(12) United States Patent
Desai et al.

(10) Patent No.: US 8,759,379 B2
(45) Date of Patent: Jun. 24, 2014

(54) INHIBITORS OF CYTOCHROME P450

(75) Inventors: Manoj C. Desai, Pleasant Hill, CA (US);
Hon C. Hui, San Mateo, CA (US);
Hongtao Liu, Cupertino, CA (US);
Lianhong Xu, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 366 days.

(21) Appl. No.: 12/340,419

(22) Filed: Dec. 19, 2008

(65) Prior Publication Data

US 2009/0175820 A1    Jul. 9, 2009

Related U.S. Application Data

(60) Provisional application No. 61/019,079, filed on Jan. 4, 2008.

(51) Int. Cl.
| | | |
|---|---|---|
| A61K 31/341 | (2006.01) | |
| A61K 31/34 | (2006.01) | |
| A61K 31/5377 | (2006.01) | |
| A61K 31/427 | (2006.01) | |
| C07D 417/12 | (2006.01) | |
| C07D 417/14 | (2006.01) | |
| C07D 493/04 | (2006.01) | |
| C07D 307/20 | (2006.01) | |

(52) U.S. Cl.
CPC ........... *A61K 31/427* (2013.01); *A61K 31/5377* (2013.01); *A61K 31/34* (2013.01); *A61K 31/341* (2013.01); *C07D 417/12* (2013.01); *C07D 417/14* (2013.01); *C07D 493/04* (2013.01); *C07D 307/20* (2013.01)
USPC ........ 514/365; 514/236.8; 514/470; 514/471; 544/133; 548/204; 549/464; 549/475

(58) Field of Classification Search
CPC . A61K 31/341; A61K 31/34; A61K 31/5377; A61K 31/427; C07D 417/12; C07D 417/14; C07D 493/04; C07D 307/20
USPC ............... 514/365, 236.8, 470, 471; 544/133; 548/204; 549/464, 475
See application file for complete search history.

(56) References Cited

U.S. PATENT DOCUMENTS

| | | | |
|---|---|---|---|
| 5,142,056 A | | 8/1992 | Kempe et al. |
| 5,354,866 A | | 10/1994 | Kempf et al. |
| 5,362,912 A | | 11/1994 | Sowin et al. |
| 5,470,816 A | * | 11/1995 | Satake et al. ................. 503/201 |
| 5,539,122 A | | 7/1996 | Kempf et al. |
| 5,541,206 A | | 7/1996 | Kempf et al. |
| 5,552,558 A | | 9/1996 | Kempf et al. |
| 5,565,418 A | | 10/1996 | Kempf et al. |
| 5,580,984 A | | 12/1996 | Kempf et al. |
| 5,583,232 A | | 12/1996 | Kempf et al. |
| 5,583,233 A | | 12/1996 | Kempf et al. |
| 5,591,860 A | | 1/1997 | Kempf et al. |
| 5,597,927 A | | 1/1997 | Kempf et al. |
| 5,597,928 A | | 1/1997 | Kempf et al. |
| 5,608,072 A | | 3/1997 | Kempf et al. |
| 5,616,720 A | | 4/1997 | Kempf et al. |
| 5,625,072 A | | 4/1997 | Kempf et al. |
| 5,635,523 A | | 6/1997 | Kempf et al. |
| 5,659,044 A | | 8/1997 | Kempf et al. |
| 5,659,045 A | | 8/1997 | Kempf et al. |
| 5,674,882 A | | 10/1997 | Kempf et al. |
| 5,679,797 A | | 10/1997 | Kempf et al. |
| 5,696,270 A | | 12/1997 | Kempf et al. |
| 5,763,464 A | | 6/1998 | Randad et al. |
| 5,892,052 A | | 4/1999 | Kempf et al. |
| 6,448,245 B1 | | 9/2002 | DePetrillo et al. |
| 2002/0115665 A1 | | 8/2002 | DePetrillo et al. |
| 2003/0191319 A1 | | 10/2003 | Vazquez et al. |
| 2004/0127689 A1 | | 7/2004 | Sigler et al. |
| 2006/0199851 A1 | | 9/2006 | Kempf et al. |
| 2008/0108617 A1 | | 5/2008 | Desai et al. |
| 2008/0207620 A1 | | 8/2008 | Desai et al. |
| 2009/0181902 A1 | | 7/2009 | Desai et al. |

FOREIGN PATENT DOCUMENTS

| | | |
|---|---|---|
| EP | 0428849 | 5/1991 |
| EP | 0674513 | 10/1995 |
| EP | 1090914 | 4/2001 |
| EP | 1183026 | 3/2002 |
| EP | 1302468 | 4/2003 |
| FR | 2773994 | 7/1999 |

(Continued)

OTHER PUBLICATIONS

Giron, D. J. Therm. Anal. Cal. 2001, 64, pp. 37-60.*
Giron, D. J. Therm. Anal. Cal. 2002, 68, pp. 335-357.*
B. Rodriquez-Spong et al. Advanced Drug Delivery Reviews, 2004, 56, pp. 241-274.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*

(Continued)

*Primary Examiner* — Joseph Kosack
*Assistant Examiner* — Matthew Coughlin
(74) *Attorney, Agent, or Firm* — Joel B. Silver

(57) ABSTRACT

The present application provides for a compound of Formula I,

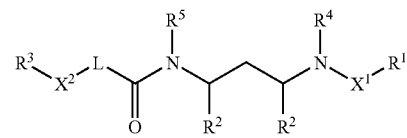

Formula I or a pharmaceutically acceptable salt, solvate, and/or ester thereof, compositions containing such compounds, therapeutic methods that include the administration of such compounds, and therapeutic methods and include the administration of such compounds with at least one additional therapeutic agent.

24 Claims, No Drawings

(56) References Cited

FOREIGN PATENT DOCUMENTS

| WO | WO-94/14436 | 7/1994 |
|----|----|----|
| WO | WO-97/01349 | 1/1997 |
| WO | WO-01/25240 | 4/2001 |
| WO | WO 2006029210 A2 * | 3/2006 |
| WO | WO-2008/010921 | 1/2008 |

OTHER PUBLICATIONS

Merriam-Webster Online Dictionary entry for "derivative", (http://www.merriam-webster.com/dictionary/derivative), last accessed Nov. 12, 2010.*

Merriam-Webster Online Dictionary entry for "analogue", (http://www.merriam-webster.com/dictionary/derivative), last accessed May 12, 2010.*

Gurjar et al. (1997) "Synthesis of Novel C2-symmetric and Pseudo C2-symmetric Based Diols, Epoxides and Dideoxy Derivatives of HIV Protease Inhibitors," *Tetrahedron* 53(13):4769-4778.

Kempf et al. (1998) "Discovery of Ritonavir, a Patent Inhibitor of HIV Protease with High Oral Bioavailability and Clinical Efficacy," *J. Med. Chem.* 41:602-617.

Molla et al. (1996) "Ordered Accumulation of Mutations in HIV Protease Confers Resistance to Ritonavir," *Nature Medicine* 2:(7):760-766.

* cited by examiner

INHIBITORS OF CYTOCHROME P450

This application is filed under 35 U.S.C. 111(a) claiming the benefit under 35 U.S.C. 119(e) to provisional application 61/019,079 filed Jan. 4, 2008 which is herein incorporated by reference in its entirety.

FIELD OF THE INVENTION

This application relates generally to compounds and pharmaceutical compositions which modify, e.g., improve, the pharmacokinetics of a co-administered drug, and methods of modifying, e.g., improving, the pharmacokinetics of a drug by co-administration of the compounds with the drug.

BACKGROUND OF THE INVENTION

Oxidative metabolism by cytochrome P450 enzymes is one of the primary mechanisms of drug metabolism. It can be difficult to maintain therapeutically effective blood plasma levels of drugs which are rapidly metabolized by cytochrome P450 enzymes. Accordingly, the blood plasma levels of drugs which are susceptible to cytochrome P450 enzyme degradation can be maintained or enhanced by co-administration of cytochrome P450 inhibitors, thereby improving the pharmacokinetics of the drug.

While certain drugs are known to inhibit cytochrome P450 enzymes, more and/or improved inhibitors for cytochrome P450 monooxygenase are desirable. Particularly, it would be desirable to have cytochrome P450 monooxygenase inhibitors which do not have appreciable biological activity other than cytochrome P450 inhibition. Such inhibitors can be useful for minimizing undesirable biological activity, e.g., side effects. In addition, it would be desirable to have P450 monooxygenase inhibitors that lack significant or have a reduced level of protease inhibitor activity. Such inhibitors could be useful for enhancing the effectiveness of antiretroviral drugs, while minimizing the possibility of eliciting viral resistance, especially against protease inhibitors.

SUMMARY OF THE INVENTION

One aspect of the present application is directed to compounds and pharmaceutical compositions which modify, e.g., improve, the pharmacokinetics of a co-administered drug, e.g., by inhibiting cytochrome P450 monooxygenase.

In one embodiment, the present application provides for a compound according to Formula I,

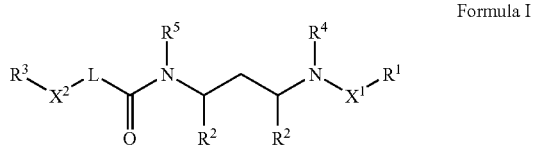

Formula I or a pharmaceutically acceptable salt, solvate, and/or ester thereof, wherein, $X^1$ is selected from the group consisting of —C(O)—O—, —S(O)—, and —S(O$_2$)—, —C(O)NR$^6$—;

$X^2$ is selected from the group consisting of —O—, —NR$^6$—C(O)—NR$^6$—, —OC(O)NR$^6$—, —NR$^6$—, and —NR$^6$C(O)O—;

L is selected from the group consisting of a covalent bond, alkylene, and —CHR$^7$—;

$R^1$ is selected from the group consisting of aryl, heteroaryl, arylalkyl, and heteroarylalkyl;

each $R^2$ is independently selected from the group consisting of H, alkyl, arylalkyl, heterocyclylalkyl, and cycloalkylalkyl wherein at least one $R^2$ is alkyl, arylalkyl, heterocyclylalkyl or cycloalkylalkyl;

$R^3$ is selected from the group consisting of heterocyclyl, aryl, heteroaryl, arylalkyl, and heteroarylalkyl;

$R^4$ and $R^5$ are each independently selected from the group consisting of H, alkyl, cycloalkyl, heterocyclyl, cycloalkylalkyl, arylalkyl, and heteroarylalkyl;

each $R^6$ is independently selected from the group consisting of H, alkyl, and cycloalkyl; and $R^7$ is H, alkyl, substituted alkyl, and heterocyclylalkyl;

wherein each aryl, heteroaryl, heterocyclyl, heterocyclylalkyl, arylalkyl, and heteroarylalkyl of $R^1$, $R^2$, $R^3$, $R^4$, $R^5$ and $R^7$ is unsubstituted or substituted.

In another embodiment, the present application provides for a pharmaceutical composition comprising a compound of Formula I, and a pharmaceutically acceptable carrier or excipient.

In another embodiment, the present application provides for a pharmaceutical composition comprising a compound of Formula I, at least one additional therapeutic agent, and a pharmaceutically acceptable carrier or excipient.

In another embodiment, the present application provides for a method for improving the pharmacokinetics of a drug, comprising administering to a patient treated with said drug, a therapeutically effective amount of a compound of Formula I, or a pharmaceutically acceptable salt solvate, and/or ester thereof.

In another embodiment, the present application provides for a method for inhibiting cytochrome P450 monooxygenase in a patient comprising administering to a patient in need thereof an amount of a compound of Formula I, or a pharmaceutically acceptable salt solvate, and/or ester thereof, effective to inhibit cytochrome P450 monooxygenase.

In another embodiment, the present application provides for a method for treating a viral infection, e.g., HIV, comprising administering to a patient in need thereof a therapeutically effective amount of a compound of Formula I, or a pharmaceutically acceptable salt, solvate, and/or ester thereof, in combination with a therapeutically effective amount of, at least one or more additional therapeutic agents which are metabolized by cytochrome P450 monooxygenase, and are suitable for treating a viral infection, e.g., HIV.

In another embodiment, the present application provides for a combination pharmaceutical agent comprising:
a) a first pharmaceutical composition comprising a compound of Formula I, or a pharmaceutically acceptable salt, solvate, and/or ester thereof; and
b) a second pharmaceutical composition comprising at least one additional active agent which is metabolized by cytochrome P450 monooxygenase.

DETAILED DESCRIPTION

Reference will now be made in detail to certain claims of the invention, examples of which are illustrated in the accompanying structures and formulas. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

DEFINITIONS

Unless otherwise indicated, all documents, patents, and patent applications referenced herein are incorporated by reference in their entirety for all purposes.

Unless stated otherwise, the following terms and phrases as used herein are intended to have the following meanings:

When trade names are used herein, applicants intend to independently include the tradename product and the active pharmaceutical ingredients) of the tradename product.

As used herein, "a compound of the invention" or "a compound of Formula I" means a compound of Formula I or a pharmaceutically acceptable salt, solvate, ester or stereoisomer thereof, or a physiologically functional derivative thereof. Similarly, with respect to isolatable intermediates, the phrase "a compound of Formula (number)" means a compound of that formula and pharmaceutically acceptable salts, solvates and physiologically functional derivatives thereof.

"Alkyl" is hydrocarbon containing normal, secondary, tertiary or cyclic carbon atoms. For example, an alkyl group can have 1 to 20 carbon atoms (i.e., $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl(Me, —$CH_3$), ethyl(Et, —$CH_2CH_3$), 1-propyl(n-Pr, n-propyl, —$CH_2CH_2CH_3$), 2-propyl(i-Pr, i-propyl, —$CH(CH_3)_2$), 1-butyl(n-Bu, n-butyl, —$CH_2CH_2CH_2CH_3$), 2-methyl-1-propyl(i-Bu, i-butyl, —$CH_2CH(CH_3)_2$), 2-butyl (s-Bu, s-butyl, —$CH(CH_3)CH_2CH_3$), 2-methyl-2-propyl(t-Bu, t-butyl, —$C(CH_3)_3$), 1-pentyl(n-pentyl, —$CH_2CH_2CH_2CH_2CH_3$), 2-pentyl(—$CH(CH_3)CH_2CH_2CH_3$), 3-pentyl(—$CH(CH_2CH_3)_2$), 2-methyl-2-butyl(—$C(CH_3)_2CH_2CH_3$), 3-methyl-2-butyl(—$CH(CH_3)CH(CH_3)_2$), 3-methyl-1-butyl(—$CH_2CH_2CH(CH_3)_2$), 2-methyl-1-butyl(—$CH_2CH(CH_3)CH_2CH_3$), 1-hexyl(—$CH_2CH_2CH_2CH_2CH_2CH_3$), 2-hexyl(—$CH(CH_3)CH_2CH_2CH_2CH_3$), 3-hexyl(—$CH(CH_2CH_3)(CH_2CH_2CH_3)$), 2-methyl-2-pentyl(—$C(CH_3)_2CH_2CH_2CH_3$), 3-methyl-2-pentyl(—$CH(CH_3)CH(CH_3)CH_2CH_3$), 4-methyl-2-pentyl(—$CH(CH_3)CH_2CH(CH_3)_2$), 3-methyl-3-pentyl(—$C(CH_3)(CH_2CH_3)_2$), 2-methyl-3-pentyl(—$CH(CH_2CH_3)CH(CH_3)_2$), 2,3-dimethyl-2-butyl(—$C(CH_3)_2CH(CH_3)_2$), 3,3-dimethyl-2-butyl(—$CH(CH_3)C(CH_3)_3$, and octyl(—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_5$ alkoxy). Examples of suitable alkoxy groups include, but are not limited to, methoxy(—O—$CH_3$ or —OMe), ethoxy(—$OCH_2CH_3$ or —OEt), t-butoxy (—O—$C(CH_3)_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl(—$CH_2CH$=$CH_2$), cyclopentenyl(—$C_5H_7$), and 5-hexenyl(—$CH_2CH_2CH_2CH_2CH$=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne), or 2 to 6 carbon atoms (i.e., $C_2$-$C_6$ alkynyl). Examples of suitable alkynyl groups include, but are not limited to, acetylenic (—C≡CH), propargyl(—$CH_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethyl(—$CH(CH_3)$—), 1,2-ethyl(—$CH_2CH_2$—), 1,1-propyl(—$CH(CH_2CH_3)$—), 1,2-propyl(—$CH_2CH(CH_3)$—), 1,3-propyl(—$CH_2CH_2CH_2$—), 1,4-butyl(—$CH_2CH_2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl(—$CH_2$C≡C—), and 4-pentynyl(—$CH_2CH_2CH_2$C≡CH—).

"Amino" means an —$NH_2$ or a —$NR_2$ group in which the "R" groups are independently H, alkyl, carbocyclyl (substituted or unsubstituted, including saturated or partially unsaturated cycloalkyl and aryl groups), heterocyclyl (substituted or unsubstituted, including saturated or unsaturated heterocycloalkyl and heteroaryl groups), arylalkyl (substituted or unsubstituted) or arylalkyl (substituted or unsubstituted) groups. Non-limiting examples of amino groups include —$NH_2$, —NH(alkyl), —NH(carbocyclyl), —NH(heterocyclyl), —N(alkyl)$_2$, —N(carbocyclyl)$_2$, —N(heterocyclyl)$_2$, —N(alkyl)(carbocyclyl), —N(alkyl)(heterocyclyl), —N(carbocyclyl)(heterocyclyl), etc., wherein alkyl, carbocyclyl, and heterocyclyl can be substituted or unsubstituted and as defined and described herein. "Substituted" or "protected" amino means an aminoalkyl as described and defined herein in which a H of the amino group is replaced with e.g., acyl groups, for example conventional amine protecting groups such as 9-Fluorenylmethyl carbamate ("Fmoc"), t-Butyl carbamate ("Boc"), Benzyl carbamate ("Cbz"), acetyl, trifluoracetyl, phthalimidyl, triphenylmethyl, p-Toluenesulfonyl ("Tosyl"), methylsulfonyl ("mesyl"), etc.

"Aminoalkyl" means an acyclic alkyl radical in which one of the hydrogen atoms bonded to a carbon atom, typically a terminal or $sp^3$ carbon atom, is replaced with an amino radical as defined and described herein. Non-limiting examples of aminoalkyl include —$CH_2$—$NH_2$, —$CH_2CH_2$—$NH_2$, —$CH_2CH_2CH_2$—$NH_2$, —$CH_2CH_2CH_2CH_2$—$NH_2$, —$CH_2CH(CH_3)$—$NH_2$, —$CH_2CH_2CH(CH_3)$—$NH_2$, —CH$_2$—NH(CH$_3$), —CH$_2$CH$_2$—NH(CH$_3$), —CH$_2$CH$_2$CH$_2$—NH(CH$_3$), —CH$_2$CH$_2$CH$_2$CH$_2$—NH(CH$_3$), —CH$_2$CH(CH$_3$)—NH(CH$_3$), —CH$_2$CH$_2$CH(CH$_3$)—NH(CH$_3$), CH$_2$—N(CH$_3$)$_2$, —CH$_2$CH$_2$—N(CH$_3$)$_2$, —CH$_2$CH$_2$CH$_2$—N(CH$_3$)$_2$, —CH$_2$CH$_2$CH$_2$CH$_2$—N(CH$_3$)$_2$, —CH$_2$CH(CH$_3$)—N(CH$_3$)$_2$, —CH$_2$CH$_2$CH(CH$_3$)—N(CH$_3$)$_2$, —CH$_2$—NH(CH$_2$CH$_3$), —CH$_2$CH$_2$—NH(CH$_2$CH$_3$), —CH$_2$CH$_2$CH$_2$NH(CH$_2$CH$_3$), —CH$_2$CH$_2$CH$_2$CH$_2$—NH(CH$_2$CH$_3$), —CH$_2$CH(CH$_3$)—NH(CH$_2$CH$_3$), —CH$_2$CH$_2$CH(CH$_3$)—NH(CH$_2$CH$_3$), —CH$_2$—N(CH$_2$CH$_3$)$_2$, —CH$_2$CH$_2$—N(CH$_2$CH$_3$)$_2$, —CH$_2$CH$_2$CH$_2$—N(CH$_2$CH$_3$)$_2$, —CH$_2$CH$_2$CH$_2$CH$_2$—N(CH$_2$CH$_3$)$_2$, —CH$_2$CH(CH$_3$)—N(CH$_2$CH$_3$)$_2$, —CH$_2$CH$_2$CH(CH$_3$)—N(CH$_2$CH$_3$)$_2$, etc. "Substituted" or "protected" aminoalkyl means an aminoalkyl as described and defined herein in which the H of the amino group is replaced with e.g., acyl groups, for example conventional amine protecting groups such as 9-fluorenylmethyl carbamate ("Fmoc"), t-butyl carbamate ("Boc"), benzyl carbamate ("Cbz"), acetyl, trifluoracetyl, phthalimidyl, triphenylmethyl, p-toluenesulfonyl ("Tosyl"), methylsulfonyl ("mesyl"), etc.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl and the like.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp$^3$ carbon atom, but also an sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 6 to 20 carbon atoms, e.g., the alkenyl moiety is 1 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 6 to 20 carbon atoms, e.g., the alkynyl moiety is 1 to 6 carbon atoms and the aryl moiety is 6 to 14 carbon atoms.

The term "substituted" in reference to alkyl, alkylene, aryl, arylalkyl, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R, —O$^-$, =O, —OR, —SR, —S$^-$, —NR$_2$, —N$^+$R$_3$, =NR, —CX$_3$, —CN, —OCN, —SCN, —N=C=O, —NCS, —NO, —NO$_2$, =N$_2$, —N$_3$, —NHC(=O)R, —NHS(=O)$_2$R, —C(=O)R, —C(=O)NRR, —S(=O)$_2$O$^-$, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —P(=O)(O$^-$)$_2$, —P(=O)(OH)$_2$, —P(O)(OR)(O$^-$), —C(=O)R, —C(=O)OR, —C(=O)X, —C(S)R, —C(O)OR, —C(O)O$^-$, —C(S)OR, —C(O)SR, —C(S)SR, —C(O)NRR, —C(S)NRR, —C(=NR)NRR, where each X is independently a halogen: F, Cl, Br, or I; and each R is independently H, alkyl, aryl, arylalkyl, heteroarylalkyl, a heterocycle, or a protecting group or prodrug moiety. Alkylene, alkenylene, and alkynylene groups may also be similarly substituted. When the number of carbon atoms is designated for a substituted group, the number of carbon atoms refers to the group, not the substituent (unless otherwise indicated). For example, a C$_{1-4}$ substituted alkyl refers to a C$_{1-4}$ alkyl, which can be substituted with groups having more the, e.g., 4 carbon atoms.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula I should be selected in order to provide a compound which is sufficiently stable to provide a pharmaceutically useful compound which can be formulated into an acceptably stable pharmaceutical composition. Compounds of Formula I which have such stability are contemplated as falling within the scope of the present invention.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

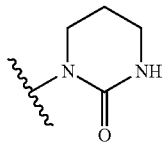 [SMILES: *N1CCCNC1=O]

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

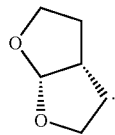

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylalkyl" refers to an acyclic alkyl radical in which one of the hydrogen atoms bonded to a carbon atom, typically a terminal or $sp^3$ carbon atom, is replaced with a heterocyclyl radical (i.e., a heterocyclyl-alkylene-moiety). Typical heterocyclyl alkyl groups include, but are not limited to heterocyclyl-$CH_2$—, heterocyclyl-$CH(CH_3)$—, heterocyclyl-$CH_2CH_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclylalkyl group comprises 2 to 20 carbon atoms, e.g., the alkyl portion of the heterocyclylalkyl group is 1 to 6 carbon atoms and the heterocyclyl moiety is 1 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or $sp^3$ carbon atom, but also a $sp^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclylalkenyl group comprises 3 to 20 carbon atoms, e.g., the alkenyl portion of the heterocyclyl alkenyl group is 2 to 6 carbon atoms and the heterocyclyl moiety is 1 to 14 carbon atoms.

"Heterocyclylalkynyl" refers to an acyclic alkynyl radical in which one of the hydrogen atoms bonded to a carbon atom, typically a terminal or $sp^3$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclylalkynyl group comprises 3 to 20 carbon atoms, e.g., the alkynyl portion of the heterocyclylalkynyl group is 2 to 6 carbon atoms and the heterocyclyl moiety is 1 to 14 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo[4,5], [5,5], [5,6] or [6,6] system, 9 or 10 ring atoms arranged as a bicyclo[5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl.

"Cycloalkylalkyl" refers to an alkyl as defined herein, in which a hydrogen atom has been replaced with a cycloalkyl or carbocyclyl as defined herein.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —$CH_2$-pyridinyl, —$CH_2$-pyrrolyl, —$CH_2$-oxazolyl, —$CH_2$-indolyl, —$CH_2$-isoindolyl, —$CH_2$-purinyl, —$CH_2$-furanyl, —$CH_2$-thienyl, —$CH_2$-benzofuranyl, —$CH_2$-benzothiophenyl, —$CH_2$-carbazolyl, —$CH_2$-imidazolyl, —$CH_2$-thiazolyl, —$CH_2$-isoxazolyl, —$CH_2$-pyrazolyl, —$CH_2$-isothiazolyl, —$CH_2$-quinolyl, —$CH_2$-isoquinolyl, —$CH_2$-pyridazyl, —$CH_2$-pyrimidyl, —$CH_2$-pyrazyl, —$CH(CH_3)$-pyridinyl, —$CH(CH_3)$-pyrrolyl, —$CH(CH_3)$-oxazolyl, —$CH(CH_3)$-indolyl, —$CH(CH_3)$-isoindolyl, —$CH(CH_3)$-purinyl, —$CH(CH_3)$-furanyl, —$CH(CH_3)$-thienyl, —$CH(CH_3)$-benzofuranyl, —$CH(CH_3)$-benzothiophenyl, —$CH(CH_3)$-carbazolyl, —$CH(CH_3)$-imidazolyl, —$CH(CH_3)$-thiazolyl, —$CH(CH_3)$-isoxazolyl, —$CH(CH_3)$-pyrazolyl, —$CH(CH_3)$-isothiazolyl, —$CH(CH_3)$-quinolyl, —$CH(CH_3)$-isoquinolyl, —$CH(CH_3)$-pyridazyl, —$CH(CH_3)$-pyrimidyl, —$CH(CH_3)$-pyrazyl, etc.

The term "optionally substituted" in reference to a particular moiety of the compound of Formula I (e.g., an optionally substituted aryl group) refers to a moiety having 0, 1, 2, or more substituents.

"Ac" means acetyl(—$C(O)CH_3$).
"$Ac_2O$" means acetic anhydride.
"DCM" means dichloromethane ($CH_2Cl_2$).
"DIBAL" means diisobutylaluminum hydride.
"DMAP" means dimethylaminopyridine.
"EDC" means 1-(3-Dimethylaminopropyl)-3-ethylcarbodiimide.
"Et" means ethyl.
"EtOAc" means ethylacetate.
"HOBt" means N-hydroxybenzotriazole.
"Me" means methyl(—$CH_3$).
"MeOH" means methanol.
"MeCN" means acetonitrile.
"Pr" means propyl.
"i-Pr" means isopropyl(—$CH(CH_3)_2$).
"i-PrOH" means isopropanol.
"rt" or "RT" means room temperature.
"TFA" means trifluoroacetic acid.
"THF" means tetrahydrofuran.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The modifier "about" used in connection with a quantity is inclusive of the stated value and has the meaning dictated by the context (e.g., includes the degree of error associated with measurement of the particular quantity).

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG groups. In general, PG groups will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether-nor ester-forming groups, as will be understood by those skilled in the art and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

Compounds of Formula I

In another embodiment of the compounds of Formula I, $R^1$ is substituted or unsubstituted aryl.

In another embodiment of the compounds of Formula I, $R^1$ is substituted or unsubstituted phenyl.

In another embodiment of the compounds of Formula I, $R^1$ is substituted phenyl.

In another embodiment of the compounds of Formula I, $R^1$ is mono-substituted phenyl.

In another embodiment of the compounds of Formula I, $R^1$ is phenyl substituted with one or more substituents selected from the group consisting of alkyl, substituted alkyl, halo, hydroxyl, amino, haloalkyl, and cyano.

In another embodiment of the compounds of Formula I, $R^1$ is 4-aminophenyl.

In another embodiment of the compounds of Formula I, $R^1$ is substituted or unsubstituted heteroaryl.

In another embodiment of the compounds of Formula I, $R^1$ is substituted or unsubstituted thiazolyl.

In another embodiment of the compounds of Formula I, $R^1$ is substituted or unsubstituted arylalkyl.

In another embodiment of the compounds of Formula I, $R^1$ is substituted or unsubstituted benzyl.

In another embodiment of the compounds of Formula I, $R^1$ is substituted or unsubstituted heteroarylalkyl.

In another embodiment of the compounds of Formula I, $R^1$ is substituted or unsubstituted heteroarylalkyl, wherein the alkyl portion thereof is any of the alkylene groups defined or disclosed herein.

In another embodiment of the compounds of Formula I, $R^1$ is substituted or unsubstituted heteroarylalkyl, wherein the alkyl portion thereof is —$CH_2$—.

In another embodiment of the compounds of Formula I, $R^1$ is substituted or unsubstituted heteroarylalkyl, wherein the heteroaryl portion thereof is any of the heteroaryl groups defined or disclosed herein.

In another embodiment of the compounds of Formula I, $R^1$ is substituted or unsubstituted heteroarylalkyl, wherein the heteroaryl portion thereof is thiazolyl.

In another embodiment of the compounds of Formula I, $R^1$ is substituted or unsubstituted thiazolylmethyl.

In another embodiment of the compounds of Formula I, $R^1$ is thiazol-5-ylmethyl.

In another embodiment of the compounds of Formula I, $R^1$ is substituted heteroarylalkyl, wherein the heteroaryl portion thereof is any of the heteroaryl groups defined or disclosed herein, and the substituent is one or more substituents selected from the group consisting of alkyl, substituted alkyl, halo, hydroxyl, amino, haloalkyl, and cyano.

In another embodiment of the compounds of Formula I, R¹ is substituted heteroarylalkyl, wherein the heteroaryl portion thereof is thiazolyl substituted with one or more substituents selected from the group consisting of alkyl, substituted alkyl, halo, hydroxyl, amino, haloalkyl, and cyano.

In another embodiment of the compounds of Formula I, R¹ is thiazolylmethyl substituted with one or more substituents selected from the group consisting of alkyl, substituted alkyl, halo, hydroxyl, amino, haloalkyl, and cyano.

In one embodiment, the present application provides compounds according to Formula I, as described herein.

In another embodiment of the compounds of Formula I, at least one R² is substituted or unsubstituted arylalkyl.

In another embodiment of the compounds of Formula I, at least one R² is substituted or unsubstituted benzyl.

In another embodiment of the compounds of Formula I, at least one R² is H.

In another embodiment of the compounds of Formula I, at least one R² is alkyl.

In another embodiment of the compounds of Formula I, one R² is substituted or unsubstituted arylalkyl, and the other R² is H.

In another embodiment of the compounds of Formula I, one R² is substituted or unsubstituted benzyl, and the other R² is H.

In another embodiment of the compounds of Formula I, one R² is substituted or unsubstituted arylalkyl, and the other R² is alkyl.

In another embodiment of the compounds of Formula I, one R² is substituted or unsubstituted benzyl, and the other R² is alkyl.

In another embodiment of the compounds of Formula I, one R² is H, and the other R² is alkyl.

In another embodiment of the compounds of Formula I, X¹ is —C(O)—O—.

In another embodiment of the compounds of Formula I, X¹ is —S(O)—.

In another embodiment of the compounds of Formula I, X¹ is —S(O₂)—.

In another embodiment of the compounds of Formula I, X¹ is —C(O)NR⁶—.

In another embodiment of the compounds of Formula I, X¹ is —NR⁶C(O)—.

In another embodiment of the compounds of Formula I, X¹ is —C(O)NH—,

In another embodiment of the compounds of Formula I, X¹ is —C(O)N(alkyl)-.

In another embodiment of the compounds of Formula I, X² is —O—.

In another embodiment of the compounds of Formula I, X² is —NR⁶—C(O)—NR⁶—.

In another embodiment of the compounds of Formula I, X² is —NR⁶—C(O)—NH—.

In another embodiment of the compounds of Formula I, X² is NH—C(O)—NR—.

In another embodiment of the compounds of Formula I, X² is —N(alkyl)-C(O)—N(alkyl)-.

In another embodiment of the compounds of Formula I, X² is —N(alkyl)-C(O)—NH—.

In another embodiment of the compounds of Formula I, X² is —N(cycloalkyl)-C(O)—NH—.

In another embodiment of the compounds of Formula I, X² is —NH—C(O)—N(alkyl)-.

In another embodiment of the compounds of Formula I, X² is NH—C(O)—N(cycloalkyl)-.

In another embodiment of the compounds of Formula I, X² is —NH—C(O)—NH—.

In another embodiment of the compounds of Formula I, X² is —NR⁶—.

In another embodiment of the compounds of Formula I, X² is —NH—.

In another embodiment of the compounds of Formula I, X² is —N(alkyl)-.

In another embodiment of the compounds of Formula I, X² is —N(cycloalkyl)-.

In another embodiment of the compounds of Formula I, X² is —OC(O)NR⁶—.

In another embodiment of the compounds of Formula I, X² is —OC(O)NH—.

In another embodiment of the compounds of Formula I, X² is —OC(O)N(alkyl)-.

In another embodiment of the compounds of Formula I, X² is —OC(O)N(cycloalkyl)-.

In another embodiment of the compounds of Formula I, X² is —NR⁶C(O)O—.

In another embodiment of the compounds of Formula I, X² is —NHC(O)O—.

In another embodiment of the compounds of Formula I, X² is —N(alkyl)C(O)O—.

In another embodiment of the compounds of Formula I, X² is —N(cycloalkyl)C(O)O—.

In another embodiment of the compounds of Formula I, L is a covalent bond.

In another embodiment of the compounds of Formula I, L is —CHR⁷—, wherein R⁷ is heterocyclylalkyl.

In another embodiment of the compounds of Formula I, L is —CHR⁷—, wherein R⁷ is heterocyclylalkyl, the alkyl portion of which is any alkylene as defined or described herein.

In another embodiment of the compounds of Formula I, L is —CHR⁷—, wherein R⁷ is heterocyclylalkyl, the heterocyclyl portion of which is any heterocyclyl as defined herein.

In another embodiment of the compounds of Formula I, L is —CHR⁷—, wherein R⁷ is heterocyclylalkyl, the heterocyclyl portion of which is a morpholinyl group.

In another embodiment of the compounds of Formula I, L is —CHR⁷— and R⁷ is:

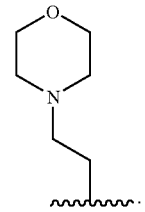 [SMILES: *CCN1CCOCC1]

In another embodiment of the compounds of Formula I, L is an alkylene.

In another embodiment of the compounds of Formula I, R³ is substituted or unsubstituted heterocyclyl.

In another embodiment of the compounds of Formula I, R³ is substituted or unsubstituted tetrahydro-2H-furo[2,3-b]furanyl.

In another embodiment of the compounds of Formula I, R³ is unsubstituted tetrahydro-2H-furo[2,3-b]furanyl.

In another embodiment of the compounds of Formula I, R³ is tetrahydro-2H-furo[2,3-b]furan-3-yl.

In another embodiment of the compounds of Formula I, R³ is substituted or unsubstituted tetrahydrofuranyl.

In another embodiment of the compounds of Formula I, R³ is unsubstituted tetrahydrofuranyl.

In another embodiment of the compounds of Formula I, $R^3$ is tetrahydrofuran-3-yl.

In another embodiment of the compounds of Formula I, $R^3$ is substituted or unsubstituted aryl.

In another embodiment of the compounds of Formula I, $R^3$ is substituted or unsubstituted phenyl.

In another embodiment of the compounds of Formula I, $R^3$ is substituted or unsubstituted heteroaryl.

In another embodiment of the compounds of Formula I, $R^3$ is substituted or unsubstituted heteroaryl, wherein said heteroaryl is any heteroaryl described or defined herein.

In another embodiment of the compounds of Formula I, $R^3$ is substituted or unsubstituted thiazolyl.

In another embodiment of the compounds of Formula I, $R^3$ is thiazolyl substituted with one or more substituents selected from the group consisting of alkyl, substituted alkyl, halo, hydroxyl, amino, haloalkyl, and cyano.

In another embodiment of the compounds of Formula I, $R^3$ is substituted or unsubstituted arylalkyl.

In another embodiment of the compounds of Formula I, $R^3$ is substituted or unsubstituted benzyl.

In another embodiment of the compounds of Formula I, $R^3$ is substituted benzyl.

In another embodiment of the compounds of Formula I, $R^3$ is benzyl substituted with one or more substituents selected from the group consisting of alkyl, substituted alkyl, halo, hydroxyl, amino, haloalkyl, and cyano.

In another embodiment of the compounds of Formula I, $R^3$ is substituted or unsubstituted heteroarylalkyl.

In another embodiment of the compounds of Formula I, $R^3$ is substituted or unsubstituted heteroarylalkyl, wherein the alkyl portion thereof is any alkylene described or disclosed herein.

In another embodiment of the compounds of Formula I, $R^3$ is substituted or unsubstituted heteroarylalkyl, wherein the alkyl portion thereof is —$CH_2$—.

In another embodiment of the compounds of Formula I, $R^3$ is substituted or unsubstituted heteroarylalkyl, wherein the heteroaryl portion thereof is any heteroaryl described or disclosed herein.

In another embodiment of the compounds of Formula I, $R^3$ is substituted or unsubstituted heteroarylalkyl, wherein the heteroaryl portion thereof is thiazolyl.

In another embodiment of the compounds of Formula I, $R^3$ is substituted or unsubstituted thiazolylmethyl.

In another embodiment of the compounds of Formula I, $R^3$ is substituted or unsubstituted thiazol-5-ylmethyl.

In another embodiment of the compounds of Formula I, $R^3$ is substituted or unsubstituted thiazol-4-ylmethyl.

In another embodiment of the compounds of Formula I, $R^3$ is substituted thiazolylmethyl.

In another embodiment of the compounds of Formula I, $R^3$ is thiazolylmethyl substituted with one or more substituents selected from the group consisting of alkyl, substituted alkyl, halo, hydroxyl, amino, haloalkyl, and cyano.

In another embodiment of the compounds of Formula I, $R^3$ is substituted thiazolylmethyl, and the substituent is an alkyl group.

In another embodiment of the compounds of Formula I, $R^3$ is 2-isopropylthiazol-4-ylmethyl.

In another embodiment of the compounds of Formula I, $R^3$ is thiazol-5-ylmethyl.

In another embodiment of the compounds of Formula I, $R^4$ is H.

In another embodiment of the compounds of Formula I, $R^4$ is alkyl.

In another embodiment of the compounds of Formula I, $R^4$ is any of the alkyl groups described or disclosed herein.

In another embodiment of the compounds of Formula I, $R^4$ is 2-methylpropyl.

In another embodiment of the compounds of Formula I, $R^4$ is n-propyl.

In another embodiment of the compounds of Formula I, $R^4$ is substituted or unsubstituted arylalkyl.

In another embodiment of the compounds of Formula I, $R^4$ is substituted or unsubstituted benzyl.

In another embodiment of the compounds of Formula I, $R^4$ is unsubstituted benzyl.

In another embodiment of the compounds of Formula I, $R^4$ is benzyl substituted with one or more substituents selected from the group consisting of alkyl, substituted alkyl, benzyl, alkoxy, benzyloxy, —O—$CH_2$-pyridyl, halo, hydroxyl, amino, haloalkyl, and cyano.

In another embodiment of the compounds of Formula I, $R^4$ is halo substituted benzyl.

In another embodiment of the compounds of Formula I, $R^4$ is chloro substituted benzyl.

In another embodiment of the compounds of Formula I, $R^4$ is substituted or unsubstituted heterocyclylalkyl.

In another embodiment of the compounds of Formula I, $R^4$ is substituted or unsubstituted heterocyclylalkyl, wherein the alkyl portion thereof is any of the alkylene groups described or defined herein.

In another embodiment of the compounds of Formula I, $R^4$ is substituted or unsubstituted heterocyclylalkyl, wherein the alkyl portion thereof is —$CH_2$—.

In another embodiment of the compounds of Formula I, $R^4$ is substituted or unsubstituted heterocyclylalkyl, wherein the heterocyclyl portion thereof is any of the heterocyclyl groups described or defined herein.

In another embodiment of the compounds of Formula I, $R^4$ is substituted or unsubstituted heterocyclylalkyl, wherein the heterocyclyl portion thereof is morpholinyl.

In another embodiment of the compounds of Formula I, $R^4$ is substituted or unsubstituted heteroarylalkyl.

In another embodiment of the compounds of Formula I, $R^4$ is substituted or unsubstituted heteroarylalkyl, wherein the alkyl portion thereof is any of the alkylene groups described or defined herein.

In another embodiment of the compounds of Formula I, $R^4$ is substituted or unsubstituted heteroarylalkyl, wherein the alkyl portion thereof is —$CH_2$—.

In another embodiment of the compounds of Formula I, $R^4$ is substituted or unsubstituted heteroarylalkyl, wherein the heteroaryl portion thereof is any of the heteroaryl groups described or defined herein.

In another embodiment of the compounds of Formula I, $R^4$ is substituted or unsubstituted —$CH_2$-pyridyl.

In another embodiment of the compounds of Formula I, $R^4$ is substituted or unsubstituted heterocyclyl, wherein the heterocyclyl is any heterocyclyl described or disclosed herein.

In another embodiment of the compounds of Formula I, $R^4$ is substituted or unsubstituted cycloalkyl, wherein the cycloalkyl is any cycloalkyl or carbocyclyl described or defined herein.

In another embodiment of the compounds of Formula I, $R^4$ is substituted or unsubstituted cycloalkylalkyl, wherein the cycloalkyl portion thereof is any cycloalkyl or carbocyclyl described or defined herein, and the alkyl portion thereof is any alkyl (or alkylene) described or disclosed herein.

In a particular embodiment, $R^4$ is —$CH_2$-cyclohexyl.

In another embodiment of the compounds of Formula I, $R^4$ is cyclopropyl.

In another embodiment of the compounds of Formula I, $R^5$ is H.

In another embodiment of the compounds of Formula I, $R^5$ is alkyl.

In another embodiment of the compounds of Formula I, $R^5$ is any of the alkyl groups described or disclosed herein.

In another embodiment of the compounds of Formula I, $R^5$ is 2-methylpropyl.

In another embodiment of the compounds of Formula I, $R^5$ is n-propyl.

In another embodiment of the compounds of Formula I, $R^5$ is substituted or unsubstituted arylalkyl.

In another embodiment of the compounds of Formula I, $R^5$ is substituted or unsubstituted benzyl.

In another embodiment of the compounds of Formula I, $R^5$ is unsubstituted benzyl.

In another embodiment of the compounds of Formula I, $R^5$ is benzyl substituted with one or more substituents selected from the group consisting of alkyl, substituted alkyl, benzyl, alkoxy, benzyloxy, —O—$CH_2$-pyridyl, halo, hydroxyl, amino, haloalkyl, and cyano.

In another embodiment of the compounds of Formula I, $R^5$ is halo substituted benzyl.

In another embodiment of the compounds of Formula I, $R^5$ is substituted or unsubstituted heterocyclylalkyl.

In another embodiment of the compounds of Formula I, $R^5$ is substituted or unsubstituted heterocyclylalkyl, wherein the alkyl portion thereof is any of the alkylene groups described or defined herein.

In another embodiment of the compounds of Formula I, $R^5$ is substituted or unsubstituted heterocyclylalkyl, wherein the alkyl portion thereof is —$CH_2$—.

In another embodiment of the compounds of Formula I, $R^5$ is substituted or unsubstituted heterocyclylalkyl, wherein the heterocyclyl portion thereof is any of the heterocyclyl groups described or defined herein.

In another embodiment of the compounds of Formula I, $R^5$ is substituted or unsubstituted heterocyclylalkyl, wherein the heterocyclyl portion thereof is morpholinyl.

In another embodiment of the compounds of Formula I, $R^5$ is substituted or unsubstituted heteroarylalkyl.

In another embodiment of the compounds of Formula I, $R^5$ is substituted or unsubstituted heteroarylalkyl, wherein the alkyl portion thereof is any of the alkylene groups described or defined herein.

In another embodiment of the compounds of Formula I, $R^5$ is substituted or unsubstituted heteroarylalkyl, wherein the alkyl portion thereof is —$CH_2$—.

In another embodiment of the compounds of Formula I, $R^5$ is substituted or unsubstituted heteroarylalkyl, wherein the heteroaryl portion thereof is any of the heteroaryl groups described or defined herein.

In another embodiment of the compounds of Formula I, $R^5$ is substituted or unsubstituted —$CH_2$-pyridyl.

In another embodiment of the compounds of Formula I, $R^5$ is substituted or unsubstituted heterocyclyl, wherein the heterocyclyl is any heterocyclyl described or disclosed herein.

In another embodiment of the compounds of Formula I, $R^5$ is substituted or unsubstituted cycloalkyl, wherein the cycloalkyl is any cycloalkyl or carbocyclyl described or defined herein.

In another embodiment of the compounds of Formula I, $R^5$ is substituted or unsubstituted cycloalkylalkyl, wherein the cycloalkyl portion thereof is any cycloalkyl or carbocyclyl described or defined herein, and the alkyl portion thereof is any alkyl (or alkylene) described or disclosed herein.

In a particular embodiment, $R^5$ is —$CH_2$-cyclohexyl.

In another embodiment of the compounds of Formula I, $R^5$ is cyclopropyl.

In another embodiment of the compounds of Formula I, $R^4$ and $R^5$ are different.

In another embodiment of the compounds of Formula I, $R^4$ and $R^5$ are the same.

In another embodiment of the compounds of Formula I, one of $R^4$ and $R^5$ is H.

In another embodiment of the compounds of Formula I, $R^4$ is H and $R^5$ is benzyl or substituted benzyl.

In another embodiment of the compounds of Formula I, —$X^1$—$R^1$ is substituted or unsubstituted —C(O)—O-aryl.

In another embodiment of the compounds of Formula I, —$X^1$—$R^1$ is substituted or unsubstituted —C(O)—O-phenyl.

In another embodiment of the compounds of Formula I, —$X^1$—$R^1$ is substituted —C(O)—O-phenyl.

In another embodiment of the compounds of Formula I, —$X^1$—$R^1$ is mono-substituted —C(O)—O-phenyl.

In another embodiment of the compounds of Formula I, —$X^1$—$R^1$ is —C(O)—O-phenyl substituted with one or more substituents selected from the group consisting of alkyl, substituted alkyl, halo, hydroxyl, amino, haloalkyl, and cyano.

In another embodiment of the compounds of Formula I, —$X^1$—$R^1$ is —C(O)—O-(4-aminophenyl).

In another embodiment of the compounds of Formula I, —$X^1$—$R^1$ is substituted or unsubstituted —C(O)—O-heteroaryl.

In another embodiment of the compounds of Formula I, —$X^1$—$R^1$ is substituted or unsubstituted —C(O)—O-thiazolyl.

In another embodiment of the compounds of Formula I, —$X^1$—$R^1$ is substituted or unsubstituted —C(O)—O-arylalkyl.

In another embodiment of the compounds of Formula I, —$X^1$—$R^1$ is substituted or unsubstituted —C(O)—O-benzyl.

In another embodiment of the compounds of Formula I, —$X^1$—$R^1$ is substituted or unsubstituted —C(O)—O-heteroarylalkyl.

In another embodiment of the compounds of Formula I, —$X^1$—$R^1$ is substituted or unsubstituted —C(O)—O-heteroarylalkyl, wherein the alkyl portion thereof is any of the alkylene groups defined or disclosed herein.

In another embodiment of the compounds of Formula I, —$X^1$—$R^1$ is substituted or unsubstituted —C(O)—O-heteroarylalkyl, wherein the alkyl portion thereof is —$CH_2$—.

In another embodiment of the compounds of Formula I, —$X^1$—$R^1$ is substituted or unsubstituted —C(O)—O-heteroarylalkyl, wherein the heteroaryl portion thereof is any of the heteroaryl groups defined or disclosed herein.

In another embodiment of the compounds of Formula I, —$X^1$—$R^1$ is substituted or unsubstituted —C(O)—O-heteroarylalkyl, wherein the heteroaryl portion thereof is thiazolyl.

In another embodiment of the compounds of Formula I, —$X^1$—$R^1$ is substituted or unsubstituted —C(O)—O-thiazolylmethyl.

In another embodiment of the compounds of Formula I, —$X^1$—$R^1$ is —C(O)—O-thiazol-5-ylmethyl.

In another embodiment of the compounds of Formula I, —$X^1$—$R^1$ is substituted —C(O)—O-heteroarylalkyl, wherein the heteroaryl portion thereof is any of the heteroaryl groups defined or disclosed herein, and the substituent is one or more substituents selected from the group consisting of alkyl, substituted alkyl, halo, hydroxyl, amino, haloalkyl, and cyano.

In another embodiment of the compounds of Formula I, —$X^1$—$R^1$ is substituted —C(O)—O-heteroarylalkyl, wherein the heteroaryl portion thereof is thiazolyl substituted with one or more substituents selected from the group consisting of alkyl, substituted alkyl, halo, hydroxyl, amino, haloalkyl, and cyano.

In another embodiment of the compounds of Formula I, —$X^1$—$R^1$ is —C(O)—O-thiazolylmethyl substituted with one or more substituents selected from the group consisting of alkyl, substituted alkyl, halo, hydroxyl, amino, haloalkyl, and cyano.

In another embodiment of the compounds of Formula I, —$X^1$—$R^1$ is substituted or unsubstituted —S(O)-aryl.

In another embodiment of the compounds of Formula I, —$X^1$—$R^1$ is substituted or unsubstituted —S(O)-phenyl.

In another embodiment of the compounds of Formula I, —$X^1$—$R^1$ is substituted —S(O)-phenyl.

In another embodiment of the compounds of Formula I, —$X^1$—$R^1$ is mono-substituted —S(O)-phenyl.

In another embodiment of the compounds of Formula I, —$X^1$—$R^1$ is —S(O)-phenyl substituted with one or more substituents selected from the group consisting of alkyl, substituted alkyl, halo, hydroxyl, amino, haloalkyl, and cyano.

In another embodiment of the compounds of Formula I, —$X^1$—$R^1$ is —S(O)-(4-aminophenyl).

In another embodiment of the compounds of Formula I, —$X^1$—$R^1$ is substituted or unsubstituted —S(O)-heteroaryl.

In another embodiment of the compounds of Formula I, —$X^1$—$R^1$ is substituted or unsubstituted —S(O)-thiazolyl.

In another embodiment of the compounds of Formula I, —$X^1$—$R^1$ is substituted or unsubstituted —S(O)-arylalkyl.

In another embodiment of the compounds of Formula I, —$X^1$—$R^1$ is substituted or unsubstituted —S(O)-benzyl.

In another embodiment of the compounds of Formula I, —$X^1$—$R^1$ is substituted or unsubstituted —S(O)-heteroarylalkyl.

In another embodiment of the compounds of Formula I, —$X^1$—$R^1$ is substituted or unsubstituted —S(O)-heteroarylalkyl, wherein the alkyl portion thereof is any of the alkylene groups defined or disclosed herein.

In another embodiment of the compounds of Formula I, —$X^1$—$R^1$ is substituted or unsubstituted —S(O)-heteroarylalkyl, wherein the alkyl portion thereof is —$CH_2$—.

In another embodiment of the compounds of Formula I, —$X^1$—$R^1$ is substituted or unsubstituted —S(O)-heteroarylalkyl wherein the heteroaryl portion thereof is any of the heteroaryl groups defined or disclosed herein.

In another embodiment of the compounds of Formula I, —$X^1$—$R^1$ is substituted or unsubstituted —S(O)-heteroarylalkyl, wherein the heteroaryl portion thereof is thiazolyl.

In another embodiment of the compounds of Formula I, —$X^1$—$R^1$ is substituted or unsubstituted —S(O)-thiazolylmethyl.

In another embodiment of the compounds of Formula I, —$X^1$—$R^1$ is substituted —S(O)-heteroarylalkyl, wherein the heteroaryl portion thereof is any of the heteroaryl groups defined or disclosed herein, and the substituent is one or more substituents selected from the group consisting of alkyl, substituted alkyl, halo, hydroxyl, amino, haloalkyl, and cyano.

In another embodiment of the compounds of Formula I, —$X^1$—$R^1$ is substituted —S(O)-heteroarylalkyl, wherein the heteroaryl portion thereof is thiazolyl substituted with one or more substituents selected from the group consisting of alkyl, substituted alkyl, halo, hydroxyl, amino, haloalkyl, and cyano.

In another embodiment of the compounds of Formula I, —$X^1$—$R^1$ is —S(O)-thiazolylmethyl substituted with one or more substituents selected from the group consisting of alkyl, substituted alkyl, halo, hydroxyl, amino haloalkyl, and cyano.

In another embodiment of the compounds of Formula I, —$X^1$—$R^1$ is substituted or unsubstituted —$S(O_2)$-aryl.

In another embodiment of the compounds of Formula I, —$X^1$—$R^1$ is substituted or unsubstituted —$S(O_2)$-phenyl.

In another embodiment of the compounds of Formula I, —$X^1$—$R^1$ is substituted —$S(O_2)$-phenyl.

In another embodiment of the compounds of Formula I, —$X^1$—$R^1$ is mono-substituted —$S(O_2)$-phenyl.

In another embodiment of the compounds of Formula I, —$X^1$—$R^1$ is —$S(O_2)$-phenyl substituted with one or more substituents selected from the group consisting of alkyl, substituted alkyl, halo, hydroxyl, amino, haloalkyl, and cyano.

In another embodiment of the compounds of Formula I, —$X^1$—$R^1$ is —$S(O_2)$-(4-aminophenyl).

In another embodiment of the compounds of Formula I, —$X^1$—$R^1$ is substituted or unsubstituted —$S(O_2)$-heteroaryl.

In another embodiment of the compounds of Formula I, —$X^1$—$R^1$ is substituted or unsubstituted —$S(O_2)$-thiazolyl.

In another embodiment of the compounds of Formula I, —$X^1$—$R^1$ is substituted or unsubstituted —$S(O_2)$-arylalkyl.

In another embodiment of the compounds of Formula I, —$X^1$—$R^1$ is substituted or unsubstituted —$S(O_2)$-benzyl.

In another embodiment of the compounds of Formula I, —$X^1$—$R^1$ is substituted or unsubstituted —$S(O_2)$-heteroarylalkyl.

In another embodiment of the compounds of Formula I, —$X^1$—$R^1$ is substituted or unsubstituted —$S(O_2)$-heteroarylalkyl, wherein the alkyl portion thereof is any of the alkylene groups defined or disclosed herein.

In another embodiment of the compounds of Formula I, —$X^1$—$R^1$ is substituted or unsubstituted —$S(O_2)$-heteroarylalkyl, wherein the alkyl portion thereof is —$CH_2$—.

In another embodiment of the compounds of Formula I, —$X^1$—$R^1$ is substituted or unsubstituted —$S(O_2)$-heteroarylalkyl, wherein the heteroaryl portion thereof is any of the heteroaryl groups defined or disclosed herein.

In another embodiment of the compounds of Formula I, —$X^1$—$R^1$ is substituted or unsubstituted —$S(O_2)$-heteroarylalkyl, wherein the heteroaryl portion thereof is thiazolyl.

In another embodiment of the compounds of Formula I, —$X^1$—$R^1$ is substituted or unsubstituted —$S(O_2)$-thiazolylmethyl.

In another embodiment of the compounds of Formula I, —$X^1$—$R^1$ is substituted —$S(O_2)$-heteroarylalkyl, wherein the heteroaryl portion thereof is any of the heteroaryl groups defined or disclosed herein, and the substituent is one or more substituents selected from the group consisting of alkyl, substituted alkyl, halo, hydroxyl amino, haloalkyl and cyano.

In another embodiment of the compounds of Formula I, —$X^1$—$R^1$ is substituted —$S(O_2)$-heteroarylalkyl, wherein the heteroaryl portion thereof is thiazolyl substituted with one or more substituents selected from the group consisting of alkyl, substituted alkyl, halo, hydroxyl, amino, haloalkyl, and cyano.

In another embodiment of the compounds of Formula I, —$X^1$—$R^1$ is —$S(O_2)$-thiazolylmethyl substituted with one or more substituents selected from the group consisting of alkyl, substituted alkyl, halo, hydroxyl, amino, haloalkyl, and cyano.

In another embodiment of the compounds of Formula I, —$X^1$—$R^1$ is substituted or unsubstituted —C(O)$NR^6$-aryl.

In another embodiment of the compounds of Formula I, —$X^1$—$R^1$ is substituted or unsubstituted —C(O)$NR^6$-phenyl.

In another embodiment of the compounds of Formula I, —$X^1$—$R^1$ is substituted —C(O)$NR^6$-phenyl.

In another embodiment of the compounds of Formula I, —$X^1$—$R^1$ is mono-substituted —C(O)$NR^6$-phenyl.

In another embodiment of the compounds of Formula I, —$X^1$—$R^1$ is —C(O)$NR^6$-phenyl substituted with one or more substituents selected from the group consisting of alkyl, substituted alkyl, halo, hydroxyl, amino, haloalkyl, and cyano.

In another embodiment of the compounds of Formula I, —$X^1$—$R^1$ is —C(O)$NR^6$-(4-aminophenyl).

In another embodiment of the compounds of Formula I, —$X^1$—$R^1$ is substituted or unsubstituted —C(O)$NR^6$-heteroaryl.

In another embodiment of the compounds of Formula I, —$X^1$—$R^1$ is substituted or unsubstituted —C(O)$NR^6$-thiazolyl.

In another embodiment of the compounds of Formula I, —$X^1$—$R^1$ is substituted or unsubstituted —C(O)$NR^6$-arylalkyl.

In another embodiment of the compounds of Formula I, —$X^1$—$R^1$ is substituted or unsubstituted —C(O)$NR^6$-benzyl.

In another embodiment of the compounds of Formula I, —$X^1$—$R^1$ is substituted or unsubstituted —C(O)$NR^6$-heteroarylalkyl.

In another embodiment of the compounds of Formula I, —$X^1$—$R^1$ is substituted or unsubstituted —C(O)$NR^6$-heteroarylalkyl, wherein the alkyl portion thereof is any of the alkylene groups defined or disclosed herein.

In another embodiment of the compounds of Formula I, —$X^1$—$R^1$ is substituted or unsubstituted —C(O)$NR^6$-heteroarylalkyl, wherein the alkyl portion thereof is —$CH_2$—.

In another embodiment of the compounds of Formula I, —$X^1$—$R^1$ is substituted or unsubstituted —C(O)$NR^6$-heteroarylalkyl, wherein the heteroaryl portion thereof is any of the heteroaryl groups defined or disclosed herein.

In another embodiment of the compounds of Formula I, —$X^1$—$R^1$ is substituted or unsubstituted —C(O)$NR^6$-heteroarylalkyl, wherein the heteroaryl portion thereof is thiazolyl.

In another embodiment of the compounds of Formula I, —$X^1$—$R^1$ is substituted or unsubstituted —C(O)$NR^6$-thiazolylmethyl.

In another embodiment of the compounds of Formula I, —$X^1$—$R^1$ is substituted —C(O)$NR^6$-heteroarylalkyl, wherein the heteroaryl portion thereof is any of the heteroaryl groups defined or disclosed herein, and the substituent is one or more substituents selected from the group consisting of alkyl, substituted alkyl, halo, hydroxyl, amino, haloalkyl, and cyano.

In another embodiment of the compounds of Formula I, —$X^1$—$R^1$ is substituted —C(O)$NR^6$-heteroarylalkyl, wherein the heteroaryl portion thereof is thiazolyl substituted with one or more substituents selected from the group consisting of alkyl, substituted alkyl, halo, hydroxyl, amino, haloalkyl, and cyano.

In another embodiment of the compounds of Formula I, —$X^1$—$R^1$ is —C(O)$NR^6$-thiazolylmethyl substituted with one or more substituents selected from the group consisting of alkyl, substituted alkyl, halo, hydroxyl, amino, haloalkyl, and cyano.

In another embodiment of the compounds of Formula I, —$X^2$—$R^3$ is substituted or unsubstituted —$NR^6$—C(O)—$NR^6$-heterocyclyl.

In another embodiment of the compounds of Formula I, —$X^2$—$R^3$ is substituted or unsubstituted —$NR^6$—C(O)—$NR^6$-aryl.

In another embodiment of the compounds of Formula I, —$X^2$—$R^3$ is substituted or unsubstituted —$NR^6$—C(O)—$NR^6$-phenyl.

In another embodiment of the compounds of Formula I, —$X^2$—$R^3$ is substituted or unsubstituted —$NR^6$—C(O)—$NR^6$-heteroaryl.

In another embodiment of the compounds of Formula I, —$X^2$—$R^3$ is substituted or unsubstituted —$NR^6$—C(O)—$NR^6$-heteroaryl, wherein said heteroaryl is any heteroaryl described or defined herein.

In another embodiment of the compounds of Formula I, —$X^2$—$R^3$ is substituted or unsubstituted —$NR^6$—C(O)—$NR^6$-thiazolyl.

In another embodiment of the compounds of Formula I, —$X^2$—$R^3$ is substituted or unsubstituted —$NR^6$—C(O)—$NR^6$-arylalkyl.

In another embodiment of the compounds of Formula I, —$X^2$—$R^3$ is substituted or unsubstituted —$NR^6$—C(O)—$NR^6$-benzyl.

In another embodiment of the compounds of Formula I, —$X^2$—$R^3$ is substituted —$NR^6$—C(O)—$NR^6$-benzyl.

In another embodiment of the compounds of Formula I, —$X^2$—$R^3$ is —$NR^6$—C(O)—$NR^6$-benzyl substituted with one or more substituents selected from the group consisting of alkyl, substituted alkyl, halo, hydroxyl, amino, haloalkyl, and cyano.

In another embodiment of the compounds of Formula I, —$X^2$—$R^3$ is substituted or unsubstituted —$NR^6$—C(O)—$NR^6$-heteroarylalkyl.

In another embodiment of the compounds of Formula I, —$X^2$—$R^3$ is substituted or unsubstituted —$NR^6$—C(O)—$NR^6$-heteroarylalkyl, wherein the alkyl portion thereof is any alkylene described or disclosed herein.

In another embodiment of the compounds of Formula I, —$X^2$—$R^3$ is substituted or unsubstituted —$NR^6$—C(O)—$NR^6$-heteroarylalkyl, wherein the alkyl portion thereof is —$CH_2$—.

In another embodiment of the compounds of Formula I, —$X^2$—$R^3$ is substituted or unsubstituted —$NR^6$—C(O)—$NR^6$-heteroarylalkyl, wherein the heteroaryl portion thereof is any heteroaryl described or disclosed herein.

In another embodiment of the compounds of Formula I, —$X^2$—$R^3$ is substituted or unsubstituted —$NR^6$—C(O)—$NR^6$-heteroarylalkyl, wherein the heteroaryl portion thereof is thiazolyl.

In another embodiment of the compounds of Formula I, —$X^2$—$R^3$ is substituted or unsubstituted —$NR^6$—C(O)—$NR^6$-thiazolylmethyl.

In another embodiment of the compounds of Formula I, —$X^2$—$R^3$ is —$NR^6$—C(O)—$NR^6$-thiazol-5-ylmethyl.

In another embodiment of the compounds of Formula I, —$X^2$—$R^3$ is substituted —$NR^6$—C(O)—$NR^6$-thiazolylmethyl.

In another embodiment of the compounds of Formula I, —$X^2$—$R^3$ is —$NR^6$—C(O)—$NR^6$-thiazolylmethyl substituted with one or more substituents selected from the group consisting of alkyl, substituted alkyl, halo, hydroxyl, amino, haloalkyl, and cyano.

In another embodiment of the compounds of Formula I, —$X^2$—$R^3$ is substituted —$NR^6$—C(O)—$NR^6$-thiazolylmethyl, and the substituent is an alkyl group.

In another embodiment of the compounds of Formula I, —$X^2$—$R^3$ is —$NR^6$—C(O)—$NR^6$-(2-isopropylthiazolyl-4-yl)methyl.

In another embodiment of the compounds of Formula I, —$X^2$—$R^3$ is substituted or unsubstituted —NH—C(O)—$NR^6$-heterocyclyl.

In another embodiment of the compounds of Formula I, —$X^2$—$R^3$ is substituted or unsubstituted —NH—C(O)—$NR^6$-aryl.

In another embodiment of the compounds of Formula I, —$X^2$—$R^3$ is substituted or unsubstituted —NH—C(O)—$NR^6$-phenyl.

In another embodiment of the compounds of Formula I, —$X^2$—$R^3$ is substituted or unsubstituted —NH—C(O)—$NR^6$-heteroaryl.

In another embodiment of the compounds of Formula I, —$X^2$—$R^3$ is substituted or unsubstituted —NH—C(O)—$NR^6$-heteroaryl, wherein said heteroaryl is any heteroaryl described or defined herein.

In another embodiment of the compounds of Formula I, —$X^2$—$R^3$ is substituted or unsubstituted —NH—C(O)—$NR^6$-thiazolyl.

In another embodiment of the compounds of Formula I, —$X^2$—$R^3$ is substituted or unsubstituted —NH—C(O)—$NR^6$-arylalkyl.

In another embodiment of the compounds of Formula I, —$X^2$—$R^3$ is substituted or unsubstituted —NH—C(O)—$NR^6$-benzyl.

In another embodiment of the compounds of Formula I, —$X^2$—$R^3$ is substituted —NH—C(O)—$NR^6$-benzyl.

In another embodiment of the compounds of Formula I, —$X^2$—$R^3$ is —NH—C(O)—$NR^6$-benzyl substituted with one or more substituents selected from the group consisting of alkyl, substituted alkyl, halo, hydroxyl, amino, haloalkyl, and cyano.

In another embodiment of the compounds of Formula I, —$X^2$—$R^3$ is substituted or unsubstituted —NH—C(O)—$NR^6$-heteroarylalkyl.

In another embodiment of the compounds of Formula I, —$X^2$—$R^3$ is substituted or unsubstituted —NH—C(O)—$NR^6$-heteroarylalkyl, wherein the alkyl portion thereof is any alkylene described or disclosed herein.

In another embodiment of the compounds of Formula I, —$X^2$—$R^3$ is substituted or unsubstituted —NH—C(O)—$NR^6$-heteroarylalkyl, wherein the alkyl portion thereof is —$CH_2$—.

In another embodiment of the compounds of Formula I, —$X^2$—$R^3$ is substituted or unsubstituted —NH—C(O)—$NR^6$-heteroarylalkyl, wherein the heteroaryl portion thereof is any heteroaryl described or disclosed herein.

In another embodiment of the compounds of Formula I, —$X^2$—$R^3$ is substituted or unsubstituted —NH—C(O)—$NR^6$-heteroarylalkyl, wherein the heteroaryl portion thereof is thiazolyl.

In another embodiment of the compounds of Formula I, —$X^2$—$R^3$ is substituted or unsubstituted —NH—C(O)—$NR^6$-thiazolylmethyl.

In another embodiment of the compounds of Formula I, —$X^2$—$R^3$ is —NH—C(O)—$NR^6$-thiazol-5-ylmethyl.

In another embodiment of the compounds of Formula I, —$X^2$—$R^3$ is substituted —NH—C(O)—$NR^6$-thiazolylmethyl.

In another embodiment of the compounds of Formula I, —$X^2$—$R^3$ is —NH—C(O)—$NR^6$-thiazolylmethyl substituted with one or more substituents selected from the group consisting of alkyl, substituted alkyl, halo, hydroxyl, amino, haloalkyl, and cyano.

In another embodiment of the compounds of Formula I, —$X^2$—$R^3$ is substituted —NH—C(O)—$NR^6$-thiazolylmethyl, and the substituent is an alkyl group.

In another embodiment of the compounds of Formula I, —$X^2$—$R^3$ is —NH—C(O)—$NR^6$-(2-isopropylthiazolyl-4-yl)methyl.

In another embodiment of the compounds of Formula I, —$X^2$—$R^3$ is substituted or unsubstituted —$NR^6$-heterocyclyl.

In another embodiment of the compounds of Formula I, —$X^2$—$R^3$ is substituted or unsubstituted —$NR^6$-aryl.

In another embodiment of the compounds of Formula I, —$X^2$—$R^3$ is substituted or unsubstituted —$NR^6$-phenyl.

In another embodiment of the compounds of Formula I, —$X^2$—$R^3$ is substituted or unsubstituted —$NR^6$-heteroaryl.

In another embodiment of the compounds of Formula I, —$X^2$—$R^3$ is substituted or unsubstituted —$NR^6$-heteroaryl, wherein said heteroaryl is any heteroaryl described or defined herein.

In another embodiment of the compounds of Formula I, —$X^2$—$R^3$ is substituted or unsubstituted —$NR^6$-thiazolyl.

In another embodiment of the compounds of Formula I, —$X^2$—$R^3$ is substituted or unsubstituted —$NR^6$-arylalkyl.

In another embodiment of the compounds of Formula I, —$X^2$—$R^3$ is substituted or unsubstituted —$NR^6$-benzyl.

In another embodiment of the compounds of Formula I, —$X^2$—$R^3$ is substituted —$NR^6$-benzyl.

In another embodiment of the compounds of Formula I, —$X^2$—$R^3$ is —$NR^6$-benzyl substituted with one or more substituents selected from the group consisting of alkyl, substituted alkyl, halo, hydroxyl, amino, haloalkyl, and cyano.

In another embodiment of the compounds of Formula I, —$X^2$—$R^3$ is substituted or unsubstituted —$NR^6$-heteroarylalkyl.

In another embodiment of the compounds of Formula I, —$X^2$—$R^3$ is substituted or unsubstituted —$NR^6$-heteroarylalkyl, wherein the alkyl portion thereof is any alkylene described or disclosed herein.

In another embodiment of the compounds of Formula I, —$X^2$—$R^3$ is substituted or unsubstituted —$NR^6$-heteroarylalkyl, wherein the alkyl portion thereof is —$CH_2$—.

In another embodiment of the compounds of Formula I, —$X^2$—$R^3$ is substituted or unsubstituted —$NR^6$-heteroarylalkyl, wherein the heteroaryl portion thereof is any heteroaryl described or disclosed herein.

In another embodiment of the compounds of Formula I, —$X^2$—$R^3$ is substituted or unsubstituted —$NR^6$-heteroarylalkyl, wherein the heteroaryl portion thereof is thiazolyl.

In another embodiment of the compounds of Formula I, —$X^2$—$R^3$ is substituted or unsubstituted —$NR^6$-thiazolylmethyl.

In another embodiment of the compounds of Formula I, —$X^2$—$R^3$ is substituted —$NR^6$-thiazolylmethyl.

In another embodiment of the compounds of Formula I, —$X^2$—$R^3$ is —$NR^6$-thiazolylmethyl substituted with one or more substituents selected from the group consisting of alkyl, substituted alkyl, halo, hydroxyl, amino, haloalkyl, and cyano.

In another embodiment of the compounds of Formula I, —$X^2$—$R^3$ is substituted —$NR^6$-thiazolylmethyl, and the substituent is an alkyl group.

In another embodiment of the compounds of Formula I, —$X^2$—$R^3$ is substituted or unsubstituted —NH-heterocyclyl.

In another embodiment of the compounds of Formula I, —$X^2$—$R^3$ is substituted or unsubstituted —NH-aryl.

In another embodiment of the compounds of Formula I, —$X^2$—$R^3$ is substituted or unsubstituted —NH-phenyl.

In another embodiment of the compounds of Formula I, —$X^2$—$R^3$ is substituted or unsubstituted —NH-heteroaryl.

In another embodiment of the compounds of Formula I, —$X^2$—$R^3$ is substituted or unsubstituted —NH-heteroaryl, wherein said heteroaryl is any heteroaryl described or defined herein.

In another embodiment of the compounds of Formula I, —$X^2$—$R^3$ is substituted or unsubstituted —NH-thiazolyl.

In another embodiment of the compounds of Formula I, —$X^2$—$R^3$ is substituted or unsubstituted —NH-arylalkyl.

In another embodiment of the compounds of Formula I, —$X^2$—$R^3$ is substituted or unsubstituted —NH-benzyl.

In another embodiment of the compounds of Formula I, —$X^2$—$R^3$ is substituted —NH-benzyl.

In another embodiment of the compounds of Formula I, —$X^2$—$R^3$ is —NH-benzyl substituted with one or more substituents selected from the group consisting of alkyl, substituted alkyl, halo, hydroxyl, amino, haloalkyl, and cyano.

In another embodiment of the compounds of Formula I, —$X^2$—$R^3$ is substituted or unsubstituted —NH-heteroarylalkyl.

In another embodiment of the compounds of Formula I, —$X^2$—$R^3$ is substituted or unsubstituted —NH-heteroarylalkyl, wherein the alkyl portion thereof is any alkylene described or disclosed herein.

In another embodiment of the compounds of Formula I, —$X^2$—$R^3$ is substituted or unsubstituted —NH-heteroarylalkyl, wherein the alkyl portion thereof is —$CH_2$—.

In another embodiment of the compounds of Formula I, —$X^2$—$R^3$ is substituted or unsubstituted —NH-heteroarylalkyl, wherein the heteroaryl portion thereof is any heteroaryl described or disclosed herein.

In another embodiment of the compounds of Formula I, —$X^2$—$R^3$ is substituted or unsubstituted —NH-heteroarylalkyl, wherein the heteroaryl portion thereof is thiazolyl.

In another embodiment of the compounds of Formula I, —$X^2$—$R^3$ is substituted or unsubstituted —NH-thiazolylmethyl.

In another embodiment of the compounds of Formula I, —$X^2$—$R^3$ is substituted —NH-thiazolylmethyl.

In another embodiment of the compounds of Formula I, —$X^2$—$R^3$ is —NH-thiazolylmethyl substituted with one or more substituents selected from the group consisting of alkyl, substituted alkyl, halo, hydroxyl, amino, haloalkyl, and cyano.

In another embodiment of the compounds of Formula I, —$X^2$—$R^1$ is substituted —NH-thiazolylmethyl, and the substituent is an alkyl group.

In another embodiment of the compounds of Formula I, —$X^2$—$R^3$ is substituted or unsubstituted —N(alkyl)-heterocyclyl.

In another embodiment of the compounds of Formula I, —$X^2$—$R^3$ is substituted or unsubstituted —N(alkyl)-aryl.

In another embodiment of the compounds of Formula I, —$X^2$—$R^3$ is substituted or unsubstituted —N(alkyl)-phenyl.

In another embodiment of the compounds of Formula I, —$X^2$—$R^3$ is substituted or unsubstituted —N(alkyl)-heteroaryl.

In another embodiment of the compounds of Formula I, —$X^2$—$R^3$ is substituted or unsubstituted —N(alkyl)-heteroaryl, wherein said heteroaryl is any heteroaryl described or defined herein.

In another embodiment of the compounds of Formula I, —$X^2$—$R^3$ is substituted or unsubstituted —N(alkyl)-thiazolyl.

In another embodiment of the compounds of Formula I, —$X^2$—$R^3$ is substituted or unsubstituted —N(alkyl)-arylalkyl.

In another embodiment of the compounds of Formula I, —$X^2$—$R^3$ is substituted or unsubstituted —N(alkyl)-benzyl.

In another embodiment of the compounds of Formula I, —$X^2$—$R^3$ is substituted —N(alkyl)-benzyl.

In another embodiment of the compounds of Formula I, —$X^2$—$R^3$ is —N(alkyl)-benzyl substituted with one or more substituents selected from the group consisting of alkyl, substituted alkyl, halo, hydroxyl, amino, haloalkyl, and cyano.

In another embodiment of the compounds of Formula I, —$X^2$—$R^3$ is substituted or unsubstituted —N(alkyl)-heteroarylalkyl.

In another embodiment of the compounds of Formula I, —$X^2$—$R^3$ is substituted or unsubstituted —N(alkyl)-heteroarylalkyl, wherein the alkyl portion thereof is any alkylene described or disclosed herein.

In another embodiment of the compounds of Formula I, —$X^2$—$R^3$ is substituted or unsubstituted —N(alkyl)-heteroarylalkyl, wherein the alkyl portion thereof is —$CH_2$—.

In another embodiment of the compounds of Formula I, —$X^2$—$R^3$ is substituted or unsubstituted —N(alkyl)-heteroarylalkyl, wherein the heteroaryl portion thereof is any heteroaryl described or disclosed herein.

In another embodiment of the compounds of Formula I, —$X^2$—$R^3$ is substituted or unsubstituted —N(alkyl)-heteroarylalkyl, wherein the heteroaryl portion thereof is thiazolyl.

In another embodiment of the compounds of Formula I, —$X^2$—$R^3$ is substituted or unsubstituted —N(alkyl)-thiazolylmethyl.

In another embodiment of the compounds of Formula I, —$X^2$—$R^3$ is substituted —N(alkyl)-thiazolylmethyl.

In another embodiment of the compounds of Formula I, —$X^2$—$R^3$ is —N(alkyl)-thiazolylmethyl substituted with one or more substituents selected from the group consisting of alkyl, substituted alkyl, halo, hydroxyl, amino, haloalkyl, and cyano.

In another embodiment of the compounds of Formula I, —$X^2$—$R^3$ is substituted —N(alkyl)-thiazolylmethyl, and the substituent is an alkyl group.

In another embodiment of the compounds of Formula I, —$X^2$—$R^3$ is substituted or unsubstituted —N(cycloalkyl)-heterocyclyl.

In another embodiment of the compounds of Formula I, —$X^2$—$R^3$ is substituted or unsubstituted —N(cycloalkyl)-aryl.

In another embodiment of the compounds of Formula I, —$X^2$—$R^3$ is substituted or unsubstituted —N(cycloalkyl)-phenyl.

In another embodiment of the compounds of Formula I, —$X^2$—$R^3$ is substituted or unsubstituted —N(cycloalkyl)-heteroaryl.

In another embodiment of the compounds of Formula I, —$X^2$—$R^3$ is substituted or unsubstituted —N(cycloalkyl)-heteroaryl, wherein said heteroaryl is any heteroaryl described or defined herein.

In another embodiment of the compounds of Formula I, —$X^2$—$R^3$ is substituted or unsubstituted —N(cycloalkyl)-thiazolyl.

In another embodiment of the compounds of Formula I, —$X^2$—$R^3$ is substituted or unsubstituted —N(cycloalkyl)-arylalkyl.

In another embodiment of the compounds of Formula I, —$X^2$—$R^3$ is substituted or unsubstituted —N(cycloalkyl)-benzyl.

In another embodiment of the compounds of Formula I, —$X^2$—$R^3$ is substituted —N(cycloalkyl)-benzyl.

In another embodiment of the compounds of Formula I, —$X^2$—$R^3$ is —N(cycloalkyl)-benzyl substituted with one or more substituents selected from the group consisting of alkyl, substituted alkyl, halo, hydroxyl, amino, haloalkyl, and cyano.

In another embodiment of the compounds of Formula I, —$X^2$—$R^3$ is substituted or unsubstituted —N(cycloalkyl)-heteroarylalkyl.

In another embodiment of the compounds of Formula I, —$X^2$—$R^3$ is substituted or unsubstituted —N(cycloalkyl)-heteroarylalkyl, wherein the alkyl portion thereof is any alkylene described or disclosed herein.

In another embodiment of the compounds of Formula I, —$X^2$—$R^3$ is substituted or unsubstituted —N(cycloalkyl)-heteroarylalkyl, wherein the alkyl portion thereof is —$CH_2$—.

In another embodiment of the compounds of Formula I, —$X^2$—$R^3$ is substituted or unsubstituted —N(cycloalkyl)-heteroarylalkyl, wherein the heteroaryl portion thereof is any heteroaryl described or disclosed herein.

In another embodiment of the compounds of Formula I, —$X^2$—$R^3$ is substituted or unsubstituted —N(cycloalkyl)-heteroarylalkyl, wherein the heteroaryl portion thereof is thiazolyl.

In another embodiment of the compounds of Formula I, —$X^2$—$R^3$ is substituted or unsubstituted —N(cycloalkyl)-thiazolylmethyl.

In another embodiment of the compounds of Formula I, —$X^2$—$R^3$ is substituted —N(cycloalkyl)-thiazolylmethyl.

In another embodiment of the compounds of Formula I, —$X^2$—$R^3$ is —N(cycloalkyl)-thiazolylmethyl substituted with one or more substituents selected from the group consisting of alkyl, substituted alkyl, halo, hydroxyl, amino, haloalkyl, and cyano.

In another embodiment of the compounds of Formula I, —$X^2$—$R^3$ is substituted —N(cycloalkyl)-thiazolylmethyl, and the substituent is an alkyl group.

In another embodiment of the compounds of Formula I, —$X^2$—$R^3$ is substituted or unsubstituted —$NR^6$—C(O)—NH-heterocyclyl.

In another embodiment of the compounds of Formula I, —$X^2$—$R^3$ is substituted or unsubstituted —$NR^6$—C(O)—NH-aryl.

In another embodiment of the compounds of Formula I, —$X^2$—$R^3$ is substituted or unsubstituted —$NR^6$—C(O)—NH-phenyl.

In another embodiment of the compounds of Formula I, —$X^2$—$R^3$ is substituted or unsubstituted —$NR^6$—C(O)—NH-heteroaryl.

In another embodiment of the compounds of Formula I, —$X^2$—$R^3$ is substituted or unsubstituted —$NR^6$—C(O)—NH-heteroaryl, wherein said heteroaryl is any heteroaryl described or defined herein.

In another embodiment of the compounds of Formula I, —$X^2$—$R^3$ is substituted or unsubstituted —$NR^6$—C(O)—NH-thiazolyl.

In another embodiment of the compounds of Formula I, —$X^2$—$R^3$ is substituted or unsubstituted —$NR^6$—C(O)—NH-arylalkyl.

In another embodiment of the compounds of Formula I, —$X^2$—$R^3$ is substituted or unsubstituted —$NR^6$—C(O)—NH-benzyl.

In another embodiment of the compounds of Formula I, —$X^2$—$R^3$ is substituted —$NR^6$—C(O)—NH-benzyl.

In another embodiment of the compounds of Formula I, —$X^2$—$R^3$ is —$NR^6$—C(O)—NH-benzyl substituted with one or more substituents selected from the group consisting of alkyl, substituted alkyl, halo, hydroxyl, amino, haloalkyl, and cyano.

In another embodiment of the compounds of Formula I, —$X^2$—$R^3$ is substituted or unsubstituted —$NR^6$—C(O)—NH-heteroarylalkyl.

In another embodiment of the compounds of Formula I, —$X^2$—$R^3$ is substituted or unsubstituted —$NR^6$—C(O)—NH-heteroarylalkyl, wherein the alkyl portion thereof is any alkylene described or disclosed herein.

In another embodiment of the compounds of Formula I, —$X^2$—$R^3$ is substituted or unsubstituted —$NR^6$—C(O)—NH-heteroarylalkyl, wherein the alkyl portion thereof is —$CH_2$—.

In another embodiment of the compounds of Formula I, —$X^2$—$R^3$ is substituted or unsubstituted —$NR^6$—C(O)—NH-heteroarylalkyl, wherein the heteroaryl portion thereof is any heteroaryl described or disclosed herein.

In another embodiment of the compounds of Formula I, —$X^2$—$R^3$ is substituted or unsubstituted —$NR^6$—C(O)—NH-heteroarylalkyl, wherein the heteroaryl portion thereof is thiazolyl.

In another embodiment of the compounds of Formula I, —$X^2$—$R^3$ is substituted or unsubstituted —$NR^6$—C(O)—NH-thiazolylmethyl.

In another embodiment of the compounds of Formula I, —$X^2$—$R^3$ is substituted —$NR^6$—C(O)—NH-thiazolylmethyl.

In another embodiment of the compounds of Formula I, —$X^2$—$R^3$ is —$NR^6$—C(O)—NH-thiazolylmethyl substituted with one or more substituents selected from the group consisting of alkyl, substituted alkyl, halo, hydroxyl, amino, haloalkyl, and cyano.

In another embodiment of the compounds of Formula I, —$X^2$—$R^3$ is substituted —$NR^6$—C(O)—NH-thiazolylmethyl, and the substituent is an alkyl group.

In another embodiment of the compounds of Formula I, —$X^2$—$R^3$ is substituted or unsubstituted —N(alkyl)-C(O)—$NR^6$-heterocyclyl.

In another embodiment of the compounds of Formula I, —$X^2$—$R^3$ is substituted or unsubstituted —N(alkyl)-C(O)—$NR^6$-aryl.

In another embodiment of the compounds of Formula I, —$X^2$—$R^3$ is substituted or unsubstituted —N(alkyl)-C(O)—$NR^6$-phenyl.

In another embodiment of the compounds of Formula I, —$X^2$—$R^3$ is substituted or unsubstituted —N(alkyl)-C(O)—$NR^6$-heteroaryl.

In another embodiment of the compounds of Formula I, —$X^2$—$R^3$ is substituted or unsubstituted —N(alkyl)-C(O)—$NR^6$-heteroaryl, wherein said heteroaryl is any heteroaryl described or defined herein.

In another embodiment of the compounds of Formula I, —$X^2$—$R^3$ is substituted or unsubstituted —N(alkyl)-C(O)—$NR^6$-thiazolyl.

In another embodiment of the compounds of Formula I, —$X^2$—$R^3$ is substituted or unsubstituted —N(alkyl)-C(O)—$NR^6$-arylalkyl.

In another embodiment of the compounds of Formula I, —$X^2$—$R^3$ is substituted or unsubstituted —N(alkyl)-C(O)—$NR^6$-benzyl.

In another embodiment of the compounds of Formula I, —$X^2$—$R^3$ is substituted —N(alkyl)-C(O)—$NR^6$-benzyl.

In another embodiment of the compounds of Formula I, —$X^2$—$R^3$ is —N(alkyl)-C(O)—$NR^6$-benzyl substituted In another embodiment of the compounds of Formula I, —X²—R³ is substituted or unsubstituted —N(alkyl)-C(O)—NR⁶-heteroarylalkyl.

In another embodiment of the compounds of Formula I, —X²—R³ is substituted or unsubstituted —N(alkyl)-C(O)—NR⁶-heteroarylalkyl, wherein the alkyl portion thereof is any alkylene described or disclosed herein.

In another embodiment of the compounds of Formula I, —X²—R³ is substituted or unsubstituted —N(alkyl)-C(O)—NR⁶-heteroarylalkyl, wherein the alkyl portion thereof is —CH₂—.

In another embodiment of the compounds of Formula I, —X²—R³ is substituted or unsubstituted —N(alkyl)-C(O)—NR⁶-heteroarylalkyl, wherein the heteroaryl portion thereof is any heteroaryl described or disclosed herein.

In another embodiment of the compounds of Formula I, —X²—R³ is substituted or unsubstituted —N(alkyl)-C(O)—NR⁶-heteroarylalkyl, wherein the heteroaryl portion thereof is thiazolyl.

In another embodiment of the compounds of Formula I, —X²—R³ is substituted or unsubstituted —N(alkyl)-C(O)—NR⁶-thiazolylmethyl.

In another embodiment of the compounds of Formula I, —X²—R³ is substituted —N(alkyl)-C(O)—NR⁶-thiazolylmethyl.

In another embodiment of the compounds of Formula I, —X²—R³ is —N(alkyl)-C(O)—NR⁶-thiazolylmethyl substituted with one or more substituents selected from the group consisting of alkyl, substituted alkyl, halo, hydroxyl, amino, haloalkyl, and cyano.

In another embodiment of the compounds of Formula I, —X²—R³ is substituted —N(alkyl)-C(O)—NR⁶-thiazolylmethyl, and the substituent is an alkyl group.

In another embodiment of the compounds of Formula I, —X²—R³ is substituted or unsubstituted —NR⁶—C(O)—N(alkyl)-heterocyclyl.

In another embodiment of the compounds of Formula I, —X²—R³ is substituted or unsubstituted —NR⁶—C(O)—N(alkyl)-aryl.

In another embodiment of the compounds of Formula I, —X²—R³ is substituted or unsubstituted —NR⁶—C(O)—N(alkyl)-phenyl.

In another embodiment of the compounds of Formula I, —X²—R³ is substituted or unsubstituted —NR⁶—C(O)—N(alkyl)-heteroaryl.

In another embodiment of the compounds of Formula I, —X²—R³ is substituted or unsubstituted —NR⁶—C(O)—N(alkyl)-heteroaryl, wherein said heteroaryl is any heteroaryl described or defined herein.

In another embodiment of the compounds of Formula I, —X²—R³ is substituted or unsubstituted —NR⁶—C(O)—N(alkyl)-thiazolyl.

In another embodiment of the compounds of Formula I, —X²—R³ is substituted or unsubstituted —NR⁶—C(O)—N(alkyl)-arylalkyl.

In another embodiment of the compounds of Formula I, —X²—R³ is substituted or unsubstituted —NR⁶—C(O)—N(alkyl)-benzyl.

In another embodiment of the compounds of Formula I, —X²—R³ is substituted —NR⁶—C(O)—N(alkyl)-benzyl.

In another embodiment of the compounds of Formula I, —X²—R³ is —NR⁶—C(O)—N(alkyl)-benzyl substituted with one or more substituents selected from the group consisting of alkyl, substituted alkyl, halo, hydroxyl, amino, haloalkyl and cyano.

In another embodiment of the compounds of Formula I, —X²—R³ is substituted or unsubstituted —NR⁶—C(O)—N(alkyl)-heteroarylalkyl.

In another embodiment of the compounds of Formula I, —X²—R³ is substituted or unsubstituted —NR⁶—C(O)—N(alkyl)-heteroarylalkyl, wherein the alkyl portion thereof is any alkylene described or disclosed herein.

In another embodiment of the compounds of Formula I, —X²—R³ is substituted or unsubstituted —NR⁶—C(O)—N(alkyl)-heteroarylalkyl, wherein the alkyl portion thereof is —CH₂—.

In another embodiment of the compounds of Formula I, —X²—R³ is substituted or unsubstituted —NR⁶—C(O)—N(alkyl)-heteroarylalkyl, wherein the heteroaryl portion thereof is any heteroaryl described or disclosed herein.

In another embodiment of the compounds of Formula I, —X²—R³ is substituted or unsubstituted —NR⁶—C(O)—N(alkyl)-heteroarylalkyl, wherein the heteroaryl portion thereof is thiazolyl.

In another embodiment of the compounds of Formula I, —X²—R³ is substituted or unsubstituted —NR⁶—C(O)—N(alkyl)-thiazolylmethyl.

In another embodiment of the compounds of Formula I, —X²—R³ is —NR⁶—C(O)—N(alkyl)-thiazol-5-ylmethyl.

In another embodiment of the compounds of Formula I, —X²—R³ is substituted —NR⁶—C(O)—N(alkyl)-thiazolylmethyl.

In another embodiment of the compounds of Formula I, —X²—R³ is —NR⁶—C(O)—N(alkyl)-thiazolylmethyl substituted with one or more substituents selected from the group consisting of alkyl, substituted alkyl, halo, hydroxyl, amino, haloalkyl, and cyano.

In another embodiment of the compounds of Formula I, —X²—R³ is substituted —NR⁶—C(O)—N(alkyl)-thiazolylmethyl, and the substituent is an alkyl group.

In another embodiment of the compounds of Formula I, —X²—R³ is —NR⁶—C(O)—N(alkyl)-(2-isopropylthiazolyl-4-yl)methyl.

In another embodiment of the compounds of Formula I, —X²—R³ is substituted or unsubstituted —N(alkyl)-C(O)—N(alkyl)-heterocyclyl.

In another embodiment of the compounds of Formula I, —X²—R³ is substituted or unsubstituted —N(alkyl)-C(O)—N(alkyl)-aryl.

In another embodiment of the compounds of Formula I, —X²—R³ is substituted or unsubstituted —N(alkyl)-C(O)—N(alkyl)-phenyl.

In another embodiment of the compounds of Formula I, —X²—R³ is substituted or unsubstituted —N(alkyl)-C(O)—N(alkyl)-heteroaryl.

In another embodiment of the compounds of Formula I, —X²—R³ is substituted or unsubstituted —N(alkyl)-C(O)—N(alkyl)-heteroaryl, wherein said heteroaryl is any heteroaryl described or defined herein.

In another embodiment of the compounds of Formula I, —X²—R³ is substituted or unsubstituted —N(alkyl)-C(O)—N(alkyl)-thiazolyl.

In another embodiment of the compounds of Formula I, —X²—R³ is substituted or unsubstituted —N(alkyl)-C(O)—N(alkyl)-arylalkyl.

In another embodiment of the compounds of Formula I, —X²—R³ is substituted or unsubstituted —N(alkyl)-C(O)—N(alkyl)-benzyl.

In another embodiment of the compounds of Formula I, —$X^2$—$R^3$ is substituted —N(alkyl)-C(O)—N(alkyl)-benzyl.

In another embodiment of the compounds of Formula I, —$X^2$—$R^3$ is —N(alkyl)-C(O)—N(alkyl)-benzyl substituted with one or more substituents selected from the group consisting of alkyl, substituted alkyl, halo, hydroxyl, amino, haloalkyl, and cyano.

In another embodiment of the compounds of Formula I, —$X^2$—$R^3$ is substituted or unsubstituted —N(alkyl)-C(O)—N(alkyl)-heteroarylalkyl.

In another embodiment of the compounds of Formula I, —$X^2$—$R^3$ is substituted or unsubstituted —N(alkyl)-C(O)—N(alkyl)-heteroarylalkyl, wherein the alkyl portion thereof is any alkylene described or disclosed herein.

In another embodiment of the compounds of Formula I, —$X^2$—$R^3$ is substituted or unsubstituted —N(alkyl)-C(O)—N(alkyl)-heteroarylalkyl, wherein the alkyl portion thereof is —$CH_2$—.

In another embodiment of the compounds of Formula I, —$X^2$—$R^3$ is substituted or unsubstituted —N(alkyl)-C(O)—N(alkyl)-heteroarylalkyl, wherein the heteroaryl portion thereof is any heteroaryl described or disclosed herein.

In another embodiment of the compounds of Formula I, —$X^2$—$R^3$ is substituted or unsubstituted —N(alkyl)-C(O)—N(alkyl)-heteroarylalkyl, wherein the heteroaryl portion thereof is thiazolyl.

In another embodiment of the compounds of Formula I, —$X^2$—$R^3$ is substituted or unsubstituted —N(alkyl)-C(O)—N(alkyl)-thiazolylmethyl.

In another embodiment of the compounds of Formula I, —$X^2$—$R^3$ is substituted —N(alkyl)-C(O)—N(alkyl)-thiazolylmethyl.

In another embodiment of the compounds of Formula I, —$X^2$—$R^3$ is —N(alkyl)-C(O)—N(alkyl)-thiazolylmethyl substituted with one or more substituents selected from the group consisting of alkyl, substituted alkyl, halo, hydroxyl, amino, haloalkyl, and cyano.

In another embodiment of the compounds of Formula I, —$X^2$—$R^3$ is substituted —N(alkyl)-C(O)—N(alkyl)-thiazolylmethyl, and the substituent is an alkyl group.

In another embodiment of the compounds of Formula I, —$X^2$—$R^3$ is substituted or unsubstituted —NH—C(O)—N($CH_3$)-heterocyclyl.

In another embodiment of the compounds of Formula I, —$X^2$—$R^3$ is substituted or unsubstituted —NH—C(O)—N($CH_3$)-aryl.

In another embodiment of the compounds of Formula I, —$X^2$—$R^3$ is substituted or unsubstituted —NH—C(O)—N($CH_3$)-phenyl.

In another embodiment of the compounds of Formula I, —$X^2$—$R^3$ is substituted or unsubstituted —NH—C(O)—N($CH_3$)-heteroaryl.

In another embodiment of the compounds of Formula I, —$X^2$—$R^3$ is substituted or unsubstituted —NH—C(O)—N($CH_3$)-heteroaryl, wherein said heteroaryl is any heteroaryl described or defined herein.

In another embodiment of the compounds of Formula I, —$X^2$—$R^3$ is substituted or unsubstituted —NH—C(O)—N($CH_3$)-thiazolyl.

In another embodiment of the compounds of Formula I, —$X^2$—$R^3$ is substituted or unsubstituted —NH—C(O)—N($CH_3$)-arylalkyl.

In another embodiment of the compounds of Formula I, —$X^2$—$R^3$ is substituted or unsubstituted —NH—C(O)—N($CH_3$)-benzyl.

In another embodiment of the compounds of Formula I, —$X^2$—$R^3$ is substituted —NH—C(O)—N($CH_3$)-benzyl.

In another embodiment of the compounds of Formula I, —$X^2$—$R^3$ is —NH—C(O)—N($CH_3$)-benzyl substituted with one or more substituents selected from the group consisting of alkyl, substituted alkyl, halo, hydroxyl, amino, haloalkyl, and cyano.

In another embodiment of the compounds of Formula I, —$X^2$—$R^3$ is substituted or unsubstituted —NH—C(O)—N($CH_3$)-heteroarylalkyl.

In another embodiment of the compounds of Formula I, —$X^2$—$R^3$ is substituted or unsubstituted —NH—C(O)—N($CH_3$)-heteroarylalkyl, wherein the alkyl portion thereof is any alkylene described or disclosed herein.

In another embodiment of the compounds of Formula I, —$X^2$—$R^3$ is substituted or unsubstituted —NH—C(O)—N($CH_3$)-heteroarylalkyl, wherein the alkyl portion thereof is —$CH_2$—.

In another embodiment of the compounds of Formula I, —$X^2$—$R^3$ is substituted or unsubstituted —NH—C(O)—N($CH_3$)-heteroarylalkyl, wherein the heteroaryl portion thereof is any heteroaryl described or disclosed herein.

In another embodiment of the compounds of Formula I, —$X^2$—$R^3$ is substituted or unsubstituted —NH—C(O)—N($CH_3$)-heteroarylalkyl, wherein the heteroaryl portion thereof is thiazolyl.

In another embodiment of the compounds of Formula I, —$X^2$—$R^3$ is substituted or unsubstituted —NH—C(O)—N($CH_3$)-thiazolylmethyl.

In another embodiment of the compounds of Formula I, —$X^2$—$R^3$ is —NH—C(O)—N($CH_3$)-thiazol-5-ylmethyl.

In another embodiment of the compounds of Formula I, —$X^2$—$R^3$ is substituted —NH—C(O)—N($CH_3$)-thiazolylmethyl.

In another embodiment of the compounds of Formula I, —$X^2$—$R^3$ is —NH—C(O)—N($CH_3$)-thiazolylmethyl substituted with one or more substituents selected from the group consisting of alkyl, substituted alkyl, halo, hydroxyl, amino, haloalkyl, and cyano.

In another embodiment of the compounds of Formula I, —$X^2$—$R^3$ is substituted —NH—C(O)—N($CH_3$)-thiazolylmethyl, and the substituent is an alkyl group.

In another embodiment of the compounds of Formula I, —$X^2$—$R^3$ is —NH—C(O)—N($CH_3$)-(2-isopropylthiazolyl-4-yl)methyl.

In another embodiment of the compounds of Formula I, —$X^2$—$R^3$ is substituted or unsubstituted —O—C(O)—$NR^6$-heterocyclyl.

In another embodiment of the compounds of Formula I, —$X^2$—$R^3$ is substituted or unsubstituted —O—C(O)—$NR^6$-aryl.

In another embodiment of the compounds of Formula I, —$X^2$—$R^3$ is substituted or unsubstituted —O—C(O)—$NR^6$-phenyl.

In another embodiment of the compounds of Formula I, —$X^2$—$R^3$ is substituted or unsubstituted —O—C(O)—$NR^6$-heteroaryl.

In another embodiment of the compounds of Formula I, —$X^2$—$R^3$ is substituted or unsubstituted —O—C(O)—$NR^6$-heteroaryl, wherein said heteroaryl is any heteroaryl described or defined herein.

In another embodiment of the compounds of Formula I, —$X^2$—$R^3$ is substituted or unsubstituted —O—C(O)—$NR^6$-thiazolyl.

In another embodiment of the compounds of Formula I, —$X^2$—$R^3$ is substituted or unsubstituted —O—C(O)—$NR^6$-arylalkyl.

In another embodiment of the compounds of Formula I, —X$^2$—R$^3$ is substituted or unsubstituted —O—C(O)—NR$^6$-benzyl.

In another embodiment of the compounds of Formula I, —X$^2$—R$^3$ is substituted —O—C(O)—NR$^6$-benzyl.

In another embodiment of the compounds of Formula I, —X$^2$—R$^3$ is O—C(O)—NR$^6$-benzyl substituted with one or more substituents selected from the group consisting of alkyl, substituted alkyl, halo, hydroxyl, amino, haloalkyl, and cyano.

In another embodiment of the compounds of Formula I, —X$^2$—R$^3$ is substituted or unsubstituted —O—C(O)—NR$^6$-heteroarylalkyl.

In another embodiment of the compounds of Formula I, —X$^2$—R$^3$ is substituted or unsubstituted —O—C(O)—NR$^6$-heteroarylalkyl, wherein the alkyl portion thereof is any alkylene described or disclosed herein.

In another embodiment of the compounds of Formula I, —X$^2$—R$^3$ is substituted or unsubstituted —O—C(O)—NR$^6$-heteroarylalkyl, wherein the alkyl portion thereof is —CH$_2$—.

In another embodiment of the compounds of Formula I, —X$^2$—R$^3$ is substituted or unsubstituted —O—C(O)—NR$^6$-heteroarylalkyl, wherein the heteroaryl portion thereof is any heteroaryl described or disclosed herein.

In another embodiment of the compounds of Formula I, —X$^2$—R$^3$ is substituted or unsubstituted —O—C(O)—NR$^6$-heteroarylalkyl, wherein the heteroaryl portion thereof is thiazolyl.

In another embodiment of the compounds of Formula I, —X$^2$—R$^3$ is substituted or unsubstituted —O—C(O)—NR$^6$-thiazolylmethyl.

In another embodiment of the compounds of Formula I, —X$^2$—R$^3$ is substituted —O—C(O)—NR$^6$-thiazolylmethyl.

In another embodiment of the compounds of Formula I, —X$^2$—R$^3$ is —O—C(O)—NR$^6$-thiazolylmethyl substituted with one or more substituents selected from the group consisting of alkyl, substituted alkyl, halo, hydroxyl, amino, haloalkyl, and cyano.

In another embodiment of the compounds of Formula I, —X$^2$—R$^3$ is substituted —O—C(O)—NR$^6$-thiazolylmethyl, and the substituent is an alkyl group.

In another embodiment of the compounds of Formula I, —X$^2$—R$^3$ is substituted or unsubstituted —O—C(O)—NH-heterocyclyl.

In another embodiment of the compounds of Formula I, —X$^2$—R$^3$ is substituted or unsubstituted —O—C(O)—NH-aryl.

In another embodiment of the compounds of Formula I, —X$^2$—R$^3$ is substituted or unsubstituted —O—C(O)—NH-phenyl.

In another embodiment of the compounds of Formula I, —X$^2$—R$^3$ is substituted or unsubstituted —O—C(O)—NH-heteroaryl.

In another embodiment of the compounds of Formula I, —X$^2$—R$^3$ is substituted or unsubstituted —O—C(O)—NH-heteroaryl, wherein said heteroaryl is any heteroaryl described or defined herein.

In another embodiment of the compounds of Formula I, —X$^2$—R$^3$ is substituted or unsubstituted —O—C(O)—NH-thiazolyl.

In another embodiment of the compounds of Formula I, —X$^2$—R$^3$ is substituted or unsubstituted —O—C(O)—NH-arylalkyl.

In another embodiment of the compounds of Formula I, —X$^2$—R$^3$ is substituted or unsubstituted —O—C(O)—NH-benzyl.

In another embodiment of the compounds of Formula I, —X$^2$—R$^3$ is substituted —O—C(O)—NH-benzyl.

In another embodiment of the compounds of Formula I, —X$^2$—R$^3$ is —O—C(O)—NH-benzyl substituted with one or more substituents selected from the group consisting of alkyl, substituted alkyl, halo, hydroxyl, amino, haloalkyl, and cyano.

In another embodiment of the compounds of Formula I, —X$^2$—R$^3$ is substituted or unsubstituted —O—C(O)—NH-heteroarylalkyl.

In another embodiment of the compounds of Formula I, —X$^2$—R$^3$ is substituted or unsubstituted —O—C(O)—NH-heteroarylalkyl, wherein the alkyl portion thereof is any alkylene described or disclosed herein.

In another embodiment of the compounds of Formula I, —X$^2$—R$^3$ is substituted or unsubstituted —O—C(O)—NH-heteroarylalkyl, wherein the alkyl portion thereof is —CH$_2$—.

In another embodiment of the compounds of Formula I, —X$^2$—R$^3$ is substituted or unsubstituted —O—C(O)—NH-heteroarylalkyl, wherein the heteroaryl portion thereof is any heteroaryl described or disclosed herein.

In another embodiment of the compounds of Formula I, —X$^2$—R$^3$ is substituted or unsubstituted —O—C(O)—NH-heteroarylalkyl, wherein the heteroaryl portion thereof is thiazolyl.

In another embodiment of the compounds of Formula I, —X$^2$—R$^3$ is substituted or unsubstituted —O—C(O)—NH-thiazolylmethyl.

In another embodiment of the compounds of Formula I, —X$^2$—R$^3$ is substituted —O—C(O)—NH-thiazolylmethyl.

In another embodiment of the compounds of Formula I, —X$^2$—R$^3$ is —O—C(O)—NH-thiazolylmethyl substituted with one or more substituents selected from the group consisting of alkyl, substituted alkyl halo, hydroxyl, amino, haloalkyl, and cyano.

In another embodiment of the compounds of Formula I, —X$^2$—R$^3$ is substituted —O—C(O)—NH-thiazolylmethyl, and the substituent is an alkyl group.

In another embodiment of the compounds of Formula I, —X$^2$—R$^3$ is substituted or unsubstituted —O—C(O)—N(alkyl)-heterocyclyl.

In another embodiment of the compounds of Formula I, —X$^2$—R$^3$ is substituted or unsubstituted —O—C(O)—N(alkyl)-aryl.

In another embodiment of the compounds of Formula I, —X$^2$—R$^3$ is substituted or unsubstituted —O—C(O)—N(alkyl)-phenyl.

In another embodiment of the compounds of Formula I, —X$^2$—R$^3$ is substituted or unsubstituted —O—C(O)—N(alkyl)-heteroaryl.

In another embodiment of the compounds of Formula I, —X$^2$—R$^3$ is substituted or unsubstituted —O—C(O)—N(alkyl)-heteroaryl, wherein said heteroaryl is any heteroaryl described or defined herein.

In another embodiment of the compounds of Formula I, —X$^2$—R$^3$ is substituted or unsubstituted —O—C(O)—N(alkyl)-thiazolyl.

In another embodiment of the compounds of Formula I, —X$^2$—R$^3$ is substituted or unsubstituted —O—C(O)—N(alkyl)-arylalkyl.

In another embodiment of the compounds of Formula I, —X$^2$—R$^3$ is substituted or unsubstituted —O—C(O)—N(alkyl)-benzyl.

In another embodiment of the compounds of Formula I, —X$^2$—R$^3$ is substituted —O—C(O)—N(alkyl)-benzyl.

In another embodiment of the compounds of Formula I, $-X^2-R^3$ is $-O-C(O)-N$(alkyl)-benzyl substituted with one or more substituents selected from the group consisting of alkyl, substituted alkyl, halo, hydroxyl, amino, haloalkyl, and cyano.

In another embodiment of the compounds of Formula I, $-X^2-R^3$ is substituted or unsubstituted $-O-C(O)-N$(alkyl)-heteroarylalkyl.

In another embodiment of the compounds of Formula I, $-X^2-R^3$ is substituted or unsubstituted $-O-C(O)-N$(alkyl)-heteroarylalkyl, wherein the alkyl portion thereof is any alkylene described or disclosed herein.

In another embodiment of the compounds of Formula I, $-X^2-R^3$ is substituted or unsubstituted $-O-C(O)-N$(alkyl)-heteroarylalkyl, wherein the alkyl portion thereof is $-CH_2-$.

In another embodiment of the compounds of Formula I, $-X^2-R^3$ is substituted or unsubstituted $-O-C(O)-N$(alkyl)-heteroarylalkyl, wherein the heteroaryl portion thereof is any heteroaryl described or disclosed herein.

In another embodiment of the compounds of Formula I, $-X^2-R^3$ is substituted or unsubstituted $-O-C(O)-N$(alkyl)-heteroarylalkyl, wherein the heteroaryl portion thereof is thiazolyl.

In another embodiment of the compounds of Formula I, $-X^2-R^3$ is substituted or unsubstituted $-O-C(O)-N$(alkyl)-thiazolylmethyl.

In another embodiment of the compounds of Formula I, $-X^2-R^3$ is substituted $-O-C(O)-N$(alkyl)-thiazolylmethyl.

In another embodiment of the compounds of Formula I, $-X^2-R^3$ is $-O-C(O)-N$(alkyl)-thiazolylmethyl substituted with one or more substituents selected from the group consisting of alkyl, substituted alkyl, halo, hydroxyl, amino, haloalkyl, and cyano.

In another embodiment of the compounds of Formula I, $-X^2-R^3$ is substituted $-O-C(O)-N$(alkyl)-thiazolylmethyl, and the substituent is an alkyl group.

In another embodiment of the compounds of Formula I, $-X^2-R^3$ is substituted or unsubstituted $-NR^6-C(O)-O-$heterocyclyl.

In another embodiment of the compounds of Formula I, $-X^2-R^3$ is substituted or unsubstituted $-NR^6-C(O)-O-$aryl.

In another embodiment of the compounds of Formula I, $-X^2-R^3$ is substituted or unsubstituted $-NR^6-C(O)-O-$phenyl.

In another embodiment of the compounds of Formula I, $-X^2-R^3$ is substituted or unsubstituted $-NR^6-C(O)-O-$heteroaryl.

In another embodiment of the compounds of Formula I, $-X^2-R^3$ is substituted or unsubstituted $-NR^6-C(O)-O-$heteroaryl, wherein said heteroaryl is any heteroaryl described or defined herein.

In another embodiment of the compounds of Formula I, $-X^2-R^3$ is substituted or unsubstituted $-NR^6-C(O)-O-$thiazolyl.

In another embodiment of the compounds of Formula I, $-X^2-R^3$ is substituted or unsubstituted $-NR^6-C(O)-O-$arylalkyl.

In another embodiment of the compounds of Formula I, $-X^2-R^3$ is substituted or unsubstituted $-NR^6-C(O)-O-$benzyl.

In another embodiment of the compounds of Formula I, $-X^2-R^3$ is substituted $-NR^6-C(O)-O-$benzyl.

In another embodiment of the compounds of Formula I, $-X^2-R^3$ is $-NR^6-C(O)-O-$benzyl substituted with one or more substituents selected from the group consisting of alkyl, substituted alkyl, halo, hydroxyl, amino, haloalkyl, and cyano.

In another embodiment of the compounds of Formula I, $-X^2-R^3$ is substituted or unsubstituted $-NR^6-C(O)-O-$heteroarylalkyl.

In another embodiment of the compounds of Formula I, $-X^2-R^3$ is substituted or unsubstituted $-NR^6-C(O)-O-$heteroarylalkyl, wherein the alkyl portion thereof is any alkylene described or disclosed herein.

In another embodiment of the compounds of Formula I, $-X^2-R^3$ is substituted or unsubstituted $-NR^6-C(O)-O-$heteroarylalkyl, wherein the alkyl portion thereof is $-CH_2-$.

In another embodiment of the compounds of Formula I, $-X^2-R^3$ is substituted or unsubstituted $-NR^6-C(O)-O-$heteroarylalkyl, wherein the heteroaryl portion thereof is any heteroaryl described or disclosed herein.

In another embodiment of the compounds of Formula I, $-X^2-R^3$ is substituted or unsubstituted $-NR^6-C(O)-O-$heteroarylalkyl, wherein the heteroaryl portion thereof is thiazolyl.

In another embodiment of the compounds of Formula I, $-X^2-R^3$ is substituted or unsubstituted $-NR^6-C(O)-O-$thiazolylmethyl.

In another embodiment of the compounds of Formula I, $-X^2-R^3$ is substituted $-NR^6-C(O)-O-$thiazolylmethyl.

In another embodiment of the compounds of Formula I, $-X^2-R^3$ is $-NR^6-C(O)O-$thiazolylmethyl substituted with one or more substituents selected from the group consisting of alkyl, substituted alkyl, halo, hydroxyl, amino, haloalkyl, and cyano.

In another embodiment of the compounds of Formula I, $-X^2-R^3$ is substituted $-NR^6-C(O)-O-$thiazolylmethyl, and the substituent is an alkyl group.

In another embodiment of the compounds of Formula I, $-X^2-R^3$ is substituted or unsubstituted $-O-$heterocyclyl.

In another embodiment of the compounds of Formula I, $-X^2-R^3$ is $-O-$(tetrahydro-2H-furo[2,3-b]furan-3-yl).

In another embodiment of the compounds of Formula I, $-X^2-R^3$ is $-O-$(tetrahydrofuran-3-yl).

In another embodiment of the compounds of Formula I, $-X^2-R^3$ is substituted or unsubstituted $-O-$aryl.

In another embodiment of the compounds of Formula I, $-X^2-R^3$ is substituted or unsubstituted $-O-$phenyl.

In another embodiment of the compounds of Formula I, $-X^2-R^3$ is substituted or unsubstituted $-O-$heteroaryl.

In another embodiment of the compounds of Formula I, $-X^2-R^3$ is substituted or unsubstituted $-O-$heteroaryl, wherein said heteroaryl is any heteroaryl described or defined herein.

In another embodiment of the compounds of Formula I, $-X^2-R^3$ is substituted or unsubstituted $-O-$thiazolyl.

In another embodiment of the compounds of Formula I, $-X^2-R^3$ is substituted or unsubstituted $-O-$arylalkyl.

In another embodiment of the compounds of Formula I, $-X^2-R^3$ is substituted or unsubstituted $-O-$benzyl.

In another embodiment of the compounds of Formula I, $-X^2-R^3$ is substituted $-O-$benzyl.

In another embodiment of the compounds of Formula I, $-X^2-R^3$ is $-O-$benzyl substituted with one or more substituents selected from the group consisting of alkyl, substituted alkyl, halo, hydroxyl, amino, haloalkyl, and cyano.

In another embodiment of the compounds of Formula I, $-X^2-R^3$ is substituted or unsubstituted $-O-$heteroarylalkyl.

In another embodiment of the compounds of Formula I, —$X^2$—$R^3$ is substituted or unsubstituted —O-heteroarylalkyl, wherein the alkyl portion thereof is any alkylene described or disclosed herein.

In another embodiment of the compounds of Formula I, —$X^2$—$R^3$ is substituted or unsubstituted —O-heteroarylalkyl, wherein the alkyl portion thereof is —$CH_2$—.

In another embodiment of the compounds of Formula I, —$X^2$—$R^3$ is substituted or unsubstituted —O-heteroarylalkyl, wherein the heteroaryl portion thereof is any heteroaryl described or disclosed herein.

In another embodiment of the compounds of Formula I, —$X^2$—$R^3$ is substituted or unsubstituted —O-heteroarylalkyl, wherein the heteroaryl portion thereof is thiazolyl.

In another embodiment of the compounds of Formula I, —$X^2$—$R^3$ is substituted or unsubstituted —O-thiazolylmethyl.

In another embodiment of the compounds of Formula I, —$X^2$—$R^3$ is substituted —O-thiazolylmethyl.

In another embodiment of the compounds of Formula I, —$X^2$—$R^3$ is —O-thiazolylmethyl substituted with one or more substituents selected from the group consisting of alkyl, substituted alkyl, halo, hydroxyl, amino, haloalkyl, and cyano.

In another embodiment of the compounds of Formula I, —$X^2$—$R^3$ is substituted —O-thiazolylmethyl, and the substituent is an alkyl group.

In another embodiment of the compounds of Formula I, -L-$X^2$—$R^3$ is substituted or unsubstituted —$NR^6$—C(O)—$NR^6$-heterocyclyl.

In another embodiment of the compounds of Formula I, -L-$X^2$—$R^3$ is substituted or unsubstituted —$NR^6$—C(O)—$NR^6$-aryl.

In another embodiment of the compounds of Formula I, -L-$X^2$—$R^3$ is substituted or unsubstituted —$NR^6$—C(O)—$NR^6$-phenyl.

In another embodiment of the compounds of Formula I, -L-$X^2$—$R^3$ is substituted or unsubstituted —$NR^6$—C(O)—$NR^6$-heteroaryl.

In another embodiment of the compounds of Formula I, -L-$X^2$—$R^3$ is substituted or unsubstituted —$NR^6$—C(O)—$NR^6$-heteroaryl, wherein said heteroaryl is any heteroaryl described or defined herein.

In another embodiment of the compounds of Formula I, -L-$X^2$—$R^3$ is substituted or unsubstituted —$NR^6$—C(O)—$NR^6$-thiazolyl.

In another embodiment of the compounds of Formula I, -L-$X^2$—$R^3$ is substituted or unsubstituted —$NR^6$—C(O)—$NR^6$-arylalkyl.

In another embodiment of the compounds of Formula I, -L-$X^2$—$R^3$ is substituted or unsubstituted —$NR^6$—C(O)—$NR^6$-benzyl.

In another embodiment of the compounds of Formula I, -L-$X^2$—$R^3$ is substituted —$NR^6$—C(O)—$NR^6$-benzyl.

In another embodiment of the compounds of Formula I, -L-$X^2$—$R^3$ is —$NR^6$—C(O)—$NR^6$-benzyl substituted with one or more substituents selected from the group consisting of alkyl, substituted alkyl, halo, hydroxyl, amino, haloalkyl, and cyano.

In another embodiment of the compounds of Formula I, -L-$X^2$—$R^3$ is substituted or unsubstituted —$NR^6$—C(O)—$NR^6$-heteroarylalkyl.

In another embodiment of the compounds of Formula I, -L-$X^2$—$R^3$ is substituted or unsubstituted —$NR^6$—C(O)—$NR^6$-heteroarylalkyl, wherein the alkyl portion thereof is any alkylene described or disclosed herein.

In another embodiment of the compounds of Formula I, -L-$X^2$—$R^3$ is substituted or unsubstituted —$NR^6$—C(O)—$NR^6$-heteroarylalkyl, wherein the alkyl portion thereof is —$CH_2$—.

In another embodiment of the compounds of Formula I, -L-$X^2$—$R^3$ is substituted or unsubstituted —$NR^6$—C(O)—$NR^6$-heteroarylalkyl, wherein the heteroaryl portion thereof is any heteroaryl described or disclosed herein.

In another embodiment of the compounds of Formula I, -L-$X^2$—$R^3$ is substituted or unsubstituted —$NR^6$—C(O)—$NR^6$-heteroarylalkyl, wherein the heteroaryl portion thereof is thiazolyl.

In another embodiment of the compounds of Formula , -L-$X^2$—$R^3$ is substituted or unsubstituted —$NR^6$—C(O)—$NR^6$-thiazolylmethyl.

In another embodiment of the compounds of Formula I, -L-$X^2$—$R^3$ is substituted —$NR^6$—C(O)—$NR^6$-thiazolylmethyl.

In another embodiment of the compounds of Formula I, -L-$X^2$—$R^3$ is —$NR^6$—C(O)—$NR^6$-thiazolylmethyl substituted with one or more substituents selected from the group consisting of alkyl, substituted alkyl, halo, hydroxyl, amino, haloalkyl, and cyano.

In another embodiment of the compounds of Formula I, -L-$X^2$—$R^3$ is substituted —$NR^6$—C(O)—$NR^6$-thiazolylmethyl, and the substituent is an alkyl group.

In another embodiment of the compounds of Formula I, -L-$X^2$—$R^3$ is substituted or unsubstituted —$CHR^7$—$NR^6$—C(O)—$NR^6$-heterocyclyl.

In another embodiment of the compounds of Formula I, -L-$X^2$—$R^3$ is substituted or unsubstituted —$CHR^7$—$NR^6$—C(O)—$NR^6$-aryl.

In another embodiment of the compounds of Formula I, -L-$X^2$—$R^3$ is substituted or unsubstituted —$CHR^7$—$NR^6$—C(O)—$NR^6$-phenyl.

In another embodiment of the compounds of Formula I, -L-$X^2$—$R^3$ is substituted or unsubstituted —$CHR^7$—$NR^6$—C(O)—$NR^6$-heteroaryl.

In another embodiment of the compounds of Formula I, -L-$X^2$—$R^3$ is substituted or unsubstituted —$CHR^7$—$NR^6$—C(O)—$NR^6$-heteroaryl, wherein said heteroaryl is any heteroaryl described or defined herein.

In another embodiment of the compounds of Formula I, -L-$X^2$—$R^3$ is substituted or unsubstituted —$CHR^7$—$NR^6$—C(O)—$NR^6$-thiazolyl.

In another embodiment of the compounds of Formula I, -L-$X^2$—$R^3$ is substituted or unsubstituted —$CHR^7$—$NR^6$—C(O)—$NR^6$-arylalkyl.

In another embodiment of the compounds of Formula I, -L-$X^2$—$R^3$ is substituted or unsubstituted —$CHR^7$—$NR^6$—C(O)—$NR^6$-benzyl.

In another embodiment of the compounds of Formula I, -L-$X^2$—$R^3$ is substituted —$CHR^7$—$NR^6$—C(O)—$NR^6$-benzyl.

In another embodiment of the compounds of Formula I, -L-$X^2$—$R^3$ is —$CHR^7$—$NR^6$—C(O)—$NR^6$-benzyl wherein the benzyl is substituted with one or more substituents selected from the group consisting of alkyl, substituted alkyl, halo, hydroxyl, amino, haloalkyl, and cyano.

In another embodiment of the compounds of Formula I, -L-$X^2$—$R^3$ is substituted or unsubstituted —$CHR^7$—$NR^6$—C(O)—$NR^6$-heteroarylalkyl.

In another embodiment of the compounds of Formula I, -L-$X^2$—$R^3$ is substituted or unsubstituted —$CHR^7$—$NR^6$—C(O)—$NR^6$-heteroarylalkyl, wherein the alkyl portion thereof is any alkylene described or disclosed herein.

In another embodiment of the compounds of Formula I, -L-$X^2$—$R^3$ is substituted or unsubstituted —$CHR^7$—$NR^6$—C(O)—$NR^6$-heteroarylalkyl, wherein the alkyl portion thereof is —$CH_2$—.

In another embodiment of the compounds of Formula I, -L-$X^2$—$R^3$ is substituted or unsubstituted —$CHR^7$—$NR^6$—C(O)—$NR^6$-heteroarylalkyl, wherein the heteroaryl portion thereof is any heteroaryl described or disclosed herein.

In another embodiment of the compounds of Formula I, -L-$X^2$—$R^3$ is substituted or unsubstituted —$CHR^7$—$NR^6$—C(O)—$NR^6$-heteroarylalkyl, wherein the heteroaryl portion thereof is thiazolyl.

In another embodiment of the compounds of Formula I, -L-$X^2$—$R^3$ is substituted or unsubstituted —$CHR^7$—$NR^6$—C(O)—$NR^6$-thiazolylmethyl.

In another embodiment of the compounds of Formula I, -L-$X^2$—$R^3$ is $CHR^7$—$NR^6$—C(O)—$NR^6$-thiazol-5-ylmethyl.

In another embodiment of the compounds of Formula I, -L-$X^2$—$R^3$ is substituted —$CHR^7$—$NR^6$—C(O)—$NR^6$-thiazolylmethyl.

In another embodiment of the compounds of Formula I, -L-$X^2$—$R^3$ is —$CHR^7$—$NR^6$—C(O)—$NR^6$-thiazolylmethyl wherein the thiazolylmethyl is substituted with one or more substituents selected from the group consisting of alkyl, substituted alkyl, halo, hydroxyl, amino, haloalkyl, and cyano.

In another embodiment of the compounds of Formula I, -L-$X^2$—$R^3$ is substituted —$CHR^7$—$NR^6$—C(O)—$NR^6$-thiazolylmethyl wherein the thiazolylmethyl substituent is an alkyl group.

In another embodiment of the compounds of Formula I, -L-$X^2$—$R^3$ is substituted —$CHR^7$—$NR^6$—C(O)—$NR^6$-(2-isopropylthiazolyl-4-yl)methyl.

In another embodiment of the compounds of Formula I, -L-$X^2$—$R^3$ is $CHR^7$—$NR^6$—C(O)—$NR^6$-heterocyclyl wherein the heterocyclyl is substituted or unsubstituted and $R^7$ is morpholinylalkyl.

In another embodiment of the compounds of Formula I, -L-$X^2$—$R^3$ is —$CHR^7$—$NR^6$—C(O)—$NR^6$-aryl wherein the aryl is substituted or unsubstituted and $R^7$ is morpholinylalkyl.

In another embodiment of the compounds of Formula I, -L-$X^2$—$R^3$ is —$CHR^7$—$NR^6$—C(O)—$NR^6$-phenyl wherein the phenyl is substituted or unsubstituted and $R^7$ is morpholinylalkyl.

In another embodiment of the compounds of Formula I, -L-$X^2$—$R^3$ is —$CHR^7$—$NR^6$—C(O)—$NR^6$-heteroaryl wherein the heteroaryl is substituted or unsubstituted and $R^7$ is morpholinylalkyl.

In another embodiment of the compounds of Formula I, -L-$X^2$—$R^3$ is —$CHR^7$—$NR^6$—C(O)—$NR^6$-heteroaryl wherein the heteroaryl is substituted or unsubstituted, said heteroaryl is any heteroaryl described or defined herein, and $R^7$ is morpholinylalkyl.

In another embodiment of the compounds of Formula I, -L-$X^2$—$R^3$ is —$CHR^7$—$NR^6$—C(O)—$NR^6$-thiazolyl wherein thiazolyl is substituted or unsubstituted and $R^7$ is morpholinylalkyl.

In another embodiment of the compounds of Formula I, -L-$X^2$—$R^3$ is —$CHR^7$—$NR^6$—C(O)—$NR^6$-arylalkyl wherein the arylalkyl is substituted or unsubstituted and $R^7$ is morpholinylalkyl.

In another embodiment of the compounds of Formula I, -L-$X^2$—$R^3$ is —$CHR^7$—$NR^6$—C(O)—$NR^6$-benzyl wherein the benzyl is substituted or unsubstituted and $R^7$ is morpholinylalkyl.

In another embodiment of the compounds of Formula I, -L-$X^2$—$R^3$ is —$CHR^7$—$NR^6$—C(O)—$NR^6$-benzyl wherein the benzyl is substituted and $R^7$ is morpholinylalkyl.

In another embodiment of the compounds of Formula I, -L-$X^2$—$R^3$ is —$CHR^7$—$NR^6$—C(O)—$NR^6$-benzyl wherein the benzyl is substituted with one or more substituents selected from the group consisting of alkyl, substituted alkyl, halo, hydroxyl, amino, haloalkyl, and cyano and $R^7$ is morpholinylalkyl.

In another embodiment of the compounds of Formula I, -L-$X^2$—$R^3$ is —$CHR^7$—$NR^6$—C(O)—$NR^6$-heteroarylalkyl wherein the heteroarylalkyl is substituted or unsubstituted and $R^7$ is morpholinylalkyl.

In another embodiment of the compounds of Formula I, -L-$X^2$—$R^3$ is —$CHR^7$—$NR^6$—C(O)—$NR^6$-heteroarylalkyl wherein the heteroarylalkyl is substituted or unsubstituted, the alkyl portion thereof is any alkylene described or disclosed herein and $R^7$ is morpholinylalkyl.

In another embodiment of the compounds of Formula I, -L-$X^2$—$R^3$ is —$CHR^7$—$NR^6$—C(O)—$NR^6$-heteroarylalkyl wherein the heteroarylalkyl is substituted or unsubstituted, the alkyl portion thereof is —$CH_2$—, and $R^7$ is morpholinylalkyl.

In another embodiment of the compounds of Formula I, -L-$X^2$—$R^3$ is —$CHR^7$—$NR^6$—C(O)—$NR^6$-heteroarylalkyl wherein the heteroarylalkyl is substituted or unsubstituted, the heteroaryl portion thereof is any heteroaryl described or disclosed herein, and $R^7$ is morpholinylalkyl.

In another embodiment of the compounds of Formula I, -L-$X^2$—$R^3$ is —$CHR^7$—$NR^6$—C(O)—$NR^6$-heteroarylalkyl wherein the heteroarylalkyl is substituted or unsubstituted, the heteroaryl portion thereof is thiazolyl, and $R^7$ is morpholinylalkyl.

In another embodiment of the compounds of Formula I, -L-$X^2$—$R^3$—$CHR^7$—$NR^6$—C(O)—$NR^6$-thiazolylmethyl wherein the thiazolylmethyl is substituted or unsubstituted and $R^7$ is morpholinylalkyl.

In another embodiment of the compounds of Formula I, -L-$X^2$—$R^3$ is —$CHR^7$—$NR^6$—C(O)—$NR^6$-thiazolyl-5-ylmethyl wherein $R^7$ is morpholinylalkyl.

In another embodiment of the compounds of Formula I, -L-$X^2$—$R^3$ is substituted —$CHR^7$—$NR^6$—C(O)—$NR^6$-thiazolylmethyl wherein the thiazolylmethyl is substituted and $R^7$ is morpholinylalkyl.

In another embodiment of the compounds of Formula I, -L-$X^2$—$R^3$ is —$CHR^7$—$NR^6$—C(O)—$NR^6$-thiazolylmethyl wherein the thiazolylmethyl is substituted with one or more substituents selected from the group consisting of alkyl, substituted alkyl, halo, hydroxyl, amino, haloalkyl, and cyano, and $R^7$ is morpholinylalkyl.

In another embodiment of the compounds of Formula I, -L-$X^2$—$R^3$ is —$CHR^7$—$NR^6$—C(O)—$NR^6$-thiazolylmethyl wherein the thiazolylmethyl is substituted, the substituent is an alkyl group, and $R^7$ is morpholinylalkyl.

In another embodiment of the compounds of Formula I, -L-$X^2$—$R^3$ is —$CHR^7$—$NR^6$—C(O)—$NR^6$-(2-isopropylthiazolyl-4-yl)methyl and $R^7$ is morpholinylalkyl.

In another embodiment of the compounds of Formula i, -L-$X^2$—$R^3$ is —$CHR^7$—$NR^6$—C(O)—$NR^6$-heterocyclyl wherein the heterocyclyl is substituted or unsubstituted and $R^7$ is —$CH_2CH_2$-morpholinyl.

In another embodiment of the compounds of Formula I, -L-$X^2$—$R^3$ is —$CHR^7$—$NR^6$—C(O)—$NR^6$-aryl wherein the aryl is substituted or unsubstituted and $R^7$ is —$CH_2CH_2$-morpholinyl.

In another embodiment of the compounds of Formula I, -L-X²—R³ is —CHR⁷—NR⁶—C(O)—NR⁶-phenyl wherein the phenyl is substituted or unsubstituted and R⁷ is —CH₂CH₂-morpholinyl.

In another embodiment of the compounds of Formula I, -L-X²—R³ is —CHR⁷—NR⁶—C(O)—NR⁶-heteroaryl wherein the heteroaryl is substituted or unsubstituted and R⁷ is —CH₂CH₂-morpholinyl.

In another embodiment of the compounds of Formula I, -L-X²—R³ is —CHR⁷—NR⁶—C(O)—NR⁶-heteroaryl wherein the heteroaryl is substituted or unsubstituted, said heteroaryl is any heteroaryl described or defined herein and R⁷ is —CH₂CH₂-morpholinyl.

In another embodiment of the compounds of Formula I, -L-X²—R³ is —CHR⁷—NR⁶—C(O)—NR⁶-thiazolyl wherein the thiazolyl is substituted or unsubstituted and R⁷ is —CH₂CH₂-morpholinyl.

In another embodiment of the compounds of Formula I, -L-X²—R³ is —CHR⁷—NR⁶—C(O)—NR⁶-arylalkyl wherein the arylalkyl is substituted or unsubstituted and R⁷ is —CH₂CH₂-morpholinyl.

In another embodiment of the compounds of Formula I, -L-X²—R³ is —CHR⁷—NR⁶—C(O)—NR⁶-benzyl wherein the benzyl is substituted or unsubstituted and R⁷ is —CH₂CH₂-morpholinyl.

In another embodiment of the compounds of Formula I, -L-X²—R³ is —CHR₇—NR⁶—C(O)—NR⁶-benzyl wherein the benzyl is substituted and R⁷ is —CH₂CH₂-morpholinyl.

In another embodiment of the compounds of Formula I, -L-X²—R³ is —CHR⁷—NR⁶—C(O)—NR⁶-benzyl wherein the benzyl is substituted with one or more substituents selected from the group consisting of alkyl, substituted alkyl, halo, hydroxyl, amino, haloalkyl, and cyano and R⁷ is —CH₂CH₂-morpholinyl.

In another embodiment of the compounds of Formula I, -L-X²—R³ is —CHR⁷—NR⁶—C(O)—NR⁶-heteroarylalkyl wherein the heteroarylalkyl is substituted or unsubstituted and R⁷ is —CH₂CH₂-morpholinyl.

In another embodiment of the compounds of Formula I, -L-X²—R³ is —CHR⁷—NR⁶—C(O)—NR⁶-heteroarylalkyl wherein the heteroarylalkyl is substituted or unsubstituted, the alkyl portion thereof is any alkylene described or disclosed herein, and R⁷ is —CH₂CH₂-morpholinyl.

In another embodiment of the compounds of Formula I, -L-X²—R³ is substituted or unsubstituted —CHR⁷—NR⁶—C(O)—NR⁶-heteroarylalkyl wherein the heteroarylalkyl is substituted or unsubstituted, the alkyl portion thereof is —CH₂—, and R⁷ is —CH₂CH₂-morpholinyl.

In another embodiment of the compounds of Formula I, -L-X²—R³ is —CHR⁷—NR⁶—C(O)—NR⁶-heteroarylalkyl wherein the heteroarylalkyl is substituted or unsubstituted, the heteroaryl portion thereof is any heteroaryl described or disclosed herein, and R⁷ is —CH₂CH₂-morpholinyl.

In another embodiment of the compounds of Formula I, -L-X²—R³ is —CHR⁷—NR⁶—C(O)—NR⁶-heteroarylalkyl wherein the heteroarylalkyl is substituted or unsubstituted, the heteroaryl portion thereof is thiazolyl, and R⁷ is —CH₂CH₂-morpholinyl.

In another embodiment of the compounds of Formula I, -L-X²—R³ is —CHR⁷—NR⁶—C(O)—NR⁶-thiazolylmethyl wherein the thiazolylmethyl is substituted or unsubstituted and R⁷ is —CH₂CH₂-morpholinyl.

In another embodiment of the compounds of Formula I, -L-X²—R³ is —CHR⁷—NR⁶—C(O)—NR⁶-thiazol-5-ylmethyl wherein R⁷ is —CH₂CH₂-morpholinyl.

In another embodiment of the compounds of Formula I, -L-X²—R³ is —CHR⁷—NR⁶—C(O)—NR⁶-thiazoylmethyl wherein the thiazoylmethyl is substituted and R⁷ is —CH₂CH₂-morpholinyl.

In another embodiment of the compounds of Formula I, -L-X²—R³ is —CHR⁷—NR⁶—C(O)—NR⁶-thiazolylmethyl wherein thiazolylmethyl is substituted with one or more substituents selected from the group consisting of alkyl, substituted alkyl, halo, hydroxyl, amino, haloalkyl, and cyano and R⁷ is —CH₂CH₂-morpholinyl.

In another embodiment of the compounds of Formula I, -L-X²—R³ is —CHR⁷—NR⁶—C(O)—NR⁶-thiazolylmethyl wherein the thiazolylmethyl is substituted, the substituent is an alkyl group, and R⁷ is —CH₂CH₂-morpholinyl.

In another embodiment of the compounds of Formula I, -L-X²—R³ is —CHR⁷—NR⁶—C(O)—NR⁶-(2-isopropylthiazolyl-4-yl)methyl wherein R⁷ is —CH₂CH₂-morpholinyl.

In another embodiment, the compounds of Formula I have the structure of Formula Ia:

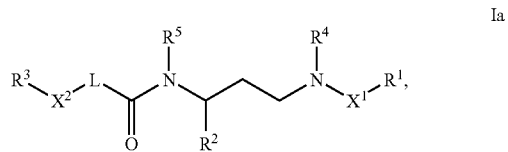

wherein X¹, X², L, R₁, R², R³, R⁴, and R⁵ are as defined herein.

In another embodiment of the compounds of Formula Ia, R² is substituted or unsubstituted arylalkyl.

In another embodiment of the compounds of Formula Ia, R² is substituted or unsubstituted benzyl.

In another embodiment of the compounds of Formula Ia, R² is alkyl.

In another embodiment of the compounds of Formula Ia, X¹ is —C(O)—O—.

In another embodiment of the compounds of Formula Ia, X¹ is —S(O)—.

In another embodiment of the compounds of Formula Ia, X¹ is —S(O₂)—.

In another embodiment of the compounds of Formula Ia, X¹ is —C(O)NR⁶—.

In another embodiment of the compounds of Formula Ia, X¹ is —C(O)NH—.

In another embodiment of the compounds of Formula Ia, X¹ is —C(O)N(alkyl)-.

In another embodiment of the compounds of Formula Ia, X² is —O—.

In another embodiment of the compounds of Formula Ia, X² is —NR⁶—C(O)—NR⁶—.

In another embodiment of the compounds of Formula Ia, X² is —NR⁶—C(O)—NH—.

In another embodiment of the compounds of Formula Ia, X² is —NH—C(O)—NR⁶—.

In another embodiment of the compounds of Formula Ia, X² is —N(alkyl)-C(O)-(alkyl)-.

In another embodiment of the compounds of Formula Ia, X² is —N(alkyl)-C(O)—NH—.

In another embodiment of the compounds of Formula Ia, X² is —NH—C(O)—N(alkyl)-.

In another embodiment of the compounds of Formula Ia, X² is —NH—C(O)—NH—.

In another embodiment of the compounds of Formula Ia, $X^2$ is —OC(O)$NR^6$—.

In another embodiment of the compounds of Formula Ia, $X^2$ is —OC(O)NH—.

In another embodiment of the compounds of Formula Ia, $X^2$ is —OC(O)N(alkyl)-.

In another embodiment of the compounds of Formula Ia, $X^2$ is —$NR^6$C(O)O—.

In another embodiment of the compounds of Formula Ia, $X^2$ is —NHC(O)O—.

In another embodiment of the compounds of Formula Ia, $X^2$ is —N(alkyl)C(O)O—.

In another embodiment of the compounds of Formula Ia, $X^2$ is —$NR^6$—.

In another embodiment of the compounds of Formula Ia, $X^2$ is —NH—.

In another embodiment of the compounds of Formula Ia, $X^2$ is —N(alkyl)-.

In another embodiment of the compounds of Formula Ia, L is a covalent bond.

In another embodiment of the compounds of Formula Ia, L is —$CHR^7$—, wherein $R^7$ is heterocyclylalkyl.

In another embodiment of the compounds of Formula Ia, L is —$CHR^7$—, wherein $R^7$ is heterocyclylalkyl, the alkyl portion of which is any alkylene as defined or described herein.

In another embodiment of the compounds of Formula IIa L is —$CHR^7$—, wherein $R^7$ is heterocyclylalkyl, the heterocyclyl portion of which is any heterocyclyl as defined herein.

In another embodiment of the compounds of Formula Ia, L is —$CHR^7$—, wherein $R^7$ is heterocyclylalkyl, the heterocyclyl portion of which is a morpholinyl group.

In another embodiment of the compounds of Formula Ia, L is —$CHR^7$— and $R^7$ is:

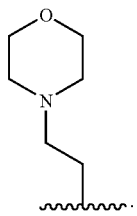 [SMILES: *CCN1CCOCC1]

In another embodiment of the compounds of Formula Ia, $R^1$ is substituted or unsubstituted aryl.

In another embodiment of the compounds of Formula Ia, $R^1$ is substituted or unsubstituted phenyl.

In another embodiment of the compounds of Formula Ia, $R^1$ is substituted phenyl.

In another embodiment of the compounds of Formula Ia, $R^1$ is mono-substituted phenyl.

In another embodiment of the compounds of Formula Ia, $R^1$ is phenyl substituted with one or more substituents selected from the group consisting of alkyl, substituted alkyl, halo, hydroxyl, amino, haloalkyl, and cyano.

In another embodiment of the compounds of Formula Ia, $R^1$ is 4-aminophenyl.

In another embodiment of the compounds of Formula Ia, $R^1$ is substituted or unsubstituted heteroaryl.

In another embodiment of the compounds of Formula Ia, $R^1$ is substituted or unsubstituted thiazolyl.

In another embodiment of the compounds of Formula Ia, $R^1$ is substituted or unsubstituted arylalkyl.

In another embodiment of the compounds of Formula Ia, $R^1$ is substituted or unsubstituted benzyl.

In another embodiment of the compounds of Formula Ia, $R^1$ is substituted or unsubstituted heteroarylalkyl.

In another embodiment of the compounds of Formula Ia, $R^1$ is substituted or unsubstituted heteroarylalkyl, wherein the alkyl portion thereof is any of the alkylene groups defined or disclosed herein.

In another embodiment of the compounds of Formula Ia, $R^1$ is substituted or unsubstituted heteroarylalkyl, wherein the alkyl portion thereof is —$CH_2$—.

In another embodiment of the compounds of Formula Ia, $R^1$ is substituted or unsubstituted heteroarylalkyl, wherein the heteroaryl portion thereof is any of the heteroaryl groups defined or disclosed herein.

In another embodiment of the compounds of Formula Ia, $R^1$ is substituted or unsubstituted heteroarylalkyl, wherein the heteroaryl portion thereof is thiazolyl.

In another embodiment of the compounds of Formula Ia, $R^1$ is substituted or unsubstituted thiazolylmethyl.

In another embodiment of the compounds of Formula Ia, $R^1$ is thiazol-5-ylmethyl.

In another embodiment of the compounds of Formula Ia, $R^1$ is substituted heteroarylalkyl, wherein the heteroaryl portion thereof is any of the heteroaryl groups defined or disclosed herein, and the substituent is one or more substituents selected from the group consisting of alkyl, substituted alkyl, halo, hydroxyl, amino, haloalkyl, and cyano.

In another embodiment of the compounds of Formula Ia, $R^1$ is substituted heteroarylalkyl, wherein the heteroaryl portion thereof is thiazolyl substituted with one or more substituents selected from the group consisting of alkyl, substituted alkyl, halo, hydroxyl, amino, haloalkyl, and cyano.

In another embodiment of the compounds of Formula Ia, $R^1$ is thiazolylmethyl substituted with one or more substituents selected from the group consisting of alkyl, substituted alkyl, halo, hydroxyl, amino, haloalkyl, and cyano.

In another embodiment of the compounds of Formula Ia, $R^3$ is substituted or unsubstituted heterocyclyl.

In another embodiment of the compounds of Formula Ia, $R^3$ is substituted or unsubstituted tetrahydro-2H-furo[2,3-b]furanyl.

In another embodiment of the compounds of Formula Ia, $R^3$ is unsubstituted tetrahydro-2H-furo[2,3-b]furanyl.

In another embodiment of the compounds of Formula Ia, $R^3$ is tetrahydro-2H-furo[2,3-b]furan-3-yl.

In another embodiment of the compounds of Formula Ia, $R^3$ is substituted or unsubstituted tetrahydrofuranyl.

In another embodiment of the compounds of Formula Ia, $R^3$ is unsubstituted tetrahydrofuranyl.

In another embodiment of the compounds of Formula Ia, $R^3$ is tetrahydrofuran-3-yl.

In another embodiment of the compounds of Formula Ia, $R^3$ is substituted or unsubstituted aryl.

In another embodiment of the compounds of Formula Ia, $R^3$ is substituted or unsubstituted phenyl.

In another embodiment of the compounds of Formula Ia, $R^3$ is substituted or unsubstituted heteroaryl.

In another embodiment of the compounds of Formula Ia, $R^3$ is substituted or unsubstituted heteroaryl, wherein said heteroaryl is any heteroaryl described or defined herein.

In another embodiment of the compounds of Formula Ia, $R^3$ is substituted or unsubstituted thiazolyl.

In another embodiment of the compounds of Formula Ia, $R^3$ is thiazolyl substituted with one or more substituents selected from the group consisting of alkyl, substituted alkyl, halo, hydroxyl, amino, haloalkyl, and cyano.

In another embodiment of the compounds of Formula Ia, $R^3$ is substituted or unsubstituted arylalkyl.

In another embodiment of the compounds of Formula Ia, $R^3$ is substituted or unsubstituted benzyl.

In another embodiment of the compounds of Formula Ia, $R^3$ is substituted benzyl.

In another embodiment of the compounds of Formula Ia, $R^3$ is benzyl substituted with one or more substituents selected from the group consisting of alkyl, substituted alkyl, halo, hydroxyl, amino, haloalkyl, and cyano.

In another embodiment of the compounds of Formula Ia, $R^3$ is substituted or unsubstituted heteroarylalkyl.

In another embodiment of the compounds of Formula Ia, $R^3$ is substituted or unsubstituted heteroarylalkyl, wherein the alkyl portion thereof is any alkylene described or disclosed herein.

In another embodiment of the compounds of Formula Ia, $R^3$ is substituted or unsubstituted heteroarylalkyl, wherein the alkyl portion thereof is —$CH_2$—.

In another embodiment of the compounds of Formula Ia, $R^3$ is substituted or unsubstituted heteroarylalkyl, wherein the heteroaryl portion thereof is any heteroaryl described or disclosed herein.

In another embodiment of the compounds of Formula Ia, $R^3$ is substituted or unsubstituted heteroarylalkyl, wherein the heteroaryl portion thereof is thiazolyl.

In another embodiment of the compounds of Formula Ia, $R^3$ is substituted or unsubstituted thiazolylmethyl.

In another embodiment of the compounds of Formula Ia, $R^3$ is thiazol-5-ylmethyl.

In another embodiment of the compounds of Formula Ia, $R^3$ is substituted thiazolylmethyl.

In another embodiment of the compounds of Formula Ia, $R^3$ is thiazolylmethyl substituted with one or more substituents selected from the group consisting of alkyl, substituted alkyl, halo, hydroxyl, amino, haloalkyl, and cyano.

In another embodiment of the compounds of Formula Ia, $R^3$ is substituted thiazolylmethyl, and the substituent is an alkyl group.

In another embodiment of the compounds of Formula Ia, $R^3$ is (2-isopropylthiazolyl-4-yl)methyl.

In another embodiment of the compounds of Formula Ia, $R^4$ is H.

In another embodiment of the compounds of Formula Ia, $R^4$ is alkyl.

In another embodiment of the compounds of Formula Ia, $R^4$ is any of the alkyl groups described or disclosed herein.

In another embodiment of the compounds of Formula Ia, $R^4$ is 2-methylpropyl.

In another embodiment of the compounds of Formula Ia, $R^4$ is substituted or unsubstituted arylalkyl.

In another embodiment of the compounds of Formula Ia, $R^4$ is substituted or unsubstituted benzyl.

In another embodiment of the compounds of Formula Ia, $R^4$ is unsubstituted benzyl.

In another embodiment of the compounds of Formula Ia, $R^4$ is benzyl substituted with one or more substituents selected from the group consisting of alkyl, substituted alkyl, halo, hydroxyl, amino, haloalkyl, and cyano.

In another embodiment of the compounds of Formula Ia, $R^4$ is halo substituted benzyl.

In another embodiment of the compounds of Formula Ia, $R^4$ is chloro substituted benzyl.

In another embodiment of the compounds of Formula Ia, $R^4$ is substituted or unsubstituted heteroarylalkyl.

In another embodiment of the compounds of Formula Ia, $R^4$ is substituted or unsubstituted heteroarylalkyl, wherein the alkyl portion thereof is any of the alkylene groups described or defined herein.

In another embodiment of the compounds of Formula Ia, $R^4$ is substituted or unsubstituted heteroarylalkyl, wherein the alkyl portion thereof is —$CH_2$—.

In another embodiment of the compounds of Formula Ia, $R^4$ is substituted or unsubstituted heteroarylalkyl, wherein the heteroaryl portion thereof is any of the heteroaryl groups described or defined herein.

In another embodiment of the compounds of Formula Ia, $R^5$ is H.

In another embodiment of the compounds of Formula Ia, $R^5$ is alkyl.

In another embodiment of the compounds of Formula Ia, $R^5$ is any of the alkyl groups described or disclosed herein.

In another embodiment of the compounds of Formula Ia, $R^5$ is 2-methylpropyl.

In another embodiment of the compounds of Formula Ia, $R^5$ is substituted or unsubstituted arylalkyl.

In another embodiment of the compounds of Formula Ia, $R^5$ is substituted or unsubstituted benzyl.

In another embodiment of the compounds of Formula Ia, $R^5$ is unsubstituted benzyl.

In another embodiment of the compounds of Formula Ia, $R^5$ is benzyl substituted with one or more substituents selected from the group consisting of alkyl, substituted alkyl, halo, hydroxyl, amino, haloalkyl, and cyano.

In another embodiment of the compounds of Formula Ia, $R^5$ is halo substituted benzyl.

In another embodiment of the compounds of Formula Ia, $R^5$ is substituted or unsubstituted heteroarylalkyl.

In another embodiment of the compounds of Formula Ia, $R^5$ is substituted or unsubstituted heteroarylalkyl, wherein the alkyl portion thereof is any of the alkylene groups described or defined herein.

In another embodiment of the compounds of Formula Ia, $R^5$ is substituted or unsubstituted heteroarylalkyl, wherein the alkyl portion thereof is —$CH_2$—.

In another embodiment of the compounds of Formula Ia, $R^5$ is substituted or unsubstituted heteroarylalkyl, wherein the heteroaryl portion thereof is any of the heteroaryl groups described or defined herein.

In another embodiment of the compounds of Formula Ia, $R^4$ and $R^5$ are different.

In another embodiment of the compounds of Formula Ia, $R^4$ and $R^5$ are the same.

In another embodiment of the compounds of Formula Ia, one of $R^4$ and $R^5$ is H.

In another embodiment of the compounds of Formula Ia, $R^4$ is H and $R^5$ is benzyl or substituted benzyl.

In another embodiment of the compounds of Formula Ia, —$X^1$—$R^1$ is substituted or unsubstituted —C(O)—O-aryl.

In another embodiment of the compounds of Formula Ia, —$X^1$—$R^1$ is substituted or unsubstituted —C(O)—O-phenyl.

In another embodiment of the compounds of Formula Ia, —$X^1$—$R^1$ is substituted —C(O)—O-phenyl.

In another embodiment of the compounds of Formula Ia, —$X^1$—$R^1$ is mono-substituted —C(O)—O-phenyl.

In another embodiment of the compounds of Formula Ia, —$X^1$—$R^1$ is C(O)—O-phenyl substituted with one or more substituents selected from the group consisting of alkyl, substituted alkyl, halo, hydroxyl, amino, haloalkyl, and cyano.

In another embodiment of the compounds of Formula Ia, —$X^1$—$R^1$ is —C(O)—O-(4-aminophenyl).

In another embodiment of the compounds of Formula Ia, —$X^1$—$R^1$ is substituted or unsubstituted —C(O)—O-heteroaryl.

In another embodiment of the compounds of Formula Ia, —X¹—R¹ is substituted or unsubstituted —C(O)—O-thiazolyl.

In another embodiment of the compounds of Formula Ia, —X¹—R¹ is substituted or unsubstituted —C(O)—O-arylalkyl.

In another embodiment of the compounds of Formula Ia, —X¹—R¹ is substituted or unsubstituted —C(O)—O-benzyl.

In another embodiment of the compounds of Formula Ia, —X¹—R¹ is substituted or unsubstituted —C(O)—O-heteroarylalkyl.

In another embodiment of the compounds of Formula Ia, —X¹—R¹ is substituted or unsubstituted —C(O)—O-heteroarylalkyl, wherein the alkyl portion thereof is any of the alkylene groups defined or disclosed herein.

In another embodiment of the compounds of Formula Ia, —X¹—R¹ is substituted or unsubstituted —C(O)—O-heteroarylalkyl, wherein the alkyl portion thereof is —CH₂—.

In another embodiment of the compounds of Formula Ia, —X¹—R¹ is substituted or unsubstituted —C(O)—O-heteroarylalkyl, wherein the heteroaryl portion thereof is any of the heteroaryl groups defined or disclosed herein.

In another embodiment of the compounds of Formula Ia, —X¹—R¹ is substituted or unsubstituted —C(O)—O-heteroarylalkyl, wherein the heteroaryl portion thereof is thiazolyl.

In another embodiment of the compounds of Formula Ia, —X¹—R¹ is substituted or unsubstituted —C(O)—O-thiazolylmethyl.

In another embodiment of the compounds of Formula Ia, —X¹—R¹ is —C(O)—O-thiazol-5-ylmethyl.

In another embodiment of the compounds of Formula Ia, —X¹—R¹ is substituted —C(O)—O-heteroarylalkyl, wherein the heteroaryl portion thereof is any of the heteroaryl groups defined or disclosed herein, and the substituent is one or more substituents selected from the group consisting of alkyl, substituted alkyl, halo, hydroxyl, amino, haloalkyl, and cyano.

In another embodiment of the compounds of Formula Ia, —X¹—R¹ is substituted —C(O)—O-heteroarylalkyl, wherein the heteroaryl portion thereof is thiazolyl substituted with one or more substituents selected from the group consisting of alkyl, substituted alkyl, halo, hydroxyl, amino, haloalkyl, and cyano.

In another embodiment of the compounds of Formula Ia, —X¹—R¹ is —C(O)—O-thiazolylmethyl substituted with one or more substituents selected from the group consisting of alkyl, substituted alkyl, halo, hydroxyl, amino, haloalkyl, and cyano.

In another embodiment of the compounds of Formula Ia, —X¹—R¹ is substituted or unsubstituted —S(O)-aryl.

In another embodiment of the compounds of Formula Ia, —X¹—R¹ is substituted or unsubstituted —S(O)-phenyl.

In another embodiment of the compounds of Formula Ia, —X¹—R¹ is substituted —S(O)-phenyl.

In another embodiment of the compounds of Formula Ia, —X¹—R¹ is mono-substituted —S(O)-phenyl.

In another embodiment of the compounds of Formula Ia, —X¹—R¹ is —S(O)-phenyl substituted with one or more substituents selected from the group consisting of alkyl, substituted alkyl, halo, hydroxyl, amino, haloalkyl, and cyano.

In another embodiment of the compounds of Formula Ia, —X¹—R¹ is —S(O)-(4-aminophenyl).

In another embodiment of the compounds of Formula Ia, —X¹—R¹ is substituted or unsubstituted —S(O)-heteroaryl.

In another embodiment of the compounds of Formula Ia, —X¹—R¹ is substituted or unsubstituted —S(O)-thiazolyl.

In another embodiment of the compounds of Formula Ia, —X¹—R¹ is substituted or unsubstituted —S(O)-arylalkyl.

In another embodiment of the compounds of Formula Ia, —X¹—R¹ is substituted or unsubstituted —S(O)-benzyl.

In another embodiment of the compounds of Formula Ia, —X¹—R¹ is substituted or unsubstituted —S(O)-heteroarylalkyl.

In another embodiment of the compounds of Formula Ia, —X¹—R¹ is substituted or unsubstituted —S(O)-heteroarylalkyl, wherein the alkyl portion thereof is any of the alkylene groups defined or disclosed herein.

In another embodiment of the compounds of Formula Ia, —X¹—R¹ is substituted or unsubstituted —S(O)-heteroarylalkyl, wherein the alkyl portion thereof is —CH₂—.

In another embodiment of the compounds of Formula Ia, —X¹—R¹ is substituted or unsubstituted —S(O)-heteroarylalkyl, wherein the heteroaryl portion thereof is any of the heteroaryl groups defined or disclosed herein.

In another embodiment of the compounds of Formula Ia, —X¹—R¹ is substituted or unsubstituted —S(O)-heteroarylalkyl, wherein the heteroaryl portion thereof is thiazolyl.

In another embodiment of the compounds of Formula Ia, —X¹—R¹ is substituted or unsubstituted —S(O)-thiazolylmethyl.

In another embodiment of the compounds of Formula Ia, —X¹—R¹ is substituted —S(O)-heteroarylalkyl, wherein the heteroaryl portion thereof is any of the heteroaryl groups defined or disclosed herein, and the substituent is one or more substituents selected from the group consisting of alkyl, substituted alkyl, halo, hydroxyl, amino, haloalkyl, and cyano.

In another embodiment of the compounds of Formula Ia, —X¹—R¹ is substituted —S(O)-heteroarylalkyl, wherein the heteroaryl portion thereof is thiazolyl substituted with one or more substituents selected from the group consisting of alkyl, substituted alkyl, halo, hydroxyl, amino, haloalkyl, and cyano.

In another embodiment of the compounds of Formula Ia, —X¹—R¹ is —S(O)-thiazolylmethyl substituted with one or more substituents selected from the group consisting of alkyl, substituted alkyl, halo, hydroxyl, amino, haloalkyl, and cyano.

In another embodiment of the compounds of Formula Ia, —X¹—R¹ is substituted or unsubstituted —S(O₂)-aryl.

In another embodiment of the compounds of Formula Ia, —X¹—R¹ is substituted or unsubstituted —S(O₂)-phenyl.

In another embodiment of the compounds of Formula Ia, —X¹—R¹ is substituted —S(O₂)-phenyl.

In another embodiment of the compounds of Formula Ia, —X¹—R¹ is mono-substituted —S(O₂)-phenyl.

In another embodiment of the compounds of Formula Ia, —X¹—R¹ is —S(O₂)-phenyl substituted with one or more substituents selected from the group consisting of alkyl, substituted alkyl, halo, hydroxyl, amino, haloalkyl, and cyano.

In another embodiment of the compounds of Formula Ia, —X¹—R¹ is —S(O₂)-(4-aminophenyl).

In another embodiment of the compounds of Formula Ia, —X¹—R¹ is substituted or unsubstituted —S(O₂)-heteroaryl.

In another embodiment of the compounds of Formula Ia, —X¹—R¹ is substituted or unsubstituted —S(O₂)-thiazolyl.

In another embodiment of the compounds of Formula Ia, —X¹—R¹ is substituted or unsubstituted —S(O₂)-arylalkyl.

In another embodiment of the compounds of Formula Ia, —X¹—R¹ is substituted or unsubstituted —S(O₂)-benzyl.

In another embodiment of the compounds of Formula Ia, —$X^1$—$R^1$ is substituted or unsubstituted —$S(O_2)$-heteroarylalkyl.

In another embodiment of the compounds of Formula Ia, —$X^1$—$R^1$ is substituted or unsubstituted —$S(O_2)$-heteroarylalkyl, wherein the alkyl portion thereof is any of the alkylene groups defined or disclosed herein.

In another embodiment of the compounds of Formula Ia, —$X^1$—$R^1$ is substituted or unsubstituted —$S(O_2)$-heteroarylalkyl, wherein the alkyl portion thereof is —$CH_2$—.

In another embodiment of the compounds of Formula Ia, —$X^1$—$R^1$ is substituted or unsubstituted —$S(O_2)$-heteroarylalkyl, wherein the heteroaryl portion thereof is any of the heteroaryl groups defined or disclosed herein.

In another embodiment of the compounds of Formula Ia, —$X^1$—$R^1$ is substituted or unsubstituted —$S(O_2)$-heteroarylalkyl, wherein the heteroaryl portion thereof is thiazolyl.

In another embodiment of the compounds of Formula Ia, —$X^1$—$R^1$ is substituted or unsubstituted —$S(O_2)$-thiazolylmethyl.

In another embodiment of the compounds of Formula Ia, —$X^1$—$R^1$ is substituted —$S(O_2)$-heteroarylalkyl, wherein the heteroaryl portion thereof is any of the heteroaryl groups defined or disclosed herein, and the substituent is one or more substituents selected from the group consisting of alkyl, substituted alkyl, halo, hydroxyl, amino, haloalkyl, and cyano.

In another embodiment of the compounds of Formula Ia, —$X^1$—$R^1$ is substituted —$S(O_2)$-heteroarylalkyl, wherein the heteroaryl portion thereof is thiazolyl substituted with one or more substituents selected from the group consisting of alkyl, substituted alkyl, halo, hydroxyl, amino, haloalkyl, and cyano.

In another embodiment of the compounds of Formula Ia, —$X^1$—$R^1$ is —$S(O_2)$-thiazolylmethyl substituted with one or more substituents selected from the group consisting of alkyl, substituted alkyl, halo, hydroxyl, amino, haloalkyl, and cyano.

In another embodiment of the compounds of Formula Ia, —$X^1$—$R^1$ is substituted or unsubstituted —$C(O)NR^6$-aryl.

In another embodiment of the compounds of Formula Ia, —$X^1$—$R^1$ is substituted or unsubstituted —$C(O)NR^6$-phenyl.

In another embodiment of the compounds of Formula Ia, —$X^1$—$R^1$ is substituted —$C(O)NR^6$-phenyl.

In another embodiment of the compounds of Formula Ia, —$X^1$—$R^1$ is mono-substituted —$C(O)NR^6$-phenyl.

In another embodiment of the compounds of Formula Ia, —$X^1$—$R^1$ is —$C(O)NR^6$-phenyl substituted with one or more substituents selected from the group consisting of alkyl, substituted alkyl, halo, hydroxyl, amino, haloalkyl, and cyano.

In another embodiment of the compounds of Formula Ia, —$X^1$—$R^1$ is —$C(O)NR^6$(4-aminophenyl).

In another embodiment of the compounds of Formula Ia, —$X^1$—$R^1$ is substituted or unsubstituted —$C(O)NR^6$-heteroaryl.

In another embodiment of the compounds of Formula Ia, —$X^1$—$R^1$ is substituted or unsubstituted —$C(O)NR^6$-thiazolyl.

In another embodiment of the compounds of Formula Ia, —$X^1$—$R^1$ is substituted or unsubstituted —$C(O)NR^6$-arylalkyl.

In another embodiment of the compounds of Formula Ia, —$X^1$—$R^1$ is substituted or unsubstituted —$C(O)NR^6$-benzyl.

In another embodiment of the compounds of Formula Ia, —$X^1$—$R^1$ is substituted or unsubstituted —$C(O)NR^6$-heteroarylalkyl.

In another embodiment of the compounds of Formula Ia, —$X^1$—$R^1$ is substituted or unsubstituted —$C(O)NR^6$-heteroarylalkyl, wherein the alkyl portion thereof is any of the alkylene groups defined or disclosed herein.

In another embodiment of the compounds of Formula Ia, —$X^1$—$R^1$ is substituted or unsubstituted —$C(O)NR^6$-heteroarylalkyl, wherein the alkyl portion thereof is —$CH_2$—.

In another embodiment of the compounds of Formula Ia, —$X^1$—$R^1$ is substituted or unsubstituted —$C(O)NR^6$-heteroarylalkyl, wherein the heteroaryl portion thereof is any of the heteroaryl groups defined or disclosed herein.

In another embodiment of the compounds of Formula Ia, —$X^1$—$R^1$ is substituted or unsubstituted —$C(O)NR^6$-heteroarylalkyl, wherein the heteroaryl portion thereof is thiazolyl.

In another embodiment of the compounds of Formula Ia, —$X^1$—$R^1$ is substituted or unsubstituted —$C(O)NR^6$-thiazolylmethyl.

In another embodiment of the compounds of Formula Ia, —$X^1$—$R^1$ is substituted —$C(O)NR^6$-heteroarylalkyl, wherein the heteroaryl portion thereof is any of the heteroaryl groups defined or disclosed herein, and the substituent is one or more substituents selected from the group consisting of alkyl, substituted alkyl, halo, hydroxyl, amino, haloalkyl, and cyano.

In another embodiment of the compounds of Formula Ia, —$X^1$—$R^1$ is substituted —$C(O)NR^6$-heteroarylalkyl, wherein the heteroaryl portion thereof is thiazolyl substituted with one or more substituents selected from the group consisting of alkyl, substituted alkyl, halo, hydroxyl, amino, haloalkyl, and cyano.

In another embodiment of the compounds of Formula Ia, —$X^1$—$R^1$ is —$C(O)NR^6$-thiazolylmethyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted or unsubstituted —$NR^6$—$C(O)$—$NR^6$-heterocyclyl.

In another embodiment of the compounds of Formula Ia, —$X^2$—$R^3$ is substituted or unsubstituted —$NR^6$—$C(O)$—$NR^6$-aryl.

In another embodiment of the compounds of Formula Ia, —$X^2$—$R^3$ is substituted or unsubstituted —$NR^6$—$C(O)$—$NR^6$-phenyl.

In another embodiment of the compounds of Formula Ia, —$X^2$—$R^3$ is substituted or unsubstituted —$NR^6$—$C(O)$—$NR^6$-heteroaryl.

In another embodiment of the compounds of Formula Ia, —$X^2$—$R^3$ is substituted or unsubstituted —$NR^6$—$C(O)$—$NR^6$-heteroaryl, wherein said heteroaryl is any heteroaryl described or defined herein.

In another embodiment of the compounds of Formula Ia, —$X^2$—$R^3$ is substituted or unsubstituted —$NR^6$—$C(O)$—$NR^6$-thiazolyl.

In another embodiment of the compounds of Formula Ia, —$X^2$—$R^3$ is substituted or unsubstituted —$NR^6$—$C(O)$—$NR^6$-arylalkyl.

In another embodiment of the compounds of Formula Ia, —$X^2$—$R^3$ is substituted or unsubstituted —$NR^6$—$C(O)$—$NR^6$-benzyl.

In another embodiment of the compounds of Formula Ia, —$X^2$—$R^3$ is substituted —$NR^6$—$C(O)$—$NR^6$-benzyl.

In another embodiment of the compounds of Formula Ia, —$X^2$—$R^3$ is —$NR^6$—C(O)—$NR^6$-benzyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted or unsubstituted —$NR^6$—C(O)—$NR^6$-heteroarylalkyl.

In another embodiment of the compounds of Formula Ia, —$X^2$—$R^3$ is substituted or unsubstituted —$NR^6$—C(O)—$NR^6$-heteroarylalkyl, wherein the alkyl portion thereof is any alkylene described or disclosed herein.

In another embodiment of the compounds of Formula Ia, —$X^2$—$R^3$ is substituted or unsubstituted —$NR^6$—C(O)—$NR^6$-heteroarylalkyl, wherein the alkyl portion thereof is —$CH_2$—.

In another embodiment of the compounds of Formula Ia, —$X^2$—$R^3$ is substituted or unsubstituted —$NR^6$—C(O)—$NR^6$-heteroarylalkyl, wherein the heteroaryl portion thereof is any heteroaryl described or disclosed herein.

In another embodiment of the compounds of Formula Ia, —$X^2$—$R^3$ is substituted or unsubstituted —$NR^6$—C(O)—$NR^6$-heteroarylalkyl, wherein the heteroaryl portion thereof is thiazolyl.

In another embodiment of the compounds of Formula Ia, —$X^2$—$R^3$ is substituted or unsubstituted —$NR^6$—C(O)—$NR^6$-thiazolylmethyl.

In another embodiment of the compounds of Formula Ia, —$X^2$—$R^3$ is —$NR^6$—C(O)—$NR^6$-thiazol-5-ylmethyl.

In another embodiment of the compounds of Formula Ia, —$X^2$—$R^3$ is substituted —$NR^6$—C(O)—$NR^6$-thiazolylmethyl.

In another embodiment of the compounds of Formula Ia, —$X^2$—$R^3$ is —$NR^6$—C(O)—$NR^6$-thiazolylmethyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted —$NR^6$—C(O)—$NR^6$-thiazolylmethyl, and the substituent is an alkyl group.

In another embodiment of the compounds of Formula Ia, —$X^2$—$R^3$ is —$NR^6$—C(O)—$NR^5$-(2-isopropylthiazolyl-4-yl)methyl.

In another embodiment of the compounds of Formula Ia, —$X^2$—$R^3$ is substituted or unsubstituted —NH—C(O)—$NR^6$-heterocyclyl.

In another embodiment of the compounds of Formula Ia, —$X^2$—$R^3$ is substituted or unsubstituted —NH—C(O)—$NR^6$-aryl.

In another embodiment of the compounds of Formula Ia, —$X^2$—$R^3$ is substituted or unsubstituted —NH—C(O)—$NR^6$-phenyl.

In another embodiment of the compounds of Formula Ia, —$X^2$—$R^3$ is substituted or unsubstituted —NH—C(O)—$NR^6$-heteroaryl.

In another embodiment of the compounds of Formula Ia, —$X^2$—$R^3$ is substituted or unsubstituted —NH—C(O)—$NR^6$-heteroaryl, wherein said heteroaryl is any heteroaryl described or defined herein.

In another embodiment of the compounds of Formula Ia, —$X^2$—$R^3$ is substituted or unsubstituted —NH—C(O)—$NR^6$-thiazolyl.

In another embodiment of the compounds of Formula Ia, —$X^2$—$R^3$ is substituted or unsubstituted —NH—C(O)—$NR^6$-arylalkyl.

In another embodiment of the compounds of Formula Ia, —$X^2$—$R^3$ is substituted or unsubstituted —NH—C(O)—$NR^6$-benzyl.

In another embodiment of the compounds of Formula Ia, —$X^2$—$R^3$ is substituted —NH—C(O)—$NR^6$-benzyl.

In another embodiment of the compounds of Formula Ia, —$X^2$—$R^3$ is —NH—C(O)—$NR^6$-benzyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted or unsubstituted —NH—C(O)—$NR^6$-heteroarylalkyl.

In another embodiment of the compounds of Formula Ia, —$X^2$—$R^3$ is substituted or unsubstituted —NH—C(O)—$NR^6$-heteroarylalkyl, wherein the alkyl portion thereof is any alkylene described or disclosed herein.

In another embodiment of the compounds of Formula Ia, —$X^2$—$R^3$ is substituted or unsubstituted —NH—C(O)—$NR^6$-heteroarylalkyl, wherein the alkyl portion thereof is —$CH_2$—.

In another embodiment of the compounds of Formula Ia, —$X^2$—$R^3$ is substituted or unsubstituted —NH—C(O)—$NR^6$-heteroarylalkyl, wherein the heteroaryl portion thereof is any heteroaryl described or disclosed herein.

In another embodiment of the compounds of Formula Ia, —$X^2$—$R^3$ is substituted or unsubstituted —NH—C(O)—$NR^6$-heteroarylalkyl, wherein the heteroaryl portion thereof is thiazolyl.

In another embodiment of the compounds of Formula Ia, —$X^2$—$R^3$ is substituted or unsubstituted —NH—C(O)—$NR^6$-thiazolylmethyl.

In another embodiment of the compounds of Formula Ia, —$X^2$—$R^3$ is —NH—C(O)—$NR^6$-thiazol-5-ylmethyl.

In another embodiment of the compounds of Formula Ia, —$X^2$—$R^3$ is substituted —NH—C(O)—$NR^6$-thiazolylmethyl.

In another embodiment of the compounds of Formula Ia, —$X^2$—$R^3$ is —NH—C(O)—$NR^6$-thiazolylmethyl substituted with one or more substituents selected from the group consisting of alkyl, substituted alkyl, halo, hydroxyl, amino, haloalkyl and cyano.

In another embodiment of the compounds of Formula Ia, —$X^2$—$R^3$ is substituted —NH—C(O)—$NR^6$-thiazolylmethyl, and the substituent is an alkyl group.

In another embodiment of the compounds of Formula Ia, —$X^2$—$R^3$ is —NH—C(O)—$NR^6$-(2-isopropylthiazolyl-4-yl)methyl.

In another embodiment of the compounds of Formula Ia, —$X^2$—$R^3$ is substituted or unsubstituted —$NR^6$—C(O)—NH-heterocyclyl.

In another embodiment of the compounds of Formula Ia, —$X^2$—$R^3$ is substituted or unsubstituted —$NR^6$—C(O)—NH-aryl.

In another embodiment of the compounds of Formula Ia, —$X^2$—$R^3$ is substituted or unsubstituted —$NR^6$—C(O)—NH-phenyl.

In another embodiment of the compounds of Formula Ia, —$X^2$—$R^3$ is substituted or unsubstituted —$NR^6$—C(O)—NH-heteroaryl.

In another embodiment of the compounds of Formula Ia, —$X^2$—$R^3$ is substituted or unsubstituted —$NR^6$—C(O)—NH-heteroaryl, wherein said heteroaryl is any heteroaryl described or defined herein.

In another embodiment of the compounds of Formula Ia, —$X^2$—$R^3$ is substituted or unsubstituted —$NR^6$—C(O)—NH-thiazolyl.

In another embodiment of the compounds of Formula Ia, —$X^2$—$R^3$ is substituted or unsubstituted —$NR^6$—C(O)—NH-arylalkyl.

In another embodiment of the compounds of Formula Ia, —$X^2$—$R^3$ is substituted or unsubstituted —$NR^6$—C(O)—NH-benzyl.

In another embodiment of the compounds of Formula Ia, —$X^2$—$R^3$ is substituted —$NR^6$—C(O)—NH-benzyl.

In another embodiment of the compounds of Formula Ia, —$X^2$—$R^3$ is —$NR^6$—C(O)—NH-benzyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted or unsubstituted —$NR^6$—C(O)—NH-heteroarylalkyl.

In another embodiment of the compounds of Formula Ia, —$X^2$—$R^3$ is substituted or unsubstituted —$NR^6$—C(O)—NH-heteroarylalkyl, wherein the alkyl portion thereof is any alkylene described or disclosed herein.

In another embodiment of the compounds of Formula Ia, —$X^2$—$R^3$ is substituted or unsubstituted —$NR^6$—C(O)—NH-heteroarylalkyl, wherein the alkyl portion thereof is —$CH_2$—.

In another embodiment of the compounds of Formula Ia, —$X^2$—$R^3$ is substituted or unsubstituted —$NR^6$—C(O)—NH-heteroarylalkyl, wherein the heteroaryl portion thereof is any heteroaryl described or disclosed herein.

In another embodiment of the compounds of Formula Ia, —$X^2$—$R^3$ is substituted or unsubstituted —$NR^6$—C(O)—NH-heteroarylalkyl, wherein the heteroaryl portion thereof is thiazolyl.

In another embodiment of the compounds of Formula Ia, —$X^2$—$R^3$ is substituted or unsubstituted —$NR^6$—C(O)—NH-thiazolylmethyl.

In another embodiment of the compounds of Formula Ia, —$X^2$—$R^3$ is substituted —$NR^6$—C(O)—NH-thiazolylmethyl.

In another embodiment of the compounds of Formula Ia, —$X^2$—$R^3$ is —$NR^6$—C(O)—NH-thiazolylmethyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted —$NR^6$—C(O)—NH-thiazolylmethyl, and the substituent is an alkyl group.

In another embodiment of the compounds of Formula Ia, —$X^2$—$R^3$ is substituted or unsubstituted —N(alkyl)-C(O)—$NR^6$-heterocyclyl.

In another embodiment of the compounds of Formula Ia, —$X^2$—$R^3$ is substituted or unsubstituted —N(alkyl)-C(O)—$NR^6$-aryl.

In another embodiment of the compounds of Formula Ia, —$X^2$—$R^3$ is substituted or unsubstituted —N(alkyl)-C(O)—$NR^6$-phenyl.

In another embodiment of the compounds of Formula Ia, —$X^2$—$R^3$ is substituted or unsubstituted —N(alkyl)-C(O)—$NR^6$-heteroaryl.

In another embodiment of the compounds of Formula Ia, —$X^2$—$R^3$ is substituted or unsubstituted —N(alkyl)-C(O)—$NR^6$-heteroaryl, wherein said heteroaryl is any heteroaryl described or defined herein.

In another embodiment of the compounds of Formula Ia, —$X^2$—$R^3$ is substituted or unsubstituted —N(alkyl)-C(O)—$NR^6$-thiazolyl.

In another embodiment of the compounds of Formula Ia, —$X^2$—$R^3$ is substituted or unsubstituted —N(alkyl)-C(O)—$NR^6$-arylalkyl.

In another embodiment of the compounds of Formula Ia, —$X^2$—$R^3$ is substituted or unsubstituted —N(alkyl)-C(O)—$NR^6$-benzyl.

In another embodiment of the compounds of Formula Ia, —$X^2$—$R^3$ is substituted —N(alkyl)-C(O)—$NR^6$-benzyl.

In another embodiment of the compounds of Formula Ia, —$X^2$—$R^3$ is N(alkyl)-C(O)—$NR^6$-benzyl substituted with one or more substituents selected from the group consisting of alkyl, substituted alkyl, halo hydroxyl, amino, haloalkyl, and cyano.

In another embodiment of the compounds of Formula Ia, —$X^2$—$R^3$ is substituted or unsubstituted —N(alkyl)-C(O)—$NR^6$-heteroarylalkyl.

In another embodiment of the compounds of Formula Ia, —$X^2$—$R^3$ is substituted or unsubstituted —N(alkyl)-C(O)—$NR^6$-heteroarylalkyl, wherein the alkyl portion thereof is any alkylene described or disclosed herein.

In another embodiment of the compounds of Formula Ia, —$X^2$—$R^3$ is substituted or unsubstituted —N(alkyl)-C(O)—$NR^6$-heteroarylalkyl, wherein the alkyl portion thereof is —$CH_2$—.

In another embodiment of the compounds of Formula Ia, —$X^2$—$R^3$ is substituted or unsubstituted —N(alkyl)-C(O)—$NR^6$-heteroarylalkyl, wherein the heteroaryl portion thereof is any heteroaryl described or disclosed herein.

In another embodiment of the compounds of Formula Ia, —$X^2$—$R^3$ is substituted or unsubstituted —N(alkyl)-C(O)—$NR^6$-heteroarylalkyl, wherein the heteroaryl portion thereof is thiazolyl.

In another embodiment of the compounds of Formula Ia, —$X^2$—$R^3$ is substituted or unsubstituted —N(alkyl)-C(O)—$NR^6$-thiazolylmethyl.

In another embodiment of the compounds of Formula Ia, —$X^2$—$R^3$ is substituted —N(alkyl)-C(O)—$NR^6$-thiazolylmethyl.

In another embodiment of the compounds of Formula Ia, —$X^2$—$R^3$ is —N(alkyl)-C(O)—$NR^6$-thiazolylmethyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted —N(alkyl)-C(O)—$NR^6$-thiazolylmethyl, and the substituent is an alkyl group.

In another embodiment of the compounds of Formula Ia, —$X^2$—$R^3$ is substituted or unsubstituted —$NR^6$—C(O)—N(alkyl)-heterocyclyl.

In another embodiment of the compounds of Formula Ia, —$X^2$—$R^3$ is substituted or unsubstituted —$NR^6$—C(O)—N(alkyl)-aryl.

In another embodiment of the compounds of Formula Ia, —$X^2$—$R^3$ is substituted or unsubstituted —$NR^6$—C(O)—N(alkyl)-phenyl.

In another embodiment of the compounds of Formula Ia, —$X^2$—$R^3$ is substituted or unsubstituted —$NR^6$—C(O)—N(alkyl)-heteroaryl.

In another embodiment of the compounds of Formula Ia, —$X^2$—$R^3$ is substituted or unsubstituted —$NR^6$—C(O)—N(alkyl)-heteroaryl, wherein said heteroaryl is any heteroaryl described or defined herein.

In another embodiment of the compounds of Formula Ia, —$X^2$—$R^3$ is substituted or unsubstituted —$NR^6$—C(O)—N(alkyl)-thiazolyl.

In another embodiment of the compounds of Formula Ia, —$X^2$—$R^3$ is substituted or unsubstituted —$NR^6$—C(O)—N(alkyl)-arylalkyl.

In another embodiment of the compounds of Formula Ia, —$X^2$—$R^3$ is substituted or unsubstituted —$NR^6$—C(O)—N(alkyl)-benzyl.

In another embodiment of the compounds of Formula Ia, —$X^2$—$R^3$ is substituted —$NR^6$—C(O)—N(alkyl)-benzyl.

In another embodiment of the compounds of Formula Ia, —$X^2$—$R^3$ is —$NR^6$—C(O)—N(alkyl)-benzyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted or unsubstituted —$NR^6$—C(O)—N(alkyl)-heteroarylalkyl.

In another embodiment of the compounds of Formula Ia, —$X^2$—$R^3$ is substituted or unsubstituted —$NR^6$—C(O)—N(alkyl)-heteroarylalkyl, wherein the alkyl portion thereof is any alkylene described or disclosed herein.

In another embodiment of the compounds of Formula Ia, —$X^2$—$R^3$ is substituted or unsubstituted —$NR^6$—C(O)—N(alkyl)-heteroarylalkyl, wherein the alkyl portion thereof is —$CH_2$—.

In another embodiment of the compounds of Formula Ia, —$X^2$—$R^3$ is substituted or unsubstituted —$NR^6$—C(O)—N(alkyl)-heteroarylalkyl, wherein the heteroaryl portion thereof is any heteroaryl described or disclosed herein.

In another embodiment of the compounds of Formula Ia, —$X^2$—$R^3$ is substituted or unsubstituted —$NR^6$—C(O)—N(alkyl)-heteroarylalkyl, wherein the heteroaryl portion thereof is thiazolyl.

In another embodiment of the compounds of Formula Ia, —$X^2$—$R^3$ is substituted or unsubstituted —$NR^6$—C(O)—N(alkyl)-thiazolylmethyl.

In another embodiment of the compounds of Formula Ia, —$X^2$—$R^3$ is —$NR^6$—C(O)—N(alkyl)-thiazol-5-ylmethyl.

In another embodiment of the compounds of Formula Ia, —$X^2$—$R^3$ is substituted —$NR^6$—C(O)—N(alkyl)-thiazolylmethyl.

In another embodiment of the compounds of Formula Ia, —$X^2$—$R^3$ is —$NR^6$—C(O)—N(alkyl)-thiazolylmethyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted —$NR^6$—C(O)—N(alkyl)-thiazolylmethyl, and the substituent is an alkyl group.

In another embodiment of the compounds of Formula Ia, —$X^2$—$R^3$ is —$NR^6$—C(O)—N(alkyl)-(2-isopropylthiazolyl-4-yl)methyl.

In another embodiment of the compounds of Formula Ia, —$X^2$—$R^3$ is substituted or unsubstituted —N(alkyl)-C(O)—N(alkyl)-heterocyclyl.

In another embodiment of the compounds of Formula Ia, —$X^2$—$R^3$ is substituted or unsubstituted —N(alkyl)-C(O)—N(alkyl)-aryl.

In another embodiment of the compounds of Formula Ia, —$X^2$—$R^3$ is substituted or unsubstituted —N(alkyl)-C(O)—N(alkyl)-phenyl.

In another embodiment of the compounds of Formula Ia, —$X^2$—$R^3$ is substituted or unsubstituted —N(alkyl)-C(O)—N(alkyl)-heteroaryl.

In another embodiment of the compounds of Formula Ia, —$X^2$—$R^3$ is substituted or unsubstituted —N(alkyl)-C(O)—N(alkyl)-heteroaryl, wherein said heteroaryl is any heteroaryl described or defined herein.

In another embodiment of the compounds of Formula Ia, —$X^2$—$R^3$ is substituted or unsubstituted —N(alkyl)-C(O)—N(alkyl)-thiazolyl.

In another embodiment of the compounds of Formula Ia, —$X^2$—$R^3$ is substituted or unsubstituted —N(alkyl)-C(O)—N(alkyl)-arylalkyl.

In another embodiment of the compounds of Formula Ia, —$X^2$—$R^3$ is substituted or unsubstituted —N(alkyl)-C(O)—N(alkyl)-benzyl.

In another embodiment of the compounds of Formula Ia, —$X^2$—$R^3$ is substituted —N(alkyl)-C(O)—N(alkyl)-benzyl.

In another embodiment of the compounds of Formula Ia, —$X^2$—$R^3$ is —N(alkyl)-C(O)—N(alkyl)-benzyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted or unsubstituted —N(alkyl)-C(O)—N(alkyl)-heteroarylalkyl.

In another embodiment of the compounds of Formula Ia, —$X^2$—$R^3$ is substituted or unsubstituted —N(alkyl)-C(O)—N(alkyl)-heteroarylalkyl, wherein the alkyl portion thereof is any alkylene described or disclosed herein.

In another embodiment of the compounds of Formula Ia, —$X^2$—$R^3$ is substituted or unsubstituted —N(alkyl)-C(O)—N(alkyl)-heteroarylalkyl, wherein the alkyl portion thereof is —$CH_2$—.

In another embodiment of the compounds of Formula Ia, —$X^2$—$R^3$ is substituted or unsubstituted —N(alkyl)-C(O)—N(alkyl)-heteroarylalkyl, wherein the heteroaryl portion thereof is any heteroaryl described or disclosed herein.

In another embodiment of the compounds of Formula Ia, —$X^2$—$R^3$ is substituted or unsubstituted —N(alkyl)-C(O)—N(alkyl)-heteroarylalkyl, wherein the heteroaryl portion thereof is thiazolyl.

In another embodiment of the compounds of Formula Ia, —$X^2$—$R^3$ is substituted or unsubstituted —N(alkyl)-C(O)—N(alkyl)-thiazolylmethyl.

In another embodiment of the compounds of Formula Ia, —$X^2$—$R^3$ is substituted —N(alkyl)-C(O)—N(alkyl)-thiazolylmethyl.

In another embodiment of the compounds of Formula Ia, —$X^2$—$R^3$ is —N(alkyl)-C(O)—N(alkyl)-thiazolylmethyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted —N(alkyl)-C(O)—N(alkyl)-thiazolylmethyl, and the substituent is an alkyl group.

In another embodiment of the compounds of Formula Ia, —$X^2$—$R^3$ is substituted or unsubstituted —NH—C(O)—N($CH_3$)-heterocyclyl.

In another embodiment of the compounds of Formula Ia, —$X^2$—$R^3$ is substituted or unsubstituted —NH—C(O)—N($CH_3$)-aryl.

In another embodiment of the compounds of Formula Ia, —$X^2$—$R^3$ is substituted or unsubstituted —NH—C(O)—N($CH_3$)-phenyl.

In another embodiment of the compounds of Formula Ia, —$X^2$—$R^3$ is substituted or unsubstituted —NH—C(O)—N($CH_3$)-heteroaryl.

In another embodiment of the compounds of Formula Ia, —$X^2$—$R^3$ is substituted or unsubstituted —NH—C(O)—N($CH_3$)-heteroaryl, wherein said heteroaryl is any heteroaryl described or defined herein.

In another embodiment of the compounds of Formula Ia, $-X^2-R^3$ is substituted or unsubstituted $-NH-C(O)-N(CH_3)$-thiazolyl.

In another embodiment of the compounds of Formula Ia, $-X^2-R^3$ is substituted or unsubstituted $-NH-C(O)-N(CH_3)$-arylalkyl.

In another embodiment of the compounds of Formula Ia, $-X^2-R^3$ is substituted or unsubstituted $-NH-C(O)-N(CH_3)$-benzyl.

In another embodiment of the compounds of Formula Ia, $-X^2-R^3$ is substituted $-NH-C(O)-N(CH_3)$-benzyl.

In another embodiment of the compounds of Formula Ia, $-X^2-R^3$ is $-NH-C(O)-N(CH_3)$-benzyl substituted with one or more substituents selected from the group consisting of alkyl, substituted alkyl, halo, hydroxyl, amino, haloalkyl, and cyano.

In another embodiment of the compounds of Formula Ia, $-X^2-R^3$ is substituted or unsubstituted $-NH-C(O)-N(CH_3)$-heteroarylalkyl.

In another embodiment of the compounds of Formula Ia, $-X^2-R^3$ is substituted or unsubstituted $-NH-C(O)-N(CH_3)$-heteroarylalkyl, wherein the alkyl portion thereof is any alkylene described or disclosed herein.

In another embodiment of the compounds of Formula Ia, $-X^2-R^3$ is substituted or unsubstituted $-NH-C(O)-N(CH_3)$-heteroarylalkyl, wherein the alkyl portion thereof is $-CH_2-$.

In another embodiment of the compounds of Formula Ia, $-X^2-R^3$ is substituted or unsubstituted $-NH-C(O)-N(CH_3)$-heteroarylalkyl, wherein the heteroaryl portion thereof is any heteroaryl described or disclosed herein.

In another embodiment of the compounds of Formula Ia, $-X^2-R^3$ is substituted or unsubstituted $-NH-C(O)-N(CH_3)$-heteroarylalkyl, wherein the heteroaryl portion thereof is thiazolyl.

In another embodiment of the compounds of Formula Ia, $-X^2-R^3$ is substituted or unsubstituted $-NH-C(O)-N(CH_3)$-thiazolylmethyl.

In another embodiment of the compounds of Formula Ia, $-X^2-R^3$ is $-NH-C(O)-N(CH_3)$-thiazol-5-ylmethyl.

In another embodiment of the compounds of Formula Ia, $-X^2-R^3$ is substituted $-NH-C(O)-N(CH_3)$-thiazolylmethyl.

In another embodiment of the compounds of Formula Ia, $-X^2-R^3$ is $-NH-C(O)-N(CH_3)$-thiazolylmethyl substituted with one or more substituents selected from the group consisting of alkyl, substituted alkyl, halo, hydroxyl, amino, haloalkyl, and cyano.

In another embodiment of the compounds of Formula Ia, $-X^2-R^3$ is substituted $-NH-C(O)-N(CH_3)$-thiazolylmethyl, and the substituent is an alkyl group.

In another embodiment of the compounds of Formula Ia, $-X^2-R^3$ is $-NH-C(O)-N(CH_3)$-(2-isopropylthiazolyl-4-yl)methyl.

In another embodiment of the compounds of Formula Ia, $-X^2-R^3$ is substituted or unsubstituted $-NR^6$-heterocyclyl.

In another embodiment of the compounds of Formula Ia, $-X^2-R^3$ is substituted or unsubstituted $-NR^6$-aryl.

In another embodiment of the compounds of Formula Ia, $-X^2-R^3$ is substituted or unsubstituted $-NR^6$-phenyl.

In another embodiment of the compounds of Formula Ia, $-X^2-R^3$ is substituted or unsubstituted $-NR^6$-heteroaryl.

In another embodiment of the compounds of Formula Ia, $-X^2-R^3$ is substituted or unsubstituted $-NR^6$-heteroaryl, wherein said heteroaryl is any heteroaryl described or defined herein.

In another embodiment of the compounds of Formula Ia, $-X^2-R^3$ is substituted or unsubstituted $-NR^6$-thiazolyl.

In another embodiment of the compounds of Formula Ia, $-X^2-R^3$ is substituted or unsubstituted $-NR^6$-arylalkyl.

In another embodiment of the compounds of Formula Ia, $-X^2-R^3$ is substituted or unsubstituted $-NR^6$-benzyl.

In another embodiment of the compounds of Formula Ia, $-X^2-R^3$ is substituted $-NR^6$-benzyl.

In another embodiment of the compounds of Formula Ia, $-X^2-R^3$ is $-NR^6$-benzyl substituted with one or more substituents selected from the group consisting of alkyl, substituted alkyl, halo, hydroxyl, amino, haloalkyl, and cyano.

In another embodiment of the compounds of Formula Ia, $-X^2-R^3$ is substituted or unsubstituted $-NR^6$-heteroarylalkyl.

In another embodiment of the compounds of Formula Ia, $-X^2-R^3$ is substituted or unsubstituted $-NR^6$-heteroarylalkyl, wherein the alkyl portion thereof is any alkylene described or disclosed herein.

In another embodiment of the compounds of Formula Ia, $-X^2-R^3$ is substituted or unsubstituted $-NR^6$-heteroarylalkyl, wherein the alkyl portion thereof is $-CH_2-$.

In another embodiment of the compounds of Formula Ia, $-X^2-R^3$ is substituted or unsubstituted $-NR^6$-heteroarylalkyl, wherein the heteroaryl portion thereof is any heteroaryl described or disclosed herein.

In another embodiment of the compounds of Formula Ia, $-X^2-R^3$ is substituted or unsubstituted $-NR^6$-heteroarylalkyl, wherein the heteroaryl portion thereof is thiazolyl.

In another embodiment of the compounds of Formula Ia, $-X^2-R^3$ is substituted or unsubstituted $-NR^6$-thiazolylmethyl.

In another embodiment of the compounds of Formula Ia, $-X^2-R^3$ is substituted $-NR^6$-thiazolylmethyl.

In another embodiment of the compounds of Formula Ia, $-X^2-R^3$ is $-NR^6$-thiazolylmethyl substituted with one or more substituents selected from the group consisting of alkyl, substituted alkyl, halo, hydroxyl, amino, haloalkyl, and cyano.

In another embodiment of the compounds of Formula Ia, $-X^2-R^3$ is substituted $-NR^6$-thiazolylmethyl, and the substituent is an alkyl group.

In another embodiment of the compounds of Formula Ia, $-X^2-R^3$ is substituted or unsubstituted $-NH$-heterocyclyl.

In another embodiment of the compounds of Formula Ia, $-X^2-R^3$ is substituted or unsubstituted $-NH$-aryl.

In another embodiment of the compounds of Formula Ia, $-X^2-R^3$ is substituted or unsubstituted $-NH$-phenyl.

In another embodiment of the compounds of Formula Ia, $-X^2-R^3$ is substituted or unsubstituted $-NH$-heteroaryl.

In another embodiment of the compounds of Formula Ia, $-X^2-R^3$ is substituted or unsubstituted $-NH$-heteroaryl, wherein said heteroaryl is any heteroaryl described or defined herein.

In another embodiment of the compounds of Formula Ia, $-X^2-R^3$ is substituted or unsubstituted $-NH$-thiazolyl.

In another embodiment of the compounds of Formula Ia, $-X^2-R^3$ is substituted or unsubstituted $-NH$-arylalkyl.

In another embodiment of the compounds of Formula Ia, $-X^2-R^3$ is substituted or unsubstituted $-NH$-benzyl.

In another embodiment of the compounds of Formula Ia, $-X^2-R^3$ is substituted $-NH$-benzyl.

In another embodiment of the compounds of Formula Ia, $-X^2-R^3$ is $-NH$-benzyl substituted with one or more substituents selected from the group consisting of alkyl, substituted alkyl, halo, hydroxyl, amino, haloalkyl, and cyano.

In another embodiment of the compounds of Formula Ia, $-X^2-R^3$ is substituted or unsubstituted —NH-heteroarylalkyl.

In another embodiment of the compounds of Formula Ia, $-X^2-R^3$ is substituted or unsubstituted —NH-heteroarylalkyl, wherein the alkyl portion thereof is any alkylene described or disclosed herein.

In another embodiment of the compounds of Formula Ia, $-X^2-R^3$ is substituted or unsubstituted —NH-heteroarylalkyl, wherein the alkyl portion thereof is —CH$_2$—.

In another embodiment of the compounds of Formula Ia, $-X^2-R^3$ is substituted or unsubstituted —NH-heteroarylalkyl, wherein the heteroaryl portion thereof is any heteroaryl described or disclosed herein.

In another embodiment of the compounds of Formula Ia, $-X^2-R^3$ is substituted or unsubstituted —NH-heteroarylalkyl, wherein the heteroaryl portion thereof is thiazolyl.

In another embodiment of the compounds of Formula Ia, $-X^2-R^3$ is substituted or unsubstituted —NH-thiazolylmethyl.

In another embodiment of the compounds of Formula Ia, $-X^2-R^3$ is substituted —NH-thiazolylmethyl.

In another embodiment of the compounds of Formula Ia, $-X^2-R^3$ is —NH-thiazolylmethyl substituted with one or more substituents selected from the group consisting of alkyl, substituted alkyl, halo, hydroxyl, amino, haloalkyl, and cyano.

In another embodiment of the compounds of Formula Ia, $-X^2-R^3$ is substituted —NH-thiazolylmethyl, and the substituent is an alkyl group.

In another embodiment of the compounds of Formula Ia, $-X^2-R^3$ is substituted or unsubstituted —N(alkyl)-heterocyclyl.

In another embodiment of the compounds of Formula Ia, $-X^2-R^3$ is substituted or unsubstituted —N(alkyl)-aryl.

In another embodiment of the compounds of Formula Ia, $-X^2-R^3$ is substituted or unsubstituted —N(alkyl)-phenyl.

In another embodiment of the compounds of Formula Ia, $-X^2-R^3$ is substituted or unsubstituted —N(alkyl)-heteroaryl.

In another embodiment of the compounds of Formula Ia, $-X^2-R^3$ is substituted or unsubstituted —N(alkyl)-heteroaryl, wherein said heteroaryl is any heteroaryl described or defined herein.

In another embodiment of the compounds of Formula Ia, $-X^2-R^3$ is substituted or unsubstituted —N(alkyl)-thiazolyl.

In another embodiment of the compounds of Formula Ia, $-X^2-R^3$ is substituted or unsubstituted —N(alkyl)-arylalkyl.

In another embodiment of the compounds of Formula Ia, $-X^2-R^3$ is substituted or unsubstituted —N(alkyl)-benzyl.

In another embodiment of the compounds of Formula Ia, $-X^2-R^3$ is substituted —N(alkyl)-benzyl.

In another embodiment of the compounds of Formula Ia, $-X^2-R^3$ is —N(alkyl)-benzyl substituted with one or more substituents selected from the group consisting of alkyl, substituted alkyl, halo, hydroxyl, amino, haloalkyl, and cyano.

In another embodiment of the compounds of Formula Ia, $-X^2-R^3$ is substituted or unsubstituted —N(alkyl)-heteroarylalkyl.

In another embodiment of the compounds of Formula Ia, $-X^2-R^3$ is substituted or unsubstituted —N(alkyl)-heteroarylalkyl, wherein the alkyl portion thereof is any alkylene described or disclosed herein.

In another embodiment of the compounds of Formula Ia, $-X^2-R^3$ is substituted or unsubstituted —N(alkyl)-heteroarylalkyl, wherein the alkyl portion thereof is —CH$_2$—.

In another embodiment of the compounds of Formula Ia, $-X^2-R^3$ is substituted or unsubstituted —N(alkyl)-heteroarylalkyl, wherein the heteroaryl portion thereof is any heteroaryl described or disclosed herein.

In another embodiment of the compounds of Formula Ia, $-X^2-R^3$ is substituted or unsubstituted —N(alkyl)-heteroarylalkyl, wherein the heteroaryl portion thereof is thiazolyl.

In another embodiment of the compounds of Formula Ia, $-X^2-R^3$ is substituted or unsubstituted —N(alkyl)-thiazolylmethyl.

In another embodiment of the compounds of Formula Ia, $-X^2-R^3$ is substituted —N(alkyl)-thiazolylmethyl.

In another embodiment of the compounds of Formula Ia, $-X^2-R^3$ is —N(alkyl)-thiazolylmethyl substituted with one or more substituents selected from the group consisting of alkyl, substituted alkyl, halo, hydroxyl, amino, haloalkyl, and cyano.

In another embodiment of the compounds of Formula Ia, $-X^2-R^3$ is substituted —N(alkyl)-thiazolylmethyl, and the substituent is an alkyl group.

In another embodiment of the compounds of Formula Ia, $-X^2-R^3$ is substituted or unsubstituted —N(cycloalkyl)-heterocyclyl.

In another embodiment of the compounds of Formula Ia, $-X^2-R^3$ is substituted or unsubstituted —N(cycloalkyl)-aryl.

In another embodiment of the compounds of Formula Ia, $-X^2-R^3$ is substituted or unsubstituted —N(cycloalkyl)-phenyl.

In another embodiment of the compounds of Formula Ia, $-X^2-R^3$ is substituted or unsubstituted —N(cycloalkyl)-heteroaryl.

In another embodiment of the compounds of Formula Ia, $-X^2-R^3$ is substituted or unsubstituted —N(cycloalkyl)-heteroaryl, wherein said heteroaryl is any heteroaryl described or defined herein.

In another embodiment of the compounds of Formula Ia, $-X^2-R^3$ is substituted or unsubstituted —N(cycloalkyl)-thiazolyl.

In another embodiment of the compounds of Formula Ia, $-X^2-R^3$ is substituted or unsubstituted —N(cycloalkyl)-arylalkyl.

In another embodiment of the compounds of Formula Ia, $-X^2-R^3$ is substituted or unsubstituted —N(cycloalkyl)-benzyl.

In another embodiment of the compounds of Formula Ia, $-X^2-R^3$ is substituted —N(cycloalkyl)-benzyl.

In another embodiment of the compounds of Formula Ia, $-X^2-R^3$ is —N(cycloalkyl)-benzyl substituted with one or more substituents selected from the group consisting of alkyl, substituted alkyl, halo, hydroxyl, amino, haloalkyl, and cyano.

In another embodiment of the compounds of Formula Ia, $-X^2-R^3$ is substituted or unsubstituted —N(cycloalkyl)-heteroarylalkyl.

In another embodiment of the compounds of Formula Ia, $-X^2-R^3$ is substituted or unsubstituted —N(cycloalkyl)-heteroarylalkyl, wherein the alkyl portion thereof is any alkylene described or disclosed herein.

In another embodiment of the compounds of Formula Ia, $-X^2-R^3$ is substituted or unsubstituted —N(cycloalkyl)-heteroarylalkyl, wherein the alkyl portion thereof is —CH$_2$—.

In another embodiment of the compounds of Formula Ia, —$X^2$—$R^3$ is substituted or unsubstituted —N(cycloalkyl)-heteroarylalkyl, wherein the heteroaryl portion thereof is any heteroaryl described or disclosed herein.

In another embodiment of the compounds of Formula Ia, —$X^2$—$R^3$ is substituted or unsubstituted —N(cycloalkyl)-heteroarylalkyl, wherein the heteroaryl portion thereof is thiazolyl.

In another embodiment of the compounds of Formula Ia, —$X^2$—$R^3$ is substituted or unsubstituted —N(cycloalkyl)-thiazolylmethyl.

In another embodiment of the compounds of Formula Ia, —$X^2$—$R^3$ is substituted —N(cycloalkyl)-thiazolylmethyl.

In another embodiment of the compounds of Formula Ia, —$X^2$—$R^3$ is —N(cycloalkyl)-thiazolylmethyl substituted with one or more substituents selected from the group consisting of alkyl substituted alkyl, halo, hydroxyl, amino, haloalkyl, and cyano.

In another embodiment of the compounds of Formula Ia, —$X^2$—$R^3$ is substituted —N(cycloalkyl)-thiazolylmethyl, and the substituent is an alkyl group.

In another embodiment of the compounds of Formula Ia, —$X^2$—$R^3$ is substituted or unsubstituted —O—C(O)—$NR^6$-heterocyclyl.

In another embodiment of the compounds of Formula Ia, —$X^2$—$R^3$ is substituted or unsubstituted —O—C(O)—$NR^6$-aryl.

In another embodiment of the compounds of Formula Ia, —$X^2$—$R^3$ is substituted or unsubstituted —O—C(O)—$NR^6$-phenyl.

In another embodiment of the compounds of Formula Ia, —$X^2$—$R^3$ is substituted or unsubstituted —O—C(O)—$NR^6$-heteroaryl.

In another embodiment of the compounds of Formula Ia, —$X^2$—$R^3$ is substituted or unsubstituted —O—C(O)—$NR^6$-heteroaryl, wherein said heteroaryl is any heteroaryl described or defined herein.

In another embodiment of the compounds of Formula Ia, —$X^2$—$R^3$ is substituted or unsubstituted —O—C(O)—$NR^6$-thiazolyl.

In another embodiment of the compounds of Formula Ia, —$X^2$—$R^3$ is substituted or unsubstituted —O—C(O)—$NR^6$-arylalkyl.

In another embodiment of the compounds of Formula Ia, —$X^2$—$R^3$ is substituted or unsubstituted —O—C(O)—$NR^6$-benzyl.

In another embodiment of the compounds of Formula Ia, —$X^2$—$R^3$ is substituted —O—C(O)—$NR^6$-benzyl.

In another embodiment of the compounds of Formula Ia, —$X^2$—$R^3$ is —O—C(O)—$NR^6$-benzyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted or unsubstituted —O—C(O)—$NR^6$-heteroarylalkyl.

In another embodiment of the compounds of Formula Ia, —$X^2$—$R^3$ is substituted or unsubstituted —O—C(O)—$NR^6$-heteroarylalkyl, wherein the alkyl portion thereof is any alkylene described or disclosed herein.

In another embodiment of the compounds of Formula Ia, —$X^2$—$R^3$ is substituted or unsubstituted —O—C(O)—$NR^6$-heteroarylalkyl, wherein the alkyl portion thereof is —$CH_2$—.

In another embodiment of the compounds of Formula Ia, —$X^2$—$R^3$ is substituted or unsubstituted —O—C(O)—$NR^6$-heteroarylalkyl, wherein the heteroaryl portion thereof is any heteroaryl described or disclosed herein.

In another embodiment of the compounds of Formula Ia, —$X^2$—$R^3$ is substituted or unsubstituted —O—C(O)—$NR^6$-heteroarylalkyl, wherein the heteroaryl portion thereof is thiazolyl.

In another embodiment of the compounds of Formula Ia, —$X^2$—$R^3$ is substituted or unsubstituted —O—C(O)—$NR^6$-thiazolylmethyl.

In another embodiment of the compounds of Formula Ia, —$X^2$—$R^3$ is substituted —O—C(O)—$NR^6$-thiazolylmethyl.

In another embodiment of the compounds of Formula Ia, —$X^2$—$R^3$ is —O—C(O)—$NR^6$-thiazolylmethyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted —O—C(O)—$NR^6$-thiazolylmethyl, and the substituent is an alkyl group.

In another embodiment of the compounds of Formula Ia, —$X^2$—$R^3$ is substituted or unsubstituted —O—C(O)—NH-heterocyclyl.

In another embodiment of the compounds of Formula Ia, —$X^2$—$R^3$ is substituted or unsubstituted —O—C(O)—NH-aryl.

In another embodiment of the compounds of Formula Ia, —$X^2$—$R^3$ is substituted or unsubstituted —O—C(O)—NH-phenyl.

In another embodiment of the compounds of Formula Ia, —$X^2$—$R^3$ is substituted or unsubstituted —O—C(O)—NH-heteroaryl.

In another embodiment of the compounds of Formula Ia, —$X^2$—$R^3$ is substituted or unsubstituted —O—C(O)—NH-heteroaryl, wherein said heteroaryl is any heteroaryl described or defined herein.

In another embodiment of the compounds of Formula Ia, —$X^2$—$R^3$ is substituted or unsubstituted —O—C(O)—NH-thiazolyl.

In another embodiment of the compounds of Formula Ia, —$X^2$—$R^3$ is substituted or unsubstituted —O—C(O)—NH-arylalkyl.

In another embodiment of the compounds of Formula Ia, —$X^2$—$R^3$ is substituted or unsubstituted —O—C(O)—NH-benzyl.

In another embodiment of the compounds of Formula Ia, —$X^2$—$R^3$ is substituted —O—C(O)—NH-benzyl.

In another embodiment of the compounds of Formula Ia, —$X^2$—$R^3$ is —O—C(O)—NH-benzyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted or unsubstituted —O—C(O)—NH-heteroarylalkyl.

In another embodiment of the compounds of Formula Ia, —$X^2$—$R^3$ is substituted or unsubstituted —O—C(O)—NH-heteroarylalkyl, wherein the alkyl portion thereof is any alkylene described or disclosed herein.

In another embodiment of the compounds of Formula Ia, —$X^2$—$R^3$ is substituted or unsubstituted —O—C(O)—NH-heteroarylalkyl, wherein the alkyl portion thereof is —$CH_2$—.

In another embodiment of the compounds of Formula Ia, —$X^2$—$R^3$ is substituted or unsubstituted —O—C(O)—NH-heteroarylalkyl, wherein the heteroaryl portion thereof is any heteroaryl described or disclosed herein.

In another embodiment of the compounds of Formula Ia, —$X^2$—$R^3$ is substituted or unsubstituted —O—C(O)—NH-heteroarylalkyl, wherein the heteroaryl portion thereof is thiazolyl.

In another embodiment of the compounds of Formula Ia, —$X^2$—$R^3$ is substituted or unsubstituted —O—C(O)—NH-thiazolylmethyl.

In another embodiment of the compounds of Formula Ia, —$X^2$—$R^3$ is substituted —O—C(O)—NH-thiazolylmethyl.

In another embodiment of the compounds of Formula Ia, —$X^2$—$R^3$ is —O—C(O)—NH-thiazolylmethyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted —O—C(O)—NH-thiazolylmethyl, and the substituent is an alkyl group.

In another embodiment of the compounds of Formula Ia, —$X^2$—$R^3$ is substituted or unsubstituted —O—C(O)—N(alkyl)-heterocyclyl.

In another embodiment of the compounds of Formula Ia, —$X^2$—$R^3$ is substituted or unsubstituted —O—C(O)—N(alkyl)-aryl.

In another embodiment of the compounds of Formula Ia, —$X^2$—$R^3$ is substituted or unsubstituted —O—C(O)—N(alkyl)-phenyl.

In another embodiment of the compounds of Formula Ia, —$X^2$—$R^3$ is substituted or unsubstituted —O—C(O)—N(alkyl)-heteroaryl.

In another embodiment of the compounds of Formula Ia, —$X^2$—$R^3$ is substituted or unsubstituted —O—C(O)—N(alkyl)-heteroaryl, wherein said heteroaryl is any heteroaryl described or defined herein.

In another embodiment of the compounds of Formula Ia, —$X^2$—$R^3$ is substituted or unsubstituted —O—C(O)—N(alkyl)-thiazolyl.

In another embodiment of the compounds of Formula Ia, —$X^2$—$R^3$ is substituted or unsubstituted —O—C(O)—N(alkyl)-arylalkyl.

In another embodiment of the compounds of Formula Ia, —$X^2$—$R^3$ is substituted or unsubstituted —O—C(O)—N(alkyl)-benzyl.

In another embodiment of the compounds of Formula Ia, —$X^2$—$R^3$ is substituted —O—C(O)—N(alkyl)-benzyl.

In another embodiment of the compounds of Formula Ia, —$X^2$—$R^3$ is —O—C(O)—N(alkyl)-benzyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted or unsubstituted —O—C(O)—N(alkyl)-heteroarylalkyl.

In another embodiment of the compounds of Formula Ia, —$X^2$—$R^3$ is substituted or unsubstituted —O—C(O)—N(alkyl)-heteroarylalkyl, wherein the alkyl portion thereof is any alkylene described or disclosed herein.

In another embodiment of the compounds of Formula Ia, —$X^2$—$R^3$ is substituted or unsubstituted —O—C(O)—N(alkyl)-heteroarylalkyl, wherein the alkyl portion thereof is —$CH_2$—.

In another embodiment of the compounds of Formula Ia, —$X^2$—$R^3$ is substituted or unsubstituted —O—C(O)—N(alkyl)-heteroarylalkyl, wherein the heteroaryl portion thereof is any heteroaryl described or disclosed herein.

In another embodiment of the compounds of Formula Ia, —$X^2$—$R^3$ is substituted or unsubstituted —O—C(O)—N(alkyl)-heteroarylalkyl, wherein the heteroaryl portion thereof is thiazolyl.

In another embodiment of the compounds of Formula Ia, —$X^2$—$R^3$ is substituted or unsubstituted —O—C(O)—N(alkyl)-thiazolylmethyl.

In another embodiment of the compounds of Formula Ia, —$X^2$—$R^3$ is substituted —O—C(O)—N(alkyl)-thiazolylmethyl.

In another embodiment of the compounds of Formula Ia, —$X^2$—$R^3$ is —O—C(O)—N(alkyl)-thiazolylmethyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted —O—C(O)—N(alkyl)-thiazolylmethyl, and the substituent is an alkyl group.

In another embodiment of the compounds of Formula Ia, —$X^2$—$R^3$ is substituted or unsubstituted —$NR^6$—C(O)—O-heterocyclyl.

In another embodiment of the compounds of Formula Ia, —$X^2$—$R^3$ is substituted or unsubstituted —$NR^6$—C(O)—O-aryl.

In another embodiment of the compounds of Formula Ia, —$X^2$—$R^3$ is substituted or unsubstituted —$NR^6$—C(O)—O-phenyl.

In another embodiment of the compounds of Formula Ia, —$X^2$—$R^3$ is substituted or unsubstituted —$NR^6$—C(O)—O-heteroaryl.

In another embodiment of the compounds of Formula Ia, —$X^2$—$R^3$ is substituted or unsubstituted —$NR^6$—C(O)—O-heteroaryl, wherein said heteroaryl is any heteroaryl described or defined herein.

In another embodiment of the compounds of Formula Ia, —$X^2$—$R^3$ is substituted or unsubstituted —$NR^6$—C(O)—O-thiazolyl.

In another embodiment of the compounds of Formula Ia, —$X^2$—$R^3$ is substituted or unsubstituted —$NR^6$—C(O)—O-arylalkyl.

In another embodiment of the compounds of Formula Ia, —$X^2$—$R^3$ is substituted or unsubstituted —$NR^6$—C(O)—O-benzyl.

In another embodiment of the compounds of Formula Ia, —$X^2$—$R^3$ is substituted —$NR^6$—C(O)—O-benzyl.

In another embodiment of the compounds of Formula Ia, —$X^2$—$R^3$ is —$NR^6$—C(O)—O-benzyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted or unsubstituted —$NR^6$—C(O)—O-heteroarylalkyl.

In another embodiment of the compounds of Formula Ia, —$X^2$—$R^3$ is substituted or unsubstituted —$NR^6$—C(O)—O-heteroarylalkyl, wherein the alkyl portion thereof is any alkylene described or disclosed herein.

In another embodiment of the compounds of Formula Ia, —$X^2$—$R^3$ is substituted or unsubstituted —$NR^6$—C(O)—O-heteroarylalkyl, wherein the alkyl portion thereof is —$CH_2$—.

In another embodiment of the compounds of Formula Ia, —$X^2$—$R^3$ is substituted or unsubstituted —$NR^6$—C(O)—O-heteroarylalkyl, wherein the heteroaryl portion thereof is any heteroaryl described or disclosed herein.

In another embodiment of the compounds of Formula Ia, —$X^2$—$R^3$ is substituted or unsubstituted —$NR^6$—C(O)—O-heteroarylalkyl, wherein the heteroaryl portion thereof is thiazolyl.

In another embodiment of the compounds of Formula Ia, —$X^2$—$R^3$ is substituted or unsubstituted —$NR^6$—C(O)—O-thiazolylmethyl.

In another embodiment of the compounds of Formula Ia, —$X^2$—$R^3$ is substituted —$NR^6$—C(O)—O-thiazolylmethyl.

In another embodiment of the compounds of Formula Ia, —$X^2$—$R^3$ is —$NR^6$—C(O)—O-thiazolylmethyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted —$NR^6$—C(O)—O-thiazolylmethyl, and the substituent is an alkyl group.

In another embodiment of the compounds of Formula Ia, —$X^2$—$R^3$ is substituted or unsubstituted —O-heterocyclyl.

In another embodiment of the compounds of Formula Ia, —$X^2$—$R^3$ is —O-(tetrahydro-2H-furo[2,3-b]furan-3-yl).

In another embodiment of the compounds of Formula Ia, —$X^2$—$R^3$ is —O-(tetrahydrofuran-3-yl).

In another embodiment of the compounds of Formula Ia, —$X^2$—$R^3$ is substituted or unsubstituted —O-aryl.

In another embodiment of the compounds of Formula Ia, —$X^2$—$R^3$ is substituted or unsubstituted —O-phenyl.

In another embodiment of the compounds of Formula Ia, —$X^2$—$R^3$ is substituted or unsubstituted —O-heteroaryl.

In another embodiment of the compounds of Formula Ia, —$X^2$—$R^3$ is substituted or unsubstituted —O-heteroaryl, wherein said heteroaryl is any heteroaryl described or defined herein.

In another embodiment of the compounds of Formula Ia, —$X^2$—$R^3$ is substituted or unsubstituted —O-thiazolyl.

In another embodiment of the compounds of Formula Ia, —$X^2$—$R^3$ is substituted or unsubstituted —O-arylalkyl.

In another embodiment of the compounds of Formula Ia, —$X^2$—$R^3$ is substituted or unsubstituted —O-benzyl.

In another embodiment of the compounds of Formula Ia, —$X^2$—$R^3$ is substituted —O-benzyl.

In another embodiment of the compounds of Formula Ia, —$X^2$—$R^3$ is —O-benzyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted or unsubstituted —O-heteroarylalkyl.

In another embodiment of the compounds of Formula Ia, —$X^2$—$R^3$ is substituted or unsubstituted —O-heteroarylalkyl, wherein the alkyl portion thereof is any alkylene described or disclosed herein.

In another embodiment of the compounds of Formula Ia, —$X^2$—$R^3$ is substituted or unsubstituted —O-heteroarylalkyl, wherein the alkyl portion thereof is —$CH_2$—.

In another embodiment of the compounds of Formula Ia, —$X^2$—$R^3$ is substituted or unsubstituted —O-heteroarylalkyl, wherein the heteroaryl portion thereof is any heteroaryl described or disclosed herein.

In another embodiment of the compounds of Formula Ia, —$X^2$—$R^3$ is substituted or unsubstituted —O-heteroarylalkyl, wherein the heteroaryl portion thereof is thiazolyl.

In another embodiment of the compounds of Formula Ia, —$X^2$—$R^3$ is substituted or unsubstituted —O-thiazolylmethyl.

In another embodiment of the compounds of Formula Ia, —$X^2$—$R^3$ is substituted —O-thiazolylmethyl.

In another embodiment of the compounds of Formula Ia, —$X^2$—$R^3$ is —O-thiazolylmethyl substituted with one or more substituents selected from the group consisting of alkyl, substituted alkyl, halo, hydroxyl, amino, haloalkyl, and cyano.

In another embodiment of the compounds of Formula Ia, —$X^2$—$R^3$ is substituted —O-thiazolylmethyl, and the substituent is an alkyl group.

In another embodiment of the compounds of Formula Ia, -L-$X^2$—$R^3$ is substituted or unsubstituted —$NR^6$—C(O)—$NR^6$-heterocyclyl.

In another embodiment of the compounds of Formula Ia, -L-$X^2$—$R^3$ is substituted or unsubstituted —$NR^6$—C(O)—$NR^6$-aryl.

In another embodiment of the compounds of Formula Ia, -L-$X^2$—$R^3$ is substituted or unsubstituted —$NR^6$—C(O)—$NR^6$-phenyl.

In another embodiment of the compounds of Formula Ia, -L-$X^2$—$R^3$ is substituted or unsubstituted —$NR^6$—C(O)—$NR^6$-heteroaryl.

In another embodiment of the compounds of Formula Ia, -L-$X^2$—$R^3$ is substituted or unsubstituted —$NR^6$—C(O)—$NR^6$-heteroaryl, wherein said heteroaryl is any heteroaryl described or defined herein.

In another embodiment of the compounds of Formula Ia, -L-$X^2$—$R^3$ is substituted or unsubstituted —$NR^6$—C(O)—$NR^6$-thiazolyl.

In another embodiment of the compounds of Formula Ia, -L-$X^2$—$R^3$ is substituted or unsubstituted —$NR^6$—C(O)—$NR^6$-arylalkyl.

In another embodiment of the compounds of Formula Ia, -L-$X^2$—$R^3$ is substituted or unsubstituted —$NR^6$—C(O)—$NR^6$-benzyl.

In another embodiment of the compounds of Formula Ia, -L-$X^2$—$R^3$ is substituted —$NR^6$—C(O)—$NR^6$-benzyl.

In another embodiment of the compounds of Formula Ia, -L-$X^2$—$R^3$ is —$NR^6$—C(O)—$NR^6$-benzyl substituted with one or more substituents selected from the group consisting of alkyl, substituted alkyl, halo, hydroxyl, amino, haloalkyl, and cyano.

In another embodiment of the compounds of Formula Ia, -L-$X^2$—$R^3$ is substituted or unsubstituted —$NR^6$—C(O)—$NR^6$-heteroarylalkyl.

In another embodiment of the compounds of Formula Ia, -L-$X^2$—$R^3$ is substituted or unsubstituted —$NR^6$—C(O)—$NR^6$-heteroarylalkyl, wherein the alkyl portion thereof is any alkylene described or disclosed herein.

In another embodiment of the compounds of Formula Ia, -L-$X^2$—$R^3$ is substituted or unsubstituted —$NR^6$—C(O)—$NR^6$-heteroarylalkyl, wherein the alkyl portion thereof is —$CH_2$—.

In another embodiment of the compounds of Formula Ia, -L-$X^2$—$R^3$ is substituted or unsubstituted —$NR^6$—C(O)—$NR^6$-heteroarylalkyl, wherein the heteroaryl portion thereof is any heteroaryl described or disclosed herein.

In another embodiment of the compounds of Formula Ia, -L-$X^2$—$R^3$ is substituted or unsubstituted —$NR^6$—C(O)—$NR^6$-heteroarylalkyl, wherein the heteroaryl portion thereof is thiazolyl.

In another embodiment of the compounds of Formula Ia, -L-$X^2$—$R^3$ is substituted or unsubstituted —$NR^6$—C(O)—$NR^6$-thiazolylmethyl.

In another embodiment of the compounds of Formula Ia, -L-$X^2$—$R^3$ is substituted —$NR^6$—C(O)—$NR^6$-thiazolylmethyl.

In another embodiment of the compounds of Formula Ia, -L-$X^2$—$R^3$ is —$NR^6$—C(O)—$NR^6$-thiazolylmethyl substituted with one or more substituents selected from the group consisting of alkyl, substituted alkyl, halo, hydroxyl, amino, haloalkyl, and cyano.

In another embodiment of the compounds of Formula Ia, -L-$X^2$-$R^3$ is substituted —$NR^6$—C(O)—$NR^6$-thiazolylmethyl, and the substituent is an alkyl group.

In another embodiment of the compounds of Formula Ia, -L-$X^2$-$R^3$ is substituted or unsubstituted —$CHR^7$—$NR^6$—C(O)—$NR^6$-heterocyclyl.

In another embodiment of the compounds of Formula Ia, -L-$X^2$-$R^3$ is substituted or unsubstituted —$CHR^7$—$NR^6$—C(O)—$NR^6$-aryl.

In another embodiment of the compounds of Formula Ia, -L-$X^2$-$R^3$ is substituted or unsubstituted —$CHR^7$—$NR^6$—C(O)—$NR^6$-phenyl.

In another embodiment of the compounds of Formula Ia, -L-$X^2$-$R^3$ is substituted or unsubstituted —$CHR^7$—$NR^6$—C(O)—$NR^6$-heteroaryl.

In another embodiment of the compounds of Formula Ia, -L-$X^2$-$R^3$ is substituted or unsubstituted —$CHR^7$—$NR^6$—C(O)—$NR^6$-heteroaryl, wherein said heteroaryl is any heteroaryl described or defined herein.

In another embodiment of the compounds of Formula Ia, -L-$X^2$-$R^3$ is substituted or unsubstituted —$CHR^7$—$NR^6$—C(O)—$NR^6$-thiazolyl.

In another embodiment of the compounds of Formula Ia, -L-$X^2$-$R^3$ is substituted or unsubstituted —$CHR^7$—$NR^6$—C(O)—$NR^6$-arylalkyl.

In another embodiment of the compounds of Formula Ia, -L-$X^2$-$R^3$ is substituted or unsubstituted —$CHR^7$—$NR^6$—C(O)—$NR^6$-benzyl.

In another embodiment of the compounds of Formula Ia, -L-$X^2$-$R^3$ is substituted —$CHR^7$—$NR^6$—C(O)—$NR^6$-benzyl.

In another embodiment of the compounds of Formula Ia, -L-$X^2$-$R^3$ is —$CHR^7$—$NR^6$—C(O)—$NR^6$-benzyl wherein the benzyl is substituted with one or more substituents selected from the group consisting of alkyl, substituted alkyl, halo, hydroxyl, amino, haloalkyl, and cyano.

In another embodiment of the compounds of Formula Ia, -L-$X^2$-$R^3$ is substituted or unsubstituted —$CHR^7$—$NR^6$—C(O)—$NR^6$-heteroarylalkyl.

In another embodiment of the compounds of Formula Ia, -L-$X^2$-$R^3$ is substituted or unsubstituted —$CHR^7$—$NR^6$—C(O)—$NR^6$-heteroarylalkyl, wherein the alkyl portion thereof is any alkylene described or disclosed herein.

In another embodiment of the compounds of Formula Ia, -L-$X^2$-$R^3$ is substituted or unsubstituted —$CHR^7$—$NR^6$—C(O)—$NR^6$-heteroarylalkyl, wherein the alkyl portion thereof is —$CH_2$—.

In another embodiment of the compounds of Formula Ia, -L-$X^2$-$R^3$ is substituted or unsubstituted —$CHR^7$—$NR^6$—C(O)—$NR^6$-heteroarylalkyl, wherein the heteroaryl portion thereof is any heteroaryl described or disclosed herein.

In another embodiment of the compounds of Formula Ia, -L-$X^2$-$R^3$ is substituted or unsubstituted —$CHR^7$—$NR^6$—C(O)—$NR^6$-heteroarylalkyl, wherein the heteroaryl portion thereof is thiazolyl.

In another embodiment of the compounds of Formula Ia, -L-$X^2$-$R^3$ is substituted or unsubstituted —$CHR^7$—$NR^6$—C(O)—$NR^6$-thiazolylmethyl.

In another embodiment of the compounds of Formula Ia, -L-$X^2$-$R^3$ is —$CHR^7$—$NR^6$—C(O)—$NR^6$-thiazol-5-ylmethyl.

In another embodiment of the compounds of Formula Ia, -L-$X^2$-$R^3$ is substituted —$CHR^7$—$NR^6$—C(O)—$NR^6$-thiazolylmethyl.

In another embodiment of the compounds of Formula Ia, -L-$X^2$-$R^3$ is —$CHR^7$—$NR^6$—C(O)—$NR^6$-thiazolylmethyl wherein the thiazolylmethyl is substituted with one or more substituents selected from the group consisting of alkyl, substituted alkyl, halo, hydroxyl, amino, haloalkyl, and cyano.

In another embodiment of the compounds of Formula Ia, -L-$X^2$-$R^3$ is substituted —$CHR^7$—$NR^6$—C(O)—$NR^6$-thiazolylmethyl wherein the thiazolylmethyl substituent is an alkyl group.

In another embodiment of the compounds of Formula Ia, -L-$X^2$-$R^3$ is substituted —$CHR^7$—$NR^6$—C(O)—$NR^6$-(2-isopropylthiazolyl-4-yl)methyl.

In another embodiment of the compounds of Formula Ia, -L-$X^2$-$R^3$ is —$CHR^7$—$NR^6$—C(O)—$NR^6$-heterocyclyl wherein the heterocyclyl is substituted or unsubstituted and $R^7$ is morpholinylalkyl.

In another embodiment of the compounds of Formula Ia, -L-$X^2$-$R^3$ is —$CHR^7$—$NR^6$—C(O)—$NR^6$-aryl wherein the aryl is substituted or unsubstituted and $R^7$ is morpholinylalkyl.

In another embodiment of the compounds of Formula Ia, -L-$X^2$-$R^3$ is —$CHR^7$—$NR^6$—C(O)—$NR^6$-phenyl wherein the phenyl is substituted or unsubstituted and $R^7$ is morpholinylalkyl.

In another embodiment of the compounds of Formula Ia, -L-$X^2$-$R^3$ is —$CHR^7$—$NR^6$—C(O)—$NR^6$-heteroaryl wherein the heteroaryl is substituted or unsubstituted and $R^7$ is morpholinylalkyl.

In another embodiment of the compounds of Formula Ia, -L-$X^2$-$R^3$ is —$CHR^7$—$NR^6$—C(O)—$NR^6$-heteroaryl wherein the heteroaryl is substituted or unsubstituted, said heteroaryl is any heteroaryl described or defined herein and $R^7$ is morpholinylalkyl.

In another embodiment of the compounds of Formula Ia, -L-$X^2$-$R^3$ is —$CHR^7$—$NR^6$—C(O)—$NR^6$-thiazolyl wherein thiazolyl is substituted or unsubstituted and $R^7$ is morpholinylalkyl.

In another embodiment of the compounds of Formula Ia, -L-$X^2$-$R^3$ is —$CHR^7$—$NR^6$—C(O)—$NR^6$-arylalkyl wherein the arylalkyl is substituted or unsubstituted and $R^7$ is morpholinylalkyl.

In another embodiment of the compounds of Formula Ia, -L-$X^2$-$R^3$ is —$CHR^7$—$NR^6$—C(O)—$NR^6$-benzyl wherein the benzyl is substituted or unsubstituted and $R^7$ is morpholinylalkyl.

In another embodiment of the compounds of Formula Ia, -L-$X^2$-$R^3$ is —$CHR^7$—$NR^6$—C(O)—$NR^6$-benzyl wherein the benzyl is substituted and $R^7$ is morpholinylalkyl.

In another embodiment of the compounds of Formula Ia, -L-$X^2$-$R^3$ is —$CHR^7$—$NR^6$—C(O)—$NR^6$-benzyl wherein the benzyl is substituted with one or more substituents selected from the group consisting of alkyl, substituted alkyl, halo, hydroxyl, amino, haloalkyl, and cyano, and $R^7$ is morpholinylalkyl.

In another embodiment of the compounds of Formula Ia, -L-$X^2$-$R^3$ is —$CHR^7$—$NR^6$—C(O)—$NR^6$-heteroarylalkyl wherein the heteroarylalkyl is substituted or unsubstituted and $R^7$ is morpholinylalkyl.

In another embodiment of the compounds of Formula Ia, -L-$X^2$-$R^3$ is —$CHR^7$—$NR^6$—C(O)—$NR^6$-heteroarylalkyl wherein the heteroarylalkyl is substituted or unsubstituted, the alkyl portion thereof is any alkylene described or disclosed herein and $R^7$ is morpholinylalkyl.

In another embodiment of the compounds of Formula Ia, -L-$X^2$-$R^3$ is —$CHR^7$—$NR^6$—C(O)—$NR^6$-heteroarylalkyl wherein the heteroarylalkyl is substituted or unsubstituted, the alkyl portion thereof is —CH$_2$—, and R$^7$ is morpholinylalkyl.

In another embodiment of the compounds of Formula Ia, -L-X$^2$—R$^3$ is —CHR$^7$—NR$^6$—C(O)—NR$^6$-heteroarylalkyl wherein the heteroarylalkyl is substituted or unsubstituted, the heteroaryl portion thereof is any heteroaryl described or disclosed herein, and R$^7$ is morpholinylalkyl.

In another embodiment of the compounds of Formula Ia, -L-X$^2$—R$^3$ is —CHR$^7$—NR$^6$—C(O)—NR$^6$-heteroarylalkyl wherein the heteroarylalkyl is substituted or unsubstituted, the heteroaryl portion thereof is thiazolyl, and R$^7$ is morpholinylalkyl.

In another embodiment of the compounds of Formula Ia, -L-X$^2$—R$^3$ is —CHR$^7$—NR$^6$—C(O)—NR$^6$-thiazolylmethyl wherein the thiazolylmethyl is substituted or unsubstituted and R$^7$ is morpholinylalkyl.

In another embodiment of the compounds of Formula Ia, -L-X$^2$—R$^3$ is —CHR$^7$—NR$^6$—C(O)—NR$^6$-thiazolyl-5-ylmethyl wherein R$^7$ is morpholinylalkyl.

In another embodiment of the compounds of Formula Ia, -L-X$^2$—R$^3$ is —CHR$^7$—NR$^6$—C(O)—NR$^6$-thiazolylmethyl wherein the thiazolylmethyl is substituted and R$^7$ is morpholinylalkyl.

In another embodiment of the compounds of Formula Ia, -L-X$^2$—R$^3$ is —CHR$^7$—NR$^6$—C(O)—NR$^6$-thiazolylmethyl wherein the thiazolylmethyl is substituted with one or more substituents selected from the group consisting of alkyl, substituted alkyl, halo, hydroxyl, amino, haloalkyl, and cyano and R$^7$ is morpholinylalkyl.

In another embodiment of the compounds of Formula Ia, -L-X$^2$—R$^3$—CHR$^7$—NR$^6$—C(O)—NR$^6$-thiazolylmethyl wherein the thiazolylmethyl is substituted, the substituent is an alkyl group, and R$^7$ is morpholinylalkyl.

In another embodiment of the compounds of Formula Ia, -L-X$^2$—R$^3$ is —CHR$^7$—NR$^6$—C(O)—NR$^6$-(2-isopropylthiazolyl-4-yl)methyl and R$^7$ is morpholinylalkyl.

In another embodiment of the compounds of Formula Ia, -L-X$^2$—R$^3$ is —CHR$^7$—NR$^6$—C(O)—NR$^6$-heterocyclyl the heterocyclyl is substituted or unsubstituted and R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-aryl wherein the aryl is substituted or unsubstituted and R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-phenyl wherein the phenyl is substituted or unsubstituted and R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-heteroaryl wherein the heteroaryl is substituted or unsubstituted and R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-heteroaryl, wherein the heteroaryl is substituted or unsubstituted, said heteroaryl is any heteroaryl described or defined herein, and R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-thiazolyl wherein the thiazolyl is substituted or unsubstituted and R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-arylalkyl wherein the arylalkyl is substituted or unsubstituted and R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-benzyl wherein the benzyl is substituted or unsubstituted and R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-benzyl wherein the benzyl is substituted and R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-benzyl wherein the benzyl is substituted with one or more substituents selected from the group consisting of alkyl, substituted alkyl, halo, hydroxyl, amino, haloalkyl, and cyano and R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-heteroarylalkyl wherein the heteroarylalkyl is substituted or unsubstituted and R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-heteroarylalkyl wherein the heteroarylalkyl is substituted or unsubstituted, the alkyl portion thereof is any alkylene described or disclosed herein, and R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-heteroarylalkyl wherein the heteroarylalkyl is substituted or unsubstituted, the alkyl portion thereof is —CH$_2$—, and R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-heteroarylalkyl wherein wherein the heteroarylalkyl is substituted or unsubstituted, the heteroaryl portion thereof is any heteroaryl described or disclosed herein, and R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-heteroarylalkyl wherein the heteroarylalkyl is substituted or unsubstituted, the heteroaryl portion thereof is thiazolyl, and R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-thiazolylmethyl wherein the thiazolylmethyl is substituted or unsubstituted and R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-thiazol-5-ylmethyl wherein R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-thiazolylmethyl wherein the thiazoylmethyl is substituted and R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-thiazolylmethyl wherein thiazolylmethyl is substituted with one or more substituents selected from the group consisting of alkyl, substituted alkyl, halo, hydroxyl, amino, haloalkyl, and cyano and R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-thiazolylmethyl wherein the thiazolylmethyl is substituted, the substituent is an alkyl group, and R$^7$ is —CH$_2$CH$_2$-morpholinyl.

In another embodiment of the compounds of Formula Ia, -L-X$^2$—R$^3$ is —CHR$^7$—NR$^6$—C(O)—NR$^6$-(2-isopropylthiazolyl-4-yl)methyl wherein R$^7$ is —CH$_2$CH$_2$-morpholinyl.

In another embodiment, the compounds of Formula I have the structure of Formula Ib:

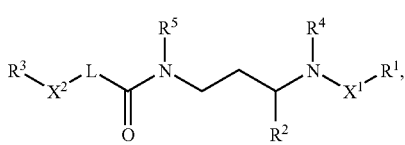

wherein X1, $X^2$, L, $R^1$, $R^2$, $R^3$, $R^4$, and $R^5$ are as defined herein.

In another embodiment of the compounds of Formula Ib, $R^2$ is substituted or unsubstituted arylalkyl.

In another embodiment of the compounds of Formula Ib, $R^2$ is substituted or unsubstituted benzyl.

In another embodiment of the compounds of Formula Ib, $R^2$ is alkyl.

In another embodiment of the compounds of Formula Ib, $X^1$ is —C(O)—O—.

In another embodiment of the compounds of Formula Ib, $X^1$ is —S(O)—.

In another embodiment of the compounds of Formula Ib, $X^1$ is —S(O$_2$)—.

In another embodiment of the compounds of Formula Ib, $X^1$ is —C(O)NR$^6$—.

In another embodiment of the compounds of Formula Ib, $X^1$ is —C(O)NH—.

In another embodiment of the compounds of Formula Ib, $X^1$ is —C(O)N(alkyl)-.

In another embodiment of the compounds of Formula Ib, $X^2$ is —O—.

In another embodiment of the compounds of Formula Ib, $X^2$ is —NR$^6$—C(O)—NR$^6$—.

In another embodiment of the compounds of Formula Ib, $X^2$ is —NR$^6$—C(O)—NH—.

In another embodiment of the compounds of Formula Ib, $X^2$ is NH—C(O)—NR—.

In another embodiment of the compounds of Formula Ib, $X^2$ is —N(alkyl)-C(O)-(alkyl)-.

In another embodiment of the compounds of Formula Ib, $X^2$ is —N(alkyl)-C(O)—NH—.

In another embodiment of the compounds of Formula Ib, $X^2$ is —NH—C(O)—N(alkyl)-.

In another embodiment of the compounds of Formula Ib, $X^2$ is —NH—C(O)—NH—.

In another embodiment of the compounds of Formula Ib, $X^2$ is —OC(O)NR$^6$—.

In another embodiment of the compounds of Formula Ib, $X^2$ is —OC(O)NH—.

In another embodiment of the compounds of Formula Ib, $X^2$ is —OC(O)N(alkyl)-.

In another embodiment of the compounds of Formula Ib, $X^2$ is —NR$^6$C(O)O—.

In another embodiment of the compounds of Formula Ib, $X^2$ is —NHC(O)O—.

In another embodiment of the compounds of Formula Ib, $X^2$ is —N(alkyl)C(O)O—.

In another embodiment of the compounds of Formula Ib, $X^2$ is —NR$^6$—.

In another embodiment of the compounds of Formula Ib, $X^2$ is —NH—.

In another embodiment of the compounds of Formula Ib, $X^2$ is —N(alkyl)-.

In another embodiment of the compounds of Formula Ib, L is a covalent bond.

In another embodiment of the compounds of Formula Ib, L is —CHR$^7$—, wherein R$^7$ is heterocyclylalkyl.

In another embodiment of the compounds of Formula Ib, L is —CHR$^7$—, wherein R$^7$ is heterocyclylalkyl, the alkyl portion of which is any alkylene as defined or described herein.

In another embodiment of the compounds of Formula Ib, L is —CHR$^7$—, wherein R$^7$ is heterocyclylalkyl, the heterocyclyl portion of which is any heterocyclyl as defined herein.

In another embodiment of the compounds of Formula Ib, L is —CHR$^7$—, wherein R$^7$ is heterocyclylalkyl, the heterocyclyl portion of which is a morpholinyl group.

In another embodiment of the compounds of Formula Ib, L is —CHR$^7$—, and R$^7$ is:

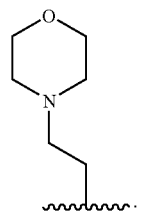 [SMILES: *CCN1CCOCC1]

In another embodiment of the compounds of Formula Ib, $R^1$ is substituted or unsubstituted aryl.

In another embodiment of the compounds of Formula Ib, $R^1$ is substituted or unsubstituted phenyl In another embodiment of the compounds of Formula Ib, $R^1$ is substituted phenyl.

In another embodiment of the compounds of Formula Ib, $R^1$ is mono-substituted phenyl.

In another embodiment of the compounds of Formula Ib, $R^1$ is phenyl substituted with one or more substituents selected from the group consisting of alkyl, substituted alkyl, halo, hydroxyl, amino, haloalkyl, and cyano.

In another embodiment of the compounds of Formula Ib, $R^1$ is 4-aminophenyl.

In another embodiment of the compounds of Formula Ib, $R^1$ is substituted or unsubstituted heteroaryl.

In another embodiment of the compounds of Formula Ib, $R^1$ is substituted or unsubstituted thiazolyl.

In another embodiment of the compounds of Formula Ib, $R^1$ is substituted or unsubstituted arylalkyl.

In another embodiment of the compounds of Formula Ib, $R^1$ is substituted or unsubstituted benzyl.

In another embodiment of the compounds of Formula Ib, $R^1$ is substituted or unsubstituted heteroarylalkyl.

In another embodiment of the compounds of Formula Ib, $R^1$ is substituted or unsubstituted heteroarylalkyl, wherein the alkyl portion thereof is any of the alkylene groups defined or disclosed herein.

In another embodiment of the compounds of Formula Ib, $R^1$ is substituted or unsubstituted heteroarylalkyl, wherein the alkyl portion thereof is —CH$_2$—.

In another embodiment of the compounds of Formula Ib, $R^1$ is substituted or unsubstituted heteroarylalkyl, wherein the heteroaryl portion thereof is any of the heteroaryl groups defined or disclosed herein.

In another embodiment of the compounds of Formula Ib, $R^1$ is substituted or unsubstituted heteroarylalkyl, wherein the heteroaryl portion thereof is thiazolyl.

In another embodiment of the compounds of Formula Ib, $R^1$ is substituted or unsubstituted thiazolylmethyl.

In another embodiment of the compounds of Formula Ib, $R^1$ is thiazol-5-ylmethyl.

In another embodiment of the compounds of Formula Ib, $R^1$ is substituted heteroarylalkyl, wherein the heteroaryl portion thereof is any of the heteroaryl groups defined or disclosed herein, and the substituent is one or more substituents selected from the group consisting of alkyl, substituted alkyl, halo, hydroxyl, amino, haloalkyl, and cyano.

In another embodiment of the compounds of Formula Ib, $R^1$ is substituted heteroarylalkyl, wherein the heteroaryl portion thereof is thiazolyl substituted with one or more substituents selected from the group consisting of alkyl, substituted alkyl, halo, hydroxyl, amino, haloalkyl, and cyano.

In another embodiment of the compounds of Formula Ib, $R^1$ is thiazolylmethyl substituted with one or more substituents selected from the group consisting of alkyl, substituted alkyl, halo, hydroxyl, amino, haloalkyl, and cyano.

In another embodiment of the compounds of Formula Ib, $R^3$ is substituted or unsubstituted heterocyclyl.

In another embodiment of the compounds of Formula Ib, $R^3$ is substituted or unsubstituted tetrahydro-2H-furo[2,3-b]furanyl.

In another embodiment of the compounds of Formula Ib, $R^3$ is unsubstituted tetrahydro-2H-furo[2,3-b]furanyl.

In another embodiment of the compounds of Formula Ib, $R^3$ is tetrahydro-2H-furo[2,3-b]furan-3-yl.

In another embodiment of the compounds of Formula Ib, $R^3$ is substituted or unsubstituted tetrahydrofuranyl.

In another embodiment of the compounds of Formula Ib, $R^3$ is unsubstituted tetrahydrofuranyl.

In another embodiment of the compounds of Formula Ib, $R^3$ is tetrahydrofuran-3-yl.

In another embodiment of the compounds of Formula Ib, $R^3$ is substituted or unsubstituted aryl.

In another embodiment of the compounds of Formula Ib, $R^3$ is substituted or unsubstituted phenyl.

In another embodiment of the compounds of Formula Ib, $R^3$ is substituted or unsubstituted heteroaryl.

In another embodiment of the compounds of Formula Ib, $R^3$ is substituted or unsubstituted heteroaryl, wherein said heteroaryl is any heteroaryl described or defined herein.

In another embodiment of the compounds of Formula Ib, $R^3$ is substituted or unsubstituted thiazolyl.

In another embodiment of the compounds of Formula Ib, $R^3$ is thiazolyl substituted with one or more substituents selected from the group consisting of alkyl, substituted alkyl, halo, hydroxyl, amino, haloalkyl, and cyano.

In another embodiment of the compounds of Formula Ib, $R^3$ is substituted or unsubstituted arylalkyl.

In another embodiment of the compounds of Formula Ib, $R^3$ is substituted or unsubstituted benzyl.

In another embodiment of the compounds of Formula Ib, $R^3$ is substituted benzyl.

In another embodiment of the compounds of Formula Ib, $R^3$ is benzyl substituted with one or more substituents selected from the group consisting of alkyl, substituted alkyl, halo, hydroxyl, amino, haloalkyl, and cyano.

In another embodiment of the compounds of Formula Ib, $R^3$ is substituted or unsubstituted heteroarylalkyl.

In another embodiment of the compounds of Formula Ib, $R^3$ is substituted or unsubstituted heteroarylalkyl, wherein the alkyl portion thereof is any alkylene described or disclosed herein.

In another embodiment of the compounds of Formula Ib, $R^3$ is substituted or unsubstituted heteroarylalkyl, wherein the alkyl portion thereof is —CH$_2$—.

In another embodiment of the compounds of Formula Ib, $R^3$ is substituted or unsubstituted heteroarylalkyl, wherein the heteroaryl portion thereof is any heteroaryl described or disclosed herein.

In another embodiment of the compounds of Formula Ib, $R^3$ is substituted or unsubstituted heteroarylalkyl, wherein the heteroaryl portion thereof is thiazolyl.

In another embodiment of the compounds of Formula Ib, $R^3$ is substituted or unsubstituted thiazolylmethyl.

In another embodiment of the compounds of Formula Ib, $R^3$ is thiazol-5-ylmethyl.

In another embodiment of the compounds of Formula Ib, $R^3$ is substituted thiazolylmethyl.

In another embodiment of the compounds of Formula Ib, $R^3$ is thiazolylmethyl substituted with one or more substituents selected from the group consisting of alkyl, substituted alkyl, halo, hydroxyl, amino, haloalkyl, and cyano.

In another embodiment of the compounds of Formula Ib, $R^3$ is substituted thiazolylmethyl, and the substituent is an alkyl group.

In another embodiment of the compounds of Formula Ib, $R^3$ is (2-isopropylthiazolyl-4-yl)methyl.

In another embodiment of the compounds of Formula Ib, $R^4$ is H.

In another embodiment of the compounds of Formula Ib, $R^4$ is alkyl.

In another embodiment of the compounds of Formula Ib, $R^4$ is any of the alkyl groups described or disclosed herein.

In another embodiment of the compounds of Formula Ib, $R^4$ is 2-methylpropyl.

In another embodiment of the compounds of Formula Ib, $R^4$ is substituted or unsubstituted arylalkyl.

In another embodiment of the compounds of Formula Ib, $R^4$ is substituted or unsubstituted benzyl.

In another embodiment of the compounds of Formula Ib, $R^4$ is unsubstituted benzyl.

In another embodiment of the compounds of Formula Ib, $R^4$ is benzyl substituted with one or more substituents selected from the group consisting of alkyl, substituted alkyl, halo, hydroxyl, amino, haloalkyl, and cyano.

In another embodiment of the compounds of Formula Ib, $R^4$ is halo substituted benzyl.

In another embodiment of the compounds of Formula Ib, $R^4$ is chloro substituted benzyl.

In another embodiment of the compounds of Formula Ib, $R^4$ is substituted or unsubstituted heteroarylalkyl.

In another embodiment of the compounds of Formula Ib, $R^4$ is substituted or unsubstituted heteroarylalkyl, wherein the alkyl portion thereof is any of the alkylene groups described or defined herein.

In another embodiment of the compounds of Formula Ib, $R^4$ is substituted or unsubstituted heteroarylalkyl, wherein the alkyl portion thereof is —CH$_2$—.

In another embodiment of the compounds of Formula Ib, $R^4$ is substituted or unsubstituted heteroarylalkyl, wherein the heteroaryl portion thereof is any of the heteroaryl groups described or defined herein.

In another embodiment of the compounds of Formula Ib, $R^5$ is H.

In another embodiment of the compounds of Formula Ib, $R^5$ is alkyl.

In another embodiment of the compounds of Formula Ib, $R^5$ is any of the alkyl groups described or disclosed herein.

In another embodiment of the compounds of Formula Ib, $R^5$ is 2-methylpropyl.

In another embodiment of the compounds of Formula Ib, $R^5$ is substituted or unsubstituted arylalkyl.

In another embodiment of the compounds of Formula Ib, $R^5$ is substituted or unsubstituted benzyl.

In another embodiment of the compounds of Formula Ib, $R^5$ is unsubstituted benzyl.

In another embodiment of the compounds of Formula Ib, $R^5$ is benzyl substituted with one or more substituents selected from the group consisting of alkyl, substituted alkyl, halo, hydroxyl, amino, haloalkyl, and cyano.

In another embodiment of the compounds of Formula Ib, $R^5$ is halo substituted benzyl.

In another embodiment of the compounds of Formula Ib, $R^5$ is substituted or unsubstituted heteroarylalkyl.

In another embodiment of the compounds of Formula Ib, $R^5$ is substituted or unsubstituted heteroarylalkyl, wherein the alkyl portion thereof is any of the alkylene groups described or defined herein.

In another embodiment of the compounds of Formula Ib, $R^5$ is substituted or unsubstituted heteroarylalkyl, wherein the alkyl portion thereof is —$CH_2$—.

In another embodiment of the compounds of Formula Ib, $R^5$ is substituted or unsubstituted heteroarylalkyl, wherein the heteroaryl portion thereof is any of the heteroaryl groups described or defined herein.

In another embodiment of the compounds of Formula Ib, $R^4$ and $R^5$ are different.

In another embodiment of the compounds of Formula Ib, $R^4$ and $R^5$ are the same.

In another embodiment of the compounds of Formula Ib, one of $R^4$ and $R^5$ is H.

In another embodiment of the compounds of Formula Ib, $R^4$ is H and $R^5$ is benzyl or substituted benzyl.

In another embodiment of the compounds of Formula Ib, —$X^1$—$R^1$ is substituted or unsubstituted —C(O)—O-aryl.

In another embodiment of the compounds of Formula Ib, —$X^1$—$R^1$ is substituted or unsubstituted —C(O)—O-phenyl.

In another embodiment of the compounds of Formula Ib, —$X^1$—$R^1$ is substituted —C(O)—O-phenyl.

In another embodiment of the compounds of Formula Ib, —$X^1$—$R^1$ is mono-substituted —C(O)—O-phenyl.

In another embodiment of the compounds of Formula Ib, —$X^1$—$R^1$ is —C(O)—O-phenyl substituted with one or more substituents selected from the group consisting of alkyl, substituted alkyl, halo, hydroxyl, amino, haloalkyl, and cyano.

In another embodiment of the compounds of Formula Ib, —$X^1$—$R^1$ is —C(O)—O-(4-aminophenyl).

In another embodiment of the compounds of Formula Ib, —$X^1$—$R^1$ is substituted or unsubstituted —C(O)—O-heteroaryl.

In another embodiment of the compounds of Formula Ib, —$X^1$—$R^1$ is substituted or unsubstituted —C(O)—O-thiazolyl.

In another embodiment of the compounds of Formula Ib, —$X^1$—$R^1$ is substituted or unsubstituted —C(O)—O-arylalkyl.

In another embodiment of the compounds of Formula Ib, —$X^1$—$R^1$ is substituted or unsubstituted —C(O)—O-benzyl.

In another embodiment of the compounds of Formula Ib, —$X^1$—$R^1$ is substituted or unsubstituted —C(O)—O-heteroarylalkyl.

In another embodiment of the compounds of Formula Ib, —$X^1$—$R^1$ is substituted or unsubstituted —C(O)—O-heteroarylalkyl, wherein the alkyl portion thereof is any of the alkylene groups defined or disclosed herein.

In another embodiment of the compounds of Formula Ib, —$X^1$—$R^1$ is substituted or unsubstituted —C(O)—O-heteroarylalkyl, wherein the alkyl portion thereof is —$CH_2$—.

In another embodiment of the compounds of Formula Ib, —$X^1$—$R^1$ is substituted or unsubstituted —C(O)—O-heteroarylalkyl, wherein the heteroaryl portion thereof is any of the heteroaryl groups defined or disclosed herein.

In another embodiment of the compounds of Formula Ib, —$X^1$—$R^1$ is substituted or unsubstituted —C(O)—O-heteroarylalkyl, wherein the heteroaryl portion thereof is thiazolyl.

In another embodiment of the compounds of Formula Ib, —$X^1$—$R^1$ is substituted or unsubstituted —C(O)—O-thiazolylmethyl.

In another embodiment of the compounds of Formula Ib, —$X^1$—$R^1$ is —C(O)—O-thiazol-5-ylmethyl.

In another embodiment of the compounds of Formula Ib, —$X^1$—$R^1$ is substituted —C(O)—O-heteroarylalkyl, wherein the heteroaryl portion thereof is any of the heteroaryl groups defined or disclosed herein, and the substituent is one or more substituents selected from the group consisting of alkyl, substituted alkyl, halo, hydroxyl, amino, haloalkyl, and cyano.

In another embodiment of the compounds of Formula Ib, —$X^1$—$R^1$ is substituted —C(O)—O-heteroarylalkyl, wherein the heteroaryl portion thereof is thiazolyl substituted with one or more substituents selected from the group consisting of alkyl, substituted alkyl, halo, hydroxyl, amino, haloalkyl, and cyano.

In another embodiment of the compounds of Formula Ib, —$X^1$—$R^1$ is —C(O)—O-thiazolylmethyl substituted with one or more substituents selected from the group consisting of alkyl, substituted alkyl, halo, hydroxyl, amino, haloalkyl, and cyano.

In another embodiment of the compounds of Formula Ib, —$X^1$—$R^1$ is substituted or unsubstituted —S(O)-aryl.

In another embodiment of the compounds of Formula Ib, —$X^1$—$R^1$ is substituted or unsubstituted —S(O)-phenyl.

In another embodiment of the compounds of Formula Ib, —$X^1$—$R^1$ is substituted —S(O)-phenyl.

In another embodiment of the compounds of Formula Ib, —$X^1$—$R^1$ is mono-substituted —S(O)-phenyl.

In another embodiment of the compounds of Formula Ib, —$X^1$—$R^1$ is —S(O)-phenyl substituted with one or more substituents selected from the group consisting of alkyl, substituted alkyl, halo, hydroxyl, amino, haloalkyl, and cyano.

In another embodiment of the compounds of Formula Ib, —$X^1$—$R^1$ is —S(O)-(4-aminophenyl).

In another embodiment of the compounds of Formula Ib, —$X^1$—$R^1$ is substituted or unsubstituted —S(O)-heteroaryl.

In another embodiment of the compounds of Formula Ib, —$X^1$—$R^1$ is substituted or unsubstituted —S(O)-thiazolyl.

In another embodiment of the compounds of Formula Ib, —$X^1$—$R^1$ is substituted or unsubstituted —S(O)-arylalkyl.

In another embodiment of the compounds of Formula Ib, —$X^1$—$R^1$ is substituted or unsubstituted —S(O)-benzyl.

In another embodiment of the compounds of Formula Ib, —$X^1$—$R^1$ is substituted or unsubstituted —S(O)-heteroarylalkyl.

In another embodiment of the compounds of Formula Ib, —$X^1$—$R^1$ is substituted or unsubstituted —S(O)-heteroarylalkyl, wherein the alkyl portion thereof is any of the alkylene groups defined or disclosed herein.

In another embodiment of the compounds of Formula Ib, —$X^1$—$R^1$ is substituted or unsubstituted —S(O)-heteroarylalkyl, wherein the alkyl portion thereof is —$CH_2$—.

In another embodiment of the compounds of Formula Ib, —$X^1$—$R^1$ is substituted or unsubstituted —S(O)-heteroarylalkyl, wherein the heteroaryl portion thereof is any of the heteroaryl groups defined or disclosed herein.

In another embodiment of the compounds of Formula Ib, —$X^1$—$R^1$ is substituted or unsubstituted —S(O)-heteroarylalkyl, wherein the heteroaryl portion thereof is thiazolyl.

In another embodiment of the compounds of Formula Ib, —$X^1$—$R^1$ is substituted or unsubstituted —S(O)-thiazolylmethyl.

In another embodiment of the compounds of Formula Ib, —$X^1$—$R^1$ is substituted —S(O)-heteroarylalkyl, wherein the heteroaryl portion thereof is any of the heteroaryl groups defined or disclosed herein, and the substituent is one or more substituents selected from the group consisting of alkyl, substituted alkyl, halo, hydroxyl, amino, haloalkyl, and cyano.

In another embodiment of the compounds of Formula Ib, —$X^1$—$R^1$ is substituted —S(O)-heteroarylalkyl, wherein the heteroaryl portion thereof is thiazolyl substituted with one or more substituents selected from the group consisting of alkyl, substituted alkyl, halo, hydroxyl, amino, haloalkyl, and cyano.

In another embodiment of the compounds of Formula Ib, —$X^1$—$R^1$ is —S(O)-thiazolylmethyl substituted with one or more substituents selected from the group consisting of alkyl, substituted alkyl, halo, hydroxyl, amino, haloalkyl, and cyano.

In another embodiment of the compounds of Formula Ib, —$X^1$—$R^1$ is substituted or unsubstituted —$S(O_2)$-aryl.

In another embodiment of the compounds of Formula Ib, —$X^1$—$R^1$ is substituted or unsubstituted —$S(O_2)$-phenyl.

In another embodiment of the compounds of Formula Ib, —$X^1$—$R^1$ is substituted —$S(O_2)$-phenyl.

In another embodiment of the compounds of Formula Ib, —$X^1$—$R^1$ is mono-substituted —$S(O_2)$-phenyl.

In another embodiment of the compounds of Formula Ib, —$X^1$—$R^1$ is —$S(O_2)$-phenyl substituted with one or more substituents selected from the group consisting of alkyl, substituted alkyl, halo, hydroxyl, amino, haloalkyl, and cyano.

In another embodiment of the compounds of Formula Ib, —$X^1$—$R^1$ is —$S(O_2)$-(4-aminophenyl).

In another embodiment of the compounds of Formula Ib, —$X^1$—$R^1$ is substituted or unsubstituted —$S(O_2)$-heteroaryl.

In another embodiment of the compounds of Formula Ib, —$X^1$—$R^1$ is substituted or unsubstituted —$S(O_2)$-thiazolyl.

In another embodiment of the compounds of Formula Ib, —$X^1$—$R^1$ is substituted or unsubstituted —$S(O_2)$-arylalkyl.

In another embodiment of the compounds of Formula Ib, —$X^1$—$R^1$ is substituted or unsubstituted —$S(O_2)$-benzyl.

In another embodiment of the compounds of Formula Ib, —$X^1$—$R^1$ is substituted or unsubstituted —$S(O_2)$-heteroarylalkyl.

In another embodiment of the compounds of Formula Ib, —$X^1$—$R^1$ is substituted or unsubstituted —$S(O_2)$-heteroarylalkyl, wherein the alkyl portion thereof is any of the alkylene groups defined or disclosed herein.

In another embodiment of the compounds of Formula Ib, —$X^1$—$R^1$ is substituted or unsubstituted —$S(O_2)$-heteroarylalkyl, wherein the alkyl portion thereof is —$CH_2$—.

In another embodiment of the compounds of Formula Ib, —$X^1$—$R^1$ is substituted or unsubstituted —$S(O_2)$-heteroarylalkyl, wherein the heteroaryl portion thereof is any of the heteroaryl groups defined or disclosed herein.

In another embodiment of the compounds of Formula Ib, —$X^1$—$R^1$ is substituted or unsubstituted —$S(O_2)$-heteroarylalkyl, wherein the heteroaryl portion thereof is thiazolyl.

In another embodiment of the compounds of Formula Ib, —$X^1$—$R^1$ is substituted or unsubstituted —$S(O_2)$-thiazolylmethyl.

In another embodiment of the compounds of Formula Ib, —$X^1$—$R^1$ is substituted —$S(O_2)$-heteroarylalkyl, wherein the heteroaryl portion thereof is any of the heteroaryl groups defined or disclosed herein, and the substituent is one or more substituents selected from the group consisting of alkyl, substituted alkyl, halo, hydroxyl, amino, haloalkyl, and cyano.

In another embodiment of the compounds of Formula Ib, —$X^1$—$R^1$ is substituted —$S(O_2)$-heteroarylalkyl, wherein the heteroaryl portion thereof is thiazolyl substituted with one or more substituents selected from the group consisting of alkyl, substituted alkyl, halo, hydroxyl, amino, haloalkyl, and cyano.

In another embodiment of the compounds of Formula Ib, —$X^1$—$R^1$ is —$S(O_2)$-thiazolylmethyl substituted with one or more substituents selected from the group consisting of alkyl, substituted alkyl, halo, hydroxyl, amino, haloalkyl, and cyano.

In another embodiment of the compounds of Formula Ib, —$X^1$—$R^1$ is substituted or unsubstituted —$C(O)NR^6$-aryl.

In another embodiment of the compounds of Formula Ib, —$X^1$—$R^1$ is substituted or unsubstituted —$C(O)NR^6$-phenyl.

In another embodiment of the compounds of Formula Ib, —$X^1$—$R^1$ is substituted —$C(O)NR^6$-phenyl.

In another embodiment of the compounds of Formula Ib, —$X^1$—$R^1$ is mono-substituted —$C(O)NR^6$-phenyl.

In another embodiment of the compounds of Formula Ib, —$X^1$—$R^1$ is —$C(O)NR^6$-phenyl substituted with one or more substituents selected from the group consisting of alkyl, substituted alkyl, halo, hydroxyl, amino, haloalkyl, and cyano.

In another embodiment of the compounds of Formula Ib, —$X^1$—$R^1$ is —$C(O)NR^6$-(4-aminophenyl).

In another embodiment of the compounds of Formula Ib, —$X^1$—$R^1$ is substituted or unsubstituted —$C(O)NR^6$-heteroaryl.

In another embodiment of the compounds of Formula Ib, —$X^1$—$R^1$ is substituted or unsubstituted —$C(O)NR^6$-thiazolyl.

In another embodiment of the compounds of Formula Ib, —$X^1$—$R^1$ is substituted or unsubstituted —$C(O)NR^6$-arylalkyl.

In another embodiment of the compounds of Formula Ib, —$X^1$—$R^1$ is substituted or unsubstituted —$C(O)NR^6$-benzyl.

In another embodiment of the compounds of Formula Ib, —$X^1$—$R^1$ is substituted or unsubstituted —$C(O)NR^6$-heteroarylalkyl.

In another embodiment of the compounds of Formula Ib, —$X^1$—$R^1$ is substituted or unsubstituted —$C(O)NR^6$-heteroarylalkyl, wherein the alkyl portion thereof is any of the alkylene groups defined or disclosed herein.

In another embodiment of the compounds of Formula Ib, —$X^1$—$R^1$ is substituted or unsubstituted —$C(O)NR^6$-heteroarylalkyl, wherein the alkyl portion thereof is —$CH_2$—.

In another embodiment of the compounds of Formula Ib, —$X^1$—$R^1$ is substituted or unsubstituted —$C(O)NR^6$-heteroarylalkyl, wherein the heteroaryl portion thereof is any of the heteroaryl groups defined or disclosed herein.

In another embodiment of the compounds of Formula Ib, —$X^1$—$R^1$ is substituted or unsubstituted —$C(O)NR^6$-heteroarylalkyl, wherein the heteroaryl portion thereof is thiazolyl.

In another embodiment of the compounds of Formula Ib, —$X^1$—$R^1$ is substituted or unsubstituted —$C(O)NR^6$-thiazolylmethyl.

In another embodiment of the compounds of Formula Ib, —$X^1$—$R^1$ is substituted —C(O)$NR^6$-heteroarylalkyl, wherein the heteroaryl portion thereof is any of the heteroaryl groups defined or disclosed herein, and the substituent is one or more substituents selected from the group consisting of alkyl, substituted alkyl, halo, hydroxyl, amino, haloalkyl, and cyano.

In another embodiment of the compounds of Formula Ib, —$X^1$—$R^1$ is substituted —C(O)$NR^6$-heteroarylalkyl, wherein the heteroaryl portion thereof is thiazolyl substituted with one or more substituents selected from the group consisting of alkyl, substituted alkyl, halo, hydroxyl, amino, haloalkyl, and cyano.

In another embodiment of the compounds of Formula Ib, —$X^1$—$R^1$ is —C(O)$NR^6$-thiazolylmethyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted or unsubstituted —$NR^6$—C(O)—$NR^6$-heterocyclyl.

In another embodiment of the compounds of Formula Ib, —$X^2$—$R^3$ is substituted or unsubstituted —$NR^6$—C(O)—$NR^6$-aryl.

In another embodiment of the compounds of Formula Ib, —$X^2$—$R^3$ is substituted or unsubstituted —$NR^6$—C(O)—$NR^6$-phenyl.

In another embodiment of the compounds of Formula Ib, —$X^2$—$R^3$ is substituted or unsubstituted —$NR^6$—C(O)—$NR^6$-heteroaryl.

In another embodiment of the compounds of Formula Ib, —$X^2$—$R^3$ is substituted or unsubstituted —$NR^6$—C(O)—$NR^6$-heteroaryl, wherein said heteroaryl is any heteroaryl described or defined herein.

In another embodiment of the compounds of Formula Ib, —$X^2$—$R^3$ is substituted or unsubstituted —$NR^6$—C(O)—$NR^6$-thiazolyl.

In another embodiment of the compounds of Formula Ib, —$X^2$—$R^3$ is substituted or unsubstituted —$NR^6$—C(O)—$NR^6$-arylalkyl.

In another embodiment of the compounds of Formula Ib, —$X^2$—$R^3$ is substituted or unsubstituted —$NR^6$—C(O)—$NR^6$-benzyl.

In another embodiment of the compounds of Formula Ib, —$X^2$—$R^3$ is substituted —$NR^6$—C(O)—$NR^6$-benzyl.

In another embodiment of the compounds of Formula Ib, —$X^2$—$R^3$ is —$NR^6$—C(O)—$NR^6$-benzyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted or unsubstituted —$NR^6$—C(O)—$NR^6$-heteroarylalkyl.

In another embodiment of the compounds of Formula Ib, —$X^2$—$R^3$ is substituted or unsubstituted —$NR^6$—C(O)—$NR^6$-heteroarylalkyl, wherein the alkyl portion thereof is any alkylene described or disclosed herein.

In another embodiment of the compounds of Formula Ib, —$X^2$—$R^3$ is substituted or unsubstituted —$NR^6$—C(O)—$NR^6$-heteroarylalkyl, wherein the alkyl portion thereof is —$CH_2$—.

In another embodiment of the compounds of Formula Ib, —$X^2$—$R^3$ is substituted or unsubstituted —$NR^6$—C(O)—$NR^6$-heteroarylalkyl, wherein the heteroaryl portion thereof is any heteroaryl described or disclosed herein.

In another embodiment of the compounds of Formula Ib, —$X^2$—$R^3$ is substituted or unsubstituted —$NR^6$—C(O)—$NR^6$-heteroarylalkyl, wherein the heteroaryl portion thereof is thiazolyl.

In another embodiment of the compounds of Formula Ib, —$X^2$—$R^3$ is substituted or unsubstituted —$NR^6$—C(O)—$NR^6$-thiazolylmethyl.

In another embodiment of the compounds of Formula Ib, —$X^2$—$R^3$ is —$NR^6$—C(O)—$NR^6$-thiazol-5-ylmethyl.

In another embodiment of the compounds of Formula Ib, —$X^2$—$R^3$ is substituted —$NR^6$—C(O)$NR^6$-thiazolylmethyl.

In another embodiment of the compounds of Formula Ib, —$X^2$—$R^3$ is —$NR^6$—C(O)—$NR^6$-thiazolylmethyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted —$NR^6$—C(O)—$NR^6$-thiazolylmethyl, and the substituent is an alkyl group.

In another embodiment of the compounds of Formula Ib, —$X^2$—$R^3$ is —$NR^6$—C(O)—$NR^6$-(2-isopropylthiazolyl-4-yl)methyl.

In another embodiment of the compounds of Formula Ib, —$X^2$—$R^3$ is substituted or unsubstituted —NH—C(O)—$NR^6$-heterocyclyl.

In another embodiment of the compounds of Formula Ib, —$X^2$—$R^3$ is substituted or unsubstituted —NH—C(O)—$NR^6$-aryl.

In another embodiment of the compounds of Formula Ib, —$X^2$—$R^3$ is substituted or unsubstituted —NH—C(O)—$NR^6$-phenyl.

In another embodiment of the compounds of Formula Ib, —$X^2$—$R^3$ is substituted or unsubstituted —NH—C(O)—$NR^6$-heteroaryl.

In another embodiment of the compounds of Formula Ib, —$X^2$—$R^3$ is substituted or unsubstituted —NH—C(O)—$NR^6$-heteroaryl, wherein said heteroaryl is any heteroaryl described or defined herein.

In another embodiment of the compounds of Formula Ib, —$X^2$—$R^3$ is substituted or unsubstituted —NH—C(O)—$NR^6$-thiazolyl.

In another embodiment of the compounds of Formula Ib, —$X^2$—$R^3$ is substituted or unsubstituted —NH—C(O)—$NR^6$-arylalkyl.

In another embodiment of the compounds of Formula Ib, —$X^2$—$R^3$ is substituted or unsubstituted —NH—C(O)—$NR^6$-benzyl.

In another embodiment of the compounds of Formula Ib, —$X^2$—$R^3$ is substituted —NH—C(O)—$NR^6$-benzyl.

In another embodiment of the compounds of Formula Ib, —$X^2$—$R^3$ is —NH—C(O)—$NR^6$-benzyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted or unsubstituted —NH—C(O)—$NR^6$-heteroarylalkyl.

In another embodiment of the compounds of Formula Ib, —$X^2$—$R^3$ is substituted or unsubstituted —NH—C(O)—$NR^6$-heteroarylalkyl, wherein the alkyl portion thereof is any alkylene described or disclosed herein.

In another embodiment of the compounds of Formula Ib, —$X^2$—$R^3$ is substituted or unsubstituted —NH—C(O)—$NR^6$-heteroarylalkyl, wherein the alkyl portion thereof is —$CH_2$—.

In another embodiment of the compounds of Formula Ib, —$X^2$—$R^3$ is substituted or unsubstituted —NH—C(O)—N$R^6$-heteroarylalkyl, wherein the heteroaryl portion thereof is any heteroaryl described or disclosed herein.

In another embodiment of the compounds of Formula Ib, —$X^2$—$R^3$ is substituted or unsubstituted —NH—C(O)—N$R^6$-heteroarylalkyl, wherein the heteroaryl portion thereof is thiazolyl.

In another embodiment of the compounds of Formula Ib, —$X^2$—$R^3$ is substituted or unsubstituted —NH—C(O)—N$R^6$-thiazolylmethyl.

In another embodiment of the compounds of Formula Ib, —$X^2$—$R^3$ is —NH—C(O)—N$R^6$-thiazol-5-ylmethyl.

In another embodiment of the compounds of Formula Ib, —$X^2$—$R^3$ is substituted —NH—C(O)—N$R^6$-thiazolylmethyl.

In another embodiment of the compounds of Formula Ib, —$X^2$—$R^3$ is —NH—C(O)—N$R^6$-thiazolylmethyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted —NH—C(O)—N$R^6$-thiazolylmethyl, and the substituent is an alkyl group.

In another embodiment of the compounds of Formula Ib, —$X^2$—$R^3$ is —NH—C(O)—N$R^6$-(2-isopropylthiazolyl-4-yl)methyl.

In another embodiment of the compounds of Formula Ib, —$X^2$—$R^3$ is substituted or unsubstituted —N$R^6$—C(O)—NH-heterocyclyl.

In another embodiment of the compounds of Formula Ib, —$X^2$—$R^3$ is substituted or unsubstituted —N$R^6$—C(O)—NH-aryl.

In another embodiment of the compounds of Formula Ib, —$X^2$—$R^3$ is substituted or unsubstituted —N$R^6$—C(O)—NH-phenyl.

In another embodiment of the compounds of Formula Ib, —$X^2$—$R^3$ is substituted or unsubstituted —N$R^6$—C(O)—NH-heteroaryl.

In another embodiment of the compounds of Formula Ib, —$X^2$—$R^3$ is substituted or unsubstituted —N$R^6$—C(O)—NH-heteroaryl, wherein said heteroaryl is any heteroaryl described or defined herein.

In another embodiment of the compounds of Formula Ib, —$X^2$—$R^3$ is substituted or unsubstituted —N$R^6$—C(O)—NH-thiazolyl.

In another embodiment of the compounds of Formula Ib, —$X^2$—$R^3$ is substituted or unsubstituted —N$R^6$—C(O)—NH-arylalkyl.

In another embodiment of the compounds of Formula Ib, —$X^2$—$R^3$ is substituted or unsubstituted —N$R^6$—C(O)—NH-benzyl.

In another embodiment of the compounds of Formula Ib, —$X^2$—$R^3$ is substituted —N$R^6$—C(O)—NH-benzyl.

In another embodiment of the compounds of Formula Ib, —$X^2$—$R^3$ is —N$R^6$—C(O)—NH-benzyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted or unsubstituted —N$R^6$—C(O)—NH-heteroarylalkyl.

In another embodiment of the compounds of Formula Ib, —$X^2$—$R^3$ is substituted or unsubstituted —N$R^6$—C(O)—NH-heteroarylalkyl, wherein the alkyl portion thereof is any alkylene described or disclosed herein.

In another embodiment of the compounds of Formula Ib, —$X^2$—$R^3$ is substituted or unsubstituted —N$R^6$—C(O)—NH-heteroarylalkyl, wherein the alkyl portion thereof is —$CH_2$—.

In another embodiment of the compounds of Formula Ib, —$X^2$—$R^3$ is substituted or unsubstituted —N$R^6$—C(O)—NH-heteroarylalkyl, wherein the heteroaryl portion thereof is any heteroaryl described or disclosed herein.

In another embodiment of the compounds of Formula Ib, —$X^2$—$R^3$ is substituted or unsubstituted —N$R^6$—C(O)—NH-heteroarylalkyl, wherein the heteroaryl portion thereof is thiazolyl.

In another embodiment of the compounds of Formula Ib, —$X^2$—$R^3$ is substituted or unsubstituted —N$R^6$—C(O)—NH-thiazolylmethyl.

In another embodiment of the compounds of Formula Ib, —$X^2$—$R^3$ is substituted —N$R^6$—C(O)—NH-thiazolylmethyl.

In another embodiment of the compounds of Formula Ib, —$X^2$—$R^3$ is —N$R^6$—C(O)—NH-thiazolylmethyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted —N$R^6$—C(O)—NH-thiazolylmethyl, and the substituent is an alkyl group.

In another embodiment of the compounds of Formula Ib, —$X^2$—$R^3$ is substituted or unsubstituted —N(alkyl)-C(O)—N$R^6$-heterocyclyl.

In another embodiment of the compounds of Formula Ib, —$X^2$—$R^3$ is substituted or unsubstituted —N(alkyl)-C(O)—N$R^6$-aryl.

In another embodiment of the compounds of Formula Ib, —$X^2$—$R^3$ is substituted or unsubstituted —N(alkyl)-C(O)—N$R^6$-phenyl.

In another embodiment of the compounds of Formula Ib, —$X^2$—$R^3$ is substituted or unsubstituted —N(alkyl)-C(O)—N$R^6$-heteroaryl.

In another embodiment of the compounds of Formula Ib, —$X^2$—$R^3$ is substituted or unsubstituted —N(alkyl)-C(O)—N$R^6$-heteroaryl, wherein said heteroaryl is any heteroaryl described or defined herein.

In another embodiment of the compounds of Formula Ib, —$X^2$—$R^3$ is substituted or unsubstituted —N(alkyl)-C(O)—N$R^6$-thiazolyl.

In another embodiment of the compounds of Formula Ib, —$X^2$—$R^3$ is substituted or unsubstituted —N(alkyl)-C(O)—N$R^6$-arylalkyl.

In another embodiment of the compounds of Formula Ib, —$X^2$—$R^3$ is substituted or unsubstituted —N(alkyl)-C(O)—N$R^6$-benzyl.

In another embodiment of the compounds of Formula Ib, —$X^2$—$R^3$ is substituted —N(alkyl)-C(O)—N$R^6$-benzyl.

In another embodiment of the compounds of Formula Ib, —$X^2$—$R^3$ is —N(alkyl)-C(O)—N$R^6$-benzyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted or unsubstituted —N(alkyl)-C(O)—N$R^6$-heteroarylalkyl.

In another embodiment of the compounds of Formula Ib, —$X^2$—$R^3$ is substituted or unsubstituted —N(alkyl)-C(O)—N$R^6$-heteroarylalkyl, wherein the alkyl portion thereof is any alkylene described or disclosed herein.

In another embodiment of the compounds of Formula Ib, —$X^2$—$R^3$ is substituted or unsubstituted —N(alkyl)-C(O)—N$R^6$-heteroarylalkyl wherein the alkyl portion thereof is —$CH_2$—.

In another embodiment of the compounds of Formula Ib, —$X^2$—$R^1$ is substituted or unsubstituted —N(alkyl)-C(O)—N$R^6$-heteroarylalkyl, wherein the heteroaryl portion thereof is any heteroaryl described or disclosed herein.

In another embodiment of the compounds of Formula Ib, —$X^2$—$R^3$ is substituted or unsubstituted —N(alkyl)-C(O)—N$R^6$-heteroarylalkyl, wherein the heteroaryl portion thereof is thiazolyl.

In another embodiment of the compounds of Formula Ib, —$X^2$—$R^3$ is substituted or unsubstituted —N(alkyl)-C(O)—N$R^6$-thiazolylmethyl.

In another embodiment of the compounds of Formula Ib, —$X^2$—$R^3$ is substituted —N(alkyl)-C(O)—N$R^6$-thiazolyl-methyl.

In another embodiment of the compounds of Formula Ib, —$X^2$—$R^3$ is —N(alkyl)-C(O)—N$R^6$-thiazolylmethyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted —N(alkyl)-C(O)—N$R^6$-thiazolyl-methyl, and the substituent is an alkyl group.

In another embodiment of the compounds of Formula Ib, —$X^2$—$R^3$ is substituted or unsubstituted —N$R^6$—C(O)—N(alkyl)-heterocyclyl.

In another embodiment of the compounds of Formula Ib, —$X^2$—$R^3$ is substituted or unsubstituted —N$R^6$—C(O)—N(alkyl)-aryl.

In another embodiment of the compounds of Formula Ib, —$X^2$—$R^3$ is substituted or unsubstituted —N$R^6$—C(O)—N(alkyl)-phenyl.

In another embodiment of the compounds of Formula Ib, —$X^2$—$R^3$ is substituted or unsubstituted —N$R^6$—C(O)—N(alkyl)-heteroaryl.

In another embodiment of the compounds of Formula Ib, —$X^2$—$R^3$ is substituted or unsubstituted —N$R^6$—C(O)—N(alkyl)-heteroaryl, wherein said heteroaryl is any heteroaryl described or defined herein.

In another embodiment of the compounds of Formula Ib, —$X^2$—$R^3$ is substituted or unsubstituted —N$R^6$—C(O)—N(alkyl)-thiazolyl.

In another embodiment of the compounds of Formula Ib, —$X^2$—$R^3$ is substituted or unsubstituted —N$R^6$—C(O)—N(alkyl)-arylalkyl.

In another embodiment of the compounds of Formula Ib, —$X^2$—$R^3$ is substituted or unsubstituted —N$R^6$—C(O)—N(alkyl)-benzyl.

In another embodiment of the compounds of Formula Ib, —$X^2$—$R^3$ is substituted —N$R^6$—C(O)—N(alkyl)-benzyl.

In another embodiment of the compounds of Formula Ib, —$X^2$—$R^3$ is —N$R^6$—C(O)—N(alkyl)-benzyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted or unsubstituted —N$R^6$—C(O)—N(alkyl)-heteroarylalkyl.

In another embodiment of the compounds of Formula Ib, —$X^2$—$R^3$ is substituted or unsubstituted —N$R^6$—C(O)—N(alkyl)-heteroarylalkyl, wherein the alkyl portion thereof is any alkylene described or disclosed herein.

In another embodiment of the compounds of Formula Ib, —$X^2$—$R^3$ is substituted or unsubstituted —N$R^6$—C(O)—N(alkyl)-heteroarylalkyl, wherein the alkyl portion thereof is —$CH_2$—.

In another embodiment of the compounds of Formula Ib, —$X^2$—$R^3$ is substituted or unsubstituted —N$R^6$—C(O)—N(alkyl)-heteroarylalkyl, wherein the heteroaryl portion thereof is any heteroaryl described or disclosed herein.

In another embodiment of the compounds of Formula Ib, —$X^2$—$R^3$ is substituted or unsubstituted —N$R^6$—C(O)—N(alkyl)-heteroarylalkyl, wherein the heteroaryl portion thereof is thiazolyl.

In another embodiment of the compounds of Formula Ib, —$X^2$—$R^3$ is substituted or unsubstituted —N$R^6$—C(O)—N(alkyl)-thiazolylmethyl.

In another embodiment of the compounds of Formula Ia, —$X^2$—$R^3$ is —N$R^6$—C(O)—N(alkyl)-thiazol-5-ylmethyl.

In another embodiment of the compounds of Formula Ib, —$X^2$—$R^3$ is substituted —N$R^6$—C(O)—N(alkyl)-thiazolyl-methyl.

In another embodiment of the compounds of Formula Ib, —$X^2$—$R^3$ is —N$R^6$—C(O)—N(alkyl)-thiazolylmethyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted —N$R^6$—C(O)—N(alkyl)-thiazolyl-methyl, and the substituent is an alkyl group.

In another embodiment of the compounds of Formula Ib, —$X^2$—$R^3$ is —N$R^6$—C(O)—N(alkyl)-(2-isopropylthiaz-olyl-4-yl)methyl.

In another embodiment of the compounds of Formula Ib, —$X^2$—$R^3$ is substituted or unsubstituted —N(alkyl)-C(O)—N(alkyl)-heterocyclyl.

In another embodiment of the compounds of Formula Ib, —$X^2$—$R^3$ is substituted or unsubstituted —N(alkyl)-C(O)—N(alkyl)-aryl.

In another embodiment of the compounds of Formula Ib, —$X^2$—$R^3$ is substituted or unsubstituted —N(alkyl)-C(O)—N(alkyl)-phenyl.

In another embodiment of the compounds of Formula Ib, —$X^2$—$R^3$ is substituted or unsubstituted —N(alkyl)-C(O)—N(alkyl)-heteroaryl.

In another embodiment of the compounds of Formula Ib, —$X^2$—$R^3$ is substituted or unsubstituted —N(alkyl)-C(O)—N(alkyl)-heteroaryl, wherein said heteroaryl is any heteroaryl described or defined herein.

In another embodiment of the compounds of Formula Ib, —$X^2$—$R^3$ is substituted or unsubstituted —N(alkyl)-C(O)—N(alkyl)-thiazolyl.

In another embodiment of the compounds of Formula Ib, —$X^2$—$R^3$ is substituted or unsubstituted —N(alkyl)-C(O)—N(alkyl)-arylalkyl.

In another embodiment of the compounds of Formula Ib, —$X^2$—$R^3$ is substituted or unsubstituted —N(alkyl)-C(O)—N(alkyl)-benzyl.

In another embodiment of the compounds of Formula Ib, —$X^2$—$R^3$ is substituted —N(alkyl)-C(O)—N(alkyl)-benzyl.

In another embodiment of the compounds of Formula Ib, —$X^2$—$R^3$ is —N(alkyl)-C(O)—N(alkyl)-benzyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted or unsubstituted —N(alkyl)-C(O)—N(alkyl)-heteroarylalkyl.

In another embodiment of the compounds of Formula Ib, —$X^2$—$R^3$ is substituted or unsubstituted —N(alkyl)-C(O)—N(alkyl)-heteroarylalkyl, wherein the alkyl portion thereof is any alkylene described or disclosed herein.

In another embodiment of the compounds of Formula Ib, —$X^2$—$R^3$ is substituted or unsubstituted —N(alkyl)-C(O)—N(alkyl)-heteroarylalkyl, wherein the alkyl portion thereof is —$CH_2$—.

In another embodiment of the compounds of Formula Ib, —$X^2$—$R^3$ is substituted or unsubstituted —N(alkyl)-C(O)—N(alkyl)-heteroarylalkyl, wherein the heteroaryl portion thereof is any heteroaryl described or disclosed herein.

In another embodiment of the compounds of Formula Ib, —$X^2$—$R^3$ is substituted or unsubstituted —N(alkyl)-C(O)—N(alkyl)-heteroarylalkyl, wherein the heteroaryl portion thereof is thiazolyl.

In another embodiment of the compounds of Formula Ib, —$X^2$—$R^3$ is substituted or unsubstituted —N(alkyl)-C(O)—N(alkyl)-thiazolylmethyl.

In another embodiment of the compounds of Formula Ib, —$X^2$—$R^3$ is substituted —N(alkyl)-C(O)—N(alkyl)-thiazolylmethyl.

In another embodiment of the compounds of Formula Ib, —$X^2$—$R^3$ is —N(alkyl)-C(O)—N(alkyl)-thiazolylmethyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted —N(alkyl)-C(O)—N(alkyl)-thiazolylmethyl, and the substituent is an alkyl group.

In another embodiment of the compounds of Formula Ib, —$X^2$—$R^3$ is substituted or unsubstituted —NH—C(O)—N($CH_3$)-heterocyclyl.

In another embodiment of the compounds of Formula Ib, —$X^2$—$R^3$ is substituted or unsubstituted —NH—C(O)—N($CH_3$)-aryl.

In another embodiment of the compounds of Formula Ib, —$X^2$—$R^3$ is substituted or unsubstituted —NH—C(O)—N($CH_3$)-phenyl.

In another embodiment of the compounds of Formula Ib, —$X^2$—$R^3$ is substituted or unsubstituted —NH—C(O)—N($CH_3$)-heteroaryl.

In another embodiment of the compounds of Formula Ib, —$X^2$—$R^3$ is substituted or unsubstituted —NH—C(O)—N($CH_3$)-heteroaryl, wherein said heteroaryl is any heteroaryl described or defined herein.

In another embodiment of the compounds of Formula Ib, —$X^2$—$R^3$ is substituted or unsubstituted —NH—C(O)—N($CH_3$)-thiazolyl.

In another embodiment of the compounds of Formula Ib, —$X^2$—$R^3$ is substituted or unsubstituted —NH—C(O)—N($CH_3$)-arylalkyl.

In another embodiment of the compounds of Formula Ib, —$X^2$—$R^3$ is substituted or unsubstituted —NH—C(O)—N($CH_3$)-benzyl.

In another embodiment of the compounds of Formula Ib, —$X^2$—$R^3$ is substituted —NH—C(O)—N($CH_3$)-benzyl.

In another embodiment of the compounds of Formula Ib, —$X^2$—$R^3$ is —NH—C(O)—N($CH_3$)-benzyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted or unsubstituted —NH—C(O)—N($CH_3$)-heteroarylalkyl.

In another embodiment of the compounds of Formula Ib, —$X^2$—$R^3$ is substituted or unsubstituted —NH—C(O)—N($CH_3$)-heteroarylalkyl, wherein the alkyl portion thereof is any alkylene described or disclosed herein.

In another embodiment of the compounds of Formula Ib, —$X^2$—$R^3$ is substituted or unsubstituted —NH—C(O)—N($CH_3$)-heteroarylalkyl, wherein the alkyl portion thereof is —$CH_2$—.

In another embodiment of the compounds of Formula Ib, —$X^2$—$R^3$ is substituted or unsubstituted —NH—C(O)—N($CH_3$)-heteroarylalkyl, wherein the heteroaryl portion thereof is any heteroaryl described or disclosed herein.

In another embodiment of the compounds of Formula Ib, —$X^2$—$R^3$ is substituted or unsubstituted —NH—C(O)—N($CH_3$)-heteroarylalkyl, wherein the heteroaryl portion thereof is thiazolyl.

In another embodiment of the compounds of Formula Ib, —$X^2$—$R^3$ is substituted or unsubstituted —NH—C(O)—N($CH_3$)-thiazolylmethyl.

In another embodiment of the compounds of Formula Ib, —$X^2$—$R^3$ is —NH—C(O)—N($CH_3$)-thiazol-5-ylmethyl.

In another embodiment of the compounds of Formula Ib, —$X^2$—$R^3$ is substituted —NH—C(O)—N($CH_3$)-thiazolylmethyl.

In another embodiment of the compounds of Formula Ib, —$X^1$—$R^1$ is —NH—C(O)—N($CH_3$)-thiazolylmethyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted —NH—C(O)—N($CH_3$)-thiazolylmethyl, and the substituent is an alkyl group.

In another embodiment of the compounds of Formula Ib, —$X^2$—$R^3$ is —NH—C(O)—N($CH_3$)-(2-isopropylthiazolyl-4-yl)methyl.

In another embodiment of the compounds of Formula Ib, —$X^2$—$R^3$ is substituted or unsubstituted —$NR^6$-heterocyclyl.

In another embodiment of the compounds of Formula Ib, —$X^2$—$R^3$ is substituted or unsubstituted —$NR^6$-aryl.

In another embodiment of the compounds of Formula Ib, —$X^2$—$R^3$ is substituted or unsubstituted —$NR^6$-phenyl.

In another embodiment of the compounds of Formula Ib, —$X^2$—$R^3$ is substituted or unsubstituted —$NR^6$-heteroaryl.

In another embodiment of the compounds of Formula Ib, —$X^2$—$R^3$ is substituted or unsubstituted —$NR^6$-heteroaryl, wherein said heteroaryl is any heteroaryl described or defined herein.

In another embodiment of the compounds of Formula Ib, —$X^2$—$R^3$ is substituted or unsubstituted —$NR^6$-thiazolyl.

In another embodiment of the compounds of Formula Ib, —$X^2$—$R^3$ is substituted or unsubstituted —$NR^6$-arylalkyl.

In another embodiment of the compounds of Formula Ib, —$X^2$—$R^3$ is substituted or unsubstituted —$NR^6$-benzyl.

In another embodiment of the compounds of Formula Ib, —$X^2$—$R^3$ is substituted —$NR^6$-benzyl.

In another embodiment of the compounds of Formula Ib, —$X^2$—$R^3$ is —$NR^6$-benzyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted or unsubstituted —$NR^6$-heteroarylalkyl.

In another embodiment of the compounds of Formula Ib, —$X^2$—$R^3$ is substituted or unsubstituted —$NR^6$-heteroarylalkyl, wherein the alkyl portion thereof is any alkylene described or disclosed herein.

In another embodiment of the compounds of Formula Ib, —$X^2$—$R^3$ is substituted or unsubstituted —$NR^6$-heteroarylalkyl, wherein the alkyl portion thereof is —$CH_2$—.

In another embodiment of the compounds of Formula Ib, —$X^2$—$R^3$ is substituted or unsubstituted —$NR^6$-heteroarylalkyl wherein the heteroaryl portion thereof is any heteroaryl described or disclosed herein.

In another embodiment of the compounds of Formula Ib, —$X^2$—$R^3$ is substituted or unsubstituted —$NR^6$-heteroarylalkyl, wherein the heteroaryl portion thereof is thiazolyl.

In another embodiment of the compounds of Formula Ib, —$X^2$—$R^3$ is substituted or unsubstituted —$NR^6$-thiazolylmethyl.

In another embodiment of the compounds of Formula Ib, —$X^2$—$R^3$ is substituted —$NR^6$-thiazolylmethyl.

In another embodiment of the compounds of Formula Ib, —$X^2$—$R^3$ is —$NR^6$-thiazolylmethyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted —$NR^6$-thiazolylmethyl, and the substituent is an alkyl group.

In another embodiment of the compounds of Formula Ib, —$X^2$—$R^3$ is substituted or unsubstituted —NH-heterocyclyl.

In another embodiment of the compounds of Formula Ib, —$X^2$—$R^3$ is substituted or unsubstituted —NH-aryl.

In another embodiment of the compounds of Formula Ib, —$X^2$—$R^3$ is substituted or unsubstituted —NH-phenyl.

In another embodiment of the compounds of Formula Ib, —$X^2$—$R^3$ is substituted or unsubstituted —NH-heteroaryl.

In another embodiment of the compounds of Formula Ib, —$X^2$—$R^3$ is substituted or unsubstituted —NH-heteroaryl, wherein said heteroaryl is any heteroaryl described or defined herein.

In another embodiment of the compounds of Formula Ib, —$X^2$—$R^3$ is substituted or unsubstituted —NH-thiazolyl.

In another embodiment of the compounds of Formula Ib, —$X^2$—$R^3$ is substituted or unsubstituted —NH-arylalkyl.

In another embodiment of the compounds of Formula Ib, —$X^2$—$R^3$ is substituted or unsubstituted —NH-benzyl.

In another embodiment of the compounds of Formula Ib, —$X^2$—$R^3$ is substituted —NH-benzyl.

In another embodiment of the compounds of Formula Ib, —$X^2$—$R^3$ is —NH-benzyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted or unsubstituted —NH-heteroarylalkyl.

In another embodiment of the compounds of Formula Ib, —$X^2$—$R^3$ is substituted or unsubstituted —NH-heteroarylalkyl, wherein the alkyl portion thereof is any alkylene described or disclosed herein.

In another embodiment of the compounds of Formula Ib, —$X^2$—$R^3$ is substituted or unsubstituted —NH-heteroarylalkyl, wherein the alkyl portion thereof is —$CH_2$—.

In another embodiment of the compounds of Formula Ib, —$X^2$—$R^3$ is substituted or unsubstituted —NH-heteroarylalkyl, wherein the heteroaryl portion thereof is any heteroaryl described or disclosed herein.

In another embodiment of the compounds of Formula Ib, —$X^2$—$R^3$ is substituted or unsubstituted —NH-heteroarylalkyl, wherein the heteroaryl portion thereof is thiazolyl.

In another embodiment of the compounds of Formula Ib, —$X^2$—$R^3$ is substituted or unsubstituted —NH-thiazolylmethyl.

In another embodiment of the compounds of Formula Ib, —$X^2$—$R^3$ is substituted —NH-thiazolylmethyl.

In another embodiment of the compounds of Formula Ib, —$X^2$—$R^3$ is —NH-thiazolylmethyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted —NH-thiazolylmethyl, and the substituent is an alkyl group.

In another embodiment of the compounds of Formula Ib, —$X^2$—$R^3$ is substituted or unsubstituted —N(alkyl)-heterocyclyl.

In another embodiment of the compounds of Formula Ib, —$X^2$—$R^3$ is substituted or unsubstituted —N(alkyl)-aryl.

In another embodiment of the compounds of Formula Ib, —$X^2$—$R^3$ is substituted or unsubstituted —N(alkyl)-phenyl.

In another embodiment of the compounds of Formula Ib, —$X^2$—$R^3$ is substituted or unsubstituted —N(alkyl)-heteroaryl.

In another embodiment of the compounds of Formula Ib, —$X^2$—$R^3$ is substituted or unsubstituted —N(alkyl)-heteroaryl, wherein said heteroaryl is any heteroaryl described or defined herein.

In another embodiment of the compounds of Formula Ib, —$X^2$—$R^3$ is substituted or unsubstituted —N(alkyl)-thiazolyl.

In another embodiment of the compounds of Formula Ib, —$X^2$—$R^3$ is substituted or unsubstituted —N(alkyl)-arylalkyl.

In another embodiment of the compounds of Formula Ib, —$X^2$—$R^3$ is substituted or unsubstituted —N(alkyl)-benzyl.

In another embodiment of the compounds of Formula Ib, —$X^2$—$R^3$ is substituted —N(alkyl)-benzyl.

In another embodiment of the compounds of Formula Ib, —$X^2$—$R^3$ is —N(alkyl)-benzyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted or unsubstituted —N(alkyl)-heteroarylalkyl.

In another embodiment of the compounds of Formula Ib, —$X^2$—$R^3$ is substituted or unsubstituted —N(alkyl)-heteroarylalkyl, wherein the alkyl portion thereof is any alkylene described or disclosed herein.

In another embodiment of the compounds of Formula Ib, —$X^2$—$R^3$ is substituted or unsubstituted —N(alkyl)-heteroarylalkyl, wherein the alkyl portion thereof is —$CH_2$—.

In another embodiment of the compounds of Formula Ib, —$X^2$—$R^3$ is substituted or unsubstituted —N(alkyl)-heteroarylalkyl, wherein the heteroaryl portion thereof is any heteroaryl described or disclosed herein.

In another embodiment of the compounds of Formula Ib, —$X^2$—$R^3$ is substituted or unsubstituted —N(alkyl)-heteroarylalkyl, wherein the heteroaryl portion thereof is thiazolyl.

In another embodiment of the compounds of Formula Ib, —$X^2$—$R^3$ is substituted or unsubstituted —N(alkyl)-thiazolylmethyl.

In another embodiment of the compounds of Formula Ib, —$X^2$—$R^3$ is substituted —N(alkyl)-thiazolylmethyl.

In another embodiment of the compounds of Formula Ib, —$X^2$—$R^3$ is —N(alkyl)-thiazolylmethyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted —N(alkyl)-thiazolylmethyl, and the substituent is an alkyl group.

In another embodiment of the compounds of Formula Ib, —$X^2$—$R^3$ is substituted or unsubstituted —N(cycloalkyl)-heterocyclyl.

In another embodiment of the compounds of Formula Ib, —$X^2$—$R^3$ is substituted or unsubstituted —N(cycloalkyl)-aryl.

In another embodiment of the compounds of Formula Ib, —$X^2$—$R^3$ is substituted or unsubstituted —N(cycloalkyl)-phenyl.

In another embodiment of the compounds of Formula Ib, —$X^2$—$R^3$ is substituted or unsubstituted —N(cycloalkyl)-heteroaryl.

In another embodiment of the compounds of Formula Ib, —$X^2$—$R^3$ is substituted or unsubstituted —N(cycloalkyl)-heteroaryl, wherein said heteroaryl is any heteroaryl described or defined herein.

In another embodiment of the compounds of Formula Ib, —$X^2$—$R^3$ is substituted or unsubstituted —N(cycloalkyl)-thiazolyl.

In another embodiment of the compounds of Formula Ib, —$X^2$—$R^3$ is substituted or unsubstituted —N(cycloalkyl)-arylalkyl.

In another embodiment of the compounds of Formula Ib, —$X^2$—$R^3$ is substituted or unsubstituted —N(cycloalkyl)-benzyl.

In another embodiment of the compounds of Formula Ib, —$X^2$—$R^3$ is substituted —N(cycloalkyl)-benzyl.

In another embodiment of the compounds of Formula Ib, —$X^2$—$R^3$ is —N(cycloalkyl)-benzyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted or unsubstituted —N(cycloalkyl)-heteroarylalkyl.

In another embodiment of the compounds of Formula Ib, —$X^2$—$R^3$ is substituted or unsubstituted —N(cycloalkyl)-heteroarylalkyl, wherein the alkyl portion thereof is any alkylene described or disclosed herein.

In another embodiment of the compounds of Formula Ib, —$X^2$—$R^3$ is substituted or unsubstituted —N(cycloalkyl)-heteroarylalkyl, wherein the alkyl portion thereof is —$CH_2$—.

In another embodiment of the compounds of Formula Ib, —$X^2$—$R^3$ is substituted or unsubstituted —N(cycloalkyl)-heteroarylalkyl, wherein the heteroaryl portion thereof is any heteroaryl described or disclosed herein.

In another embodiment of the compounds of Formula Ib, —$X^2$—$R^3$ is substituted or unsubstituted —N(cycloalkyl)-heteroarylalkyl, wherein the heteroaryl portion thereof is thiazolyl.

In another embodiment of the compounds of Formula Ib, —$X^2$—$R^3$ is substituted or unsubstituted —N(cycloalkyl)-thiazolylmethyl.

In another embodiment of the compounds of Formula Ib, —$X^2$—$R^3$ is substituted —N(cycloalkyl)-thiazolylmethyl.

In another embodiment of the compounds of Formula Ib, —$X^2$—$R^3$ is —N(cycloalkyl)-thiazolylmethyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted —N(cycloalkyl)-thiazolylmethyl, and the substituent is an alkyl group.

In another embodiment of the compounds of Formula Ib, —$X^2$—$R^3$ is substituted or unsubstituted —O—C(O)—$NR^6$-heterocyclyl.

In another embodiment of the compounds of Formula Ib, —$X^2$—$R^3$ is substituted or unsubstituted —O—C(O)—$NR^6$-aryl.

In another embodiment of the compounds of Formula Ib, —$X^2$—$R^3$ is substituted or unsubstituted —O—C(O)—$NR^6$-phenyl.

In another embodiment of the compounds of Formula Ib, —$X^2$—$R^3$ is substituted or unsubstituted —O—C(O)—$NR^6$-heteroaryl.

In another embodiment of the compounds of Formula Ib, —$X^2$—$R^3$ is substituted or unsubstituted —O—C(O)—$NR^6$-heteroaryl, wherein said heteroaryl is any heteroaryl described or defined herein.

In another embodiment of the compounds of Formula Ib, —$X^2$—$R^3$ is substituted or unsubstituted —O—C(O)—$NR^6$-thiazolyl.

In another embodiment of the compounds of Formula Ib, —$X^2$—$R^3$ is substituted or unsubstituted —O—C(O)—$NR^6$-arylalkyl.

In another embodiment of the compounds of Formula Ib, —$X^2$—$R^3$ is substituted or unsubstituted —O—C(O)—$NR^6$-benzyl.

In another embodiment of the compounds of Formula Ib, —$X^2$—$R^3$ is substituted —O—C(O)—$NR^6$-benzyl.

In another embodiment of the compounds of Formula Ib, —$X^2$—$R^3$ is —O—C(O)—$NR^6$-benzyl substituted with one or more substituents selected from the group consisting of alkyl, substituted alkyl halo, hydroxyl, amino, haloalkyl, and cyano.

In another embodiment of the compounds of Formula Ib, —$X^2$—$R^3$ is substituted or unsubstituted —O—C(O)—$NR^6$-heteroarylalkyl.

In another embodiment of the compounds of Formula Ib, —$X^2$—$R^3$ is substituted or unsubstituted —O—C(O)—$NR^6$-heteroarylalkyl, wherein the alkyl portion thereof is any alkylene described or disclosed herein.

In another embodiment of the compounds of Formula Ib, —$X^2$—$R^3$ is substituted or unsubstituted —O—C(O)—$NR^6$-heteroarylalkyl, wherein the alkyl portion thereof is —$CH_2$—.

In another embodiment of the compounds of Formula Ib, —$X^2$—$R^3$ is substituted or unsubstituted —O—C(O)—$NR^6$-heteroarylalkyl, wherein the heteroaryl portion thereof is any heteroaryl described or disclosed herein.

In another embodiment of the compounds of Formula Ib, —$X^2$—$R^3$ is substituted or unsubstituted —O—C(O)—$NR^6$-heteroarylalkyl, wherein the heteroaryl portion thereof is thiazolyl.

In another embodiment of the compounds of Formula Ib, —$X^2$—$R^3$ is substituted or unsubstituted —O—C(O)—$NR^6$-thiazolylmethyl.

In another embodiment of the compounds of Formula Ib, —$X^2$—$R^3$ is substituted —O—C(O)—$NR^6$-thiazolylmethyl.

In another embodiment of the compounds of Formula Ib, —$X^2$—$R^3$ is —O—C(O)—$NR^6$-thiazolylmethyl substituted with one or more substituents selected from the group consisting of alkyl, substituted alkyl halo, hydroxyl, amino, haloalkyl, and cyano.

In another embodiment of the compounds of Formula Ib, —$X^2$—$R^3$ is substituted —O—C(O)—$NR^6$-thiazolylmethyl, and the substituent is an alkyl group.

In another embodiment of the compounds of Formula Ib, —$X^2$—$R^3$ is substituted or unsubstituted —O—C(O)—NH-heterocyclyl.

In another embodiment of the compounds of Formula Ib, —$X^2$—$R^3$ is substituted or unsubstituted —O—C(O)—NH-aryl.

In another embodiment of the compounds of Formula Ib, —$X^2$—$R^3$ is substituted or unsubstituted —O—C(O)—NH-phenyl.

In another embodiment of the compounds of Formula Ib, —$X^2$—$R^3$ is substituted or unsubstituted —O—C(O)—NH-heteroaryl.

In another embodiment of the compounds of Formula Ib, —$X^2$—$R^3$ is substituted or unsubstituted —O—C(O)—NH-heteroaryl, wherein said heteroaryl is any heteroaryl described or defined herein.

In another embodiment of the compounds of Formula Ib, —$X^2$—$R^3$ is substituted or unsubstituted —O—C(O)—NH-thiazolyl.

In another embodiment of the compounds of Formula Ib, —$X^2$—$R^3$ is substituted or unsubstituted —O—C(O)—NH-arylalkyl.

In another embodiment of the compounds of Formula Ib, —$X^2$—$R^3$ is substituted or unsubstituted —O—C(O)—NH-benzyl.

In another embodiment of the compounds of Formula Ib, —$X^2$—$R^3$ is substituted —O—C(O)—NH-benzyl.

In another embodiment of the compounds of Formula Ib, —$X^2$—$R^3$ is —O—C(O)—NH-benzyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted or unsubstituted —O—C(O)—NH-heteroarylalkyl.

In another embodiment of the compounds of Formula Ib, —$X^2$—$R^3$ is substituted or unsubstituted —O—C(O)—NH-heteroarylalkyl, wherein the alkyl portion thereof is any alkylene described or disclosed herein.

In another embodiment of the compounds of Formula Ib, —$X^2$—$R^3$ is substituted or unsubstituted —O—C(O)—NH-heteroarylalkyl, wherein the alkyl portion thereof is —$CH_2$—.

In another embodiment of the compounds of Formula Ib, —$X^2$—$R^3$ is substituted or unsubstituted —O—C(O)—NH-heteroarylalkyl, wherein the heteroaryl portion thereof is any heteroaryl described or disclosed herein.

In another embodiment of the compounds of Formula Ib, —$X^2$—$R^3$ is substituted or unsubstituted —O—C(O)—NH-heteroarylalkyl, wherein the heteroaryl portion thereof is thiazolyl.

In another embodiment of the compounds of Formula Ib, —$X^2$—$R^3$ is substituted or unsubstituted —O—C(O)—NH-thiazolylmethyl.

In another embodiment of the compounds of Formula Ib, —$X^2$—$R^3$ is substituted —O—C(O)—NH-thiazolylmethyl.

In another embodiment of the compounds of Formula Ib, —$X^2$—$R^3$ is —O—C(O)—NH-thiazolylmethyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted —O—C(O)—NH-thiazolylmethyl, and the substituent is an alkyl group.

In another embodiment of the compounds of Formula Ib, —$X^2$—$R^3$ is substituted or unsubstituted —O—C(O)—N(alkyl)-heterocyclyl.

In another embodiment of the compounds of Formula Ib, —$X^2$—$R^3$ is substituted or unsubstituted —O—C(O)—N(alkyl)-aryl.

In another embodiment of the compounds of Formula Ib, —$X^2$—$R^3$ is substituted or unsubstituted —O—C(O)—N(alkyl)-phenyl.

In another embodiment of the compounds of Formula Ib, —$X^2$—$R^3$ is substituted or unsubstituted —O—C(O)—N(alkyl)-heteroaryl.

In another embodiment of the compounds of Formula Ib, —$X^2$—$R^3$ is substituted or unsubstituted —O—C(O)—N(alkyl)-heteroaryl, wherein said heteroaryl is any heteroaryl described or defined herein.

In another embodiment of the compounds of Formula Ib, —$X^2$—$R^3$ is substituted or unsubstituted —O—C(O)—N(alkyl)-thiazolyl.

In another embodiment of the compounds of Formula Ib, —$X^2$—$R^3$ is substituted or unsubstituted —O—C(O)—N(alkyl)-arylalkyl.

In another embodiment of the compounds of Formula Ib, —$X^2$—$R^3$ is substituted or unsubstituted —O—C(O)—N(alkyl)-benzyl.

In another embodiment of the compounds of Formula Ib, —$X^2$—$R^3$ is substituted —O—C(O)—N(alkyl)-benzyl.

In another embodiment of the compounds of Formula Ib, —$X^2$—$R^3$ is —O—C(O)—N(alkyl)-benzyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted or unsubstituted —O—C(O)—N(alkyl)-heteroarylalkyl.

In another embodiment of the compounds of Formula Ib, —$X^2$—$R^3$ is substituted or unsubstituted —O—C(O)—N(alkyl)-heteroarylalkyl, wherein the alkyl portion thereof is any alkylene described or disclosed herein.

In another embodiment of the compounds of Formula Ib, —$X^2$—$R^3$ is substituted or unsubstituted —O—C(O)—N(alkyl)-heteroarylalkyl, wherein the alkyl portion thereof is —$CH_2$—.

In another embodiment of the compounds of Formula Ib, —$X^2$—$R^3$ is substituted or unsubstituted —O—C(O)—N(alkyl)-heteroarylalkyl, wherein the heteroaryl portion thereof is any heteroaryl described or disclosed herein.

In another embodiment of the compounds of Formula Ib, —$X^2$—$R^3$ is substituted or unsubstituted —O—C(O)—N(alkyl)-heteroarylalkyl, wherein the heteroaryl portion thereof is thiazolyl.

In another embodiment of the compounds of Formula Ib, —$X^2$—$R^3$ is substituted or unsubstituted —O—C(O)—N(alkyl)-thiazolylmethyl.

In another embodiment of the compounds of Formula Ib, —$X^2$—$R^3$ is substituted —O—C(O)—N(alkyl)-thiazolylmethyl.

In another embodiment of the compounds of Formula Ib, —$X^2$—$R^3$ is —O—C(O)—N(alkyl)-thiazolylmethyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted —O—C(O)—N(alkyl)-thiazolylmethyl, and the substituent is an alkyl group.

In another embodiment of the compounds of Formula Ib, —$X^2$—$R^3$ is substituted or unsubstituted —$NR^6$—C(O)—O-heterocyclyl.

In another embodiment of the compounds of Formula Ib, —$X^2$—$R^3$ is substituted or unsubstituted —$NR^6$—C(O)—O-aryl.

In another embodiment of the compounds of Formula Ib, —$X^2$—$R^3$ is substituted or unsubstituted —$NR^6$—C(O)—O-phenyl.

In another embodiment of the compounds of Formula Ib, —$X^2$—$R^3$ is substituted or unsubstituted —$NR^6$—C(O)—O-heteroaryl.

In another embodiment of the compounds of Formula Ib, —$X^2$—$R^3$ is substituted or unsubstituted —$NR^6$—C(O)—O-heteroaryl, wherein said heteroaryl is any heteroaryl described or defined herein.

In another embodiment of the compounds of Formula Ib, —$X^2$—$R^3$ is substituted or unsubstituted —$NR^6$—C(O)—O-thiazolyl.

In another embodiment of the compounds of Formula Ib, —$X^2$—$R^3$ is substituted or unsubstituted —$NR^6$—C(O)—O-arylalkyl.

In another embodiment of the compounds of Formula Ib, —$X^2$—$R^3$ is substituted or unsubstituted —$NR^6$—C(O)—O-benzyl.

In another embodiment of the compounds of Formula Ib, —$X^2$—$R^3$ is substituted —$NR^6$—C(O)—O-benzyl.

In another embodiment of the compounds of Formula Ib, —$X^2$—$R^3$ is —$NR^6$—C(O)—O-benzyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted or unsubstituted —$NR^6$—C(O)—O-heteroarylalkyl.

In another embodiment of the compounds of Formula Ib, —$X^2$—$R^3$ is substituted or unsubstituted —$NR^6$—C(O)—O-heteroarylalkyl, wherein the alkyl portion thereof is any alkylene described or disclosed herein.

In another embodiment of the compounds of Formula Ib, —$X^2$—$R^3$ is substituted or unsubstituted —$NR^6$—C(O)—O-heteroarylalkyl, wherein the alkyl portion thereof is —$CH_2$—.

In another embodiment of the compounds of Formula Ib, —$X^2$—$R^3$ is substituted or unsubstituted —$NR^6$—C(O)—O-heteroarylalkyl, wherein the heteroaryl portion thereof is any heteroaryl described or disclosed herein.

In another embodiment of the compounds of Formula Ib, —$X^2$—$R^3$ is substituted or unsubstituted —$NR^6$—C(O)—O-heteroarylalkyl, wherein the heteroaryl portion thereof is thiazolyl.

In another embodiment of the compounds of Formula Ib, —$X^2$—$R^3$ is substituted or unsubstituted —$NR^6$—C(O)—O-thiazolylmethyl.

In another embodiment of the compounds of Formula Ib, —$X^2$—$R^3$ is substituted —$NR^6$—C(O)—O-thiazolylmethyl.

In another embodiment of the compounds of Formula Ib, —$X^2$—$R^3$ is —$NR^6$—C(O)—O-thiazolylmethyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted —$NR^6$—C(O)—O-thiazolylmethyl, and the substituent is an alkyl group.

In another embodiment of the compounds of Formula Ib, —$X^2$—$R^3$ is substituted or unsubstituted —O-heterocyclyl.

In another embodiment of the compounds of Formula Ib, —$X^2$—$R^3$ is —O-(tetrahydro-2H-furo[2,3-b]furan-3-yl).

In another embodiment of the compounds of Formula Ib, —$X^2$—$R^3$ is —O-(tetrahydrofuran-3-yl).

In another embodiment of the compounds of Formula Ib, —$X^2$—$R^3$ is substituted or unsubstituted —O-aryl.

In another embodiment of the compounds of Formula Ib, —$X^2$—$R^3$ is substituted or unsubstituted —O-phenyl.

In another embodiment of the compounds of Formula Ib, —$X^2$—$R^3$ is substituted or unsubstituted —O-heteroaryl.

In another embodiment of the compounds of Formula Ib, —$X^2$—$R^3$ is substituted or unsubstituted —O-heteroaryl, wherein said heteroaryl is any heteroaryl described or defined herein.

In another embodiment of the compounds of Formula Ib, —$X^2$—$R^3$ is substituted or unsubstituted —O-thiazolyl.

In another embodiment of the compounds of Formula Ib, —$X^2$—$R^3$ is substituted or unsubstituted —O-arylalkyl.

In another embodiment of the compounds of Formula Ib, —$X^2$—$R^3$ is substituted or unsubstituted —O-benzyl.

In another embodiment of the compounds of Formula Ib, —$X^2$—$R^3$ is substituted —O-benzyl.

In another embodiment of the compounds of Formula Ib, —$X^2$—$R^3$ is —O-benzyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted or unsubstituted —O-heteroarylalkyl.

In another embodiment of the compounds of Formula Ib, —$X^2$—$R^3$ is substituted or unsubstituted —O-heteroarylalkyl, wherein the alkyl portion thereof is any alkylene described or disclosed herein.

In another embodiment of the compounds of Formula Ib, —$X^2$—$R^3$ is substituted or unsubstituted —O-heteroarylalkyl, wherein the alkyl portion thereof is —$CH_2$—.

In another embodiment of the compounds of Formula Ib, —$X^2$—$R^3$ is substituted or unsubstituted —O-heteroarylalkyl, wherein the heteroaryl portion thereof is any heteroaryl described or disclosed herein.

In another embodiment of the compounds of Formula Ib, —$X^2$—$R^3$ is substituted or unsubstituted —O-heteroarylalkyl, wherein the heteroaryl portion thereof is thiazolyl.

In another embodiment of the compounds of Formula Ib, —$X^2$—$R^3$ is substituted or unsubstituted —O-thiazolylmethyl.

In another embodiment of the compounds of Formula Ib, —$X^2$—$R^3$ is substituted —O-thiazolylmethyl.

In another embodiment of the compounds of Formula Ib, —$X^2$—$R^3$ is —O-thiazolylmethyl substituted with one or more substituents selected from the group consisting of alkyl, substituted alkyl, halo, hydroxyl, amino, haloalkyl, and cyano.

In another embodiment of the compounds of Formula Ib, —$X^2$—$R^3$ is substituted —O-thiazolylmethyl, and the substituent is an alkyl group.

In another embodiment of the compounds of Formula Ib, -L-$X^2$—$R^3$ is substituted or unsubstituted —$NR^6$—C(O)—$NR^6$-heterocyclyl.

In another embodiment of the compounds of Formula Ib, -L-$X^2$—$R^3$ is substituted or unsubstituted —$NR^6$—C(O)—$NR^6$-aryl.

In another embodiment of the compounds of Formula Ib, -L-$X^2$—$R^3$ is substituted or unsubstituted —$NR^6$—C(O)—$NR^6$-phenyl.

In another embodiment of the compounds of Formula Ib, -L-$X^2$—$R^3$ is substituted or unsubstituted —$NR^6$—C(O)—$NR^6$-heteroaryl.

In another embodiment of the compounds of Formula Ib, -L-$X^2$—$R^3$ is substituted or unsubstituted —$NR^6$—C(O)—$NR^6$-heteroaryl, wherein said heteroaryl is any heteroaryl described or defined herein.

In another embodiment of the compounds of Formula Ib, -L-$X^2$—$R^3$ is substituted or unsubstituted —$NR^6$—C(O)—$NR^6$-thiazolyl.

In another embodiment of the compounds of Formula Ib, -L-$X^2$—$R^3$ is substituted or unsubstituted —$NR^6$—C(O)—$NR^6$-arylalkyl.

In another embodiment of the compounds of Formula Ib, -L-$X^2$—$R^3$ is substituted or unsubstituted —$NR^6$—C(O)—$NR^6$-benzyl.

In another embodiment of the compounds of Formula Ib, -L-$X^2$—$R^3$ is substituted —$NR^6$—C(O)—$NR^6$-benzyl.

In another embodiment of the compounds of Formula Ib, -L-$X^2$—$R^3$ is —$NR^6$—C(O)—$NR^6$-benzyl substituted with one or more substituents selected from the group consisting of alkyl, substituted alkyl, halo, hydroxyl, amino, haloalkyl, and cyano.

In another embodiment of the compounds of Formula Ib, -L-$X^2$—$R^3$ is substituted or unsubstituted —$NR^6$—C(O)—$NR^6$-heteroarylalkyl.

In another embodiment of the compounds of Formula Ib, -L-$X^2$—$R^3$ is substituted or unsubstituted —$NR^6$—C(O)—$NR^6$-heteroarylalkyl, wherein the alkyl portion thereof is any alkylene described or disclosed herein.

In another embodiment of the compounds of Formula Ib, -L-$X^2$—$R^3$ is substituted or unsubstituted —$NR^6$—C(O)—$NR^6$-heteroarylalkyl, wherein the alkyl portion thereof is —$CH_2$—.

In another embodiment of the compounds of Formula Ib, -L-$X^2$—$R^3$ is substituted or unsubstituted —$NR^6$—C(O)—$NR^6$-heteroarylalkyl, wherein the heteroaryl portion thereof is any heteroaryl described or disclosed herein.

In another embodiment of the compounds of Formula Ib, -L-$X^2$—$R^3$ is substituted or unsubstituted —$NR^6$—C(O)—$NR^6$-heteroarylalkyl, wherein the heteroaryl portion thereof is thiazolyl.

In another embodiment of the compounds of Formula Ib, -L-$X^2$—$R^3$ is substituted or unsubstituted —$NR^6$—C(O)—$NR^6$-thiazolylmethyl.

In another embodiment of the compounds of Formula Ib, -L-$X^2$—$R^3$ is substituted —$NR^6$—C(O)—$NR^6$-thiazolylmethyl.

In another embodiment of the compounds of Formula Ib, -L-$X^2$—$R^3$ is —$NR^6$—C(O)—$NR^6$-thiazolylmethyl substituted with one or more substituents selected from the group consisting of alkyl, substituted alkyl, halo, hydroxyl, amino, haloalkyl, and cyano.

In another embodiment of the compounds of Formula Ib, -L-$X^2$—$R^3$ is substituted —$NR^6$—C(O)—$NR^6$-thiazolylmethyl, and the substituent is an alkyl group.

In another embodiment of the compounds of Formula Ib, -L-$X^2$—$R^3$ is substituted or unsubstituted —$CHR^7$—$NR^6$—C(O)—$NR^6$-heterocyclyl.

In another embodiment of the compounds of Formula Ib, -L-$X^2$—$R^3$ is substituted or unsubstituted —$CHR^7$—$NR^6$—C(O)—$NR^6$-aryl.

In another embodiment of the compounds of Formula Ib, -L-$X^2$—$R^3$ is substituted or unsubstituted —$CHR^7$—$NR^6$—C(O)—$NR^6$-phenyl.

In another embodiment of the compounds of Formula Ib, -L-$X^2$—$R^3$ is substituted or unsubstituted —$CHR^7$—$NR^6$—C(O)—$NR^6$-heteroaryl.

In another embodiment of the compounds of Formula Ib, -L-$X^2$—$R^3$ is substituted or unsubstituted —$CHR^7$—$NR^6$—C(O)—$NR^6$-heteroaryl, wherein said heteroaryl is any heteroaryl described or defined herein.

In another embodiment of the compounds of Formula Ib, -L-$X^2$—$R^3$ is substituted or unsubstituted —$CHR^7$—$NR^6$—C(O)—$NR^6$-thiazolyl.

In another embodiment of the compounds of Formula Ib, -L-$X^2$—$R^3$ is substituted or unsubstituted —$CHR^7$—$NR^6$—C(O)—$NR^6$-arylalkyl.

In another embodiment of the compounds of Formula Ib, -L-$X^2$—$R^3$ is substituted or unsubstituted —$CHR^7$—$NR^6$—C(O)—$NR^6$-benzyl.

In another embodiment of the compounds of Formula Ib, -L-$X^2$—$R^3$ is substituted —$CHR^7$—$NR^6$—C(O)—$NR^6$-benzyl.

In another embodiment of the compounds of Formula Ib, -L-$X^2$—$R^3$ is —$CHR^7$—$NR^6$—C(O)—$NR^6$-benzyl wherein the benzyl is substituted with one or more substituents selected from the group consisting of alkyl, substituted alkyl, halo, hydroxyl, amino, haloalkyl, and cyano.

In another embodiment of the compounds of Formula Ib, -L-$X^2$—$R^3$ is substituted or unsubstituted —$CHR^7$—$NR^6$—C(O)—$NR^6$-heteroarylalkyl.

In another embodiment of the compounds of Formula Ib, -L-$X^2$—$R^3$ is substituted or unsubstituted —$CHR^7$—$NR^6$—C(O)—$NR^6$-heteroarylalkyl, wherein the alkyl portion thereof is any alkylene described or disclosed herein.

In another embodiment of the compounds of Formula Ib, -L-$X^2$—$R^3$ is substituted or unsubstituted —$CHR^7$—$NR^6$—C(O)—$NR^6$-heteroarylalkyl, wherein the alkyl portion thereof is —$CH_2$—.

In another embodiment of the compounds of Formula Ib, -L-$X^2$—$R^3$ is substituted or unsubstituted —$CHR^7$—$NR^6$—C(O)—$NR^6$-heteroarylalkyl, wherein the heteroaryl portion thereof is any heteroaryl described or disclosed herein.

In another embodiment of the compounds of Formula Ib, -L-$X^2$—$R^3$ is substituted or unsubstituted —$CHR^7$—$NR^6$—C(O)—$NR^6$-heteroarylalkyl, wherein the heteroaryl portion thereof is thiazolyl.

In another embodiment of the compounds of Formula Ib, -L-$X^2$—$R^3$ is substituted or unsubstituted —$CHR^7$—$NR^6$—C(O)—$NR^6$-thiazolylmethyl.

In another embodiment of the compounds of Formula Ib, -L-$X^2$—$R^3$ is —$CHR^7$—$NR^6$—C(O)—$NR^6$-thiazol-5-ylmethyl.

In another embodiment of the compounds of Formula Ib, -L-$X^2$—$R^3$ is substituted —$CHR^7$—$NR^6$—C(O)—$NR^6$-thiazolylmethyl.

In another embodiment of the compounds of Formula Ib, -L-$X^2$—$R^3$ is $CHR^7$—$NR^6$—C(O)—$NR^6$-thiazolylmethyl wherein the thiazolylmethyl is substituted with one or more substituents selected from the group consisting of alkyl, substituted alkyl, halo, hydroxyl, amino, haloalkyl, and cyano.

In another embodiment of the compounds of Formula Ib, -L-$X^2$—$R^3$ is substituted —$CHR^7$—$NR^6$—C(O)—$NR^6$-thiazolylmethyl wherein the thiazolylmethyl substituent is an alkyl group.

In another embodiment of the compounds of Formula Ib, -L-$X^2$—$R^3$ is substituted —$CHR^7$—$NR^6$—C(O)—$NR^6$-(2-isopropylthiazolyl-4-yl)methyl.

In another embodiment of the compounds of Formula Ib, -L-$X^2$—$R^3$ is —$CHR^7$—$NR^6$—C(O)—$NR^6$-heterocyclyl wherein the heterocyclyl is substituted or unsubstituted and $R^7$ is morpholinylalkyl.

In another embodiment of the compounds of Formula Ib, -L-$X^2$—$R^3$ is —$CHR^7$—$NR^6$—C(O)—$NR^6$-aryl wherein the aryl is substituted or unsubstituted and $R^7$ is morpholinylalkyl.

In another embodiment of the compounds of Formula Ib, -L-$X^2$—$R^3$ is —$CHR^7$—$NR^6$—C(O)—$NR^6$-phenyl wherein the phenyl is substituted or unsubstituted and $R^7$ is morpholinylalkyl.

In another embodiment of the compounds of Formula Ib, -L-$X^2$—$R^3$ is —$CHR^7$—$NR^6$—C(O)—$NR^6$-heteroaryl wherein the heteroaryl is substituted or unsubstituted and $R^7$ is morpholinylalkyl.

In another embodiment of the compounds of Formula Ib, -L-$X^2$—$R^3$ is —$CHR^7$—$NR^6$—C(O)—$NR^6$-heteroaryl wherein the heteroaryl is substituted or unsubstituted, said heteroaryl is any heteroaryl described or defined herein and $R^7$ is morpholinylalkyl.

In another embodiment of the compounds of Formula Ib, -L-$X^2$—$R^3$ is —$CHR^7$—$NR^6$—C(O)—$NR^6$-thiazolyl wherein thiazolyl is substituted or unsubstituted and $R^7$ is morpholinylalkyl.

In another embodiment of the compounds of Formula Ib, -L-$X^2$—$R^3$ is —$CHR^7$—$NR^6$—C(O)—$NR^6$-arylalkyl wherein the arylalkyl is substituted or unsubstituted and $R^7$ is morpholinylalkyl.

In another embodiment of the compounds of Formula Ib, -L-$X^2$—$R^3$ is —$CHR^7$—$NR^6$—C(O)—$NR^6$-benzyl wherein the benzyl is substituted or unsubstituted and $R^7$ is morpholinylalkyl.

In another embodiment of the compounds of Formula Ib, -L-$X^2$—$R^3$ is —$CHR^7$—$NR^6$—C(O)—$NR^6$-benzyl wherein the benzyl is substituted and $R^7$ is morpholinylalkyl.

In another embodiment of the compounds of Formula Ib, -L-$X^2$—$R^3$ is —$CHR^7$—$NR^6$—C(O)—$NR^6$-benzyl wherein the benzyl is substituted with one or more substituents selected from the group consisting of alkyl, substituted alkyl, halo, hydroxyl, amino, haloalkyl, and cyano, and $R^7$ is morpholinylalkyl.

In another embodiment of the compounds of Formula Ib, -L-$X^2$—$R^3$ is —$CHR^7$—$NR^6$—C(O)—$NR^6$-heteroarylalkyl wherein the heteroarylalkyl is substituted or unsubstituted and $R^7$ is morpholinylalkyl.

In another embodiment of the compounds of Formula Ib, -L-$X^2$—$R^3$ is —$CHR^7$—$NR^6$—C(O)—$NR^6$-heteroarylalkyl wherein the heteroarylalkyl is substituted or unsubstituted, the alkyl portion thereof is any alkylene described or disclosed herein and $R^7$ is morpholinylalkyl.

In another embodiment of the compounds of Formula Ib, -L-$X^2$—$R^3$ is —$CHR^7$—$NR^6$—C(O)—$NR^6$-heteroarylalkyl wherein the heteroarylalkyl is substituted or unsubstituted, the alkyl portion thereof is —$CH_2$—, and $R^7$ is morpholinylalkyl.

In another embodiment of the compounds of Formula Ib, -L-$X^2$—$R^3$ is —$CHR^7$—$NR^6$—C(O)—$NR^6$-heteroarylalkyl wherein the heteroarylalkyl is substituted or unsubstituted, the heteroaryl portion thereof is any heteroaryl described or disclosed herein, and $R^7$ is morpholinylalkyl.

In another embodiment of the compounds of Formula Ib, -L-$X^2$—$R^3$ is —$CHR^7$—$NR^6$—C(O)—$NR^6$-heteroarylalkyl wherein the heteroarylalkyl is substituted or unsubstituted, the heteroaryl portion thereof is thiazolyl, and $R^7$ is morpholinylalkyl.

In another embodiment of the compounds of Formula Ib, -L-$X^2$—$R^3$ is —$CHR^7$—$NR^6$—C(O)—$NR^6$-thiazolylmethyl wherein the thiazolylmethyl is substituted or unsubstituted and $R^7$ is morpholinylalkyl.

In another embodiment of the compounds of Formula Ib, -L-$X^2$—$R^3$ is —$CHR^7$—$NR^6$—C(O)—$NR^6$-thiazolyl-5-yl-methyl wherein $R^7$ is morpholinylalkyl.

In another embodiment of the compounds of Formula Ib, -L-$X^2$—$R^3$ is —$CHR^7$—$NR^6$—C(O)—$NR^6$-thiazolylmethyl wherein the thiazolylmethyl is substituted and $R^7$ is morpholinylalkyl.

In another embodiment of the compounds of Formula Ib, -L-$X^2$—$R^3$ is —$CHR^7$—$NR^6$—C(O)—$NR^6$-thiazolylmethyl wherein the thiazolylmethyl is substituted with one or more substituents selected from the group consisting of alkyl, substituted alkyl, halo, hydroxyl, amino, haloalkyl, and cyano and $R^7$ is morpholinylalkyl.

In another embodiment of the compounds of Formula Ib, -L-$X^2$—$R^3$—$CHR^7$—$NR^6$—C(O)—$NR^6$-thiazolylmethyl wherein the thiazolylmethyl is substituted, the substituent is an alkyl group, and $R^7$ is morpholinylalkyl.

In another embodiment of the compounds of Formula Ib, -L-$X^2$—$R^3$ is —$CHR^7$—$NR^6$—C(O)—$NR^6$-(2-isopropylthiazolyl-4-yl)methyl and $R^7$ is morpholinylalkyl.

In another embodiment of the compounds of Formula Ib, -L-$X^2$—$R^3$ is —$CHR^7$—$NR^6$—C(O)—$NR^6$-heterocyclyl the heterocyclyl is substituted or unsubstituted and $R^7$ is —$CH_2CH_2$-morpholinyl.

In another embodiment of the compounds of Formula Ib, -L-$X^2$—$R^3$ is —$CHR^7$—$NR^6$—C(O)—$NR^6$-aryl wherein the aryl is substituted or unsubstituted and $R^7$ is —$CH_2CH_2$-morpholinyl.

In another embodiment of the compounds of Formula Ib, -L-$X^2$—$R^3$ is —$CHR^7$—$NR^6$—C(O)—$NR^6$-phenyl wherein the phenyl is substituted or unsubstituted and $R^7$ is —$CH_2CH_2$-morpholinyl.

In another embodiment of the compounds of Formula Ib, -L-$X^2$—$R^3$ is —$CHR^7$—$NR^6$—C(O)—$NR^6$-heteroaryl wherein the heteroaryl is substituted or unsubstituted and $R^7$ is —$CH_2CH_2$-morpholinyl.

In another embodiment of the compounds of Formula Ib, -L-$X^2$—$R^3$ is —$CHR^7$—$NR^6$—C(O)—$NR^6$-heteroaryl, wherein the heteroaryl is substituted or unsubstituted, said heteroaryl is any heteroaryl described or defined herein, and $R^7$ is —$CH_2CH_2$-morpholinyl.

In another embodiment of the compounds of Formula Ib, -L-$X^2$—$R^3$ is —$CHR^7$—$NR^6$—C(O)—$NR^6$-thiazolyl wherein the thiazolyl is substituted or unsubstituted and $R^7$ is —$CH_2CH_2$-morpholinyl.

In another embodiment of the compounds of Formula Ib, -L-$X^2$—$R^3$ is —$CHR^7$—$NR^6$—C(O)—$NR^6$-arylalkyl wherein the arylalkyl is substituted or unsubstituted and $R^7$ is —$CH_2CH_2$-morpholinyl.

In another embodiment of the compounds of Formula Ib, -L-$X^2$—$R^3$ is —$CHR^7$—$NR^6$—C(O)—$NR^6$-benzyl wherein the benzyl is substituted or unsubstituted and $R^7$ is —$CH_2CH_2$-morpholinyl.

In another embodiment of the compounds of Formula Ib, -L-$X^2$—$R^3$ is —$CHR^7$—$NR^6$—C(O)—$NR^6$-benzyl wherein the benzyl is substituted and $R^7$ is —$CH_2CH_2$-morpholinyl.

In another embodiment of the compounds of Formula Ib, -L-$X^2$—$R^3$ is —$CHR^7$—$NR^6$—C(O)—$NR^6$-benzyl wherein the benzyl is substituted with one or more substituents selected from the group consisting of alkyl, substituted alkyl, halo, hydroxyl, amino, haloalkyl, and cyano and $R^7$ is —$CH_2CH_2$-morpholinyl.

In another embodiment of the compounds of Formula Ib, -L-$X^2$—$R^3$ is —$CHR^7$—$NR^6$—C(O)—$NR^6$-heteroarylalkyl wherein the heteroarylalkyl is substituted or unsubstituted and $R^7$ is —$CH_2CH_2$-morpholinyl.

In another embodiment of the compounds of Formula Ib, -L-$X^2$—$R^3$ is —$CHR^7$—$NR^6$—C(O)—$NR^6$-heteroarylalkyl wherein the heteroarylalkyl is substituted or unsubstituted, the alkyl portion thereof is any alkylene described or disclosed herein, and $R^7$ is —$CH_2CH_2$-morpholinyl.

In another embodiment of the compounds of Formula Ib, -L-$X^2$—$R^3$ is —$CHR^7$—$NR^6$—C(O)—$NR^6$-heteroarylalkyl wherein the heteroarylalkyl is substituted or unsubstituted, the alkyl portion thereof is —$CH_2$—, and $R^7$ is —$CH_2CH_2$-morpholinyl.

In another embodiment of the compounds of Formula Ia, -L-$X^2$—$R^3$ is —$CHR^7$—$NR^6$—C(O)—$NR^6$-heteroarylalkyl wherein wherein the heteroarylalkyl is substituted or unsubstituted, the heteroaryl portion thereof is any heteroaryl described or disclosed herein, and $R^7$ is —$CH_2CH_2$-morpholinyl.

In another embodiment of the compounds of Formula Ib, -L-$X^2$—$R^3$ is —$CHR^7$—$NR^6$—C(O)—$NR^6$-heteroarylalkyl wherein the heteroarylalkyl is substituted or unsubstituted, the heteroaryl portion thereof is thiazolyl, and $R^7$ is —$CH_2CH_2$-morpholinyl.

In another embodiment of the compounds of Formula Ib, -L-$X^2$—$R^3$ is —$CHR^7$—$NR^6$—C(O)—$NR^6$-thiazolylmethyl wherein the thiazolylmethyl is substituted or unsubstituted and $R^7$ is —$CH_2CH_2$-morpholinyl.

In another embodiment of the compounds of Formula Ib, -L-$X^2$—$R^3$ is —$CHR^7$—$NR^6$—C(O)—$NR^6$-thiazol-5-ylmethyl wherein $R^7$ is —$CH_2CH_2$-morpholinyl.

In another embodiment of the compounds of Formula Ib, -L-$X^2$—$R^3$ is —$CHR^7$—$NR^6$—C(O)—$NR^6$-thiazolylmethyl wherein the thiazoylmethyl is substituted and $R^7$ is —$CH_2CH_2$-morpholinyl.

In another embodiment of the compounds of Formula Ib, -L-$X^2$—$R^3$ is —$CHR^7$—$NR^6$—C(O)—$NR^6$-thiazolylmethyl wherein thiazolylmethyl is substituted with one or more substituents selected from the group consisting of alkyl, substituted alkyl, halo, hydroxyl, amino, haloalkyl, and cyano and $R^7$ is —$CH_2CH_2$-morpholinyl.

In another embodiment of the compounds of Formula Ib, -L-$X^2$—$R^3$ is —$CHR^7$—$NR^6$—C(O)—$NR^6$-thiazolylmethyl wherein the thiazolylmethyl is substituted, the substituent is an alkyl group, and $R^7$ is —$CH_2CH_2$-morpholinyl.

In another embodiment of the compounds of Formula Ib, -L-$X^2$—$R^3$ is —$CHR^7$—$NR^6$—C(O)—$NR^6$-(2-isopropylthiazolyl-4-yl)methyl wherein $R^7$ is —$CH_2CH_2$-morpholinyl.

In another embodiment, the compounds of Formula I have the structure of Formula II:

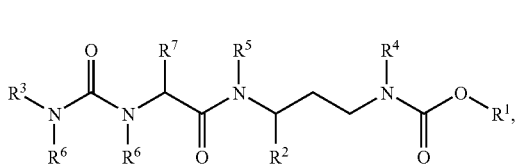

II wherein $R^1$, $R^2$, $R^3$, $R^4$, $R^5$, $R^6$, and $R^7$ are as defined herein.

In another embodiment of the compounds of Formula II, $R^1$ is substituted or unsubstituted aryl.

In another embodiment of the compounds of Formula II, $R^1$ is substituted or unsubstituted phenyl.

In another embodiment of the compounds of Formula II, $R^1$ is substituted phenyl.

In another embodiment of the compounds of Formula II, $R^1$ is mono-substituted phenyl.

In another embodiment of the compounds of Formula II, $R^1$ is phenyl substituted with one or more substituents selected from the group consisting of alkyl, substituted alkyl, halo, hydroxyl, amino, haloalkyl, and cyano.

In another embodiment of the compounds of Formula II, $R^1$ is 4-aminophenyl.

In another embodiment of the compounds of Formula II, $R^1$ is substituted or unsubstituted heteroaryl.

In another embodiment of the compounds of Formula II, $R^1$ is substituted or unsubstituted thiazolyl.

In another embodiment of the compounds of Formula II, $R^1$ is substituted or unsubstituted arylalkyl.

In another embodiment of the compounds of Formula II, $R^1$ is substituted or unsubstituted benzyl.

In another embodiment of the compounds of Formula II, $R^1$ is substituted or unsubstituted heteroarylalkyl.

In another embodiment of the compounds of Formula II, $R^1$ is substituted or unsubstituted heteroarylalkyl, wherein the alkyl portion thereof is any of the alkylene groups defined or disclosed herein.

In another embodiment of the compounds of Formula II, $R^1$ is substituted or unsubstituted heteroarylalkyl, wherein the alkyl portion thereof is —$CH_2$—.

In another embodiment of the compounds of Formula II, $R^1$ is substituted or unsubstituted heteroarylalkyl, wherein the heteroaryl portion thereof is any of the heteroaryl groups defined or disclosed herein.

In another embodiment of the compounds of Formula II, $R^1$ is substituted or unsubstituted heteroarylalkyl, wherein the heteroaryl portion thereof is thiazolyl.

In another embodiment of the compounds of Formula II, $R^1$ is substituted or unsubstituted thiazolylmethyl.

In another embodiment of the compounds of Formula II, $R^1$ is thiazol-5-ylmethyl.

In another embodiment of the compounds of Formula II, $R^1$ is substituted heteroarylalkyl wherein the heteroaryl portion thereof is any of the heteroaryl groups defined or disclosed herein, and the substituent is one or more substituents selected from the group consisting of alkyl, substituted alkyl, halo, hydroxyl, amino, haloalkyl, and cyano.

In another embodiment of the compounds of Formula II, $R^1$ is substituted heteroarylalkyl, wherein the heteroaryl portion thereof is thiazolyl substituted with one or more substituents selected from the group consisting of alkyl, substituted alkyl, halo, hydroxyl, amino, haloalkyl, and cyano.

In another embodiment of the compounds of Formula II, $R^1$ is thiazolylmethyl substituted with one or more substituents selected from the group consisting of alkyl, substituted alkyl, halo, hydroxyl, amino, haloalkyl, and cyano.

In another embodiment of the compounds of Formula II, $R^2$ is substituted or unsubstituted arylalkyl.

In another embodiment of the compounds of Formula II, $R^2$ is substituted or unsubstituted benzyl.

In another embodiment of the compounds of Formula II, $R^2$ is benzyl substituted with one or more substituents selected from the group consisting of alkyl, substituted alkyl, halo, hydroxyl, amino, haloalkyl, and cyano.

In another embodiment of the compounds of Formula II, $R^2$ is unsubstituted benzyl.

In another embodiment of the compounds of Formula II, $R^2$ is substituted or unsubstituted heteroarylalkyl.

In another embodiment of the compounds of Formula II, $R^2$ is unsubstituted heteroarylalkyl.

In another embodiment of the compounds of Formula II, $R^2$ is heteroarylalkyl substituted with one or more substituents selected from the group consisting of alkyl, substituted alkyl, halo, hydroxyl, amino, haloalkyl, and cyano.

In another embodiment of the compounds of Formula II, $R^3$ is substituted or unsubstituted heterocyclyl.

In another embodiment of the compounds of Formula II, $R^3$ is substituted or unsubstituted hexahydrofuro[2,3-b]furanyl.

In another embodiment of the compounds of Formula II, $R^3$ is unsubstituted hexahydrofuro[2,3-b]furanyl.

In another embodiment of the compounds of Formula II, $R^3$ is substituted or unsubstituted furanyl.

In another embodiment of the compounds of Formula II, $R^3$ is unsubstituted furanyl.

In another embodiment of the compounds of Formula II, $R^3$ is substituted or unsubstituted aryl.

In another embodiment of the compounds of Formula II, $R^3$ is substituted or unsubstituted phenyl.

In another embodiment of the compounds of Formula II, $R^3$ is substituted or unsubstituted heteroaryl.

In another embodiment of the compounds of Formula II, $R^3$ is substituted or unsubstituted heteroaryl, wherein said heteroaryl is any heteroaryl described or defined herein.

In another embodiment of the compounds of Formula II, $R^3$ is substituted or unsubstituted thiazolyl.

In another embodiment of the compounds of Formula II, $R^3$ is thiazolyl substituted with one or more substituents selected from the group consisting of alkyl, substituted alkyl, halo, hydroxyl, amino, haloalkyl, and cyano.

In another embodiment of the compounds of Formula II, $R^3$ is substituted or unsubstituted arylalkyl.

In another embodiment of the compounds of Formula II, $R^3$ is substituted or unsubstituted benzyl.

In another embodiment of the compounds of Formula II, $R^3$ is substituted benzyl.

In another embodiment of the compounds of Formula II, $R^3$ is benzyl substituted with one or more substituents selected from the group consisting of alkyl, substituted alkyl, halo, hydroxyl, amino, haloalkyl, and cyano.

In another embodiment of the compounds of Formula II, $R^3$ is substituted or unsubstituted heteroarylalkyl.

In another embodiment of the compounds of Formula II, $R^3$ is substituted or unsubstituted heteroarylalkyl, wherein the alkyl portion thereof is any alkylene described or disclosed herein.

In another embodiment of the compounds of Formula II, $R^3$ is substituted or unsubstituted heteroarylalkyl, wherein the alkyl portion thereof is —CH$_2$—.

In another embodiment of the compounds of Formula II, $R^3$ is substituted or unsubstituted heteroarylalkyl, wherein the heteroaryl portion thereof is any heteroaryl described or disclosed herein.

In another embodiment of the compounds of Formula II, $R^3$ is substituted or unsubstituted heteroarylalkyl, wherein the heteroaryl portion thereof is thiazolyl.

In another embodiment of the compounds of Formula II, $R^3$ is substituted or unsubstituted thiazolylmethyl.

In another embodiment of the compounds of Formula II, $R^3$ is thiazol-5-ylmethyl.

In another embodiment of the compounds of Formula II, $R^3$ is substituted thiazolylmethyl.

In another embodiment of the compounds of Formula II, $R^3$ is thiazolylmethyl substituted with one or more substituents selected from the group consisting of alkyl, substituted alkyl, halo, hydroxyl, amino, haloalkyl, and cyano.

In another embodiment of the compounds of Formula II, $R^3$ is substituted thiazolylmethyl, and the substituent is an alkyl group.

In another embodiment of the compounds of Formula II, $R^3$ is (2-isopropylthiazolyl-4-yl)methyl.

In another embodiment of the compounds of Formula II, $R^4$ is H.

In another embodiment of the compounds of Formula II, $R^4$ is alkyl.

In another embodiment of the compounds of Formula II, $R^4$ is any of the alkyl groups described or disclosed herein.

In another embodiment of the compounds of Formula II, $R^4$ is 2-methylpropyl.

In another embodiment of the compounds of Formula II, $R^4$ is substituted or unsubstituted arylalkyl.

In another embodiment of the compounds of Formula II, $R^4$ is substituted or unsubstituted benzyl.

In another embodiment of the compounds of Formula II, $R^4$ is unsubstituted benzyl.

In another embodiment of the compounds of Formula II, $R^4$ is benzyl substituted with one or more substituents selected from the group consisting of alkyl, substituted alkyl, halo, hydroxyl, amino, haloalkyl, and cyano.

In another embodiment of the compounds of Formula II, $R^4$ is halo substituted benzyl.

In another embodiment of the compounds of Formula II, $R^4$ is chloro substituted benzyl.

In another embodiment of the compounds of Formula II, $R^4$ is substituted or unsubstituted heteroarylalkyl.

In another embodiment of the compounds of Formula II, $R^4$ is substituted or unsubstituted heteroarylalkyl, wherein the alkyl portion thereof is any of the alkylene groups described or defined herein.

In another embodiment of the compounds of Formula II, $R^4$ is substituted or unsubstituted heteroarylalkyl, wherein the alkyl portion thereof is —CH$_2$—.

In another embodiment of the compounds of Formula II, $R^4$ is substituted or unsubstituted heteroarylalkyl, wherein the heteroaryl portion thereof is any of the heteroaryl groups described or defined herein.

In another embodiment of the compounds of Formula II, $R^5$ is H.

In another embodiment of the compounds of Formula II, $R^5$ is alkyl

In another embodiment of the compounds of Formula II, $R^5$ is any of the alkyl groups described or disclosed herein.

In another embodiment of the compounds of Formula II, $R^5$ is 2-methylpropyl.

In another embodiment of the compounds of Formula II, $R^5$ is substituted or unsubstituted arylalkyl.

In another embodiment of the compounds of Formula II, $R^5$ is substituted or unsubstituted benzyl.

In another embodiment of the compounds of Formula II, $R^5$ is unsubstituted benzyl.

In another embodiment of the compounds of Formula II, $R^5$ is benzyl substituted with one or more substituents selected from the group consisting of alkyl, substituted alkyl, halo, hydroxyl, amino, haloalkyl, and cyano.

In another embodiment of the compounds of Formula II, $R^5$ is halo substituted benzyl.

In another embodiment of the compounds of Formula II, $R^5$ is substituted or unsubstituted heteroarylalkyl.

In another embodiment of the compounds of Formula II, $R^5$ is substituted or unsubstituted heteroarylalkyl, wherein the alkyl portion thereof is any of the alkylene groups described or defined herein.

In another embodiment of the compounds of Formula II, $R^5$ is substituted or unsubstituted heteroarylalkyl, wherein the alkyl portion thereof is —CH$_2$—.

In another embodiment of the compounds of Formula II, $R^5$ is substituted or unsubstituted heteroarylalkyl, wherein the heteroaryl portion thereof is any of the heteroaryl groups described or defined herein.

In another embodiment of the compounds of Formula II, $R^4$ and $R^5$ are different.

In another embodiment of the compounds of Formula II, $R^4$ and $R^5$ are the same.

In another embodiment of the compounds of Formula II, one of $R^4$ and $R^5$ is H.

In another embodiment of the compounds of Formula II, $R^4$ is H and $R^5$ is benzyl or substituted benzyl.

In another embodiment of the compounds of Formula II, at least one $R^6$ is H.

In another embodiment of the compounds of Formula II, at least one $R^6$ is alkyl.

In another embodiment of the compounds of Formula II, one $R^6$ is H and the other $R^6$ is alkyl.

In another embodiment of the compounds of Formula II, $R^7$ is substituted or unsubstituted heterocyclylalkyl.

In another embodiment of the compounds of Formula II, $R^7$ is unsubstituted heterocyclylalkyl.

In another embodiment of the compounds of Formula II, $R^7$ is heterocyclylalkyl substituted with one or more substituents selected from the group consisting of alkyl, substituted alkyl, halo, hydroxyl, amino, haloalkyl, and cyano.

In another embodiment of the compounds of Formula II, $R^7$ is:

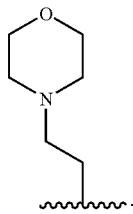 [SMILES: *CCN1CCOCC1]

In another embodiment, the compounds of Formula I have the structure of Formula III:

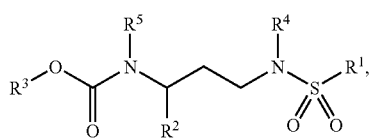

wherein $R^1$, $R^2$, $R^3$, $R^4$, and $R^5$ are as defined herein.

In another embodiment of the compounds of Formula III, $R^1$ is substituted or unsubstituted aryl.

In another embodiment of the compounds of Formula III, $R^1$ is substituted or unsubstituted phenyl.

In another embodiment of the compounds of Formula III, $R^1$ is substituted phenyl.

In another embodiment of the compounds of Formula III, $R^1$ is mono-substituted phenyl.

In another embodiment of the compounds of Formula III, $R^1$ is phenyl substituted with one or more substituents selected from the group consisting of alkyl, substituted alkyl, halo, hydroxyl, amino, haloalkyl, and cyano.

In another embodiment of the compounds of Formula III, $R^1$ is 4-aminophenyl.

In another embodiment of the compounds of Formula III, $R^1$ is substituted or unsubstituted heteroaryl.

In another embodiment of the compounds of Formula III, $R^1$ is substituted or unsubstituted thiazolyl.

In another embodiment of the compounds of Formula III, $R^1$ is substituted or unsubstituted arylalkyl.

In another embodiment of the compounds of Formula III, $R^1$ is substituted or unsubstituted benzyl.

In another embodiment of the compounds of Formula III, $R^1$ is substituted or unsubstituted heteroarylalkyl.

In another embodiment of the compounds of Formula III, $R^1$ is substituted or unsubstituted heteroarylalkyl, wherein the alkyl portion thereof is any of the alkylene groups defined or disclosed herein.

In another embodiment of the compounds of Formula III, $R^1$ is substituted or unsubstituted heteroarylalkyl, wherein the alkyl portion thereof is —$CH_2$—.

In another embodiment of the compounds of Formula III, $R^1$ is substituted or unsubstituted heteroarylalkyl, wherein the heteroaryl portion thereof is any of the heteroaryl groups defined or disclosed herein.

In another embodiment of the compounds of Formula III, $R^1$ is substituted or unsubstituted heteroarylalkyl, wherein the heteroaryl portion thereof is thiazolyl.

In another embodiment of the compounds of Formula III, $R^1$ is substituted or unsubstituted thiazolylmethyl.

In another embodiment of the compounds of Formula III, $R^1$ is substituted heteroarylalkyl, wherein the heteroaryl portion thereof is any of the heteroaryl groups defined or disclosed herein, and the substituent is one or more substituents selected from the group consisting of alkyl, substituted alkyl, halo, hydroxyl, amino, haloalkyl, and cyano.

In another embodiment of the compounds of Formula III, $R^1$ is substituted heteroarylalkyl, wherein the heteroaryl portion thereof is thiazolyl substituted with one or more substituents selected from the group consisting of alkyl, substituted alkyl, halo, hydroxyl, amino, haloalkyl, and cyano.

In another embodiment of the compounds of Formula III, $R^1$ is thiazolylmethyl substituted with one or more substituents selected from the group consisting of alkyl, substituted alkyl, halo, hydroxyl, amino, haloalkyl, and cyano.

In another embodiment of the compounds of Formula III, $R^2$ is substituted or unsubstituted arylalkyl.

In another embodiment of the compounds of Formula III, $R^2$ is substituted or unsubstituted benzyl.

In another embodiment of the compounds of Formula III, $R^2$ is benzyl substituted with one or more substituents selected from the group consisting of alkyl, substituted alkyl, halo, hydroxyl, amino, haloalkyl and cyano.

In another embodiment of the compounds of Formula III, $R^2$ is unsubstituted benzyl.

In another embodiment of the compounds of Formula III, $R^2$ is substituted or unsubstituted heteroarylalkyl.

In another embodiment of the compounds of Formula III, $R^2$ is unsubstituted heteroarylalkyl.

In another embodiment of the compounds of Formula III, $R^2$ is heteroarylalkyl substituted with one or more substituents selected from the group consisting of alkyl, substituted alkyl, halo, hydroxyl, amino, haloalkyl, and cyano.

In another embodiment of the compounds of Formula III, $R^3$ is substituted or unsubstituted heterocyclyl.

In another embodiment of the compounds of Formula III, $R^3$ is substituted or unsubstituted tetrahydro-2H-furo[2,3-b]furanyl.

In another embodiment of the compounds of Formula III, $R^3$ is unsubstituted tetrahydro-2H-furo[2,3-b]furanyl.

In another embodiment of the compounds of Formula III, $R^3$ is tetrahydro-2H-furo[2,3-b]furan-3-yl.

In another embodiment of the compounds of Formula III, $R^3$ is substituted or unsubstituted tetrahydrofuranyl.

In another embodiment of the compounds of Formula III, $R^3$ is unsubstituted tetrahydrofuranyl.

In another embodiment of the compounds of Formula III, $R^3$ is tetrahydrofuran-3-yl.

In another embodiment of the compounds of Formula III, $R^3$ is substituted or unsubstituted aryl.

In another embodiment of the compounds of Formula III, $R^3$ is substituted or unsubstituted phenyl.

In another embodiment of the compounds of Formula III, $R^3$ is substituted or unsubstituted heteroaryl.

In another embodiment of the compounds of Formula III, $R^3$ is substituted or unsubstituted heteroaryl, wherein said heteroaryl is any heteroaryl described or defined herein.

In another embodiment of the compounds of Formula III, $R^3$ is substituted or unsubstituted thiazolyl.

In another embodiment of the compounds of Formula III, $R^3$ is thiazolyl substituted with one or more substituents selected from the group consisting of alkyl, substituted alkyl, halo, hydroxyl, amino, haloalkyl, and cyano.

In another embodiment of the compounds of Formula III, $R^3$ is substituted or unsubstituted arylalkyl.

In another embodiment of the compounds of Formula III, $R^3$ is substituted or unsubstituted benzyl.

In another embodiment of the compounds of Formula III, $R^3$ is substituted benzyl.

In another embodiment of the compounds of Formula III, $R^3$ is benzyl substituted with one or more substituents selected from the group consisting of alkyl, substituted alkyl, halo, hydroxyl, amino, haloalkyl, and cyano.

In another embodiment of the compounds of Formula III, $R^3$ is substituted or unsubstituted heteroarylalkyl.

In another embodiment of the compounds of Formula III, $R^3$ is substituted or unsubstituted heteroarylalkyl, wherein the alkyl portion thereof is any alkylene described or disclosed herein.

In another embodiment of the compounds of Formula III, $R^3$ is substituted or unsubstituted heteroarylalkyl, wherein the alkyl portion thereof is $-CH_2-$.

In another embodiment of the compounds of Formula III, $R^3$ is substituted or unsubstituted heteroarylalkyl, wherein the heteroaryl portion thereof is any heteroaryl described or disclosed herein.

In another embodiment of the compounds of Formula III, $R^3$ is substituted or unsubstituted heteroarylalkyl, wherein the heteroaryl portion thereof is thiazolyl.

In another embodiment of the compounds of Formula III, $R^3$ is substituted or unsubstituted thiazolylmethyl.

In another embodiment of the compounds of Formula III, $R^3$ is substituted thiazolylmethyl.

In another embodiment of the compounds of Formula III, $R^3$ is thiazolylmethyl substituted with one or more substituents selected from the group consisting of alkyl, substituted alkyl, halo, hydroxyl, amino, haloalkyl, and cyano.

In another embodiment of the compounds of Formula III, $R^3$ is substituted thiazolylmethyl, and the substituent is an alkyl group.

In another embodiment of the compounds of Formula III, $R^4$ is H.

In another embodiment of the compounds of Formula III, $R^4$ is alkyl.

In another embodiment of the compounds of Formula III, $R^4$ is any of the alkyl groups described or disclosed herein.

In another embodiment of the compounds of Formula III, $R^4$ is 2-methylpropyl.

In another embodiment of the compounds of Formula III, $R^4$ is substituted or unsubstituted arylalkyl.

In another embodiment of the compounds of Formula III, $R^4$ is substituted or unsubstituted benzyl.

In another embodiment of the compounds of Formula III, $R^4$ is unsubstituted benzyl.

In another embodiment of the compounds of Formula III, $R^4$ is benzyl substituted with one or more substituents selected from the group consisting of alkyl, substituted alkyl, halo, hydroxyl, amino, haloalkyl, and cyano.

In another embodiment of the compounds of Formula III, $R^4$ is halo substituted benzyl.

In another embodiment of the compounds of Formula III, $R^4$ is substituted or unsubstituted heteroarylalkyl.

In another embodiment of the compounds of Formula III, $R^4$ is substituted or unsubstituted heteroarylalkyl, wherein the alkyl portion thereof is any of the alkylene groups described or defined herein.

In another embodiment of the compounds of Formula III, $R^4$ is substituted or unsubstituted heteroarylalkyl, wherein the alkyl portion thereof is $-CH_2-$.

In another embodiment of the compounds of Formula III, $R^4$ is substituted or unsubstituted heteroarylalkyl, wherein the heteroaryl portion thereof is any of the heteroaryl groups described or defined herein.

In another embodiment of the compounds of Formula III, $R^5$ is H.

In another embodiment of the compounds of Formula III, $R^5$ is alkyl.

In another embodiment of the compounds of Formula III, $R^5$ is any of the alkyl groups described or disclosed herein.

In another embodiment of the compounds of Formula III, $R^5$ is 2-methylpropyl.

In another embodiment of the compounds of Formula III, $R^5$ is substituted or unsubstituted arylalkyl.

In another embodiment of the compounds of Formula III, $R^5$ is substituted or unsubstituted benzyl.

In another embodiment of the compounds of Formula III, $R^5$ is unsubstituted benzyl.

In another embodiment of the compounds of Formula III, $R^5$ is benzyl substituted with one or more substituents selected from the group consisting of alkyl, substituted alkyl, halo, hydroxyl, amino, haloalkyl, and cyano.

In another embodiment of the compounds of Formula III, $R^5$ is halo substituted benzyl.

In another embodiment of the compounds of Formula III, $R^5$ is substituted or unsubstituted heteroarylalkyl.

In another embodiment of the compounds of Formula III, $R^5$ is substituted or unsubstituted heteroarylalkyl, wherein the alkyl portion thereof is any of the alkylene groups described or defined herein.

In another embodiment of the compounds of Formula III, $R^5$ is substituted or unsubstituted heteroarylalkyl, wherein the alkyl portion thereof is $-CH_2-$.

In another embodiment of the compounds of Formula III, $R^5$ is substituted or unsubstituted heteroarylalkyl, wherein the heteroaryl portion thereof is any of the heteroaryl groups described or defined herein.

In another embodiment of the compounds of Formula III, $R^4$ and $R^5$ are different.

In another embodiment of the compounds of Formula III, $R^4$ and $R^5$ are the same.

In another embodiment of the compounds of Formula III, one of $R^4$ and $R^5$ is H.

In another embodiment of the compounds of Formula III, at least one $R^6$ is H.

In another embodiment of the compounds of Formula III, at least one $R^6$ is alkyl.

In another embodiment, the compounds of Formula I have one of the following structures:
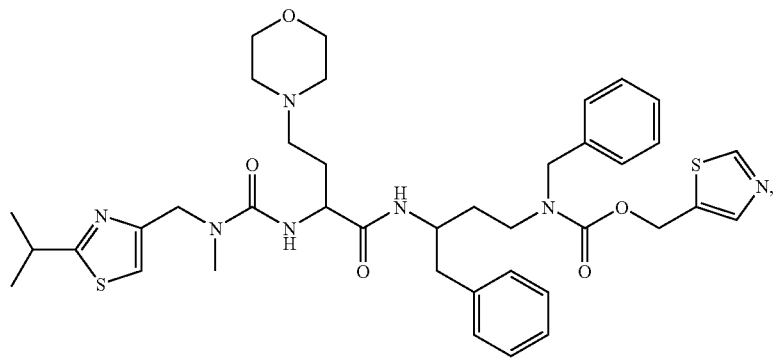
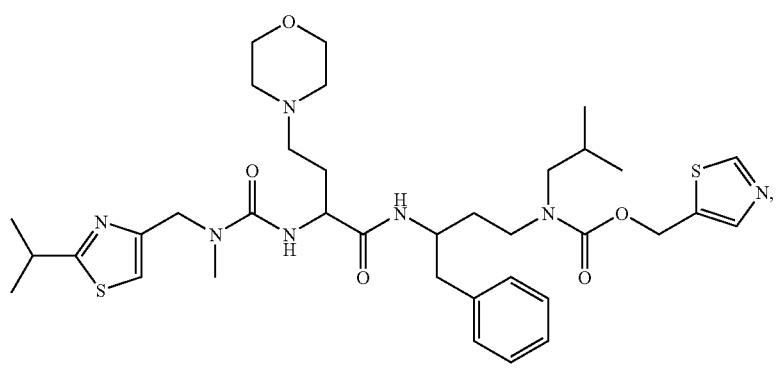
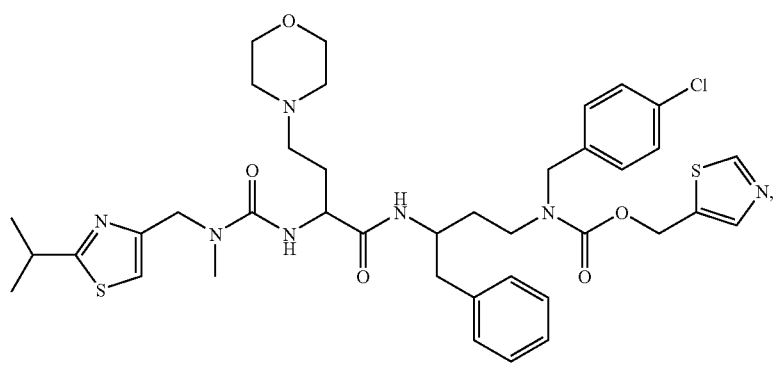
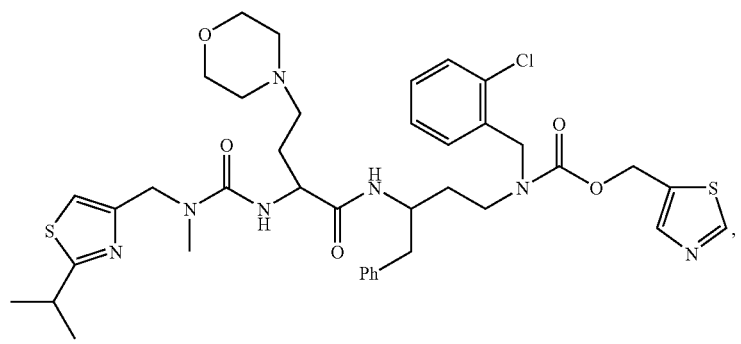

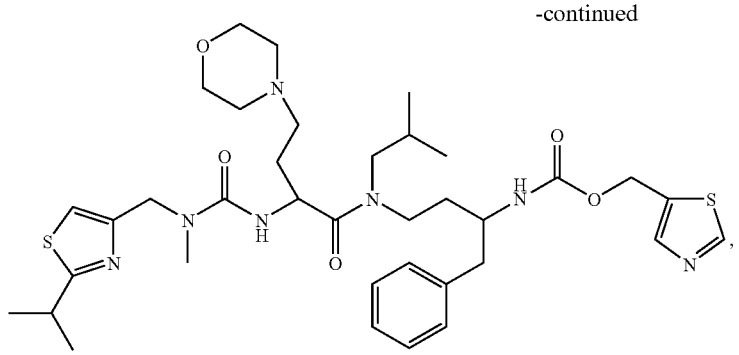
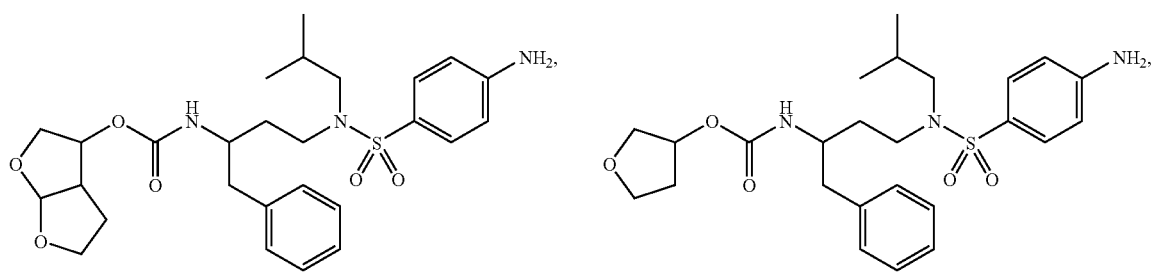
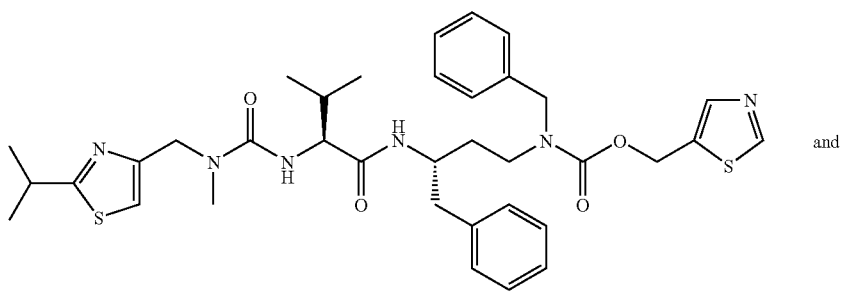
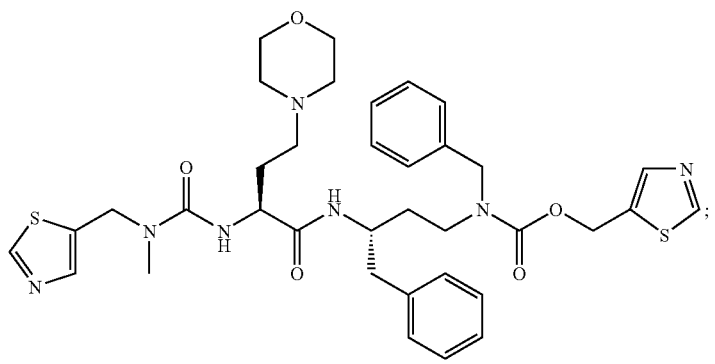
including stereoisomers or mixtures of stereoisomers thereof.
One skilled in the art will recognize that stereoisomers or mixtures of stereoisomers of the compounds of the present application include enantiomers, diastereomers, and other stereoisomers. For example, for:

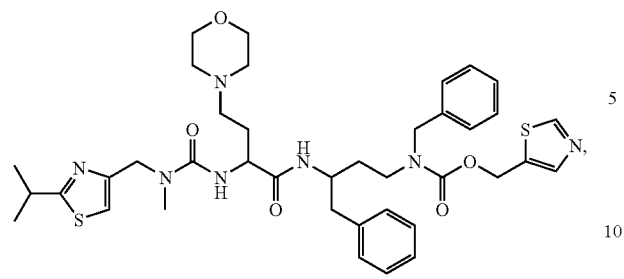
contemplated stereoisomers include at least:
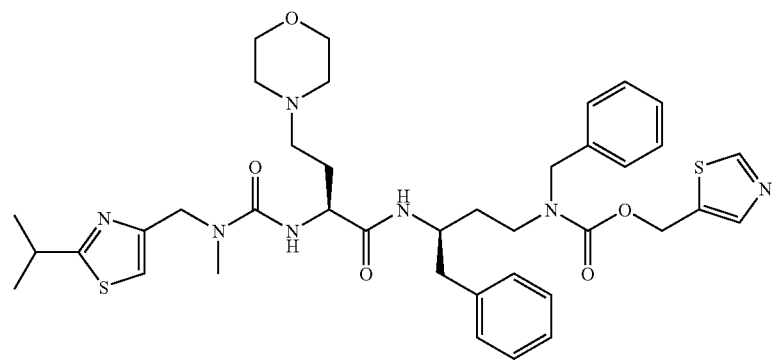
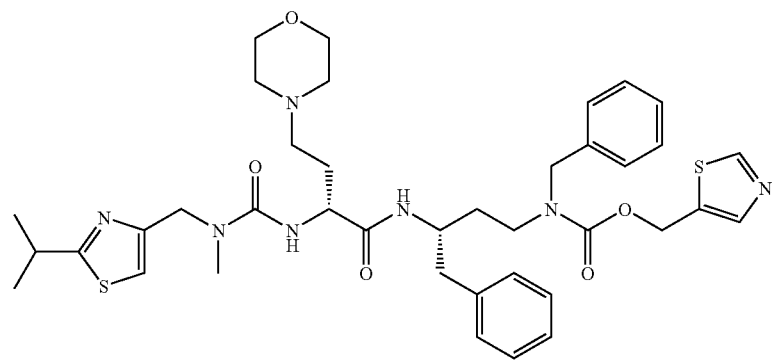
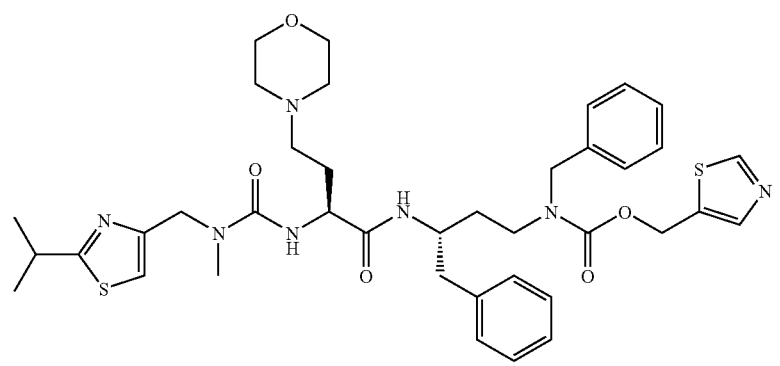

-continued

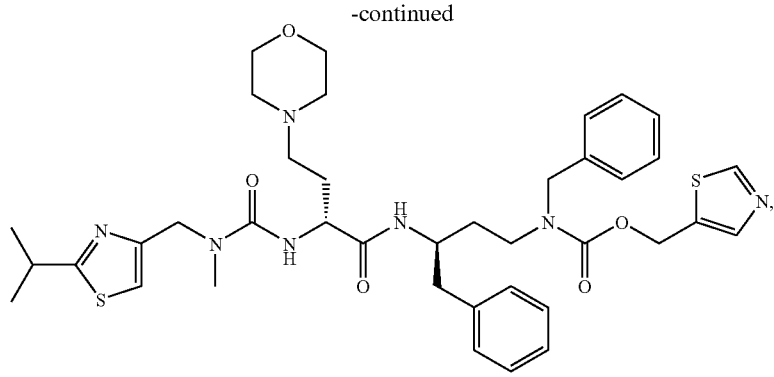

as well as mixtures of two or more of these stereoisomers.

In still yet another embodiment, the compounds of Formula I are named below in tabular format (Table 6) as compounds of general Formula IV:

Formula IV

Compounds of general Formula IV are depicted as a "core" structure (Z) substituted with four moieties T1, T2, Y1 and Y2. The core structures Z are depicted in Table 1. The points of attachment of T1, T2, Y1 and Y2 are indicated on each of the core structures depicted in Table 1. Tables 2-5, respectively, show the structures of the T1, T2, Y1 and Y2 moieties. The point of attachment of the core structure Z is indicated in each of the structures of T1, T2, Y1 and Y2. Each core structure Z in Table 1, and each substituent T1, T2, Y1 and Y2 and Tables 2-5 is represented by a "code" comprising a letter and a number. Each structure of a compound of Formula I can be designated in tabular form by combining the "code" representing each structural moiety using the following syntax: Z.T1.T2.Y1.Y2. Thus, for example, Z1.T1A.T2B.Y1A.Y2A represents the following structure:

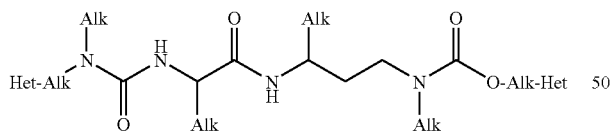

In the structures depicted in Tables 1-5, the term "Alk" means a substituted or unsubstituted alkyl, cycloalkyl, or alkylene group, wherein the terms "alkyl", "cycloalkyl", and "alkylene" are as defined herein. "Alk" means an alkyl or cycloalkyl group when depicted as monovalent, and an alkylene group when depicted as divalent. "Het" is a substituted or unsubstituted heterocyclyl or heterocyclylene group, wherein the term "heterocyclyl" is as defined herein, and the term "heterocyclylene" means a heterocyclyl group as defined herein, in which a hydrogen atom has been replaced by an open valence (in analogy to alkylene), thereby defining a divalent heterocyclyl. "Het" is a heterocyclyl when depicted as monovalent, and heterocyclylene when depicted as divalent. "Ar" is a substitute or unsubstituted aryl or arylene group, wherein the term "aryl" is as defined herein, and the term "arylene" means an aryl group as defined herein, in which a hydrogen atom has been replaced by an open valence (in analogy to alkylene), thereby defining a divalent aryl. "Ar" is aryl when depicted as monovalent, and arylene when depicted as divalent. When substituted, "Alk", "Het", and "Ar" can be substituted with any of the substituents defined or exemplified herein. For example, substituents of "Alk" can include ether, halogen, —OH, amide, amine, etc., substituents of "Het" can include alkyl, aryl, carbonyl, —OH, halogen, and substituents of "Ar" can include alkyl, aryl, —OH, halogen, etc., with the proviso that the resulting structure is chemically reasonable and would provide compounds which are sufficiently stable for formulation in a pharmaceutically acceptable composition. When a structure or substructure shown in the tables below contains more than one "Alk", "Het" or "Ar" group, these groups are independently selected and can be the same or different. So, for example, each of the "Alk" groups of substructure T1A are independently selected and may be the same or different.

TABLE 1

Core Structures

| Code | Core Structure |
|---|---|
| Z1 |  |
| Z2 |  |
| Z3 |  |
| Z4 |  |

TABLE 1-continued

Core Structures

| Code | Core Structure |
|---|---|
| Z5 | T1-NH-C(Y1)(Alk)-CH2-N(Y2)-C(=O)-T2 |
| Z6 | T1-NH-C(Y1)-CH2-N(Y2)-S(=O)2-T2 |
| Z7 | T1-N(Alk)-C(Y1)-CH2-N(Y2)-S(=O)2-T2 |

TABLE 2

T1 Structures

| Code | T1 Structure |
|---|---|
| T1A | Het-Alk-N(Alk)-C(=O)-NH-CH(Alk)-C(=O)- |
| T1B | Het-Alk-NH-C(=O)-N(Alk)-CH(Alk)-C(=O)- |
| T1C | Het-Alk-N(Alk)-C(=O)-N(Alk)-CH(Alk)-C(=O)- |
| T1D | Het-Alk-O-C(=O)-N(Alk)-CH(Alk)-C(=O)- |
| T1E | Het-Alk-NH-C(=O)-O-CH(Alk)-C(=O)- |
| T1F | Het-Alk-C(=O)- |
| T1G | Het-O-C(=O)- |

TABLE 3

T2 Structures

| Code | T2 Structure |
|---|---|
| T2A | —O-Alk-Het |
| T2B | —NH-Alk-Het |
| T2C | —N(Alk)-Alk-Het |

TABLE 4

Y1 Structures

| Code | Y1 Structure |
|---|---|
| Y1A | -Alk |
| Y1B | -Alk-Ar |
| Y1C | -Alk-Het |
| Y1D | -Alk-Ar—O-Alk-Ar |
| Y1E | -Alk-Ar—O-Alk-Het |

TABLE 5

Y2 Structures

| Code | Y2 Structure |
|---|---|
| Y2A | -Alk |
| Y2B | -Alk-Ar |
| Y2C | -Alk-Het |
| Y2D | -Alk-Ar—O-Alk-Het |

TABLE 6

List of Compound Structures of Formula I

Z1.T1A.T2A.Y1A.Y2A, Z1.T1A.T2A.Y1A.Y2B, Z1.T1A.T2A.Y1A.Y2C,
Z1.T1A.T2A.Y1A.Y2D, Z1.T1A.T2A.Y1B.Y2A, Z1.T1A.T2A.Y1B.Y2B,
Z1.T1A.T2A.Y1B.Y2C, Z1.T1A.T2A.Y1B.Y2D, Z1.T1A.T2A.Y1C.Y2A,
Z1.T1A.T2A.Y1C.Y2B, Z1.T1A.T2A.Y1C.Y2C, Z1.T1A.T2A.Y1C.Y2D,
Z1.T1A.T2A.Y1D.Y2A, Z1.T1A.T2A.Y1D.Y2B, Z1.T1A.T2A.Y1D.Y2C,
Z1.T1A.T2A.Y1D.Y2D, Z1.T1A.T2A.Y1E.Y2A, Z1.T1A.T2A.Y1E.Y2B,
Z1.T1A.T2A.Y1E.Y2C, Z1.T1A.T2A.Y1E.Y2D, Z1.T1A.T2B.Y1A.Y2A,
Z1.T1A.T2B.Y1A.Y2B, Z1.T1A.T2B.Y1A.Y2C, Z1.T1A.T2B.Y1A.Y2D,

TABLE 6-continued

List of Compound Structures of Formula I

Z1.T1A.T2B.Y1B.Y2A, Z1.T1A.T2B.Y1B.Y2B, Z1.T1A.T2B.Y1B.Y2C,
Z1.T1A.T2B.Y1B.Y2D, Z1.T1A.T2B.Y1C.Y2A, Z1.T1A.T2B.Y1C.Y2B,
Z1.T1A.T2B.Y1C.Y2C, Z1.T1A.T2B.Y1C.Y2D, Z1.T1A.T2B.Y1D.Y2A,
Z1.T1A.T2B.Y1D.Y2B, Z1.T1A.T2B.Y1D.Y2C, Z1.T1A.T2B.Y1D.Y2D,
Z1.T1A.T2B.Y1E.Y2A, Z1.T1A.T2B.Y1E.Y2B, Z1.T1A.T2B.Y1E.Y2C,
Z1.T1A.T2B.Y1E.Y2D, Z1.T1A.T2C.Y1A.Y2A, Z1.T1A.T2C.Y1A.Y2B,
Z1.T1A.T2C.Y1A.Y2C, Z1.T1A.T2C.Y1A.Y2D, Z1.T1A.T2C.Y1B.Y2A,
Z1.T1A.T2C.Y1B.Y2B, Z1.T1A.T2C.Y1B.Y2C, Z1.T1A.T2C.Y1B.Y2D,
Z1.T1A.T2C.Y1C.Y2A, Z1.T1A.T2C.Y1C.Y2B, Z1.T1A.T2C.Y1C.Y2C,
Z1.T1A.T2C.Y1C.Y2D, Z1.T1A.T2C.Y1D.Y2A, Z1.T1A.T2C.Y1D.Y2B,
Z1.T1A.T2C.Y1D.Y2C, Z1.T1A.T2C.Y1D.Y2D, Z1.T1A.T2C.Y1E.Y2A,
Z1.T1A.T2C.Y1E.Y2B, Z1.T1A.T2C.Y1E.Y2C, Z1.T1A.T2C.Y1E.Y2D,
Z1.T1B.T2A.Y1A.Y2A, Z1.T1B.T2A.Y1A.Y2B, Z1.T1B.T2A.Y1A.Y2C,
Z1.T1B.T2A.Y1A.Y2D, Z1.T1B.T2A.Y1B.Y2A, Z1.T1B.T2A.Y1B.Y2B,
Z1.T1B.T2A.Y1B.Y2C, Z1.T1B.T2A.Y1B.Y2D, Z1.T1B.T2A.Y1C.Y2A,
Z1.T1B.T2A.Y1C.Y2B, Z1.T1B.T2A.Y1C.Y2C, Z1.T1B.T2A.Y1C.Y2D,
Z1.T1B.T2A.Y1D.Y2A, Z1.T1B.T2A.Y1D.Y2B, Z1.T1B.T2A.Y1D.Y2C,
Z1.T1B.T2A.Y1D.Y2D, Z1.T1B.T2A.Y1E.Y2A, Z1.T1B.T2A.Y1E.Y2B,
Z1.T1B.T2A.Y1E.Y2C, Z1.T1B.T2A.Y1E.Y2D, Z1.T1B.T2B.Y1A.Y2A,
Z1.T1B.T2B.Y1A.Y2B, Z1.T1B.T2B.Y1A.Y2C, Z1.T1B.T2B.Y1A.Y2D,
Z1.T1B.T2B.Y1B.Y2A, Z1.T1B.T2B.Y1B.Y2B, Z1.T1B.T2B.Y1B.Y2C,
Z1.T1B.T2B.Y1B.Y2D, Z1.T1B.T2B.Y1C.Y2A, Z1.T1B.T2B.Y1C.Y2B,
Z1.T1B.T2B.Y1C.Y2C, Z1.T1B.T2B.Y1C.Y2D, Z1.T1B.T2B.Y1D.Y2A,
Z1.T1B.T2B.Y1D.Y2B, Z1.T1B.T2B.Y1D.Y2C, Z1.T1B.T2B.Y1D.Y2D,
Z1.T1B.T2B.Y1E.Y2A, Z1.T1B.T2B.Y1E.Y2B, Z1.T1B.T2B.Y1E.Y2C,
Z1.T1B.T2B.Y1E.Y2D, Z1.T1B.T2C.Y1A.Y2A, Z1.T1B.T2C.Y1A.Y2B,
Z1.T1B.T2C.Y1A.Y2C, Z1.T1B.T2C.Y1A.Y2D, Z1.T1B.T2C.Y1B.Y2A,
Z1.T1B.T2C.Y1B.Y2B, Z1.T1B.T2C.Y1B.Y2C, Z1.T1B.T2C.Y1B.Y2D,
Z1.T1B.T2C.Y1C.Y2A, Z1.T1B.T2C.Y1C.Y2B, Z1.T1B.T2C.Y1C.Y2C,
Z1.T1B.T2C.Y1C.Y2D, Z1.T1B.T2C.Y1D.Y2A, Z1.T1B.T2C.Y1D.Y2B,
Z1.T1B.T2C.Y1D.Y2C, Z1.T1B.T2C.Y1D.Y2D, Z1.T1B.T2C.Y1E.Y2A,
Z1.T1B.T2C.Y1E.Y2B, Z1.T1B.T2C.Y1E.Y2C, Z1.T1B.T2C.Y1E.Y2D,
Z1.T1C.T2A.Y1A.Y2A, Z1.T1C.T2A.Y1A.Y2B, Z1.T1C.T2A.Y1A.Y2C,
Z1.T1C.T2A.Y1A.Y2D, Z1.T1C.T2A.Y1B.Y2A, Z1.T1C.T2A.Y1B.Y2B,
Z1.T1C.T2A.Y1B.Y2C, Z1.T1C.T2A.Y1B.Y2D, Z1.T1C.T2A.Y1C.Y2A,
Z1.T1C.T2A.Y1C.Y2B, Z1.T1C.T2A.Y1C.Y2C, Z1.T1C.T2A.Y1C.Y2D,
Z1.T1C.T2A.Y1D.Y2A, Z1.T1C.T2A.Y1D.Y2B, Z1.T1C.T2A.Y1D.Y2C,
Z1.T1C.T2A.Y1D.Y2D, Z1.T1C.T2A.Y1E.Y2A, Z1.T1C.T2A.Y1E.Y2B,
Z1.T1C.T2A.Y1E.Y2C, Z1.T1C.T2A.Y1E.Y2D, Z1.T1C.T2B.Y1A.Y2A,
Z1.T1C.T2B.Y1A.Y2B, Z1.T1C.T2B.Y1A.Y2C, Z1.T1C.T2B.Y1A.Y2D,
Z1.T1C.T2B.Y1B.Y2A, Z1.T1C.T2B.Y1B.Y2B, Z1.T1C.T2B.Y1B.Y2C,
Z1.T1C.T2B.Y1B.Y2D, Z1.T1C.T2B.Y1C.Y2A, Z1.T1C.T2B.Y1C.Y2B,
Z1.T1C.T2B.Y1C.Y2C, Z1.T1C.T2B.Y1C.Y2D, Z1.T1C.T2B.Y1D.Y2A,
Z1.T1C.T2B.Y1D.Y2B, Z1.T1C.T2B.Y1D.Y2C, Z1.T1C.T2B.Y1D.Y2D,
Z1.T1C.T2B.Y1E.Y2A, Z1.T1C.T2B.Y1E.Y2B, Z1.T1C.T2B.Y1E.Y2C,
Z1.T1C.T2B.Y1E.Y2D, Z1.T1C.T2C.Y1A.Y2A, Z1.T1C.T2C.Y1A.Y2B,
Z1.T1C.T2C.Y1A.Y2C, Z1.T1C.T2C.Y1A.Y2D, Z1.T1C.T2C.Y1B.Y2A,
Z1.T1C.T2C.Y1B.Y2B, Z1.T1C.T2C.Y1B.Y2C, Z1.T1C.T2C.Y1B.Y2D,
Z1.T1C.T2C.Y1C.Y2A, Z1.T1C.T2C.Y1C.Y2B, Z1.T1C.T2C.Y1C.Y2C,
Z1.T1C.T2C.Y1C.Y2D, Z1.T1C.T2C.Y1D.Y2A, Z1.T1C.T2C.Y1D.Y2B,
Z1.T1C.T2C.Y1D.Y2C, Z1.T1C.T2C.Y1D.Y2D, Z1.T1C.T2C.Y1E.Y2A,
Z1.T1C.T2C.Y1E.Y2B, Z1.T1C.T2C.Y1E.Y2C, Z1.T1C.T2C.Y1E.Y2D,
Z1.T1D.T2A.Y1A.Y2A, Z1.T1D.T2A.Y1A.Y2B, Z1.T1D.T2A.Y1A.Y2C,
Z1.T1D.T2A.Y1A.Y2D, Z1.T1D.T2A.Y1B.Y2A, Z1.T1D.T2A.Y1B.Y2B,
Z1.T1D.T2A.Y1B.Y2C, Z1.T1D.T2A.Y1B.Y2D, Z1.T1D.T2A.Y1C.Y2A,
Z1.T1D.T2A.Y1C.Y2B, Z1.T1D.T2A.Y1C.Y2C, Z1.T1D.T2A.Y1C.Y2D,
Z1.T1D.T2A.Y1D.Y2A, Z1.T1D.T2A.Y1D.Y2B, Z1.T1D.T2A.Y1D.Y2C,
Z1.T1D.T2A.Y1D.Y2D, Z1.T1D.T2A.Y1E.Y2A, Z1.T1D.T2A.Y1E.Y2B,
Z1.T1D.T2A.Y1E.Y2C, Z1.T1D.T2A.Y1E.Y2D, Z1.T1D.T2B.Y1A.Y2A,
Z1.T1D.T2B.Y1A.Y2B, Z1.T1D.T2B.Y1A.Y2C, Z1.T1D.T2B.Y1A.Y2D,
Z1.T1D.T2B.Y1B.Y2A, Z1.T1D.T2B.Y1B.Y2B, Z1.T1D.T2B.Y1B.Y2C,
Z1.T1D.T2B.Y1B.Y2D, Z1.T1D.T2B.Y1C.Y2A, Z1.T1D.T2B.Y1C.Y2B,
Z1.T1D.T2B.Y1C.Y2C, Z1.T1D.T2B.Y1C.Y2D, Z1.T1D.T2B.Y1D.Y2A,
Z1.T1D.T2B.Y1D.Y2B, Z1.T1D.T2B.Y1D.Y2C, Z1.T1D.T2B.Y1D.Y2D,
Z1.T1D.T2B.Y1E.Y2A, Z1.T1D.T2B.Y1E.Y2B, Z1.T1D.T2B.Y1E.Y2C,
Z1.T1D.T2B.Y1E.Y2D, Z1.T1D.T2C.Y1A.Y2A, Z1.T1D.T2C.Y1A.Y2B,
Z1.T1D.T2C.Y1A.Y2C, Z1.T1D.T2C.Y1A.Y2D, Z1.T1D.T2C.Y1B.Y2A,
Z1.T1D.T2C.Y1B.Y2B, Z1.T1D.T2C.Y1B.Y2C, Z1.T1D.T2C.Y1B.Y2D,
Z1.T1D.T2C.Y1C.Y2A, Z1.T1D.T2C.Y1C.Y2B, Z1.T1D.T2C.Y1C.Y2C,
Z1.T1D.T2C.Y1C.Y2D, Z1.T1D.T2C.Y1D.Y2A, Z1.T1D.T2C.Y1D.Y2B,
Z1.T1D.T2C.Y1D.Y2C, Z1.T1D.T2C.Y1D.Y2D, Z1.T1D.T2C.Y1E.Y2A,
Z1.T1D.T2C.Y1E.Y2B, Z1.T1D.T2C.Y1E.Y2C, Z1.T1D.T2C.Y1E.Y2D,
Z1.T1E.T2A.Y1A.Y2A, Z1.T1E.T2A.Y1A.Y2B, Z1.T1E.T2A.Y1A.Y2C,
Z1.T1E.T2A.Y1A.Y2D, Z1.T1E.T2A.Y1B.Y2A, Z1.T1E.T2A.Y1B.Y2B,
Z1.T1E.T2A.Y1B.Y2C, Z1.T1E.T2A.Y1B.Y2D, Z1.T1E.T2A.Y1C.Y2A,
Z1.T1E.T2A.Y1C.Y2B, Z1.T1E.T2A.Y1C.Y2C, Z1.T1E.T2A.Y1C.Y2D,
Z1.T1E.T2A.Y1D.Y2A, Z1.T1E.T2A.Y1D.Y2B, Z1.T1E.T2A.Y1D.Y2C,
Z1.T1E.T2A.Y1D.Y2D, Z1.T1E.T2A.Y1E.Y2A, Z1.T1E.T2A.Y1E.Y2B,

TABLE 6-continued

List of Compound Structures of Formula I

Z1.T1E.T2A.Y1E.Y2C, Z1.T1E.T2A.Y1E.Y2D, Z1.T1E.T2B.Y1A.Y2A,
Z1.T1E.T2B.Y1A.Y2B, Z1.T1E.T2B.Y1A.Y2C, Z1.T1E.T2B.Y1A.Y2D,
Z1.T1E.T2B.Y1B.Y2A, Z1.T1E.T2B.Y1B.Y2B, Z1.T1E.T2B.Y1B.Y2C,
Z1.T1E.T2B.Y1B.Y2D, Z1.T1E.T2B.Y1C.Y2A, Z1.T1E.T2B.Y1C.Y2B,
Z1.T1E.T2B.Y1C.Y2C, Z1.T1E.T2B.Y1C.Y2D, Z1.T1E.T2B.Y1D.Y2A,
Z1.T1E.T2B.Y1D.Y2B, Z1.T1E.T2B.Y1D.Y2C, Z1.T1E.T2B.Y1D.Y2D,
Z1.T1E.T2B.Y1E.Y2A, Z1.T1E.T2B.Y1E.Y2B, Z1.T1E.T2B.Y1E.Y2C,
Z1.T1E.T2B.Y1E.Y2D, Z1.T1E.T2C.Y1A.Y2A, Z1.T1E.T2C.Y1A.Y2B,
Z1.T1E.T2C.Y1A.Y2C, Z1.T1E.T2C.Y1A.Y2D, Z1.T1E.T2C.Y1B.Y2A,
Z1.T1E.T2C.Y1B.Y2B, Z1.T1E.T2C.Y1B.Y2C, Z1.T1E.T2C.Y1B.Y2D,
Z1.T1E.T2C.Y1C.Y2A, Z1.T1E.T2C.Y1C.Y2B, Z1.T1E.T2C.Y1C.Y2C,
Z1.T1E.T2C.Y1C.Y2D, Z1.T1E.T2C.Y1D.Y2A, Z1.T1E.T2C.Y1D.Y2B,
Z1.T1E.T2C.Y1D.Y2C, Z1.T1E.T2C.Y1D.Y2D, Z1.T1E.T2C.Y1E.Y2A,
Z1.T1E.T2C.Y1E.Y2B, Z1.T1E.T2C.Y1E.Y2C, Z1.T1E.T2C.Y1E.Y2D,
Z1.T1F.T2A.Y1A.Y2A, Z1.T1F.T2A.Y1A.Y2B, Z1.T1F.T2A.Y1A.Y2C,
Z1.T1F.T2A.Y1A.Y2D, Z1.T1F.T2A.Y1B.Y2A, Z1.T1F.T2A.Y1B.Y2B,
Z1.T1F.T2A.Y1B.Y2C, Z1.T1F.T2A.Y1B.Y2D, Z1.T1F.T2A.Y1C.Y2A,
Z1.T1F.T2A.Y1C.Y2B, Z1.T1F.T2A.Y1C.Y2C, Z1.T1F.T2A.Y1C.Y2D,
Z1.T1F.T2A.Y1D.Y2A, Z1.T1F.T2A.Y1D.Y2B, Z1.T1F.T2A.Y1D.Y2C,
Z1.T1F.T2A.Y1D.Y2D, Z1.T1F.T2A.Y1E.Y2A, Z1.T1F.T2A.Y1E.Y2B,
Z1.T1F.T2A.Y1E.Y2C, Z1.T1F.T2A.Y1E.Y2D, Z1.T1F.T2B.Y1A.Y2A,
Z1.T1F.T2B.Y1A.Y2B, Z1.T1F.T2B.Y1A.Y2C, Z1.T1F.T2B.Y1A.Y2D,
Z1.T1F.T2B.Y1B.Y2A, Z1.T1F.T2B.Y1B.Y2B, Z1.T1F.T2B.Y1B.Y2C,
Z1.T1F.T2B.Y1B.Y2D, Z1.T1F.T2B.Y1C.Y2A, Z1.T1F.T2B.Y1C.Y2B,
Z1.T1F.T2B.Y1C.Y2C, Z1.T1F.T2B.Y1C.Y2D, Z1.T1F.T2B.Y1D.Y2A,
Z1.T1F.T2B.Y1D.Y2B, Z1.T1F.T2B.Y1D.Y2C, Z1.T1F.T2B.Y1D.Y2D,
Z1.T1F.T2B.Y1E.Y2A, Z1.T1F.T2B.Y1E.Y2B, Z1.T1F.T2B.Y1E.Y2C,
Z1.T1F.T2B.Y1E.Y2D, Z1.T1F.T2C.Y1A.Y2A, Z1.T1F.T2C.Y1A.Y2B,
Z1.T1F.T2C.Y1A.Y2C, Z1.T1F.T2C.Y1A.Y2D, Z1.T1F.T2C.Y1B.Y2A,
Z1.T1F.T2C.Y1B.Y2B, Z1.T1F.T2C.Y1B.Y2C, Z1.T1F.T2C.Y1B.Y2D,
Z1.T1F.T2C.Y1C.Y2A, Z1.T1F.T2C.Y1C.Y2B, Z1.T1F.T2C.Y1C.Y2C,
Z1.T1F.T2C.Y1C.Y2D, Z1.T1F.T2C.Y1D.Y2A, Z1.T1F.T2C.Y1D.Y2B,
Z1.T1F.T2C.Y1D.Y2C, Z1.T1F.T2C.Y1D.Y2D, Z1.T1F.T2C.Y1E.Y2A,
Z1.T1F.T2C.Y1E.Y2B, Z1.T1F.T2C.Y1E.Y2C, Z1.T1F.T2C.Y1E.Y2D,
Z1.T1G.T2A.Y1A.Y2A, Z1.T1G.T2A.Y1A.Y2B, Z1.T1G.T2A.Y1A.Y2C,
Z1.T1G.T2A.Y1A.Y2D, Z1.T1G.T2A.Y1B.Y2A, Z1.T1G.T2A.Y1B.Y2B,
Z1.T1G.T2A.Y1B.Y2C, Z1.T1G.T2A.Y1B.Y2D, Z1.T1G.T2A.Y1C.Y2A,
Z1.T1G.T2A.Y1C.Y2B, Z1.T1G.T2A.Y1C.Y2C, Z1.T1G.T2A.Y1C.Y2D,
Z1.T1G.T2A.Y1D.Y2A, Z1.T1G.T2A.Y1D.Y2B, Z1.T1G.T2A.Y1D.Y2C,
Z1.T1G.T2A.Y1D.Y2D, Z1.T1G.T2A.Y1E.Y2A, Z1.T1G.T2A.Y1E.Y2B,
Z1.T1G.T2A.Y1E.Y2C, Z1.T1G.T2A.Y1E.Y2D, Z1.T1G.T2B.Y1A.Y2A,
Z1.T1G.T2B.Y1A.Y2B, Z1.T1G.T2B.Y1A.Y2C, Z1.T1G.T2B.Y1A.Y2D,
Z1.T1G.T2B.Y1B.Y2A, Z1.T1G.T2B.Y1B.Y2B, Z1.T1G.T2B.Y1B.Y2C,
Z1.T1G.T2B.Y1B.Y2D, Z1.T1G.T2B.Y1C.Y2A, Z1.T1G.T2B.Y1C.Y2B,
Z1.T1G.T2B.Y1C.Y2C, Z1.T1G.T2B.Y1C.Y2D, Z1.T1G.T2B.Y1D.Y2A,
Z1.T1G.T2B.Y1D.Y2B, Z1.T1G.T2B.Y1D.Y2C, Z1.T1G.T2B.Y1D.Y2D,
Z1.T1G.T2B.Y1E.Y2A, Z1.T1G.T2B.Y1E.Y2B, Z1.T1G.T2B.Y1E.Y2C,
Z1.T1G.T2B.Y1E.Y2D, Z1.T1G.T2C.Y1A.Y2A, Z1.T1G.T2C.Y1A.Y2B,
Z1.T1G.T2C.Y1A.Y2C, Z1.T1G.T2C.Y1A.Y2D, Z1.T1G.T2C.Y1B.Y2A,
Z1.T1G.T2C.Y1B.Y2B, Z1.T1G.T2C.Y1B.Y2C, Z1.T1G.T2C.Y1B.Y2D,
Z1.T1G.T2C.Y1C.Y2A, Z1.T1G.T2C.Y1C.Y2B, Z1.T1G.T2C.Y1C.Y2C,
Z1.T1G.T2C.Y1C.Y2D, Z1.T1G.T2C.Y1D.Y2A, Z1.T1G.T2C.Y1D.Y2B,
Z1.T1G.T2C.Y1D.Y2C, Z1.T1G.T2C.Y1D.Y2D, Z1.T1G.T2C.Y1E.Y2A,
Z1.T1G.T2C.Y1E.Y2B, Z1.T1G.T2C.Y1E.Y2C, Z1.T1G.T2C.Y1E.Y2D,
Z2.T1A.T2A.Y1A.Y2A, Z2.T1A.T2A.Y1A.Y2B, Z2.T1A.T2A.Y1A.Y2C,
Z2.T1A.T2A.Y1A.Y2D, Z2.T1A.T2A.Y1B.Y2A, Z2.T1A.T2A.Y1B.Y2B,
Z2.T1A.T2A.Y1B.Y2C, Z2.T1A.T2A.Y1B.Y2D, Z2.T1A.T2A.Y1C.Y2A,
Z2.T1A.T2A.Y1C.Y2B, Z2.T1A.T2A.Y1C.Y2C, Z2.T1A.T2A.Y1C.Y2D,
Z2.T1A.T2A.Y1D.Y2A, Z2.T1A.T2A.Y1D.Y2B, Z2.T1A.T2A.Y1D.Y2C,
Z2.T1A.T2A.Y1D.Y2D, Z2.T1A.T2A.Y1E.Y2A, Z2.T1A.T2A.Y1E.Y2B,
Z2.T1A.T2A.Y1E.Y2C, Z2.T1A.T2A.Y1E.Y2D, Z2.T1A.T2B.Y1A.Y2A,
Z2.T1A.T2B.Y1A.Y2B, Z2.T1A.T2B.Y1A.Y2C, Z2.T1A.T2B.Y1A.Y2D,
Z2.T1A.T2B.Y1B.Y2A, Z2.T1A.T2B.Y1B.Y2B, Z2.T1A.T2B.Y1B.Y2C,
Z2.T1A.T2B.Y1B.Y2D, Z2.T1A.T2B.Y1C.Y2A, Z2.T1A.T2B.Y1C.Y2B,
Z2.T1A.T2B.Y1C.Y2C, Z2.T1A.T2B.Y1C.Y2D, Z2.T1A.T2B.Y1D.Y2A,
Z2.T1A.T2B.Y1D.Y2B, Z2.T1A.T2B.Y1D.Y2C, Z2.T1A.T2B.Y1D.Y2D,
Z2.T1A.T2B.Y1E.Y2A, Z2.T1A.T2B.Y1E.Y2B, Z2.T1A.T2B.Y1E.Y2C,
Z2.T1A.T2B.Y1E.Y2D, Z2.T1A.T2C.Y1A.Y2A, Z2.T1A.T2C.Y1A.Y2B,
Z2.T1A.T2C.Y1A.Y2C, Z2.T1A.T2C.Y1A.Y2D, Z2.T1A.T2C.Y1B.Y2A,
Z2.T1A.T2C.Y1B.Y2B, Z2.T1A.T2C.Y1B.Y2C, Z2.T1A.T2C.Y1B.Y2D,
Z2.T1A.T2C.Y1C.Y2A, Z2.T1A.T2C.Y1C.Y2B, Z2.T1A.T2C.Y1C.Y2C,
Z2.T1A.T2C.Y1C.Y2D, Z2.T1A.T2C.Y1D.Y2A, Z2.T1A.T2C.Y1D.Y2B,
Z2.T1A.T2C.Y1D.Y2C, Z2.T1A.T2C.Y1D.Y2D, Z2.T1A.T2C.Y1E.Y2A,
Z2.T1A.T2C.Y1E.Y2B, Z2.T1A.T2C.Y1E.Y2C, Z2.T1A.T2C.Y1E.Y2D,
Z2.T1B.T2A.Y1A.Y2A, Z2.T1B.T2A.Y1A.Y2B, Z1.T1B.T2A.Y1A.Y2C,
Z2.T1B.T2A.Y1A.Y2D, Z2.T1B.T2A.Y1B.Y2A, Z2.T1B.T2A.Y1B.Y2B,
Z2.T1B.T2A.Y1B.Y2C, Z2.T1B.T2A.Y1B.Y2D, Z2.T1B.T2A.Y1C.Y2A,
Z2.T1B.T2A.Y1C.Y2B, Z2.T1B.T2A.Y1C.Y2C, Z2.T1B.T2A.Y1C.Y2D,

TABLE 6-continued

List of Compound Structures of Formula I

Z2.T1B.T2A.Y1D.Y2A, Z2.T1B.T2A.Y1D.Y2B, Z2.T1B.T2A.Y1D.Y2C,
Z2.T1B.T2A.Y1D.Y2D, Z2.T1B.T2A.Y1E.Y2A, Z2.T1B.T2A.Y1E.Y2B,
Z2.T1B.T2A.Y1E.Y2C, Z2.T1B.T2A.Y1E.Y2D, Z2.T1B.T2B.Y1A.Y2A,
Z2.T1B.T2B.Y1A.Y2B, Z2.T1B.T2B.Y1A.Y2C, Z2.T1B.T2B.Y1A.Y2D,
Z2.T1B.T2B.Y1B.Y2A, Z2.T1B.T2B.Y1B.Y2B, Z2.T1B.T2B.Y1B.Y2C,
Z2.T1B.T2B.Y1B.Y2D, Z2.T1B.T2B.Y1C.Y2A, Z2.T1B.T2B.Y1C.Y2B,
Z2.T1B.T2B.Y1C.Y2C, Z2.T1B.T2B.Y1C.Y2D, Z2.T1B.T2B.Y1D.Y2A,
Z2.T1B.T2B.Y1D.Y2B, Z2.T1B.T2B.Y1D.Y2C, Z2.T1B.T2B.Y1D.Y2D,
Z2.T1B.T2B.Y1E.Y2A, Z2.T1B.T2B.Y1E.Y2B, Z2.T1B.T2B.Y1E.Y2C,
Z2.T1B.T2B.Y1E.Y2D, Z2.T1B.T2C.Y1A.Y2A, Z2.T1B.T2C.Y1A.Y2B,
Z2.T1B.T2C.Y1A.Y2C, Z2.T1B.T2C.Y1A.Y2D, Z2.T1B.T2C.Y1B.Y2A,
Z2.T1B.T2C.Y1B.Y2B, Z2.T1B.T2C.Y1B.Y2C, Z2.T1B.T2C.Y1B.Y2D,
Z2.T1B.T2C.Y1C.Y2A, Z2.T1B.T2C.Y1C.Y2B, Z2.T1B.T2C.Y1C.Y2C,
Z2.T1B.T2C.Y1C.Y2D, Z2.T1B.T2C.Y1D.Y2A, Z2.T1B.T2C.Y1D.Y2B,
Z2.T1B.T2C.Y1D.Y2C, Z2.T1B.T2C.Y1D.Y2D, Z2.T1B.T2C.Y1E.Y2A,
Z2.T1B.T2C.Y1E.Y2B, Z2.T1B.T2C.Y1E.Y2C, Z2.T1B.T2C.Y1E.Y2D,
Z2.T1C.T2A.Y1A.Y2A, Z2.T1C.T2A.Y1A.Y2B, Z2.T1C.T2A.Y1A.Y2C,
Z2.T1C.T2A.Y1A.Y2D, Z2.T1C.T2A.Y1B.Y2A, Z2.T1C.T2A.Y1B.Y2B,
Z2.T1C.T2A.Y1B.Y2C, Z2.T1C.T2A.Y1B.Y2D, Z2.T1C.T2A.Y1C.Y2A,
Z2.T1C.T2A.Y1C.Y2B, Z2.T1C.T2A.Y1C.Y2C, Z2.T1C.T2A.Y1C.Y2D,
Z2.T1C.T2A.Y1D.Y2A, Z2.T1C.T2A.Y1D.Y2B, Z2.T1C.T2A.Y1D.Y2C,
Z2.T1C.T2A.Y1D.Y2D, Z2.T1C.T2A.Y1E.Y2A, Z2.T1C.T2A.Y1E.Y2B,
Z2.T1C.T2A.Y1E.Y2C, Z2.T1C.T2A.Y1E.Y2D, Z2.T1C.T2B.Y1A.Y2A,
Z2.T1C.T2B.Y1A.Y2B, Z2.T1C.T2B.Y1A.Y2C, Z2.T1C.T2B.Y1A.Y2D,
Z2.T1C.T2B.Y1B.Y2A, Z2.T1C.T2B.Y1B.Y2B, Z2.T1C.T2B.Y1B.Y2C,
Z2.T1C.T2B.Y1B.Y2D, Z2.T1C.T2B.Y1C.Y2A, Z2.T1C.T2B.Y1C.Y2B,
Z2.T1C.T2B.Y1C.Y2C, Z2.T1C.T2B.Y1C.Y2D, Z2.T1C.T2B.Y1D.Y2A,
Z2.T1C.T2B.Y1D.Y2B, Z2.T1C.T2B.Y1D.Y2C, Z2.T1C.T2B.Y1D.Y2D,
Z2.T1C.T2B.Y1E.Y2A, Z2.T1C.T2B.Y1E.Y2B, Z2.T1C.T2B.Y1E.Y2C,
Z2.T1C.T2B.Y1E.Y2D, Z2.T1C.T2C.Y1A.Y2A, Z2.T1C.T2C.Y1A.Y2B,
Z2.T1C.T2C.Y1A.Y2C, Z2.T1C.T2C.Y1A.Y2D, Z2.T1C.T2C.Y1B.Y2A,
Z2.T1C.T2C.Y1B.Y2B, Z2.T1C.T2C.Y1B.Y2C, Z2.T1C.T2C.Y1B.Y2D,
Z2.T1C.T2C.Y1C.Y2A, Z2.T1C.T2C.Y1C.Y2B, Z2.T1C.T2C.Y1C.Y2C,
Z2.T1C.T2C.Y1C.Y2D, Z2.T1C.T2C.Y1D.Y2A, Z2.T1C.T2C.Y1D.Y2B,
Z2.T1C.T2C.Y1D.Y2C, Z2.T1C.T2C.Y1D.Y2D, Z2.T1C.T2C.Y1E.Y2A,
Z2.T1C.T2C.Y1E.Y2B, Z2.T1C.T2C.Y1E.Y2C, Z2.T1C.T2C.Y1E.Y2D,
Z2.T1D.T2A.Y1A.Y2A, Z2.T1D.T2A.Y1A.Y2B, Z2.T1D.T2A.Y1A.Y2C,
Z2.T1D.T2A.Y1A.Y2D, Z2.T1D.T2A.Y1B.Y2A, Z2.T1D.T2A.Y1B.Y2B,
Z2.T1D.T2A.Y1B.Y2C, Z2.T1D.T2A.Y1B.Y2D, Z2.T1D.T2A.Y1C.Y2A,
Z2.T1D.T2A.Y1C.Y2B, Z2.T1D.T2A.Y1C.Y2C, Z2.T1D.T2A.Y1C.Y2D,
Z2.T1D.T2A.Y1D.Y2A, Z2.T1D.T2A.Y1D.Y2B, Z2.T1D.T2A.Y1D.Y2C,
Z2.T1D.T2A.Y1D.Y2D, Z2.T1D.T2A.Y1E.Y2A, Z2.T1D.T2A.Y1E.Y2B,
Z2.T1D.T2A.Y1E.Y2C, Z2.T1D.T2A.Y1E.Y2D, Z2.T1D.T2B.Y1A.Y2A,
Z2.T1D.T2B.Y1A.Y2B, Z2.T1D.T2B.Y1A.Y2C, Z2.T1D.T2B.Y1A.Y2D,
Z2.T1D.T2B.Y1B.Y2A, Z2.T1D.T2B.Y1B.Y2B, Z2.T1D.T2B.Y1B.Y2C,
Z2.T1D.T2B.Y1B.Y2D, Z2.T1D.T2B.Y1C.Y2A, Z2.T1D.T2B.Y1C.Y2B,
Z2.T1D.T2B.Y1C.Y2C, Z2.T1D.T2B.Y1C.Y2D, Z2.T1D.T2B.Y1D.Y2A,
Z2.T1D.T2B.Y1D.Y2B, Z2.T1D.T2B.Y1D.Y2C, Z2.T1D.T2B.Y1D.Y2D,
Z2.T1D.T2B.Y1E.Y2A, Z2.T1D.T2B.Y1E.Y2B, Z2.T1D.T2B.Y1E.Y2C,
Z2.T1D.T2B.Y1E.Y2D, Z2.T1D.T2C.Y1A.Y2A, Z2.T1D.T2C.Y1A.Y2B,
Z2.T1D.T2C.Y1A.Y2C, Z2.T1D.T2C.Y1A.Y2D, Z2.T1D.T2C.Y1B.Y2A,
Z2.T1D.T2C.Y1B.Y2B, Z2.T1D.T2C.Y1B.Y2C, Z2.T1D.T2C.Y1B.Y2D,
Z2.T1D.T2C.Y1C.Y2A, Z2.T1D.T2C.Y1C.Y2B, Z2.T1D.T2C.Y1C.Y2C,
Z2.T1D.T2C.Y1C.Y2D, Z2.T1D.T2C.Y1D.Y2A, Z2.T1D.T2C.Y1D.Y2B,
Z2.T1D.T2C.Y1D.Y2C, Z2.T1D.T2C.Y1D.Y2D, Z2.T1D.T2C.Y1E.Y2A,
Z2.T1D.T2C.Y1E.Y2B, Z2.T1D.T2C.Y1E.Y2C, Z2.T1D.T2C.Y1E.Y2D,
Z2.T1E.T2A.Y1A.Y2A, Z2.T1E.T2A.Y1A.Y2B, Z2.T1E.T2A.Y1A.Y2C,
Z2.T1E.T2A.Y1A.Y2D, Z2.T1E.T2A.Y1B.Y2A, Z2.T1E.T2A.Y1B.Y2B,
Z2.T1E.T2A.Y1B.Y2C, Z2.T1E.T2A.Y1B.Y2D, Z2.T1E.T2A.Y1C.Y2A,
Z2.T1E.T2A.Y1C.Y2B, Z2.T1E.T2A.Y1C.Y2C, Z2.T1E.T2A.Y1C.Y2D,
Z2.T1E.T2A.Y1D.Y2A, Z2.T1E.T2A.Y1D.Y2B, Z2.T1E.T2A.Y1D.Y2C,
Z2.T1E.T2A.Y1D.Y2D, Z2.T1E.T2A.Y1E.Y2A, Z2.T1E.T2A.Y1E.Y2B,
Z2.T1E.T2A.Y1E.Y2C, Z2.T1E.T2A.Y1E.Y2D, Z2.T1E.T2B.Y1A.Y2A,
Z2.T1E.T2B.Y1A.Y2B, Z2.T1E.T2B.Y1A.Y2C, Z2.T1E.T2B.Y1A.Y2D,
Z2.T1E.T2B.Y1B.Y2A, Z2.T1E.T2B.Y1B.Y2B, Z2.T1E.T2B.Y1B.Y2C,
Z2.T1E.T2B.Y1B.Y2D, Z2.T1E.T2B.Y1C.Y2A, Z2.T1E.T2B.Y1C.Y2B,
Z2.T1E.T2B.Y1C.Y2C, Z2.T1E.T2B.Y1C.Y2D, Z2.T1E.T2B.Y1D.Y2A,
Z2.T1E.T2B.Y1D.Y2B, Z2.T1E.T2B.Y1D.Y2C, Z2.T1E.T2B.Y1D.Y2D,
Z2.T1E.T2B.Y1E.Y2A, Z2.T1E.T2B.Y1E.Y2B, Z2.T1E.T2B.Y1E.Y2C,
Z2.T1E.T2B.Y1E.Y2D, Z2.T1E.T2C.Y1A.Y2A, Z2.T1E.T2C.Y1A.Y2B,
Z2.T1E.T2C.Y1A.Y2C, Z2.T1E.T2C.Y1A.Y2D, Z2.T1E.T2C.Y1B.Y2A,
Z2.T1E.T2C.Y1B.Y2B, Z2.T1E.T2C.Y1B.Y2C, Z2.T1E.T2C.Y1B.Y2D,
Z2.T1E.T2C.Y1C.Y2A, Z2.T1E.T2C.Y1C.Y2B, Z2.T1E.T2C.Y1C.Y2C,
Z2.T1E.T2C.Y1C.Y2D, Z2.T1E.T2C.Y1D.Y2A, Z2.T1E.T2C.Y1D.Y2B,
Z2.T1E.T2C.Y1D.Y2C, Z2.T1E.T2C.Y1D.Y2D, Z2.T1E.T2C.Y1E.Y2A,
Z2.T1E.T2C.Y1E.Y2B, Z2.T1E.T2C.Y1E.Y2C, Z2.T1E.T2C.Y1E.Y2D,
Z2.T1F.T2A.Y1A.Y2A, Z2.T1F.T2A.Y1A.Y2B, Z2.T1F.T2A.Y1A.Y2C,
Z2.T1F.T2A.Y1A.Y2D, Z2.T1F.T2A.Y1B.Y2A, Z2.T1F.T2A.Y1B.Y2B,

TABLE 6-continued

List of Compound Structures of Formula I

Z2.T1F.T2A.Y1B.Y2C, Z2.T1F.T2A.Y1B.Y2D, Z2.T1F.T2A.Y1C.Y2A,
Z2.T1F.T2A.Y1C.Y2B, Z2.T1F.T2A.Y1C.Y2C, Z2.T1F.T2A.Y1C.Y2D,
Z2.T1F.T2A.Y1D.Y2A, Z2.T1F.T2A.Y1D.Y2B, Z2.T1F.T2A.Y1D.Y2C,
Z2.T1F.T2A.Y1D.Y2D, Z2.T1F.T2A.Y1E.Y2A, Z2.T1F.T2A.Y1E.Y2B,
Z2.T1F.T2A.Y1E.Y2C, Z2.T1F.T2A.Y1E.Y2D, Z2.T1F.T2B.Y1A.Y2A,
Z2.T1F.T2B.Y1A.Y2B, Z2.T1F.T2B.Y1A.Y2C, Z2.T1F.T2B.Y1A.Y2D,
Z2.T1F.T2B.Y1B.Y2A, Z2.T1F.T2B.Y1B.Y2B, Z2.T1F.T2B.Y1B.Y2C,
Z2.T1F.T2B.Y1B.Y2D, Z2.T1F.T2B.Y1C.Y2A, Z2.T1F.T2B.Y1C.Y2B,
Z2.T1F.T2B.Y1C.Y2C, Z2.T1F.T2B.Y1C.Y2D, Z2.T1F.T2B.Y1D.Y2A,
Z2.T1F.T2B.Y1D.Y2B, Z2.T1F.T2B.Y1D.Y2C, Z2.T1F.T2B.Y1D.Y2D,
Z2.T1F.T2B.Y1E.Y2A, Z2.T1F.T2B.Y1E.Y2B, Z2.T1F.T2B.Y1E.Y2C,
Z2.T1F.T2B.Y1E.Y2D, Z2.T1F.T2C.Y1A.Y2A, Z2.T1F.T2C.Y1A.Y2B,
Z2.T1F.T2C.Y1A.Y2C, Z2.T1F.T2C.Y1A.Y2D, Z2.T1F.T2C.Y1B.Y2A,
Z2.T1F.T2C.Y1B.Y2B, Z2.T1F.T2C.Y1B.Y2C, Z2.T1F.T2C.Y1B.Y2D,
Z2.T1F.T2C.Y1C.Y2A, Z2.T1F.T2C.Y1C.Y2B, Z2.T1F.T2C.Y1C.Y2C,
Z2.T1F.T2C.Y1C.Y2D, Z2.T1F.T2C.Y1D.Y2A, Z2.T1F.T2C.Y1D.Y2B,
Z2.T1F.T2C.Y1D.Y2C, Z2.T1F.T2C.Y1D.Y2D, Z2.T1F.T2C.Y1E.Y2A,
Z2.T1F.T2C.Y1E.Y2B, Z2.T1F.T2C.Y1E.Y2C, Z2.T1F.T2C.Y1E.Y2D,
Z2.T1G.T2A.Y1A.Y2A, Z2.T1G.T2A.Y1A.Y2B, Z2.T1G.T2A.Y1A.Y2C,
Z2.T1G.T2A.Y1A.Y2D, Z2.T1G.T2A.Y1B.Y2A, Z2.T1G.T2A.Y1B.Y2B,
Z2.T1G.T2A.Y1B.Y2C, Z2.T1G.T2A.Y1B.Y2D, Z2.T1G.T2A.Y1C.Y2A,
Z2.T1G.T2A.Y1C.Y2B, Z2.T1G.T2A.Y1C.Y2C, Z2.T1G.T2A.Y1C.Y2D,
Z2.T1G.T2A.Y1D.Y2A, Z2.T1G.T2A.Y1D.Y2B, Z2.T1G.T2A.Y1D.Y2C,
Z2.T1G.T2A.Y1D.Y2D, Z2.T1G.T2A.Y1E.Y2A, Z2.T1G.T2A.Y1E.Y2B,
Z2.T1G.T2A.Y1E.Y2C, Z2.T1G.T2A.Y1E.Y2D, Z2.T1G.T2B.Y1A.Y2A,
Z2.T1G.T2B.Y1A.Y2B, Z2.T1G.T2B.Y1A.Y2C, Z2.T1G.T2B.Y1A.Y2D,
Z2.T1G.T2B.Y1B.Y2A, Z2.T1G.T2B.Y1B.Y2B, Z2.T1G.T2B.Y1B.Y2C,
Z2.T1G.T2B.Y1B.Y2D, Z2.T1G.T2B.Y1C.Y2A, Z2.T1G.T2B.Y1C.Y2B,
Z2.T1G.T2B.Y1C.Y2C, Z2.T1G.T2B.Y1C.Y2D, Z2.T1G.T2B.Y1D.Y2A,
Z2.T1G.T2B.Y1D.Y2B, Z2.T1G.T2B.Y1D.Y2C, Z2.T1G.T2B.Y1D.Y2D,
Z2.T1G.T2B.Y1E.Y2A, Z2.T1G.T2B.Y1E.Y2B, Z2.T1G.T2B.Y1E.Y2C,
Z2.T1G.T2B.Y1E.Y2D, Z2.T1G.T2C.Y1A.Y2A, Z2.T1G.T2C.Y1A.Y2B,
Z2.T1G.T2C.Y1A.Y2C, Z2.T1G.T2C.Y1A.Y2D, Z2.T1G.T2C.Y1B.Y2A,
Z2.T1G.T2C.Y1B.Y2B, Z2.T1G.T2C.Y1B.Y2C, Z2.T1G.T2C.Y1B.Y2D,
Z2.T1G.T2C.Y1C.Y2A, Z2.T1G.T2C.Y1C.Y2B, Z2.T1G.T2C.Y1C.Y2C,
Z2.T1G.T2C.Y1C.Y2D, Z2.T1G.T2C.Y1D.Y2A, Z2.T1G.T2C.Y1D.Y2B,
Z2.T1G.T2C.Y1D.Y2C, Z2.T1G.T2C.Y1D.Y2D, Z2.T1G.T2C.Y1E.Y2A,
Z2.T1G.T2C.Y1E.Y2B, Z2.T1G.T2C.Y1E.Y2C, Z2.T1G.T2C.Y1E.Y2D,
Z3.T1A.T2A.Y1A.Y2A, Z3.T1A.T2A.Y1A.Y2B, Z3.T1A.T2A.Y1A.Y2C,
Z3.T1A.T2A.Y1A.Y2D, Z3.T1A.T2A.Y1B.Y2A, Z3.T1A.T2A.Y1B.Y2B,
Z3.T1A.T2A.Y1B.Y2C, Z3.T1A.T2A.Y1B.Y2D, Z3.T1A.T2A.Y1C.Y2A,
Z3.T1A.T2A.Y1C.Y2B, Z3.T1A.T2A.Y1C.Y2C, Z3.T1A.T2A.Y1C.Y2D,
Z3.T1A.T2A.Y1D.Y2A, Z3.T1A.T2A.Y1D.Y2B, Z3.T1A.T2A.Y1D.Y2C,
Z3.T1A.T2A.Y1D.Y2D, Z3.T1A.T2A.Y1E.Y2A, Z3.T1A.T2A.Y1E.Y2B,
Z3.T1A.T2A.Y1E.Y2C, Z3.T1A.T2A.Y1E.Y2D, Z3.T1A.T2B.Y1A.Y2A,
Z3.T1A.T2B.Y1A.Y2B, Z3.T1A.T2B.Y1A.Y2C, Z3.T1A.T2B.Y1A.Y2D,
Z3.T1A.T2B.Y1B.Y2A, Z3.T1A.T2B.Y1B.Y2B, Z3.T1A.T2B.Y1B.Y2C,
Z3.T1A.T2B.Y1B.Y2D, Z3.T1A.T2B.Y1C.Y2A, Z3.T1A.T2B.Y1C.Y2B,
Z3.T1A.T2B.Y1C.Y2C, Z3.T1A.T2B.Y1C.Y2D, Z3.T1A.T2B.Y1D.Y2A,
Z3.T1A.T2B.Y1D.Y2B, Z3.T1A.T2B.Y1D.Y2C, Z3.T1A.T2B.Y1D.Y2D,
Z3.T1A.T2B.Y1E.Y2A, Z3.T1A.T2B.Y1E.Y2B, Z3.T1A.T2B.Y1E.Y2C,
Z3.T1A.T2B.Y1E.Y2D, Z3.T1A.T2C.Y1A.Y2A, Z3.T1A.T2C.Y1A.Y2B,
Z3.T1A.T2C.Y1A.Y2C, Z3.T1A.T2C.Y1A.Y2D, Z3.T1A.T2C.Y1B.Y2A,
Z3.T1A.T2C.Y1B.Y2B, Z3.T1A.T2C.Y1B.Y2C, Z3.T1A.T2C.Y1B.Y2D,
Z3.T1A.T2C.Y1C.Y2A, Z3.T1A.T2C.Y1C.Y2B, Z3.T1A.T2C.Y1C.Y2C,
Z3.T1A.T2C.Y1C.Y2D, Z3.T1A.T2C.Y1D.Y2A, Z3.T1A.T2C.Y1D.Y2B,
Z3.T1A.T2C.Y1D.Y2C, Z3.T1A.T2C.Y1D.Y2D, Z3.T1A.T2C.Y1E.Y2A,
Z3.T1A.T2C.Y1E.Y2B, Z3.T1A.T2C.Y1E.Y2C, Z3.T1A.T2C.Y1E.Y2D,
Z3.T1B.T2A.Y1A.Y2A, Z3.T1B.T2A.Y1A.Y2B, Z3.T1B.T2A.Y1A.Y2C,
Z3.T1B.T2A.Y1A.Y2D, Z3.T1B.T2A.Y1B.Y2A, Z3.T1B.T2A.Y1B.Y2B,
Z3.T1B.T2A.Y1B.Y2C, Z3.T1B.T2A.Y1B.Y2D, Z3.T1B.T2A.Y1C.Y2A,
Z3.T1B.T2A.Y1C.Y2B, Z3.T1B.T2A.Y1C.Y2C, Z3.T1B.T2A.Y1C.Y2D,
Z3.T1B.T2A.Y1D.Y2A, Z3.T1B.T2A.Y1D.Y2B, Z3.T1B.T2A.Y1D.Y2C,
Z3.T1B.T2A.Y1D.Y2D, Z3.T1B.T2A.Y1E.Y2A, Z3.T1B.T2A.Y1E.Y2B,
Z3.T1B.T2A.Y1E.Y2C, Z3.T1B.T2A.Y1E.Y2D, Z3.T1B.T2B.Y1A.Y2A,
Z3.T1B.T2B.Y1A.Y2B, Z3.T1B.T2B.Y1A.Y2C, Z3.T1B.T2B.Y1A.Y2D,
Z3.T1B.T2B.Y1B.Y2A, Z3.T1B.T2B.Y1B.Y2B, Z3.T1B.T2B.Y1B.Y2C,
Z3.T1B.T2B.Y1B.Y2D, Z3.T1B.T2B.Y1C.Y2A, Z3.T1B.T2B.Y1C.Y2B,
Z3.T1B.T2B.Y1C.Y2C, Z3.T1B.T2B.Y1C.Y2D, Z3.T1B.T2B.Y1D.Y2A,
Z3.T1B.T2B.Y1D.Y2B, Z3.T1B.T2B.Y1D.Y2C, Z3.T1B.T2B.Y1D.Y2D,
Z3.T1B.T2B.Y1E.Y2A, Z3.T1B.T2B.Y1E.Y2B, Z3.T1B.T2B.Y1E.Y2C,
Z3.T1B.T2B.Y1E.Y2D, Z3.T1B.T2C.Y1A.Y2A, Z3.T1B.T2C.Y1A.Y2B,
Z3.T1B.T2C.Y1A.Y2C, Z3.T1B.T2C.Y1A.Y2D, Z3.T1B.T2C.Y1B.Y2A,
Z3.T1B.T2C.Y1B.Y2B, Z3.T1B.T2C.Y1B.Y2C, Z3.T1B.T2C.Y1B.Y2D,
Z3.T1B.T2C.Y1C.Y2A, Z3.T1B.T2C.Y1C.Y2B, Z3.T1B.T2C.Y1C.Y2C,
Z3.T1B.T2C.Y1C.Y2D, Z3.T1B.T2C.Y1D.Y2A, Z3.T1B.T2C.Y1D.Y2B,
Z3.T1B.T2C.Y1D.Y2C, Z3.T1B.T2C.Y1D.Y2D, Z3.T1B.T2C.Y1E.Y2A,
Z3.T1B.T2C.Y1E.Y2B, Z3.T1B.T2C.Y1E.Y2C, Z3.T1B.T2C.Y1E.Y2D,

TABLE 6-continued

List of Compound Structures of Formula I

Z3.T1C.T2A.Y1A.Y2A, Z3.T1C.T2A.Y1A.Y2B, Z3.T1C.T2A.Y1A.Y2C,
Z3.T1C.T2A.Y1A.Y2D, Z3.T1C.T2A.Y1B.Y2A, Z3.T1C.T2A.Y1B.Y2B,
Z3.T1C.T2A.Y1B.Y2C, Z3.T1C.T2A.Y1B.Y2D, Z3.T1C.T2A.Y1C.Y2A,
Z3.T1C.T2A.Y1C.Y2B, Z3.T1C.T2A.Y1C.Y2C, Z3.T1C.T2A.Y1C.Y2D,
Z3.T1C.T2A.Y1D.Y2A, Z3.T1C.T2A.Y1D.Y2B, Z3.T1C.T2A.Y1D.Y2C,
Z3.T1C.T2A.Y1D.Y2D, Z3.T1C.T2A.Y1E.Y2A, Z3.T1C.T2A.Y1E.Y2B,
Z3.T1C.T2A.Y1E.Y2C, Z3.T1C.T2A.Y1E.Y2D, Z3.T1C.T2B.Y1A.Y2A,
Z3.T1C.T2B.Y1A.Y2B, Z3.T1C.T2B.Y1A.Y2C, Z3.T1C.T2B.Y1A.Y2D,
Z3.T1C.T2B.Y1B.Y2A, Z3.T1C.T2B.Y1B.Y2B, Z3.T1C.T2B.Y1B.Y2C,
Z3.T1C.T2B.Y1B.Y2D, Z3.T1C.T2B.Y1C.Y2A, Z3.T1C.T2B.Y1C.Y2B,
Z3.T1C.T2B.Y1C.Y2C, Z3.T1C.T2B.Y1C.Y2D, Z3.T1C.T2B.Y1D.Y2A,
Z3.T1C.T2B.Y1D.Y2B, Z3.T1C.T2B.Y1D.Y2C, Z3.T1C.T2B.Y1D.Y2D,
Z3.T1C.T2B.Y1E.Y2A, Z3.T1C.T2B.Y1E.Y2B, Z3.T1C.T2B.Y1E.Y2C,
Z3.T1C.T2B.Y1E.Y2D, Z3.T1C.T2C.Y1A.Y2A, Z3.T1C.T2C.Y1A.Y2B,
Z3.T1C.T2C.Y1A.Y2C, Z3.T1C.T2C.Y1A.Y2D, Z3.T1C.T2C.Y1B.Y2A,
Z3.T1C.T2C.Y1B.Y2B, Z3.T1C.T2C.Y1B.Y2C, Z3.T1C.T2C.Y1B.Y2D,
Z3.T1C.T2C.Y1C.Y2A, Z3.T1C.T2C.Y1C.Y2B, Z3.T1C.T2C.Y1C.Y2C,
Z3.T1C.T2C.Y1C.Y2D, Z3.T1C.T2C.Y1D.Y2A, Z3.T1C.T2C.Y1D.Y2B,
Z3.T1C.T2C.Y1D.Y2C, Z3.T1C.T2C.Y1D.Y2D, Z3.T1C.T2C.Y1E.Y2A,
Z3.T1C.T2C.Y1E.Y2B, Z3.T1C.T2C.Y1E.Y2C, Z3.T1C.T2C.Y1E.Y2D,
Z3.T1D.T2A.Y1A.Y2A, Z3.T1D.T2A.Y1A.Y2B, Z3.T1D.T2A.Y1A.Y2C,
Z3.T1D.T2A.Y1A.Y2D, Z3.T1D.T2A.Y1B.Y2A, Z3.T1D.T2A.Y1B.Y2B,
Z3.T1D.T2A.Y1B.Y2C, Z3.T1D.T2A.Y1B.Y2D, Z3.T1D.T2A.Y1C.Y2A,
Z3.T1D.T2A.Y1C.Y2B, Z3.T1D.T2A.Y1C.Y2C, Z3.T1D.T2A.Y1C.Y2D,
Z3.T1D.T2A.Y1D.Y2A, Z3.T1D.T2A.Y1D.Y2B, Z3.T1D.T2A.Y1D.Y2C,
Z3.T1D.T2A.Y1D.Y2D, Z3.T1D.T2A.Y1E.Y2A, Z3.T1D.T2A.Y1E.Y2B,
Z3.T1D.T2A.Y1E.Y2C, Z3.T1D.T2A.Y1E.Y2D, Z3.T1D.T2B.Y1A.Y2A,
Z3.T1D.T2B.Y1A.Y2B, Z3.T1D.T2B.Y1A.Y2C, Z3.T1D.T2B.Y1A.Y2D,
Z3.T1D.T2B.Y1B.Y2A, Z3.T1D.T2B.Y1B.Y2B, Z3.T1D.T2B.Y1B.Y2C,
Z3.T1D.T2B.Y1B.Y2D, Z3.T1D.T2B.Y1C.Y2A, Z3.T1D.T2B.Y1C.Y2B,
Z3.T1D.T2B.Y1C.Y2C, Z3.T1D.T2B.Y1C.Y2D, Z3.T1D.T2B.Y1D.Y2A,
Z3.T1D.T2B.Y1D.Y2B, Z3.T1D.T2B.Y1D.Y2C, Z3.T1D.T2B.Y1D.Y2D,
Z3.T1D.T2B.Y1E.Y2A, Z3.T1D.T2B.Y1E.Y2B, Z3.T1D.T2B.Y1E.Y2C,
Z3.T1D.T2B.Y1E.Y2D, Z3.T1D.T2C.Y1A.Y2A, Z3.T1D.T2C.Y1A.Y2B,
Z3.T1D.T2C.Y1A.Y2C, Z3.T1D.T2C.Y1A.Y2D, Z3.T1D.T2C.Y1B.Y2A,
Z3.T1D.T2C.Y1B.Y2B, Z3.T1D.T2C.Y1B.Y2C, Z3.T1D.T2C.Y1B.Y2D,
Z3.T1D.T2C.Y1C.Y2A, Z3.T1D.T2C.Y1C.Y2B, Z3.T1D.T2C.Y1C.Y2C,
Z3.T1D.T2C.Y1C.Y2D, Z3.T1D.T2C.Y1D.Y2A, Z3.T1D.T2C.Y1D.Y2B,
Z3.T1D.T2C.Y1D.Y2C, Z3.T1D.T2C.Y1D.Y2D, Z3.T1D.T2C.Y1E.Y2A,
Z3.T1D.T2C.Y1E.Y2B, Z3.T1D.T2C.Y1E.Y2C, Z3.T1D.T2C.Y1E.Y2D,
Z3.T1E.T2A.Y1A.Y2A, Z3.T1E.T2A.Y1A.Y2B, Z3.T1E.T2A.Y1A.Y2C,
Z3.T1E.T2A.Y1A.Y2D, Z3.T1E.T2A.Y1B.Y2A, Z3.T1E.T2A.Y1B.Y2B,
Z3.T1E.T2A.Y1B.Y2C, Z3.T1E.T2A.Y1B.Y2D, Z3.T1E.T2A.Y1C.Y2A,
Z3.T1E.T2A.Y1C.Y2B, Z3.T1E.T2A.Y1C.Y2C, Z3.T1E.T2A.Y1C.Y2D,
Z3.T1E.T2A.Y1D.Y2A, Z3.T1E.T2A.Y1D.Y2B, Z3.T1E.T2A.Y1D.Y2C,
Z3.T1E.T2A.Y1D.Y2D, Z3.T1E.T2A.Y1E.Y2A, Z3.T1E.T2A.Y1E.Y2B,
Z3.T1E.T2A.Y1E.Y2C, Z3.T1E.T2A.Y1E.Y2D, Z3.T1E.T2B.Y1A.Y2A,
Z3.T1E.T2B.Y1A.Y2B, Z3.T1E.T2B.Y1A.Y2C, Z3.T1E.T2B.Y1A.Y2D,
Z3.T1E.T2B.Y1B.Y2A, Z3.T1E.T2B.Y1B.Y2B, Z3.T1E.T2B.Y1B.Y2C,
Z3.T1E.T2B.Y1B.Y2D, Z3.T1E.T2B.Y1C.Y2A, Z3.T1E.T2B.Y1C.Y2B,
Z3.T1E.T2B.Y1C.Y2C, Z3.T1E.T2B.Y1C.Y2D, Z3.T1E.T2B.Y1D.Y2A,
Z3.T1E.T2B.Y1D.Y2B, Z3.T1E.T2B.Y1D.Y2C, Z3.T1E.T2B.Y1D.Y2D,
Z3.T1E.T2B.Y1E.Y2A, Z3.T1E.T2B.Y1E.Y2B, Z3.T1E.T2B.Y1E.Y2C,
Z3.T1E.T2B.Y1E.Y2D, Z3.T1E.T2C.Y1A.Y2A, Z3.T1E.T2C.Y1A.Y2B,
Z3.T1E.T2C.Y1A.Y2C, Z3.T1E.T2C.Y1A.Y2D, Z3.T1E.T2C.Y1B.Y2A,
Z3.T1E.T2C.Y1B.Y2B, Z3.T1E.T2C.Y1B.Y2C, Z3.T1E.T2C.Y1B.Y2D,
Z3.T1E.T2C.Y1C.Y2A, Z3.T1E.T2C.Y1C.Y2B, Z3.T1E.T2C.Y1C.Y2C,
Z3.T1E.T2C.Y1C.Y2D, Z3.T1E.T2C.Y1D.Y2A, Z3.T1E.T2C.Y1D.Y2B,
Z3.T1E.T2C.Y1D.Y2C, Z3.T1E.T2C.Y1D.Y2D, Z3.T1E.T2C.Y1E.Y2A,
Z3.T1E.T2C.Y1E.Y2B, Z3.T1E.T2C.Y1E.Y2C, Z3.T1E.T2C.Y1E.Y2D,
Z3.T1F.T2A.Y1A.Y2A, Z3.T1F.T2A.Y1A.Y2B, Z3.T1F.T2A.Y1A.Y2C,
Z3.T1F.T2A.Y1A.Y2D, Z3.T1F.T2A.Y1B.Y2A, Z3.T1F.T2A.Y1B.Y2B,
Z3.T1F.T2A.Y1B.Y2C, Z3.T1F.T2A.Y1B.Y2D, Z3.T1F.T2A.Y1C.Y2A,
Z3.T1F.T2A.Y1C.Y2B, Z3.T1F.T2A.Y1C.Y2C, Z3.T1F.T2A.Y1C.Y2D,
Z3.T1F.T2A.Y1D.Y2A, Z3.T1F.T2A.Y1D.Y2B, Z3.T1F.T2A.Y1D.Y2C,
Z3.T1F.T2A.Y1D.Y2D, Z3.T1F.T2A.Y1E.Y2A, Z3.T1F.T2A.Y1E.Y2B,
Z3.T1F.T2A.Y1E.Y2C, Z3.T1F.T2A.Y1E.Y2D, Z3.T1F.T2B.Y1A.Y2A,
Z3.T1F.T2B.Y1A.Y2B, Z3.T1F.T2B.Y1A.Y2C, Z3.T1F.T2B.Y1A.Y2D,
Z3.T1F.T2B.Y1B.Y2A, Z3.T1F.T2B.Y1B.Y2B, Z3.T1F.T2B.Y1B.Y2C,
Z3.T1F.T2B.Y1B.Y2D, Z3.T1F.T2B.Y1C.Y2A, Z3.T1F.T2B.Y1C.Y2B,
Z3.T1F.T2B.Y1C.Y2C, Z3.T1F.T2B.Y1C.Y2D, Z3.T1F.T2B.Y1D.Y2A,
Z3.T1F.T2B.Y1D.Y2B, Z3.T1F.T2B.Y1D.Y2C, Z3.T1F.T2B.Y1D.Y2D,
Z3.T1F.T2B.Y1E.Y2A, Z3.T1F.T2B.Y1E.Y2B, Z3.T1F.T2B.Y1E.Y2C,
Z3.T1F.T2B.Y1E.Y2D, Z3.T1F.T2C.Y1A.Y2A, Z3.T1F.T2C.Y1A.Y2B,
Z3.T1F.T2C.Y1A.Y2C, Z3.T1F.T2C.Y1A.Y2D, Z3.T1F.T2C.Y1B.Y2A,
Z3.T1F.T2C.Y1B.Y2B, Z3.T1F.T2C.Y1B.Y2C, Z3.T1F.T2C.Y1B.Y2D,
Z3.T1F.T2C.Y1C.Y2A, Z3.T1F.T2C.Y1C.Y2B, Z3.T1F.T2C.Y1C.Y2C,
Z3.T1F.T2C.Y1C.Y2D, Z3.T1F.T2C.Y1D.Y2A, Z3.T1F.T2C.Y1D.Y2B,

TABLE 6-continued

List of Compound Structures of Formula I

Z3.T1F.T2C.Y1D.Y2C, Z3.T1F.T2C.Y1D.Y2D, Z3.T1F.T2C.Y1E.Y2A,
Z3.T1F.T2C.Y1E.Y2B, Z3.T1F.T2C.Y1E.Y2C, Z3.T1F.T2C.Y1E.Y2D,
Z3.T1G.T2A.Y1A.Y2A, Z3.T1G.T2A.Y1A.Y2B, Z3.T1G.T2A.Y1A.Y2C,
Z3.T1G.T2A.Y1A.Y2D, Z3.T1G.T2A.Y1B.Y2A, Z3.T1G.T2A.Y1B.Y2B,
Z3.T1G.T2A.Y1B.Y2C, Z3.T1G.T2A.Y1B.Y2D, Z3.T1G.T2A.Y1C.Y2A,
Z3.T1G.T2A.Y1C.Y2B, Z3.T1G.T2A.Y1C.Y2C, Z3.T1G.T2A.Y1C.Y2D,
Z3.T1G.T2A.Y1D.Y2A, Z3.T1G.T2A.Y1D.Y2B, Z3.T1G.T2A.Y1D.Y2C,
Z3.T1G.T2A.Y1D.Y2D, Z3.T1G.T2A.Y1E.Y2A, Z3.T1G.T2A.Y1E.Y2B,
Z3.T1G.T2A.Y1E.Y2C, Z3.T1G.T2A.Y1E.Y2D, Z3.T1G.T2B.Y1A.Y2A,
Z3.T1G.T2B.Y1A.Y2B, Z3.T1G.T2B.Y1A.Y2C, Z3.T1G.T2B.Y1A.Y2D,
Z3.T1G.T2B.Y1B.Y2A, Z3.T1G.T2B.Y1B.Y2B, Z3.T1G.T2B.Y1B.Y2C,
Z3.T1G.T2B.Y1B.Y2D, Z3.T1G.T2B.Y1C.Y2A, Z3.T1G.T2B.Y1C.Y2B,
Z3.T1G.T2B.Y1C.Y2C, Z3.T1G.T2B.Y1C.Y2D, Z3.T1G.T2B.Y1D.Y2A,
Z3.T1G.T2B.Y1D.Y2B, Z3.T1G.T2B.Y1D.Y2C, Z3.T1G.T2B.Y1D.Y2D,
Z3.T1G.T2B.Y1E.Y2A, Z3.T1G.T2B.Y1E.Y2B, Z3.T1G.T2B.Y1E.Y2C,
Z3.T1G.T2B.Y1E.Y2D, Z3.T1G.T2C.Y1A.Y2A, Z3.T1G.T2C.Y1A.Y2B,
Z3.T1G.T2C.Y1A.Y2C, Z3.T1G.T2C.Y1A.Y2D, Z3.T1G.T2C.Y1B.Y2A,
Z3.T1G.T2C.Y1B.Y2B, Z3.T1G.T2C.Y1B.Y2C, Z3.T1G.T2C.Y1B.Y2D,
Z3.T1G.T2C.Y1C.Y2A, Z3.T1G.T2C.Y1C.Y2B, Z3.T1G.T2C.Y1C.Y2C,
Z3.T1G.T2C.Y1C.Y2D, Z3.T1G.T2C.Y1D.Y2A, Z3.T1G.T2C.Y1D.Y2B,
Z3.T1G.T2C.Y1D.Y2C, Z3.T1G.T2C.Y1D.Y2D, Z3.T1G.T2C.Y1E.Y2A,
Z3.T1G.T2C.Y1E.Y2B, Z3.T1G.T2C.Y1E.Y2C, Z3.T1G.T2C.Y1E.Y2D,
Z4.T1A.T2A.Y1A.Y2A, Z4.T1A.T2A.Y1A.Y2B, Z4.T1A.T2A.Y1A.Y2C,
Z4.T1A.T2A.Y1A.Y2D, Z4.T1A.T2A.Y1B.Y2A, Z4.T1A.T2A.Y1B.Y2B,
Z4.T1A.T2A.Y1B.Y2C, Z4.T1A.T2A.Y1B.Y2D, Z4.T1A.T2A.Y1C.Y2A,
Z4.T1A.T2A.Y1C.Y2B, Z4.T1A.T2A.Y1C.Y2C, Z4.T1A.T2A.Y1C.Y2D,
Z4.T1A.T2A.Y1D.Y2A, Z4.T1A.T2A.Y1D.Y2B, Z4.T1A.T2A.Y1D.Y2C,
Z4.T1A.T2A.Y1D.Y2D, Z4.T1A.T2A.Y1E.Y2A, Z4.T1A.T2A.Y1E.Y2B,
Z4.T1A.T2A.Y1E.Y2C, Z4.T1A.T2A.Y1E.Y2D, Z4.T1A.T2B.Y1A.Y2A,
Z4.T1A.T2B.Y1A.Y2B, Z4.T1A.T2B.Y1A.Y2C, Z4.T1A.T2B.Y1A.Y2D,
Z4.T1A.T2B.Y1B.Y2A, Z4.T1A.T2B.Y1B.Y2B, Z4.T1A.T2B.Y1B.Y2C,
Z4.T1A.T2B.Y1B.Y2D, Z4.T1A.T2B.Y1C.Y2A, Z4.T1A.T2B.Y1C.Y2B,
Z4.T1A.T2B.Y1C.Y2C, Z4.T1A.T2B.Y1C.Y2D, Z4.T1A.T2B.Y1D.Y2A,
Z4.T1A.T2B.Y1D.Y2B, Z4.T1A.T2B.Y1D.Y2C, Z4.T1A.T2B.Y1D.Y2D,
Z4.T1A.T2B.Y1E.Y2A, Z4.T1A.T2B.Y1E.Y2B, Z4.T1A.T2B.Y1E.Y2C,
Z4.T1A.T2B.Y1E.Y2D, Z4.T1A.T2C.Y1A.Y2A, Z4.T1A.T2C.Y1A.Y2B,
Z4.T1A.T2C.Y1A.Y2C, Z4.T1A.T2C.Y1A.Y2D, Z4.T1A.T2C.Y1B.Y2A,
Z4.T1A.T2C.Y1B.Y2B, Z4.T1A.T2C.Y1B.Y2C, Z4.T1A.T2C.Y1B.Y2D,
Z4.T1A.T2C.Y1C.Y2A, Z4.T1A.T2C.Y1C.Y2B, Z4.T1A.T2C.Y1C.Y2C,
Z4.T1A.T2C.Y1C.Y2D, Z4.T1A.T2C.Y1D.Y2A, Z4.T1A.T2C.Y1D.Y2B,
Z4.T1A.T2C.Y1D.Y2C, Z4.T1A.T2C.Y1D.Y2D, Z4.T1A.T2C.Y1E.Y2A,
Z4.T1A.T2C.Y1E.Y2B, Z4.T1A.T2C.Y1E.Y2C, Z4.T1A.T2C.Y1E.Y2D,
Z4.T1B.T2A.Y1A.Y2A, Z4.T1B.T2A.Y1A.Y2B, Z4.T1B.T2A.Y1A.Y2C,
Z4.T1B.T2A.Y1A.Y2D, Z4.T1B.T2A.Y1B.Y2A, Z4.T1B.T2A.Y1B.Y2B,
Z4.T1B.T2A.Y1B.Y2C, Z4.T1B.T2A.Y1B.Y2D, Z4.T1B.T2A.Y1C.Y2A,
Z4.T1B.T2A.Y1C.Y2B, Z4.T1B.T2A.Y1C.Y2C, Z4.T1B.T2A.Y1C.Y2D,
Z4.T1B.T2A.Y1D.Y2A, Z4.T1B.T2A.Y1D.Y2B, Z4.T1B.T2A.Y1D.Y2C,
Z4.T1B.T2A.Y1D.Y2D, Z4.T1B.T2A.Y1E.Y2A, Z4.T1B.T2A.Y1E.Y2B,
Z4.T1B.T2A.Y1E.Y2C, Z4.T1B.T2A.Y1E.Y2D, Z4.T1B.T2B.Y1A.Y2A,
Z4.T1B.T2B.Y1A.Y2B, Z4.T1B.T2B.Y1A.Y2C, Z4.T1B.T2B.Y1A.Y2D,
Z4.T1B.T2B.Y1B.Y2A, Z4.T1B.T2B.Y1B.Y2B, Z4.T1B.T2B.Y1B.Y2C,
Z4.T1B.T2B.Y1B.Y2D, Z4.T1B.T2B.Y1C.Y2A, Z4.T1B.T2B.Y1C.Y2B,
Z4.T1B.T2B.Y1C.Y2C, Z4.T1B.T2B.Y1C.Y2D, Z4.T1B.T2B.Y1D.Y2A,
Z4.T1B.T2B.Y1D.Y2B, Z4.T1B.T2B.Y1D.Y2C, Z4.T1B.T2B.Y1D.Y2D,
Z4.T1B.T2B.Y1E.Y2A, Z4.T1B.T2B.Y1E.Y2B, Z4.T1B.T2B.Y1E.Y2C,
Z4.T1B.T2B.Y1E.Y2D, Z4.T1B.T2C.Y1A.Y2A, Z4.T1B.T2C.Y1A.Y2B,
Z4.T1B.T2C.Y1A.Y2C, Z4.T1B.T2C.Y1A.Y2D, Z4.T1B.T2C.Y1B.Y2A,
Z4.T1B.T2C.Y1B.Y2B, Z4.T1B.T2C.Y1B.Y2C, Z4.T1B.T2C.Y1B.Y2D,
Z4.T1B.T2C.Y1C.Y2A, Z4.T1B.T2C.Y1C.Y2B, Z4.T1B.T2C.Y1C.Y2C,
Z4.T1B.T2C.Y1C.Y2D, Z4.T1B.T2C.Y1D.Y2A, Z4.T1B.T2C.Y1D.Y2B,
Z4.T1B.T2C.Y1D.Y2C, Z4.T1B.T2C.Y1D.Y2D, Z4.T1B.T2C.Y1E.Y2A,
Z4.T1B.T2C.Y1E.Y2B, Z4.T1B.T2C.Y1E.Y2C, Z4.T1B.T2C.Y1E.Y2D,
Z4.T1C.T2A.Y1A.Y2A, Z4.T1C.T2A.Y1A.Y2B, Z4.T1C.T2A.Y1A.Y2C,
Z4.T1C.T2A.Y1A.Y2D, Z4.T1C.T2A.Y1B.Y2A, Z4.T1C.T2A.Y1B.Y2B,
Z4.T1C.T2A.Y1B.Y2C, Z4.T1C.T2A.Y1B.Y2D, Z4.T1C.T2A.Y1C.Y2A,
Z4.T1C.T2A.Y1C.Y2B, Z4.T1C.T2A.Y1C.Y2C, Z4.T1C.T2A.Y1C.Y2D,
Z4.T1C.T2A.Y1D.Y2A, Z4.T1C.T2A.Y1D.Y2B, Z4.T1C.T2A.Y1D.Y2C,
Z4.T1C.T2A.Y1D.Y2D, Z4.T1C.T2A.Y1E.Y2A, Z4.T1C.T2A.Y1E.Y2B,
Z4.T1C.T2A.Y1E.Y2C, Z4.T1C.T2A.Y1E.Y2D, Z4.T1C.T2B.Y1A.Y2A,
Z4.T1C.T2B.Y1A.Y2B, Z4.T1C.T2B.Y1A.Y2C, Z4.T1C.T2B.Y1A.Y2D,
Z4.T1C.T2B.Y1B.Y2A, Z4.T1C.T2B.Y1B.Y2B, Z4.T1C.T2B.Y1B.Y2C,
Z4.T1C.T2B.Y1B.Y2D, Z4.T1C.T2B.Y1C.Y2A, Z4.T1C.T2B.Y1C.Y2B,
Z4.T1C.T2B.Y1C.Y2C, Z4.T1C.T2B.Y1C.Y2D, Z4.T1C.T2B.Y1D.Y2A,
Z4.T1C.T2B.Y1D.Y2B, Z4.T1C.T2B.Y1D.Y2C, Z4.T1C.T2B.Y1D.Y2D,
Z4.T1C.T2B.Y1E.Y2A, Z4.T1C.T2B.Y1E.Y2B, Z4.T1C.T2B.Y1E.Y2C,
Z4.T1C.T2B.Y1E.Y2D, Z4.T1C.T2C.Y1A.Y2A, Z4.T1C.T2C.Y1A.Y2B,
Z4.T1C.T2C.Y1A.Y2C, Z4.T1C.T2C.Y1A.Y2D, Z4.T1C.T2C.Y1B.Y2A,
Z4.T1C.T2C.Y1B.Y2B, Z4.T1C.T2C.Y1B.Y2C, Z4.T1C.T2C.Y1B.Y2D,

TABLE 6-continued

List of Compound Structures of Formula I

Z4.T1C.T2C.Y1C.Y2A, Z4.T1C.T2C.Y1C.Y2B, Z4.T1C.T2C.Y1C.Y2C,
Z4.T1C.T2C.Y1C.Y2D, Z4.T1C.T2C.Y1D.Y2A, Z4.T1C.T2C.Y1D.Y2B,
Z4.T1C.T2C.Y1D.Y2C, Z4.T1C.T2C.Y1D.Y2D, Z4.T1C.T2C.Y1E.Y2A,
Z4.T1C.T2C.Y1E.Y2B, Z4.T1C.T2C.Y1E.Y2C, Z4.T1C.T2C.Y1E.Y2D,
Z4.T1D.T2A.Y1A.Y2A, Z4.T1D.T2A.Y1A.Y2B, Z4.T1D.T2A.Y1A.Y2C,
Z4.T1D.T2A.Y1A.Y2D, Z4.T1D.T2A.Y1B.Y2A, Z4.T1D.T2A.Y1B.Y2B,
Z4.T1D.T2A.Y1B.Y2C, Z4.T1D.T2A.Y1B.Y2D, Z4.T1D.T2A.Y1C.Y2A,
Z4.T1D.T2A.Y1C.Y2B, Z4.T1D.T2A.Y1C.Y2C, Z4.T1D.T2A.Y1C.Y2D,
Z4.T1D.T2A.Y1D.Y2A, Z4.T1D.T2A.Y1D.Y2B, Z4.T1D.T2A.Y1D.Y2C,
Z4.T1D.T2A.Y1D.Y2D, Z4.T1D.T2A.Y1E.Y2A, Z4.T1D.T2A.Y1E.Y2B,
Z4.T1D.T2A.Y1E.Y2C, Z4.T1D.T2A.Y1E.Y2D, Z4.T1D.T2B.Y1A.Y2A,
Z4.T1D.T2B.Y1A.Y2B, Z4.T1D.T2B.Y1A.Y2C, Z4.T1D.T2B.Y1A.Y2D,
Z4.T1D.T2B.Y1B.Y2A, Z4.T1D.T2B.Y1B.Y2B, Z4.T1D.T2B.Y1B.Y2C,
Z4.T1D.T2B.Y1B.Y2D, Z4.T1D.T2B.Y1C.Y2A, Z4.T1D.T2B.Y1C.Y2B,
Z4.T1D.T2B.Y1C.Y2C, Z4.T1D.T2B.Y1C.Y2D, Z4.T1D.T2B.Y1D.Y2A,
Z4.T1D.T2B.Y1D.Y2B, Z4.T1D.T2B.Y1D.Y2C, Z4.T1D.T2B.Y1D.Y2D,
Z4.T1D.T2B.Y1E.Y2A, Z4.T1D.T2B.Y1E.Y2B, Z4.T1D.T2B.Y1E.Y2C,
Z4.T1D.T2B.Y1E.Y2D, Z4.T1D.T2C.Y1A.Y2A, Z4.T1D.T2C.Y1A.Y2B,
Z4.T1D.T2C.Y1A.Y2C, Z4.T1D.T2C.Y1A.Y2D, Z4.T1D.T2C.Y1B.Y2A,
Z4.T1D.T2C.Y1B.Y2B, Z4.T1D.T2C.Y1B.Y2C, Z4.T1D.T2C.Y1B.Y2D,
Z4.T1D.T2C.Y1C.Y2A, Z4.T1D.T2C.Y1C.Y2B, Z4.T1D.T2C.Y1C.Y2C,
Z4.T1D.T2C.Y1C.Y2D, Z4.T1D.T2C.Y1D.Y2A, Z4.T1D.T2C.Y1D.Y2B,
Z4.T1D.T2C.Y1D.Y2C, Z4.T1D.T2C.Y1D.Y2D, Z4.T1D.T2C.Y1E.Y2A,
Z4.T1D.T2C.Y1E.Y2B, Z4.T1D.T2C.Y1E.Y2C, Z4.T1D.T2C.Y1E.Y2D,
Z4.T1E.T2A.Y1A.Y2A, Z4.T1E.T2A.Y1A.Y2B, Z4.T1E.T2A.Y1A.Y2C,
Z4.T1E.T2A.Y1A.Y2D, Z4.T1E.T2A.Y1B.Y2A, Z4.T1E.T2A.Y1B.Y2B,
Z4.T1E.T2A.Y1B.Y2C, Z4.T1E.T2A.Y1B.Y2D, Z4.T1E.T2A.Y1C.Y2A,
Z4.T1E.T2A.Y1C.Y2B, Z4.T1E.T2A.Y1C.Y2C, Z4.T1E.T2A.Y1C.Y2D,
Z4.T1E.T2A.Y1D.Y2A, Z4.T1E.T2A.Y1D.Y2B, Z4.T1E.T2A.Y1D.Y2C,
Z4.T1E.T2A.Y1D.Y2D, Z4.T1E.T2A.Y1E.Y2A, Z4.T1E.T2A.Y1E.Y2B,
Z4.T1E.T2A.Y1E.Y2C, Z4.T1E.T2A.Y1E.Y2D, Z4.T1E.T2B.Y1A.Y2A,
Z4.T1E.T2B.Y1A.Y2B, Z4.T1E.T2B.Y1A.Y2C, Z4.T1E.T2B.Y1A.Y2D,
Z4.T1E.T2B.Y1B.Y2A, Z4.T1E.T2B.Y1B.Y2B, Z4.T1E.T2B.Y1B.Y2C,
Z4.T1E.T2B.Y1B.Y2D, Z4.T1E.T2B.Y1C.Y2A, Z4.T1E.T2B.Y1C.Y2B,
Z4.T1E.T2B.Y1C.Y2C, Z4.T1E.T2B.Y1C.Y2D, Z4.T1E.T2B.Y1D.Y2A,
Z4.T1E.T2B.Y1D.Y2B, Z4.T1E.T2B.Y1D.Y2C, Z4.T1E.T2B.Y1D.Y2D,
Z4.T1E.T2B.Y1E.Y2A, Z4.T1E.T2B.Y1E.Y2B, Z4.T1E.T2B.Y1E.Y2C,
Z4.T1E.T2B.Y1E.Y2D, Z4.T1E.T2C.Y1A.Y2A, Z4.T1E.T2C.Y1A.Y2B,
Z4.T1E.T2C.Y1A.Y2C, Z4.T1E.T2C.Y1A.Y2D, Z4.T1E.T2C.Y1B.Y2A,
Z4.T1E.T2C.Y1B.Y2B, Z4.T1E.T2C.Y1B.Y2C, Z4.T1E.T2C.Y1B.Y2D,
Z4.T1E.T2C.Y1C.Y2A, Z4.T1E.T2C.Y1C.Y2B, Z4.T1E.T2C.Y1C.Y2C,
Z4.T1E.T2C.Y1C.Y2D, Z4.T1E.T2C.Y1D.Y2A, Z4.T1E.T2C.Y1D.Y2B,
Z4.T1E.T2C.Y1D.Y2C, Z4.T1E.T2C.Y1D.Y2D, Z4.T1E.T2C.Y1E.Y2A,
Z4.T1E.T2C.Y1E.Y2B, Z4.T1E.T2C.Y1E.Y2C, Z4.T1E.T2C.Y1E.Y2D,
Z4.T1F.T2A.Y1A.Y2A, Z4.T1F.T2A.Y1A.Y2B, Z4.T1F.T2A.Y1A.Y2C,
Z4.T1F.T2A.Y1A.Y2D, Z4.T1F.T2A.Y1B.Y2A, Z4.T1F.T2A.Y1B.Y2B,
Z4.T1F.T2A.Y1B.Y2C, Z4.T1F.T2A.Y1B.Y2D, Z4.T1F.T2A.Y1C.Y2A,
Z4.T1F.T2A.Y1C.Y2B, Z4.T1F.T2A.Y1C.Y2C, Z4.T1F.T2A.Y1C.Y2D,
Z4.T1F.T2A.Y1D.Y2A, Z4.T1F.T2A.Y1D.Y2B, Z4.T1F.T2A.Y1D.Y2C,
Z4.T1F.T2A.Y1D.Y2D, Z4.T1F.T2A.Y1E.Y2A, Z4.T1F.T2A.Y1E.Y2B,
Z4.T1F.T2A.Y1E.Y2C, Z4.T1F.T2A.Y1E.Y2D, Z4.T1F.T2B.Y1A.Y2A,
Z4.T1F.T2B.Y1A.Y2B, Z4.T1F.T2B.Y1A.Y2C, Z4.T1F.T2B.Y1A.Y2D,
Z4.T1F.T2B.Y1B.Y2A, Z4.T1F.T2B.Y1B.Y2B, Z4.T1F.T2B.Y1B.Y2C,
Z4.T1F.T2B.Y1B.Y2D, Z4.T1F.T2B.Y1C.Y2A, Z4.T1F.T2B.Y1C.Y2B,
Z4.T1F.T2B.Y1C.Y2C, Z4.T1F.T2B.Y1C.Y2D, Z4.T1F.T2B.Y1D.Y2A,
Z4.T1F.T2B.Y1D.Y2B, Z4.T1F.T2B.Y1D.Y2C, Z4.T1F.T2B.Y1D.Y2D,
Z4.T1F.T2B.Y1E.Y2A, Z4.T1F.T2B.Y1E.Y2B, Z4.T1F.T2B.Y1E.Y2C,
Z4.T1F.T2B.Y1E.Y2D, Z4.T1F.T2C.Y1A.Y2A, Z4.T1F.T2C.Y1A.Y2B,
Z4.T1F.T2C.Y1A.Y2C, Z4.T1F.T2C.Y1A.Y2D, Z4.T1F.T2C.Y1B.Y2A,
Z4.T1F.T2C.Y1B.Y2B, Z4.T1F.T2C.Y1B.Y2C, Z4.T1F.T2C.Y1B.Y2D,
Z4.T1F.T2C.Y1C.Y2A, Z4.T1F.T2C.Y1C.Y2B, Z4.T1F.T2C.Y1C.Y2C,
Z4.T1F.T2C.Y1C.Y2D, Z4.T1F.T2C.Y1D.Y2A, Z4.T1F.T2C.Y1D.Y2B,
Z4.T1F.T2C.Y1D.Y2C, Z4.T1F.T2C.Y1D.Y2D, Z4.T1F.T2C.Y1E.Y2A,
Z4.T1F.T2C.Y1E.Y2B, Z4.T1F.T2C.Y1E.Y2C, Z4.T1F.T2C.Y1E.Y2D,
Z4.T1G.T2A.Y1A.Y2A, Z4.T1G.T2A.Y1A.Y2B, Z4.T1G.T2A.Y1A.Y2C,
Z4.T1G.T2A.Y1A.Y2D, Z4.T1G.T2A.Y1B.Y2A, Z4.T1G.T2A.Y1B.Y2B,
Z4.T1G.T2A.Y1B.Y2C, Z4.T1G.T2A.Y1B.Y2D, Z4.T1G.T2A.Y1C.Y2A,
Z4.T1G.T2A.Y1C.Y2B, Z4.T1G.T2A.Y1C.Y2C, Z4.T1G.T2A.Y1C.Y2D,
Z4.T1G.T2A.Y1D.Y2A, Z4.T1G.T2A.Y1D.Y2B, Z4.T1G.T2A.Y1D.Y2C,
Z4.T1G.T2A.Y1D.Y2D, Z4.T1G.T2A.Y1E.Y2A, Z4.T1G.T2A.Y1E.Y2B,
Z4.T1G.T2A.Y1E.Y2C, Z4.T1G.T2A.Y1E.Y2D, Z4.T1G.T2B.Y1A.Y2A,
Z4.T1G.T2B.Y1A.Y2B, Z4.T1G.T2B.Y1A.Y2C, Z4.T1G.T2B.Y1A.Y2D,
Z4.T1G.T2B.Y1B.Y2A, Z4.T1G.T2B.Y1B.Y2B, Z4.T1G.T2B.Y1B.Y2C,
Z4.T1G.T2B.Y1B.Y2D, Z4.T1G.T2B.Y1C.Y2A, Z4.T1G.T2B.Y1C.Y2B,
Z4.T1G.T2B.Y1C.Y2C, Z4.T1G.T2B.Y1C.Y2D, Z4.T1G.T2B.Y1D.Y2A,
Z4.T1G.T2B.Y1D.Y2B, Z4.T1G.T2B.Y1D.Y2C, Z4.T1G.T2B.Y1D.Y2D,
Z4.T1G.T2B.Y1E.Y2A, Z4.T1G.T2B.Y1E.Y2B, Z4.T1G.T2B.Y1E.Y2C,
Z4.T1G.T2B.Y1E.Y2D, Z4.T1G.T2C.Y1A.Y2A, Z4.T1G.T2C.Y1A.Y2B,

TABLE 6-continued

List of Compound Structures of Formula I

Z4.T1G.T2C.Y1A.Y2C, Z4.T1G.T2C.Y1A.Y2D, Z4.T1G.T2C.Y1B.Y2A,
Z4.T1G.T2C.Y1B.Y2B, Z4.T1G.T2C.Y1B.Y2C, Z4.T1G.T2C.Y1B.Y2D,
Z4.T1G.T2C.Y1C.Y2A, Z4.T1G.T2C.Y1C.Y2B, Z4.T1G.T2C.Y1C.Y2C,
Z4.T1G.T2C.Y1C.Y2D, Z4.T1G.T2C.Y1D.Y2A, Z4.T1G.T2C.Y1D.Y2B,
Z4.T1G.T2C.Y1D.Y2C, Z4.T1G.T2C.Y1D.Y2D, Z4.T1G.T2C.Y1E.Y2A,
Z4.T1G.T2C.Y1E.Y2B, Z4.T1G.T2C.Y1E.Y2C, Z4.T1G.T2C.Y1E.Y2D,
Z5.T1A.T2A.Y1A.Y2A, Z5.T1A.T2A.Y1A.Y2B, Z5.T1A.T2A.Y1A.Y2C,
Z5.T1A.T2A.Y1A.Y2D, Z5.T1A.T2A.Y1B.Y2A, Z5.T1A.T2A.Y1B.Y2B,
Z5.T1A.T2A.Y1B.Y2C, Z5.T1A.T2A.Y1B.Y2D, Z5.T1A.T2A.Y1C.Y2A,
Z5.T1A.T2A.Y1C.Y2B, Z5.T1A.T2A.Y1C.Y2C, Z5.T1A.T2A.Y1C.Y2D,
Z5.T1A.T2A.Y1D.Y2A, Z5.T1A.T2A.Y1D.Y2B, Z5.T1A.T2A.Y1D.Y2C,
Z5.T1A.T2A.Y1D.Y2D, Z5.T1A.T2A.Y1E.Y2A, Z5.T1A.T2A.Y1E.Y2B,
Z5.T1A.T2A.Y1E.Y2C, Z5.T1A.T2A.Y1E.Y2D, Z5.T1A.T2B.Y1A.Y2A,
Z5.T1A.T2B.Y1A.Y2B, Z5.T1A.T2B.Y1A.Y2C, Z5.T1A.T2B.Y1A.Y2D,
Z5.T1A.T2B.Y1B.Y2A, Z5.T1A.T2B.Y1B.Y2B, Z5.T1A.T2B.Y1B.Y2C,
Z5.T1A.T2B.Y1B.Y2D, Z5.T1A.T2B.Y1C.Y2A, Z5.T1A.T2B.Y1C.Y2B,
Z5.T1A.T2B.Y1C.Y2C, Z5.T1A.T2B.Y1C.Y2D, Z5.T1A.T2B.Y1D.Y2A,
Z5.T1A.T2B.Y1D.Y2B, Z5.T1A.T2B.Y1D.Y2C, Z5.T1A.T2B.Y1D.Y2D,
Z5.T1A.T2B.Y1E.Y2A, Z5.T1A.T2B.Y1E.Y2B, Z5.T1A.T2B.Y1E.Y2C,
Z5.T1A.T2B.Y1E.Y2D, Z5.T1A.T2C.Y1A.Y2A, Z5.T1A.T2C.Y1A.Y2B,
Z5.T1A.T2C.Y1A.Y2C, Z5.T1A.T2C.Y1A.Y2D, Z5.T1A.T2C.Y1B.Y2A,
Z5.T1A.T2C.Y1B.Y2B, Z5.T1A.T2C.Y1B.Y2C, Z5.T1A.T2C.Y1B.Y2D,
Z5.T1A.T2C.Y1C.Y2A, Z5.T1A.T2C.Y1C.Y2B, Z5.T1A.T2C.Y1C.Y2C,
Z5.T1A.T2C.Y1C.Y2D, Z5.T1A.T2C.Y1D.Y2A, Z5.T1A.T2C.Y1D.Y2B,
Z5.T1A.T2C.Y1D.Y2C, Z5.T1A.T2C.Y1D.Y2D, Z5.T1A.T2C.Y1E.Y2A,
Z5.T1A.T2C.Y1E.Y2B, Z5.T1A.T2C.Y1E.Y2C, Z5.T1A.T2C.Y1E.Y2D,
Z5.T1B.T2A.Y1A.Y2A, Z5.T1B.T2A.Y1A.Y2B, Z5.T1B.T2A.Y1A.Y2C,
Z5.T1B.T2A.Y1A.Y2D, Z5.T1B.T2A.Y1B.Y2A, Z5.T1B.T2A.Y1B.Y2B,
Z5.T1B.T2A.Y1B.Y2C, Z5.T1B.T2A.Y1B.Y2D, Z5.T1B.T2A.Y1C.Y2A,
Z5.T1B.T2A.Y1C.Y2B, Z5.T1B.T2A.Y1C.Y2C, Z5.T1B.T2A.Y1C.Y2D,
Z5.T1B.T2A.Y1D.Y2A, Z5.T1B.T2A.Y1D.Y2B, Z5.T1B.T2A.Y1D.Y2C,
Z5.T1B.T2A.Y1D.Y2D, Z5.T1B.T2A.Y1E.Y2A, Z5.T1B.T2A.Y1E.Y2B,
Z5.T1B.T2A.Y1E.Y2C, Z5.T1B.T2A.Y1E.Y2D, Z5.T1B.T2B.Y1A.Y2A,
Z5.T1B.T2B.Y1A.Y2B, Z5.T1B.T2B.Y1A.Y2C, Z5.T1B.T2B.Y1A.Y2D,
Z5.T1B.T2B.Y1B.Y2A, Z5.T1B.T2B.Y1B.Y2B, Z5.T1B.T2B.Y1B.Y2C,
Z5.T1B.T2B.Y1B.Y2D, Z5.T1B.T2B.Y1C.Y2A, Z5.T1B.T2B.Y1C.Y2B,
Z5.T1B.T2B.Y1C.Y2C, Z5.T1B.T2B.Y1C.Y2D, Z5.T1B.T2B.Y1D.Y2A,
Z5.T1B.T2B.Y1D.Y2B, Z5.T1B.T2B.Y1D.Y2C, Z5.T1B.T2B.Y1D.Y2D,
Z5.T1B.T2B.Y1E.Y2A, Z5.T1B.T2B.Y1E.Y2B, Z5.T1B.T2B.Y1E.Y2C,
Z5.T1B.T2B.Y1E.Y2D, Z5.T1B.T2C.Y1A.Y2A, Z5.T1B.T2C.Y1A.Y2B,
Z5.T1B.T2C.Y1A.Y2C, Z5.T1B.T2C.Y1A.Y2D, Z5.T1B.T2C.Y1B.Y2A,
Z5.T1B.T2C.Y1B.Y2B, Z5.T1B.T2C.Y1B.Y2C, Z5.T1B.T2C.Y1B.Y2D,
Z5.T1B.T2C.Y1C.Y2A, Z5.T1B.T2C.Y1C.Y2B, Z5.T1B.T2C.Y1C.Y2C,
Z5.T1B.T2C.Y1C.Y2D, Z5.T1B.T2C.Y1D.Y2A, Z5.T1B.T2C.Y1D.Y2B,
Z5.T1B.T2C.Y1D.Y2C, Z5.T1B.T2C.Y1D.Y2D, Z5.T1B.T2C.Y1E.Y2A,
Z5.T1B.T2C.Y1E.Y2B, Z5.T1B.T2C.Y1E.Y2C, Z5.T1B.T2C.Y1E.Y2D,
Z5.T1C.T2A.Y1A.Y2A, Z5.T1C.T2A.Y1A.Y2B, Z5.T1C.T2A.Y1A.Y2C,
Z5.T1C.T2A.Y1A.Y2D, Z5.T1C.T2A.Y1B.Y2A, Z5.T1C.T2A.Y1B.Y2B,
Z5.T1C.T2A.Y1B.Y2C, Z5.T1C.T2A.Y1B.Y2D, Z5.T1C.T2A.Y1C.Y2A,
Z5.T1C.T2A.Y1C.Y2B, Z5.T1C.T2A.Y1C.Y2C, Z5.T1C.T2A.Y1C.Y2D,
Z5.T1C.T2A.Y1D.Y2A, Z5.T1C.T2A.Y1D.Y2B, Z5.T1C.T2A.Y1D.Y2C,
Z5.T1C.T2A.Y1D.Y2D, Z5.T1C.T2A.Y1E.Y2A, Z5.T1C.T2A.Y1E.Y2B,
Z5.T1C.T2A.Y1E.Y2C, Z5.T1C.T2A.Y1E.Y2D, Z5.T1C.T2B.Y1A.Y2A,
Z5.T1C.T2B.Y1A.Y2B, Z5.T1C.T2B.Y1A.Y2C, Z5.T1C.T2B.Y1A.Y2D,
Z5.T1C.T2B.Y1B.Y2A, Z5.T1C.T2B.Y1B.Y2B, Z5.T1C.T2B.Y1B.Y2C,
Z5.T1C.T2B.Y1B.Y2D, Z5.T1C.T2B.Y1C.Y2A, Z5.T1C.T2B.Y1C.Y2B,
Z5.T1C.T2B.Y1C.Y2C, Z5.T1C.T2B.Y1C.Y2D, Z5.T1C.T2B.Y1D.Y2A,
Z5.T1C.T2B.Y1D.Y2B, Z5.T1C.T2B.Y1D.Y2C, Z5.T1C.T2B.Y1D.Y2D,
Z5.T1C.T2B.Y1E.Y2A, Z5.T1C.T2B.Y1E.Y2B, Z5.T1C.T2B.Y1E.Y2C,
Z5.T1C.T2B.Y1E.Y2D, Z5.T1C.T2C.Y1A.Y2A, Z5.T1C.T2C.Y1A.Y2B,
Z5.T1C.T2C.Y1A.Y2C, Z5.T1C.T2C.Y1A.Y2D, Z5.T1C.T2C.Y1B.Y2A,
Z5.T1C.T2C.Y1B.Y2B, Z5.T1C.T2C.Y1B.Y2C, Z5.T1C.T2C.Y1B.Y2D,
Z5.T1C.T2C.Y1C.Y2A, Z5.T1C.T2C.Y1C.Y2B, Z5.T1C.T2C.Y1C.Y2C,
Z5.T1C.T2C.Y1C.Y2D, Z5.T1C.T2C.Y1D.Y2A, Z5.T1C.T2C.Y1D.Y2B,
Z5.T1C.T2C.Y1D.Y2C, Z5.T1C.T2C.Y1D.Y2D, Z5.T1C.T2C.Y1E.Y2A,
Z5.T1C.T2C.Y1E.Y2B, Z5.T1C.T2C.Y1E.Y2C, Z5.T1C.T2C.Y1E.Y2D,
Z5.T1D.T2A.Y1A.Y2A, Z5.T1D.T2A.Y1A.Y2B, Z5.T1D.T2A.Y1A.Y2C,
Z5.T1D.T2A.Y1A.Y2D, Z5.T1D.T2A.Y1B.Y2A, Z5.T1D.T2A.Y1B.Y2B,
Z5.T1D.T2A.Y1B.Y2C, Z5.T1D.T2A.Y1B.Y2D, Z5.T1D.T2A.Y1C.Y2A,
Z5.T1D.T2A.Y1C.Y2B, Z5.T1D.T2A.Y1C.Y2C, Z5.T1D.T2A.Y1C.Y2D,
Z5.T1D.T2A.Y1D.Y2A, Z5.T1D.T2A.Y1D.Y2B, Z5.T1D.T2A.Y1D.Y2C,
Z5.T1D.T2A.Y1D.Y2D, Z5.T1D.T2A.Y1E.Y2A, Z5.T1D.T2A.Y1E.Y2B,
Z5.T1D.T2A.Y1E.Y2C, Z5.T1D.T2A.Y1E.Y2D, Z5.T1D.T2B.Y1A.Y2A,
Z5.T1D.T2B.Y1A.Y2B, Z5.T1D.T2B.Y1A.Y2C, Z5.T1D.T2B.Y1A.Y2D,
Z5.T1D.T2B.Y1B.Y2A, Z5.T1D.T2B.Y1B.Y2B, Z5.T1D.T2B.Y1B.Y2C,
Z5.T1D.T2B.Y1B.Y2D, Z5.T1D.T2B.Y1C.Y2A, Z5.T1D.T2B.Y1C.Y2B,
Z5.T1D.T2B.Y1C.Y2C, Z5.T1D.T2B.Y1C.Y2D, Z5.T1D.T2B.Y1D.Y2A,
Z5.T1D.T2B.Y1D.Y2B, Z5.T1D.T2B.Y1D.Y2C, Z5.T1D.T2B.Y1D.Y2D,

TABLE 6-continued

List of Compound Structures of Formula I

Z5.T1D.T2B.Y1E.Y2A, Z5.T1D.T2B.Y1E.Y2B, Z5.T1D.T2B.Y1E.Y2C,
Z5.T1D.T2B.Y1E.Y2D, Z5.T1D.T2C.Y1A.Y2A, Z5.T1D.T2C.Y1A.Y2B,
Z5.T1D.T2C.Y1A.Y2C, Z5.T1D.T2C.Y1A.Y2D, Z5.T1D.T2C.Y1B.Y2A,
Z5.T1D.T2C.Y1B.Y2B, Z5.T1D.T2C.Y1B.Y2C, Z5.T1D.T2C.Y1B.Y2D,
Z5.T1D.T2C.Y1C.Y2A, Z5.T1D.T2C.Y1C.Y2B, Z5.T1D.T2C.Y1C.Y2C,
Z5.T1D.T2C.Y1C.Y2D, Z5.T1D.T2C.Y1D.Y2A, Z5.T1D.T2C.Y1D.Y2B,
Z5.T1D.T2C.Y1D.Y2C, Z5.T1D.T2C.Y1D.Y2D, Z5.T1D.T2C.Y1E.Y2A,
Z5.T1D.T2C.Y1E.Y2B, Z5.T1D.T2C.Y1E.Y2C, Z5.T1D.T2C.Y1E.Y2D,
Z5.T1E.T2A.Y1A.Y2A, Z5.T1E.T2A.Y1A.Y2B, Z5.T1E.T2A.Y1A.Y2C,
Z5.T1E.T2A.Y1A.Y2D, Z5.T1E.T2A.Y1B.Y2A, Z5.T1E.T2A.Y1B.Y2B,
Z5.T1E.T2A.Y1B.Y2C, Z5.T1E.T2A.Y1B.Y2D, Z5.T1E.T2A.Y1C.Y2A,
Z5.T1E.T2A.Y1C.Y2B, Z5.T1E.T2A.Y1C.Y2C, Z5.T1E.T2A.Y1C.Y2D,
Z5.T1E.T2A.Y1D.Y2A, Z5.T1E.T2A.Y1D.Y2B, Z5.T1E.T2A.Y1D.Y2C,
Z5.T1E.T2A.Y1D.Y2D, Z5.T1E.T2A.Y1E.Y2A, Z5.T1E.T2A.Y1E.Y2B,
Z5.T1E.T2A.Y1E.Y2C, Z5.T1E.T2A.Y1E.Y2D, Z5.T1E.T2B.Y1A.Y2A,
Z5.T1E.T2B.Y1A.Y2B, Z5.T1E.T2B.Y1A.Y2C, Z5.T1E.T2B.Y1A.Y2D,
Z5.T1E.T2B.Y1B.Y2A, Z5.T1E.T2B.Y1B.Y2B, Z5.T1E.T2B.Y1B.Y2C,
Z5.T1E.T2B.Y1B.Y2D, Z5.T1E.T2B.Y1C.Y2A, Z5.T1E.T2B.Y1C.Y2B,
Z5.T1E.T2B.Y1C.Y2C, Z5.T1E.T2B.Y1C.Y2D, Z5.T1E.T2B.Y1D.Y2A,
Z5.T1E.T2B.Y1D.Y2B, Z5.T1E.T2B.Y1D.Y2C, Z5.T1E.T2B.Y1D.Y2D,
Z5.T1E.T2B.Y1E.Y2A, Z5.T1E.T2B.Y1E.Y2B, Z5.T1E.T2B.Y1E.Y2C,
Z5.T1E.T2B.Y1E.Y2D, Z5.T1E.T2C.Y1A.Y2A, Z5.T1E.T2C.Y1A.Y2B,
Z5.T1E.T2C.Y1A.Y2C, Z5.T1E.T2C.Y1A.Y2D, Z5.T1E.T2C.Y1B.Y2A,
Z5.T1E.T2C.Y1B.Y2B, Z5.T1E.T2C.Y1B.Y2C, Z5.T1E.T2C.Y1B.Y2D,
Z5.T1E.T2C.Y1C.Y2A, Z5.T1E.T2C.Y1C.Y2B, Z5.T1E.T2C.Y1C.Y2C,
Z5.T1E.T2C.Y1C.Y2D, Z5.T1E.T2C.Y1D.Y2A, Z5.T1E.T2C.Y1D.Y2B,
Z5.T1E.T2C.Y1D.Y2C, Z5.T1E.T2C.Y1D.Y2D, Z5.T1E.T2C.Y1E.Y2A,
Z5.T1E.T2C.Y1E.Y2B, Z5.T1E.T2C.Y1E.Y2C, Z5.T1E.T2C.Y1E.Y2D,
Z5.T1F.T2A.Y1A.Y2A, Z5.T1F.T2A.Y1A.Y2B, Z5.T1F.T2A.Y1A.Y2C,
Z5.T1F.T2A.Y1A.Y2D, Z5.T1F.T2A.Y1B.Y2A, Z5.T1F.T2A.Y1B.Y2B,
Z5.T1F.T2A.Y1B.Y2C, Z5.T1F.T2A.Y1B.Y2D, Z5.T1F.T2A.Y1C.Y2A,
Z5.T1F.T2A.Y1C.Y2B, Z5.T1F.T2A.Y1C.Y2C, Z5.T1F.T2A.Y1C.Y2D,
Z5.T1F.T2A.Y1D.Y2A, Z5.T1F.T2A.Y1D.Y2B, Z5.T1F.T2A.Y1D.Y2C,
Z5.T1F.T2A.Y1D.Y2D, Z5.T1F.T2A.Y1E.Y2A, Z5.T1F.T2A.Y1E.Y2B,
Z5.T1F.T2A.Y1E.Y2C, Z5.T1F.T2A.Y1E.Y2D, Z5.T1F.T2B.Y1A.Y2A,
Z5.T1F.T2B.Y1A.Y2B, Z5.T1F.T2B.Y1A.Y2C, Z5.T1F.T2B.Y1A.Y2D,
Z5.T1F.T2B.Y1B.Y2A, Z5.T1F.T2B.Y1B.Y2B, Z5.T1F.T2B.Y1B.Y2C,
Z5.T1F.T2B.Y1B.Y2D, Z5.T1F.T2B.Y1C.Y2A, Z5.T1F.T2B.Y1C.Y2B,
Z5.T1F.T2B.Y1C.Y2C, Z5.T1F.T2B.Y1C.Y2D, Z5.T1F.T2B.Y1D.Y2A,
Z5.T1F.T2B.Y1D.Y2B, Z5.T1F.T2B.Y1D.Y2C, Z5.T1F.T2B.Y1D.Y2D,
Z5.T1F.T2B.Y1E.Y2A, Z5.T1F.T2B.Y1E.Y2B, Z5.T1F.T2B.Y1E.Y2C,
Z5.T1F.T2B.Y1E.Y2D, Z5.T1F.T2C.Y1A.Y2A, Z5.T1F.T2C.Y1A.Y2B,
Z5.T1F.T2C.Y1A.Y2C, Z5.T1F.T2C.Y1A.Y2D, Z5.T1F.T2C.Y1B.Y2A,
Z5.T1F.T2C.Y1B.Y2B, Z5.T1F.T2C.Y1B.Y2C, Z5.T1F.T2C.Y1B.Y2D,
Z5.T1F.T2C.Y1C.Y2A, Z5.T1F.T2C.Y1C.Y2B, Z5.T1F.T2C.Y1C.Y2C,
Z5.T1F.T2C.Y1C.Y2D, Z5.T1F.T2C.Y1D.Y2A, Z5.T1F.T2C.Y1D.Y2B,
Z5.T1F.T2C.Y1D.Y2C, Z5.T1F.T2C.Y1D.Y2D, Z5.T1F.T2C.Y1E.Y2A,
Z5.T1F.T2C.Y1E.Y2B, Z5.T1F.T2C.Y1E.Y2C, Z5.T1F.T2C.Y1E.Y2D,
Z5.T1G.T2A.Y1A.Y2A, Z5.T1G.T2A.Y1A.Y2B, Z5.T1G.T2A.Y1A.Y2C,
Z5.T1G.T2A.Y1A.Y2D, Z5.T1G.T2A.Y1B.Y2A, Z5.T1G.T2A.Y1B.Y2B,
Z5.T1G.T2A.Y1B.Y2C, Z5.T1G.T2A.Y1B.Y2D, Z5.T1G.T2A.Y1C.Y2A,
Z5.T1G.T2A.Y1C.Y2B, Z5.T1G.T2A.Y1C.Y2C, Z5.T1G.T2A.Y1C.Y2D,
Z5.T1G.T2A.Y1D.Y2A, Z5.T1G.T2A.Y1D.Y2B, Z5.T1G.T2A.Y1D.Y2C,
Z5.T1G.T2A.Y1D.Y2D, Z5.T1G.T2A.Y1E.Y2A, Z5.T1G.T2A.Y1E.Y2B,
Z5.T1G.T2A.Y1E.Y2C, Z5.T1G.T2A.Y1E.Y2D, Z5.T1G.T2B.Y1A.Y2A,
Z5.T1G.T2B.Y1A.Y2B, Z5.T1G.T2B.Y1A.Y2C, Z5.T1G.T2B.Y1A.Y2D,
Z5.T1G.T2B.Y1B.Y2A, Z5.T1G.T2B.Y1B.Y2B, Z5.T1G.T2B.Y1B.Y2C,
Z5.T1G.T2B.Y1B.Y2D, Z5.T1G.T2B.Y1C.Y2A, Z5.T1G.T2B.Y1C.Y2B,
Z5.T1G.T2B.Y1C.Y2C, Z5.T1G.T2B.Y1C.Y2D, Z5.T1G.T2B.Y1D.Y2A,
Z5.T1G.T2B.Y1D.Y2B, Z5.T1G.T2B.Y1D.Y2C, Z5.T1G.T2B.Y1D.Y2D,
Z5.T1G.T2B.Y1E.Y2A, Z5.T1G.T2B.Y1E.Y2B, Z5.T1G.T2B.Y1E.Y2C,
Z5.T1G.T2B.Y1E.Y2D, Z5.T1G.T2C.Y1A.Y2A, Z5.T1G.T2C.Y1A.Y2B,
Z5.T1G.T2C.Y1A.Y2C, Z5.T1G.T2C.Y1A.Y2D, Z5.T1G.T2C.Y1B.Y2A,
Z5.T1G.T2C.Y1B.Y2B, Z5.T1G.T2C.Y1B.Y2C, Z5.T1G.T2C.Y1B.Y2D,
Z5.T1G.T2C.Y1C.Y2A, Z5.T1G.T2C.Y1C.Y2B, Z5.T1G.T2C.Y1C.Y2C,
Z5.T1G.T2C.Y1C.Y2D, Z5.T1G.T2C.Y1D.Y2A, Z5.T1G.T2C.Y1D.Y2B,
Z5.T1G.T2C.Y1D.Y2C, Z5.T1G.T2C.Y1D.Y2D, Z5.T1G.T2C.Y1E.Y2A,
Z5.T1G.T2C.Y1E.Y2B, Z5.T1G.T2C.Y1E.Y2C, Z5.T1G.T2C.Y1E.Y2D,
Z6.T1A.T2A.Y1A.Y2A, Z6.T1A.T2A.Y1A.Y2B, Z6.T1A.T2A.Y1A.Y2C,
Z6.T1A.T2A.Y1A.Y2D, Z6.T1A.T2A.Y1B.Y2A, Z6.T1A.T2A.Y1B.Y2B,
Z6.T1A.T2A.Y1B.Y2C, Z6.T1A.T2A.Y1B.Y2D, Z6.T1A.T2A.Y1C.Y2A,
Z6.T1A.T2A.Y1C.Y2B, Z6.T1A.T2A.Y1C.Y2C, Z6.T1A.T2A.Y1C.Y2D,
Z6.T1A.T2A.Y1D.Y2A, Z6.T1A.T2A.Y1D.Y2B, Z6.T1A.T2A.Y1D.Y2C,
Z6.T1A.T2A.Y1D.Y2D, Z6.T1A.T2A.Y1E.Y2A, Z6.T1A.T2A.Y1E.Y2B,
Z6.T1A.T2A.Y1E.Y2C, Z6.T1A.T2A.Y1E.Y2D, Z6.T1A.T2B.Y1A.Y2A,
Z6.T1A.T2B.Y1A.Y2B, Z6.T1A.T2B.Y1A.Y2C, Z6.T1A.T2B.Y1A.Y2D,
Z6.T1A.T2B.Y1B.Y2A, Z6.T1A.T2B.Y1B.Y2B, Z6.T1A.T2B.Y1B.Y2C,
Z6.T1A.T2B.Y1B.Y2D, Z6.T1A.T2B.Y1C.Y2A, Z6.T1A.T2B.Y1C.Y2B,

TABLE 6-continued

List of Compound Structures of Formula I

Z6.T1A.T2B.Y1C.Y2C, Z6.T1A.T2B.Y1C.Y2D, Z6.T1A.T2B.Y1D.Y2A,
Z6.T1A.T2B.Y1D.Y2B, Z6.T1A.T2B.Y1D.Y2C, Z6.T1A.T2B.Y1D.Y2D,
Z6.T1A.T2B.Y1E.Y2A, Z6.T1A.T2B.Y1E.Y2B, Z6.T1A.T2B.Y1E.Y2C,
Z6.T1A.T2B.Y1E.Y2D, Z6.T1A.T2C.Y1A.Y2A, Z6.T1A.T2C.Y1A.Y2B,
Z6.T1A.T2C.Y1A.Y2C, Z6.T1A.T2C.Y1A.Y2D, Z6.T1A.T2C.Y1B.Y2A,
Z6.T1A.T2C.Y1B.Y2B, Z6.T1A.T2C.Y1B.Y2C, Z6.T1A.T2C.Y1B.Y2D,
Z6.T1A.T2C.Y1C.Y2A, Z6.T1A.T2C.Y1C.Y2B, Z6.T1A.T2C.Y1C.Y2C,
Z6.T1A.T2C.Y1C.Y2D, Z6.T1A.T2C.Y1D.Y2A, Z6.T1A.T2C.Y1D.Y2B,
Z6.T1A.T2C.Y1D.Y2C, Z6.T1A.T2C.Y1D.Y2D, Z6.T1A.T2C.Y1E.Y2A,
Z6.T1A.T2C.Y1E.Y2B, Z6.T1A.T2C.Y1E.Y2C, Z6.T1A.T2C.Y1E.Y2D,
Z6.T1B.T2A.Y1A.Y2A, Z6.T1B.T2A.Y1A.Y2B, Z6.T1B.T2A.Y1A.Y2C,
Z6.T1B.T2A.Y1A.Y2D, Z6.T1B.T2A.Y1B.Y2A, Z6.T1B.T2A.Y1B.Y2B,
Z6.T1B.T2A.Y1B.Y2C, Z6.T1B.T2A.Y1B.Y2D, Z6.T1B.T2A.Y1C.Y2A,
Z6.T1B.T2A.Y1C.Y2B, Z6.T1B.T2A.Y1C.Y2C, Z6.T1B.T2A.Y1C.Y2D,
Z6.T1B.T2A.Y1D.Y2A, Z6.T1B.T2A.Y1D.Y2B, Z6.T1B.T2A.Y1D.Y2C,
Z6.T1B.T2A.Y1D.Y2D, Z6.T1B.T2A.Y1E.Y2A, Z6.T1B.T2A.Y1E.Y2B,
Z6.T1B.T2A.Y1E.Y2C, Z6.T1B.T2A.Y1E.Y2D, Z6.T1B.T2B.Y1A.Y2A,
Z6.T1B.T2B.Y1A.Y2B, Z6.T1B.T2B.Y1A.Y2C, Z6.T1B.T2B.Y1A.Y2D,
Z6.T1B.T2B.Y1B.Y2A, Z6.T1B.T2B.Y1B.Y2B, Z6.T1B.T2B.Y1B.Y2C,
Z6.T1B.T2B.Y1B.Y2D, Z6.T1B.T2B.Y1C.Y2A, Z6.T1B.T2B.Y1C.Y2B,
Z6.T1B.T2B.Y1C.Y2C, Z6.T1B.T2B.Y1C.Y2D, Z6.T1B.T2B.Y1D.Y2A,
Z6.T1B.T2B.Y1D.Y2B, Z6.T1B.T2B.Y1D.Y2C, Z6.T1B.T2B.Y1D.Y2D,
Z6.T1B.T2B.Y1E.Y2A, Z6.T1B.T2B.Y1E.Y2B, Z6.T1B.T2B.Y1E.Y2C,
Z6.T1B.T2B.Y1E.Y2D, Z6.T1B.T2C.Y1A.Y2A, Z6.T1B.T2C.Y1A.Y2B,
Z6.T1B.T2C.Y1A.Y2C, Z6.T1B.T2C.Y1A.Y2D, Z6.T1B.T2C.Y1B.Y2A,
Z6.T1B.T2C.Y1B.Y2B, Z6.T1B.T2C.Y1B.Y2C, Z6.T1B.T2C.Y1B.Y2D,
Z6.T1B.T2C.Y1C.Y2A, Z6.T1B.T2C.Y1C.Y2B, Z6.T1B.T2C.Y1C.Y2C,
Z6.T1B.T2C.Y1C.Y2D, Z6.T1B.T2C.Y1D.Y2A, Z6.T1B.T2C.Y1D.Y2B,
Z6.T1B.T2C.Y1D.Y2C, Z6.T1B.T2C.Y1D.Y2D, Z6.T1B.T2C.Y1E.Y2A,
Z6.T1B.T2C.Y1E.Y2B, Z6.T1B.T2C.Y1E.Y2C, Z6.T1B.T2C.Y1E.Y2D,
Z6.T1C.T2A.Y1A.Y2A, Z6.T1C.T2A.Y1A.Y2B, Z6.T1C.T2A.Y1A.Y2C,
Z6.T1C.T2A.Y1A.Y2D, Z6.T1C.T2A.Y1B.Y2A, Z6.T1C.T2A.Y1B.Y2B,
Z6.T1C.T2A.Y1B.Y2C, Z6.T1C.T2A.Y1B.Y2D, Z6.T1C.T2A.Y1C.Y2A,
Z6.T1C.T2A.Y1C.Y2B, Z6.T1C.T2A.Y1C.Y2C, Z6.T1C.T2A.Y1C.Y2D,
Z6.T1C.T2A.Y1D.Y2A, Z6.T1C.T2A.Y1D.Y2B, Z6.T1C.T2A.Y1D.Y2C,
Z6.T1C.T2A.Y1D.Y2D, Z6.T1C.T2A.Y1E.Y2A, Z6.T1C.T2A.Y1E.Y2B,
Z6.T1C.T2A.Y1E.Y2C, Z6.T1C.T2A.Y1E.Y2D, Z6.T1C.T2B.Y1A.Y2A,
Z6.T1C.T2B.Y1A.Y2B, Z6.T1C.T2B.Y1A.Y2C, Z6.T1C.T2B.Y1A.Y2D,
Z6.T1C.T2B.Y1B.Y2A, Z6.T1C.T2B.Y1B.Y2B, Z6.T1C.T2B.Y1B.Y2C,
Z6.T1C.T2B.Y1B.Y2D, Z6.T1C.T2B.Y1C.Y2A, Z6.T1C.T2B.Y1C.Y2B,
Z6.T1C.T2B.Y1C.Y2C, Z6.T1C.T2B.Y1C.Y2D, Z6.T1C.T2B.Y1D.Y2A,
Z6.T1C.T2B.Y1D.Y2B, Z6.T1C.T2B.Y1D.Y2C, Z6.T1C.T2B.Y1D.Y2D,
Z6.T1C.T2B.Y1E.Y2A, Z6.T1C.T2B.Y1E.Y2B, Z6.T1C.T2B.Y1E.Y2C,
Z6.T1C.T2B.Y1E.Y2D, Z6.T1C.T2C.Y1A.Y2A, Z6.T1C.T2C.Y1A.Y2B,
Z6.T1C.T2C.Y1A.Y2C, Z6.T1C.T2C.Y1A.Y2D, Z6.T1C.T2C.Y1B.Y2A,
Z6.T1C.T2C.Y1B.Y2B, Z6.T1C.T2C.Y1B.Y2C, Z6.T1C.T2C.Y1B.Y2D,
Z6.T1C.T2C.Y1C.Y2A, Z6.T1C.T2C.Y1C.Y2B, Z6.T1C.T2C.Y1C.Y2C,
Z6.T1C.T2C.Y1C.Y2D, Z6.T1C.T2C.Y1D.Y2A, Z6.T1C.T2C.Y1D.Y2B,
Z6.T1C.T2C.Y1D.Y2C, Z6.T1C.T2C.Y1D.Y2D, Z6.T1C.T2C.Y1E.Y2A,
Z6.T1C.T2C.Y1E.Y2B, Z6.T1C.T2C.Y1E.Y2C, Z6.T1C.T2C.Y1E.Y2D,
Z6.T1D.T2A.Y1A.Y2A, Z6.T1D.T2A.Y1A.Y2B, Z6.T1D.T2A.Y1A.Y2C,
Z6.T1D.T2A.Y1A.Y2D, Z6.T1D.T2A.Y1B.Y2A, Z6.T1D.T2A.Y1B.Y2B,
Z6.T1D.T2A.Y1B.Y2C, Z6.T1D.T2A.Y1B.Y2D, Z6.T1D.T2A.Y1C.Y2A,
Z6.T1D.T2A.Y1C.Y2B, Z6.T1D.T2A.Y1C.Y2C, Z6.T1D.T2A.Y1C.Y2D,
Z6.T1D.T2A.Y1D.Y2A, Z6.T1D.T2A.Y1D.Y2B, Z6.T1D.T2A.Y1D.Y2C,
Z6.T1D.T2A.Y1D.Y2D, Z6.T1D.T2A.Y1E.Y2A, Z6.T1D.T2A.Y1E.Y2B,
Z6.T1D.T2A.Y1E.Y2C, Z6.T1D.T2A.Y1E.Y2D, Z6.T1D.T2B.Y1A.Y2A,
Z6.T1D.T2B.Y1A.Y2B, Z6.T1D.T2B.Y1A.Y2C, Z6.T1D.T2B.Y1A.Y2D,
Z6.T1D.T2B.Y1B.Y2A, Z6.T1D.T2B.Y1B.Y2B, Z6.T1D.T2B.Y1B.Y2C,
Z6.T1D.T2B.Y1B.Y2D, Z6.T1D.T2B.Y1C.Y2A, Z6.T1D.T2B.Y1C.Y2B,
Z6.T1D.T2B.Y1C.Y2C, Z6.T1D.T2B.Y1C.Y2D, Z6.T1D.T2B.Y1D.Y2A,
Z6.T1D.T2B.Y1D.Y2B, Z6.T1D.T2B.Y1D.Y2C, Z6.T1D.T2B.Y1D.Y2D,
Z6.T1D.T2B.Y1E.Y2A, Z6.T1D.T2B.Y1E.Y2B, Z6.T1D.T2B.Y1E.Y2C,
Z6.T1D.T2B.Y1E.Y2D, Z6.T1D.T2C.Y1A.Y2A, Z6.T1D.T2C.Y1A.Y2B,
Z6.T1D.T2C.Y1A.Y2C, Z6.T1D.T2C.Y1A.Y2D, Z6.T1D.T2C.Y1B.Y2A,
Z6.T1D.T2C.Y1B.Y2B, Z6.T1D.T2C.Y1B.Y2C, Z6.T1D.T2C.Y1B.Y2D,
Z6.T1D.T2C.Y1C.Y2A, Z6.T1D.T2C.Y1C.Y2B, Z6.T1D.T2C.Y1C.Y2C,
Z6.T1D.T2C.Y1C.Y2D, Z6.T1D.T2C.Y1D.Y2A, Z6.T1D.T2C.Y1D.Y2B,
Z6.T1D.T2C.Y1D.Y2C, Z6.T1D.T2C.Y1D.Y2D, Z6.T1D.T2C.Y1E.Y2A,
Z6.T1D.T2C.Y1E.Y2B, Z6.T1D.T2C.Y1E.Y2C, Z6.T1D.T2C.Y1E.Y2D,
Z6.T1E.T2A.Y1A.Y2A, Z6.T1E.T2A.Y1A.Y2B, Z6.T1E.T2A.Y1A.Y2C,
Z6.T1E.T2A.Y1A.Y2D, Z6.T1E.T2A.Y1B.Y2A, Z6.T1E.T2A.Y1B.Y2B,
Z6.T1E.T2A.Y1B.Y2C, Z6.T1E.T2A.Y1B.Y2D, Z6.T1E.T2A.Y1C.Y2A,
Z6.T1E.T2A.Y1C.Y2B, Z6.T1E.T2A.Y1C.Y2C, Z6.T1E.T2A.Y1C.Y2D,
Z6.T1E.T2A.Y1D.Y2A, Z6.T1E.T2A.Y1D.Y2B, Z6.T1E.T2A.Y1D.Y2C,
Z6.T1E.T2A.Y1D.Y2D, Z6.T1E.T2A.Y1E.Y2A, Z6.T1E.T2A.Y1E.Y2B,
Z6.T1E.T2A.Y1E.Y2C, Z6.T1E.T2A.Y1E.Y2D, Z6.T1E.T2B.Y1A.Y2A,
Z6.T1E.T2B.Y1A.Y2B, Z6.T1E.T2B.Y1A.Y2C, Z6.T1E.T2B.Y1A.Y2D,

TABLE 6-continued

List of Compound Structures of Formula I

Z6.T1E.T2B.Y1B.Y2A, Z6.T1E.T2B.Y1B.Y2B, Z6.T1E.T2B.Y1B.Y2C,
Z6.T1E.T2B.Y1B.Y2D, Z6.T1E.T2B.Y1C.Y2A, Z6.T1E.T2B.Y1C.Y2B,
Z6.T1E.T2B.Y1C.Y2C, Z6.T1E.T2B.Y1C.Y2D, Z6.T1E.T2B.Y1D.Y2A,
Z6.T1E.T2B.Y1D.Y2B, Z6.T1E.T2B.Y1D.Y2C, Z6.T1E.T2B.Y1D.Y2D,
Z6.T1E.T2B.Y1E.Y2A, Z6.T1E.T2B.Y1E.Y2B, Z6.T1E.T2B.Y1E.Y2C,
Z6.T1E.T2B.Y1E.Y2D, Z6.T1E.T2C.Y1A.Y2A, Z6.T1E.T2C.Y1A.Y2B,
Z6.T1E.T2C.Y1A.Y2C, Z6.T1E.T2C.Y1A.Y2D, Z6.T1E.T2C.Y1B.Y2A,
Z6.T1E.T2C.Y1B.Y2B, Z6.T1E.T2C.Y1B.Y2C, Z6.T1E.T2C.Y1B.Y2D,
Z6.T1E.T2C.Y1C.Y2A, Z6.T1E.T2C.Y1C.Y2B, Z6.T1E.T2C.Y1C.Y2C,
Z6.T1E.T2C.Y1C.Y2D, Z6.T1E.T2C.Y1D.Y2A, Z6.T1E.T2C.Y1D.Y2B,
Z6.T1E.T2C.Y1D.Y2C, Z6.T1E.T2C.Y1D.Y2D, Z6.T1E.T2C.Y1E.Y2A,
Z6.T1E.T2C.Y1E.Y2B, Z6.T1E.T2C.Y1E.Y2C, Z6.T1E.T2C.Y1E.Y2D,
Z6.T1F.T2A.Y1A.Y2A, Z6.T1F.T2A.Y1A.Y2B, Z6.T1F.T2A.Y1A.Y2C,
Z6.T1F.T2A.Y1A.Y2D, Z6.T1F.T2A.Y1B.Y2A, Z6.T1F.T2A.Y1B.Y2B,
Z6.T1F.T2A.Y1B.Y2C, Z6.T1F.T2A.Y1B.Y2D, Z6.T1F.T2A.Y1C.Y2A,
Z6.T1F.T2A.Y1C.Y2B, Z6.T1F.T2A.Y1C.Y2C, Z6.T1F.T2A.Y1C.Y2D,
Z6.T1F.T2A.Y1D.Y2A, Z6.T1F.T2A.Y1D.Y2B, Z6.T1F.T2A.Y1D.Y2C,
Z6.T1F.T2A.Y1D.Y2D, Z6.T1F.T2A.Y1E.Y2A, Z6.T1F.T2A.Y1E.Y2B,
Z6.T1F.T2A.Y1E.Y2C, Z6.T1F.T2A.Y1E.Y2D, Z6.T1F.T2B.Y1A.Y2A,
Z6.T1F.T2B.Y1A.Y2B, Z6.T1F.T2B.Y1A.Y2C, Z6.T1F.T2B.Y1A.Y2D,
Z6.T1F.T2B.Y1B.Y2A, Z6.T1F.T2B.Y1B.Y2B, Z6.T1F.T2B.Y1B.Y2C,
Z6.T1F.T2B.Y1B.Y2D, Z6.T1F.T2B.Y1C.Y2A, Z6.T1F.T2B.Y1C.Y2B,
Z6.T1F.T2B.Y1C.Y2C, Z6.T1F.T2B.Y1C.Y2D, Z6.T1F.T2B.Y1D.Y2A,
Z6.T1F.T2B.Y1D.Y2B, Z6.T1F.T2B.Y1D.Y2C, Z6.T1F.T2B.Y1D.Y2D,
Z6.T1F.T2B.Y1E.Y2A, Z6.T1F.T2B.Y1E.Y2B, Z6.T1F.T2B.Y1E.Y2C,
Z6.T1F.T2B.Y1E.Y2D, Z6.T1F.T2C.Y1A.Y2A, Z6.T1E.T2C.Y1A.Y2B,
Z6.T1F.T2C.Y1A.Y2C, Z6.T1F.T2C.Y1A.Y2D, Z6.T1F.T2C.Y1B.Y2A,
Z6.T1F.T2C.Y1B.Y2B, Z6.T1F.T2C.Y1B.Y2C, Z6.T1F.T2C.Y1B.Y2D,
Z6.T1F.T2C.Y1C.Y2A, Z6.T1F.T2C.Y1C.Y2B, Z6.T1F.T2C.Y1C.Y2C,
Z6.T1F.T2C.Y1C.Y2D, Z6.T1F.T2C.Y1D.Y2A, Z6.T1F.T2C.Y1D.Y2B,
Z6.T1F.T2C.Y1D.Y2C, Z6.T1F.T2C.Y1D.Y2D, Z6.T1F.T2C.Y1E.Y2A,
Z6.T1F.T2C.Y1E.Y2B, Z6.T1F.T2C.Y1E.Y2C, Z6.T1F.T2C.Y1E.Y2D,
Z6.T1G.T2A.Y1A.Y2A, Z6.T1G.T2A.Y1A.Y2B, Z6.T1G.T2A.Y1A.Y2C,
Z6.T1G.T2A.Y1A.Y2D, Z6.T1G.T2A.Y1B.Y2A, Z6.T1G.T2A.Y1B.Y2B,
Z6.T1G.T2A.Y1B.Y2C, Z6.T1G.T2A.Y1B.Y2D, Z6.T1G.T2A.Y1C.Y2A,
Z6.T1G.T2A.Y1C.Y2B, Z6.T1G.T2A.Y1C.Y2C, Z6.T1G.T2A.Y1C.Y2D,
Z6.T1G.T2A.Y1D.Y2A, Z6.T1G.T2A.Y1D.Y2B, Z6.T1G.T2A.Y1D.Y2C,
Z6.T1G.T2A.Y1D.Y2D, Z6.T1G.T2A.Y1E.Y2A, Z6.T1G.T2A.Y1E.Y2B,
Z6.T1G.T2A.Y1E.Y2C, Z6.T1G.T2A.Y1E.Y2D, Z6.T1G.T2B.Y1A.Y2A,
Z6.T1G.T2B.Y1A.Y2B, Z6.T1G.T2B.Y1A.Y2C, Z6.T1G.T2B.Y1A.Y2D,
Z6.T1G.T2B.Y1B.Y2A, Z6.T1G.T2B.Y1B.Y2B, Z6.T1G.T2B.Y1B.Y2C,
Z6.T1G.T2B.Y1B.Y2D, Z6.T1G.T2B.Y1C.Y2A, Z6.T1G.T2B.Y1C.Y2B,
Z6.T1G.T2B.Y1C.Y2C, Z6.T1G.T2B.Y1C.Y2D, Z6.T1G.T2B.Y1D.Y2A,
Z6.T1G.T2B.Y1D.Y2B, Z6.T1G.T2B.Y1D.Y2C, Z6.T1G.T2B.Y1D.Y2D,
Z6.T1G.T2B.Y1E.Y2A, Z6.T1G.T2B.Y1E.Y2B, Z6.T1G.T2B.Y1E.Y2C,
Z6.T1G.T2B.Y1E.Y2D, Z6.T1G.T2C.Y1A.Y2A, Z6.T1G.T2C.Y1A.Y2B,
Z6.T1G.T2C.Y1A.Y2C, Z6.T1G.T2C.Y1A.Y2D, Z6.T1G.T2C.Y1B.Y2A,
Z6.T1G.T2C.Y1B.Y2B, Z6.T1G.T2C.Y1B.Y2C, Z6.T1G.T2C.Y1B.Y2D,
Z6.T1G.T2C.Y1C.Y2A, Z6.T1G.T2C.Y1C.Y2B, Z6.T1G.T2C.Y1C.Y2C,
Z6.T1G.T2C.Y1C.Y2D, Z6.T1G.T2C.Y1D.Y2A, Z6.T1G.T2C.Y1D.Y2B,
Z6.T1G.T2C.Y1D.Y2C, Z6.T1G.T2C.Y1D.Y2D, Z6.T1G.T2C.Y1E.Y2A,
Z6.T1G.T2C.Y1E.Y2B, Z6.T1G.T2C.Y1E.Y2C, Z6.T1G.T2C.Y1E.Y2D,
Z7.T1A.T2A.Y1A.Y2A, Z7.T1A.T2A.Y1A.Y2B, Z7.T1A.T2A.Y1A.Y2C,
Z7.T1A.T2A.Y1A.Y2D, Z7.T1A.T2A.Y1B.Y2A, Z7.T1A.T2A.Y1B.Y2B,
Z7.T1A.T2A.Y1B.Y2C, Z7.T1A.T2A.Y1B.Y2D, Z7.T1A.T2A.Y1C.Y2A,
Z7.T1A.T2A.Y1C.Y2B, Z7.T1A.T2A.Y1C.Y2C, Z7.T1A.T2A.Y1C.Y2D,
Z7.T1A.T2A.Y1D.Y2A, Z7.T1A.T2A.Y1D.Y2B, Z7.T1A.T2A.Y1D.Y2C,
Z7.T1A.T2A.Y1D.Y2D, Z7.T1A.T2A.Y1E.Y2A, Z7.T1A.T2A.Y1E.Y2B,
Z7.T1A.T2A.Y1E.Y2C, Z7.T1A.T2A.Y1E.Y2D, Z7.T1A.T2B.Y1A.Y2A,
Z7.T1A.T2B.Y1A.Y2B, Z7.T1A.T2B.Y1A.Y2C, Z7.T1A.T2B.Y1A.Y2D,
Z7.T1A.T2B.Y1B.Y2A, Z7.T1A.T2B.Y1B.Y2B, Z7.T1A.T2B.Y1B.Y2C,
Z7.T1A.T2B.Y1B.Y2D, Z7.T1A.T2B.Y1C.Y2A, Z7.T1A.T2B.Y1C.Y2B,
Z7.T1A.T2B.Y1C.Y2C, Z7.T1A.T2B.Y1C.Y2D, Z7.T1A.T2B.Y1D.Y2A,
Z7.T1A.T2B.Y1D.Y2B, Z7.T1A.T2B.Y1D.Y2C, Z7.T1A.T2B.Y1D.Y2D,
Z7.T1A.T2B.Y1E.Y2A, Z7.T1A.T2B.Y1E.Y2B, Z7.T1A.T2B.Y1E.Y2C,
Z7.T1A.T2B.Y1E.Y2D, Z7.T1A.T2C.Y1A.Y2A, Z7.T1A.T2C.Y1A.Y2B,
Z7.T1A.T2C.Y1A.Y2C, Z7.T1A.T2C.Y1A.Y2D, Z7.T1A.T2C.Y1B.Y2A,
Z7.T1A.T2C.Y1B.Y2B, Z7.T1A.T2C.Y1B.Y2C, Z7.T1A.T2C.Y1B.Y2D,
Z7.T1A.T2C.Y1C.Y2A, Z7.T1A.T2C.Y1C.Y2B, Z7.T1A.T2C.Y1C.Y2C,
Z7.T1A.T2C.Y1C.Y2D, Z7.T1A.T2C.Y1D.Y2A, Z7.T1A.T2C.Y1D.Y2B,
Z7.T1A.T2C.Y1D.Y2C, Z7.T1A.T2C.Y1D.Y2D, Z7.T1A.T2C.Y1E.Y2A,
Z7.T1A.T2C.Y1E.Y2B, Z7.T1A.T2C.Y1E.Y2C, Z7.T1A.T2C.Y1E.Y2D,
Z7.T1B.T2A.Y1A.Y2A, Z7.T1B.T2A.Y1A.Y2B, Z7.T1B.T2A.Y1A.Y2C,
Z7.T1B.T2A.Y1A.Y2D, Z7.T1B.T2A.Y1B.Y2A, Z7.T1B.T2A.Y1B.Y2B,
Z7.T1B.T2A.Y1B.Y2C, Z7.T1B.T2A.Y1B.Y2D, Z7.T1B.T2A.Y1C.Y2A,
Z7.T1B.T2A.Y1C.Y2B, Z7.T1B.T2A.Y1C.Y2C, Z7.T1B.T2A.Y1C.Y2D,
Z7.T1B.T2A.Y1D.Y2A, Z7.T1B.T2A.Y1D.Y2B, Z7.T1B.T2A.Y1D.Y2C,
Z7.T1B.T2A.Y1D.Y2D, Z7.T1B.T2A.Y1E.Y2A, Z7.T1B.T2A.Y1E.Y2B,

TABLE 6-continued

List of Compound Structures of Formula I

Z7.T1B.T2A.Y1E.Y2C, Z7.T1B.T2A.Y1E.Y2D, Z7.T1B.T2B.Y1A.Y2A,
Z7.T1B.T2B.Y1A.Y2B, Z7.T1B.T2B.Y1A.Y2C, Z7.T1B.T2B.Y1A.Y2D,
Z7.T1B.T2B.Y1B.Y2A, Z7.T1B.T2B.Y1B.Y2B, Z7.T1B.T2B.Y1B.Y2C,
Z7.T1B.T2B.Y1B.Y2D, Z7.T1B.T2B.Y1C.Y2A, Z7.T1B.T2B.Y1C.Y2B,
Z7.T1B.T2B.Y1C.Y2C, Z7.T1B.T2B.Y1C.Y2D, Z7.T1B.T2B.Y1D.Y2A,
Z7.T1B.T2B.Y1D.Y2B, Z7.T1B.T2B.Y1D.Y2C, Z7.T1B.T2B.Y1D.Y2D,
Z7.T1B.T2B.Y1E.Y2A, Z7.T1B.T2B.Y1E.Y2B, Z7.T1B.T2B.Y1E.Y2C,
Z7.T1B.T2B.Y1E.Y2D, Z7.T1B.T2C.Y1A.Y2A, Z7.T1B.T2C.Y1A.Y2B,
Z7.T1B.T2C.Y1A.Y2C, Z7.T1B.T2C.Y1A.Y2D, Z7.T1B.T2C.Y1B.Y2A,
Z7.T1B.T2C.Y1B.Y2B, Z7.T1B.T2C.Y1B.Y2C, Z7.T1B.T2C.Y1B.Y2D,
Z7.T1B.T2C.Y1C.Y2A, Z7.T1B.T2C.Y1C.Y2B, Z7.T1B.T2C.Y1C.Y2C,
Z7.T1B.T2C.Y1C.Y2D, Z7.T1B.T2C.Y1D.Y2A, Z7.T1B.T2C.Y1D.Y2B,
Z7.T1B.T2C.Y1D.Y2C, Z7.T1B.T2C.Y1D.Y2D, Z7.T1B.T2C.Y1E.Y2A,
Z7.T1B.T2C.Y1E.Y2B, Z7.T1B.T2C.Y1E.Y2C, Z7.T1B.T2C.Y1E.Y2D,
Z7.T1C.T2A.Y1A.Y2A, Z7.T1C.T2A.Y1A.Y2B, Z7.T1C.T2A.Y1A.Y2C,
Z7.T1C.T2A.Y1A.Y2D, Z7.T1C.T2A.Y1B.Y2A, Z7.T1C.T2A.Y1B.Y2B,
Z7.T1C.T2A.Y1B.Y2C, Z7.T1C.T2A.Y1B.Y2D, Z7.T1C.T2A.Y1C.Y2A,
Z7.T1C.T2A.Y1C.Y2B, Z7.T1C.T2A.Y1C.Y2C, Z7.T1C.T2A.Y1C.Y2D,
Z7.T1C.T2A.Y1D.Y2A, Z7.T1C.T2A.Y1D.Y2B, Z7.T1C.T2A.Y1D.Y2C,
Z7.T1C.T2A.Y1D.Y2D, Z7.T1C.T2A.Y1E.Y2A, Z7.T1C.T2A.Y1E.Y2B,
Z7.T1C.T2A.Y1E.Y2C, Z7.T1C.T2A.Y1E.Y2D, Z7.T1C.T2B.Y1A.Y2A,
Z7.T1C.T2B.Y1A.Y2B, Z7.T1C.T2B.Y1A.Y2C, Z7.T1C.T2B.Y1A.Y2D,
Z7.T1C.T2B.Y1B.Y2A, Z7.T1C.T2B.Y1B.Y2B, Z7.T1C.T2B.Y1B.Y2C,
Z7.T1C.T2B.Y1B.Y2D, Z7.T1C.T2B.Y1C.Y2A, Z7.T1C.T2B.Y1C.Y2B,
Z7.T1C.T2B.Y1C.Y2C, Z7.T1C.T2B.Y1C.Y2D, Z7.T1C.T2B.Y1D.Y2A,
Z7.T1C.T2B.Y1D.Y2B, Z7.T1C.T2B.Y1D.Y2C, Z7.T1C.T2B.Y1D.Y2D,
Z7.T1C.T2B.Y1E.Y2A, Z7.T1C.T2B.Y1E.Y2B, Z7.T1C.T2B.Y1E.Y2C,
Z7.T1C.T2B.Y1E.Y2D, Z7.T1C.T2C.Y1A.Y2A, Z7.T1C.T2C.Y1A.Y2B,
Z7.T1C.T2C.Y1A.Y2C, Z7.T1C.T2C.Y1A.Y2D, Z7.T1C.T2C.Y1B.Y2A,
Z7.T1C.T2C.Y1B.Y2B, Z7.T1C.T2C.Y1B.Y2C, Z7.T1C.T2C.Y1B.Y2D,
Z7.T1C.T2C.Y1C.Y2A, Z7.T1C.T2C.Y1C.Y2B, Z7.T1C.T2C.Y1C.Y2C,
Z7.T1C.T2C.Y1C.Y2D, Z7.T1C.T2C.Y1D.Y2A, Z7.T1C.T2C.Y1D.Y2B,
Z7.T1C.T2C.Y1D.Y2C, Z7.T1C.T2C.Y1D.Y2D, Z7.T1C.T2C.Y1E.Y2A,
Z7.T1C.T2C.Y1E.Y2B, Z7.T1C.T2C.Y1E.Y2C, Z7.T1C.T2C.Y1E.Y2D,
Z7.T1D.T2A.Y1A.Y2A, Z7.T1D.T2A.Y1A.Y2B, Z7.T1D.T2A.Y1A.Y2C,
Z7.T1D.T2A.Y1A.Y2D, Z7.T1D.T2A.Y1B.Y2A, Z7.T1D.T2A.Y1B.Y2B,
Z7.T1D.T2A.Y1B.Y2C, Z7.T1D.T2A.Y1B.Y2D, Z7.T1D.T2A.Y1C.Y2A,
Z7.T1D.T2A.Y1C.Y2B, Z7.T1D.T2A.Y1C.Y2C, Z7.T1D.T2A.Y1C.Y2D,
Z7.T1D.T2A.Y1D.Y2A, Z7.T1D.T2A.Y1D.Y2B, Z7.T1D.T2A.Y1D.Y2C,
Z7.T1D.T2A.Y1D.Y2D, Z7.T1D.T2A.Y1E.Y2A, Z7.T1D.T2A.Y1E.Y2B,
Z7.T1D.T2A.Y1E.Y2C, Z7.T1D.T2A.Y1E.Y2D, Z7.T1D.T2B.Y1A.Y2A,
Z7.T1D.T2B.Y1A.Y2B, Z7.T1D.T2B.Y1A.Y2C, Z7.T1D.T2B.Y1A.Y2D,
Z7.T1D.T2B.Y1B.Y2A, Z7.T1D.T2B.Y1B.Y2B, Z7.T1D.T2B.Y1B.Y2C,
Z7.T1D.T2B.Y1B.Y2D, Z7.T1D.T2B.Y1C.Y2A, Z7.T1D.T2B.Y1C.Y2B,
Z7.T1D.T2B.Y1C.Y2C, Z7.T1D.T2B.Y1C.Y2D, Z7.T1D.T2B.Y1D.Y2A,
Z7.T1D.T2B.Y1D.Y2B, Z7.T1D.T2B.Y1D.Y2C, Z7.T1D.T2B.Y1D.Y2D,
Z7.T1D.T2B.Y1E.Y2A, Z7.T1D.T2B.Y1E.Y2B, Z7.T1D.T2B.Y1E.Y2C,
Z7.T1D.T2B.Y1E.Y2D, Z7.T1D.T2C.Y1A.Y2A, Z7.T1D.T2C.Y1A.Y2B,
Z7.T1D.T2C.Y1A.Y2C, Z7.T1D.T2C.Y1A.Y2D, Z7.T1D.T2C.Y1B.Y2A,
Z7.T1D.T2C.Y1B.Y2B, Z7.T1D.T2C.Y1B.Y2C, Z7.T1D.T2C.Y1B.Y2D,
Z7.T1D.T2C.Y1C.Y2A, Z7.T1D.T2C.Y1C.Y2B, Z7.T1D.T2C.Y1C.Y2C,
Z7.T1D.T2C.Y1C.Y2D, Z7.T1D.T2C.Y1D.Y2A, Z7.T1D.T2C.Y1D.Y2B,
Z7.T1D.T2C.Y1D.Y2C, Z7.T1D.T2C.Y1D.Y2D, Z7.T1D.T2C.Y1E.Y2A,
Z7.T1D.T2C.Y1E.Y2B, Z7.T1D.T2C.Y1E.Y2C, Z7.T1D.T2C.Y1E.Y2D,
Z7.T1E.T2A.Y1A.Y2A, Z7.T1E.T2A.Y1A.Y2B, Z7.T1E.T2A.Y1A.Y2C,
Z7.T1E.T2A.Y1A.Y2D, Z7.T1E.T2A.Y1B.Y2A, Z7.T1E.T2A.Y1B.Y2B,
Z7.T1E.T2A.Y1B.Y2C, Z7.T1E.T2A.Y1B.Y2D, Z7.T1E.T2A.Y1C.Y2A,
Z7.T1E.T2A.Y1C.Y2B, Z7.T1E.T2A.Y1C.Y2C, Z7.T1E.T2A.Y1C.Y2D,
Z7.T1E.T2A.Y1D.Y2A, Z7.T1E.T2A.Y1D.Y2B, Z7.T1E.T2A.Y1D.Y2C,
Z7.T1E.T2A.Y1D.Y2D, Z7.T1E.T2A.Y1E.Y2A, Z7.T1E.T2A.Y1E.Y2B,
Z7.T1E.T2A.Y1E.Y2C, Z7.T1E.T2A.Y1E.Y2D, Z7.T1E.T2B.Y1A.Y2A,
Z7.T1E.T2B.Y1A.Y2B, Z7.T1E.T2B.Y1A.Y2C, Z7.T1E.T2B.Y1A.Y2D,
Z7.T1E.T2B.Y1B.Y2A, Z7.T1E.T2B.Y1B.Y2B, Z7.T1E.T2B.Y1B.Y2C,
Z7.T1E.T2B.Y1B.Y2D, Z7.T1E.T2B.Y1C.Y2A, Z7.T1E.T2B.Y1C.Y2B,
Z7.T1E.T2B.Y1C.Y2C, Z7.T1E.T2B.Y1C.Y2D, Z7.T1E.T2B.Y1D.Y2A,
Z7.T1E.T2B.Y1D.Y2B, Z7.T1E.T2B.Y1D.Y2C, Z7.T1E.T2B.Y1D.Y2D,
Z7.T1E.T2B.Y1E.Y2A, Z7.T1E.T2B.Y1E.Y2B, Z7.T1E.T2B.Y1E.Y2C,
Z7.T1E.T2B.Y1E.Y2D, Z7.T1E.T2C.Y1A.Y2A, Z7.T1E.T2C.Y1A.Y2B,
Z7.T1E.T2C.Y1A.Y2C, Z7.T1E.T2C.Y1A.Y2D, Z7.T1E.T2C.Y1B.Y2A,
Z7.T1E.T2C.Y1B.Y2B, Z7.T1E.T2C.Y1B.Y2C, Z7.T1E.T2C.Y1B.Y2D,
Z7.T1E.T2C.Y1C.Y2A, Z7.T1E.T2C.Y1C.Y2B, Z7.T1E.T2C.Y1C.Y2C,
Z7.T1E.T2C.Y1C.Y2D, Z7.T1E.T2C.Y1D.Y2A, Z7.T1E.T2C.Y1D.Y2B,
Z7.T1E.T2C.Y1D.Y2C, Z7.T1E.T2C.Y1D.Y2D, Z7.T1E.T2C.Y1E.Y2A,
Z7.T1E.T2C.Y1E.Y2B, Z7.T1E.T2C.Y1E.Y2C, Z7.T1E.T2C.Y1E.Y2D,
Z7.T1F.T2A.Y1A.Y2A, Z7.T1F.T2A.Y1A.Y2B, Z7.T1F.T2A.Y1A.Y2C,
Z7.T1F.T2A.Y1A.Y2D, Z7.T1F.T2A.Y1B.Y2A, Z7.T1F.T2A.Y1B.Y2B,
Z7.T1F.T2A.Y1B.Y2C, Z7.T1F.T2A.Y1B.Y2D, Z7.T1F.T2A.Y1C.Y2A,
Z7.T1F.T2A.Y1C.Y2B, Z7.T1F.T2A.Y1C.Y2C, Z7.T1F.T2A.Y1C.Y2D,

TABLE 6-continued

List of Compound Structures of Formula I

Z7.T1F.T2A.Y1D.Y2A, Z7.T1F.T2A.Y1D.Y2B, Z7.T1F.T2A.Y1D.Y2C,
Z7.T1F.T2A.Y1D.Y2D, Z7.T1F.T2A.Y1E.Y2A, Z7.T1F.T2A.Y1E.Y2B,
Z7.T1F.T2A.Y1E.Y2C, Z7.T1F.T2A.Y1E.Y2D, Z7.T1F.T2B.Y1A.Y2A,
Z7.T1F.T2B.Y1A.Y2B, Z7.T1F.T2B.Y1A.Y2C, Z7.T1F.T2B.Y1A.Y2D,
Z7.T1F.T2B.Y1B.Y2A, Z7.T1F.T2B.Y1B.Y2B, Z7.T1F.T2B.Y1B.Y2C,
Z7.T1F.T2B.Y1B.Y2D, Z7.T1F.T2B.Y1C.Y2A, Z7.T1F.T2B.Y1C.Y2B,
Z7.T1F.T2B.Y1C.Y2C, Z7.T1F.T2B.Y1C.Y2D, Z7.T1F.T2B.Y1D.Y2A,
Z7.T1F.T2B.Y1D.Y2B, Z7.T1F.T2B.Y1D.Y2C, Z7.T1F.T2B.Y1D.Y2D,
Z7.T1F.T2B.Y1E.Y2A, Z7.T1F.T2B.Y1E.Y2B, Z7.T1F.T2B.Y1E.Y2C,
Z7.T1F.T2B.Y1E.Y2D, Z7.T1F.T2C.Y1A.Y2A, Z7.T1F.T2C.Y1A.Y2B,
Z7.T1F.T2C.Y1A.Y2C, Z7.T1F.T2C.Y1A.Y2D, Z7.T1F.T2C.Y1B.Y2A,
Z7.T1F.T2C.Y1B.Y2B, Z7.T1F.T2C.Y1B.Y2C, Z7.T1F.T2C.Y1B.Y2D,
Z7.T1F.T2C.Y1C.Y2A, Z7.T1F.T2C.Y1C.Y2B, Z7.T1F.T2C.Y1C.Y2C,
Z7.T1F.T2C.Y1C.Y2D, Z7.T1F.T2C.Y1D.Y2A, Z7.T1F.T2C.Y1D.Y2B,
Z7.T1F.T2C.Y1D.Y2C, Z7.T1F.T2C.Y1D.Y2D, Z7.T1F.T2C.Y1E.Y2A,
Z7.T1F.T2C.Y1E.Y2B, Z7.T1F.T2C.Y1E.Y2C, Z7.T1F.T2C.Y1E.Y2D,
Z7.T1G.T2A.Y1A.Y2A, Z7.T1G.T2A.Y1A.Y2B, Z7.T1G.T2A.Y1A.Y2C,
Z7.T1G.T2A.Y1A.Y2D, Z7.T1G.T2A.Y1B.Y2A, Z7.T1G.T2A.Y1B.Y2B,
Z7.T1G.T2A.Y1B.Y2C, Z7.T1G.T2A.Y1B.Y2D, Z7.T1G.T2A.Y1C.Y2A,
Z7.T1G.T2A.Y1C.Y2B, Z7.T1G.T2A.Y1C.Y2C, Z7.T1G.T2A.Y1C.Y2D,
Z7.T1G.T2A.Y1D.Y2A, Z7.T1G.T2A.Y1D.Y2B, Z7.T1G.T2A.Y1D.Y2C,
Z7.T1G.T2A.Y1D.Y2D, Z7.T1G.T2A.Y1E.Y2A, Z7.T1G.T2A.Y1E.Y2B,
Z7.T1G.T2A.Y1E.Y2C, Z7.T1G.T2A.Y1E.Y2D, Z7.T1G.T2B.Y1A.Y2A,
Z7.T1G.T2B.Y1A.Y2B, Z7.T1G.T2B.Y1A.Y2C, Z7.T1G.T2B.Y1A.Y2D,
Z7.T1G.T2B.Y1B.Y2A, Z7.T1G.T2B.Y1B.Y2B, Z7.T1G.T2B.Y1B.Y2C,
Z7.T1G.T2B.Y1B.Y2D, Z7.T1G.T2B.Y1C.Y2A, Z7.T1G.T2B.Y1C.Y2B,
Z7.T1G.T2B.Y1C.Y2C, Z7.T1G.T2B.Y1C.Y2D, Z7.T1G.T2B.Y1D.Y2A,
Z7.T1G.T2B.Y1D.Y2B, Z7.T1G.T2B.Y1D.Y2C, Z7.T1G.T2B.Y1D.Y2D,
Z7.T1G.T2B.Y1E.Y2A, Z7.T1G.T2B.Y1E.Y2B, Z7.T1G.T2B.Y1E.Y2C,
Z7.T1G.T2B.Y1E.Y2D, Z7.T1G.T2C.Y1A.Y2A, Z7.T1G.T2C.Y1A.Y2B,
Z7.T1G.T2C.Y1A.Y2C, Z7.T1G.T2C.Y1A.Y2D, Z7.T1G.T2C.Y1B.Y2A,
Z7.T1G.T2C.Y1B.Y2B, Z7.T1G.T2C.Y1B.Y2C, Z7.T1G.T2C.Y1B.Y2D,
Z7.T1G.T2C.Y1C.Y2A, Z7.T1G.T2C.Y1C.Y2B, Z7.T1G.T2C.Y1C.Y2C,
Z7.T1G.T2C.Y1C.Y2D, Z7.T1G.T2C.Y1D.Y2A, Z7.T1G.T2C.Y1D.Y2B,
Z7.T1G.T2C.Y1D.Y2C, Z7.T1G.T2C.Y1D.Y2D, Z7.T1G.T2C.Y1E.Y2A,
Z7.T1G.T2C.Y1E.Y2B, Z7.T1G.T2C.Y1E.Y2C, Z7.T1G.T2C.Y1E.Y2D,

In still another embodiment, selected compounds of Formula I are named below in tabular format (Table 12) as compounds of general Formula V (below):

Formula V

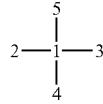

where 1, 2, 3, 4 and 5 are defined in Tables 7-11, below. Each compound is designated in tabular form by combining the "code" representing each structural moiety using the following syntax: 1.2.3.4.5. Thus, for example, 1a.2a.3a.4a.5a represents the following structure:

TABLE 7

"1" Structures

| Code | "1" Structure |
|---|---|
| 1a | 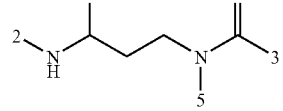 |

TABLE 7-continued

"1" Structures

| Code | "1" Structure |
|---|---|
| 1b | 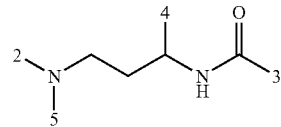 |
| 1c | 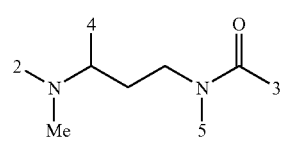 |

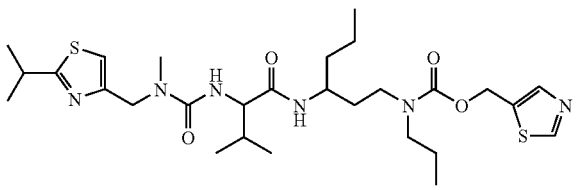

TABLE 7-continued

"1" Structures

| Code | "1" Structure |
|------|---------------|
| 1d | 2-NH-CH(4)-CH2-CH2-N(5)H-S(=O)2-3 |
| 1e | 2-N(5)-CH2-CH2-CH(4)-N H-S(=O)2-3 |
| 1f | 2-N(5)-CH(Me)-CH2-CH(4)-N H-S(=O)2-3 |
| 1g | 2-N(cyclopropyl)-CH(4)-CH2-CH2-N(5)-C(=O)-3 |
| 1h | 2-N(Me)-CH(4)-CH2-CH2-N(5)-S(=O)2-3 |
| 1i | 2-N(5)-CH2-CH2-CH(4)-N(cyclopropyl)-C(=O)-3 |

TABLE 8

"2" Structures

| Code | "2" Structure |
|------|---------------|
| 2a | isopropyl-thiazole-CH2-N(CH3)-C(=O)-NH-CH(iPr)-C(=O)- |
| 2b | isopropyl-thiazole-CH2-N(CH3)-C(=O)-NH-CH(iPr)-C(=O)- |
| 2c | pyridin-2-yl-CH2-N(CH3)-C(=O)-NH-CH(iPr)-C(=O)- |
| 2d | pyrazin-2-yl-CH2-N(CH3)-C(=O)-NH-CH(iPr)-C(=O)- |
| 2e | isopropyl-thiazol-4-yl-CH2-N(CH3)-C(=O)-NH-CH(CH(OH)CH3)-C(=O)- |
| 2f | isopropyl-thiazol-5-yl-CH2-N(CH3)-C(=O)-NH-CH(CH(OH)CH3)-C(=O)- |
| 2g | isopropyl-thiazol-4-yl-CH2-N(CH3)-C(=O)-NH-CH(CH2CH2-imidazol-1-yl)-C(=O)- |
| 2h | isopropyl-thiazol-4-yl-CH2-N(CH3)-C(=O)-NH-CH(CH2CH2-(4,4-difluoropiperidin-1-yl))-C(=O)- |

TABLE 8-continued

"2" Structures

| Code | "2" Structure |
|---|---|
| 2i | |
| 2j | |
| 2k | |
| 2l | |
| 2m | |
| 2n | |
| 2o | |
| 2p | |
| 2q | |
| 2r | |
| 2s | |
| 2t | |

TABLE 8-continued

"2" Structures

| Code | "2" Structure |
|------|---------------|
| 2u | (structure: isopropyl-thiazole-CH2-N(Me)-C(O)-NH-CH(CH2CH2NHAc)-C(O)-) |
| 2v | (structure: isopropyl-thiazole-CH2-O-C(O)-N(Me)-CH(iPr)-C(O)-) |
| 2w | (structure: isopropyl-thiazole-CH2-N(Me)-C(O)-NH-CH(CH2C(O)NH2)-C(O)-) |
| 2x | (structure: isopropyl-thiazole-CH2-N(Me)-C(O)-NH-CH(CH2-C(O)-morpholinyl)-C(O)-) |
| 2y | (structure: isopropyl-thiazole-CH2-N(Me)-C(O)-NH-CH(CH2CH2NH-2-pyridyl)-C(O)-) |
| 2z | (structure: tetrahydrofuran-3-yl-O-C(O)-) |

TABLE 9

"3" Structures

| Code | "3" Structure |
|------|---------------|
| 3a | —O—CH2-(5-thiazolyl) |
| 3b | —O—CH2-(3-pyridyl) |
| 3c | —NH—CH2-(5-thiazolyl) |
| 3d | —NH—CH2-(3-pyridyl) |
| 3e | —N(CH3)—CH2-(5-thiazolyl) |
| 3f | —N(CH3)—CH2-(3-pyridyl) |
| 3g | —N(CH3)-(5-thiazolyl) |
| 3h | —N(CH3)-(3-pyridyl) |

TABLE 10

"4" Structures

| Code | "4" Structure |
|------|---------------|
| 4a | n-propyl |
| 4b | i-butyl |
| 4c | —CH$_2$-cyclohexyl |
| 4d | —CH$_2$-phenyl |
| 4e | —CH$_2$-(4-methoxyphenyl) |
| 4f | —CH$_2$-(3-fluorophenyl) |
| 4g | —CH$_2$-(4-pyridyl) |
| 4h | —CH$_2$-(3-pyridyl) |
| 4i | —CH$_2$-(2-pyridyl) |
| 4j | —CH$_2$CH$_2$-(4-morpholinyl) |
| 4k | (structure: -CH2-(3-benzyloxyphenyl)) |
| 4l | (structure: -CH2-(4-benzyloxyphenyl)) |
| 4m | (structure: -CH2-(4-(3-pyridylmethoxy)phenyl)) |
| 4n | (structure: -CH2-(3-(2-pyridylmethoxy)phenyl)) |
| 4o | (structure: -CH2-(4-benzylphenyl)) |

TABLE 10-continued

"4" Structures

| Code | "4" Structure |
|---|---|
| 4p | 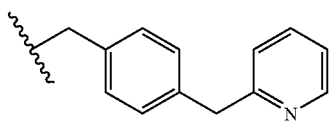 [SMILES: *Cc1ccc(Cc2ccccn2)cc1] |

TABLE 11

"5" Structures

| Code | "5" Structure |
|---|---|
| 5a | n-propyl |
| 5b | i-butyl |
| 5c | —CH$_2$-cyclohexyl |
| 5d | —CH$_2$-phenyl |
| 5e | —CH$_2$-(4-methoxyphenyl) |
| 5f | —CH$_2$-(3-fluorophenyl) |
| 5g | —CH$_2$-(4-pyridyl) |
| 5h | —CH$_2$-(3-pyridyl) |
| 5i | —CH$_2$-(2-pyridyl) |
| 5j | —CH$_2$CH$_2$-(4-morpholinyl) |
| 5k | 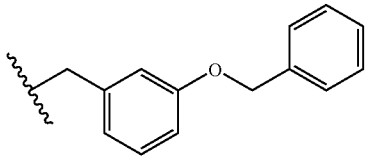 [SMILES: *Cc1cccc(OCc2ccccc2)c1] |

TABLE 11-continued

"5" Structures

| Code | "5" Structure |
|---|---|
| 5l | |
| 5m | |
| 5n | |
| 5o | |

TABLE 12

List of Compound Structures of Formula II 1a.2a.3a.4a.5a, 1a.2a.3a.4a.5b, 1a.2a.3a.4a.5d, 1a.2a.3a.4a.5f, 1a.2a.3a.4a.5h,
1a.2a.3a.4a.5i, 1a.2a.3a.4a.5n, 1a.2a.3a.4b.5a, 1a.2a.3a.4b.5b, 1a.2a.3a.4b.5d,
1a.2a.3a.4b.5f, 1a.2a.3a.4b.5h, 1a.2a.3a.4b.5i, 1a.2a.3a.4b.5n, 1a.2a.3a.4d.5a,
1a.2a.3a.4d.5b, 1a.2a.3a.4d.5d, 1a.2a.3a.4d.5f, 1a.2a.3a.4d.5h, 1a.2a.3a.4d.5i,
1a.2a.3a.4d.5n, 1a.2a.3a.4f.5a, 1a.2a.3a.4f.5b, 1a.2a.3a.4f.5d, 1a.2a.3a.4f.5f,
1a.2a.3a.4f.5h, 1a.2a.3a.4f.5i, 1a.2a.3a.4f.5n, 1a.2a.3a.4i.5a, 1a.2a.3a.4i.5b,
1a.2a.3a.4i.5d, 1a.2a.3a.4i.5f, 1a.2a.3a.4i.5h, 1a.2a.3a.4i.5i, 1a.2a.3a.4i.5n,
1a.2a.3a.4n.5a, 1a.2a.3a.4n.5b, 1a.2a.3a.4n.5d, 1a.2a.3a.4n.5f, 1a.2a.3a.4n.5h,
1a.2a.3a.4n.5i, 1a.2a.3a.4n.5n, 1a.2a.3a.4p.5a, 1a.2a.3a.4p.5b, 1a.2a.3a.4p.5d,
1a.2a.3a.4p.5f, 1a.2a.3a.4p.5h, 1a.2a.3a.4p.5i, 1a.2a.3a.4p.5n, 1a.2a.3c.4a.5a,
1a.2a.3c.4a.5b, 1a.2a.3c.4a.5d, 1a.2a.3c.4a.5f, 1a.2a.3c.4a.5h, 1a.2a.3c.4a.5i,
1a.2a.3c.4a.5n, 1a.2a.3c.4b.5a, 1a.2a.3c.4b.5b, 1a.2a.3c.4b.5d, 1a.2a.3c.4b.5f,
1a.2a.3c.4b.5h, 1a.2a.3c.4b.5i, 1a.2a.3c.4b.5n, 1a.2a.3c.4d.5a, 1a.2a.3c.4d.5b,
1a.2a.3c.4d.5d, 1a.2a.3c.4d.5f, 1a.2a.3c.4d.5h, 1a.2a.3c.4d.5i, 1a.2a.3c.4d.5n,
1a.2a.3c.4f.5a, 1a.2a.3c.4f.5b, 1a.2a.3c.4f.5d, 1a.2a.3c.4f.5f, 1a.2a.3c.4f.5h,
1a.2a.3c.4f.5i, 1a.2a.3c.4f.5n, 1a.2a.3c.4i.5a, 1a.2a.3c.4i.5b, 1a.2a.3c.4i.5d,
1a.2a.3c.4i.5f, 1a.2a.3c.4i.5h, 1a.2a.3c.4i.5i, 1a.2a.3c.4i.5n, 1a.2a.3c.4n.5a,
1a.2a.3c.4n.5b, 1a.2a.3c.4n.5d, 1a.2a.3c.4n.5f, 1a.2a.3c.4n.5h, 1a.2a.3c.4n.5i,
1a.2a.3c.4n.5n, 1a.2a.3c.4p.5a, 1a.2a.3c.4p.5b, 1a.2a.3c.4p.5d, 1a.2a.3c.4p.5f,
1a.2a.3c.4p.5h, 1a.2a.3c.4p.5i, 1a.2a.3c.4p.5n, 1a.2a.3e.4a.5a, 1a.2a.3e.4a.5b,
1a.2a.3e.4a.5d, 1a.2a.3e.4a.5f, 1a.2a.3e.4a.5h, 1a.2a.3e.4a.5i, 1a.2a.3e.4a.5n,
1a.2a.3e.4b.5a, 1a.2a.3e.4b.5b, 1a.2a.3e.4b.5d, 1a.2a.3e.4b.5f, 1a.2a.3e.4b.5h,
1a.2a.3e.4b.5i, 1a.2a.3e.4b.5n, 1a.2a.3e.4d.5a, 1a.2a.3e.4d.5b, 1a.2a.3e.4d.5d,
1a.2a.3e.4d.5f, 1a.2a.3e.4d.5h, 1a.2a.3e.4d.5i, 1a.2a.3e.4d.5n, 1a.2a.3e.4f.5a,
1a.2a.3e.4f.5b, 1a.2a.3e.4f.5d, 1a.2a.3e.4f.5f, 1a.2a.3e.4f.5h, 1a.2a.3e.4f.5i,
1a.2a.3e.4f.5n, 1a.2a.3e.4i.5a, 1a.2a.3e.4i.5b, 1a.2a.3e.4i.5d, 1a.2a.3e.4i.5f,
1a.2a.3e.4i.5h, 1a.2a.3e.4i.5i, 1a.2a.3e.4i.5n, 1a.2a.3e.4n.5a, 1a.2a.3e.4n.5b,
1a.2a.3e.4n.5d, 1a.2a.3e.4n.5f, 1a.2a.3e.4n.5h, 1a.2a.3e.4n.5i, 1a.2a.3e.4n.5n,
1a.2a.3e.4p.5a, 1a.2a.3e.4p.5b, 1a.2a.3e.4p.5d, 1a.2a.3e.4p.5f, 1a.2a.3e.4p.5h,
1a.2a.3e.4p.5i, 1a.2a.3e.4p.5n, 1a.2a.3g.4a.5a, 1a.2a.3g.4a.5b, 1a.2a.3g.4a.5d,
1a.2a.3g.4a.5f, 1a.2a.3g.4a.5h, 1a.2a.3g.4a.5i, 1a.2a.3g.4a.5n, 1a.2a.3g.4b.5a,
1a.2a.3g.4b.5b, 1a.2a.3g.4b.5d, 1a.2a.3g.4b.5f, 1a.2a.3g.4b.5h, 1a.2a.3g.4b.5i,
1a.2a.3g.4b.5n, 1a.2a.3g.4d.5a, 1a.2a.3g.4d.5b, 1a.2a.3g.4d.5d, 1a.2a.3g.4d.5f,
1a.2a.3g.4d.5h, 1a.2a.3g.4d.5i, 1a.2a.3g.4d.5n, 1a.2a.3g.4f.5a, 1a.2a.3g.4f.5b,
1a.2a.3g.4f.5d, 1a.2a.3g.4f.5f, 1a.2a.3g.4f.5h, 1a.2a.3g.4f.5i, 1a.2a.3g.4f.5n, TABLE 12-continued List of Compound Structures of Formula II 1a.2a.3g.4i.5a, 1a.2a.3g.4i.5b, 1a.2a.3g.4i.5d, 1a.2a.3g.4i.5f, 1a.2a.3g.4i.5h,
1a.2a.3g.4i.5i, 1a.2a.3g.4i.5n, 1a.2a.3g.4n.5a, 1a.2a.3g.4n.5b, 1a.2a.3g.4n.5d,
1a.2a.3g.4n.5f, 1a.2a.3g.4n.5h, 1a.2a.3g.4n.5i, 1a.2a.3g.4n.5n, 1a.2a.3g.4p.5a,
1a.2a.3g.4p.5b, 1a.2a.3g.4p.5d, 1a.2a.3g.4p.5f, 1a.2a.3g.4p.5h, 1a.2a.3g.4p.5i,
1a.2a.3g.4p.5n, 1a.2b.3a.4a.5a, 1a.2b.3a.4a.5b, 1a.2b.3a.4a.5d, 1a.2b.3a.4a.5f,
1a.2b.3a.4a.5h, 1a.2b.3a.4a.5i, 1a.2b.3a.4a.5n, 1a.2b.3a.4b.5a, 1a.2b.3a.4b.5b,
1a.2b.3a.4b.5d, 1a.2b.3a.4b.5f, 1a.2b.3a.4b.5h, 1a.2b.3a.4b.5i, 1a.2b.3a.4b.5n,
1a.2b.3a.4d.5a, 1a.2b.3a.4d.5b, 1a.2b.3a.4d.5d, 1a.2b.3a.4d.5f, 1a.2b.3a.4d.5h,
1a.2b.3a.4d.5i, 1a.2b.3a.4d.5n, 1a.2b.3a.4f.5a, 1a.2b.3a.4f.5b, 1a.2b.3a.4f.5d,
1a.2b.3a.4f.5f, 1a.2b.3a.4f.5h, 1a.2b.3a.4f.5i, 1a.2b.3a.4f.5n, 1a.2b.3a.4i.5a,
1a.2b.3a.4i.5b, 1a.2b.3a.4i.5d, 1a.2b.3a.4i.5f, 1a.2b.3a.4i.5h, 1a.2b.3a.4i.5i,
1a.2b.3a.4i.5n, 1a.2b.3a.4n.5a, 1a.2b.3a.4n.5b, 1a.2b.3a.4n.5d, 1a.2b.3a.4n.5f,
1a.2b.3a.4n.5h, 1a.2b.3a.4n.5i, 1a.2b.3a.4n.5n, 1a.2b.3a.4p.5a, 1a.2b.3a.4p.5b,
1a.2b.3a.4p.5d, 1a.2b.3a.4p.5f, 1a.2b.3a.4p.5h, 1a.2b.3a.4p.5i, 1a.2b.3a.4p.5n,
1a.2b.3c.4a.5a, 1a.2b.3c.4a.5b, 1a.2b.3c.4a.5d, 1a.2b.3c.4a.5f, 1a.2b.3c.4a.5h,
1a.2b.3c.4a.5i, 1a.2b.3c.4a.5n, 1a.2b.3c.4b.5a, 1a.2b.3c.4b.5b, 1a.2b.3c.4b.5d,
1a.2b.3c.4b.5f, 1a.2b.3c.4b.5h, 1a.2b.3c.4b.5i, 1a.2b.3c.4b.5n, 1a.2b.3c.4d.5a,
1a.2b.3c.4d.5b, 1a.2b.3c.4d.5d, 1a.2b.3c.4d.5f, 1a.2b.3c.4d.5h, 1a.2b.3c.4d.5i,
1a.2b.3c.4d.5n, 1a.2b.3c.4f.5a, 1a.2b.3c.4f.5b, 1a.2b.3c.4f.5d, 1a.2b.3c.4f.5f,
1a.2b.3c.4f.5h, 1a.2b.3c.4f.5i, 1a.2b.3c.4f.5n, 1a.2b.3c.4i.5a, 1a.2b.3c.4i.5b,
1a.2b.3c.4i.5d, 1a.2b.3c.4i.5f, 1a.2b.3c.4i.5h, 1a.2b.3c.4i.5i, 1a.2b.3c.4i.5n,
1a.2b.3c.4n.5a, 1a.2b.3c.4n.5b, 1a.2b.3c.4n.5d, 1a.2b.3c.4n.5f, 1a.2b.3c.4n.5h,
1a.2b.3c.4n.5i, 1a.2b.3c.4n.5n, 1a.2b.3c.4p.5a, 1a.2b.3c.4p.5b, 1a.2b.3c.4p.5d,
1a.2b.3c.4p.5f, 1a.2b.3c.4p.5h, 1a.2b.3c.4p.5i, 1a.2b.3c.4p.5n, 1a.2b.3e.4a.5a,
1a.2b.3e.4a.5b, 1a.2b.3e.4a.5d, 1a.2b.3e.4a.5f, 1a.2b.3e.4a.5h, 1a.2b.3e.4a.5i,
1a.2b.3e.4a.5n, 1a.2b.3e.4b.5a, 1a.2b.3e.4b.5b, 1a.2b.3e.4b.5d, 1a.2b.3e.4b.5f,
1a.2b.3e.4b.5h, 1a.2b.3e.4b.5i, 1a.2b.3e.4b.5n, 1a.2b.3e.4d.5a, 1a.2b.3e.4d.5b,
1a.2b.3e.4d.5d, 1a.2b.3e.4d.5f, 1a.2b.3e.4d.5h, 1a.2b.3e.4d.5i, 1a.2b.3e.4d.5n,
1a.2b.3e.4f.5a, 1a.2b.3e.4f.5b, 1a.2b.3e.4f.5d, 1a.2b.3e.4f.5f, 1a.2b.3e.4f.5h,
1a.2b.3e.4f.5i, 1a.2b.3e.4f.5n, 1a.2b.3e.4i.5a, 1a.2b.3e.4i.5b, 1a.2b.3e.4i.5d,
1a.2b.3e.4i.5f, 1a.2b.3e.4i.5h, 1a.2b.3e.4i.5i, 1a.2b.3e.4i.5n, 1a.2b.3e.4n.5a,
1a.2b.3e.4n.5b, 1a.2b.3e.4n.5d, 1a.2b.3e.4n.5f, 1a.2b.3e.4n.5h, 1a.2b.3e.4n.5i,
1a.2b.3e.4n.5n, 1a.2b.3e.4p.5a, 1a.2b.3e.4p.5b, 1a.2b.3e.4p.5d, 1a.2b.3e.4p.5f,
1a.2b.3e.4p.5h, 1a.2b.3e.4p.5i, 1a.2b.3e.4p.5n, 1a.2b.3g.4a.5a, 1a.2b.3g.4a.5b,
1a.2b.3g.4a.5d, 1a.2b.3g.4a.5f, 1a.2b.3g.4a.5h, 1a.2b.3g.4a.5i, 1a.2b.3g.4a.5n,
1a.2b.3g.4b.5a, 1a.2b.3g.4b.5b, 1a.2b.3g.4b.5d, 1a.2b.3g.4b.5f, 1a.2b.3g.4b.5h,
1a.2b.3g.4b.5i, 1a.2b.3g.4b.5n, 1a.2b.3g.4d.5a, 1a.2b.3g.4d.5b, 1a.2b.3g.4d.5d,
1a.2b.3g.4d.5f, 1a.2b.3g.4d.5h, 1a.2b.3g.4d.5i, 1a.2b.3g.4d.5n, 1a.2b.3g.4f.5a,
1a.2b.3g.4f.5b, 1a.2b.3g.4f.5d, 1a.2b.3g.4f.5f, 1a.2b.3g.4f.5h, 1a.2b.3g.4f.5i,
1a.2b.3g.4f.5n, 1a.2b.3g.4i.5a, 1a.2b.3g.4i.5b, 1a.2b.3g.4i.5d, 1a.2b.3g.4i.5f,
1a.2b.3g.4i.5h, 1a.2b.3g.4i.5i, 1a.2b.3g.4i.5n, 1a.2b.3g.4n.5a, 1a.2b.3g.4n.5b,
1a.2b.3g.4n.5d, 1a.2b.3g.4n.5f, 1a.2b.3g.4n.5h, 1a.2b.3g.4n.5i, 1a.2b.3g.4n.5n,
1a.2b.3g.4p.5a, 1a.2b.3g.4p.5b, 1a.2b.3g.4p.5d, 1a.2b.3g.4p.5f, 1a.2b.3g.4p.5h,
1a.2b.3g.4p.5i, 1a.2b.3g.4p.5n, 1a.2e.3a.4a.5a, 1a.2e.3a.4a.5b, 1a.2e.3a.4a.5d,
1a.2e.3a.4a.5f, 1a.2e.3a.4a.5h, 1a.2e.3a.4a.5i, 1a.2e.3a.4a.5n, 1a.2e.3a.4b.5a,
1a.2e.3a.4b.5b, 1a.2e.3a.4b.5d, 1a.2e.3a.4b.5f, 1a.2e.3a.4b.5h, 1a.2e.3a.4b.5i,
1a.2e.3a.4b.5n, 1a.2e.3a.4d.5a, 1a.2e.3a.4d.5b, 1a.2e.3a.4d.5d, 1a.2e.3a.4d.5f,
1a.2e.3a.4d.5h, 1a.2e.3a.4d.5i, 1a.2e.3a.4d.5n, 1a.2e.3a.4f.5a, 1a.2e.3a.4f.5b,
1a.2e.3a.4f.5d, 1a.2e.3a.4f.5f, 1a.2e.3a.4f.5h, 1a.2e.3a.4f.5i, 1a.2e.3a.4f.5n,
1a.2e.3a.4i.5a, 1a.2e.3a.4i.5b, 1a.2e.3a.4i.5d, 1a.2e.3a.4i.5f, 1a.2e.3a.4i.5h,
1a.2e.3a.4i.5i, 1a.2e.3a.4i.5n, 1a.2e.3a.4n.5a, 1a.2e.3a.4n.5b, 1a.2e.3a.4n.5d,
1a.2e.3a.4n.5f, 1a.2e.3a.4n.5h, 1a.2e.3a.4n.5i, 1a.2e.3a.4n.5n, 1a.2e.3a.4p.5a,
1a.2e.3a.4p.5b, 1a.2e.3a.4p.5d, 1a.2e.3a.4p.5f, 1a.2e.3a.4p.5h, 1a.2e.3a.4p.5i,
1a.2e.3a.4p.5n, 1a.2e.3c.4a.5a, 1a.2e.3c.4a.5b, 1a.2e.3c.4a.5d, 1a.2e.3c.4a.5f,
1a.2e.3c.4a.5h, 1a.2e.3c.4a.5i, 1a.2e.3c.4a.5n, 1a.2e.3c.4b.5a, 1a.2e.3c.4b.5b,
1a.2e.3c.4b.5d, 1a.2e.3c.4b.5f, 1a.2e.3c.4b.5h, 1a.2e.3c.4b.5i, 1a.2e.3c.4b.5n,
1a.2e.3c.4d.5a, 1a.2e.3c.4d.5b, 1a.2e.3c.4d.5d, 1a.2e.3c.4d.5f, 1a.2e.3c.4d.5h,
1a.2e.3c.4d.5i, 1a.2e.3c.4d.5n, 1a.2e.3c.4f.5a, 1a.2e.3c.4f.5b, 1a.2e.3c.4f.5d,
1a.2e.3c.4f.5f, 1a.2e.3c.4f.5h, 1a.2e.3c.4f.5i, 1a.2e.3c.4f.5n, 1a.2e.3c.4i.5a,
1a.2e.3c.4i.5b, 1a.2e.3c.4i.5d, 1a.2e.3c.4i.5f, 1a.2e.3c.4i.5h, 1a.2e.3c.4i.5i,
1a.2e.3c.4i.5n, 1a.2e.3c.4n.5a, 1a.2e.3c.4n.5b, 1a.2e.3c.4n.5d, 1a.2e.3c.4n.5f,
1a.2e.3c.4n.5h, 1a.2e.3c.4n.5i, 1a.2e.3c.4n.5n, 1a.2e.3c.4p.5a, 1a.2e.3c.4p.5b,
1a.2e.3c.4p.5d, 1a.2e.3c.4p.5f, 1a.2e.3c.4p.5h, 1a.2e.3c.4p.5i, 1a.2e.3c.4p.5n,
1a.2e.3e.4a.5a, 1a.2e.3e.4a.5b, 1a.2e.3e.4a.5d, 1a.2e.3e.4a.5f, 1a.2e.3e.4a.5h,
1a.2e.3e.4a.5i, 1a.2e.3e.4a.5n, 1a.2e.3e.4b.5a, 1a.2e.3e.4b.5b, 1a.2e.3e.4b.5d,
1a.2e.3e.4b.5f, 1a.2e.3e.4b.5h, 1a.2e.3e.4b.5i, 1a.2e.3e.4b.5n, 1a.2e.3e.4d.5a,
1a.2e.3e.4d.5b, 1a.2e.3e.4d.5d, 1a.2e.3e.4d.5f, 1a.2e.3e.4d.5h, 1a.2e.3e.4d.5i,
1a.2e.3e.4d.5n, 1a.2e.3e.4f.5a, 1a.2e.3e.4f.5b, 1a.2e.3e.4f.5d, 1a.2e.3e.4f.5f,
1a.2e.3e.4f.5h, 1a.2e.3e.4f.5i, 1a.2e.3e.4f.5n, 1a.2e.3e.4i.5a, 1a.2e.3e.4i.5b,
1a.2e.3e.4i.5d, 1a.2e.3e.4i.5f, 1a.2e.3e.4i.5h, 1a.2e.3e.4i.5i, 1a.2e.3e.4i.5n,
1a.2e.3e.4n.5a, 1a.2e.3e.4n.5b, 1a.2e.3e.4n.5d, 1a.2e.3e.4n.5f, 1a.2e.3e.4n.5h,
1a.2e.3e.4n.5i, 1a.2e.3e.4n.5n, 1a.2e.3e.4p.5a, 1a.2e.3e.4p.5b, 1a.2e.3e.4p.5d,
1a.2e.3e.4p.5f, 1a.2e.3e.4p.5h, 1a.2e.3e.4p.5i, 1a.2e.3e.4p.5n, 1a.2e.3g.4a.5a,
1a.2e.3g.4a.5b, 1a.2e.3g.4a.5d, 1a.2e.3g.4a.5f, 1a.2e.3g.4a.5h, 1a.2e.3g.4a.5i,
1a.2e.3g.4a.5n, 1a.2e.3g.4b.5a, 1a.2e.3g.4b.5b, 1a.2e.3g.4b.5d, 1a.2e.3g.4b.5f,
1a.2e.3g.4b.5h, 1a.2e.3g.4b.5i, 1a.2e.3g.4b.5n, 1a.2e.3g.4d.5a, 1a.2e.3g.4d.5b,
1a.2e.3g.4d.5d, 1a.2e.3g.4d.5f, 1a.2e.3g.4d.5h, 1a.2e.3g.4d.5i, 1a.2e.3g.4d.5n,
1a.2e.3g.4f.5a, 1a.2e.3g.4f.5b, 1a.2e.3g.4f.5d, 1a.2e.3g.4f.5f, 1a.2e.3g.4f.5h, TABLE 12-continued List of Compound Structures of Formula II 1a.2e.3g.4f.5i, 1a.2e.3g.4f.5n, 1a.2e.3g.4i.5a, 1a.2e.3g.4i.5b, 1a.2e.3g.4i.5d,
1a.2e.3g.4i.5f, 1a.2e.3g.4i.5h, 1a.2e.3g.4i.5i, 1a.2e.3g.4i.5n, 1a.2e.3g.4n.5a,
1a.2e.3g.4n.5b, 1a.2e.3g.4n.5d, 1a.2e.3g.4n.5f, 1a.2e.3g.4n.5h, 1a.2e.3g.4n.5i,
1a.2e.3g.4n.5n, 1a.2e.3g.4p.5a, 1a.2e.3g.4p.5b, 1a.2e.3g.4p.5d, 1a.2e.3g.4p.5f,
1a.2e.3g.4p.5h, 1a.2e.3g.4p.5i, 1a.2e.3g.4p.5n, 1a.2f.3a.4a.5a, 1a.2f.3a.4a.5b,
1a.2f.3a.4a.5d, 1a.2f.3a.4a.5f, 1a.2f.3a.4a.5h, 1a.2f.3a.4a.5i, 1a.2f.3a.4a.5n,
1a.2f.3a.4b.5a, 1a.2f.3a.4b.5b, 1a.2f.3a.4b.5d, 1a.2f.3a.4b.5f, 1a.2f.3a.4b.5h,
1a.2f.3a.4b.5i, 1a.2f.3a.4b.5n, 1a.2f.3a.4d.5a, 1a.2f.3a.4d.5b, 1a.2f.3a.4d.5d,
1a.2f.3a.4d.5f, 1a.2f.3a.4d.5h, 1a.2f.3a.4d.5i, 1a.2f.3a.4d.5n, 1a.2f.3a.4f.5a,
1a.2f.3a.4f.5b, 1a.2f.3a.4f.5d, 1a.2f.3a.4f.5f, 1a.2f.3a.4f.5h, 1a.2f.3a.4f.5i,
1a.2f.3a.4f.5n, 1a.2f.3a.4i.5a, 1a.2f.3a.4i.5b, 1a.2f.3a.4i.5d, 1a.2f.3a.4i.5f,
1a.2f.3a.4i.5h, 1a.2f.3a.4i.5i, 1a.2f.3a.4i.5n, 1a.2f.3a.4n.5a, 1a.2f.3a.4n.5b,
1a.2f.3a.4n.5d, 1a.2f.3a.4n.5f, 1a.2f.3a.4n.5h, 1a.2f.3a.4n.5i, 1a.2f.3a.4n.5n,
1a.2f.3a.4p.5a, 1a.2f.3a.4p.5b, 1a.2f.3a.4p.5d, 1a.2f.3a.4p.5f, 1a.2f.3a.4p.5h,
1a.2f.3a.4p.5i, 1a.2f.3a.4p.5n, 1a.2f.3c.4a.5a, 1a.2f.3c.4a.5b, 1a.2f.3c.4a.5d,
1a.2f.3c.4a.5f, 1a.2f.3c.4a.5h, 1a.2f.3c.4a.5i, 1a.2f.3c.4a.5n, 1a.2f.3c.4b.5a,
1a.2f.3c.4b.5b, 1a.2f.3c.4b.5d, 1a.2f.3c.4b.5f, 1a.2f.3c.4b.5h, 1a.2f.3c.4b.5i,
1a.2f.3c.4b.5n, 1a.2f.3c.4d.5a, 1a.2f.3c.4d.5b, 1a.2f.3c.4d.5d, 1a.2f.3c.4d.5f,
1a.2f.3c.4d.5h, 1a.2f.3c.4d.5i, 1a.2f.3c.4d.5n, 1a.2f.3c.4f.5a, 1a.2f.3c.4f.5b,
1a.2f.3c.4f.5d, 1a.2f.3c.4f.5f, 1a.2f.3c.4f.5h, 1a.2f.3c.4f.5i, 1a.2f.3c.4f.5n,
1a.2f.3c.4i.5a, 1a.2f.3c.4i.5b, 1a.2f.3c.4i.5d, 1a.2f.3c.4i.5f, 1a.2f.3c.4i.5h,
1a.2f.3c.4i.5i, 1a.2f.3c.4i.5n, 1a.2f.3c.4n.5a, 1a.2f.3c.4n.5b, 1a.2f.3c.4n.5d,
1a.2f.3c.4n.5f, 1a.2f.3c.4n.5h, 1a.2f.3c.4n.5i, 1a.2f.3c.4n.5n, 1a.2f.3c.4p.5a,
1a.2f.3c.4p.5b, 1a.2f.3c.4p.5d, 1a.2f.3c.4p.5f, 1a.2f.3c.4p.5h, 1a.2f.3c.4p.5i,
1a.2f.3c.4p.5n, 1a.2f.3e.4a.5a, 1a.2f.3e.4a.5b, 1a.2f.3e.4a.5d, 1a.2f.3e.4a.5f,
1a.2f.3e.4a.5h, 1a.2f.3e.4a.5i, 1a.2f.3e.4a.5n, 1a.2f.3e.4b.5a, 1a.2f.3e.4b.5b,
1a.2f.3e.4b.5d, 1a.2f.3e.4b.5f, 1a.2f.3e.4b.5h, 1a.2f.3e.4b.5i, 1a.2f.3e.4b.5n,
1a.2f.3e.4d.5a, 1a.2f.3e.4d.5b, 1a.2f.3e.4d.5d, 1a.2f.3e.4d.5f, 1a.2f.3e.4d.5h,
1a.2f.3e.4d.5i, 1a.2f.3e.4d.5n, 1a.2f.3e.4f.5a, 1a.2f.3e.4f.5b, 1a.2f.3e.4f.5d,
1a.2f.3e.4f.5f, 1a.2f.3e.4f.5h, 1a.2f.3e.4f.5i, 1a.2f.3e.4f.5n, 1a.2f.3e.4i.5a,
1a.2f.3e.4i.5b, 1a.2f.3e.4i.5d, 1a.2f.3e.4i.5f, 1a.2f.3e.4i.5h, 1a.2f.3e.4i.5i,
1a.2f.3e.4i.5n, 1a.2f.3e.4n.5a, 1a.2f.3e.4n.5b, 1a.2f.3e.4n.5d, 1a.2f.3e.4n.5f,
1a.2f.3e.4n.5h, 1a.2f.3e.4n.5i, 1a.2f.3e.4n.5n, 1a.2f.3e.4p.5a, 1a.2f.3e.4p.5b,
1a.2f.3e.4p.5d, 1a.2f.3e.4p.5f, 1a.2f.3e.4p.5h, 1a.2f.3e.4p.5i, 1a.2f.3e.4p.5n,
1a.2f.3g.4a.5a, 1a.2f.3g.4a.5b, 1a.2f.3g.4a.5d, 1a.2f.3g.4a.5f, 1a.2f.3g.4a.5h,
1a.2f.3g.4a.5i, 1a.2f.3g.4a.5n, 1a.2f.3g.4b.5a, 1a.2f.3g.4b.5b, 1a.2f.3g.4b.5d,
1a.2f.3g.4b.5f, 1a.2f.3g.4b.5h, 1a.2f.3g.4b.5i, 1a.2f.3g.4b.5n, 1a.2f.3g.4d.5a,
1a.2f.3g.4d.5b, 1a.2f.3g.4d.5d, 1a.2f.3g.4d.5f, 1a.2f.3g.4d.5h, 1a.2f.3g.4d.5i,
1a.2f.3g.4d.5n, 1a.2f.3g.4f.5a, 1a.2f.3g.4f.5b, 1a.2f.3g.4f.5d, 1a.2f.3g.4f.5f,
1a.2f.3g.4f.5h, 1a.2f.3g.4f.5i, 1a.2f.3g.4f.5n, 1a.2f.3g.4i.5a, 1a.2f.3g.4i.5b,
1a.2f.3g.4i.5d, 1a.2f.3g.4i.5f, 1a.2f.3g.4i.5h, 1a.2f.3g.4i.5i, 1a.2f.3g.4i.5n,
1a.2f.3g.4n.5a, 1a.2f.3g.4n.5b, 1a.2f.3g.4n.5d, 1a.2f.3g.4n.5f, 1a.2f.3g.4n.5h,
1a.2f.3g.4n.5i, 1a.2f.3g.4n.5n, 1a.2f.3g.4p.5a, 1a.2f.3g.4p.5b, 1a.2f.3g.4p.5d,
1a.2f.3g.4p.5f, 1a.2f.3g.4p.5h, 1a.2f.3g.4p.5i, 1a.2f.3g.4p.5n, 1a.2g.3a.4a.5a,
1a.2g.3a.4a.5b, 1a.2g.3a.4a.5d, 1a.2g.3a.4a.5f, 1a.2g.3a.4a.5h, 1a.2g.3a.4a.5i,
1a.2g.3a.4a.5n, 1a.2g.3a.4b.5a, 1a.2g.3a.4b.5b, 1a.2g.3a.4b.5d, 1a.2g.3a.4b.5f,
1a.2g.3a.4b.5h, 1a.2g.3a.4b.5i, 1a.2g.3a.4b.5n, 1a.2g.3a.4d.5a, 1a.2g.3a.4d.5b,
1a.2g.3a.4d.5d, 1a.2g.3a.4d.5f, 1a.2g.3a.4d.5h, 1a.2g.3a.4d.5i, 1a.2g.3a.4d.5n,
1a.2g.3a.4f.5a, 1a.2g.3a.4f.5b, 1a.2g.3a.4f.5d, 1a.2g.3a.4f.5f, 1a.2g.3a.4f.5h,
1a.2g.3a.4f.5i, 1a.2g.3a.4f.5n, 1a.2g.3a.4i.5a, 1a.2g.3a.4i.5b, 1a.2g.3a.4i.5d,
1a.2g.3a.4i.5f, 1a.2g.3a.4i.5h, 1a.2g.3a.4i.5i, 1a.2g.3a.4i.5n, 1a.2g.3a.4n.5a,
1a.2g.3a.4n.5b, 1a.2g.3a.4n.5d, 1a.2g.3a.4n.5f, 1a.2g.3a.4n.5h, 1a.2g.3a.4n.5i,
1a.2g.3a.4n.5n, 1a.2g.3a.4p.5a, 1a.2g.3a.4p.5b, 1a.2g.3a.4p.5d, 1a.2g.3a.4p.5f,
1a.2g.3a.4p.5h, 1a.2g.3a.4p.5i, 1a.2g.3a.4p.5n, 1a.2g.3c.4a.5a, 1a.2g.3c.4a.5b,
1a.2g.3c.4a.5d, 1a.2g.3c.4a.5f, 1a.2g.3c.4a.5h, 1a.2g.3c.4a.5i, 1a.2g.3c.4a.5n,
1a.2g.3c.4b.5a, 1a.2g.3c.4b.5b, 1a.2g.3c.4b.5d, 1a.2g.3c.4b.5f, 1a.2g.3c.4b.5h,
1a.2g.3c.4b.5i, 1a.2g.3c.4b.5n, 1a.2g.3c.4d.5a, 1a.2g.3c.4d.5b, 1a.2g.3c.4d.5d,
1a.2g.3c.4d.5f, 1a.2g.3c.4d.5h, 1a.2g.3c.4d.5i, 1a.2g.3c.4d.5n, 1a.2g.3c.4f.5a,
1a.2g.3c.4f.5b, 1a.2g.3c.4f.5d, 1a.2g.3c.4f.5f, 1a.2g.3c.4f.5h, 1a.2g.3c.4f.5i,
1a.2g.3c.4f.5n, 1a.2g.3c.4i.5a, 1a.2g.3c.4i.5b, 1a.2g.3c.4i.5d, 1a.2g.3c.4i.5f,
1a.2g.3c.4i.5h, 1a.2g.3c.4i.5i, 1a.2g.3c.4i.5n, 1a.2g.3c.4n.5a, 1a.2g.3c.4n.5b,
1a.2g.3c.4n.5d, 1a.2g.3c.4n.5f, 1a.2g.3c.4n.5h, 1a.2g.3c.4n.5i, 1a.2g.3c.4n.5n,
1a.2g.3c.4p.5a, 1a.2g.3c.4p.5b, 1a.2g.3c.4p.5d, 1a.2g.3c.4p.5f, 1a.2g.3c.4p.5h,
1a.2g.3c.4p.5i, 1a.2g.3c.4p.5n, 1a.2g.3e.4a.5a, 1a.2g.3e.4a.5b, 1a.2g.3e.4a.5d,
1a.2g.3e.4a.5f, 1a.2g.3e.4a.5h, 1a.2g.3e.4a.5i, 1a.2g.3e.4a.5n, 1a.2g.3e.4b.5a,
1a.2g.3e.4b.5b, 1a.2g.3e.4b.5d, 1a.2g.3e.4b.5f, 1a.2g.3e.4b.5h, 1a.2g.3e.4b.5i,
1a.2g.3e.4b.5n, 1a.2g.3e.4d.5a, 1a.2g.3e.4d.5b, 1a.2g.3e.4d.5d, 1a.2g.3e.4d.5f,
1a.2g.3e.4d.5h, 1a.2g.3e.4d.5i, 1a.2g.3e.4d.5n, 1a.2g.3e.4f.5a, 1a.2g.3e.4f.5b,
1a.2g.3e.4f.5d, 1a.2g.3e.4f.5f, 1a.2g.3e.4f.5h, 1a.2g.3e.4f.5i, 1a.2g.3e.4f.5n,
1a.2g.3e.4i.5a, 1a.2g.3e.4i.5b, 1a.2g.3e.4i.5d, 1a.2g.3e.4i.5f, 1a.2g.3e.4i.5h,
1a.2g.3e.4i.5i, 1a.2g.3e.4i.5n, 1a.2g.3e.4n.5a, 1a.2g.3e.4n.5b, 1a.2g.3e.4n.5d,
1a.2g.3e.4n.5f, 1a.2g.3e.4n.5h, 1a.2g.3e.4n.5i, 1a.2g.3e.4n.5n, 1a.2g.3e.4p.5a,
1a.2g.3e.4p.5b, 1a.2g.3e.4p.5d, 1a.2g.3e.4p.5f, 1a.2g.3e.4p.5h, 1a.2g.3e.4p.5i,
1a.2g.3e.4p.5n, 1a.2g.3g.4a.5a, 1a.2g.3g.4a.5b, 1a.2g.3g.4a.5d, 1a.2g.3g.4a.5f,
1a.2g.3g.4a.5h, 1a.2g.3g.4a.5i, 1a.2g.3g.4a.5n, 1a.2g.3g.4b.5a, 1a.2g.3g.4b.5b,
1a.2g.3g.4b.5d, 1a.2g.3g.4b.5f, 1a.2g.3g.4b.5h, 1a.2g.3g.4b.5i, 1a.2g.3g.4b.5n,
1a.2g.3g.4d.5a, 1a.2g.3g.4d.5b, 1a.2g.3g.4d.5d, 1a.2g.3g.4d.5f, 1a.2g.3g.4d.5h,
1a.2g.3g.4d.5i, 1a.2g.3g.4d.5n, 1a.2g.3g.4f.5a, 1a.2g.3g.4f.5b, 1a.2g.3g.4f.5d,

TABLE 12-continued

List of Compound Structures of Formula II 1a.2g.3g.4f.5f, 1a.2g.3g.4f.5h, 1a.2g.3g.4f.5i, 1a.2g.3g.4f.5n, 1a.2g.3g.4i.5a, 1a.2g.3g.4i.5b, 1a.2g.3g.4i.5d, 1a.2g.3g.4i.5f, 1a.2g.3g.4i.5h, 1a.2g.3g.4i.5i, 1a.2g.3g.4i.5n, 1a.2g.3g.4n.5a, 1a.2g.3g.4n.5b, 1a.2g.3g.4n.5d, 1a.2g.3g.4n.5f, 1a.2g.3g.4n.5h, 1a.2g.3g.4n.5i, 1a.2g.3g.4n.5n, 1a.2g.3g.4p.5a, 1a.2g.3g.4p.5b, 1a.2g.3g.4p.5d, 1a.2g.3g.4p.5f, 1a.2g.3g.4p.5h, 1a.2g.3g.4p.5i, 1a.2g.3g.4p.5n, 1a.2l.3a.4a.5a, 1a.2l.3a.4a.5b, 1a.2l.3a.4a.5d, 1a.2l.3a.4a.5f, 1a.2l.3a.4a.5h, 1a.2l.3a.4a.5i, 1a.2l.3a.4a.5n, 1a.2l.3a.4b.5a, 1a.2l.3a.4b.5b, 1a.2l.3a.4b.5d, 1a.2l.3a.4b.5f, 1a.2l.3a.4b.5h, 1a.2l.3a.4b.5i, 1a.2l.3a.4b.5n, 1a.2l.3a.4d.5a, 1a.2l.3a.4d.5b, 1a.2l.3a.4d.5d, 1a.2l.3a.4d.5f, 1a.2l.3a.4d.5h, 1a.2l.3a.4d.5i, 1a.2l.3a.4d.5n, 1a.2l.3a.4f.5a, 1a.2l.3a.4f.5b, 1a.2l.3a.4f.5d, 1a.2l.3a.4f.5f, 1a.2l.3a.4f.5h, 1a.2l.3a.4f.5i, 1a.2l.3a.4f.5n, 1a.2l.3a.4i.5a, 1a.2l.3a.4i.5b, 1a.2l.3a.4i.5d, 1a.2l.3a.4i.5f, 1a.2l.3a.4i.5h, 1a.2l.3a.4i.5i, 1a.2l.3a.4i.5n, 1a.2l.3a.4n.5a, 1a.2l.3a.4n.5b, 1a.2l.3a.4n.5d, 1a.2l.3a.4n.5f, 1a.2l.3a.4n.5h, 1a.2l.3a.4n.5i, 1a.2l.3a.4n.5n, 1a.2l.3a.4p.5a, 1a.2l.3a.4p.5b, 1a.2l.3a.4p.5d, 1a.2l.3a.4p.5f, 1a.2l.3a.4p.5h, 1a.2l.3a.4p.5i, 1a.2l.3a.4p.5n, 1a.2l.3c.4a.5a, 1a.2l.3c.4a.5b, 1a.2l.3c.4a.5d, 1a.2l.3c.4a.5f, 1a.2l.3c.4a.5h, 1a.2l.3c.4a.5i, 1a.2l.3c.4a.5n, 1a.2l.3c.4b.5a, 1a.2l.3c.4b.5b, 1a.2l.3c.4b.5d, 1a.2l.3c.4b.5f, 1a.2l.3c.4b.5h, 1a.2l.3c.4b.5i, 1a.2l.3c.4b.5n, 1a.2l.3c.4d.5a, 1a.2l.3c.4d.5b, 1a.2l.3c.4d.5d, 1a.2l.3c.4d.5f, 1a.2l.3c.4d.5h, 1a.2l.3c.4d.5i, 1a.2l.3c.4d.5n, 1a.2l.3c.4f.5a, 1a.2l.3c.4f.5b, 1a.2l.3c.4f.5d, 1a.2l.3c.4f.5f, 1a.2l.3c.4f.5h, 1a.2l.3c.4f.5i, 1a.2l.3c.4f.5n, 1a.2l.3c.4i.5a, 1a.2l.3c.4i.5b, 1a.2l.3c.4i.5d, 1a.2l.3c.4i.5f, 1a.2l.3c.4i.5h, 1a.2l.3c.4i.5i, 1a.2l.3c.4i.5n, 1a.2l.3c.4n.5a, 1a.2l.3c.4n.5b, 1a.2l.3c.4n.5d, 1a.2l.3c.4n.5f, 1a.2l.3c.4n.5h, 1a.2l.3c.4n.5i, 1a.2l.3c.4n.5n, 1a.2l.3c.4p.5a, 1a.2l.3c.4p.5b, 1a.2l.3c.4p.5d, 1a.2l.3c.4p.5f, 1a.2l.3c.4p.5h, 1a.2l.3c.4p.5i, 1a.2l.3c.4p.5n, 1a.2l.3e.4a.5a, 1a.2l.3e.4a.5b, 1a.2l.3e.4a.5d, 1a.2l.3e.4a.5f, 1a.2l.3e.4a.5h, 1a.2l.3e.4a.5i, 1a.2l.3e.4a.5n, 1a.2l.3e.4b.5a, 1a.2l.3e.4b.5b, 1a.2l.3e.4b.5d, 1a.2l.3e.4b.5f, 1a.2l.3e.4b.5h, 1a.2l.3e.4b.5i, 1a.2l.3e.4b.5n, 1a.2l.3e.4d.5a, 1a.2l.3e.4d.5b, 1a.2l.3e.4d.5d, 1a.2l.3e.4d.5f, 1a.2l.3e.4d.5h, 1a.2l.3e.4d.5i, 1a.2l.3e.4d.5n, 1a.2l.3e.4f.5a, 1a.2l.3e.4f.5b, 1a.2l.3e.4f.5d, 1a.2l.3e.4f.5f, 1a.2l.3e.4f.5h, 1a.2l.3e.4f.5i, 1a.2l.3e.4f.5n, 1a.2l.3e.4i.5a, 1a.2l.3e.4i.5b, 1a.2l.3e.4i.5d, 1a.2l.3e.4i.5f, 1a.2l.3e.4i.5h, 1a.2l.3e.4i.5i, 1a.2l.3e.4i.5n, 1a.2l.3e.4n.5a, 1a.2l.3e.4n.5b, 1a.2l.3e.4n.5d, 1a.2l.3e.4n.5f, 1a.2l.3e.4n.5h, 1a.2l.3e.4n.5i, 1a.2l.3e.4n.5n, 1a.2l.3e.4p.5a, 1a.2l.3e.4p.5b, 1a.2l.3e.4p.5d, 1a.2l.3e.4p.5f, 1a.2l.3e.4p.5h, 1a.2l.3e.4p.5i, 1a.2l.3e.4p.5n, 1a.2l.3g.4a.5a, 1a.2l.3g.4a.5b, 1a.2l.3g.4a.5d, 1a.2l.3g.4a.5f, 1a.2l.3g.4a.5h, 1a.2l.3g.4a.5i, 1a.2l.3g.4a.5n, 1a.2l.3g.4b.5a, 1a.2l.3g.4b.5b, 1a.2l.3g.4b.5d, 1a.2l.3g.4b.5f, 1a.2l.3g.4b.5h, 1a.2l.3g.4b.5i, 1a.2l.3g.4b.5n, 1a.2l.3g.4d.5a, 1a.2l.3g.4d.5b, 1a.2l.3g.4d.5d, 1a.2l.3g.4d.5f, 1a.2l.3g.4d.5h, 1a.2l.3g.4d.5i, 1a.2l.3g.4d.5n, 1a.2l.3g.4f.5a, 1a.2l.3g.4f.5b, 1a.2l.3g.4f.5d, 1a.2l.3g.4f.5f, 1a.2l.3g.4f.5h, 1a.2l.3g.4f.5i, 1a.2l.3g.4f.5n, 1a.2l.3g.4i.5a, 1a.2l.3g.4i.5b, 1a.2l.3g.4i.5d, 1a.2l.3g.4i.5f, 1a.2l.3g.4i.5h, 1a.2l.3g.4i.5i, 1a.2l.3g.4i.5n, 1a.2l.3g.4n.5a, 1a.2l.3g.4n.5b, 1a.2l.3g.4n.5d, 1a.2l.3g.4n.5f, 1a.2l.3g.4n.5h, 1a.2l.3g.4n.5i, 1a.2l.3g.4n.5n, 1a.2l.3g.4p.5a, 1a.2l.3g.4p.5b, 1a.2l.3g.4p.5d, 1a.2l.3g.4p.5f, 1a.2l.3g.4p.5h, 1a.2l.3g.4p.5i, 1a.2l.3g.4p.5n, 1a.2m.3a.4a.5a, 1a.2m.3a.4a.5b, 1a.2m.3a.4a.5d, 1a.2m.3a.4a.5f, 1a.2m.3a.4a.5h, 1a.2m.3a.4a.5i, 1a.2m.3a.4a.5n, 1a.2m.3a.4b.5a, 1a.2m.3a.4b.5b, 1a.2m.3a.4b.5d, 1a.2m.3a.4b.5f, 1a.2m.3a.4b.5h, 1a.2m.3a.4b.5i, 1a.2m.3a.4b.5n, 1a.2m.3a.4d.5a, 1a.2m.3a.4d.5b, 1a.2m.3a.4d.5d, 1a.2m.3a.4d.5f, 1a.2m.3a.4d.5h, 1a.2m.3a.4d.5i, 1a.2m.3a.4d.5n, 1a.2m.3a.4f.5a, 1a.2m.3a.4f.5b, 1a.2m.3a.4f.5d, 1a.2m.3a.4f.5f, 1a.2m.3a.4f.5h, 1a.2m.3a.4f.5i, 1a.2m.3a.4f.5n, 1a.2m.3a.4i.5a, 1a.2m.3a.4i.5b, 1a.2m.3a.4i.5d, 1a.2m.3a.4i.5f, 1a.2m.3a.4i.5h, 1a.2m.3a.4i.5i, 1a.2m.3a.4i.5n, 1a.2m.3a.4n.5a, 1a.2m.3a.4n.5b, 1a.2m.3a.4n.5d, 1a.2m.3a.4n.5f, 1a.2m.3a.4n.5h, 1a.2m.3a.4n.5i, 1a.2m.3a.4n.5n, 1a.2m.3a.4p.5a, 1a.2m.3a.4p.5b, 1a.2m.3a.4p.5d, 1a.2m.3a.4p.5f, 1a.2m.3a.4p.5h, 1a.2m.3a.4p.5i, 1a.2m.3a.4p.5n, 1a.2m.3c.4a.5a, 1a.2m.3c.4a.5b, 1a.2m.3c.4a.5d, 1a.2m.3c.4a.5f, 1a.2m.3c.4a.5h, 1a.2m.3c.4a.5i, 1a.2m.3c.4a.5n, 1a.2m.3c.4b.5a, 1a.2m.3c.4b.5h, 1a.2m.3c.4b.5d, 1a.2m.3c.4b.5f, 1a.2m.3c.4b.5h, 1a.2m.3c.4b.5i, 1a.2m.3c.4b.5n, 1a.2m.3c.4d.5a, 1a.2m.3c.4d.5b, 1a.2m.3c.4d.5d, 1a.2m.3c.4d.5f, 1a.2m.3c.4d.5h, 1a.2m.3c.4d.5i, 1a.2m.3c.4d.5n, 1a.2m.3c.4f.5a, 1a.2m.3c.4f.5b, 1a.2m.3c.4f.5d, 1a.2m.3c.4f.5f, 1a.2m.3c.4f.5h, 1a.2m.3c.4f.5i, 1a.2m.3c.4f.5n, 1a.2m.3c.4i.5a, 1a.2m.3c.4i.5b, 1a.2m.3c.4i.5d, 1a.2m.3c.4i.5f, 1a.2m.3c.4i.5h, 1a.2m.3c.4i.5i, 1a.2m.3c.4i.5n, 1a.2m.3c.4n.5a, 1a.2m.3c.4n.5b, 1a.2m.3c.4n.5d, 1a.2m.3c.4n.5f, 1a.2m.3c.4n.5h, 1a.2m.3c.4n.5i, 1a.2m.3c.4n.5n, 1a.2m.3c.4p.5a, 1a.2m.3c.4p.5b, 1a.2m.3c.4p.5d, 1a.2m.3c.4p.5f, 1a.2m.3c.4p.5h, 1a.2m.3c.4p.5i, 1a.2m.3c.4p.5n, 1a.2m.3e.4a.5a, 1a.2m.3e.4a.5b, 1a.2m.3e.4a.5d, 1a.2m.3e.4a.5f, 1a.2m.3e.4a.5h, 1a.2m.3e.4a.5i, 1a.2m.3e.4a.5n, 1a.2m.3e.4b.5a, 1a.2m.3e.4b.5b, 1a.2m.3e.4b.5d, 1a.2m.3e.4b.5f, 1a.2m.3e.4b.5h, 1a.2m.3e.4b.5i, 1a.2m.3e.4b.5n, 1a.2m.3e.4d.5a, 1a.2m.3e.4d.5b, 1a.2m.3e.4d.5d, 1a.2m.3e.4d.5f, 1a.2m.3e.4d.5h, 1a.2m.3e.4d.5i, 1a.2m.3e.4d.5n, 1a.2m.3e.4f.5a, 1a.2m.3e.4f.5b, 1a.2m.3e.4f.5d, 1a.2m.3e.4f.5f, 1a.2m.3e.4f.5h, 1a.2m.3e.4f.5i, 1a.2m.3e.4f.5n, 1a.2m.3e.4i.5a, 1a.2m.3e.4i.5b, 1a.2m.3e.4i.5d, 1a.2m.3e.4i.5f, 1a.2m.3e.4i.5h, 1a.2m.3e.4i.5i, 1a.2m.3e.4i.5n, 1a.2m.3e.4n.5a, 1a.2m.3e.4n.5b, 1a.2m.3e.4n.5d, 1a.2m.3e.4n.5f, 1a.2m.3e.4n.5h, 1a.2m.3e.4n.5i, 1a.2m.3e.4n.5n, 1a.2m.3e.4p.5a, 1a.2m.3e.4p.5b, 1a.2m.3e.4p.5d, 1a.2m.3e.4p.5f, 1a.2m.3e.4p.5h, 1a.2m.3e.4p.5i, 1a.2m.3e.4p.5n, 1a.2m.3g.4a.5a, 1a.2m.3g.4a.5b, 1a.2m.3g.4a.5d, 1a.2m.3g.4a.5f, 1a.2m.3g.4a.5h, 1a.2m.3g.4a.5i, 1a.2m.3g.4a.5n, 1a.2m.3g.4b.5a, 1a.2m.3g.4b.5b, 1a.2m.3g.4b.5d, 1a.2m.3g.4b.5f, 1a.2m.3g.4b.5h, 1a.2m.3g.4b.5i, 1a.2m.3g.4b.5n, 1a.2m.3g.4d.5a, 1a.2m.3g.4d.5b, 1a.2m.3g.4d.5d, 1a.2m.3g.4d.5f, 1a.2m.3g.4d.5h, 1a.2m.3g.4d.5i, 1a.2m.3g.4d.5n, 1a.2m.3g.4f.5a, TABLE 12-continued List of Compound Structures of Formula II 1a.2m.3g.4f.5b, 1a.2m.3g.4f.5d, 1a.2m.3g.4f.5f, 1a.2m.3g.4f.5h, 1a.2m.3g.4f.5i, 1a.2m.3g.4f.5n, 1a.2m.3g.4i.5a, 1a.2m.3g.4i.5b, 1a.2m.3g.4i.5d, 1a.2m.3g.4i.5f, 1a.2m.3g.4i.5h, 1a.2m.3g.4i.5i, 1a.2m.3g.4i.5n, 1a.2m.3g.4n.5a, 1a.2m.3g.4n.5b, 1a.2m.3g.4n.5d, 1a.2m.3g.4n.5f, 1a.2m.3g.4n.5h, 1a.2m.3g.4n.5i, 1a.2m.3g.4n.5n, 1a.2m.3g.4p.5a, 1a.2m.3g.4p.5b, 1a.2m.3g.4p.5d, 1a.2m.3g.4p.5f, 1a.2m.3g.4p.5h, 1a.2m.3g.4p.5i, 1a.2m.3g.4p.5n, 1a.2n.3a.4a.5a, 1a.2n.3a.4a.5b, 1a.2n.3a.4a.5d, 1a.2n.3a.4a.5f, 1a.2n.3a.4a.5h, 1a.2n.3a.4a.5i, 1a.2n.3a.4a.5n, 1a.2n.3a.4b.5a, 1a.2n.3a.4b.5b, 1a.2n.3a.4b.5d, 1a.2n.3a.4b.5f, 1a.2n.3a.4b.5h, 1a.2n.3a.4b.5i, 1a.2n.3a.4b.5n, 1a.2n.3a.4d.5a, 1a.2n.3a.4d.5b, 1a.2n.3a.4d.5d, 1a.2n.3a.4d.5f, 1a.2n.3a.4d.5h, 1a.2n.3a.4d.5i, 1a.2n.3a.4d.5n, 1a.2n.3a.4f.5a, 1a.2n.3a.4f.5b, 1a.2n.3a.4f.5d, 1a.2n.3a.4f.5f, 1a.2n.3a.4f.5h, 1a.2n.3a.4f.5i, 1a.2n.3a.4f.5n, 1a.2n.3a.4i.5a, 1a.2n.3a.4i.5b, 1a.2n.3a.4i.5d, 1a.2n.3a.4i.5f, 1a.2n.3a.4i.5h, 1a.2n.3a.4i.5i, 1a.2n.3a.4i.5n, 1a.2n.3a.4n.5a, 1a.2n.3a.4n.5b, 1a.2n.3a.4n.5d, 1a.2n.3a.4n.5f, 1a.2n.3a.4n.5h, 1a.2n.3a.4n.5i, 1a.2n.3a.4n.5n, 1a.2n.3a.4p.5a, 1a.2n.3a.4p.5b, 1a.2n.3a.4p.5d, 1a.2n.3a.4p.5f, 1a.2n.3a.4p.5h, 1a.2n.3a.4p.5i, 1a.2n.3a.4p.5n, 1a.2n.3c.4a.5a, 1a.2n.3c.4a.5b, 1a.2n.3c.4a.5d, 1a.2n.3c.4a.5f, 1a.2n.3c.4a.5h, 1a.2n.3c.4a.5i, 1a.2n.3c.4a.5n, 1a.2n.3c.4b.5a, 1a.2n.3c.4b.5b, 1a.2n.3c.4b.5d, 1a.2n.3c.4b.5f, 1a.2n.3c.4b.5h, 1a.2n.3c.4b.5i, 1a.2n.3c.4b.5n, 1a.2n.3c.4d.5a, 1a.2n.3c.4d.5b, 1a.2n.3c.4d.5d, 1a.2n.3c.4d.5f, 1a.2n.3c.4d.5h, 1a.2n.3c.4d.5i, 1a.2n.3c.4d.5n, 1a.2n.3c.4f.5a, 1a.2n.3c.4f.5b, 1a.2n.3c.4f.5d, 1a.2n.3c.4f.5f, 1a.2n.3c.4f.5h, 1a.2n.3c.4f.5i, 1a.2n.3c.4f.5n, 1a.2n.3c.4i.5a, 1a.2n.3c.4i.5b, 1a.2n.3c.4i.5d, 1a.2n.3c.4i.5f, 1a.2n.3c.4i.5h, 1a.2n.3c.4i.5i, 1a.2n.3c.4i.5n, 1a.2n.3c.4n.5a, 1a.2n.3c.4n.5b, 1a.2n.3c.4n.5d, 1a.2n.3c.4n.5f, 1a.2n.3c.4n.5h, 1a.2n.3c.4n.5i, 1a.2n.3c.4n.5n, 1a.2n.3c.4p.5a, 1a.2n.3c.4p.5b, 1a.2n.3c.4p.5d, 1a.2n.3c.4p.5f, 1a.2n.3c.4p.5h, 1a.2n.3c.4p.5i, 1a.2n.3c.4p.5n, 1a.2n.3e.4a.5a, 1a.2n.3e.4a.5b, 1a.2n.3e.4a.5d, 1a.2n.3e.4a.5f, 1a.2n.3e.4a.5h, 1a.2n.3e.4a.5i, 1a.2n.3e.4a.5n, 1a.2n.3e.4b.5a, 1a.2n.3e.4b.5b, 1a.2n.3e.4b.5d, 1a.2n.3e.4b.5f, 1a.2n.3e.4b.5h, 1a.2n.3e.4b.5i, 1a.2n.3e.4b.5n, 1a.2n.3e.4d.5a, 1a.2n.3e.4d.5b, 1a.2n.3e.4d.5d, 1a.2n.3e.4d.5f, 1a.2n.3e.4d.5h, 1a.2n.3e.4d.5i, 1a.2n.3e.4d.5n, 1a.2n.3e.4f.5a, 1a.2n.3e.4f.5b, 1a.2n.3e.4f.5d, 1a.2n.3e.4f.5f, 1a.2n.3e.4f.5h, 1a.2n.3e.4f.5i, 1a.2n.3e.4f.5n, 1a.2n.3e.4i.5a, 1a.2n.3e.4i.5b, 1a.2n.3e.4i.5d, 1a.2n.3e.4i.5f, 1a.2n.3e.4i.5h, 1a.2n.3e.4i.5i, 1a.2n.3e.4i.5n, 1a.2n.3e.4n.5a, 1a.2n.3e.4n.5b, 1a.2n.3e.4n.5d, 1a.2n.3e.4n.5f, 1a.2n.3e.4n.5h, 1a.2n.3e.4n.5i, 1a.2n.3e.4n.5n, 1a.2n.3e.4p.5a, 1a.2n.3e.4p.5b, 1a.2n.3e.4p.5d, 1a.2n.3e.4p.5f, 1a.2n.3e.4p.5h, 1a.2n.3e.4p.5i, 1a.2n.3e.4p.5n, 1a.2n.3g.4a.5a, 1a.2n.3g.4a.5b, 1a.2n.3g.4a.5d, 1a.2n.3g.4a.5f, 1a.2n.3g.4a.5h, 1a.2n.3g.4a.5i, 1a.2n.3g.4a.5n, 1a.2n.3g.4b.5a, 1a.2n.3g.4b.5b, 1a.2n.3g.4b.5d, 1a.2n.3g.4b.5f, 1a.2n.3g.4b.5h, 1a.2n.3g.4b.5i, 1a.2n.3g.4b.5n, 1a.2n.3g.4d.5a, 1a.2n.3g.4d.5b, 1a.2n.3g.4d.5d, 1a.2n.3g.4d.5f, 1a.2n.3g.4d.5h, 1a.2n.3g.4d.5i, 1a.2n.3g.4d.5n, 1a.2n.3g.4f.5a, 1a.2n.3g.4f.5b, 1a.2n.3g.4f.5d, 1a.2n.3g.4f.5f, 1a.2n.3g.4f.5h, 1a.2n.3g.4f.5i, 1a.2n.3g.4f.5n, 1a.2n.3g.4i.5a, 1a.2n.3g.4i.5b, 1a.2n.3g.4i.5d, 1a.2n.3g.4i.5f, 1a.2n.3g.4i.5h, 1a.2n.3g.4i.5i, 1a.2n.3g.4i.5n, 1a.2n.3g.4n.5a, 1a.2n.3g.4n.5b, 1a.2n.3g.4n.5d, 1a.2n.3g.4n.5f, 1a.2n.3g.4n.5h, 1a.2n.3g.4n.5i, 1a.2n.3g.4n.5n, 1a.2n.3g.4p.5a, 1a.2n.3g.4p.5b, 1a.2n.3g.4p.5d, 1a.2n.3g.4p.5f, 1a.2n.3g.4p.5h, 1a.2n.3g.4p.5i, 1a.2n.3g.4p.5n, 1a.2q.3a.4a.5a, 1a.2q.3a.4a.5b, 1a.2q.3a.4a.5d, 1a.2q.3a.4a.5f, 1a.2q.3a.4a.5h, 1a.2q.3a.4a.5i, 1a.2q.3a.4a.5n, 1a.2q.3a.4b.5a, 1a.2q.3a.4b.5b, 1a.2q.3a.4b.5d, 1a.2q.3a.4b.5f, 1a.2q.3a.4b.5h, 1a.2q.3a.4b.5i, 1a.2q.3a.4b.5n, 1a.2q.3a.4d.5a, 1a.2q.3a.4d.5b, 1a.2q.3a.4d.5d, 1a.2q.3a.4d.5f, 1a.2q.3a.4d.5h, 1a.2q.3a.4d.5i, 1a.2q.3a.4d.5n, 1a.2q.3a.4f.5a, 1a.2q.3a.4f.5b, 1a.2q.3a.4f.5d, 1a.2q.3a.4f.5f, 1a.2q.3a.4f.5h, 1a.2q.3a.4f.5i, 1a.2q.3a.4f.5n, 1a.2q.3a.4i.5a, 1a.2q.3a.4i.5b, 1a.2q.3a.4i.5d, 1a.2q.3a.4i.5f, 1a.2q.3a.4i.5h, 1a.2q.3a.4i.5i, 1a.2q.3a.4i.5n, 1a.2q.3a.4n.5a, 1a.2q.3a.4n.5b, 1a.2q.3a.4n.5d, 1a.2q.3a.4n.5f, 1a.2q.3a.4n.5h, 1a.2q.3a.4n.5i, 1a.2q.3a.4n.5n, 1a.2q.3a.4p.5a, 1a.2q.3a.4p.5b, 1a.2q.3a.4p.5d, 1a.2q.3a.4p.5f, 1a.2q.3a.4p.5h, 1a.2q.3a.4p.5i, 1a.2q.3a.4p.5n, 1a.2q.3c.4a.5a, 1a.2q.3c.4a.5b, 1a.2q.3c.4a.5d, 1a.2q.3c.4a.5f, 1a.2q.3c.4a.5h, 1a.2q.3c.4a.5i, 1a.2q.3c.4a.5n, 1a.2q.3c.4b.5a, 1a.2q.3c.4b.5b, 1a.2q.3c.4b.5d, 1a.2q.3c.4b.5f, 1a.2q.3c.4b.5h, 1a.2q.3c.4b.5i, 1a.2q.3c.4b.5n, 1a.2q.3c.4d.5a, 1a.2q.3c.4d.5b, 1a.2q.3c.4d.5d, 1a.2q.3c.4d.5f, 1a.2q.3c.4d.5h, 1a.2q.3c.4d.5i, 1a.2q.3c.4d.5n, 1a.2q.3c.4f.5a, 1a.2q.3c.4f.5b, 1a.2q.3c.4f.5d, 1a.2q.3c.4f.5f, 1a.2q.3c.4f.5h, 1a.2q.3c.4f.5i, 1a.2q.3c.4f.5n, 1a.2q.3c.4i.5a, 1a.2q.3c.4i.5b, 1a.2q.3c.4i.5d, 1a.2q.3c.4i.5f, 1a.2q.3c.4i.5h, 1a.2q.3c.4i.5i, 1a.2q.3c.4i.5n, 1a.2q.3c.4n.5a, 1a.2q.3c.4n.5b, 1a.2q.3c.4n.5d, 1a.2q.3c.4n.5f, 1a.2q.3c.4n.5h, 1a.2q.3c.4n.5i, 1a.2q.3c.4n.5n, 1a.2q.3c.4p.5a, 1a.2q.3c.4p.5b, 1a.2q.3c.4p.5d, 1a.2q.3c.4p.5f, 1a.2q.3c.4p.5h, 1a.2q.3c.4p.5i, 1a.2q.3c.4p.5n, 1a.2q.3e.4a.5a, 1a.2q.3e.4a.5b, 1a.2q.3e.4a.5d, 1a.2q.3e.4a.5f, 1a.2q.3e.4a.5h, 1a.2q.3e.4a.5i, 1a.2q.3e.4a.5n, 1a.2q.3e.4b.5a, 1a.2q.3e.4b.5b, 1a.2q.3e.4b.5d, 1a.2q.3e.4b.5f, 1a.2q.3e.4b.5h, 1a.2q.3e.4b.5i, 1a.2q.3e.4b.5n, 1a.2q.3e.4d.5a, 1a.2q.3e.4d.5b, 1a.2q.3e.4d.5d, 1a.2q.3e.4d.5f, 1a.2q.3e.4d.5h, 1a.2q.3e.4d.5i, 1a.2q.3e.4d.5n, 1a.2q.3e.4f.5a, 1a.2q.3e.4f.5b, 1a.2q.3e.4f.5d, 1a.2q.3e.4f.5f, 1a.2q.3e.4f.5h, 1a.2q.3e.4f.5i, 1a.2q.3e.4f.5n, 1a.2q.3e.4i.5a, 1a.2q.3e.4i.5b, 1a.2q.3e.4i.5d, 1a.2q.3e.4i.5f, 1a.2q.3e.4i.5h, 1a.2q.3e.4i.5i, 1a.2q.3e.4i.5n, 1a.2q.3e.4n.5a, 1a.2q.3e.4n.5b, 1a.2q.3e.4n.5d, 1a.2q.3e.4n.5f, 1a.2q.3e.4n.5h, 1a.2q.3e.4n.5i, 1a.2q.3e.4n.5n, 1a.2q.3e.4p.5a, 1a.2q.3e.4p.5b, 1a.2q.3e.4p.5d, 1a.2q.3e.4p.5f, 1a.2q.3e.4p.5h, 1a.2q.3e.4p.5i, 1a.2q.3e.4p.5n, 1a.2q.3g.4a.5a, 1a.2q.3g.4a.5b, 1a.2q.3g.4a.5d, 1a.2q.3g.4a.5f, 1a.2q.3g.4a.5h, 1a.2q.3g.4a.5i, 1a.2q.3g.4a.5n, 1a.2q.3g.4b.5a, 1a.2q.3g.4b.5b, 1a.2q.3g.4b.5d, 1a.2q.3g.4b.5f, 1a.2q.3g.4b.5h, 1a.2q.3g.4b.5i, 1a.2q.3g.4b.5n, 1a.2q.3g.4d.5a, 1a.2q.3g.4d.5b, 1a.2q.3g.4d.5d, 1a.2q.3g.4d.5f, 1a.2q.3g.4d.5h, 1a.2q.3g.4d.5i, TABLE 12-continued List of Compound Structures of Formula II 1a.2q.3g.4d.5n, 1a.2q.3g.4f.5a, 1a.2q.3g.4f.5b, 1a.2q.3g.4f.5d, 1a.2q.3g.4f.5f,
1a.2q.3g.4f.5h, 1a.2q.3g.4f.5i, 1a.2q.3g.4f.5n, 1a.2q.3g.4i.5a, 1a.2q.3g.4i.5b,
1a.2q.3g.4i.5d, 1a.2q.3g.4i.5f, 1a.2q.3g.4i.5h, 1a.2q.3g.4i.5i, 1a.2q.3g.4i.5n,
1a.2q.3g.4n.5a, 1a.2q.3g.4n.5b, 1a.2q.3g.4n.5d, 1a.2q.3g.4n.5f, 1a.2q.3g.4n.5h,
1a.2q.3g.4n.5i, 1a.2q.3g.4n.5n, 1a.2q.3g.4p.5a, 1a.2q.3g.4p.5b, 1a.2q.3g.4p.5d,
1a.2q.3g.4p.5f, 1a.2q.3g.4p.5h, 1a.2q.3g.4p.5i, 1a.2q.3g.4p.5n, 1a.2v.3a.4a.5a,
1a.2v.3a.4a.5b, 1a.2v.3a.4a.5d, 1a.2v.3a.4a.5f, 1a.2v.3a.4a.5h, 1a.2v.3a.4a.5i,
1a.2v.3a.4a.5n, 1a.2v.3a.4b.5a, 1a.2v.3a.4b.5b, 1a.2v.3a.4b.5d, 1a.2v.3a.4b.5f,
1a.2v.3a.4b.5h, 1a.2v.3a.4b.5i, 1a.2v.3a.4b.5n, 1a.2v.3a.4d.5a, 1a.2v.3a.4d.5b,
1a.2v.3a.4d.5d, 1a.2v.3a.4d.5f, 1a.2v.3a.4d.5h, 1a.2v.3a.4d.5i, 1a.2v.3a.4d.5n,
1a.2v.3a.4f.5a, 1a.2v.3a.4f.5b, 1a.2v.3a.4f.5d, 1a.2v.3a.4f.5f, 1a.2v.3a.4f.5h,
1a.2v.3a.4f.5i, 1a.2v.3a.4f.5n, 1a.2v.3a.4i.5a, 1a.2v.3a.4i.5b, 1a.2v.3a.4i.5d,
1a.2v.3a.4i.5f, 1a.2v.3a.4i.5h, 1a.2v.3a.4i.5i, 1a.2v.3a.4i.5n, 1a.2v.3a.4n.5a,
1a.2v.3a.4n.5b, 1a.2v.3a.4n.5d, 1a.2v.3a.4n.5f, 1a.2v.3a.4n.5h, 1a.2v.3a.4n.5i,
1a.2v.3a.4n.5n, 1a.2v.3a.4p.5a, 1a.2v.3a.4p.5b, 1a.2v.3a.4p.5d, 1a.2v.3a.4p.5f,
1a.2v.3a.4p.5h, 1a.2v.3a.4p.5i, 1a.2v.3a.4p.5n, 1a.2v.3c.4a.5a, 1a.2v.3c.4a.5b,
1a.2v.3c.4a.5d, 1a.2v.3c.4a.5f, 1a.2v.3c.4a.5h, 1a.2v.3c.4a.5i, 1a.2v.3c.4a.5n,
1a.2v.3c.4b.5a, 1a.2v.3c.4b.5b, 1a.2v.3c.4b.5d, 1a.2v.3c.4b.5f, 1a.2v.3c.4b.5h,
1a.2v.3c.4b.5i, 1a.2v.3c.4b.5n, 1a.2v.3c.4d.5a, 1a.2v.3c.4d.5b, 1a.2v.3c.4d.5d,
1a.2v.3c.4d.5f, 1a.2v.3c.4d.5h, 1a.2v.3c.4d.5i, 1a.2v.3c.4d.5n, 1a.2v.3c.4f.5a,
1a.2v.3c.4f.5b, 1a.2v.3c.4f.5d, 1a.2v.3c.4f.5f, 1a.2v.3c.4f.5h, 1a.2v.3c.4f.5i,
1a.2v.3c.4f.5n, 1a.2v.3c.4i.5a, 1a.2v.3c.4i.5b, 1a.2v.3c.4i.5d, 1a.2v.3c.4i.5f,
1a.2v.3c.4i.5h, 1a.2v.3c.4i.5i, 1a.2v.3c.4i.5n, 1a.2v.3c.4n.5a, 1a.2v.3c.4n.5b,
1a.2v.3c.4n.5d, 1a.2v.3c.4n.5f, 1a.2v.3c.4n.5h, 1a.2v.3c.4n.5i, 1a.2v.3c.4n.5n,
1a.2v.3c.4p.5a, 1a.2v.3c.4p.5b, 1a.2v.3c.4p.5d, 1a.2v.3c.4p.5f, 1a.2v.3c.4p.5h,
1a.2v.3c.4p.5i, 1a.2v.3c.4p.5n, 1a.2v.3e.4a.5a, 1a.2v.3e.4a.5b, 1a.2v.3e.4a.5d,
1a.2v.3e.4a.5f, 1a.2v.3e.4a.5h, 1a.2v.3e.4a.5i, 1a.2v.3e.4a.5n, 1a.2v.3e.4b.5a,
1a.2v.3e.4b.5b, 1a.2v.3e.4b.5d, 1a.2v.3e.4b.5f, 1a.2v.3e.4b.5h, 1a.2v.3e.4b.5i,
1a.2v.3e.4b.5n, 1a.2v.3e.4d.5a, 1a.2v.3e.4d.5b, 1a.2v.3e.4d.5d, 1a.2v.3e.4d.5f,
1a.2v.3e.4d.5h, 1a.2v.3e.4d.5i, 1a.2v.3e.4d.5n, 1a.2v.3e.4f.5a, 1a.2v.3e.4f.5b,
1a.2v.3e.4f.5d, 1a.2v.3e.4f.5f, 1a.2v.3e.4f.5h, 1a.2v.3e.4f.5i, 1a.2v.3e.4f.5n,
1a.2v.3e.4i.5a, 1a.2v.3e.4i.5b, 1a.2v.3e.4i.5d, 1a.2v.3e.4i.5f, 1a.2v.3e.4i.5h,
1a.2v.3e.4i.5i, 1a.2v.3e.4i.5n, 1a.2v.3e.4n.5a, 1a.2v.3e.4n.5b, 1a.2v.3e.4n.5d,
1a.2v.3e.4n.5f, 1a.2v.3e.4n.5h, 1a.2v.3e.4n.5i, 1a.2v.3e.4n.5n, 1a.2v.3e.4p.5a,
1a.2v.3e.4p.5b, 1a.2v.3e.4p.5d, 1a.2v.3e.4p.5f, 1a.2v.3e.4p.5h, 1a.2v.3e.4p.5i,
1a.2v.3e.4p.5n, 1a.2v.3g.4a.5a, 1a.2v.3g.4a.5b, 1a.2v.3g.4a.5d, 1a.2v.3g.4a.5f,
1a.2v.3g.4a.5h, 1a.2v.3g.4a.5i, 1a.2v.3g.4a.5n, 1a.2v.3g.4b.5a, 1a.2v.3g.4b.5b,
1a.2v.3g.4b.5d, 1a.2v.3g.4b.5f, 1a.2v.3g.4b.5h, 1a.2v.3g.4b.5i, 1a.2v.3g.4b.5n,
1a.2v.3g.4d.5a, 1a.2v.3g.4d.5b, 1a.2v.3g.4d.5d, 1a.2v.3g.4d.5f, 1a.2v.3g.4d.5h,
1a.2v.3g.4d.5i, 1a.2v.3g.4d.5n, 1a.2v.3g.4f.5a, 1a.2v.3g.4f.5b, 1a.2v.3g.4f.5d,
1a.2v.3g.4f.5f, 1a.2v.3g.4f.5h, 1a.2v.3g.4f.5i, 1a.2v.3g.4f.5n, 1a.2v.3g.4i.5a,
1a.2v.3g.4i.5b, 1a.2v.3g.4i.5d, 1a.2v.3g.4i.5f, 1a.2v.3g.4i.5h, 1a.2v.3g.4i.5i,
1a.2v.3g.4i.5n, 1a.2v.3g.4n.5a, 1a.2v.3g.4n.5b, 1a.2v.3g.4n.5d, 1a.2v.3g.4n.5f,
1a.2v.3g.4n.5h, 1a.2v.3g.4n.5i, 1a.2v.3g.4n.5n, 1a.2v.3g.4p.5a, 1a.2v.3g.4p.5b,
1a.2v.3g.4p.5d, 1a.2v.3g.4p.5f, 1a.2v.3g.4p.5h, 1a.2v.3g.4p.5i, 1a.2v.3g.4p.5n,
1a.2y.3a.4a.5a, 1a.2y.3a.4a.5b, 1a.2y.3a.4a.5d, 1a.2y.3a.4a.5f, 1a.2y.3a.4a.5h,
1a.2y.3a.4a.5i, 1a.2y.3a.4a.5n, 1a.2y.3a.4b.5a, 1a.2y.3a.4b.5b, 1a.2y.3a.4b.5d,
1a.2y.3a.4b.5f, 1a.2y.3a.4b.5h, 1a.2y.3a.4b.5i, 1a.2y.3a.4b.5n, 1a.2y.3a.4d.5a,
1a.2y.3a.4d.5b, 1a.2y.3a.4d.5d, 1a.2y.3a.4d.5f, 1a.2y.3a.4d.5h, 1a.2y.3a.4d.5i,
1a.2y.3a.4d.5n, 1a.2y.3a.4f.5a, 1a.2y.3a.4f.5b, 1a.2y.3a.4f.5d, 1a.2y.3a.4f.5f,
1a.2y.3a.4f.5h, 1a.2y.3a.4f.5i, 1a.2y.3a.4f.5n, 1a.2y.3a.4i.5a, 1a.2y.3a.4i.5b,
1a.2y.3a.4i.5d, 1a.2y.3a.4i.5f, 1a.2y.3a.4i.5h, 1a.2y.3a.4i.5i, 1a.2y.3a.4i.5n,
1a.2y.3a.4n.5a, 1a.2y.3a.4n.5b, 1a.2y.3a.4n.5d, 1a.2y.3a.4n.5f, 1a.2y.3a.4n.5h,
1a.2y.3a.4n.5i, 1a.2y.3a.4n.5n, 1a.2y.3a.4p.5a, 1a.2y.3a.4p.5b, 1a.2y.3a.4p.5d,
1a.2y.3a.4p.5f, 1a.2y.3a.4p.5h, 1a.2y.3a.4p.5i, 1a.2y.3a.4p.5n, 1a.2y.3c.4a.5a,
1a.2y.3c.4a.5b, 1a.2y.3c.4a.5d, 1a.2y.3c.4a.5f, 1a.2y.3c.4a.5h, 1a.2y.3c.4a.5i,
1a.2y.3c.4a.5n, 1a.2y.3c.4b.5a, 1a.2y.3c.4b.5b, 1a.2y.3c.4b.5d, 1a.2y.3c.4b.5f,
1a.2y.3c.4b.5h, 1a.2y.3c.4b.5i, 1a.2y.3c.4b.5n, 1a.2y.3c.4d.5a, 1a.2y.3c.4d.5b,
1a.2y.3c.4d.5d, 1a.2y.3c.4d.5f, 1a.2y.3c.4d.5h, 1a.2y.3c.4d.5i, 1a.2y.3c.4d.5n,
1a.2y.3c.4f.5a, 1a.2y.3c.4f.5b, 1a.2y.3c.4f.5d, 1a.2y.3c.4f.5f, 1a.2y.3c.4f.5h,
1a.2y.3c.4f.5i, 1a.2y.3c.4f.5n, 1a.2y.3c.4i.5a, 1a.2y.3c.4i.5b, 1a.2y.3c.4i.5d,
1a.2y.3c.4i.5f, 1a.2y.3c.4i.5h, 1a.2y.3c.4i.5i, 1a.2y.3c.4i.5n, 1a.2y.3c.4n.5a,
1a.2y.3c.4n.5b, 1a.2y.3c.4n.5d, 1a.2y.3c.4n.5f, 1a.2y.3c.4n.5h, 1a.2y.3c.4n.5i,
1a.2y.3c.4n.5n, 1a.2y.3c.4p.5a, 1a.2y.3c.4p.5b, 1a.2y.3c.4p.5d, 1a.2y.3c.4p.5f,
1a.2y.3c.4p.5h, 1a.2y.3c.4p.5i, 1a.2y.3c.4p.5n, 1a.2y.3e.4a.5a, 1a.2y.3e.4a.5b,
1a.2y.3e.4a.5d, 1a.2y.3c.4a.5f, 1a.2y.3e.4a.5h, 1a.2y.3e.4a.5i, 1a.2y.3e.4a.5n,
1a.2y.3e.4b.5a, 1a.2y.3e.4b.5b, 1a.2y.3e.4b.5d, 1a.2y.3e.4b.5f, 1a.2y.3e.4b.5h,
1a.2y.3e.4b.5i, 1a.2y.3e.4b.5n, 1a.2y.3e.4d.5a, 1a.2y.3e.4d.5b, 1a.2y.3e.4d.5d,
1a.2y.3e.4d.5f, 1a.2y.3e.4d.5h, 1a.2y.3e.4d.5i, 1a.2y.3e.4d.5n, 1a.2y.3e.4f.5a,
1a.2y.3e.4f.5b, 1a.2y.3e.4f.5d, 1a.2y.3e.4f.5f, 1a.2y.3e.4f.5h, 1a.2y.3e.4f.5i,
1a.2y.3e.4f.5n, 1a.2y.3e.4i.5a, 1a.2y.3e.4i.5b, 1a.2y.3e.4i.5d, 1a.2y.3e.4i.5f,
1a.2y.3e.4i.5h, 1a.2y.3e.4i.5i, 1a.2y.3e.4i.5n, 1a.2y.3e.4n.5a, 1a.2y.3e.4n.5b,
1a.2y.3e.4n.5d, 1a.2y.3e.4n.5f, 1a.2y.3e.4n.5h, 1a.2y.3e.4n.5i, 1a.2y.3e.4n.5n,
1a.2y.3e.4p.5a, 1a.2y.5e.4p.5b, 1a.2y.3e.4p.5d, 1a.2y.3e.4p.5f, 1a.2y.3e.4p.5h,
1a.2y.3e.4p.5i, 1a.2y.3e.4p.5n, 1a.2y.3g.4a.5a, 1a.2y.3g.4a.5b, 1a.2y.3g.4a.5d,
1a.2y.3g.4a.5f, 1a.2y.3g.4a.5h, 1a.2y.3g.4a.5i, 1a.2y.3g.4a.5n, 1a.2y.3g.4b.5a,
1a.2y.3g.4b.5b, 1a.2y.3g.4b.5d, 1a.2y.3g.4b.5f, 1a.2y.3g.4b.5h, 1a.2y.3g.4b.5i,
1a.2y.3g.4b.5n, 1a.2y.3g.4d.5a, 1a.2y.3g.4d.5b, 1a.2y.3g.4d.5d, 1a.2y.3g.4d.5f, TABLE 12-continued List of Compound Structures of Formula II 1a.2y.3g.4d.5h, 1a.2y.3g.4d.5i, 1a.2y.3g.4d.5n, 1a.2y.3g.4f.5a, 1a.2y.3g.4f.5b,
1a.2y.3g.4f.5d, 1a.2y.3g.4f.5f, 1a.2y.3g.4f.5h, 1a.2y.3g.4f.5i, 1a.2y.3g.4f.5n,
1a.2y.3g.4i.5a, 1a.2y.3g.4i.5b, 1a.2y.3g.4i.5d, 1a.2y.3g.4i.5f, 1a.2y.3g.4i.5h,
1a.2y.3g.4i.5i, 1a.2y.3g.4i.5n, 1a.2y.3g.4n.5a, 1a.2y.3g.4n.5b, 1a.2y.3g.4n.5d,
1a.2y.3g.4n.5f, 1a.2y.3g.4n.5h, 1a.2y.3g.4n.5i, 1a.2y.3g.4n.5n, 1a.2y.3g.4p.5a,
1a.2y.3g.4p.5b, 1a.2y.3g.4p.5d, 1a.2y.3g.4p.5f, 1a.2y.3g.4p.5h, 1a.2y.3g.4p.5i,
1a.2y.3g.4p.5n, 1a.2z.3a.4a.5a, 1a.2z.3a.4a.5b, 1a.2z.3a.4a.5d, 1a.2z.3a.4a.5f,
1a.2z.3a.4a.5h, 1a.2z.3a.4a.5i, 1a.2z.3a.4a.5n, 1a.2z.3a.4b.5a, 1a.2z.3a.4b.5b,
1a.2z.3a.4b.5d, 1a.2z.3a.4b.5f, 1a.2z.3a.4b.5h, 1a.2z.3a.4b.5i, 1a.2z.3a.4b.5n,
1a.2z.3a.4d.5a, 1a.2z.3a.4d.5b, 1a.2z.3a.4d.5d, 1a.2z.3a.4d.5f, 1a.2z.3a.4d.5h,
1a.2z.3a.4d.5i, 1a.2z.3a.4d.5n, 1a.2z.3a.4f.5a, 1a.2z.3a.4f.5b, 1a.2z.3a.4f.5d,
1a.2z.3a.4f.5f, 1a.2z.3a.4f.5h, 1a.2z.3a.4f.5i, 1a.2z.3a.4f.5n, 1a.2z.3a.4i.5a,
1a.2z.3a.4i.5b, 1a.2z.3a.4i.5d, 1a.2z.3a.4i.5f, 1a.2z.3a.4i.5h, 1a.2z.3a.4i.5i,
1a.2z.3a.4i.5n, 1a.2z.3a.4n.5a, 1a.2z.3a.4n.5b, 1a.2z.3a.4n.5d, 1a.2z.3a.4n.5f,
1a.2z.3a.4n.5h, 1a.2z.3a.4n.5i, 1a.2z.3a.4n.5n, 1a.2z.3a.4p.5a, 1a.2z.3a.4p.5b,
1a.2z.3a.4p.5d, 1a.2z.3a.4p.5f, 1a.2z.3a.4p.5h, 1a.2z.3a.4p.5i, 1a.2z.3a.4p.5n,
1a.2z.3c.4a.5a, 1a.2z.3c.4a.5b, 1a.2z.3c.4a.5d, 1a.2z.3c.4a.5f, 1a.2z.3c.4a.5h,
1a.2z.3c.4a.5i, 1a.2z.3c.4a.5n, 1a.2z.3c.4b.5a, 1a.2z.3c.4b.5b, 1a.2z.3c.4b.5d,
1a.2z.3c.4b.5f, 1a.2z.3c.4b.5h, 1a.2z.3c.4b.5i, 1a.2z.3c.4b.5n, 1a.2z.3c.4d.5a,
1a.2z.3c.4d.5b, 1a.2z.3c.4d.5d, 1a.2z.3c.4d.5f, 1a.2z.3c.4d.5h, 1a.2z.3c.4d.5i,
1a.2z.3c.4d.5n, 1a.2z.3c.4f.5a, 1a.2z.3c.4f.5b, 1a.2z.3c.4f.5d, 1a.2z.3c.4f.5f,
1a.2z.3c.4f.5h, 1a.2z.3c.4f.5i, 1a.2z.3c.4f.5n, 1a.2z.3c.4i.5a, 1a.2z.3c.4i.5b,
1a.2z.3c.4i.5d, 1a.2z.3c.4i.5f, 1a.2z.3c.4i.5h, 1a.2z.3c.4i.5i, 1a.2z.3c.4i.5n,
1a.2z.3c.4n.5a, 1a.2z.3c.4n.5b, 1a.2z.3c.4n.5d, 1a.2z.3c.4n.5f, 1a.2z.3c.4n.5h,
1a.2z.3c.4n.5i, 1a.2z.3c.4n.5n, 1a.2z.3c.4p.5a, 1a.2z.3c.4p.5b, 1a.2z.3c.4p.5d,
1a.2z.3c.4p.5f, 1a.2z.3c.4p.5h, 1a.2z.3c.4p.5i, 1a.2z.3c.4p.5n, 1a.2z.3e.4a.5a,
1a.2z.3e.4a.5b, 1a.2z.3e.4a.5d, 1a.2z.3e.4a.5f, 1a.2z.3e.4a.5h, 1a.2z.3e.4a.5i,
1a.2z.3e.4a.5n, 1a.2z.3e.4b.5a, 1a.2z.3e.4b.5b, 1a.2z.3e.4b.5d, 1a.2z.3e.4b.5f,
1a.2z.3e.4b.5h, 1a.2z.3e.4b.5i, 1a.2z.3e.4b.5n, 1a.2z.3e.4d.5a, 1a.2z.3e.4d.5b,
1a.2z.3e.4d.5d, 1a.2z.3e.4d.5f, 1a.2z.3e.4d.5h, 1a.2z.3e.4d.5i, 1a.2z.3e.4d.5n,
1a.2z.3e.4f.5a, 1a.2z.3e.4f.5b, 1a.2z.3e.4f.5d, 1a.2z.3e.4f.5f, 1a.2z.3e.4f.5h,
1a.2z.3e.4f.5i, 1a.2z.3e.4f.5n, 1a.2z.3e.4i.5a, 1a.2z.3e.4i.5b, 1a.2z.3e.4i.5d,
1a.2z.3e.4i.5f, 1a.2z.3e.4i.5h, 1a.2z.3e.4i.5i, 1a.2z.3e.4i.5n, 1a.2z.3e.4n.5a,
1a.2z.3e.4n.5b, 1a.2z.3e.4n.5d, 1a.2z.3e.4n.5f, 1a.2z.3e.4n.5h, 1a.2z.3e.4n.5i,
1a.2z.3e.4n.5n, 1a.2z.3e.4p.5a, 1a.2z.3e.4p.5b, 1a.2z.3e.4p.5d, 1a.2z.3e.4p.5f,
1a.2z.3e.4p.5h, 1a.2z.3e.4p.5i, 1a.2z.3e.4p.5n, 1a.2z.3g.4a.5a, 1a.2z.3g.4a.5b,
1a.2z.3g.4a.5d, 1a.2z.3g.4a.5f, 1a.2z.3g.4a.5h, 1a.2z.3g.4a.5i, 1a.2z.3g.4a.5n,
1a.2z.3g.4b.5a, 1a.2z.3g.4b.5b, 1a.2z.3g.4b.5d, 1a.2z.3g.4b.5f, 1a.2z.3g.4b.5h,
1a.2z.3g.4b.5i, 1a.2z.3g.4b.5n, 1a.2z.3g.4d.5a, 1a.2z.3g.4d.5b, 1a.2z.3g.4d.5d,
1a.2z.3g.4d.5f, 1a.2z.3g.4d.5h, 1a.2z.3g.4d.5i, 1a.2z.3g.4d.5n, 1a.2z.3g.4f.5a,
1a.2z.3g.4f.5b, 1a.2z.3g.4f.5d, 1a.2z.3g.4f.5f, 1a.2z.3g.4f.5h, 1a.2z.3g.4f.5i,
1a.2z.3g.4f.5n, 1a.2z.3g.4i.5a, 1a.2z.3g.4i.5b, 1a.2z.3g.4i.5d, 1a.2z.3g.4i.5f,
1a.2z.3g.4i.5h, 1a.2z.3g.4i.5i, 1a.2z.3g.4i.5n, 1a.2z.3g.4n.5a, 1a.2z.3g.4n.5b,
1a.2z.3g.4n.5d, 1a.2z.3g.4n.5f, 1a.2z.3g.4n.5h, 1a.2z.3g.4n.5i, 1a.2z.3g.4n.5n,
1a.2z.3g.4p.5a, 1a.2z.3g.4p.5b, 1a.2z.3g.4p.5d, 1a.2z.3g.4p.5f, 1a.2z.3g.4p.5h,
1a.2z.3g.4p.5i, 1a.2z.3g.4p.5n, 1b.2a.3a.4a.5a, 1b.2a.3a.4a.5b, 1b.2a.3a.4a.5d,
1b.2a.3a.4a.5f, 1b.2a.3a.4a.5h, 1b.2a.3a.4a.5i, 1b.2a.3a.4a.5n, 1b.2a.3a.4b.5a,
1b.2a.3a.4b.5b, 1b.2a.3a.4b.5d, 1b.2a.3a.4b.5f, 1b.2a.3a.4b.5h, 1b.2a.3a.4b.5i,
1b.2a.3a.4b.5n, 1b.2a.3a.4d.5a, 1b.2a.3a.4d.5b, 1b.2a.3a.4d.5d, 1b.2a.3a.4d.5f,
1b.2a.3a.4d.5h, 1b.2a.3a.4d.5i, 1b.2a.3a.4d.5n, 1b.2a.3a.4f.5a, 1b.2a.3a.4f.5b,
1b.2a.3a.4f.5d, 1b.2a.3a.4f.5f, 1b.2a.3a.4f.5h, 1b.2a.3a.4f.5i, 1b.2a.3a.4f.5n,
1b.2a.3a.4i.5a, 1b.2a.3a.4i.5b, 1b.2a.3a.4i.5d, 1b.2a.3a.4i.5f, 1b.2a.3a.4i.5h,
1b.2a.3a.4i.5i, 1b.2a.3a.4i.5n, 1b.2a.3a.4n.5a, 1b.2a.3a.4n.5b, 1b.2a.3a.4n.5d,
1b.2a.3a.4n.5f, 1b.2a.3a.4n.5h, 1b.2a.3a.4n.5i, 1b.2a.3a.4n.5n, 1b.2a.3a.4p.5a,
1b.2a.3a.4p.5b, 1b.2a.3a.4p.5d, 1b.2a.3a.4p.5f, 1b.2a.3a.4p.5h, 1b.2a.3a.4p.5i,
1b.2a.3a.4p.5n, 1b.2a.3c.4a.5a, 1b.2a.3c.4a.5b, 1b.2a.3c.4a.5d, 1b.2a.3c.4a.5f,
1b.2a.3c.4a.5h, 1b.2a.3c.4a.5i, 1b.2a.3c.4a.5n, 1b.2a.3c.4b.5a, 1b.2a.3c.4b.5b,
1b.2a.3c.4b.5d, 1b.2a.3c.4b.5f, 1b.2a.3c.4b.5h, 1b.2a.3c.4b.5i, 1b.2a.3c.4b.5n,
1b.2a.3c.4d.5a, 1b.2a.3c.4d.5b, 1b.2a.3c.4d.5d, 1b.2a.3c.4d.5f, 1b.2a.3c.4d.5h,
1b.2a.3c.4d.5i, 1b.2a.3c.4d.5n, 1b.2a.3c.4f.5a, 1b.2a.3c.4f.5b, 1b.2a.3c.4f.5d,
1b.2a.3c.4f.5f, 1b.2a.3c.4f.5h, 1b.2a.3c.4f.5i, 1b.2a.3c.4f.5n, 1b.2a.3c.4i.5a,
1b.2a.3c.4i.5b, 1b.2a.3c.4i.5d, 1b.2a.3c.4i.5f, 1b.2a.3c.4i.5h, 1b.2a.3c.4i.5i,
1b.2a.3c.4i.5n, 1b.2a.3c.4n.5a, 1b.2a.3c.4n.5b, 1b.2a.3c.4n.5d, 1b.2a.3c.4n.5f,
1b.2a.3c.4n.5h, 1b.2a.3c.4n.5i, 1b.2a.3c.4n.5n, 1b.2a.3c.4p.5a, 1b.2a.3c.4p.5b,
1b.2a.3c.4p.5d, 1b.2a.3c.4p.5f, 1b.2a.3c.4p.5h, 1b.2a.3c.4p.5i, 1b.2a.3c.4p.5n,
1b.2a.3e.4a.5a, 1b.2a.3e.4a.5b, 1b.2a.3e.4a.5d, 1b.2a.3e.4a.5f, 1b.2a.3e.4a.5h,
1b.2a.3e.4a.5i, 1b.2a.3e.4a.5n, 1b.2a.3e.4b.5a, 1b.2a.3e.4b.5b, 1b.2a.3e.4b.5d,
1b.2a.3e.4b.5f, 1b.2a.3e.4b.5h, 1b.2a.3e.4b.5i, 1b.2a.3e.4b.5n, 1b.2a.3e.4d.5a,
1b.2a.3e.4d.5b, 1b.2a.3e.4d.5d, 1b.2a.3e.4d.5f, 1b.2a.3e.4d.5h, 1b.2a.3e.4d.5i,
1b.2a.3e.4d.5n, 1b.2a.3e.4f.5a, 1b.2a.3e.4f.5b, 1b.2a.3e.4f.5d, 1b.2a.3e.4f.5f,
1b.2a.3e.4f.5h, 1b.2a.3e.4f.5i, 1b.2a.3e.4f.5n, 1b.2a.3e.4i.5a, 1b.2a.3e.4i.5b,
1b.2a.3e.4i.5d, 1b.2a.3e.4i.5f, 1b.2a.3e.4i.5h, 1b.2a.3e.4i.5i, 1b.2a.3e.4i.5n,
1b.2a.3e.4n.5a, 1b.2a.3e.4n.5b, 1b.2a.3e.4n.5d, 1b.2a.3e.4n.5f, 1b.2a.3e.4n.5h,
1b.2a.3e.4n.5i, 1b.2a.3e.4n.5n, 1b.2a.3e.4p.5a, 1b.2a.3e.4p.5b, 1b.2a.3e.4p.5d,
1b.2a.3e.4p.5f, 1b.2a.3e.4p.5h, 1b.2a.3e.4p.5i, 1b.2a.3e.4p.5n, 1b.2a.3g.4a.5a,
1b.2a.3g.4a.5b, 1b.2a.3g.4a.5d, 1b.2a.3g.4a.5f, 1b.2a.3g.4a.5h, 1b.2a.3g.4a.5i,
1b.2a.3g.4a.5n, 1b.2a.3g.4b.5a, 1b.2a.3g.4b.5b, 1b.2a.3g.4b.5d, 1b.2a.3g.4b.5f,
1b.2a.3g.4b.5h, 1b.2a.3g.4b.5i, 1b.2a.3g.4b.5n, 1b.2a.3g.4d.5a, 1b.2a.3g.4d.5b, TABLE 12-continued List of Compound Structures of Formula II 1b.2a.3g.4d.5d, 1b.2a.3g.4d.5f, 1b.2a.3g.4d.5h, 1b.2a.3g.4d.5i, 1b.2a.3g.4d.5n,
1b.2a.3g.4f.5a, 1b.2a.3g.4f.5b, 1b.2a.3g.4f.5d, 1b.2a.3g.4f.5f, 1b.2a.3g.4f.5h,
1b.2a.3g.4f.5i, 1b.2a.3g.4f.5n, 1b.2a.3g.4i.5a, 1b.2a.3g.4i.5b, 1b.2a.3g.4i.5d,
1b.2a.3g.4i.5f, 1b.2a.3g.4i.5h, 1b.2a.3g.4i.5i, 1b.2a.3g.4i.5n, 1b.2a.3g.4n.5a,
1b.2a.3g.4n.5b, 1b.2a.3g.4n.5d, 1b.2a.3g.4n.5f, 1b.2a.3g.4n.5h, 1b.2a.3g.4n.5i,
1b.2a.3g.4n.5n, 1b.2a.3g.4p.5a, 1b.2a.3g.4p.5b, 1b.2a.3g.4p.5d, 1b.2a.3g.4p.5f,
1b.2a.3g.4p.5h, 1b.2a.3g.4p.5i, 1b.2a.3g.4p.5n, 1b.2b.3a.4a.5a, 1b.2b.3a.4a.5b,
1b.2b.3a.4a.5d, 1b.2b.3a.4a.5f, 1b.2b.3a.4a.5h, 1b.2b.3a.4a.5i, 1b.2b.3a.4a.5n,
1b.2b.3a.4b.5a, 1b.2b.3a.4b.5b, 1b.2b.3a.4b.5d, 1b.2b.3a.4b.5f, 1b.2b.3a.4b.5h,
1b.2b.3a.4b.5i, 1b.2b.3a.4b.5n, 1b.2b.3a.4d.5a, 1b.2b.3a.4d.5b, 1b.2b.3a.4d.5d,
1b.2b.3a.4d.5f, 1b.2b.3a.4d.5h, 1b.2b.3a.4d.5i, 1b.2b.3a.4d.5n, 1b.2b.3a.4f.5a,
1b.2b.3a.4f.5b, 1b.2b.3a.4f.5d, 1b.2b.3a.4f.5f, 1b.2b.3a.4f.5h, 1b.2b.3a.4f.5i,
1b.2b.3a.4f.5n, 1b.2b.3a.4i.5a, 1b.2b.3a.4i.5b, 1b.2b.3a.4i.5d, 1b.2b.3a.4i.5f,
1b.2b.3a.4i.5h, 1b.2b.3a.4i.5i, 1b.2b.3a.4i.5n, 1b.2b.3a.4n.5a, 1b.2b.3a.4n.5b,
1b.2b.3a.4n.5d, 1b.2b.3a.4n.5f, 1b.2b.3a.4n.5h, 1b.2b.3a.4n.5i, 1b.2b.3a.4n.5n,
1b.2b.3a.4p.5a, 1b.2b.3a.4p.5b, 1b.2b.3a.4p.5d, 1b.2b.3a.4p.5f, 1b.2b.3a.4p.5h,
1b.2b.3a.4p.5i, 1b.2b.3a.4p.5n, 1b.2b.3c.4a.5a, 1b.2b.3c.4a.5b, 1b.2b.3c.4a.5d,
1b.2b.3c.4a.5f, 1b.2b.3c.4a.5h, 1b.2b.3c.4a.5i, 1b.2b.3c.4a.5n, 1b.2b.3c.4b.5a,
1b.2b.3c.4b.5b, 1b.2b.3c.4b.5d, 1b.2b.3c.4b.5f, 1b.2b.3c.4b.5h, 1b.2b.3c.4b.5i,
1b.2b.3c.4b.5n, 1b.2b.3c.4d.5a, 1b.2b.3c.4d.5b, 1b.2b.3c.4d.5d, 1b.2b.3c.4d.5f,
1b.2b.3c.4d.5h, 1b.2b.3c.4d.5i, 1b.2b.3c.4d.5n, 1b.2b.3c.4f.5a, 1b.2b.3c.4f.5b,
1b.2b.3c.4f.5d, 1b.2b.3c.4f.5f, 1b.2b.3c.4f.5h, 1b.2b.3c.4f.5i, 1b.2b.3c.4f.5n,
1b.2b.3c.4i.5a, 1b.2b.3c.4i.5b, 1b.2b.3c.4i.5d, 1b.2b.3c.4i.5f, 1b.2b.3c.4i.5h,
1b.2b.3c.4i.5i, 1b.2b.3c.4i.5n, 1b.2b.3c.4n.5a, 1b.2b.3c.4n.5b, 1b.2b.3c.4n.5d,
1b.2b.3c.4n.5f, 1b.2b.3c.4n.5h, 1b.2b.3c.4n.5i, 1b.2b.3c.4n.5n, 1b.2b.3c.4p.5a,
1b.2b.3c.4p.5b, 1b.2b.3c.4p.5d, 1b.2b.3c.4p.5f, 1b.2b.3c.4p.5h, 1b.2b.3c.4p.5i,
1b.2b.3c.4p.5n, 1b.2b.3e.4a.5a, 1b.2b.3e.4a.5b, 1b.2b.3e.4a.5d, 1b.2b.3e.4a.5f,
1b.2b.3e.4a.5h, 1b.2b.3e.4a.5i, 1b.2b.3e.4a.5n, 1b.2b.3e.4b.5a, 1b.2b.3e.4b.5b,
1b.2b.3e.4b.5d, 1b.2b.3e.4b.5f, 1b.2b.3e.4b.5h, 1b.2b.3e.4b.5i, 1b.2b.3e.4b.5n,
1b.2b.3e.4d.5a, 1b.2b.3e.4d.5b, 1b.2b.3e.4d.5d, 1b.2b.3e.4d.5f, 1b.2b.3e.4d.5h,
1b.2b.3e.4d.5i, 1b.2b.3e.4d.5n, 1b.2b.3e.4f.5a, 1b.2b.3e.4f.5b, 1b.2b.3e.4f.5d,
1b.2b.3e.4f.5f, 1b.2b.3e.4f.5h, 1b.2b.3e.4f.5i, 1b.2b.3e.4f.5n, 1b.2b.3e.4i.5a,
1b.2b.3e.4i.5b, 1b.2b.3e.4i.5d, 1b.2b.3e.4i.5f, 1b.2b.3e.4i.5h, 1b.2b.3e.4i.5i,
1b.2b.3e.4i.5n, 1b.2b.3e.4n.5a, 1b.2b.3e.4n.5b, 1b.2b.3e.4n.5d, 1b.2b.3e.4n.5f,
1b.2b.3e.4n.5h, 1b.2b.3e.4n.5i, 1b.2b.3e.4n.5n, 1b.2b.3e.4p.5a, 1b.2b.3e.4p.5b,
1b.2b.3e.4p.5d, 1b.2b.3e.4p.5f, 1b.2b.3e.4p.5h, 1b.2b.3e.4p.5i, 1b.2b.3e.4p.5n,
1b.2b.3g.4a.5a, 1b.2b.3g.4a.5b, 1b.2b.3g.4a.5d, 1b.2b.3g.4a.5f, 1b.2b.3g.4a.5h,
1b.2b.3g.4a.5i, 1b.2b.3g.4a.5n, 1b.2b.3g.4b.5a, 1b.2b.3g.4b.5b, 1b.2b.3g.4b.5d,
1b.2b.3g.4b.5f, 1b.2b.3g.4b.5h, 1b.2b.3g.4b.5i, 1b.2b.3g.4b.5n, 1b.2b.3g.4d.5a,
1b.2b.3g.4d.5b, 1b.2b.3g.4d.5d, 1b.2b.3g.4d.5f, 1b.2b.3g.4d.5h, 1b.2b.3g.4d.5i,
1b.2b.3g.4d.5n, 1b.2b.3g.4f.5a, 1b.2b.3g.4f.5b, 1b.2b.3g.4f.5d, 1b.2b.3g.4f.5f,
1b.2b.3g.4f.5h, 1b.2b.3g.4f.5i, 1b.2b.3g.4f.5n, 1b.2b.3g.4i.5a, 1b.2b.3g.4i.5b,
1b.2b.3g.4i.5d, 1b.2b.3g.4i.5f, 1b.2b.3g.4i.5h, 1b.2b.3g.4i.5i, 1b.2b.3g.4i.5n,
1b.2b.3g.4n.5a, 1b.2b.3g.4n.5b, 1b.2b.3g.4n.5d, 1b.2b.3g.4n.5f, 1b.2b.3g.4n.5h,
1b.2b.3g.4n.5i, 1b.2b.3g.4n.5n, 1b.2b.3g.4p.5a, 1b.2b.3g.4p.5b, 1b.2b.3g.4p.5d,
1b.2b.3g.4p.5f, 1b.2b.3g.4p.5h, 1b.2b.3g.4p.5i, 1b.2b.3g.4p.5n, 1b.2e.3a.4a.5a,
1b.2e.3a.4a.5b, 1b.2e.3a.4a.5d, 1b.2e.3a.4a.5f, 1b.2e.3a.4a.5h, 1b.2e.3a.4a.5i,
1b.2e.3a.4a.5n, 1b.2e.3a.4b.5a, 1b.2e.3a.4b.5b, 1b.2e.3a.4b.5d, 1b.2e.3a.4b.5f,
1b.2e.3a.4b.5h, 1b.2e.3a.4b.5i, 1b.2e.3a.4b.5n, 1b.2e.3a.4d.5a, 1b.2e.3a.4d.5b,
1b.2e.3a.4d.5d, 1b.2e.3a.4d.5f, 1b.2e.3a.4d.5h, 1b.2e.3a.4d.5i, 1b.2e.3a.4d.5n,
1b.2e.3a.4f.5a, 1b.2e.3a.4f.5b, 1b.2e.3a.4f.5d, 1b.2e.3a.4f.5f, 1b.2e.3a.4f.5h,
1b.2e.3a.4f.5i, 1b.2e.3a.4f.5n, 1b.2e.3a.4i.5a, 1b.2e.3a.4i.5b, 1b.2e.3a.4i.5d,
1b.2e.3a.4i.5f, 1b.2e.3a.4i.5h, 1b.2e.3a.4i.5i, 1b.2e.3a.4i.5n, 1b.2e.3a.4n.5a,
1b.2e.3a.4n.5b, 1b.2e.3a.4n.5d, 1b.2e.3a.4n.5f, 1b.2e.3a.4n.5h, 1b.2e.3a.4n.5i,
1b.2e.3a.4n.5n, 1b.2e.3a.4p.5a, 1b.2e.3a.4p.5b, 1b.2e.3a.4p.5d, 1b.2e.3a.4p.5f,
1b.2e.3a.4p.5h, 1b.2e.3a.4p.5i, 1b.2e.3a.4p.5n, 1b.2e.3c.4a.5a, 1b.2e.3c.4a.5b,
1b.2e.3c.4a.5d, 1b.2e.3c.4a.5f, 1b.2e.3c.4a.5h, 1b.2e.3c.4a.5i, 1b.2e.3c.4a.5n,
1b.2e.3c.4b.5a, 1b.2e.3c.4b.5b, 1b.2e.3c.4b.5d, 1b.2e.3c.4b.5f, 1b.2e.3c.4b.5h,
1b.2e.3c.4b.5i, 1b.2e.3c.4b.5n, 1b.2e.3c.4d.5a, 1b.2e.3c.4d.5b, 1b.2e.3c.4d.5d,
1b.2e.3c.4d.5f, 1b.2e.3c.4d.5h, 1b.2e.3c.4d.5i, 1b.2e.3c.4d.5n, 1b.2e.3c.4f.5a,
1b.2e.3c.4f.5b, 1b.2e.3c.4f.5d, 1b.2e.3c.4f.5f, 1b.2e.3c.4f.5h, 1b.2e.3c.4f.5i,
1b.2e.3c.4f.5n, 1b.2e.3c.4i.5a, 1b.2e.3c.4i.5b, 1b.2e.3c.4i.5d, 1b.2e.3c.4i.5f,
1b.2e.3c.4i.5h, 1b.2e.3c.4i.5i, 1b.2e.3c.4i.5n, 1b.2e.3c.4n.5a, 1b.2e.3c.4n.5b,
1b.2e.3c.4n.5d, 1b.2e.3c.4n.5f, 1b.2e.3c.4n.5h, 1b.2e.3c.4n.5i, 1b.2e.3c.4n.5n,
1b.2e.3c.4p.5a, 1b.2e.3c.4p.5b, 1b.2e.3c.4p.5d, 1b.2e.3c.4p.5f, 1b.2e.3c.4p.5h,
1b.2e.3c.4p.5i, 1b.2e.3c.4p.5n, 1b.2e.3e.4a.5a, 1b.2e.3e.4a.5b, 1b.2e.3e.4a.5d,
1b.2e.3e.4a.5f, 1b.2e.3e.4a.5h, 1b.2e.3e.4a.5i, 1b.2e.3e.4a.5n, 1b.2e.3e.4b.5a,
1b.2e.3e.4b.5b, 1b.2e.3e.4b.5d, 1b.2e.3e.4b.5f, 1b.2e.3e.4b.5h, 1b.2e.3e.4b.5i,
1b.2e.3e.4b.5n, 1b.2e.3e.4d.5a, 1b.2e.3e.4d.5b, 1b.2e.3e.4d.5d, 1b.2e.3e.4d.5f,
1b.2e.3e.4d.5h, 1b.2e.3e.4d.5i, 1b.2e.3e.4d.5n, 1b.2e.3e.4f.5a, 1b.2e.3e.4f.5b,
1b.2e.3e.4f.5d, 1b.2e.3e.4f.5f, 1b.2e.3e.4f.5h, 1b.2e.3e.4f.5i, 1b.2e.3e.4f.5n,
1b.2e.3e.4i.5a, 1b.2e.3e.4i.5b, 1b.2e.3e.4i.5d, 1b.2e.3e.4i.5f, 1b.2e.3e.4i.5h,
1b.2e.3e.4i.5i, 1b.2e.3e.4i.5n, 1b.2e.3e.4n.5a, 1b.2e.3e.4n.5b, 1b.2e.3e.4n.5d,
1b.2e.3e.4n.5f, 1b.2e.3e.4n.5h, 1b.2e.3e.4n.5i, 1b.2e.3e.4n.5n, 1b.2e.3e.4p.5a,
1b.2e.3e.4p.5b, 1b.2e.3e.4p.5d, 1b.2e.3e.4p.5f, 1b.2e.3e.4p.5h, 1b.2e.3e.4p.5i,
1b.2e.3e.4p.5n, 1b.2e.3g.4a.5a, 1b.2e.3g.4a.5b, 1b.2e.3g.4a.5d, 1b.2e.3g.4a.5f,
1b.2e.3g.4a.5h, 1b.2e.3g.4a.5i, 1b.2e.3g.4a.5n, 1b.2e.3g.4b.5a, 1b.2e.3g.4b.5b,
1b.2e.3g.4b.5d, 1b.2e.3g.4b.5f, 1b.2e.3g.4b.5h, 1b.2e.3g.4b.5i, 1b.2e.3g.4b.5n,

TABLE 12-continued

List of Compound Structures of Formula II 1b.2e.3g.4d.5a, 1b.2e.3g.4d.5b, 1b.2e.3g.4d.5d, 1b.2e.3g.4d.5f, 1b.2e.3g.4d.5h,
1b.2e.3g.4d.5i, 1b.2e.3g.4d.5n, 1b.2e.3g.4f.5a, 1b.2e.3g.4f.5b, 1b.2e.3g.4f.5d,
1b.2e.3g.4f.5f, 1b.2e.3g.4f.5h, 1b.2e.3g.4f.5i, 1b.2e.3g.4f.5n, 1b.2e.3g.4i.5a,
1b.2e.3g.4i.5b, 1b.2e.3g.4i.5d, 1b.2e.3g.4i.5f, 1b.2e.3g.4i.5h, 1b.2e.3g.4i.5i,
1b.2e.3g.4i.5n, 1b.2e.3g.4n.5a, 1b.2e.3g.4n.5b, 1b.2e.3g.4n.5d, 1b.2e.3g.4n.5f,
1b.2e.3g.4n.5h, 1b.2e.3g.4n.5i, 1b.2e.3g.4n.5n, 1b.2e.3g.4p.5a, 1b.2e.3g.4p.5b,
1b.2e.3g.4p.5d, 1b.2e.3g.4p.5f, 1b.2e.3g.4p.5h, 1b.2e.3g.4p.5i, 1b.2e.3g.4p.5n,
1b.2f.3a.4a.5a, 1b.2f.3a.4a.5b, 1b.2f.3a.4a.5d, 1b.2f.3a.4a.5f, 1b.2f.3a.4a.5h,
1b.2f.3a.4a.5i, 1b.2f.3a.4a.5n, 1b.2f.3a.4b.5a, 1b.2f.3a.4b.5b, 1b.2f.3a.4b.5d,
1b.2f.3a.4b.5f, 1b.2f.3a.4b.5h, 1b.2f.3a.4b.5i, 1b.2f.3a.4b.5n, 1b.2f.3a.4d.5a,
1b.2f.3a.4d.5b, 1b.2f.3a.4d.5d, 1b.2f.3a.4d.5f, 1b.2f.3a.4d.5h, 1b.2f.3a.4d.5i,
1b.2f.3a.4d.5n, 1b.2f.3a.4f.5a, 1b.2f.3a.4f.5b, 1b.2f.3a.4f.5d, 1b.2f.3a.4f.5f,
1b.2f.3a.4f.5h, 1b.2f.3a.4f.5i, 1b.2f.3a.4f.5n, 1b.2f.3a.4i.5a, 1b.2f.3a.4i.5b,
1b.2f.3a.4i.5d, 1b.2f.3a.4i.5f, 1b.2f.3a.4i.5h, 1b.2f.3a.4i.5i, 1b.2f.3a.4i.5n,
1b.2f.3a.4n.5a, 1b.2f.3a.4n.5b, 1b.2f.3a.4n.5d, 1b.2f.3a.4n.5f, 1b.2f.3a.4n.5h,
1b.2f.3a.4n.5i, 1b.2f.3a.4n.5n, 1b.2f.3a.4p.5a, 1b.2f.3a.4p.5b, 1b.2f.3a.4p.5d,
1b.2f.3a.4p.5f, 1b.2f.3a.4p.5h, 1b.2f.3a.4p.5i, 1b.2f.3a.4p.5n, 1b.2f.3c.4a.5a,
1b.2f.3c.4a.5b, 1b.2f.3c.4a.5d, 1b.2f.3c.4a.5f, 1b.2f.3c.4a.5h, 1b.2f.3c.4a.5i,
1b.2f.3c.4a.5n, 1b.2f.3c.4b.5a, 1b.2f.3c.4b.5b, 1b.2f.3c.4b.5d, 1b.2f.3c.4b.5f,
1b.2f.3c.4b.5h, 1b.2f.3c.4b.5i, 1b.2f.3c.4b.5n, 1b.2f.3c.4d.5a, 1b.2f.3c.4d.5b,
1b.2f.3c.4d.5d, 1b.2f.3c.4d.5f, 1b.2f.3c.4d.5h, 1b.2f.3c.4d.5i, 1b.2f.3c.4d.5n,
1b.2f.3c.4f.5a, 1b.2f.3c.4f.5b, 1b.2f.3c.4f.5d, 1b.2f.3c.4f.5f, 1b.2f.3c.4f.5h,
1b.2f.3c.4f.5i, 1b.2f.3c.4f.5n, 1b.2f.3c.4i.5a, 1b.2f.3c.4i.5b, 1b.2f.3c.4i.5d,
1b.2f.3c.4i.5f, 1b.2f.3c.4i.5h, 1b.2f.3c.4i.5i, 1b.2f.3c.4i.5n, 1b.2f.3c.4n.5a,
1b.2f.3c.4n.5b, 1b.2f.3c.4n.5d, 1b.2f.3c.4n.5f, 1b.2f.3c.4n.5h, 1b.2f.3c.4n.5i,
1b.2f.3c.4n.5n, 1b.2f.3c.4p.5a, 1b.2f.3c.4p.5b, 1b.2f.3c.4p.5d, 1b.2f.3c.4p.5f,
1b.2f.3c.4p.5h, 1b.2f.3c.4p.5i, 1b.2f.3c.4p.5n, 1b.2f.3e.4a.5a, 1b.2f.3e.4a.5b,
1b.2f.3e.4a.5d, 1b.2f.3e.4a.5f, 1b.2f.3e.4a.5h, 1b.2f.3e.4a.5i, 1b.2f.3e.4a.5n,
1b.2f.3e.4b.5a, 1b.2f.3e.4b.5b, 1b.2f.3e.4b.5d, 1b.2f.3e.4b.5f, 1b.2f.3e.4b.5h,
1b.2f.3e.4b.5i, 1b.2f.3e.4b.5n, 1b.2f.3e.4d.5a, 1b.2f.3e.4d.5b, 1b.2f.3e.4d.5d,
1b.2f.3e.4d.5f, 1b.2f.3e.4d.5h, 1b.2f.3e.4d.5i, 1b.2f.3e.4d.5n, 1b.2f.3e.4f.5a,
1b.2f.3e.4f.5b, 1b.2f.3e.4f.5d, 1b.2f.3e.4f.5f, 1b.2f.3e.4f.5h, 1b.2f.3e.4f.5i,
1b.2f.3e.4f.5n, 1b.2f.3e.4i.5a, 1b.2f.3e.4i.5b, 1b.2f.3e.4i.5d, 1b.2f.3e.4i.5f,
1b.2f.3e.4i.5h, 1b.2f.3e.4i.5i, 1b.2f.3e.4i.5n, 1b.2f.3e.4n.5a, 1b.2f.3e.4n.5b,
1b.2f.3e.4n.5d, 1b.2f.3e.4n.5f, 1b.2f.3e.4n.5h, 1b.2f.3e.4n.5i, 1b.2f.3e.4n.5n,
1b.2f.3e.4p.5a, 1b.2f.3e.4p.5b, 1b.2f.3e.4p.5d, 1b.2f.3e.4p.5f, 1b.2f.3e.4p.5h,
1b.2f.3e.4p.5i, 1b.2f.3e.4p.5n, 1b.2f.3g.4a.5a, 1b.2f.3g.4a.5b, 1b.2f.3g.4a.5d,
1b.2f.3g.4a.5f, 1b.2f.3g.4a.5h, 1b.2f.3g.4a.5i, 1b.2f.3g.4a.5n, 1b.2f.3g.4b.5a,
1b.2f.3g.4b.5b, 1b.2f.3g.4b.5d, 1b.2f.3g.4b.5f, 1b.2f.3g.4b.5h, 1b.2f.3g.4b.5i,
1b.2f.3g.4b.5n, 1b.2f.3g.4d.5a, 1b.2f.3g.4d.5b, 1b.2f.3g.4d.5d, 1b.2f.3g.4d.5f,
1b.2f.3g.4d.5h, 1b.2f.3g.4d.5i, 1b.2f.3g.4d.5n, 1b.2f.3g.4f.5a, 1b.2f.3g.4f.5b,
1b.2f.3g.4f.5d, 1b.2f.3g.4f.5f, 1b.2f.3g.4f.5h, 1b.2f.3g.4f.5i, 1b.2f.3g.4f.5n,
1b.2f.3g.4i.5a, 1b.2f.3g.4i.5b, 1b.2f.3g.4i.5d, 1b.2f.3g.4i.5f, 1b.2f.3g.4i.5h,
1b.2f.3g.4i.5i, 1b.2f.3g.4i.5n, 1b.2f.3g.4n.5a, 1b.2f.3g.4n.5b, 1b.2f.3g.4n.5d,
1b.2f.3g.4n.5f, 1b.2f.3g.4n.5h, 1b.2f.3g.4n.5i, 1b.2f.3g.4n.5n, 1b.2f.3g.4p.5a,
1b.2f.3g.4p.5b, 1b.2f.3g.4p.5d, 1b.2f.3g.4p.5f, 1b.2f.3g.4p.5h, 1b.2f.3g.4p.5i,
1b.2f.3g.4p.5n, 1b.2g.3a.4a.5a, 1b.2g.3a.4a.5b, 1b.2g.3a.4a.5d, 1b.2g.3a.4a.5f,
1b.2g.3a.4a.5h, 1b.2g.3a.4a.5i, 1b.2g.3a.4a.5n, 1b.2g.3a.4b.5a, 1b.2g.3a.4b.5b,
1b.2g.3a.4b.5d, 1b.2g.3a.4b.5f, 1b.2g.3a.4b.5h, 1b.2g.3a.4b.5i, 1b.2g.3a.4b.5n,
1b.2g.3a.4d.5a, 1b.2g.3a.4d.5b, 1b.2g.3a.4d.5d, 1b.2g.3a.4d.5f, 1b.2g.3a.4d.5h,
1b.2g.3a.4d.5i, 1b.2g.3a.4d.5n, 1b.2g.3a.4f.5a, 1b.2g.3a.4f.5b, 1b.2g.3a.4f.5d,
1b.2g.3a.4f.5f, 1b.2g.3a.4f.5h, 1b.2g.3a.4f.5i, 1b.2g.3a.4f.5n, 1b.2g.3a.4i.5a,
1b.2g.3a.4i.5b, 1b.2g.3a.4i.5d, 1b.2g.3a.4i.5f, 1b.2g.3a.4i.5h, 1b.2g.3a.4i.5i,
1b.2g.3a.4i.5n, 1b.2g.3a.4n.5a, 1b.2g.3a.4n.5b, 1b.2g.3a.4n.5d, 1b.2g.3a.4n.5f,
1b.2g.3a.4n.5h, 1b.2g.3a.4n.5i, 1b.2g.3a.4n.5n, 1b.2g.3a.4p.5a, 1b.2g.3a.4p.5b,
1b.2g.3a.4p.5d, 1b.2g.3a.4p.5f, 1b.2g.3a.4p.5h, 1b.2g.3a.4p.5i, 1b.2g.3a.4p.5n,
1b.2g.3c.4a.5a, 1b.2g.3c.4a.5b, 1b.2g.3c.4a.5d, 1b.2g.3c.4a.5f, 1b.2g.3c.4a.5h,
1b.2g.3c.4a.5i, 1b.2g.3c.4a.5n, 1b.2g.3c.4b.5a, 1b.2g.3c.4b.5b, 1b.2g.3c.4b.5d,
1b.2g.3c.4b.5f, 1b.2g.3c.4b.5h, 1b.2g.3c.4b.5i, 1b.2g.3c.4b.5n, 1b.2g.3c.4d.5a,
1b.2g.3c.4d.5b, 1b.2g.3c.4d.5d, 1b.2g.3c.4d.5f, 1b.2g.3c.4d.5h, 1b.2g.3c.4d.5i,
1b.2g.3c.4d.5n, 1b.2g.3c.4f.5a, 1b.2g.3c.4f.5b, 1b.2g.3c.4f.5d, 1b.2g.3c.4f.5f,
1b.2g.3c.4f.5h, 1b.2g.3c.4f.5i, 1b.2g.3c.4f.5n, 1b.2g.3c.4i.5a, 1b.2g.3c.4i.5b,
1b.2g.3c.4i.5d, 1b.2g.3c.4i.5f, 1b.2g.3c.4i.5h, 1b.2g.3c.4i.5i, 1b.2g.3c.4i.5n,
1b.2g.3c.4n.5a, 1b.2g.3c.4n.5b, 1b.2g.3c.4n.5d, 1b.2g.3c.4n.5f, 1b.2g.3c.4n.5h,
1b.2g.3c.4n.5i, 1b.2g.3c.4n.5n, 1b.2g.3c.4p.5a, 1b.2g.3c.4p.5b, 1b.2g.3c.4p.5d,
1b.2g.3c.4p.5f, 1b.2g.3c.4p.5h, 1b.2g.3c.4p.5i, 1b.2g.3c.4p.5n, 1b.2g.3e.4a.5a,
1b.2g.3e.4a.5b, 1b.2g.3e.4a.5d, 1b.2g.3e.4a.5f, 1b.2g.3e.4a.5h, 1b.2g.3e.4a.5i,
1b.2g.3e.4a.5n, 1b.2g.3e.4b.5a, 1b.2g.3e.4b.5b, 1b.2g.3e.4b.5d, 1b.2g.3e.4b.5f,
1b.2g.3e.4b.5h, 1b.2g.3e.4b.5i, 1b.2g.3e.4b.5n, 1b.2g.3e.4d.5a, 1b.2g.3e.4d.5b,
1b.2g.3e.4d.5d, 1b.2g.3e.4d.5f, 1b.2g.3e.4d.5h, 1b.2g.3e.4d.5i, 1b.2g.3e.4d.5n,
1b.2g.3e.4f.5a, 1b.2g.3e.4f.5b, 1b.2g.3e.4f.5d, 1b.2g.3e.4f.5f, 1b.2g.3e.4f.5h,
1b.2g.3e.4f.5i, 1b.2g.3e.4f.5n, 1b.2g.3e.4i.5a, 1b.2g.3e.4i.5b, 1b.2g.3e.4i.5d,
1b.2g.3e.4i.5f, 1b.2g.3e.4i.5h, 1b.2g.3e.4i.5i, 1b.2g.3e.4i.5n, 1b.2g.3e.4n.5a,
1b.2g.3e.4n.5b, 1b.2g.3e.4n.5d, 1b.2g.3e.4n.5f, 1b.2g.3e.4n.5h, 1b.2g.3e.4n.5i,
1b.2g.3e.4n.5n, 1b.2g.3e.4p.5a, 1b.2g.3e.4p.5b, 1b.2g.3e.4p.5d, 1b.2g.3e.4p.5f,
1b.2g.3e.4p.5h, 1b.2g.3e.4p.5i, 1b.2g.3e.4p.5n, 1b.2g.3g.4a.5a, 1b.2g.3g.4a.5b,
1b.2g.3g.4a.5d, 1b.2g.3g.4a.5f, 1b.2g.3g.4a.5h, 1b.2g.3g.4a.5i, 1b.2g.3g.4a.5n,
1b.2g.3g.4b.5a, 1b.2g.3g.4b.5b, 1b.2g.3g.4b.5d, 1b.2g.3g.4b.5f, 1b.2g.3g.4b.5h, TABLE 12-continued List of Compound Structures of Formula II 1b.2g.3g.4b.5i, 1b.2g.3g.4b.5n, 1b.2g.3g.4d.5a, 1b.2g.3g.4d.5b, 1b.2g.3g.4d.5d,
1b.2g.3g.4d.5f, 1b.2g.3g.4d.5h, 1b.2g.3g.4d.5i, 1b.2g.3g.4d.5n, 1b.2g.3g.4f.5a,
1b.2g.3g.4f.5b, 1b.2g.3g.4f.5d, 1b.2g.3g.4f.5f, 1b.2g.3g.4f.5h, 1b.2g.3g.4f.5i,
1b.2g.3g.4f.5n, 1b.2g.3g.4i.5a, 1b.2g.3g.4i.5b, 1b.2g.3g.4i.5d, 1b.2g.3g.4i.5f,
1b.2g.3g.4i.5h, 1b.2g.3g.4i.5i, 1b.2g.3g.4i.5n, 1b.2g.3g.4n.5a, 1b.2g.3g.4n.5b,
1b.2g.3g.4n.5d, 1b.2g.3g.4n.5f, 1b.2g.3g.4n.5h, 1b.2g.3g.4n.5i, 1b.2g.3g.4n.5n,
1b.2g.3g.4p.5a, 1b.2g.3g.4p.5b, 1b.2g.3g.4p.5d, 1b.2g.3g.4p.5f, 1b.2g.3g.4p.5h,
1b.2g.3g.4p.5i, 1b.2g.3g.4p.5n, 1b.2l.3a.4a.5a, 1b.2l.3a.4a.5b, 1b.2l.3a.4a.5d,
1b.2l.3a.4a.5f, 1b.2l.3a.4a.5h, 1b.2l.3a.4a.5i, 1b.2l.3a.4a.5n, 1b.2l.3a.4b.5a,
1b.2l.3a.4b.5b, 1b.2l.3a.4b.5d, 1b.2l.3a.4b.5f, 1b.2l.3a.4b.5h, 1b.2l.3a.4b.5i,
1b.2l.3a.4b.5n, 1b.2l.3a.4d.5a, 1b.2l.3a.4d.5b, 1b.2l.3a.4d.5d, 1b.2l.3a.4d.5f,
1b.2l.3a.4d.5h, 1b.2l.3a.4d.5i, 1b.2l.3a.4d.5n, 1b.2l.3a.4f.5a, 1b.2l.3a.4f.5b,
1b.2l.3a.4f.5d, 1b.2l.3a.4f.5f, 1b.2l.3a.4f.5h, 1b.2l.3a.4f.5i, 1b.2l.3a.4f.5n,
1b.2l.3a.4i.5a, 1b.2l.3a.4i.5b, 1b.2l.3a.4i.5d, 1b.2l.3a.4i.5f, 1b.2l.3a.4i.5h,
1b.2l.3a.4i.5i, 1b.2l.3a.4i.5n, 1b.2l.3a.4n.5a, 1b.2l.3a.4n.5b, 1b.2l.3a.4n.5d,
1b.2l.3a.4n.5f, 1b.2l.3a.4n.5h, 1b.2l.3a.4n.5i, 1b.2l.3a.4n.5n, 1b.2l.3a.4p.5a,
1b.2l.3a.4p.5b, 1b.2l.3a.4p.5d, 1b.2l.3a.4p.5f, 1b.2l.3a.4p.5h, 1b.2l.3a.4p.5i,
1b.2l.3a.4p.5n, 1b.2l.3c.4a.5a, 1b.2l.3c.4a.5b, 1b.2l.3c.4a.5d, 1b.2l.3c.4a.5f,
1b.2l.3c.4a.5h, 1b.2l.3c.4a.5i, 1b.2l.3c.4a.5n, 1b.2l.3c.4b.5a, 1b.2l.3c.4b.5b,
1b.2l.3c.4b.5d, 1b.2l.3c.4b.5f, 1b.2l.3c.4b.5h, 1b.2l.3c.4b.5i, 1b.2l.3c.4b.5n,
1b.2l.3c.4d.5a, 1b.2l.3c.4d.5b, 1b.2l.3c.4d.5d, 1b.2l.3c.4d.5f, 1b.2l.3c.4d.5h,
1b.2l.3c.4d.5i, 1b.2l.3c.4d.5n, 1b.2l.3c.4f.5a, 1b.2l.3c.4f.5b, 1b.2l.3c.4f.5d,
1b.2l.3c.4f.5f, 1b.2l.3c.4f.5h, 1b.2l.3c.4f.5i, 1b.2l.3c.4f.5n, 1b.2l.3c.4i.5a,
1b.2l.3c.4i.5b, 1b.2l.3c.4i.5d, 1b.2l.3c.4i.5f, 1b.2l.3c.4i.5h, 1b.2l.3c.4i.5i,
1b.2l.3c.4i.5n, 1b.2l.3c.4n.5a, 1b.2l.3c.4n.5b, 1b.2l.3c.4n.5d, 1b.2l.3c.4n.5f,
1b.2l.3c.4n.5h, 1b.2l.3c.4n.5i, 1b.2l.3c.4n.5n, 1b.2l.3c.4p.5a, 1b.2l.3c.4p.5b,
1b.2l.3c.4p.5d, 1b.2l.3c.4p.5f, 1b.2l.3c.4p.5h, 1b.2l.3c.4p.5i, 1b.2l.3c.4p.5n,
1b.2l.3e.4a.5a, 1b.2l.3e.4a.5b, 1b.2l.3e.4a.5d, 1b.2l.3e.4a.5f, 1b.2l.3e.4a.5h,
1b.2l.3e.4a.5i, 1b.2l.3e.4a.5n, 1b.2l.3e.4b.5a, 1b.2l.3e.4b.5b, 1b.2l.3e.4b.5d,
1b.2l.3e.4b.5f, 1b.2l.3e.4b.5h, 1b.2l.3e.4b.5i, 1b.2l.3e.4b.5n, 1b.2l.3e.4d.5a,
1b.2l.3e.4d.5b, 1b.2l.3e.4d.5d, 1b.2l.3e.4d.5f, 1b.2l.3e.4d.5h, 1b.2l.3e.4d.5i,
1b.2l.3e.4d.5n, 1b.2l.3e.4f.5a, 1b.2l.3e.4f.5b, 1b.2l.3e.4f.5d, 1b.2l.3e.4f.5f,
1b.2l.3e.4f.5h, 1b.2l.3e.4f.5i, 1b.2l.3e.4f.5n, 1b.2l.3e.4i.5a, 1b.2l.3e.4i.5b,
1b.2l.3e.4i.5d, 1b.2l.3e.4i.5f, 1b.2l.3e.4i.5h, 1b.2l.3e.4i.5i, 1b.2l.3e.4i.5n,
1b.2l.3e.4n.5a, 1b.2l.3e.4n.5b, 1b.2l.3e.4n.5d, 1b.2l.3e.4n.5f, 1b.2l.3e.4n.5h,
1b.2l.3e.4n.5i, 1b.2l.3e.4n.5n, 1b.2l.3e.4p.5a, 1b.2l.3e.4p.5b, 1b.2l.3e.4p.5d,
1b.2l.3e.4p.5f, 1b.2l.3e.4p.5h, 1b.2l.3e.4p.5i, 1b.2l.3e.4p.5n, 1b.2l.3g.4a.5a,
1b.2l.3g.4a.5b, 1b.2l.3g.4a.5d, 1b.2l.3g.4a.5f, 1b.2l.3g.4a.5h, 1b.2l.3g.4a.5i,
1b.2l.3g.4a.5n, 1b.2l.3g.4b.5a, 1b.2l.3g.4b.5b, 1b.2l.3g.4b.5d, 1b.2l.3g.4b.5f,
1b.2l.3g.4b.5h, 1b.2l.3g.4b.5i, 1b.2l.3g.4b.5n, 1b.2l.3g.4d.5a, 1b.2l.3g.4d.5b,
1b.2l.3g.4d.5d, 1b.2l.3g.4d.5f, 1b.2l.3g.4d.5h, 1b.2l.3g.4d.5i, 1b.2l.3g.4d.5n,
1b.2l.3g.4f.5a, 1b.2l.3g.4f.5b, 1b.2l.3g.4f.5d, 1b.2l.3g.4f.5f, 1b.2l.3g.4f.5h,
1b.2l.3g.4f.5i, 1b.2l.3g.4f.5n, 1b.2l.3g.4i.5a, 1b.2l.3g.4i.5b, 1b.2l.3g.4i.5d,
1b.2l.3g.4i.5f, 1b.2l.3g.4i.5h, 1b.2l.3g.4i.5i, 1b.2l.3g.4i.5n, 1b.2l.3g.4n.5a,
1b.2l.3g.4n.5b, 1b.2l.3g.4n.5d, 1b.2l.3g.4n.5f, 1b.2l.3g.4n.5h, 1b.2l.3g.4n.5i,
1b.2l.3g.4n.5n, 1b.2l.3g.4p.5a, 1b.2l.3g.4p.5b, 1b.2l.3g.4p.5d, 1b.2l.3g.4p.5f,
1b.2l.3g.4p.5h, 1b.2l.3g.4p.5i, 1b.2l.3g.4p.5n, 1b.2m.3a.4a.5a, 1b.2m.3a.4a.5b,
1b.2m.3a.4a.5d, 1b.2m.3a.4a.5f, 1b.2m.3a.4a.5h, 1b.2m.3a.4a.5i, 1b.2m.3a.4a.5n,
1b.2m.3a.4b.5a, 1b.2m.3a.4b.5b, 1b.2m.3a.4b.5d, 1b.2m.3a.4b.5f, 1b.2m.3a.4b.5h,
1b.2m.3a.4b.5i, 1b.2m.3a.4b.5n, 1b.2m.3a.4d.5a, 1b.2m.3a.4d.5b, 1b.2m.3a.4d.5d,
1b.2m.3a.4d.5f, 1b.2m.3a.4d.5h, 1b.2m.3a.4d.5i, 1b.2m.3a.4d.5n, 1b.2m.3a.4f.5a,
1b.2m.3a.4f.5b, 1b.2m.3a.4f.5d, 1b.2m.3a.4f.5f, 1b.2m.3a.4f.5h, 1b.2m.3a.4f.5i,
1b.2m.3a.4f.5n, 1b.2m.5a.4i.5a, 1b.2m.3a.4i.5b, 1b.2m.3a.4i.5d, 1b.2m.3a.4i.5f,
1b.2m.3a.4f.5h, 1b.2m.3a.4i.5i, 1b.2m.3a.4i.5n, 1b.2m.3a.4n.5a, 1b.2m.3a.4n.5b,
1b.2m.3a.4n.5d, 1b.2m.3a.4n.5f, 1b.2m.3a.4n.5h, 1b.2m.3a.4n.5i, 1b.2m.3a.4n.5n,
1b.2m.3a.4p.5a, 1b.2m.3a.4p.5b, 1b.2m.3a.4p.5d, 1b.2m.3a.4p.5f, 1b.2m.3a.4p.5h,
1b.2m.3a.4p.5i, 1b.2m.3a.4p.5n, 1b.2m.3c.4a.5a, 1b.2m.3c.4a.5b, 1b.2m.3c.4a.5d,
1b.2m.3c.4a.5f, 1b.2m.3c.4a.5h, 1b.2m.3c.4a.5i, 1b.2m.3c.4a.5n, 1b.2m.3c.4b.5a,
1b.2m.3c.4b.5b, 1b.2m.3c.4b.5d, 1b.2m.3c.4b.5f, 1b.2m.3c.4b.5h, 1b.2m.3c.4b.5i,
1b.2m.3c.4b.5n, 1b.2m.3c.4d.5a, 1b.2m.3c.4d.5b, 1b.2m.3c.4d.5d, 1b.2m.3c.4d.5f,
1b.2m.3c.4d.5h, 1b.2m.3c.4d.5i, 1b.2m.3c.4d.5n, 1b.2m.3c.4f.5a, 1b.2m.3c.4f.5b,
1b.2m.3c.4f.5d, 1b.2m.3c.4f.5f, 1b.2m.3c.4f.5h, 1b.2m.3c.4f.5i, 1b.2m.3c.4f.5n,
1b.2m.3c.4i.5a, 1b.2m.3c.4i.5b, 1b.2m.3c.4i.5d, 1b.2m.3c.4i.5f, 1b.2m.3c.4i.5h,
1b.2m.3c.4i.5i, 1b.2m.3c.4i.5n, 1b.2m.3c.4n.5a, 1b.2m.3c.4n.5b, 1b.2m.3c.4n.5d,
1b.2m.3c.4n.5f, 1b.2m.3c.4n.5h, 1b.2m.3c.4n.5i, 1b.2m.3c.4n.5n, 1b.2m.3c.4p.5a,
1b.2m.3c.4p.5b, 1b.2m.3c.4p.5d, 1b.2m.3c.4p.5f, 1b.2m.3c.4p.5h, 1b.2m.3c.4p.5i,
1b.2m.3c.4p.5n, 1b.2m.3e.4a.5a, 1b.2m.3e.4a.5b, 1b.2m.3e.4a.5d, 1b.2m.3e.4a.5f,
1b.2m.3e.4a.5h, 1b.2m.3e.4a.5i, 1b.2m.3e.4a.5n, 1b.2m.3e.4b.5a, 1b.2m.3e.4b.5b,
1b.2m.3e.4b.5d, 1b.2m.3e.4b.5f, 1b.2m.3e.4b.5h, 1b.2m.3e.4b.5i, 1b.2m.3e.4b.5n,
1b.2m.3e.4d.5a, 1b.2m.3e.4d.5b, 1b.2m.3e.4d.5d, 1b.2m.3e.4d.5f, 1b.2m.3e.4d.5h,
1b.2m.3e.4d.5i, 1b.2m.3e.4d.5n, 1b.2m.3e.4f.5a, 1b.2m.3e.4f.5b, 1b.2m.3e.4f.5d,
1b.2m.3e.4f.5f, 1b.2m.3e.4f.5h, 1b.2m.3e.4f.5i, 1b.2m.3e.4f.5n, 1b.2m.3e.4i.5a,
1b.2m.3e.4i.5b, 1b.2m.3e.4i.5d, 1b.2m.3e.4i.5f, 1b.2m.3e.4i.5h, 1b.2m.3e.4i.5i,
1b.2m.3e.4i.5n, 1b.2m.3e.4n.5a, 1b.2m.3e.4n.5b, 1b.2m.3e.4n.5d, 1b.2m.3e.4n.5f,
1b.2m.3e.4n.5h, 1b.2m.3e.4n.5i, 1b.2m.3e.4n.5n, 1b.2m.3e.4p.5a, 1b.2m.3e.4p.5b,
1b.2m.3e.4p.5d, 1b.2m.3e.4p.5f, 1b.2m.3e.4p.5h, 1b.2m.3e.4p.5i, 1b.2m.3e.4p.5n,
1b.2m.3g.4a.5a, 1b.2m.3g.4a.5b, 1b.2m.3g.4a.5d, 1b.2m.3g.4a.5f, 1b.2m.3g.4a.5h,
1b.2m.3g.4a.5i, 1b.2m.3g.4a.5n, 1b.2m.3g.4b.5a, 1b.2m.3g.4b.5b, 1b.2m.3g.4b.5d,

TABLE 12-continued

List of Compound Structures of Formula II 1b.2m.3g.4b.5f, 1b.2m.3g.4b.5h, 1b.2m.3g.4b.5i, 1b.2m.3g.4b.5n, 1b.2m.3g.4d.5a,
1b.2m.3g.4d.5b, 1b.2m.3g.4d.5d, 1b.2m.3g.4d.5f, 1b.2m.3g.4d.5h, 1b.2m.3g.4d.5i,
1b.2m.3g.4d.5n, 1b.2m.3g.4f.5a, 1b.2m.3g.4f.5b, 1b.2m.3g.4f.5d, 1b.2m.3g.4f.5f,
1b.2m.3g.4f.5h, 1b.2m.3g.4f.5i, 1b.2m.3g.4f.5n, 1b.2m.3g.4i.5a, 1b.2m.3g.4i.5b,
1b.2m.3g.4i.5d, 1b.2m.3g.4i.5f, 1b.2m.3g.4i.5h, 1b.2m.3g.4i.5i, 1b.2m.3g.4i.5n,
1b.2m.3g.4n.5a, 1b.2m.3g.4n.5b, 1b.2m.3g.4n.5d, 1b.2m.3g.4n.5f, 1b.2m.3g.4n.5h,
1b.2m.3g.4n.5i, 1b.2m.3g.4n.5n, 1b.2m.3g.4p.5a, 1b.2m.3g.4p.5b, 1b.2m.3g.4p.5d,
1b.2m.3g.4p.5f, 1b.2m.3g.4p.5h, 1b.2m.3g.4p.5i, 1b.2m.3g.4p.5n, 1b.2n.3a.4a.5a,
1b.2n.3a.4a.5b, 1b.2n.3a.4a.5d, 1b.2n.3a.4a.5f, 1b.2n.3a.4a.5h, 1b.2n.3a.4a.5i,
1b.2n.3a.4a.5n, 1b.2n.3a.4b.5a, 1b.2n.3a.4b.5b, 1b.2n.3a.4b.5d, 1b.2n.3a.4b.5f,
1b.2n.3a.4b.5h, 1b.2n.3a.4b.5i, 1b.2n.3a.4b.5n, 1b.2n.3a.4d.5a, 1b.2n.3a.4d.5b,
1b.2n.3a.4d.5d, 1b.2n.3a.4d.5f, 1b.2n.3a.4d.5h, 1b.2n.3a.4d.5i, 1b.2n.3a.4d.5n,
1b.2n.3a.4f.5a, 1b.2n.3a.4f.5b, 1b.2n.3a.4f.5d, 1b.2n.3a.4f.5f, 1b.2n.3a.4f.5h,
1b.2n.3a.4f.5i, 1b.2n.3a.4f.5n, 1b.2n.3a.4i.5a, 1b.2n.3a.4i.5b, 1b.2n.3a.4i.5d,
1b.2n.3a.4i.5f, 1b.2n.3a.4i.5h, 1b.2n.3a.4i.5i, 1b.2n.3a.4i.5n, 1b.2n.3a.4n.5a,
1b.2n.3a.4n.5b, 1b.2n.3a.4n.5d, 1b.2n.3a.4n.5f, 1b.2n.3a.4n.5h, 1b.2n.3a.4n.5i,
1b.2n.3a.4n.5n, 1b.2n.3a.4p.5a, 1b.2n.3a.4p.5b, 1b.2n.3a.4p.5d, 1b.2n.3a.4p.5f,
1b.2n.3a.4p.5h, 1b.2n.3a.4p.5i, 1b.2n.3a.4p.5n, 1b.2n.3c.4a.5a, 1b.2n.3c.4a.5b,
1b.2n.3c.4a.5d, 1b.2n.3c.4a.5f, 1b.2n.3c.4a.5h, 1b.2n.3c.4a.5i, 1b.2n.3c.4a.5n,
1b.2n.3c.4b.5a, 1b.2n.3c.4b.5b, 1b.2n.3c.4b.5d, 1b.2n.3c.4b.5f, 1b.2n.3c.4b.5h,
1b.2n.3c.4b.5i, 1b.2n.3c.4b.5n, 1b.2n.3c.4d.5a, 1b.2n.3c.4d.5b, 1b.2n.3c.4d.5d,
1b.2n.3c.4d.5f, 1b.2n.3c.4d.5h, 1b.2n.3c.4d.5i, 1b.2n.3c.4d.5n, 1b.2n.3c.4f.5a,
1b.2n.3c.4f.5b, 1b.2n.3c.4f.5d, 1b.2n.3c.4f.5f, 1b.2n.3c.4f.5h, 1b.2n.3c.4f.5i,
1b.2n.3c.4f.5n, 1b.2n.3c.4i.5a, 1b.2n.3c.4i.5b, 1b.2n.3c.4i.5d, 1b.2n.3c.4i.5f,
1b.2n.3c.4i.5h, 1b.2n.3c.4i.5i, 1b.2n.3c.4i.5n, 1b.2n.3c.4n.5a, 1b.2n.3c.4n.5b,
1b.2n.3c.4n.5d, 1b.2n.3c.4n.5f, 1b.2n.3c.4n.5h, 1b.2n.3c.4n.5i, 1b.2n.3c.4n.5n,
1b.2n.3c.4p.5a, 1b.2n.3c.4p.5b, 1b.2n.3c.4p.5d, 1b.2n.3c.4p.5f, 1b.2n.3c.4p.5h,
1b.2n.3c.4p.5i, 1b.2n.3c.4p.5n, 1b.2n.3e.4a.5a, 1b.2n.3e.4a.5b, 1b.2n.3e.4a.5d,
1b.2n.3e.4a.5f, 1b.2n.3e.4a.5h, 1b.2n.3e.4a.5i, 1b.2n.3e.4a.5n, 1b.2n.3e.4b.5a,
1b.2n.3e.4b.5b, 1b.2n.3e.4b.5d, 1b.2n.3e.4b.5f, 1b.2n.3e.4b.5h, 1b.2n.3e.4b.5i,
1b.2n.3e.4b.5n, 1b.2n.3e.4d.5a, 1b.2n.3e.4d.5b, 1b.2n.3e.4d.5d, 1b.2n.3e.4d.5f,
1b.2n.3e.4d.5h, 1b.2n.3e.4d.5i, 1b.2n.3e.4d.5n, 1b.2n.3e.4f.5a, 1b.2n.3e.4f.5b,
1b.2n.3e.4f.5d, 1b.2n.3e.4f.5f, 1b.2n.3e.4f.5h, 1b.2n.3e.4f.5i, 1b.2n.3e.4f.5n,
1b.2n.3e.4i.5a, 1b.2n.3e.4i.5b, 1b.2n.3e.4i.5d, 1b.2n.3e.4i.5f, 1b.2n.3e.4i.5h,
1b.2n.3e.4i.5i, 1b.2n.3e.4i.5n, 1b.2n.3e.4n.5a, 1b.2n.3e.4n.5b, 1b.2n.3e.4n.5d,
1b.2n.3e.4n.5f, 1b.2n.3e.4n.5h, 1b.2n.3e.4n.5i, 1b.2n.3e.4n.5n, 1b.2n.3e.4p.5a,
1b.2n.3e.4p.5b, 1b.2n.3e.4p.5d, 1b.2n.3e.4p.5f, 1b.2n.3e.4p.5h, 1b.2n.3e.4p.5i,
1b.2n.3e.4p.5n, 1b.2n.3g.4a.5a, 1b.2n.3g.4a.5b, 1b.2n.3g.4a.5d, 1b.2n.3g.4a.5f,
1b.2n.3g.4a.5h, 1b.2n.3g.4a.5i, 1b.2n.3g.4a.5n, 1b.2n.3g.4b.5a, 1b.2n.3g.4b.5b,
1b.2n.3g.4b.5d, 1b.2n.3g.4b.5f, 1b.2n.3g.4b.5h, 1b.2n.3g.4b.5i, 1b.2n.3g.4b.5n,
1b.2n.3g.4d.5a, 1b.2n.3g.4d.5b, 1b.2n.3g.4d.5d, 1b.2n.3g.4d.5f, 1b.2n.3g.4d.5h,
1b.2n.3g.4d.5i, 1b.2n.3g.4d.5n, 1b.2n.3g.4f.5a, 1b.2n.3g.4f.5b, 1b.2n.3g.4f.5d,
1b.2n.3g.4d.5f, 1b.2n.3g.4f.5h, 1b.2n.3g.4f.5i, 1b.2n.3g.4f.5n, 1b.2n.3g.4i.5a,
1b.2n.3g.4i.5b, 1b.2n.3g.4i.5d, 1b.2n.3g.4i.5f, 1b.2n.3g.4i.5h, 1b.2n.3g.4i.5i,
1b.2n.3g.4i.5n, 1b.2n.3g.4n.5a, 1b.2n.3g.4n.5b, 1b.2n.3g.4n.5d, 1b.2n.3g.4n.5f,
1b.2n.3g.4n.5h, 1b.2n.3g.4n.5i, 1b.2n.3g.4n.5n, 1b.2n.3g.4p.5a, 1b.2n.3g.4p.5b,
1b.2n.3g.4p.5d, 1b.2n.3g.4p.5f, 1b.2n.3g.4p.5h, 1b.2n.3g.4p.5i, 1b.2n.3g.4p.5n,
1b.2q.3a.4a.5a, 1b.2q.3a.4a.5b, 1b.2q.3a.4a.5d, 1b.2q.3a.4a.5f, 1b.2q.3a.4a.5h,
1b.2q.3a.4a.5i, 1b.2q.3a.4a.5n, 1b.2q.3a.4b.5a, 1b.2q.3a.4b.5b, 1b.2q.3a.4b.5d,
1b.2q.3a.4b.5f, 1b.2q.3a.4b.5h, 1b.2q.3a.4b.5i, 1b.2q.3a.4b.5n, 1b.2q.3a.4d.5a,
1b.2q.3a.4d.5b, 1b.2q.3a.4d.5d, 1b.2q.3a.4d.5f, 1b.2q.3a.4d.5h, 1b.2q.3a.4d.5i,
1b.2q.3a.4d.5n, 1b.2q.3a.4f.5a, 1b.2q.3a.4f.5b, 1b.2q.3a.4f.5d, 1b.2q.3a.4f.5f,
1b.2q.3a.4f.5h, 1b.2q.3a.4f.5i, 1b.2q.3a.4f.5n, 1b.2q.3a.4i.5a, 1b.2q.3a.4i.5b,
1b.2q.3a.4i.5d, 1b.2q.3a.4i.5f, 1b.2q.3a.4i.5h, 1b.2q.3a.4i.5i, 1b.2q.3a.4i.5n,
1b.2q.3a.4n.5a, 1b.2q.3a.4n.5b, 1b.2q.3a.4n.5d, 1b.2q.3a.4n.5f, 1b.2q.3a.4n.5h,
1b.2q.3a.4n.5i, 1b.2q.3a.4n.5n, 1b.2q.3a.4p.5a, 1b.2q.3a.4p.5b, 1b.2q.3a.4p.5d,
1b.2q.3a.4p.5f, 1b.2q.3a.4p.5h, 1b.2q.3a.4p.5i, 1b.2q.3a.4p.5n, 1b.2q.3c.4a.5a,
1b.2q.3c.4a.5b, 1b.2q.3c.4a.5d, 1b.2q.3c.4a.5f, 1b.2q.3c.4a.5h, 1b.2q.3c.4a.5i,
1b.2q.3c.4a.5n, 1b.2q.3c.4b.5a, 1b.2q.3c.4b.5b, 1b.2q.3c.4b.5d, 1b.2q.3c.4b.5f,
1b.2q.3c.4b.5h, 1b.2q.3c.4b.5i, 1b.2q.3c.4b.5n, 1b.2q.3c.4d.5a, 1b.2q.3c.4d.5b,
1b.2q.3c.4d.5d, 1b.2q.3c.4d.5f, 1b.2q.3c.4d.5h, 1b.2q.3c.4d.5i, 1b.2q.3c.4d.5n,
1b.2q.3c.4f.5a, 1b.2q.3c.4f.5b, 1b.2q.3c.4f.5d, 1b.2q.3c.4f.5f, 1b.2q.3c.4f.5h,
1b.2q.3c.4f.5i, 1b.2q.3c.4f.5n, 1b.2q.3c.4i.5a, 1b.2q.3c.4i.5b, 1b.2q.3c.4i.5d,
1b.2q.3c.4i.5f, 1b.2q.3c.4i.5h, 1b.2q.3c.4i.5i, 1b.2q.3c.4i.5n, 1b.2q.3c.4n.5a,
1b.2q.3c.4n.5b, 1b.2q.3c.4n.5d, 1b.2q.3c.4n.5f, 1b.2q.3c.4n.5h, 1b.2q.3c.4n.5i,
1b.2q.3c.4n.5n, 1b.2q.3c.4p.5a, 1b.2q.3c.4p.5b, 1b.2q.3c.4p.5d, 1b.2q.3c.4p.5f,
1b.2q.3c.4p.5h, 1b.2q.3c.4p.5i, 1b.2q.3c.4p.5n, 1b.2q.3e.4a.5a, 1b.2q.3e.4a.5b,
1b.2q.3e.4a.5d, 1b.2q.3e.4a.5f, 1b.2q.3e.4a.5h, 1b.2q.3e.4a.5i, 1b.2q.3e.4a.5n,
1b.2q.3e.4b.5a, 1b.2q.3e.4b.5b, 1b.2q.3e.4b.5d, 1b.2q.3e.4b.5f, 1b.2q.3e.4b.5h,
1b.2q.3e.4b.5i, 1b.2q.3e.4b.5n, 1b.2q.3e.4d.5a, 1b.2q.3e.4d.5b, 1b.2q.3e.4d.5d,
1b.2q.3e.4d.5f, 1b.2q.3e.4d.5h, 1b.2q.3e.4d.5i, 1b.2q.3e.4d.5n, 1b.2q.3e.4f.5a,
1b.2q.3e.4d.5b, 1b.2q.3e.4f.5d, 1b.2q.3e.4f.5f, 1b.2q.3e.4f.5h, 1b.2q.3e.4f.5i,
1b.2q.3e.4f.5n, 1b.2q.3e.4i.5a, 1b.2q.3e.4i.5b, 1b.2q.3e.4i.5d, 1b.2q.3e.4i.5f,
1b.2q.3e.4i.5h, 1b.2q.3e.4i.5i, 1b.2q.3e.4i.5n, 1b.2q.3e.4n.5a, 1b.2q.3e.4n.5b,
1b.2q.3e.4n.5d, 1b.2q.3e.4n.5f, 1b.2q.3e.4n.5h, 1b.2q.3e.4n.5i, 1b.2q.3e.4n.5n,
1b.2q.3e.4p.5a, 1b.2q.3e.4p.5b, 1b.2q.3e.4p.5d, 1b.2q.3e.4p.5f, 1b.2q.3e.4p.5h,
1b.2q.3e.4p.5i, 1b.2q.3e.4p.5n, 1b.2q.3g.4a.5a, 1b.2q.3g.4a.5b, 1b.2q.3g.4a.5d,
1b.2q.3g.4a.5f, 1b.2q.3g.4a.5h, 1b.2q.3g.4a.5i, 1b.2q.3g.4a.5n, 1b.2q.3g.4b.5a, TABLE 12-continued List of Compound Structures of Formula II 1b.2q.3g.4b.5b, 1b.2q.3g.4b.5d, 1b.2q.3g.4b.5f, 1b.2q.3g.4b.5h, 1b.2q.3g.4b.5i,
1b.2q.3g.4b.5n, 1b.2q.3g.4d.5a, 1b.2q.3g.4d.5b, 1b.2q.3g.4d.5d, 1b.2q.3g.4c.5f,
1b.2q.3g.4d.5h, 1b.2q.3g.4d.5i, 1b.2q.3g.4d.5n, 1b.2q.3g.4f.5a, 1b.2q.3g.4f.5b,
1b.2q.3g.4f.5d, 1b.2q.3g.4f.5f, 1b.2q.3g.4f.5h, 1b.2q.3g.4f.5i, 1b.2q.3g.4f.5n,
1b.2q.3g.4i.5a, 1b.2q.3g.4i.5b, 1b.2q.3g.4i.5d, 1b.2q.3g.4i.5f, 1b.2q.3g.4i.5h,
1b.2q.3g.4i.5i, 1b.2q.3g.4i.5n, 1b.2q.3g.4n.5a, 1b.2q.3g.4n.5b, 1b.2q.3g.4n.5d,
1b.2q.3g.4n.5f, 1b.2q.3g.4n.5h, 1b.2q.3g.4n.5i, 1b.2q.3g.4n.5n, 1b.2q.3g.4p.5a,
1b.2q.3g.4p.5b, 1b.2q.3g.4p.5d, 1b.2q.3g.4p.5f, 1b.2q.3g.4p.5h, 1b.2q.3g.4p.5i,
1b.2q.3g.4p.5n, 1b.2v.3a.4a.5a, 1b.2v.3a.4a.5b, 1b.2v.3a.4a.5d, 1b.2v.3a.4a.5f,
1b.2v.3a.4a.5h, 1b.2v.3a.4a.5i, 1b.2v.3a.4a.5n, 1b.2v.3a.4b.5a, 1b.2v.3a.4b.5b,
1b.2v.3a.4b.5d, 1b.2v.3a.4b.5f, 1b.2v.3a.4b.5h, 1b.2v.3a.4b.5i, 1b.2v.3a.4b.5n,
1b.2v.3a.4d.5a, 1b.2v.3a.4d.5b, 1b.2v.3a.4d.5d, 1b.2v.3a.4d.5f, 1b.2v.3a.4d.5h,
1b.2v.3a.4d.5i, 1b.2v.3a.4d.5n, 1b.2v.3a.4f.5a, 1b.2v.3a.4f.5b, 1b.2v.3a.4f.5d,
1b.2v.3a.4f.5f, 1b.2v.3a.4f.5h, 1b.2v.3a.4f.5i, 1b.2v.3a.4f.5n, 1b.2v.3a.4i.5a,
1b.2v.3a.4i.5b, 1b.2v.3a.4i.5d, 1b.2v.3a.4i.5f, 1b.2v.3a.4i.5h, 1b.2v.3a.4i.5i,
1b.2v.3a.4i.5n, 1b.2v.3a.4n.5a, 1b.2v.3a.4n.5b, 1b.2v.3a.4n.5d, 1b.2v.3a.4n.5f,
1b.2v.3a.4n.5h, 1b.2v.3a.4n.5i, 1b.2v.3a.4n.5n, 1b.2v.3a.4p.5a, 1b.2v.3a.4p.5b,
1b.2v.3a.4p.5d, 1b.2v.3a.4p.5f, 1b.2v.3a.4p.5h, 1b.2v.3a.4p.5i, 1b.2v.3a.4p.5n,
1b.2v.3c.4a.5a, 1b.2v.3c.4a.5b, 1b.2v.3c.4a.5d, 1b.2v.3c.4a.5f, 1b.2v.3c.4a.5h,
1b.2v.3c.4a.5i, 1b.2v.3c.4a.5n, 1b.2v.3c.4b.5a, 1b.2v.3c.4b.5b, 1b.2v.3c.4b.5d,
1b.2v.3c.4b.5f, 1b.2v.3c.4b.5h, 1b.2v.3c.4b.5i, 1b.2v.3c.4b.5n, 1b.2v.3c.4d.5a,
1b.2v.3c.4d.5b, 1b.2v.3c.4d.5d, 1b.2v.3c.4d.5f, 1b.2v.3c.4d.5h, 1b.2v.3c.4d.5i,
1b.2v.3c.4d.5n, 1b.2v.3c.4f.5a, 1b.2v.3c.4f.5b, 1b.2v.3c.4f.5d, 1b.2v.3c.4f.5f,
1b.2v.3c.4f.5h, 1b.2v.3c.4f.5i, 1b.2v.3c.4f.5n, 1b.2v.3c.4i.5a, 1b.2v.3c.4i.5b,
1b.2v.3c.4i.5d, 1b.2v.3c.4i.5f, 1b.2v.3c.4i.5h, 1b.2v.3c.4i.5i, 1b.2v.3c.4i.5n,
1b.2v.3c.4n.5a, 1b.2v.3c.4n.5b, 1b.2v.3c.4n.5d, 1b.2v.3c.4n.5f, 1b.2v.3c.4n.5h,
1b.2v.3c.4n.5i, 1b.2v.3c.4n.5n, 1b.2v.3c.4p.5a, 1b.2v.3c.4p.5b, 1b.2v.3c.4p.5d,
1b.2v.3c.4p.5f, 1b.2v.3c.4p.5h, 1b.2v.3c.4p.5i, 1b.2v.3c.4p.5n, 1b.2v.3e.4a.5a,
1b.2v.3e.4a.5b, 1b.2v.3e.4a.5d, 1b.2v.3e.4a.5f, 1b.2v.3e.4a.5h, 1b.2v.3e.4a.5i,
1b.2v.3e.4a.5n, 1b.2v.3e.4b.5a, 1b.2v.3e.4b.5b, 1b.2v.3e.4b.5d, 1b.2v.3e.4b.5f,
1b.2v.3e.4b.5h, 1b.2v.3e.4b.5i, 1b.2v.3e.4b.5n, 1b.2v.3e.4d.5a, 1b.2v.3e.4d.5b,
1b.2v.3e.4d.5d, 1b.2v.3e.4d.5f, 1b.2v.3e.4d.5h, 1b.2v.3e.4d.5i, 1b.2v.3e.4d.5n,
1b.2v.3e.4f.5a, 1b.2v.3e.4f.5b, 1b.2v.3e.4f.5d, 1b.2v.3e.4f.5f, 1b.2v.3e.4f.5h,
1b.2v.3e.4f.5i, 1b.2v.3e.4f.5n, 1b.2v.3e.4i.5a, 1b.2v.3e.4i.5b, 1b.2v.3e.4i.5d,
1b.2v.3e.4i.5f, 1b.2v.3e.4i.5h, 1b.2v.3e.4i.5i, 1b.2v.3e.4i.5n, 1b.2v.3e.4n.5a,
1b.2v.3e.4n.5b, 1b.2v.3e.4n.5d, 1b.2v.3e.4n.5f, 1b.2v.3e.4n.5h, 1b.2v.3e.4n.5i,
1b.2v.3e.4n.5n, 1b.2v.3e.4p.5a, 1b.2v.3e.4p.5b, 1b.2v.3e.4p.5d, 1b.2v.3e.4p.5f,
1b.2v.3e.4p.5h, 1b.2v.3e.4p.5i, 1b.2v.3e.4p.5n, 1b.2v.3g.4a.5a, 1b.2v.3g.4a.5b,
1b.2v.3g.4a.5d, 1b.2v.3g.4a.5f, 1b.2v.3g.4a.5h, 1b.2v.3g.4a.5i, 1b.2v.3g.4a.5n,
1b.2v.3g.4b.5a, 1b.2v.3g.4b.5b, 1b.2v.3g.4b.5d, 1b.2v.3g.4b.5f, 1b.2v.3g.4b.5h,
1b.2v.3g.4b.5i, 1b.2v.3g.4b.5n, 1b.2v.3g.4d.5a, 1b.2v.3g.4d.5b, 1b.2v.3g.4d.5d,
1b.2v.3g.4d.5f, 1b.2v.3g.4d.5h, 1b.2v.3g.4d.5i, 1b.2v.3g.4d.5n, 1b.2v.3g.4f.5a,
1b.2v.3g.4f.5b, 1b.2v.3g.4f.5d, 1b.2v.3g.4f.5f, 1b.2v.3g.4f.5h, 1b.2v.3g.4f.5i,
1b.2v.3g.4f.5n, 1b.2v.3g.4i.5a, 1b.2v.3g.4i.5b, 1b.2v.3g.4i.5d, 1b.2v.3g.4i.5f,
1b.2v.3g.4i.5h, 1b.2v.3g.4i.5i, 1b.2v.3g.4i.5n, 1b.2v.3g.4n.5a, 1b.2v.3g.4n.5b,
1b.2v.3g.4n.5d, 1b.2v.3g.4n.5f, 1b.2v.3g.4n.5h, 1b.2v.3g.4n.5i, 1b.2v.3g.4n.5n,
1b.2v.3g.4p.5a, 1b.2v.3g.4p.5b, 1b.2v.3g.4p.5d, 1b.2v.3g.4p.5f, 1b.2v.3g.4p.5h,
1b.2v.3g.4p.5i, 1b.2v.3g.4p.5n, 1b.2y.3a.4a.5a, 1b.2y.3a.4a.5b, 1b.2y.3a.4a.5d,
1b.2y.3a.4a.5f, 1b.2y.3a.4a.5h, 1b.2y.3a.4a.5i, 1b.2y.3a.4a.5n, 1b.2y.3a.4b.5a,
1b.2y.3a.4b.5b, 1b.2y.3a.4b.5d, 1b.2y.3a.4b.5f, 1b.2y.3a.4b.5h, 1b.2y.3a.4b.5i,
1b.2y.3a.4b.5n, 1b.2y.3a.4d.5a, 1b.2y.3a.4d.5b, 1b.2y.3a.4d.5d, 1b.2y.3a.4d.5f,
1b.2y.3a.4d.5h, 1b.2y.3a.4d.5i, 1b.2y.3a.4d.5n, 1b.2y.3a.4f.5a, 1b.2y.3a.4f.5b,
1b.2y.3a.4f.5d, 1b.2y.3a.4f.5f, 1b.2y.3a.4f.5h, 1b.2y.3a.4f.5i, 1b.2y.3a.4f.5n,
1b.2y.3a.4i.5a, 1b.2y.3a.4i.5b, 1b.2y.3a.4i.5d, 1b.2y.3a.4i.5f, 1b.2y.3a.4i.5h,
1b.2y.3a.4i.5i, 1b.2y.3a.4i.5n, 1b.2y.3a.4n.5a, 1b.2y.3a.4n.5b, 1b.2y.3a.4n.5d,
1b.2y.3a.4n.5f, 1b.2y.3a.4n.5h, 1b.2y.3a.4n.5i, 1b.2y.3a.4n.5n, 1b.2y.3a.4p.5a,
1b.2y.3a.4p.5b, 1b.2y.3a.4p.5d, 1b.2y.3a.4p.5f, 1b.2y.3a.4p.5h, 1b.2y.3a.4p.5i,
1b.2y.3a.4p.5n, 1b.2y.3c.4a.5a, 1b.2y.3c.4a.5b, 1b.2y.3c.4a.5d, 1b.2y.3c.4a.5f,
1b.2y.3c.4a.5h, 1b.2y.3c.4a.5i, 1b.2y.3c.4a.5n, 1b.2y.3c.4b.5a, 1b.2y.3c.4b.5b,
1b.2y.3c.4b.5d, 1b.2y.3c.4b.5f, 1b.2y.3c.4b.5h, 1b.2y.3c.4b.5i, 1b.2y.3c.4b.5n,
1b.2y.3c.4d.5a, 1b.2y.3c.4d.5b, 1b.2y.3c.4d.5d, 1b.2y.3c.4d.5f, 1b.2y.3c.4d.5h,
1b.2y.3c.4d.5i, 1b.2y.3c.4d.5n, 1b.2y.3c.4f.5a, 1b.2y.3c.4f.5b, 1b.2y.3c.4f.5d,
1b.2y.3c.4f.5f, 1b.2y.3c.4f.5h, 1b.2y.3c.4f.5i, 1b.2y.3c.4f.5n, 1b.2y.3c.4i.5a,
1b.2y.3c.4i.5b, 1b.2y.3c.4i.5d, 1b.2y.3c.4i.5f, 1b.2y.3c.4i.5h, 1b.2y.3c.4i.5i,
1b.2y.3c.4i.5n, 1b.2y.3c.4n.5a, 1b.2y.3c.4n.5b, 1b.2y.3c.4n.5d, 1b.2y.3c.4n.5f,
1b.2y.3c.4n.5h, 1b.2y.3c.4n.5i, 1b.2y.3c.4n.5n, 1b.2y.3c.4p.5a, 1b.2y.3c.4p.5b,
1b.2y.3c.4p.5d, 1b.2y.3c.4p.5f, 1b.2y.3c.4p.5h, 1b.2y.3c.4p.5i, 1b.2y.3c.4p.5n,
1b.2y.3e.4a.5a, 1b.2y.3e.4a.5b, 1b.2y.3e.4a.5d, 1b.2y.3e.4a.5f, 1b.2y.3e.4a.5h,
1b.2y.3e.4a.5i, 1b.2y.3e.4a.5n, 1b.2y.3e.4b.5a, 1b.2y.3e.4b.5b, 1b.2y.3e.4b.5d,
1b.2y.3e.4b.5f, 1b.2y.3e.4b.5h, 1b.2y.3e.4b.5i, 1b.2y.3e.4b.5n, 1b.2y.3e.4d.5a,
1b.2y.3e.4d.5b, 1b.2y.3e.4d.5d, 1b.2y.3e.4d.5f, 1b.2y.3e.4d.5h, 1b.2y.3e.4d.5i,
1b.2y.3e.4d.5n, 1b.2y.3e.4f.5a, 1b.2y.3e.4f.5b, 1b.2y.3e.4f.5d, 1b.2y.3e.4f.5f,
1b.2y.3e.4f.5h, 1b.2y.3e.4f.5i, 1b.2y.3e.4f.5n, 1b.2y.3e.4i.5a, 1b.2y.3e.4i.5b,
1b.2y.3e.4i.5d, 1b.2y.3e.4i.5f, 1b.2y.3e.4i.5h, 1b.2y.3e.4i.5i, 1b.2y.3e.4i.5n,
1b.2y.3e.4n.5a, 1b.2y.3e.4n.5b, 1b.2y.3e.4n.5d, 1b.2y.3e.4n.5f, 1b.2y.3e.4n.5h,
1b.2y.3e.4n.5i, 1b.2y.3e.4n.5n, 1b.2y.3e.4p.5a, 1b.2y.3e.4p.5b, 1b.2y.3e.4p.5d,
1b.2y.3e.4p.5f, 1b.2y.3e.4p.5h, 1b.2y.3e.4p.5i, 1b.2y.3e.4p.5n, 1b.2y.3g.4a.5a,
1b.2y.3g.4a.5b, 1b.2y.3g.4a.5d, 1b.2y.3g.4a.5f, 1b.2y.3g.4a.5h, 1b.2y.3g.4a.5i, TABLE 12-continued List of Compound Structures of Formula II 1b.2y.3g.4a.5n, 1b.2y.3g.4b.5a, 1b.2y.3g.4b.5b, 1b.2y.3g.4b.5d, 1b.2y.3g.4b.5f,
1b.2y.3g.4b.5h, 1b.2y.3g.4b.5i, 1b.2y.3g.4b.5n, 1b.2y.3g.4d.5a, 1b.2y.3g.4d.5b,
1b.2y.3g.4d.5d, 1b.2y.3g.4d.5f, 1b.2y.3g.4d.5h, 1b.2y.3g.4d.5i, 1b.2y.3g.4d.5n,
1b.2y.3g.4f.5a, 1b.2y.3g.4f.5b, 1b.2y.3g.4f.5d, 1b.2y.3g.4f.5f, 1b.2y.3g.4f.5h,
1b.2y.3g.4f.5i, 1b.2y.3g.4f.5n, 1b.2y.3g.4i.5a, 1b.2y.3g.4i.5b, 1b.2y.3g.4i.5d,
1b.2y.3g.4i.5f, 1b.2y.3g.4i.5h, 1b.2y.3g.4i.5i, 1b.2y.3g.4i.5n, 1b.2y.3g.4n.5a,
1b.2y.3g.4n.5b, 1b.2y.3g.4n.5d, 1b.2y.3g.4n.5f, 1b.2y.3g.4n.5h, 1b.2y.3g.4n.5i,
1b.2y.3g.4n.5n, 1b.2y.3g.4p.5a, 1b.2y.3g.4p.5b, 1b.2y.3g.4p.5d, 1b.2y.3g.4p.5f,
1b.2y.3g.4p.5h, 1b.2y.3g.4p.5i, 1b.2y.3g.4p.5n, 1b.2z.3a.4a.5a, 1b.2z.3a.4a.5b,
1b.2z.3a.4a.5d, 1b.2z.3a.4a.5f, 1b.2z.3a.4a.5h, 1b.2z.3a.4a.5i, 1b.2z.3a.4a.5n,
1b.2z.3a.4b.5a, 1b.2z.3a.4b.5b, 1b.2z.3a.4b.5d, 1b.2z.3a.4b.5f, 1b.2z.3a.4b.5h,
1b.2z.3a.4b.5i, 1b.2z.3a.4b.5n, 1b.2z.3a.4d.5a, 1b.2z.3a.4d.5b, 1b.2z.3a.4d.5d,
1b.2z.3a.4d.5f, 1b.2z.3a.4d.5h, 1b.2z.3a.4d.5i, 1b.2z.3a.4d.5n, 1b.2z.3a.4f.5a,
1b.2z.3a.4f.5b, 1b.2z.3a.4f.5d, 1b.2z.3a.4f.5f, 1b.2z.3a.4f.5h, 1b.2z.3a.4f.5i,
1b.2z.3a.4f.5n, 1b.2z.3a.4i.5a, 1b.2z.3a.4i.5b, 1b.2z.3a.4i.5d, 1b.2z.3a.4i.5f,
1b.2z.3a.4i.5h, 1b.2z.3a.4i.5i, 1b.2z.3a.4i.5n, 1b.2z.3a.4n.5a, 1b.2z.3a.4n.5b,
1b.2z.3a.4n.5d, 1b.2z.3a.4n.5f, 1b.2z.3a.4n.5h, 1b.2z.3a.4n.5i, 1b.2z.3a.4n.5n,
1b.2z.3a.4p.5a, 1b.2z.3a.4p.5b, 1b.2z.3a.4p.5d, 1b.2z.3a.4p.5f, 1b.2z.3a.4p.5h,
1b.2z.3a.4p.5i, 1b.2z.3a.4p.5n, 1b.2z.3c.4a.5a, 1b.2z.3c.4a.5b, 1b.2z.3c.4a.5d,
1b.2z.3c.4a.5f, 1b.2z.3c.4a.5h, 1b.2z.3c.4a.5i, 1b.2z.3c.4a.5n, 1b.2z.3c.4b.5a,
1b.2z.3c.4b.5b, 1b.2z.3c.4b.5d, 1b.2z.3c.4b.5f, 1b.2z.3c.4b.5h, 1b.2z.3c.4b.5i,
1b.2z.3c.4b.5n, 1b.2z.3c.4d.5a, 1b.2z.3c.4d.5b, 1b.2z.3c.4d.5d, 1b.2z.3c.4d.5f,
1b.2z.3c.4d.5h, 1b.2z.3c.4d.5i, 1b.2z.3c.4d.5n, 1b.2z.3c.4f.5a, 1b.2z.3c.4f.5b,
1b.2z.3c.4f.5d, 1b.2z.3c.4f.5f, 1b.2z.3c.4f.5h, 1b.2z.3c.4f.5i, 1b.2z.3c.4f.5n,
1b.2z.3c.4i.5a, 1b.2z.3c.4i.5b, 1b.2z.3c.4i.5d, 1b.2z.3c.4i.5f, 1b.2z.3c.4i.5h,
1b.2z.3c.4i.5i, 1b.2z.3c.4i.5n, 1b.2z.3c.4n.5a, 1b.2z.3c.4n.5b, 1b.2z.3c.4n.5d,
1b.2z.3c.4n.5f, 1b.2z.3c.4n.5h, 1b.2z.3c.4n.5i, 1b.2z.3c.4n.5n, 1b.2z.3c.4p.5a,
1b.2z.3c.4p.5b, 1b.2z.3c.4p.5d, 1b.2z.3c.4p.5f, 1b.2z.3c.4p.5h, 1b.2z.3c.4p.5i,
1b.2z.3c.4p.5n, 1b.2z.3e.4a.5a, 1b.2z.3e.4a.5b, 1b.2z.3e.4a.5d, 1b.2z.3e.4a.5f,
1b.2z.3e.4a.5h, 1b.2z.3e.4a.5i, 1b.2z.3e.4a.5n, 1b.2z.3e.4b.5a, 1b.2z.3e.4b.5b,
1b.2z.3e.4b.5d, 1b.2z.3e.4b.5f, 1b.2z.3e.4b.5h, 1b.2z.3e.4b.5i, 1b.2z.3e.4b.5n,
1b.2z.3e.4d.5a, 1b.2z.3e.4d.5b, 1b.2z.3e.4d.5d, 1b.2z.3e.4d.5f, 1b.2z.3e.4d.5h,
1b.2z.3e.4d.5i, 1b.2z.3e.4d.5n, 1b.2z.3e.4f.5a, 1b.2z.3e.4f.5b, 1b.2z.3e.4f.5d,
1b.2z.3e.4f.5f, 1b.2z.3e.4f.5h, 1b.2z.3e.4f.5i, 1b.2z.3e.4f.5n, 1b.2z.3e.4i.5a,
1b.2z.3e.4i.5b, 1b.2z.3e.4i.5d, 1b.2z.3e.4i.5f, 1b.2z.3e.4i.5h, 1b.2z.3e.4i.5i,
1b.2z.3e.4i.5n, 1b.2z.3e.4n.5a, 1b.2z.3e.4n.5b, 1b.2z.3e.4n.5d, 1b.2z.3e.4n.5f,
1b.2z.3e.4n.5h, 1b.2z.3e.4n.5i, 1b.2z.3e.4n.5n, 1b.2z.3e.4p.5a, 1b.2z.3e.4p.5b,
1b.2z.3e.4p.5d, 1b.2z.3e.4p.5f, 1b.2z.3e.4p.5h, 1b.2z.3e.4p.5i, 1b.2z.3e.4p.5n,
1b.2z.3g.4a.5a, 1b.2z.3g.4a.5b, 1b.2z.3g.4a.5d, 1b.2z.3g.4a.5f, 1b.2z.3g.4a.5h,
1b.2z.3g.4a.5i, 1b.2z.3g.4a.5n, 1b.2z.3g.4b.5a, 1b.2z.3g.4b.5b, 1b.2z.3g.4b.5d,
1b.2z.3g.4b.5f, 1b.2z.3g.4b.5h, 1b.2z.3g.4b.5i, 1b.2z.3g.4b.5n, 1b.2z.3g.4d.5a,
1b.2z.3g.4d.5b, 1b.2z.3g.4d.5d, 1b.2z.3g.4d.5f, 1b.2z.3g.4d.5h, 1b.2z.3g.4d.5i,
1b.2z.3g.4d.5n, 1b.2z.3g.4f.5a, 1b.2z.3g.4f.5b, 1b.2z.3g.4f.5d, 1b.2z.3g.4f.5f,
1b.2z.3g.4f.5h, 1b.2z.3g.4f.5i, 1b.2z.3g.4f.5n, 1b.2z.3g.4i.5a, 1b.2z.3g.4i.5b,
1b.2z.3g.4i.5d, 1b.2z.3g.4i.5f, 1b.2z.3g.4i.5h, 1b.2z.3g.4i.5i, 1b.2z.3g.4i.5n,
1b.2z.3g.4n.5a, 1b.2z.3g.4n.5b, 1b.2z.3g.4n.5d, 1b.2z.3g.4n.5f, 1b.2z.3g.4n.5h,
1b.2z.3g.4n.5i, 1b.2z.3g.4n.5n, 1b.2z.3g.4p.5a, 1b.2z.3g.4p.5b, 1b.2z.3g.4p.5d,
1b.2z.3g.4p.5f, 1b.2z.3g.4p.5h, 1b.2z.3g.4p.5i, 1b.2z.3g.4p.5n, 1c.2a.3a.4a.5a,
1c.2a.3a.4a.5b, 1c.2a.3a.4a.5d, 1c.2a.3a.4a.5f, 1c.2a.3a.4a.5h, 1c.2a.3a.4a.5i,
1c.2a.3a.4a.5n, 1c.2a.3a.4b.5a, 1c.2a.3a.4b.5b, 1c.2a.3a.4b.5d, 1c.2a.3a.4b.5f,
1c.2a.3a.4b.5h, 1c.2a.3a.4b.5i, 1c.2a.3a.4b.5n, 1c.2a.3a.4d.5a, 1c.2a.3a.4d.5b,
1c.2a.3a.4d.5d, 1c.2a.3a.4d.5f, 1c.2a.3a.4d.5h, 1c.2a.3a.4d.5i, 1c.2a.3a.4d.5n,
1c.2a.3a.4f.5a, 1c.2a.3a.4f.5b, 1c.2a.3a.4f.5d, 1c.2a.3a.4f.5f, 1c.2a.3a.4f.5h,
1c.2a.3a.4f.5i, 1c.2a.3a.4f.5n, 1c.2a.3a.4i.5a, 1c.2a.3a.4i.5b, 1c.2a.3a.4i.5d,
1c.2a.3a.4i.5f, 1c.2a.3a.4i.5h, 1c.2a.3a.4i.5i, 1c.2a.3a.4i.5n, 1c.2a.3a.4n.5a,
1c.2a.3a.4n.5b, 1c.2a.3a.4n.5d, 1c.2a.3a.4n.5f, 1c.2a.3a.4n.5h, 1c.2a.3a.4n.5i,
1c.2a.3a.4n.5n, 1c.2a.3a.4p.5a, 1c.2a.3a.4p.5b, 1c.2a.3a.4p.5d, 1c.2a.3a.4p.5f,
1c.2a.3a.4p.5h, 1c.2a.3a.4p.5i, 1c.2a.3a.4p.5n, 1c.2a.3c.4a.5a, 1c.2a.3c.4a.5b,
1c.2a.3c.4a.5d, 1c.2a.3c.4a.5f, 1c.2a.3c.4a.5h, 1c.2a.3c.4a.5i, 1c.2a.3c.4a.5n,
1c.2a.3c.4b.5a, 1c.2a.3c.4b.5b, 1c.2a.3c.4b.5d, 1c.2a.3c.4b.5f, 1c.2a.3c.4b.5h,
1c.2a.3c.4b.5i, 1c.2a.3c.4b.5n, 1c.2a.3c.4d.5a, 1c.2a.3c.4d.5b, 1c.2a.3c.4d.5d,
1c.2a.3c.4d.5f, 1c.2a.3c.4d.5h, 1c.2a.3c.4d.5i, 1c.2a.3c.4d.5n, 1c.2a.3c.4f.5a,
1c.2a.3c.4f.5b, 1c.2a.3c.4f.5d, 1c.2a.3c.4f.5f, 1c.2a.3c.4f.5h, 1c.2a.3c.4f.5i,
1c.2a.3c.4f.5n, 1c.2a.3c.4i.5a, 1c.2a.3c.4i.5b, 1c.2a.3c.4i.5d, 1c.2a.3c.4i.5f,
1c.2a.3c.4i.5h, 1c.2a.3c.4i.5i, 1c.2a.3c.4i.5n, 1c.2a.3c.4n.5a, 1c.2a.3c.4n.5b,
1c.2a.3c.4n.5d, 1c.2a.3c.4n.5f, 1c.2a.3c.4n.5h, 1c.2a.3c.4n.5i, 1c.2a.3c.4n.5n,
1c.2a.3c.4p.5a, 1c.2a.3c.4p.5b, 1c.2a.3c.4p.5d, 1c.2a.3c.4p.5f, 1c.2a.3c.4p.5h,
1c.2a.3c.4p.5i, 1c.2a.3c.4p.5n, 1c.2a.3e.4a.5a, 1c.2a.3e.4a.5b, 1c.2a.3e.4a.5d,
1c.2a.3e.4a.5f, 1c.2a.3e.4a.5h, 1c.2a.3e.4a.5i, 1c.2a.3e.4a.5n, 1c.2a.3e.4b.5a,
1c.2a.3e.4b.5b, 1c.2a.3e.4b.5d, 1c.2a.3e.4b.5f, 1c.2a.3e.4b.5h, 1c.2a.3e.4b.5i,
1c.2a.3e.4b.5n, 1c.2a.3e.4d.5a, 1c.2a.3e.4d.5b, 1c.2a.3e.4d.5d, 1c.2a.3e.4d.5f,
1c.2a.3e.4d.5h, 1c.2a.3e.4d.5i, 1c.2a.3e.4d.5n, 1c.2a.3e.4f.5a, 1c.2a.3e.4f.5b,
1c.2a.3e.4f.5d, 1c.2a.3e.4f.5f, 1c.2a.3e.4f.5h, 1c.2a.3e.4f.5i, 1c.2a.3e.4f.5n,
1c.2a.3e.4i.5a, 1c.2a.3e.4i.5b, 1c.2a.3e.4i.5d, 1c.2a.3e.4i.5f, 1c.2a.3e.4i.5h,
1c.2a.3e.4i.5i, 1c.2a.3e.4i.5n, 1c.2a.3e.4n.5a, 1c.2a.3e.4n.5b, 1c.2a.3e.4n.5d,
1c.2a.3e.4n.5f, 1c.2a.3e.4n.5h, 1c.2a.3e.4n.5i, 1c.2a.3e.4n.5n, 1c.2a.3e.4p.5a,
1c.2a.3e.4p.5b, 1c.2a.3e.4p.5d, 1c.2a.3e.4p.5f, 1c.2a.3e.4p.5h, 1c.2a.3e.4p.5i,
1c.2a.3e.4p.5n, 1c.2a.3g.4a.5a, 1c.2a.3g.4a.5b, 1c.2a.3g.4a.5d, 1c.2a.3g.4a.5f, TABLE 12-continued List of Compound Structures of Formula II 1c.2a.3g.4a.5h, 1c.2a.3g.4a.5i, 1c.2a.3g.4a.5n, 1c.2a.3g.4b.5a, 1c.2a.3g.4b.5b,
1c.2a.3g.4b.5d, 1c.2a.3g.4b.5f, 1c.2a.3g.4b.5h, 1c.2a.3g.4b.5i, 1c.2a.3g.4b.5n,
1c.2a.3g.4d.5a, 1c.2a.3g.4d.5b, 1c.2a.3g.4d.5d, 1c.2a.3g.4d.5f, 1c.2a.3g.4d.5h,
1c.2a.3g.4d.5i, 1c.2a.3g.4d.5n, 1c.2a.3g.4f.5a, 1c.2a.3g.4f.5b, 1c.2a.3g.4f.5d,
1c.2a.3g.4f.5f, 1c.2a.3g.4f.5h, 1c.2a.3g.4f.5i, 1c.2a.3g.4f.5n, 1c.2a.3g.4i.5a,
1c.2a.3g.4i.5b, 1c.2a.3g.4i.5d, 1c.2a.3g.4i.5f, 1c.2a.3g.4i.5h, 1c.2a.3g.4i.5i,
1c.2a.3g.4i.5n, 1c.2a.3g.4n.5a, 1c.2a.3g.4n.5b, 1c.2a.3g.4n.5d, 1c.2a.3g.4n.5f,
1c.2a.3g.4n.5h, 1c.2a.3g.4n.5i, 1c.2a.3g.4n.5n, 1c.2a.3g.4p.5a, 1c.2a.3g.4p.5b,
1c.2a.3g.4p.5d, 1c.2a.3g.4p.5f, 1c.2a.3g.4p.5h, 1c.2a.3g.4p.5i, 1c.2a.3g.4p.5n,
1c.2b.3a.4a.5a, 1c.2b.3a.4a.5b, 1c.2b.3a.4a.5d, 1c.2b.3a.4a.5f, 1c.2b.3a.4a.5h,
1c.2b.3a.4a.5i, 1c.2b.3a.4a.5n, 1c.2b.3a.4b.5a, 1c.2b.3a.4b.5b, 1c.2b.3a.4b.5d,
1c.2b.3a.4b.5f, 1c.2b.3a.4b.5h, 1c.2b.3a.4b.5i, 1c.2b.3a.4b.5n, 1c.2b.3a.4d.5a,
1c.2b.3a.4d.5b, 1c.2b.3a.4d.5d, 1c.2b.3a.4d.5f, 1c.2b.3a.4d.5h, 1c.2b.3a.4d.5i,
1c.2b.3a.4d.5n, 1c.2b.3a.4f.5a, 1c.2b.3a.4f.5b, 1c.2b.3a.4f.5d, 1c.2b.3a.4f.5f,
1c.2b.3a.4f.5h, 1c.2b.3a.4f.5i, 1c.2b.3a.4f.5n, 1c.2b.3a.4i.5a, 1c.2b.3a.4i.5b,
1c.2b.3a.4i.5d, 1c.2b.3a.4i.5f, 1c.2b.3a.4i.5h, 1c.2b.3a.4i.5i, 1c.2b.3a.4i.5n,
1c.2b.3a.4n.5a, 1c.2b.3a.4n.5b, 1c.2b.3a.4n.5d, 1c.2b.3a.4n.5f, 1c.2b.3a.4n.5h,
1c.2b.3a.4n.5i, 1c.2b.3a.4n.5n, 1c.2b.3a.4p.5a, 1c.2b.3a.4p.5b, 1c.2b.3a.4p.5d,
1c.2b.3a.4p.5f, 1c.2b.3a.4p.5h, 1c.2b.3a.4p.5i, 1c.2b.3a.4p.5n, 1c.2b.3c.4a.5a,
1c.2b.3c.4a.5b, 1c.2b.3c.4a.5d, 1c.2b.3c.4a.5f, 1c.2b.3c.4a.5h, 1c.2b.3c.4a.5i,
1c.2b.3c.4a.5n, 1c.2b.3c.4b.5a, 1c.2b.3c.4b.5b, 1c.2b.3c.4b.5d, 1c.2b.3c.4b.5f,
1c.2b.3c.4b.5h, 1c.2b.3c.4b.5i, 1c.2b.3c.4b.5n, 1c.2b.3c.4d.5a, 1c.2b.3c.4d.5b,
1c.2b.3c.4d.5d, 1c.2b.3c.4d.5f, 1c.2b.3c.4d.5h, 1c.2b.3c.4d.5i, 1c.2b.3c.4d.5n,
1c.2b.3c.4f.5a, 1c.2b.3c.4f.5b, 1c.2b.3c.4f.5d, 1c.2b.3c.4f.5f, 1c.2b.3c.4f.5h,
1c.2b.3c.4f.5i, 1c.2b.3c.4f.5n, 1c.2b.3c.4i.5a, 1c.2b.3c.4i.5b, 1c.2b.3c.4i.5d,
1c.2b.3c.4i.5f, 1c.2b.3c.4i.5h, 1c.2b.3c.4i.5i, 1c.2b.3c.4i.5n, 1c.2b.3c.4n.5a,
1c.2b.3c.4n.5b, 1c.2b.3c.4n.5d, 1c.2b.3c.4n.5f, 1c.2b.3c.4n.5h, 1c.2b.3c.4n.5i,
1c.2b.3c.4n.5n, 1c.2b.3c.4p.5a, 1c.2b.3c.4p.5b, 1c.2b.3c.4p.5d, 1c.2b.3c.4p.5f,
1c.2b.3c.4p.5h, 1c.2b.3c.4p.5i, 1c.2b.3c.4p.5n, 1c.2b.3e.4a.5a, 1c.2b.3e.4a.5b,
1c.2b.3e.4a.5d, 1c.2b.3e.4a.5f, 1c.2b.3e.4a.5h, 1c.2b.3e.4a.5i, 1c.2b.3e.4a.5n,
1c.2b.3e.4b.5a, 1c.2b.3e.4b.5b, 1c.2b.3e.4b.5d, 1c.2b.3e.4b.5f, 1c.2b.3e.4b.5h,
1c.2b.3e.4b.5i, 1c.2b.3e.4b.5n, 1c.2b.3e.4d.5a, 1c.2b.3e.4d.5b, 1c.2b.3e.4d.5d,
1c.2b.3e.4d.5f, 1c.2b.3e.4d.5h, 1c.2b.3e.4d.5i, 1c.2b.3e.4d.5n, 1c.2b.3e.4f.5a,
1c.2b.3e.4f.5b, 1c.2b.3e.4f.5d, 1c.2b.3e.4f.5f, 1c.2b.3e.4f.5h, 1c.2b.3e.4f.5i,
1c.2b.3e.4f.5n, 1c.2b.3e.4i.5a, 1c.2b.3e.4i.5b, 1c.2b.3e.4i.5d, 1c.2b.3e.4i.5f,
1c.2b.3e.4i.5h, 1c.2b.3e.4i.5i, 1c.2b.3e.4i.5n, 1c.2b.3e.4n.5a, 1c.2b.3e.4n.5b,
1c.2b.3e.4n.5d, 1c.2b.3e.4n.5f, 1c.2b.3e.4n.5h, 1c.2b.3e.4n.5i, 1c.2b.3e.4n.5n,
1c.2b.3e.4p.5a, 1c.2b.3e.4p.5b, 1c.2b.3e.4p.5d, 1c.2b.3e.4p.5f, 1c.2b.3e.4p.5h,
1c.2b.3e.4p.5i, 1c.2b.3e.4p.5n, 1c.2b.3g.4a.5a, 1c.2b.3g.4a.5b, 1c.2b.3g.4a.5d,
1c.2b.3g.4a.5f, 1c.2b.3g.4a.5h, 1c.2b.3g.4a.5i, 1c.2b.3g.4a.5n, 1c.2b.3g.4b.5a,
1c.2b.3g.4b.5b, 1c.2b.3g.4b.5d, 1c.2b.3g.4b.5f, 1c.2b.3g.4b.5h, 1c.2b.3g.4b.5i,
1c.2b.3g.4b.5n, 1c.2b.3g.4d.5a, 1c.2b.3g.4d.5b, 1c.2b.3g.4d.5d, 1c.2b.3g.4d.5f,
1c.2b.3g.4d.5h, 1c.2b.3g.4d.5i, 1c.2b.3g.4d.5n, 1c.2b.3g.4f.5a, 1c.2b.3g.4f.5b,
1c.2b.3g.4f.5d, 1c.2b.3g.4f.5f, 1c.2b.3g.4f.5h, 1c.2b.3g.4f.5i, 1c.2b.3g.4f.5n,
1c.2b.3g.4i.5a, 1c.2b.3g.4i.5b, 1c.2b.3g.4i.5d, 1c.2b.3g.4i.5f, 1c.2b.3g.4i.5h,
1c.2b.3g.4i.5i, 1c.2b.3g.4i.5n, 1c.2b.3g.4n.5a, 1c.2b.3g.4n.5b, 1c.2b.3g.4n.5d,
1c.2b.3g.4n.5f, 1c.2b.3g.4n.5h, 1c.2b.3g.4n.5i, 1c.2b.3g.4n.5n, 1c.2b.3g.4p.5a,
1c.2b.3g.4p.5b, 1c.2b.3g.4p.5d, 1c.2b.3g.4p.5f, 1c.2b.3g.4p.5h, 1c.2b.3g.4p.5i,
1c.2b.3g.4p.5n, 1c.2e.3a.4a.5a, 1c.2e.3a.4a.5b, 1c.2e.3a.4a.5d, 1c.2e.3a.4a.5f,
1c.2e.3a.4a.5h, 1c.2e.3a.4a.5i, 1c.2e.3a.4a.5n, 1c.2e.3a.4b.5a, 1c.2e.3a.4b.5b,
1c.2e.3a.4b.5d, 1c.2e.3a.4b.5f, 1c.2e.3a.4b.5h, 1c.2e.3a.4b.5i, 1c.2e.3a.4b.5n,
1c.2e.3a.4d.5a, 1c.2e.3a.4d.5b, 1c.2e.3a.4d.5d, 1c.2e.3a.4d.5f, 1c.2e.3a.4d.5h,
1c.2e.3a.4d.5i, 1c.2e.3a.4d.5n, 1c.2e.3a.4f.5a, 1c.2e.3a.4f.5b, 1c.2e.3a.4f.5d,
1c.2e.3a.4f.5f, 1c.2e.3a.4f.5h, 1c.2e.3a.4f.5i, 1c.2e.3a.4f.5n, 1c.2e.3a.4i.5a,
1c.2e.3a.4i.5b, 1c.2e.3a.4i.5d, 1c.2e.3a.4i.5f, 1c.2e.3a.4i.5h, 1c.2e.3a.4i.5i,
1c.2e.3a.4i.5n, 1c.2e.3a.4n.5a, 1c.2e.3a.4n.5b, 1c.2e.3a.4n.5d, 1c.2e.3a.4n.5f,
1c.2e.3a.4n.5h, 1c.2e.3a.4n.5i, 1c.2e.3a.4n.5n, 1c.2e.3a.4p.5a, 1c.2e.3a.4p.5b,
1c.2e.3a.4p.5d, 1c.2e.3a.4p.5f, 1c.2e.3a.4p.5h, 1c.2e.3a.4p.5i, 1c.2e.3a.4p.5n,
1c.2e.3c.4a.5a, 1c.2e.3c.4a.5b, 1c.2e.3c.4a.5d, 1c.2e.3c.4a.5f, 1c.2e.3c.4a.5h,
1c.2e.3c.4a.5i, 1c.2e.3c.4a.5n, 1c.2e.3c.4b.5a, 1c.2e.3c.4b.5b, 1c.2e.3c.4b.5d,
1c.2e.3c.4b.5f, 1c.2e.3c.4b.5h, 1c.2e.3c.4b.5i, 1c.2e.3c.4b.5n, 1c.2e.3c.4d.5a,
1c.2e.3c.4d.5b, 1c.2e.3c.4d.5d, 1c.2e.3c.4d.5f, 1c.2e.3c.4d.5h, 1c.2e.3c.4d.5i,
1c.2e.3c.4d.5n, 1c.2e.3c.4f.5a, 1c.2e.3c.4f.5b, 1c.2e.3c.4f.5d, 1c.2e.3c.4f.5f,
1c.2e.3c.4f.5h, 1c.2e.3c.4f.5i, 1c.2e.3c.4f.5n, 1c.2e.3c.4i.5a, 1c.2e.3c.4i.5b,
1c.2e.3c.4i.5d, 1c.2e.3c.4i.5f, 1c.2e.3c.4i.5h, 1c.2e.3c.4i.5i, 1c.2e.3c.4i.5n,
1c.2e.3c.4n.5a, 1c.2e.3c.4n.5b, 1c.2e.3c.4n.5d, 1c.2e.3c.4n.5f, 1c.2e.3c.4n.5h,
1c.2e.3c.4n.5i, 1c.2e.3c.4n.5n, 1c.2e.3c.4p.5a, 1c.2e.3c.4p.5b, 1c.2e.3c.4p.5d,
1c.2e.3c.4p.5f, 1c.2e.3c.4p.5h, 1c.2e.3c.4p.5i, 1c.2e.3c.4p.5n, 1c.2e.3e.4a.5a,
1c.2e.3e.4a.5b, 1c.2e.3e.4a.5d, 1c.2e.3e.4a.5f, 1c.2e.3e.4a.5h, 1c.2e.3e.4a.5i,
1c.2e.3e.4a.5n, 1c.2e.3e.4b.5a, 1c.2e.3e.4b.5b, 1c.2e.3e.4b.5d, 1c.2e.3e.4b.5f,
1c.2e.3e.4b.5h, 1c.2e.3e.4b.5i, 1c.2e.3e.4b.5n, 1c.2e.3e.4d.5a, 1c.2e.3e.4d.5b,
1c.2e.3e.4d.5d, 1c.2e.3e.4d.5f, 1c.2e.3e.4d.5h, 1c.2e.3e.4d.5i, 1c.2e.3e.4d.5n,
1c.2e.3e.4f.5a, 1c.2e.3e.4f.5b, 1c.2e.3e.4f.5d, 1c.2e.3e.4f.5f, 1c.2e.3e.4f.5h,
1c.2e.3e.4f.5i, 1c.2e.3e.4f.5n, 1c.2e.3e.4i.5a, 1c.2e.3e.4i.5b, 1c.2e.3e.4i.5d,
1c.2e.3e.4i.5f, 1c.2e.3e.4i.5h, 1c.2e.3e.4i.5i, 1c.2e.3e.4i.5n, 1c.2e.3e.4n.5a,
1c.2e.3e.4n.5b, 1c.2e.3e.4n.5d, 1c.2e.3e.4n.5f, 1c.2e.3e.4n.5h, 1c.2e.3e.4n.5i,
1c.2e.3e.4n.5n, 1c.2e.3e.4p.5a, 1c.2e.3e.4p.5b, 1c.2e.3e.4p.5d, 1c.2e.3e.4p.5f,
1c.2e.3e.4p.5h, 1c.2e.3e.4p.5i, 1c.2e.3e.4p.5n, 1c.2e.3g.4a.5a, 1c.2e.3g.4a.5b, TABLE 12-continued List of Compound Structures of Formula II 1c.2e.3g.4a.5d, 1c.2e.3g.4a.5f, 1c.2e.3g.4a.5h, 1c.2e.3g.4a.5i, 1c.2e.3g.4a.5n,
1c.2e.3g.4b.5a, 1c.2e.3g.4b.5b, 1c.2e.3g.4b.5d, 1c.2e.3g.4b.5f, 1c.2e.3g.4b.5h,
1c.2e.3g.4b.5i, 1c.2e.3g.4b.5n, 1c.2e.3g.4d.5a, 1c.2e.3g.4d.5b, 1c.2e.3g.4d.5d,
1c.2e.3g.4d.5f, 1c.2e.3g.4d.5h, 1c.2e.3g.4d.5i, 1c.2e.3g.4d.5n, 1c.2e.3g.4f.5a,
1c.2e.3g.4f.5b, 1c.2e.3g.4f.5d, 1c.2e.3g.4f.5f, 1c.2e.3g.4f.5h, 1c.2e.3g.4f.5i,
1c.2e.3g.4f.5n, 1c.2e.3g.4i.5a, 1c.2e.3g.4i.5b, 1c.2e.3g.4i.5d, 1c.2e.3g.4i.5f,
1c.2e.3g.4i.5h, 1c.2e.3g.4i.5i, 1c.2e.3g.4i.5n, 1c.2e.3g.4n.5a, 1c.2e.3g.4n.5b,
1c.2e.3g.4n.5d, 1c.2e.3g.4n.5f, 1c.2e.3g.4n.5h, 1c.2e.3g.4n.5i, 1c.2e.3g.4n.5n,
1c.2e.3g.4p.5a, 1c.2e.3g.4p.5b, 1c.2e.3g.4p.5d, 1c.2e.3g.4p.5f, 1c.2e.3g.4p.5h,
1c.2e.3g.4p.5i, 1c.2e.3g.4p.5n, 1c.2f.3a.4a.5a, 1c.2f.3a.4a.5b, 1c.2f.3a.4a.5d,
1c.2f.3a.4a.5f, 1c.2f.3a.4a.5h, 1c.2f.3a.4a.5i, 1c.2f.3a.4a.5n, 1c.2f.3a.4b.5a,
1c.2f.3a.4b.5b, 1c.2f.3a.4b.5d, 1c.2f.3a.4b.5f, 1c.2f.3a.4b.5h, 1c.2f.3a.4b.5i,
1c.2f.3a.4b.5n, 1c.2f.3a.4d.5a, 1c.2f.3a.4d.5b, 1c.2f.3a.4d.5d, 1c.2f.3a.4d.5f,
1c.2f.3a.4d.5h, 1c.2f.3a.4d.5i, 1c.2f.3a.4d.5n, 1c.2f.3a.4f.5a, 1c.2f.3a.4f.5b,
1c.2f.3a.4f.5d, 1c.2f.3a.4f.5f, 1c.2f.3a.4f.5h, 1c.2f.3a.4f.5i, 1c.2f.3a.4f.5n,
1c.2f.3a.4i.5a, 1c.2f.3a.4i.5b, 1c.2f.3a.4i.5d, 1c.2f.3a.4i.5f, 1c.2f.3a.4i.5h,
1c.2f.3a.4i.5i, 1c.2f.3a.4i.5n, 1c.2f.3a.4n.5a, 1c.2f.3a.4n.5b, 1c.2f.3a.4n.5d,
1c.2f.3a.4n.5f, 1c.2f.3a.4n.5h, 1c.2f.3a.4n.5i, 1c.2f.3a.4n.5n, 1c.2f.3a.4p.5a,
1c.2f.3a.4p.5b, 1c.2f.3a.4p.5d, 1c.2f.3a.4p.5f, 1c.2f.3a.4p.5h, 1c.2f.3a.4p.5i,
1c.2f.3a.4p.5n, 1c.2f.3c.4a.5a, 1c.2f.3c.4a.5b, 1c.2f.3c.4a.5d, 1c.2f.3c.4a.5f,
1c.2f.3c.4a.5h, 1c.2f.3c.4a.5i, 1c.2f.3c.4a.5n, 1c.2f.3c.4b.5a, 1c.2f.3c.4b.5b,
1c.2f.3c.4b.5d, 1c.2f.3c.4b.5f, 1c.2f.3c.4b.5h, 1c.2f.3c.4b.5i, 1c.2f.3c.4b.5n,
1c.2f.3c.4d.5a, 1c.2f.3c.4d.5b, 1c.2f.3c.4d.5d, 1c.2f.3c.4d.5f, 1c.2f.3c.4d.5h,
1c.2f.3c.4d.5i, 1c.2f.3c.4d.5n, 1c.2f.3c.4f.5a, 1c.2f.3c.4f.5b, 1c.2f.3c.4f.5d,
1c.2f.3c.4f.5f, 1c.2f.3c.4f.5h, 1c.2f.3c.4f.5i, 1c.2f.3c.4f.5n, 1c.2f.3c.4i.5a,
1c.2f.3c.4i.5b, 1c.2f.3c.4i.5d, 1c.2f.3c.4i.5f, 1c.2f.3c.4i.5h, 1c.2f.3c.4i.5i,
1c.2f.3c.4i.5n, 1c.2f.3c.4n.5a, 1c.2f.3c.4n.5b, 1c.2f.3c.4n.5d, 1c.2f.3c.4n.5f,
1c.2f.3c.4n.5h, 1c.2f.3c.4n.5i, 1c.2f.3c.4n.5n, 1c.2f.3c.4p.5a, 1c.2f.3c.4p.5b,
1c.2f.3c.4p.5d, 1c.2f.3c.4p.5f, 1c.2f.3c.4p.5h, 1c.2f.3c.4p.5i, 1c.2f.3c.4p.5n,
1c.2f.3e.4a.5a, 1c.2f.3e.4a.5b, 1c.2f.3e.4a.5d, 1c.2f.3e.4a.5f, 1c.2f.3e.4a.5h,
1c.2f.3e.4a.5i, 1c.2f.3e.4a.5n, 1c.2f.3e.4b.5a, 1c.2f.3e.4b.5b, 1c.2f.3e.4b.5d,
1c.2f.3e.4b.5f, 1c.2f.3e.4b.5h, 1c.2f.3e.4b.5i, 1c.2f.3e.4b.5n, 1c.2f.3e.4d.5a,
1c.2f.3e.4d.5b, 1c.2f.3e.4d.5d, 1c.2f.3e.4d.5f, 1c.2f.3e.4d.5h, 1c.2f.3e.4d.5i,
1c.2f.3e.4d.5n, 1c.2f.3e.4f.5a, 1c.2f.3e.4f.5b, 1c.2f.3e.4f.5d, 1c.2f.3e.4f.5f,
1c.2f.3e.4f.5h, 1c.2f.3e.4f.5i, 1c.2f.3e.4f.5n, 1c.2f.3e.4i.5a, 1c.2f.3e.4i.5b,
1c.2f.3e.4i.5d, 1c.2f.3e.4i.5f, 1c.2f.3e.4i.5h, 1c.2f.3e.4i.5i, 1c.2f.3e.4i.5n,
1c.2f.3e.4n.5a, 1c.2f.3e.4n.5b, 1c.2f.3e.4n.5d, 1c.2f.3e.4n.5f, 1c.2f.3e.4n.5h,
1c.2f.3e.4n.5i, 1c.2f.3e.4n.5n, 1c.2f.3e.4p.5a, 1c.2f.3e.4p.5b, 1c.2f.3e.4p.5d,
1c.2f.3e.4p.5f, 1c.2f.3e.4p.5h, 1c.2f.3e.4p.5i, 1c.2f.3e.4p.5n, 1c.2f.3g.4a.5a,
1c.2f.3g.4a.5b, 1c.2f.3g.4a.5d, 1c.2f.3g.4a.5f, 1c.2f.3g.4a.5h, 1c.2f.3g.4a.5i,
1c.2f.3g.4a.5n, 1c.2f.3g.4b.5a, 1c.2f.3g.4b.5b, 1c.2f.3g.4b.5d, 1c.2f.3g.4b.5f,
1c.2f.3g.4b.5h, 1c.2f.3g.4b.5i, 1c.2f.3g.4b.5n, 1c.2f.3g.4d.5a, 1c.2f.3g.4d.5b,
1c.2f.3g.4d.5d, 1c.2f.3g.4d.5f, 1c.2f.3g.4d.5h, 1c.2f.3g.4d.5i, 1c.2f.3g.4d.5n,
1c.2f.3g.4f.5a, 1c.2f.3g.4f.5b, 1c.2f.3g.4f.5d, 1c.2f.3g.4f.5f, 1c.2f.3g.4f.5h,
1c.2f.3g.4f.5i, 1c.2f.3g.4f.5n, 1c.2f.3g.4i.5a, 1c.2f.3g.4i.5b, 1c.2f.3g.4i.5d,
1c.2f.3g.4i.5f, 1c.2f.3g.4i.5h, 1c.2f.3g.4i.5i, 1c.2f.3g.4i.5n, 1c.2f.3g.4n.5a,
1c.2f.3g.4n.5b, 1c.2f.3g.4n.5d, 1c.2f.3g.4n.5f, 1c.2f.3g.4n.5h, 1c.2f.3g.4n.5i,
1c.2f.3g.4n.5n, 1c.2f.3g.4p.5a, 1c.2f.3g.4p.5b, 1c.2f.3g.4p.5d, 1c.2f.3g.4p.5f,
1c.2f.3g.4p.5h, 1c.2f.3g.4p.5i, 1c.2f.3g.4p.5n, 1c.2g.3a.4a.5a, 1c.2g.3a.4a.5b,
1c.2g.3a.4a.5d, 1c.2g.3a.4a.5f, 1c.2g.3a.4a.5h, 1c.2g.3a.4a.5i, 1c.2g.3a.4a.5n,
1c.2g.3a.4b.5a, 1c.2g.3a.4b.5b, 1c.2g.3a.4b.5d, 1c.2g.3a.4b.5f, 1c.2g.3a.4b.5h,
1c.2g.3a.4b.5i, 1c.2g.3a.4b.5n, 1c.2g.3a.4d.5a, 1c.2g.3a.4d.5b, 1c.2g.3a.4d.5d,
1c.2g.3a.4d.5f, 1c.2g.3a.4d.5h, 1c.2g.3a.4d.5i, 1c.2g.3a.4d.5n, 1c.2g.3a.4f.5a,
1c.2g.3a.4f.5b, 1c.2g.3a.4f.5d, 1c.2g.3a.4f.5f, 1c.2g.3a.4f.5h, 1c.2g.3a.4f.5i,
1c.2g.3a.4f.5n, 1c.2g.3a.4i.5a, 1c.2g.3a.4i.5b, 1c.2g.3a.4i.5d, 1c.2g.3a.4i.5f,
1c.2g.3a.4i.5h, 1c.2g.3a.4i.5i, 1c.2g.3a.4i.5n, 1c.2g.3a.4n.5a, 1c.2g.3a.4n.5b,
1c.2g.3a.4n.5d, 1c.2g.3a.4n.5f, 1c.2g.3a.4n.5h, 1c.2g.3a.4n.5i, 1c.2g.3a.4n.5n,
1c.2g.3a.4p.5a, 1c.2g.3a.4p.5b, 1c.2g.3a.4p.5d, 1c.2g.3a.4p.5f, 1c.2g.3a.4p.5h,
1c.2g.3a.4p.5i, 1c.2g.3a.4p.5n, 1c.2g.3c.4a.5a, 1c.2g.3c.4a.5b, 1c.2g.3c.4a.5d,
1c.2g.3c.4a.5f, 1c.2g.3c.4a.5h, 1c.2g.3c.4a.5i, 1c.2g.3c.4a.5n, 1c.2g.3c.4b.5a,
1c.2g.3c.4b.5b, 1c.2g.3c.4b.5d, 1c.2g.3c.4b.5f, 1c.2g.3c.4b.5h, 1c.2g.3c.4b.5i,
1c.2g.3c.4b.5n, 1c.2g.3c.4d.5a, 1c.2g.3c.4d.5b, 1c.2g.3c.4d.5d, 1c.2g.3c.4d.5f,
1c.2g.3c.4d.5h, 1c.2g.3c.4d.5i, 1c.2g.3c.4d.5n, 1c.2g.3c.4f.5a, 1c.2g.3c.4f.5b,
1c.2g.3c.4f.5d, 1c.2g.3c.4f.5f, 1c.2g.3c.4f.5h, 1c.2g.3c.4f.5i, 1c.2g.3c.4f.5n,
1c.2g.3c.4i.5a, 1c.2g.3c.4i.5b, 1c.2g.3c.4i.5d, 1c.2g.3c.4i.5f, 1c.2g.3c.4i.5h,
1c.2g.3c.4i.5i, 1c.2g.3c.4i.5n, 1c.2g.3c.4n.5a, 1c.2g.3c.4n.5b, 1c.2g.3c.4n.5d,
1c.2g.3c.4n.5f, 1c.2g.3c.4n.5h, 1c.2g.3c.4n.5i, 1c.2g.3c.4n.5n, 1c.2g.3c.4p.5a,
1c.2g.3c.4p.5b, 1c.2g.3c.4p.5d, 1c.2g.3c.4p.5f, 1c.2g.3c.4p.5h, 1c.2g.3c.4p.5i,
1c.2g.3c.4p.5n, 1c.2g.3e.4a.5a, 1c.2g.3e.4a.5b, 1c.2g.3e.4a.5d, 1c.2g.3e.4a.5f,
1c.2g.3e.4a.5h, 1c.2g.3e.4a.5i, 1c.2g.3e.4a.5n, 1c.2g.3e.4b.5a, 1c.2g.3e.4b.5b,
1c.2g.3e.4b.5d, 1c.2g.3e.4b.5f, 1c.2g.3e.4b.5h, 1c.2g.3e.4b.5i, 1c.2g.3e.4b.5n,
1c.2g.3e.4d.5a, 1c.2g.3e.4d.5b, 1c.2g.3e.4d.5d, 1c.2g.3e.4d.5f, 1c.2g.3e.4d.5h,
1c.2g.3e.4d.5i, 1c.2g.3e.4d.5n, 1c.2g.3e.4f.5a, 1c.2g.3e.4f.5b, 1c.2g.3e.4f.5d,
1c.2g.3e.4f.5f, 1c.2g.3e.4f.5h, 1c.2g.3e.4f.5i, 1c.2g.3e.4f.5n, 1c.2g.3e.4i.5a,
1c.2g.3e.4i.5b, 1c.2g.3e.4i.5d, 1c.2g.3e.4i.5f, 1c.2g.3e.4i.5h, 1c.2g.3e.4i.5i,
1c.2g.3e.4i.5n, 1c.2g.3e.4n.5a, 1c.2g.3e.4n.5b, 1c.2g.3e.4n.5d, 1c.2g.3e.4n.5f,
1c.2g.3e.4n.5h, 1c.2g.3e.4n.5i, 1c.2g.3e.4n.5n, 1c.2g.3e.4p.5a, 1c.2g.3e.4p.5b,
1c.2g.3e.4p.5d, 1c.2g.3e.4p.5f, 1c.2g.3e.4p.5h, 1c.2g.3e.4p.5i, 1c.2g.3e.4p.5n, TABLE 12-continued List of Compound Structures of Formula II 1c.2g.3g.4a.5a, 1c.2g.3g.4a.5b, 1c.2g.3g.4a.5d, 1c.2g.3g.4a.5f, 1c.2g.3g.4a.5h,
1c.2g.3g.4a.5i, 1c.2g.3g.4a.5n, 1c.2g.3g.4b.5a, 1c.2g.3g.4b.5b, 1c.2g.3g.4b.5d,
1c.2g.3g.4b.5f, 1c.2g.3g.4b.5h, 1c.2g.3g.4b.5i, 1c.2g.3g.4b.5n, 1c.2g.3g.4d.5a,
1c.2g.3g.4d.5b, 1c.2g.3g.4d.5d, 1c.2g.3g.4d.5f, 1c.2g.3g.4d.5h, 1c.2g.3g.4d.5i,
1c.2g.3g.4d.5n, 1c.2g.3g.4f.5a, 1c.2g.3g.4f.5b, 1c.2g.3g.4f.5d, 1c.2g.3g.4f.5f,
1c.2g.3g.4f.5h, 1c.2g.3g.4f.5i, 1c.2g.3g.4f.5n, 1c.2g.3g.4i.5a, 1c.2g.3g.4i.5b,
1c.2g.3g.4i.5d, 1c.2g.3g.4i.5f, 1c.2g.3g.4i.5h, 1c.2g.3g.4i.5i, 1c.2g.3g.4i.5n,
1c.2g.3g.4n.5a, 1c.2g.3g.4n.5b, 1c.2g.3g.4n.5d, 1c.2g.3g.4n.5f, 1c.2g.3g.4n.5h,
1c.2g.3g.4n.5i, 1c.2g.3g.4n.5n, 1c.2g.3g.4p.5a, 1c.2g.3g.4p.5b, 1c.2g.3g.4p.5d,
1c.2g.3g.4p.5f, 1c.2g.3g.4p.5h, 1c.2g.3g.4p.5i, 1c.2g.3g.4p.5n, 1c.2l.3a.4a.5a,
1c.2l.3a.4a.5b, 1c.2l.3a.4a.5d, 1c.2l.3a.4a.5f, 1c.2l.3a.4a.5h, 1c.2l.3a.4a.5i,
1c.2l.3a.4a.5n, 1c.2l.3a.4b.5a, 1c.2l.3a.4b.5b, 1c.2l.3a.4b.5d, 1c.2l.3a.4b.5f,
1c.2l.3a.4b.5h, 1c.2l.3a.4b.5i, 1c.2l.3a.4b.5n, 1c.2l.3a.4d.5a, 1c.2l.3a.4d.5b,
1c.2l.3a.4d.5d, 1c.2l.3a.4d.5f, 1c.2l.3a.4d.5h, 1c.2l.3a.4d.5i, 1c.2l.3a.4d.5n,
1c.2l.3a.4f.5a, 1c.2l.3a.4f.5b, 1c.2l.3a.4f.5d, 1c.2l.3a.4f.5f, 1c.2l.3a.4f.5h,
1c.2l.3a.4f.5i, 1c.2l.3a.4f.5n, 1c.2l.3a.4i.5a, 1c.2l.3a.4i.5b, 1c.2l.3a.4i.5d,
1c.2l.3a.4i.5f, 1c.2l.3a.4i.5h, 1c.2l.3a.4i.5i, 1c.2l.3a.4i.5n, 1c.2l.3a.4n.5a,
1c.2l.3a.4n.5b, 1c.2l.3a.4n.5d, 1c.2l.3a.4n.5f, 1c.2l.3a.4n.5h, 1c.2l.3a.4n.5i,
1c.2l.3a.4n.5n, 1c.2l.3a.4p.5a, 1c.2l.3a.4p.5b, 1c.2l.3a.4p.5d, 1c.2l.3a.4p.5f,
1c.2l.3a.4p.5h, 1c.2l.3a.4p.5i, 1c.2l.3a.4p.5n, 1c.2l.3c.4a.5a, 1c.2l.3c.4a.5b,
1c.2l.3c.4a.5d, 1c.2l.3c.4a.5f, 1c.2l.3c.4a.5h, 1c.2l.3c.4a.5i, 1c.2l.3c.4a.5n,
1c.2l.3c.4b.5a, 1c.2l.3c.4b.5b, 1c.2l.3c.4b.5d, 1c.2l.3c.4b.5f, 1c.2l.3c.4b.5h,
1c.2l.3c.4b.5i, 1c.2l.3c.4b.5n, 1c.2l.3c.4d.5a, 1c.2l.3c.4d.5b, 1c.2l.3c.4d.5d,
1c.2l.3c.4d.5f, 1c.2l.3c.4d.5h, 1c.2l.3c.4d.5i, 1c.2l.3c.4d.5n, 1c.2l.3c.4f.5a,
1c.2l.3c.4f.5b, 1c.2l.3c.4f.5d, 1c.2l.3c.4f.5f, 1c.2l.3c.4f.5h, 1c.2l.3c.4f.5i,
1c.2l.3c.4f.5n, 1c.2l.3c.4i.5a, 1c.2l.3c.4i.5b, 1c.2l.3c.4i.5d, 1c.2l.3c.4i.5f,
1c.2l.3c.4i.5h, 1c.2l.3c.4i.5i, 1c.2l.3c.4i.5n, 1c.2l.3c.4n.5a, 1c.2l.3c.4n.5b,
1c.2l.3c.4n.5d, 1c.2l.3c.4n.5f, 1c.2l.3c.4i.5h, 1c.2l.3c.4n.5i, 1c.2l.3c.4n.5n,
1c.2l.3c.4p.5a, 1c.2l.3c.4p.5b, 1c.2l.3c.4p.5d, 1c.2l.3c.4p.5f, 1c.2l.3c.4p.5h,
1c.2l.3c.4p.5i, 1c.2l.3c.4p.5n, 1c.2l.3e.4a.5a, 1c.2l.3e.4a.5b, 1c.2l.3e.4a.5d,
1c.2l.3e.4a.5f, 1c.2l.3e.4a.5h, 1c.2l.3e.4a.5i, 1c.2l.3e.4a.5n, 1c.2l.3e.4b.5a,
1c.2l.3e.4b.5b, 1c.2l.3e.4b.5d, 1c.2l.3e.4b.5f, 1c.2l.3e.4b.5h, 1c.2l.3e.4b.5i,
1c.2l.3e.4b.3n, 1c.2l.3e.4d.5a, 1c.2l.3e.4d.5b, 1c.2l.3e.4d.5d, 1c.2l.3e.4d.5f,
1c.2l.3e.4d.5h, 1c.2l.3e.4d.5i, 1c.2l.3e.4d.5n, 1c.2l.3e.4f.5a, 1c.2l.3e.4f.5b,
1c.2l.3e.4f.5d, 1c.2l.3e.4f.5f, 1c.2l.3e.4f.5h, 1c.2l.3e.4f.5i, 1c.2l.3e.4l.5n,
1c.2l.3e.4i.5a, 1c.2l.3e.4i.5b, 1c.2l.3e.4i.5d, 1c.2l.3e.4i.5f, 1c.2l.3e.4i.5h,
1c.2l.3e.4i.5i, 1c.2l.3e.4i.5n, 1c.2l.3e.4n.5a, 1c.2l.3e.4n.5b, 1c.2l.3e.4n.5d,
1c.2l.3e.4n.5f, 1c.2l.3e.4n.5h, 1c.2l.3e.4n.5i, 1c.2l.3e.4n.5n, 1c.2l.3e.4p.5a,
1c.2l.3e.4p.5b, 1c.2l.3e.4p.5d, 1c.2l.3e.4p.5f, 1c.2l.3e.4p.5h, 1c.2l.3e.4p.5i,
1c.2l.3e.4p.5n, 1c.2l.3g.4a.5a, 1c.2l.3g.4a.5b, 1c.2l.3g.4a.5d, 1c.2l.3g.4a.5f,
1c.2l.3g.4a.5h, 1c.2l.3g.4a.5i, 1c.2l.3g.4a.5n, 1c.2l.3g.4b.5a, 1c.2l.3g.4b.5b,
1c.2l.3g.4b.5d, 1c.2l.3g.4b.5f, 1c.2l.3g.4b.5h, 1c.2l.3g.4b.5i, 1c.2l.3g.4b.5n,
1c.2l.3g.4d.5a, 1c.2l.3g.4d.5b, 1c.2l.3g.4d.5d, 1c.2l.3g.4d.5f, 1c.2l.3g.4d.5h,
1c.2l.3g.4d.5i, 1c.2l.3g.4d.5n, 1c.2l.3g.4f.5a, 1c.2l.3g.4f.5b, 1c.2l.3g.4f.5d,
1c.2l.3g.4f.5f, 1c.2l.3g.4f.5h, 1c.2l.3g.4f.5i, 1c.2l.3g.4f.5n, 1c.2l.3g.4i.5a,
1c.2l.3g.4i.5b, 1c.2l.3g.4i.5d, 1c.2l.3g.4i.5f, 1c.2l.3g.4i.5h, 1c.2l.3g.4i.5i,
1c.2l.3g.4i.5n, 1c.2l.3g.4n.5a, 1c.2l.3g.4n.5b, 1c.2l.3g.4n.5d, 1c.2l.3g.4n.5f,
1c.2l.3g.4n.5h, 1c.2l.3g.4n.5i, 1c.2l.3g.4n.5n, 1c.2l.3g.4p.5a, 1c.2l.3g.4p.5b,
1c.2l.3g.4p.5d, 1c.2l.3g.4p.5f, 1c.2l.3g.4p.5h, 1c.2l.3g.4p.5i, 1c.2l.3g.4p.5n,
1c.2m.3a.4a.5a, 1c.2m.3a.4a.5b, 1c.2m.3a.4a.5d, 1c.2m.3a.4a.5f, 1c.2m.3a.4a.5h,
1c.2m.3a.4a.5i, 1c.2m.3a.4a.5n, 1c.2m.3a.4b.5a, 1c.2m.3a.4b.5b, 1c.2m.3a.4b.5d,
1c.2m.3a.4b.5f, 1c.2m.3a.4b.5h, 1c.2m.3a.4b.5i, 1c.2m.3a.4b.5n, 1c.2m.3a.4d.5a,
1c.2m.3a.4d.5b, 1c.2m.3a.4d.5d, 1c.2m.3a.4d.5f, 1c.2m.3a.4d.5h, 1c.2m.3a.4d.5i,
1c.2m.3a.4d.5n, 1c.2m.3a.4f.5a, 1c.2m.3a.4f.5b, 1c.2m.3a.4f.5d, 1c.2m.3a.4f.5f,
1c.2m.3a.4f.5h, 1c.2m.3a.4f.5i, 1c.2m.3a.4f.5n, 1c.2m.3a.4i.5a, 1c.2m.3a.4i.5b,
1c.2m.3a.4i.5d, 1c.2m.3a.4i.5f, 1c.2m.3a.4i.5h, 1c.2m.3a.4i.5i, 1c.2m.3a.4i.5n,
1c.2m.3a.4n.5a, 1c.2m.3a.4n.5b, 1c.2m.3a.4m.5d, 1c.2m.3a.4n.5f, 1c.2m.3a.4n.5h,
1c.2m.3a.4n.5i, 1c.2m.3a.4n.5n, 1c.2m.3a.4p.5a, 1c.2m.3a.4p.5b, 1c.2m.3a.4p.5d,
1c.2m.3a.4p.5f, 1c.2m.3a.4p.5h, 1c.2m.3a.4p.5i, 1c.2m.3a.4p.5n, 1c.2m.3c.4a.5a,
1c.2m.3c.4a.5b, 1c.2m.3c.4a.5d, 1c.2m.3c.4a.5f, 1c.2m.3c.4a.5h, 1c.2m.3c.4a.5i,
1c.2m.3c.4a.5n, 1c.2m.3c.4b.5a, 1c.2m.3c.4b.5b, 1c.2m.3c.4b.5d, 1c.2m.3c.4b.5f,
1c.2m.3c.4b.5h, 1c.2m.3c.4b.5i, 1c.2m.3c.4b.5n, 1c.2m.3c.4d.5a, 1c.2m.3c.4d.5b,
1c.2m.3c.4d.5d, 1c.2m.3c.4d.5f, 1c.2m.3c.4d.5h, 1c.2m.3c.4d.5i, 1c.2m.3c.4d.5n,
1c.2m.3c.4f.5a, 1c.2m.3c.4f.5b, 1c.2m.3c.4f.5d, 1c.2m.3c.4f.5f, 1c.2m.3c.4f.5h,
1c.2m.3c.4f.5i, 1c.2m.3c.4f.5n, 1c.2m.3c.4i.5a, 1c.2m.3c.4i.5b, 1c.2m.3c.4i.5d,
1c.2m.3c.4i.5f, 1c.2m.3c.4i.5h, 1c.2m.3c.4i.5i, 1c.2m.3c.4i.5n, 1c.2m.3c.4n.5a,
1c.2m.3c.4n.5b, 1c.2m.3c.4n.5d, 1c.2m.3c.4n.5f, 1c.2m.3c.4n.5h, 1c.2m.3c.4n.5i,
1c.2m.3c.4n.5n, 1c.2m.3c.4p.5a, 1c.2m.3c.4p.5b, 1c.2m.3c.4p.5d, 1c.2m.3c.4p.5f,
1c.2m.3c.4p.5h, 1c.2m.3c.4p.5i, 1c.2m.3c.4p.5n, 1c.2m.3e.4a.5a, 1c.2m.3e.4a.5b,
1c.2m.3e.4a.5d, 1c.2m.3e.4a.5f, 1c.2m.3e.4a.5h, 1c.2m.3e.4a.5i, 1c.2m.3e.4a.5n,
1c.2m.3e.4b.5a, 1c.2m.3e.4b.5b, 1c.2m.3e.4b.5d, 1c.2m.3e.4b.5f, 1c.2m.3e.4b.5h,
1c.2m.3e.4b.5i, 1c.2m.3e.4b.5n, 1c.2m.3e.4d.5a, 1c.2m.3e.4d.5b, 1c.2m.3e.4d.5d,
1c.2m.3e.4d.5f, 1c.2m.3e.4d.5h, 1c.2m.3e.4d.5i, 1c.2m.3e.4d.5n, 1c.2m.3e.4f.5a,
1c.2m.3e.4f.5b, 1c.2m.3e.4f.5d, 1c.2m.3e.4f.5f, 1c.2m.3e.4f.5h, 1c.2m.3e.4f.5i,
1c.2m.3e.4f.5n, 1c.2m.3e.4i.5a, 1c.2m.3e.4i.5b, 1c.2m.3e.4i.5d, 1c.2m.3e.4i.5f,
1c.2m.3e.4i.5h, 1c.2m.3e.4i.5i, 1c.2m.3e.4i.5n, 1c.2m.3e.4n.5a, 1c.2m.3e.4n.5b,
1c.2m.3e.4n.5d, 1c.2m.3e.4n.5f, 1c.2m.3e.4n.5h, 1c.2m.3e.4n.5i, 1c.2m.3e.4n.5n,
1c.2m.3e.4p.5a, 1c.2m.3e.4p.5b, 1c.2m.3e.4p.5d, 1c.2m.3e.4p.5f, 1c.2m.3e.4p.5h, TABLE 12-continued List of Compound Structures of Formula II 1c.2m.3e.4p.5i, 1c.2m.3e.4p.5n, 1c.2m.3g.4a.5a, 1c.2m.3g.4a.5b, 1c.2m.3g.4a.5d,
1c.2m.3g.4a.5f, 1c.2m.3g.4a.5h, 1c.2m.3g.4a.5i, 1c.2m.3g.4a.5n, 1c.2m.3g.4b.5a,
1c.2m.3g.4b.5b, 1c.2m.3g.4b.5d, 1c.2m.3g.4b.5f, 1c.2m.3g.4b.5h, 1c.2m.3g.4b.5i,
1c.2m.3g.4b.5n, 1c.2m.3g.4d.5a, 1c.2m.3g.4d.5b, 1c.2m.3g.4d.5d, 1c.2m.3g.4d.5f,
1c.2m.3g.4d.5h, 1c.2m.3g.4d.5i, 1c.2m.3g.4d.5n, 1c.2m.3g.4f.5a, 1c.2m.3g.4f.5b,
1c.2m.3g.4f.5d, 1c.2m.3g.4f.5f, 1c.2m.3g.4f.5h, 1c.2m.3g.4f.5i, 1c.2m.3g.4f.5n,
1c.2m.3g.4i.5a, 1c.2m.3g.4i.5b, 1c.2m.3g.4i.5d, 1c.2m.3g.4i.5f, 1c.2m.3g.4i.5h,
1c.2m.3g.4i.5i, 1c.2m.3g.4i.5n, 1c.2m.3g.4n.5a, 1c.2m.3g.4n.5b, 1c.2m.3g.4n.5d,
1c.2m.3g.4n.5f, 1c.2m.3g.4n.5h, 1c.2m.3g.4n.5i, 1c.2m.3g.4n.5n, 1c.2m.3g.4p.5a,
1c.2m.3g.4p.5b, 1c.2m.3g.4p.5d, 1c.2m.3g.4p.5f, 1c.2m.3g.4p.5h, 1c.2m.3g.4p.5i,
1c.2m.3g.4p.5n, 1c.2n.3a.4a.5a, 1c.2n.3a.4a.5b, 1c.2n.3a.4a.5d, 1c.2n.3a.4a.5f,
1c.2n.3a.4a.5h, 1c.2n.3a.4a.5i, 1c.2n.3a.4a.5n, 1c.2n.3a.4b.5a, 1c.2n.3a.4b.5b,
1c.2n.3a.4b.5d, 1c.2n.3a.4b.5f, 1c.2n.3a.4b.5h, 1c.2n.3a.4b.5i, 1c.2n.3a.4b.5n,
1c.2n.3a.4d.5a, 1c.2n.3a.4d.5b, 1c.2n.3a.4d.5d, 1c.2n.3a.4d.5f, 1c.2n.3a.4d.5h,
1c.2n.3a.4d.5i, 1c.2n.3a.4d.5n, 1c.2n.3a.4f.5a, 1c.2n.3a.4f.5b, 1c.2n.3a.4f.5d,
1c.2n.3a.4f.5f, 1c.2n.3a.4f.5h, 1c.2n.3a.4f.5i, 1c.2n.3a.4f.5n, 1c.2n.3a.4i.5a,
1c.2n.3a.4i.5b, 1c.2n.3a.4i.5d, 1c.2n.3a.4i.5f, 1c.2n.3a.4i.5h, 1c.2n.3a.4i.5i,
1c.2n.3a.4i.5n, 1c.2n.3a.4n.5a, 1c.2n.3a.4n.5b, 1c.2n.3a.4n.5d, 1c.2n.3a.4n.5f,
1c.2n.3a.4n.5h, 1c.2n.3a.4n.5i, 1c.2n.3a.4n.5n, 1c.2n.3a.4p.5a, 1c.2n.3a.4p.5b,
1c.2n.3a.4p.5d, 1c.2n.3a.4p.5f, 1c.2n.3a.4p.5h, 1c.2n.3a.4p.5i, 1c.2n.3a.4p.5n,
1c.2n.3c.4a.5a, 1c.2n.3c.4a.5b, 1c.2n.3c.4a.5d, 1c.2n.3c.4a.5f, 1c.2n.3c.4a.5h,
1c.2n.3c.4a.5i, 1c.2n.3c.4a.5n, 1c.2n.3c.4b.5a, 1c.2n.3c.4b.5b, 1c.2n.3c.4b.5d,
1c.2n.3c.4b.5f, 1c.2n.3c.4b.5h, 1c.2n.3c.4b.5i, 1c.2n.3c.4b.5n, 1c.2n.3c.4d.5a,
1c.2n.3c.4d.5b, 1c.2n.3c.4d.5d, 1c.2n.3c.4d.5f, 1c.2n.3c.4d.5h, 1c.2n.3c.4d.5i,
1c.2n.3c.4d.5n, 1c.2n.3c.4f.5a, 1c.2n.3c.4f.5b, 1c.2n.3c.4f.5d, 1c.2n.3c.4f.5f,
1c.2n.3c.4f.5h, 1c.2n.3c.4f.5i, 1c.2n.3c.4f.5n, 1c.2n.3c.4i.5a, 1c.2n.3c.4i.5b,
1c.2n.3c.4i.5d, 1c.2n.3c.4i.5f, 1c.2n.3c.4i.5h, 1c.2n.3c.4i.5i, 1c.2n.3c.4i.5n,
1c.2n.3c.4n.5a, 1c.2n.3c.4n.5b, 1c.2n.3c.4n.5d, 1c.2n.3c.4n.5f, 1c.2n.3c.4n.5h,
1c.2n.3c.4n.5i, 1c.2n.3c.4n.5n, 1c.2n.3c.4p.5a, 1c.2n.3c.4p.5b, 1c.2n.3c.4p.5d,
1c.2n.3c.4p.5f, 1c.2n.3c.4p.5h, 1c.2n.3c.4p.5i, 1c.2n.3c.4p.5n, 1c.2n.3e.4a.5a,
1c.2n.3e.4a.5b, 1c.2n.3e.4a.5d, 1c.2n.3e.4a.5f, 1c.2n.3e.4a.5h, 1c.2n.3e.4a.5i,
1c.2n.3e.4a.5n, 1c.2n.3e.4b.5a, 1c.2n.3e.4b.5b, 1c.2n.3e.4b.5d, 1c.2n.3e.4b.5f,
1c.2n.3e.4b.5h, 1c.2n.3e.4b.5i, 1c.2n.3e.4b.5n, 1c.2n.3e.4d.5a, 1c.2n.3e.4d.5b,
1c.2n.3e.4d.5d, 1c.2n.3e.4d.5f, 1c.2n.3e.4d.5h, 1c.2n.3e.4d.5i, 1c.2n.3e.4d.5n,
1c.2n.3e.4f.5a, 1c.2n.3e.4f.5b, 1c.2n.3e.4f.5d, 1c.2n.3e.4f.5f, 1c.2n.3e.4f.5h,
1c.2n.3e.4f.5i, 1c.2n.3e.4f.5n, 1c.2n.3e.4i.5a, 1c.2n.3e.4i.5b, 1c.2n.3e.4i.5d,
1c.2n.3e.4i.5f, 1c.2n.3e.4i.5h, 1c.2n.3e.4i.5i, 1c.2n.3e.4i.5n, 1c.2n.3e.4n.5a,
1c.2n.3e.4n.5b, 1c.2n.3e.4n.5d, 1c.2n.3e.4n.5f, 1c.2n.3e.4n.5h, 1c.2n.3e.4n.5i,
1c.2n.3e.4n.5n, 1c.2n.3e.4p.5a, 1c.2n.3e.4p.5b, 1c.2n.3e.4p.5d, 1c.2n.3e.4p.5f,
1c.2n.3e.4p.5h, 1c.2n.3e.4p.5i, 1c.2n.3e.4p.5n, 1c.2n.3g.4a.5a, 1c.2n.3g.4a.5b,
1c.2n.3g.4a.5d, 1c.2n.3g.4a.5f, 1c.2n.3g.4a.5h, 1c.2n.3g.4a.5i, 1c.2n.3g.4a.5n,
1c.2n.3g.4b.5a, 1c.2n.3g.4b.5b, 1c.2n.3g.4b.5d, 1c.2n.3g.4b.5f, 1c.2n.3g.4b.5h,
1c.2n.3g.4b.5i, 1c.2n.3g.4b.5n, 1c.2n.3g.4d.5a, 1c.2n.3g.4d.5b, 1c.2n.3g.4d.5d,
1c.2n.3g.4d.5f, 1c.2n.3g.4d.5h, 1c.2n.3g.4d.5i, 1c.2n.3g.4d.5n, 1c.2n.3g.4f.5a,
1c.2n.3g.4f.5b, 1c.2n.3g.4f.5d, 1c.2n.3g.4f.5f, 1c.2n.3g.4f.5h, 1c.2n.3g.4f.5i,
1c.2n.3g.4f.5n, 1c.2n.3g.4i.5a, 1c.2n.3g.4i.5b, 1c.2n.3g.4i.5d, 1c.2n.3g.4i.5f,
1c.2n.3g.4i.5h, 1c.2n.3g.4i.5i, 1c.2n.3g.4i.5n, 1c.2n.3g.4n.5a, 1c.2n.3g.4n.5b,
1c.2n.3g.4n.5d, 1c.2n.3g.4n.5f, 1c.2n.3g.4n.5h, 1c.2n.3g.4n.5i, 1c.2n.3g.4n.5n,
1c.2n.3g.4p.5a, 1c.2n.3g.4p.5b, 1c.2n.3g.4p.5d, 1c.2n.3g.4p.5f, 1c.2n.3g.4p.5h,
1c.2n.3g.4p.5i, 1c.2n.3g.4p.5n, 1c.2q.3a.4a.5a, 1c.2q.3a.4a.5b, 1c.2q.3a.4a.5d,
1c.2q.3a.4a.5f, 1c.2q.3a.4a.5h, 1c.2q.3a.4a.5i, 1c.2q.3a.4a.5n, 1c.2q.3a.4b.5a,
1c.2q.3a.4b.5b, 1c.2q.3a.4b.5d, 1c.2q.3a.4b.5f, 1c.2q.3a.4b.5h, 1c.2q.3a.4b.5i,
1c.2q.3a.4b.5n, 1c.2q.3a.4d.5a, 1c.2q.3a.4d.5b, 1c.2q.3a.4d.5d, 1c.2q.3a.4d.5f,
1c.2q.3a.4d.5h, 1c.2q.3a.4d.5i, 1c.2q.3a.4d.5n, 1c.2q.3a.4f.5a, 1c.2q.3a.4f.5b,
1c.2q.3a.4f.5d, 1c.2q.3a.4f.5f, 1c.2q.3a.4f.5h, 1c.2q.3a.4f.5i, 1c.2q.3a.4f.5n,
1c.2q.3a.4i.5a, 1c.2q.3a.4i.5b, 1c.2q.3a.4i.5d, 1c.2q.3a.4i.5f, 1c.2q.3a.4i.5h,
1c.2q.3a.4i.5i, 1c.2q.3a.4i.5n, 1c.2q.3a.4n.5a, 1c.2q.3a.4n.5b, 1c.2q.3a.4n.5d,
1c.2q.3a.4n.5f, 1c.2q.3a.4n.5h, 1c.2q.3a.4n.5i, 1c.2q.3a.4n.5n, 1c.2q.3a.4p.5a,
1c.2q.3a.4p.5b, 1c.2q.3a.4p.5d, 1c.2q.3a.4p.5f, 1c.2q.3a.4p.5h, 1c.2q.3a.4p.5i,
1c.2q.3a.4p.5n, 1c.2q.3c.4a.5a, 1c.2q.3c.4a.5b, 1c.2q.3c.4a.5d, 1c.2q.3c.4a.5f,
1c.2q.3c.4a.5h, 1c.2q.3c.4a.5i, 1c.2q.3c.4a.5n, 1c.2q.3c.4b.5a, 1c.2q.3c.4b.5b,
1c.2q.3c.4b.5d, 1c.2q.3c.4b.5f, 1c.2q.3c.4b.5h, 1c.2q.3c.4b.5i, 1c.2q.3c.4b.5n,
1c.2q.3c.4d.5a, 1c.2q.3c.4d.5b, 1c.2q.3c.4d.5d, 1c.2q.3c.4d.5f, 1c.2q.3c.4d.5h,
1c.2q.3c.4d.5i, 1c.2q.3c.4d.5n, 1c.2q.3c.4f.5a, 1c.2q.3c.4f.5b, 1c.2q.3c.4f.5d,
1c.2q.3c.4f.5f, 1c.2q.3c.4f.5h, 1c.2q.3c.4f.5i, 1c.2q.3c.4f.5n, 1c.2q.3c.4i.5a,
1c.2q.3c.4i.5b, 1c.2q.3c.4i.5d, 1c.2q.3c.4i.5f, 1c.2q.3c.4i.5h, 1c.2q.3c.4i.5i,
1c.2q.3c.4i.5n, 1c.2q.3c.4n.5a, 1c.2q.3c.4n.5b, 1c.2q.3c.4n.5d, 1c.2q.3c.4n.5f,
1c.2q.3c.4n.5h, 1c.2q.3c.4n.5i, 1c.2q.3c.4n.5n, 1c.2q.3c.4p.5a, 1c.2q.3c.4p.5b,
1c.2q.3c.4p.5d, 1c.2q.3c.4p.5f, 1c.2q.3c.4p.5h, 1c.2q.3c.4p.5i, 1c.2q.3c.4p.5n,
1c.2q.3e.4a.5a, 1c.2q.3e.4a.5b, 1c.2q.3e.4a.5d, 1c.2q.3e.4a.5f, 1c.2q.3e.4a.5h,
1c.2q.3e.4a.5i, 1c.2q.3e.4a.5n, 1c.2q.3e.4b.5a, 1c.2q.3e.4b.5b, 1c.2q.3e.4b.5d,
1c.2q.3e.4b.5f, 1c.2q.3e.4b.5h, 1c.2q.3e.4b.5i, 1c.2q.3e.4b.5n, 1c.2q.3e.4d.5a,
1c.2q.3e.4d.5b, 1c.2q.3e.4d.5d, 1c.2q.3e.4d.5f, 1c.2q.3e.4d.5h, 1c.2q.3e.4d.5i,
1c.2q.3e.4d.5n, 1c.2q.3e.4f.5a, 1c.2q.3e.4f.5b, 1c.2q.3e.4f.5d, 1c.2q.3e.4f.5f,
1c.2q.3e.4f.5h, 1c.2q.3e.4f.5i, 1c.2q.3e.4f.5n, 1c.2q.3e.4i.5a, 1c.2q.3e.4i.5b,
1c.2q.3e.4i.5d, 1c.2q.3e.4i.5f, 1c.2q.3e.4i.5h, 1c.2q.3e.4i.5i, 1c.2q.3e.4i.5n,
1c.2q.3e.4n.5a, 1c.2q.3e.4n.5b, 1c.2q.3e.4n.5d, 1c.2q.3e.4n.5f, 1c.2q.3e.4n.5h,
1c.2q.3e.4n.5i, 1c.2q.3e.4n.5n, 1c.2q.3e.4p.5a, 1c.2q.3e.4p.5b, 1c.2q.3e.4p.5d, TABLE 12-continued List of Compound Structures of Formula II 1c.2q.3e.4p.5f, 1c.2q.3e.4p.5h, 1c.2q.3e.4p.5i, 1c.2q.3e.4p.5n, 1c.2q.3g.4a.5a,
1c.2q.3g.4a.5b, 1c.2q.3g.4a.5d, 1c.2q.3g.4a.5f, 1c.2q.3g.4a.5h, 1c.2q.3g.4a.5i,
1c.2q.3g.4a.5n, 1c.2q.3g.4b.5a, 1c.2q.3g.4b.5b, 1c.2q.3g.4b.5d, 1c.2q.3g.4b.5f,
1c.2q.3g.4b.5h, 1c.2q.3g.4b.5i, 1c.2q.3g.4b.5n, 1c.2q.3g.4d.5a, 1c.2q.3g.4d.5b,
1c.2q.3g.4d.5d, 1c.2q.3g.4d.5f, 1c.2q.3g.4d.5h, 1c.2q.3g.4d.5i, 1c.2q.3g.4d.5n,
1c.2q.3g.4f.5a, 1c.2q.3g.4f.5b, 1c.2q.3g.4f.5d, 1c.2q.3g.4f.5f, 1c.2q.3g.4f.5h,
1c.2q.3g.4f.5i, 1c.2q.3g.4f.5n, 1c.2q.3g.4i.5a, 1c.2q.3g.4i.5b, 1c.2q.3g.4i.5d,
1c.2q.3g.4i.5f, 1c.2q.3g.4i.5h, 1c.2q.3g.4i.5i, 1c.2q.3g.4i.5n, 1c.2q.3g.4n.5a,
1c.2q.3g.4n.5b, 1c.2q.3g.4n.5d, 1c.2q.3g.4n.5f, 1c.2q.3g.4n.5h, 1c.2q.3g.4n.5i,
1c.2q.3g.4n.5n, 1c.2q.3g.4p.5a, 1c.2q.3g.4p.5b, 1c.2q.3g.4p.5d, 1c.2q.3g.4p.5f,
1c.2q.3g.4p.5h, 1c.2q.3g.4p.5i, 1c.2q.3g.4p.5n, 1c.2v.3a.4a.5a, 1c.2v.3a.4a.5b,
1c.2v.3a.4a.5d, 1c.2v.3a.4a.5f, 1c.2v.3a.4a.5h, 1c.2v.3a.4a.5i, 1c.2v.3a.4a.5n,
1c.2v.3a.4b.5a, 1c.2v.3a.4b.5b, 1c.2v.3a.4b.5d, 1c.2v.3a.4b.5f, 1c.2v.3a.4b.5h,
1c.2v.3a.4b.5i, 1c.2v.3a.4b.5n, 1c.2v.3a.4d.5a, 1c.2v.3a.4d.5b, 1c.2v.3a.4d.5d,
1c.2v.3a.4d.5f, 1c.2v.3a.4d.5h, 1c.2v.3a.4d.5i, 1c.2v.3a.4d.5n, 1c.2v.3a.4f.5a,
1c.2v.3a.4f.5b, 1c.2v.3a.4f.5d, 1c.2v.3a.4f.5f, 1c.2v.3a.4f.5h, 1c.2v.3a.4f.5i,
1c.2v.3a.4f.5n, 1c.2v.3a.4i.5a, 1c.2v.3a.4i.5b, 1c.2v.3a.4i.5d, 1c.2v.3a.4i.5f,
1c.2v.3a.4i.5h, 1c.2v.3a.4i.5i, 1c.2v.3a.4i.5n, 1c.2v.3a.4n.5a, 1c.2v.3a.4n.5b,
1c.2v.3a.4n.5d, 1c.2v.3a.4n.5f, 1c.2v.3a.4n.5h, 1c.2v.3a.4n.5i, 1c.2v.3a.4n.5n,
1c.2v.3a.4p.5a, 1c.2v.3a.4p.5b, 1c.2v.3a.4p.5d, 1c.2v.3a.4p.5f, 1c.2v.3a.4p.5h,
1c.2v.3a.4p.5i, 1c.2v.3a.4p.5n, 1c.2v.3c.4a.5a, 1c.2v.3c.4a.5b, 1c.2v.3c.4a.5d,
1c.2v.3c.4a.5f, 1c.2v.3c.4a.5h, 1c.2v.3c.4a.5i, 1c.2v.3c.4a.5n, 1c.2v.3c.4b.5a,
1c.2v.3c.4b.5b, 1c.2v.3c.4b.5d, 1c.2v.3c.4b.5f, 1c.2v.3c.4b.5h, 1c.2v.3c.4b.5i,
1c.2v.3c.4b.5n, 1c.2v.3c.4d.5a, 1c.2v.3c.4d.5b, 1c.2v.3c.4d.5d, 1c.2v.3c.4d.5f,
1c.2v.3c.4d.5h, 1c.2v.3c.4d.5i, 1c.2v.3c.4d.5n, 1c.2v.3c.4f.5a, 1c.2v.3c.4f.5b,
1c.2v.3c.4f.5d, 1c.2v.3c.4f.5f, 1c.2v.3c.4f.5h, 1c.2v.3c.4f.5i, 1c.2v.3c.4f.5n,
1c.2v.3c.4i.5a, 1c.2v.3c.4i.5b, 1c.2v.3c.4i.5d, 1c.2v.3c.4i.5f, 1c.2v.3c.4i.5h,
1c.2v.3c.4i.5i, 1c.2v.3c.4i.5n, 1c.2v.3c.4n.5a, 1c.2v.3c.4n.5b, 1c.2v.3c.4n.5d,
1c.2v.3c.4n.5f, 1c.2v.3c.4n.5h, 1c.2v.3c.4n.5i, 1c.2v.3c.4n.5n, 1c.2v.3c.4p.5a,
1c.2v.3c.4p.5b, 1c.2v.3c.4p.5d, 1c.2v.3c.4p.5f, 1c.2v.3c.4p.5h, 1c.2v.3c.4p.5i,
1c.2v.3c.4p.5n, 1c.2v.3e.4a.5a, 1c.2v.3e.4a.5b, 1c.2v.3e.4a.5d, 1c.2v.3c.4a.5f,
1c.2v.3e.4a.5h, 1c.2v.3e.4a.5i, 1c.2v.3e.4a.5n, 1c.2v.3e.4b.5a, 1c.2v.3e.4b.5b,
1c.2v.3e.4b.5d, 1c.2v.3e.4b.5f, 1c.2v.3e.4b.5h, 1c.2v.3e.4b.5i, 1c.2v.3e.4b.5n,
1c.2v.3e.4d.5a, 1c.2v.3e.4d.5b, 1c.2v.3e.4d.5d, 1c.2v.3e.4d.5f, 1c.2v.3e.4d.5h,
1c.2v.3e.4d.5i, 1c.2v.3e.4d.5n, 1c.2v.3e.4f.5a, 1c.2v.3e.4f.5b, 1c.2v.3e.4f.5d,
1c.2v.3e.4f.5f, 1c.2v.3e.4f.5h, 1c.2v.3e.4f.5i, 1c.2v.3e.4f.5n, 1c.2v.3e.4i.5a,
1c.2v.3e.4i.5b, 1c.2v.3e.4i.5d, 1c.2v.3e.4i.5f, 1c.2v.3e.4i.5h, 1c.2v.3e.4i.5i,
1c.2v.3e.4i.5n, 1c.2v.3e.4n.5a, 1c.2v.3e.4n.5b, 1c.2v.3e.4n.5d, 1c.2v.3e.4n.5f,
1c.2v.3e.4n.5h, 1c.2v.3e.4n.5i, 1c.2v.3e.4n.5n, 1c.2v.3e.4p.5a, 1c.2v.3e.4p.5b,
1c.2v.3e.4p.5d, 1c.2v.3e.4p.5f, 1c.2v.3e.4p.5h, 1c.2v.3e.4p.5i, 1c.2v.3e.4p.5n,
1c.2v.3g.4a.5a, 1c.2v.3g.4a.5b, 1c.2v.3g.4a.5d, 1c.2v.3g.4a.5f, 1c.2v.3g.4a.5h,
1c.2v.3g.4a.5i, 1c.2v.3g.4a.5n, 1c.2v.3g.4b.5a, 1c.2v.3g.4b.5b, 1c.2v.3g.4b.5d,
1c.2v.3g.4b.5f, 1c.2v.3g.4b.5h, 1c.2v.3g.4b.5i, 1c.2v.3g.4b.5n, 1c.2v.3g.4d.5a,
1c.2v.3g.4d.5b, 1c.2v.3g.4d.5d, 1c.2v.3g.4d.5f, 1c.2v.3g.4d.5h, 1c.2v.3g.4d.5i,
1c.2v.3g.4d.5n, 1c.2v.3g.4f.5a, 1c.2v.3g.4f.5b, 1c.2v.3g.4f.5d, 1c.2v.3g.4f.5f,
1c.2v.3g.4f.5h, 1c.2v.3g.4f.5i, 1c.2v.3g.4f.5n, 1c.2v.3g.4i.5a, 1c.2v.3g.4i.5b,
1c.2v.3g.4i.5d, 1c.2v.3g.4i.5f, 1c.2v.3g.4i.5h, 1c.2v.3g.4i.5i, 1c.2v.3g.4i.5n,
1c.2v.3g.4n.5a, 1c.2v.3g.4n.5b, 1c.2v.3g.4n.5d, 1c.2v.3g.4n.5f, 1c.2v.3g.4n.5h,
1c.2v.3g.4n.5i, 1c.2v.3g.4n.5n, 1c.2v.3g.4p.5a, 1c.2v.3g.4p.5b, 1c.2v.3g.4p.5d,
1c.2v.3g.4p.5f, 1c.2v.3g.4p.5h, 1c.2v.3g.4p.5i, 1c.2v.3g.4p.5n, 1c.2y.3a.4a.5a,
1c.2y.3a.4a.5b, 1c.2y.3a.4a.5d, 1c.2y.3a.4a.5f, 1c.2y.3a.4a.5h, 1c.2y.3a.4a.5i,
1c.2y.3a.4a.5n, 1c.2y.3a.4b.5a, 1c.2y.3a.4b.5b, 1c.2y.3a.4b.5d, 1c.2y.3a.4b.5f,
1c.2y.3a.4b.5h, 1c.2y.3a.4b.5i, 1c.2y.3a.4b.5n, 1c.2y.3a.4d.5a, 1c.2y.3a.4d.5b,
1c.2y.3a.4d.5d, 1c.2y.3a.4d.5f, 1c.2y.3a.4d.5h, 1c.2y.3a.4d.5i, 1c.2y.3a.4d.5n,
1c.2y.3a.4f.5a, 1c.2y.3a.4f.5b, 1c.2y.3a.4f.5d, 1c.2y.3a.4f.5f, 1c.2y.3a.4f.5h,
1c.2y.3a.4f.5i, 1c.2y.3a.4f.5n, 1c.2y.3a.4i.5a, 1c.2y.3a.4i.5b, 1c.2y.3a.4i.5d,
1c.2y.3a.4i.5f, 1c.2y.3a.4i.5h, 1c.2y.3a.4i.5i, 1c.2y.3a.4i.5n, 1c.2y.3a.4n.5a,
1c.2y.3a.4n.5b, 1c.2y.3a.4n.5d, 1c.2y.3a.4n.5f, 1c.2y.3a.4n.5h, 1c.2y.3a.4n.5i,
1c.2y.3a.4n.5n, 1c.2y.3a.4p.5a, 1c.2y.3a.4p.5b, 1c.2y.3a.4p.5d, 1c.2y.3a.4p.5f,
1c.2y.3a.4p.5h, 1c.2y.3a.4p.5i, 1c.2y.3a.4p.5n, 1c.2y.3c.4a.5a, 1c.2y.3c.4a.5b,
1c.2y.3c.4a.5d, 1c.2y.3c.4a.5f, 1c.2y.3c.4a.5h, 1c.2y.3c.4a.5i, 1c.2y.3c.4a.5n,
1c.2y.3c.4b.5a, 1c.2y.3c.4b.5b, 1c.2y.3c.4b.5d, 1c.2y.3c.4b.5f, 1c.2y.3c.4b.5h,
1c.2y.3c.4b.5i, 1c.2y.3c.4b.5n, 1c.2y.3c.4d.5a, 1c.2y.3c.4d.5b, 1c.2y.3c.4d.5d,
1c.2y.3c.4d.5f, 1c.2y.3c.4d.5h, 1c.2y.3c.4d.5i, 1c.2y.3c.4d.5n, 1c.2y.3c.4f.5a,
1c.2y.3c.4f.5b, 1c.2y.3c.4f.5d, 1c.2y.3c.4f.5f, 1c.2y.3c.4f.5h, 1c.2y.3c.4f.5i,
1c.2y.3c.4f.5n, 1c.2y.3c.4i.5a, 1c.2y.3c.4i.5b, 1c.2y.3c.4i.5d, 1c.2y.3c.4i.5f,
1c.2y.3c.4i.5h, 1c.2y.3c.4i.5i, 1c.2y.3c.4i.5n, 1c.2y.3c.4n.5a, 1c.2y.3c.4n.5b,
1c.2y.3c.4n.5d, 1c.2y.3c.4n.5f, 1c.2y.3c.4n.5h, 1c.2y.3c.4n.5i, 1c.2y.3c.4n.5n,
1c.2y.3c.4p.5a, 1c.2y.3c.4p.5b, 1c.2y.3c.4p.5d, 1c.2y.3c.4p.5f, 1c.2y.3c.4p.5h,
1c.2y.3c.4p.5i, 1c.2y.3c.4p.5n, 1c.2y.3e.4a.5a, 1c.2y.3e.4a.5b, 1c.2y.3e.4a.5d,
1c.2y.3e.4a.5f, 1c.2y.3e.4a.5h, 1c.2y.3e.4a.5i, 1c.2y.3e.4a.5n, 1c.2y.3e.4b.5a,
1c.2y.3e.4b.5b, 1c.2y.3e.4b.5d, 1c.2y.3e.4b.5f, 1c.2y.3e.4b.5h, 1c.2y.3e.4b.5i,
1c.2y.3e.4b.5n, 1c.2y.3e.4d.5a, 1c.2y.3e.4d.5b, 1c.2y.3e.4d.5d, 1c.2y.3e.4d.5f,
1c.2y.3e.4d.5h, 1c.2y.3e.4d.5i, 1c.2y.5e.4d.5n, 1c.2y.3e.4f.5a, 1c.2y.3e.4f.5b,
1c.2y.3e.4f.5d, 1c.2y.3e.4f.5f, 1c.2y.3e.4f.5h, 1c.2y.3e.4f.5i, 1c.2y.3e.4f.5n,
1c.2y.3e.4i.5a, 1c.2y.3e.4i.5b, 1c.2y.3e.4i.5d, 1c.2y.3e.4i.5f, 1c.2y.3e.4i.5h,
1c.2y.3e.4i.5i, 1c.2y.3e.4i.5n, 1c.2y.3e.4n.5a, 1c.2y.3e.4n.5b, 1c.2y.3e.4n.5d,
1c.2y.3e.4n.5f, 1c.2y.3e.4n.5h, 1c.2y.3e.4n.5i, 1c.2y.3e.4n.5n, 1c.2y.3e.4p.5a,

TABLE 12-continued

List of Compound Structures of Formula II 1c.2y.3e.4p.5b, 1c.2y.3e.4p.5d, 1c.2y.3e.4p.5f, 1c.2y.3e.4p.5h, 1c.2y.3e.4p.5i,
1c.2y.3e.4p.5n, 1c.2y.3g.4a.5a, 1c.2y.3g.4a.5b, 1c.2y.3g.4a.5d, 1c.2y.3g.4a.5f,
1c.2y.3g.4a.5h, 1c.2y.3g.4a.5i, 1c.2y.3g.4a.5n, 1c.2y.3g.4b.5a, 1c.2y.3g.4b.5b,
1c.2y.3g.4b.5d, 1c.2y.3g.4b.5f, 1c.2y.3g.4b.5h, 1c.2y.3g.4b.5i, 1c.2y.3g.4b.5n,
1c.2y.3g.4d.5a, 1c.2y.3g.4d.5b, 1c.2y.3g.4d.5d, 1c.2y.3g.4d.5f, 1c.2y.3g.4d.5h,
1c.2y.3g.4d.5i, 1c.2y.3g.4d.5n, 1c.2y.3g.4f.5a, 1c.2y.3g.4f.5b, 1c.2y.3g.4f.5d,
1c.2y.3g.4f.5f, 1c.2y.3g.4f.5h, 1c.2y.3g.4f.5i, 1c.2y.3g.4f.5n, 1c.2y.3g.4i.5a,
1c.2y.3g.4i.5b, 1c.2y.3g.4i.5d, 1c.2y.3g.4i.5f, 1c.2y.3g.4i.5h, 1c.2y.3g.4i.5i,
1c.2y.3g.4i.5n, 1c.2y.3g.4n.5a, 1c.2y.3g.4n.5b, 1c.2y.3g.4n.5d, 1c.2y.3g.4n.5f,
1c.2y.3g.4n.5h, 1c.2y.3g.4n.5i, 1c.2y.3g.4n.5n, 1c.2y.3g.4p.5a, 1c.2y.3g.4p.5b,
1c.2y.3g.4p.5d, 1c.2y.3g.4p.5f, 1c.2y.3g.4p.5h, 1c.2y.3g.4p.5i, 1c.2y.3g.4p.5n,
1c.2z.3a.4a.5a, 1c.2z.3a.4a.5b, 1c.2z.3a.4a.5d, 1c.2z.3a.4a.5f, 1c.2z.3a.4a.5h,
1c.2z.3a.4a.5i, 1c.2z.3a.4a.5n, 1c.2z.3a.4b.5a, 1c.2z.3a.4b.5b, 1c.2z.3a.4b.5d,
1c.2z.3a.4b.5f, 1c.2z.3a.4b.5h, 1c.2z.3a.4b.5i, 1c.2z.3a.4b.5n, 1c.2z.3a.4d.5a,
1c.2z.3a.4d.5b, 1c.2z.3a.4d.5d, 1c.2z.3a.4d.5f, 1c.2z.3a.4d.5h, 1c.2z.3a.4d.5i,
1c.2z.3a.4d.5n, 1c.2z.3a.4f.5a, 1c.2z.3a.4f.5b, 1c.2z.3a.4f.5d, 1c.2z.3a.4f.5f,
1c.2z.3a.4f.5h, 1c.2z.3a.4f.5i, 1c.2z.3a.4f.5n, 1c.2z.3a.4i.5a, 1c.2z.3a.4i.5b,
1c.2z.3a.4i.5d, 1c.2z.3a.4i.5f, 1c.2z.3a.4i.5h, 1c.2z.3a.4i.5i, 1c.2z.3a.4i.5n,
1c.2z.3a.4n.5a, 1c.2z.3a.4n.5b, 1c.2z.3a.4n.5d, 1c.2z.3a.4n.5f, 1c.2z.3a.4n.5h,
1c.2z.3a.4n.5i, 1c.2z.3a.4n.5n, 1c.2z.3a.4p.5a, 1c.2z.3a.4p.5b, 1c.2z.3a.4p.5d,
1c.2z.3a.4p.5f, 1c.2z.3a.4p.5h, 1c.2z.3a.4p.5i, 1c.2z.3a.4p.5n, 1c.2z.3c.4a.5a,
1c.2z.3c.4a.5b, 1c.2z.3c.4a.5d, 1c.2z.3c.4a.5f, 1c.2z.3c.4a.5h, 1c.2z.3c.4a.5i,
1c.2z.3c.4a.5n, 1c.2z.3c.4b.5a, 1c.2z.3c.4b.5b, 1c.2z.3c.4b.5d, 1c.2z.3c.4b.5f,
1c.2z.3c.4b.5h, 1c.2z.3c.4b.5i, 1c.2z.3c.4b.5n, 1c.2z.3c.4d.5a, 1c.2z.3c.4d.5b,
1c.2z.3c.4d.5d, 1c.2z.3c.4d.5f, 1c.2z.3c.4d.5h, 1c.2z.3c.4d.5i, 1c.2z.3c.4d.5n,
1c.2z.3c.4f.5a, 1c.2z.3c.4f.5b, 1c.2z.3c.4f.5d, 1c.2z.3c.4f.5f, 1c.2z.3c.4f.5h,
1c.2z.3c.4f.5i, 1c.2z.3c.4f.5n, 1c.2z.3c.4i.5a, 1c.2z.3c.4i.5b, 1c.2z.3c.4i.5d,
1c.2z.3c.4i.5f, 1c.2z.3c.4i.5h, 1c.2z.3c.4i.5i, 1c.2z.3c.4i.5n, 1c.2z.3c.4n.5a,
1c.2z.3c.4n.5b, 1c.2z.3c.4n.5d, 1c.2z.3c.4n.5f, 1c.2z.3c.4n.5h, 1c.2z.3c.4n.5i,
1c.2z.3c.4n.5n, 1c.2z.3c.4p.5a, 1c.2z.3c.4p.5b, 1c.2z.3c.4p.5d, 1c.2z.3c.4p.5f,
1c.2z.3c.4p.5h, 1c.2z.3c.4p.5i, 1c.2z.3c.4p.5n, 1c.2z.3e.4a.5a, 1c.2z.3e.4a.5b,
1c.2z.3e.4a.5d, 1c.2z.3e.4a.5f, 1c.2z.3e.4a.5h, 1c.2z.3e.4a.5i, 1c.2z.3e.4a.5n,
1c.2z.3e.4b.5a, 1c.2z.3e.4b.5b, 1c.2z.3e.4b.5d, 1c.2z.3e.4b.5f, 1c.2z.3e.4b.5h,
1c.2z.3e.4b.5i, 1c.2z.3e.4b.5n, 1c.2z.3e.4d.5a, 1c.2z.3e.4d.5b, 1c.2z.3e.4d.5d,
1c.2z.3e.4d.5f, 1c.2z.3e.4d.5h, 1c.2z.3e.4d.5i, 1c.2z.3e.4d.5n, 1c.2z.3e.4f.5a,
1c.2z.3e.4f.5b, 1c.2z.3e.4f.5d, 1c.2z.3e.4f.5h, 1c.2z.3e.4f.5i, 1c.2z.5e.4f.5i,
1c.2z.3e.4f.5n, 1c.2z.3e.4i.5a, 1c.2z.3e.4i.5b, 1c.2z.3e.4i.5d, 1c.2z.3e.4i.5f,
1c.2z.3e.4i.5h, 1c.2z.3e.4i.5i, 1c.2z.3e.4i.5n, 1c.2z.3e.4n.5a, 1c.2z.3e.4n.5b,
1c.2z.3e.4n.5d, 1c.2z.3e.4n.5f, 1c.2z.3e.4n.5h, 1c.2z.3e.4n.5i, 1c.2z.3e.4n.5n,
1c.2z.3e.4p.5a, 1c.2z.3e.4p.5b, 1c.2z.3e.4p.5d, 1c.2z.3e.4p.5f, 1c.2z.3e.4p.5h,
1c.2z.3e.4p.5i, 1c.2z.3e.4p.5n, 1c.2z.3g.4a.5a, 1c.2z.3g.4a.5b, 1c.2z.3g.4a.5d,
1c.2z.3g.4a.5f, 1c.2z.3g.4a.5h, 1c.2z.3g.4a.5i, 1c.2z.3g.4a.5n, 1c.2z.3g.4b.5a,
1c.2z.3g.4b.5b, 1c.2z.3g.4b.5d, 1c.2z.3g.4b.5f, 1c.2z.3g.4b.5h, 1c.2z.3g.4b.5i,
1c.2z.3g.4b.5n, 1c.2z.3g.4d.5a, 1c.2z.3g.4d.5b, 1c.2z.3g.4d.5d, 1c.2z.3g.4d.5f,
1c.2z.3g.4d.5h, 1c.2z.3g.4d.5i, 1c.2z.3g.4d.5n, 1c.2z.3g.4f.5a, 1c.2z.3g.4f.5b,
1c.2z.3g.4f.5d, 1c.2z.3g.4f.5f, 1c.2z.3g.4f.5h, 1c.2z.3g.4f.5i, 1c.2z.3g.4f.5n,
1c.2z.3g.4i.5a, 1c.2z.3g.4i.5b, 1c.2z.3g.4i.5d, 1c.2z.3g.4i.5f, 1c.2z.3g.4i.5h,
1c.2z.3g.4i.5i, 1c.2z.3g.4i.5n, 1c.2z.3g.4n.5a, 1c.2z.3g.4n.5b, 1c.2z.3g.4n.5d,
1c.2z.3g.4n.5f, 1c.2z.3g.4n.5h, 1c.2z.3g.4n.5i, 1c.2z.3g.4n.5n, 1c.2z.3g.4p.5a,
1c.2z.3g.4p.5b, 1c.2z.3g.4p.5d, 1c.2z.3g.4p.5f, 1c.2z.3g.4p.5h, 1c.2z.3g.4p.5i,
1c.2z.3g.4p.5n, 1d.2a.3a.4a.5a, 1d.2a.3a.4a.5b, 1d.2a.3a.4a.5d, 1d.2a.3a.4a.5f,
1d.2a.3a.4a.5h, 1d.2a.3a.4a.5i, 1d.2a.3a.4a.5n, 1d.2a.3a.4b.5a, 1d.2a.3a.4b.5b,
1d.2a.3a.4b.5d, 1d.2a.3a.4b.5f, 1d.2a.3a.4b.5h, 1d.2a.3a.4b.5i, 1d.2a.3a.4b.5n,
1d.2a.3a.4d.5a, 1d.2a.3a.4d.5b, 1d.2a.3a.4d.5d, 1d.2a.3a.4d.5f, 1d.2a.3a.4d.5h,
1d.2a.3a.4d.5i, 1d.2a.3a.4d.5n, 1d.2a.3a.4f.5a, 1d.2a.3a.4f.5b, 1d.2a.3a.4f.5d,
1d.2a.3a.4f.5f, 1d.2a.3a.4f.5h, 1d.2a.3a.4f.5i, 1d.2a.3a.4f.5n, 1d.2a.3a.4i.5a,
1d.2a.3a.4i.5b, 1d.2a.3a.4i.5d, 1d.2a.3a.4i.5f, 1d.2a.3a.4i.5h, 1d.2a.3a.4i.5i,
1d.2a.3a.4i.5n, 1d.2a.3a.4n.5a, 1d.2a.3a.4n.5b, 1d.2a.3a.4n.5d, 1d.2a.3a.4n.5f,
1d.2a.3a.4n.5h, 1d.2a.3a.4n.5i, 1d.2a.3a.4n.5n, 1d.2a.3a.4p.5a, 1d.2a.3a.4p.5b,
1d.2a.3a.4p.5d, 1d.2a.3a.4p.5f, 1d.2a.3a.4p.5h, 1d.2a.3a.4p.5i, 1d.2a.3a.4p.5n,
1d.2a.3c.4a.5a, 1d.2a.3c.4a.5b, 1d.2a.3c.4a.5d, 1d.2a.3c.4a.5f, 1d.2a.3c.4a.5h,
1d.2a.3c.4a.5i, 1d.2a.3c.4a.5n, 1d.2a.3c.4b.5a, 1d.2a.3c.4b.5b, 1d.2a.3c.4b.5d,
1d.2a.3c.4b.5f, 1d.2a.3c.4b.5h, 1d.2a.3c.4b.5i, 1d.2a.3c.4b.5n, 1d.2a.3c.4d.5a,
1d.2a.3c.4d.5b, 1d.2a.3c.4d.5d, 1d.2a.3c.4d.5f, 1d.2a.3c.4d.5h, 1d.2a.3c.4d.5i,
1d.2a.3c.4d.5n, 1d.2a.3c.4f.5a, 1d.2a.3c.4f.5b, 1d.2a.3c.4f.5d, 1d.2a.3c.4f.5f,
1d.2a.3c.4f.5h, 1d.2a.3c.4f.5i, 1d.2a.3c.4f.5n, 1d.2a.3c.4i.5a, 1d.2a.3c.4i.5b,
1d.2a.3c.4i.5d, 1d.2a.3c.4i.5f, 1d.2a.3c.4i.5h, 1d.2a.3c.4i.5i, 1d.2a.3c.4i.5n,
1d.2a.3c.4n.5a, 1d.2a.3c.4n.5b, 1d.2a.3c.4n.5d, 1d.2a.3c.4n.5f, 1d.2a.3c.4n.5h,
1d.2a.3c.4n.5i, 1d.2a.3c.4n.5n, 1d.2a.3c.4p.5a, 1d.2a.3c.4p.5b, 1d.2a.3c.4p.5d,
1d.2a.3c.4p.5f, 1d.2a.3c.4p.5h, 1d.2a.3c.4p.5i, 1d.2a.3c.4p.5n, 1d.2a.3e.4a.5a,
1d.2a.3e.4a.5b, 1d.2a.3e.4a.5d, 1d.2a.3e.4a.5f, 1d.2a.3e.4a.5h, 1d.2a.3e.4a.5i,
1d.2a.3e.4a.5n, 1d.2a.3e.4b.5a, 1d.2a.3e.4b.5b, 1d.2a.3e.4b.5d, 1d.2a.3e.4b.5f,
1d.2a.3e.4b.5h, 1d.2a.3e.4b.5i, 1d.2a.3e.4b.5n, 1d.2a.3e.4d.5a, 1d.2a.3e.4d.5b,
1d.2a.3e.4d.5d, 1d.2a.3e.4d.5f, 1d.2a.3e.4d.5h, 1d.2a.3e.4d.5i, 1d.2a.3e.4d.5n,
1d.2a.3e.4f.5a, 1d.2a.3e.4f.5b, 1d.2a.3e.4f.5d, 1d.2a.3e.4f.5f, 1d.2a.3e.4f.5h,
1d.2a.3e.4f.5i, 1d.2a.3e.4f.5n, 1d.2a.3e.4i.5a, 1d.2a.3e.4i.5b, 1d.2a.3e.4i.5d,
1d.2a.3e.4i.5f, 1d.2a.3e.4i.5h, 1d.2a.3e.4i.5i, 1d.2a.3e.4i.5n, 1d.2a.3e.4n.5a,
1d.2a.3e.4n.5b, 1d.2a.3e.4n.5d, 1d.2a.3e.4n.5f, 1d.2a.3e.4n.5h, 1d.2a.3e.4n.5i,

TABLE 12-continued

List of Compound Structures of Formula II 1d.2a.3e.4n.5n, 1d.2a.3e.4p.5a, 1d.2a.3e.4p.5b, 1d.2a.3e.4p.5d, 1d.2a.3e.4p.5f,
1d.2a.3e.4p.5h, 1d.2a.3e.4p.5i, 1d.2a.3e.4p.5n, 1d.2a.3g.4a.5a, 1d.2a.3g.4a.5b,
1d.2a.3g.4a.5d, 1d.2a.3g.4a.5f, 1d.2a.3g.4a.5h, 1d.2a.3g.4a.5i, 1d.2a.3g.4a.5n,
1d.2a.3g.4b.5a, 1d.2a.3g.4b.5b, 1d.2a.3g.4b.5d, 1d.2a.3g.4b.5f, 1d.2a.3g.4b.5h,
1d.2a.3g.4b.5i, 1d.2a.3g.4b.5n, 1d.2a.3g.4d.5a, 1d.2a.3g.4d.5b, 1d.2a.3g.4d.5d,
1d.2a.3g.4d.5f, 1d.2a.3g.4d.5h, 1d.2a.3g.4d.5i, 1d.2a.3g.4d.5n, 1d.2a.3g.4f.5a,
1d.2a.3g.4f.5b, 1d.2a.3g.4f.5d, 1d.2a.3g.4f.5f, 1d.2a.3g.4f.5h, 1d.2a.3g.4f.5i,
1d.2a.3g.4f.5n, 1d.2a.3g.4i.5a, 1d.2a.3g.4i.5b, 1d.2a.3g.4i.5d, 1d.2a.3g.4i.5f,
1d.2a.3g.4i.5h, 1d.2a.3g.4i.5i, 1d.2a.3g.4i.5n, 1d.2a.3g.4n.5a, 1d.2a.3g.4n.5b,
1d.2a.3g.4n.5d, 1d.2a.3g.4n.5f, 1d.2a.3g.4n.5h, 1d.2a.3g.4n.5i, 1d.2a.3g.4n.5n,
1d.2a.3g.4p.5a, 1d.2a.3g.4p.5b, 1d.2a.3g.4p.5d, 1d.2a.3g.4p.5f, 1d.2a.3g.4p.5h,
1d.2a.3g.4p.5i, 1d.2a.3g.4p.5n, 1d.2b.3a.4a.5a, 1d.2b.3a.4a.5b, 1d.2b.3a.4a.5d,
1d.2b.3a.4a.5f, 1d.2b.3a.4a.5h, 1d.2b.3a.4a.5i, 1d.2b.3a.4a.5n, 1d.2b.3a.4b.5a,
1d.2b.3a.4b.5b, 1d.2b.3a.4b.5d, 1d.2b.3a.4b.5f, 1d.2b.3a.4b.5h, 1d.2b.3a.4b.5i,
1d.2b.3a.4b.5n, 1d.2b.3a.4d.5a, 1d.2b.3a.4d.5b, 1d.2b.3a.4d.5d, 1d.2b.3a.4d.5f,
1d.2b.3a.4d.5h, 1d.2b.3a.4d.5i, 1d.2b.3a.4d.5n, 1d.2b.3a.4f.5a, 1d.2b.3a.4f.5b,
1d.2b.3a.4f.5d, 1d.2b.3a.4f.5f, 1d.2b.3a.4f.5h, 1d.2b.3a.4f.5i, 1d.2b.3a.4f.5n,
1d.2b.3a.4i.5a, 1d.2b.3a.4i.5b, 1d.2b.3a.4i.5d, 1d.2b.3a.4i.5f, 1d.2b.3a.4i.5h,
1d.2b.3a.4i.5i, 1d.2b.3a.4i.5n, 1d.2b.3a.4n.5a, 1d.2b.3a.4n.5b, 1d.2b.3a.4n.5d,
1d.2b.3a.4n.5f, 1d.2b.3a.4n.5h, 1d.2b.3a.4n.5i, 1d.2b.3a.4n.5n, 1d.2b.3a.4p.5a,
1d.2b.3a.4p.5b, 1d.2b.3a.4p.5d, 1d.2b.3a.4p.5f, 1d.2b.3a.4p.5h, 1d.2b.3a.4p.5i,
1d.2b.3a.4p.5n, 1d.2b.3c.4a.5a, 1d.2b.3c.4a.5b, 1d.2b.3c.4a.5d, 1d.2b.3c.4a.5f,
1d.2b.3c.4a.5h, 1d.2b.3c.4a.5i, 1d.2b.3c.4a.5n, 1d.2b.3c.4b.5a, 1d.2b.3c.4b.5b,
1d.2b.3c.4b.5d, 1d.2b.3c.4b.5f, 1d.2b.3c.4b.5h, 1d.2b.3c.4b.5i, 1d.2b.3c.4b.5n,
1d.2b.3c.4d.5a, 1d.2b.3c.4d.5b, 1d.2b.3c.4d.5d, 1d.2b.3c.4d.5f, 1d.2b.3c.4d.5h,
1d.2b.3c.4d.5i, 1d.2b.3c.4d.5n, 1d.2b.3c.4f.5a, 1d.2b.3c.4f.5b, 1d.2b.3c.4f.5d,
1d.2b.3c.4f.5f, 1d.2b.3c.4f.5h, 1d.2b.3c.4f.5i, 1d.2b.3c.4f.5n, 1d.2b.3c.4i.5a,
1d.2b.3c.4i.5b, 1d.2b.3c.4i.5d, 1d.2b.3c.4i.5f, 1d.2b.3c.4i.5h, 1d.2b.3c.4i.5i,
1d.2b.3c.4i.5n, 1d.2b.3c.4n.5a, 1d.2b.3c.4n.5b, 1d.2b.3c.4n.5d, 1d.2b.3c.4n.5f,
1d.2b.3c.4n.5h, 1d.2b.3c.4n.5i, 1d.2b.3c.4n.5n, 1d.2b.3c.4p.5a, 1d.2b.3c.4p.5b,
1d.2b.3c.4p.5d, 1d.2b.3c.4p.5f, 1d.2b.3c.4p.5h, 1d.2b.3c.4p.5i, 1d.2b.3c.4p.5n,
1d.2b.3e.4a.5a, 1d.2b.3e.4a.5b, 1d.2b.3e.4a.5d, 1d.2b.3e.4a.5f, 1d.2b.3e.4a.5h,
1d.2b.3e.4a.5i, 1d.2b.3e.4a.5n, 1d.2b.3e.4b.5a, 1d.2b.3e.4b.5b, 1d.2b.3e.4b.5d,
1d.2b.3e.4b.5f, 1d.2b.3e.4b.5h, 1d.2b.3e.4b.5i, 1d.2b.3e.4b.5n, 1d.2b.3e.4d.5a,
1d.2b.3e.4d.5b, 1d.2b.3e.4d.5d, 1d.2b.3e.4d.5f, 1d.2b.3e.4d.5h, 1d.2b.3e.4d.5i,
1d.2b.3e.4d.5n, 1d.2b.3e.4f.5a, 1d.2b.3e.4f.5b, 1d.2b.3e.4f.5d, 1d.2b.3e.4f.5f,
1d.2b.3e.4f.5h, 1d.2b.3e.4f.5i, 1d.2b.3e.4f.5n, 1d.2b.3e.4i.5a, 1d.2b.3e.4i.5b,
1d.2b.3e.4i.5d, 1d.2b.3e.4i.5f, 1d.2b.3e.4i.5h, 1d.2b.3e.4i.5i, 1d.2b.3e.4i.5n,
1d.2b.3e.4n.5a, 1d.2b.3e.4n.5b, 1d.2b.3e.4n.5d, 1d.2b.3e.4n.5f, 1d.2b.3e.4n.5h,
1d.2b.3e.4n.5i, 1d.2b.3e.4n.5n, 1d.2b.3e.4p.5a, 1d.2b.3e.4p.5b, 1d.2b.3e.4p.5d,
1d.2b.3e.4p.5f, 1d.2b.3e.4p.5h, 1d.2b.3e.4p.5i, 1d.2b.3e.4p.5n, 1d.2b.3g.4a.5a,
1d.2b.3g.4a.5b, 1d.2b.3g.4a.5d, 1d.2b.3g.4a.5f, 1d.2b.3g.4a.5h, 1d.2b.3g.4a.5i,
1d.2b.3g.4a.5n, 1d.2b.3g.4b.5a, 1d.2b.3g.4b.5b, 1d.2b.3g.4b.5d, 1d.2b.3g.4b.5f,
1d.2b.3g.4b.5h, 1d.2b.3g.4b.5i, 1d.2b.3g.4b.5n, 1d.2b.3g.4d.5a, 1d.2b.3g.4d.5b,
1d.2b.3g.4d.5d, 1d.2b.3g.4d.5f, 1d.2b.3g.4d.5h, 1d.2b.3g.4d.5i, 1d.2b.3g.4d.5n,
1d.2b.3g.4f.5a, 1d.2b.3g.4f.5b, 1d.2b.3g.4f.5d, 1d.2b.3g.4f.5f, 1d.2b.3g.4f.5h,
1d.2b.3g.4f.5i, 1d.2b.3g.4f.5n, 1d.2b.3g.4i.5a, 1d.2b.3g.4i.5b, 1d.2b.3g.4i.5d,
1d.2b.3g.4i.5f, 1d.2b.3g.4i.5h, 1d.2b.3g.4i.5i, 1d.2b.3g.4i.5n, 1d.2b.3g.4n.5a,
1d.2b.3g.4n.5b, 1d.2b.3g.4n.5d, 1d.2b.3g.4n.5f, 1d.2b.3g.4n.5h, 1d.2b.3g.4n.5i,
1d.2b.3g.4n.5n, 1d.2b.3g.4p.5a, 1d.2b.3g.4p.5b, 1d.2b.3g.4p.5d, 1d.2b.3g.4p.5f,
1d.2b.3g.4p.5h, 1d.2b.3g.4p.5i, 1d.2b.3g.4p.5n, 1d.2e.3a.4a.5a, 1d.2e.3a.4a.5b,
1d.2e.3a.4a.5d, 1d.2e.3a.4a.5f, 1d.2e.3a.4a.5h, 1d.2e.3a.4a.5i, 1d.2e.3a.4a.5n,
1d.2e.3a.4b.5a, 1d.2e.3a.4b.5b, 1d.2e.3a.4b.5d, 1d.2e.3a.4b.5f, 1d.2e.3a.4b.5h,
1d.2e.3a.4b.5i, 1d.2e.3a.4b.5n, 1d.2e.3a.4d.5a, 1d.2e.3a.4d.5b, 1d.2e.3a.4d.5d,
1d.2e.3a.4d.5f, 1d.2e.3a.4d.5h, 1d.2e.3a.4d.5i, 1d.2e.3a.4d.5n, 1d.2e.3a.4f.5a,
1d.2e.3a.4f.5b, 1d.2e.3a.4f.5d, 1d.2e.3a.4f.5f, 1d.2e.3a.4f.5h, 1d.2e.3a.4f.5i,
1d.2e.3a.4f.5n, 1d.2e.3a.4i.5a, 1d.2e.3a.4i.5b, 1d.2e.3a.4i.5d, 1d.2e.3a.4i.5f,
1d.2e.3a.4i.5h, 1d.2e.3a.4i.5i, 1d.2e.3a.4i.5n, 1d.2e.3a.4n.5a, 1d.2e.3a.4n.5b,
1d.2e.3a.4n.5d, 1d.2e.3a.4n.5f, 1d.2e.3a.4n.5h, 1d.2e.3a.4n.5i, 1d.2e.3a.4n.5n,
1d.2e.3a.4p.5a, 1d.2e.3a.4p.5b, 1d.2e.3a.4p.5d, 1d.2e.3a.4p.5f, 1d.2e.3a.4p.5h,
1d.2e.3a.4p.5i, 1d.2e.3a.4p.5n, 1d.2e.3c.4a.5a, 1d.2e.3c.4a.5b, 1d.2e.3c.4a.5d,
1d.2e.3c.4a.5f, 1d.2e.3c.4a.5h, 1d.2e.3c.4a.5i, 1d.2e.3c.4a.5n, 1d.2e.3c.4b.5a,
1d.2e.3c.4b.5b, 1d.2e.3c.4b.5d, 1d.2e.3c.4b.5f, 1d.2e.3c.4b.5h, 1d.2e.3c.4b.5i,
1d.2e.3c.4b.5n, 1d.2e.3c.4d.5a, 1d.2e.3c.4d.5b, 1d.2e.3c.4d.5d, 1d.2e.3c.4d.5f,
1d.2e.3c.4d.5h, 1d.2e.3c.4d.5i, 1d.2e.3c.4d.5n, 1d.2e.3c.4f.5a, 1d.2e.3c.4f.5b,
1d.2e.3c.4f.5d, 1d.2e.3c.4f.5f, 1d.2e.3c.4f.5h, 1d.2e.3c.4f.5i, 1d.2e.3c.4f.5n,
1d.2e.3c.4i.5a, 1d.2e.3c.4i.5b, 1d.2e.3c.4i.5d, 1d.2e.3c.4i.5f, 1d.2e.3c.4i.5h,
1d.2e.3c.4i.5i, 1d.2e.3c.4i.5n, 1d.2e.3c.4n.5a, 1d.2e.3c.4n.5b, 1d.2e.3c.4n.5d,
1d.2e.3c.4n.5f, 1d.2e.3c.4n.5h, 1d.2e.3c.4n.5i, 1d.2e.3c.4n.5n, 1d.2e.3c.4p.5a,
1d.2e.3c.4p.5b, 1d.2e.3c.4p.5d, 1d.2e.3c.4p.5f, 1d.2e.3c.4p.5h, 1d.2e.3c.4p.5i,
1d.2e.3c.4p.5n, 1d.2e.3e.4a.5a, 1d.2e.3e.4a.5b, 1d.2e.3e.4a.5d, 1d.2e.3e.4a.5f,
1d.2e.3e.4a.5h, 1d.2e.3e.4a.5i, 1d.2e.3e.4a.5n, 1d.2e.3e.4b.5a, 1d.2e.3e.4b.5b,
1d.2e.3e.4b.5d, 1d.2e.3e.4b.5f, 1d.2e.3e.4b.5h, 1d.2e.3e.4b.5i, 1d.2e.3e.4b.5n,
1d.2e.3e.4d.5a, 1d.2e.3e.4d.5b, 1d.2e.3e.4d.5d, 1d.2e.3e.4d.5f, 1d.2e.3e.4d.5h,
1d.2e.3e.4d.5i, 1d.2e.3e.4d.5n, 1d.2e.3e.4f.5a, 1d.2e.3e.4f.5b, 1d.2e.3e.4f.5d,
1d.2e.3e.4f.5f, 1d.2e.3e.4f.5h, 1d.2e.3e.4f.5i, 1d.2e.3e.4f.5n, 1d.2e.3e.4i.5a,
1d.2e.3e.4i.5b, 1d.2e.3e.4i.5d, 1d.2e.3e.4i.5f, 1d.2e.3e.4i.5h, 1d.2e.3e.4i.5i,
1d.2e.3e.4i.5n, 1d.2e.3e.4n.5a, 1d.2e.3e.4n.5b, 1d.2e.3e.4n.5d, 1d.2e.3e.4n.5f,

TABLE 12-continued

List of Compound Structures of Formula II 1d.2e.3e.4n.5h, 1d.2e.3e.4n.5i, 1d.2e.3e.4n.5n, 1d.2e.3e.4p.5a, 1d.2e.3e.4p.5b,
1d.2e.3e.4p.5d, 1d.2e.3e.4p.5f, 1d.2e.3e.4p.5h, 1d.2e.3e.4p.5i, 1d.2e.3e.4p.5n,
1d.2e.3g.4a.5a, 1d.2e.3g.4a.5b, 1d.2e.3g.4a.5d, 1d.2e.3g.4a.5f, 1d.2e.3g.4a.5h,
1d.2e.3g.4a.5i, 1d.2e.3g.4a.5n, 1d.2e.3g.4b.5a, 1d.2e.3g.4b.5b, 1d.2e.3g.4b.5d,
1d.2e.3g.4b.5f, 1d.2e.3g.4b.5h, 1d.2e.3g.4b.5i, 1d.2e.3g.4b.5n, 1d.2e.3g.4d.5a,
1d.2e.3g.4d.5b, 1d.2e.3g.4d.5d, 1d.2e.3g.4d.5f, 1d.2e.3g.4d.5h, 1d.2e.3g.4d.5i,
1d.2e.3g.4d.5n, 1d.2e.3g.4f.5a, 1d.2e.3g.4f.5b, 1d.2e.3g.4f.5d, 1d.2e.3g.4f.5f,
1d.2e.3g.4f.5h, 1d.2e.3g.4f.5i, 1d.2e.3g.4f.5n, 1d.2e.3g.4i.5a, 1d.2e.3g.4i.5b,
1d.2e.3g.4i.5d, 1d.2e.3g.4i.5f, 1d.2e.3g.4i.5h, 1d.2e.3g.4i.5i, 1d.2e.3g.4i.5n,
1d.2e.3g.4n.5a, 1d.2e.3g.4n.5b, 1d.2e.3g.4n.5d, 1d.2e.3g.4n.5f, 1d.2e.3g.4n.5h,
1d.2e.3g.4n.5i, 1d.2e.3g.4n.5n, 1d.2e.3g.4p.5a, 1d.2e.3g.4p.5b, 1d.2e.3g.4p.5d,
1d.2e.3g.4p.5f, 1d.2e.3g.4p.5h, 1d.2e.3g.4p.5i, 1d.2e.3g.4p.5n, 1d.2f.3a.4a.5a,
1d.2f.3a.4a.5b, 1d.2f.3a.4a.5d, 1d.2f.3a.4a.5f, 1d.2f.3a.4a.5h, 1d.2f.3a.4a.5i,
1d.2f.3a.4a.5n, 1d.2f.3a.4b.5a, 1d.2f.3a.4b.5b, 1d.2f.3a.4b.5d, 1d.2f.3a.4b.5f,
1d.2f.3a.4b.5h, 1d.2f.3a.4b.5i, 1d.2f.3a.4b.5n, 1d.2f.3a.4d.5a, 1d.2f.3a.4d.5b,
1d.2f.3a.4d.5d, 1d.2f.3a.4d.5f, 1d.2f.3a.4d.5h, 1d.2f.3a.4d.5i, 1d.2f.3a.4d.5n,
1d.2f.3a.4f.5a, 1d.2f.3a.4f.5b, 1d.2f.3a.4f.5d, 1d.2f.3a.4f.5f, 1d.2f.3a.4f.5h,
1d.2f.3a.4f.5i, 1d.2f.3a.4f.5n, 1d.2f.3a.4i.5a, 1d.2f.3a.4i.5b, 1d.2f.3a.4i.5d,
1d.2f.3a.4i.5f, 1d.2f.3a.4i.5h, 1d.2f.3a.4i.5i, 1d.2f.3a.4i.5n, 1d.2f.3a.4n.5a,
1d.2f.3a.4n.5b, 1d.2f.3a.4n.5d, 1d.2f.3a.4n.5f, 1d.2f.3a.4n.5h, 1d.2f.3a.4n.5i,
1d.2f.3a.4n.5n, 1d.2f.3a.4p.5a, 1d.2f.3a.4p.5b, 1d.2f.3a.4p.5d, 1d.2f.3a.4p.5f,
1d.2f.3a.4p.5h, 1d.2f.3a.4p.5i, 1d.2f.3a.4p.5n, 1d.2f.3c.4a.5a, 1d.2f.3c.4a.5b,
1d.2f.3c.4a.5d, 1d.2f.3c.4a.5f, 1d.2f.3c.4a.5h, 1d.2f.3c.4a.5i, 1d.2f.3c.4a.5n,
1d.2f.3c.4b.5a, 1d.2f.3c.4b.5b, 1d.2f.3c.4b.5d, 1d.2f.3c.4b.5f, 1d.2f.3c.4b.5h,
1d.2f.3c.4b.5i, 1d.2f.3c.4b.5n, 1d.2f.3c.4d.5a, 1d.2f.3c.4d.5b, 1d.2f.3c.4d.5d,
1d.2f.3c.4d.5f, 1d.2f.3c.4d.5h, 1d.2f.3c.4d.5i, 1d.2f.3c.4d.5n, 1d.2f.3c.4f.5a,
1d.2f.3c.4f.5b, 1d.2f.3c.4f.5d, 1d.2f.3c.4f.5f, 1d.2f.3c.4f.5h, 1d.2f.3c.4f.5i,
1d.2f.3c.4f.5n, 1d.2f.3c.4i.5a, 1d.2f.3c.4i.5b, 1d.2f.3c.4f.5d, 1d.2f.3c.4i.5f,
1d.2f.3c.4i.5h, 1d.2f.3c.4i.5i, 1d.2f.3c.4i.5n, 1d.2f.3c.4n.5a, 1d.2f.3c.4n.5b,
1d.2f.3c.4n.5d, 1d.2f.3c.4n.5f, 1d.2f.3c.4n.5h, 1d.2f.3c.4n.5i, 1d.2f.3c.4n.5n,
1d.2f.3c.4p.5a, 1d.2f.3c.4p.5b, 1d.2f.3c.4p.5d, 1d.2f.3c.4p.5f, 1d.2f.3c.4p.5h,
1d.2f.3c.4p.5i, 1d.2f.3c.4p.5n, 1d.2f.3e.4a.5a, 1d.2f.3e.4a.5b, 1d.2f.3e.4a.5d,
1d.2f.3e.4a.5f, 1d.2f.3e.4a.5h, 1d.2f.3e.4a.5i, 1d.2f.3e.4a.5n, 1d.2f.3e.4b.5a,
1d.2f.3e.4b.5b, 1d.2f.3e.4b.5d, 1d.2f.3e.4b.5f, 1d.2f.3e.4b.5h, 1d.2f.3e.4b.5i,
1d.2f.3e.4b.5n, 1d.2f.3e.4d.5b, 1d.2f.3e.4d.5d, 1d.2f.3e.4d.5f,
1d.2f.3e.4d.5h, 1d.2f.3e.4d.5i, 1d.2f.3e.4d.5n, 1d.2f.3e.4f.5a, 1d.2f.3e.4f.5b,
1d.2f.3e.4f.5d, 1d.2f.3e.4f.5f, 1d.2f.3e.4f.5h, 1d.2f.3e.4f.5i, 1d.2f.3e.4f.5n,
1d.2f.3e.4i.5a, 1d.2f.3e.4i.5b, 1d.2f.3e.4i.5d, 1d.2f.3e.4i.5f, 1d.2f.3e.4i.5h,
1d.2f.3e.4i.5i, 1d.2f.3e.4i.5n, 1d.2f.3e.4n.5a, 1d.2f.3e.4n.5b, 1d.2f.3e.4n.5d,
1d.2f.3e.4n.5f, 1d.2f.3e.4n.5h, 1d.2f.3e.4n.5i, 1d.2f.3e.4n.5n, 1d.2f.3e.4p.5a,
1d.2f.3e.4p.5b, 1d.2f.3e.4p.5d, 1d.2f.3e.4p.5f, 1d.2f.3e.4p.5h, 1d.2f.3e.4p.5i,
1d.2f.3e.4p.5n, 1d.2f.3g.4a.5a, 1d.2f.3g.4a.5b, 1d.2f.3g.4a.5d, 1d.2f.3g.4a.5f,
1d.2f.3g.4a.5h, 1d.2f.3g.4a.5i, 1d.2f.3g.4a.5n, 1d.2f.3g.4b.5a, 1d.2f.3g.4b.5b,
1d.2f.3g.4b.5d, 1d.2f.3g.4b.5f, 1d.2f.3g.4b.5h, 1d.2f.3g.4b.5i, 1d.2f.3g.4b.5n,
1d.2f.3g.4d.5a, 1d.2f.3g.4d.5b, 1d.2f.3g.4d.5d, 1d.2f.3g.4d.5f, 1d.2f.3g.4d.5h,
1d.2f.3g.4d.5i, 1d.2f.3g.4d.5n, 1d.2f.3g.4f.5a, 1d.2f.3g.4f.5b, 1d.2f.3g.4f.5d,
1d.2f.3g.4f.5f, 1d.2f.3g.4f.5h, 1d.2f.3g.4f.5i, 1d.2f.3g.4f.5n, 1d.2f.3g.4i.5a,
1d.2f.3g.4i.5b, 1d.2f.3g.4i.5d, 1d.2f.3g.4i.5f, 1d.2f.3g.4i.5h, 1d.2f.3g.4i.5i,
1d.2f.3g.4i.5n, 1d.2f.3g.4n.5a, 1d.2f.3g.4n.5b, 1d.2f.3g.4n.5d, 1d.2f.3g.4n.5f,
1d.2f.3g.4n.5h, 1d.2f.3g.4n.5i, 1d.2f.3g.4n.5n, 1d.2f.3g.4p.5a, 1d.2f.3g.4p.5b,
1d.2f.3g.4p.5d, 1d.2f.3g.4p.5f, 1d.2f.3g.4p.5h, 1d.2f.3g.4p.5i, 1d.2f.3g.4p.5n,
1d.2g.3a.4a.5a, 1d.2g.3a.4a.5b, 1d.2g.3a.4a.5d, 1d.2g.3a.4a.5f, 1d.2g.3a.4a.5h,
1d.2g.3a.4a.5i, 1d.2g.3a.4a.5n, 1d.2g.3a.4b.5a, 1d.2g.3a.4b.5b, 1d.2g.3a.4b.5d,
1d.2g.3a.4b.5f, 1d.2g.3a.4b.5h, 1d.2g.3a.4b.5i, 1d.2g.3a.4b.5n, 1d.2g.3a.4d.5a,
1d.2g.3a.4d.5b, 1d.2g.3a.4d.5d, 1d.2g.3a.4d.5f, 1d.2g.3a.4d.5h, 1d.2g.3a.4d.5i,
1d.2g.3a.4d.5n, 1d.2g.3a.4f.5a, 1d.2g.3a.4f.5b, 1d.2g.3a.4f.5d, 1d.2g.3a.4f.5f,
1d.2g.3a.4f.5h, 1d.2g.3a.4f.5i, 1d.2g.3a.4f.5n, 1d.2g.3a.4i.5a, 1d.2g.3a.4i.5b,
1d.2g.3a.4i.5d, 1d.2g.3a.4i.5f, 1d.2g.3a.4i.5h, 1d.2g.3a.4i.5i, 1d.2g.3a.4i.5n,
1d.2g.3a.4n.5a, 1d.2g.3a.4n.5b, 1d.2g.3a.4n.5d, 1d.2g.3a.4n.5f, 1d.2g.3a.4n.5h,
1d.2g.3a.4n.5i, 1d.2g.3a.4n.5n, 1d.2g.3a.4p.5a, 1d.2g.3a.4p.5b, 1d.2g.3a.4p.5d,
1d.2g.3a.4p.5f, 1d.2g.3a.4p.5h, 1d.2g.3a.4p.5i, 1d.2g.3a.4p.5n, 1d.2g.3c.4a.5a,
1d.2g.3c.4a.5b, 1d.2g.3c.4a.5d, 1d.2g.3c.4a.5f, 1d.2g.3c.4a.5h, 1d.2g.3c.4a.5i,
1d.2g.3c.4a.5n, 1d.2g.3c.4b.5a, 1d.2g.3c.4b.5b, 1d.2g.3c.4b.5d, 1d.2g.3c.4b.5f,
1d.2g.3c.4b.5h, 1d.2g.3c.4b.5i, 1d.2g.3c.4b.5n, 1d.2g.3c.4d.5a, 1d.2g.3c.4d.5b,
1d.2g.3c.4d.5d, 1d.2g.3c.4d.5f, 1d.2g.3c.4d.5h, 1d.2g.3c.4d.5i, 1d.2g.3c.4d.5n,
1d.2g.3c.4f.5a, 1d.2g.3c.4f.5b, 1d.2g.3c.4f.5d, 1d.2g.3c.4f.5f, 1d.2g.3c.4f.5h,
1d.2g.3c.4f.5i, 1d.2g.3c.4f.5n, 1d.2g.3c.4i.5a, 1d.2g.3c.4i.5b, 1d.2g.3c.4i.5d,
1d.2g.3c.4i.5f, 1d.2g.3c.4i.5h, 1d.2g.3c.4i.5i, 1d.2g.3c.4i.5n, 1d.2g.3c.4n.5a,
1d.2g.3c.4n.5b, 1d.2g.3c.4n.5d, 1d.2g.3c.4n.5f, 1d.2g.3c.4n.5h, 1d.2g.3c.4n.5i,
1d.2g.3c.4n.5n, 1d.2g.3c.4p.5a, 1d.2g.3c.4p.5b, 1d.2g.3c.4p.5d, 1d.2g.3c.4p.5f,
1d.2g.3c.4p.5h, 1d.2g.3c.4p.5i, 1d.2g.3c.4p.5n, 1d.2g.3e.4a.5a, 1d.2g.3e.4a.5b,
1d.2g.3e.4a.5d, 1d.2g.3e.4a.5f, 1d.2g.3e.4a.5h, 1d.2g.3e.4a.5i, 1d.2g.3e.4a.5n,
1d.2g.3e.4b.5a, 1d.2g.3e.4b.5b, 1d.2g.3e.4b.5d, 1d.2g.3e.4b.5f, 1d.2g.3e.4b.5h,
1d.2g.3e.4b.5i, 1d.2g.3e.4b.5n, 1d.2g.3e.4d.5a, 1d.2g.3e.4d.5b, 1d.2g.3e.4d.5d,
1d.2g.3e.4d.5f, 1d.2g.3e.4d.5h, 1d.2g.3e.4d.5i, 1d.2g.3e.4d.5n, 1d.2g.3e.4f.5a,
1d.2g.3e.4f.5b, 1d.2g.3e.4f.5d, 1d.2g.3e.4f.5f, 1d.2g.3e.4f.5h, 1d.2g.3e.4f.5i,
1d.2g.3e.4f.5n, 1d.2g.3e.4i.5a, 1d.2g.3e.4i.5b, 1d.2g.3e.4i.5d, 1d.2g.3e.4i.5f,
1d.2g.3e.4i.5h, 1d.2g.3e.4i.5i, 1d.2g.3e.4i.5n, 1d.2g.3e.4n.5a, 1d.2g.3e.4n.5b,

TABLE 12-continued

List of Compound Structures of Formula II 1d.2g.3e.4n.5d, 1d.2g.3e.4n.5f, 1d.2g.3e.4n.5h, 1d.2g.3e.4n.5i, 1d.2g.3e.4n.5n,
1d.2g.3e.4p.5a, 1d.2g.3e.4p.5b, 1d.2g.3e.4p.5d, 1d.2g.3e.4p.5f, 1d.2g.3e.4p.5h,
1d.2g.3e.4p.5i, 1d.2g.3e.4p.5n, 1d.2g.3g.4a.5a, 1d.2g.3g.4a.5b, 1d.2g.3g.4a.5d,
1d.2g.3g.4a.5f, 1d.2g.3g.4a.5h, 1d.2g.3g.4a.5i, 1d.2g.3g.4a.5n, 1d.2g.3g.4b.5a,
1d.2g.3g.4b.5b, 1d.2g.3g.4b.5d, 1d.2g.3g.4b.5f, 1d.2g.3g.4b.5h, 1d.2g.3g.4b.5i,
1d.2g.3g.4b.5n, 1d.2g.3g.4d.5a, 1d.2g.3g.4d.5b, 1d.2g.3g.4d.5d, 1d.2g.3g.4d.5f,
1d.2g.3g.4d.5h, 1d.2g.3g.4d.5i, 1d.2g.3g.4d.5n, 1d.2g.3g.4f.5a, 1d.2g.3g.4f.5b,
1d.2g.3g.4f.5d, 1d.2g.3g.4f.5f, 1d.2g.3g.4f.5h, 1d.2g.3g.4f.5i, 1d.2g.3g.4f.5n,
1d.2g.3g.4i.5a, 1d.2g.3g.4i.5b, 1d.2g.3g.4i.5d, 1d.2g.3g.4i.5f, 1d.2g.3g.4i.5h,
1d.2g.3g.4i.5i, 1d.2g.3g.4i.5n, 1d.2g.3g.4n.5a, 1d.2g.3g.4n.5b, 1d.2g.3g.4n.5d,
1d.2g.3g.4n.5f, 1d.2g.3g.4n.5h, 1d.2g.3g.4p.5i, 1d.2g.3g.4n.5n, 1d.2g.3g.4p.5a,
1d.2g.3g.4p.5b, 1d.2g.3g.4p.5d, 1d.2g.3g.4p.5f, 1d.2g.3g.4p.5h, 1d.2g.3g.4p.5i,
1d.2g.3g.4p.5n, 1d.2l.3a.4a.5a, 1d.2l.3a.4a.5b, 1d.2l.3a.4a.5d, 1d.2l.3a.4a.5f,
1d.2l.3a.4a.5h, 1d.2l.3a.4a.5i, 1d.2l.3a.4a.5n, 1d.2l.3a.4b.5a, 1d.2l.3a.4b.5b,
1d.2l.3a.4b.5d, 1d.2l.3a.4b.5f, 1d.2l.3a.4b.5h, 1d.2l.3a.4b.5i, 1d.2l.3a.4b.5n,
1d.2l.3a.4d.5a, 1d.2l.3a.4d.5b, 1d.2l.3a.4d.5d, 1d.2l.3a.4d.5f, 1d.2l.3a.4d.5h,
1d.2l.3a.4d.5i, 1d.2l.3a.4d.5n, 1d.2l.3a.4f.5a, 1d.2l.3a.4f.5b, 1d.2l.3a.4f.5d,
1d.2l.3a.4f.5f, 1d.2l.3a.4f.5h, 1d.2l.3a.4f.5i, 1d.2l.3a.4f.5n, 1d.2l.3a.4i.5a,
1d.2l.3a.4i.5b, 1d.2l.3a.4i.5d, 1d.2l.3a.4i.5f, 1d.2l.3a.4i.5h, 1d.2l.3a.4i.5i,
1d.2l.3a.4i.5n, 1d.2l.3a.4n.5a, 1d.2l.3a.4n.5b, 1d.2l.3a.4n.5d, 1d.2l.3a.4n.5f,
1d.2l.3a.4n.5h, 1d.2l.3a.4n.5i, 1d.2l.3a.4n.5n, 1d.2l.3a.4p.5a, 1d.2l.3a.4p.5b,
1d.2l.3a.4p.5d, 1d.2l.3a.4p.5f, 1d.2l.3a.4p.5h, 1d.2l.3a.4p.5i, 1d.2l.3a.4p.5n,
1d.2l.3c.4a.5a, 1d.2l.3c.4a.5b, 1d.2l.3c.4a.5d, 1d.2l.3c.4a.5f, 1d.2l.3c.4a.5h,
1d.2l.3c.4a.5i, 1d.2l.3c.4a.5n, 1d.2l.3c.4b.5a, 1d.2l.3c.4b.5b, 1d.2l.3c.4b.5d,
1d.2l.3c.4b.5f, 1d.2l.3c.4b.5h, 1d.2l.3c.4b.5i, 1d.2l.3c.4b.5n, 1d.2l.3c.4d.5a,
1d.2l.3c.4d.5b, 1d.2l.3c.4d.5d, 1d.2l.3c.4d.5f, 1d.2l.3c.4d.5h, 1d.2l.3c.4d.5i,
1d.2l.3c.4d.5n, 1d.2l.3c.4f.5a, 1d.2l.3c.4f.5b, 1d.2l.3c.4f.5d, 1d.2l.3c.4f.5f,
1d.2l.3c.4f.5h, 1d.2l.3c.4f.5i, 1d.2l.3c.4f.5n, 1d.2l.3c.4i.5a, 1d.2l.3c.4i.5b,
1d.2l.3c.4i.5d, 1d.2l.3c.4i.5f, 1d.2l.3c.4i.5h, 1d.2l.3c.4i.5i, 1d.2l.3c.4i.5n,
1d.2l.3c.4n.5a, 1d.2l.3c.4n.5b, 1d.2l.3c.4n.5d, 1d.2l.3c.4n.5f, 1d.2l.3c.4n.5h,
1d.2l.3c.4n.5i, 1d.2l.3c.4n.5n, 1d.2l.3c.4p.5a, 1d.2l.3c.4p.5b, 1d.2l.3c.4p.5d,
1d.2l.3c.4p.5f, 1d.2l.3c.4p.5h, 1d.2l.3c.4p.5i, 1d.2l.3c.4p.5n, 1d.2l.3e.4a.5a,
1d.2l.3e.4a.5b, 1d.2l.3e.4a.5d, 1d.2l.3e.4a.5f, 1d.2l.3e.4a.5h, 1d.2l.3e.4a.5i,
1d.2l.3e.4a.5n, 1d.2l.3e.4b.5a, 1d.2l.3e.4b.5b, 1d.2l.3e.4b.5d, 1d.2l.3e.4b.5f,
1d.2l.3e.4b.5h, 1d.2l.3e.4b.5i, 1d.2l.3e.4b.5n, 1d.2l.3e.4d.5a, 1d.2l.3e.4d.5b,
1d.2l.3e.4d.5d, 1d.2l.3e.4d.5f, 1d.2l.3e.4d.5h, 1d.2l.3e.4d.5i, 1d.2l.3e.4d.5n,
1d.2l.3e.4f.5a, 1d.2l.3e.4f.5b, 1d.2l.3e.4f.5d, 1d.2l.3e.4f.5f, 1d.2l.3e.4f.5h,
1d.2l.3e.4f.5i, 1d.2l.3e.4f.5n, 1d.2l.3e.4i.5a, 1d.2l.3e.4i.5b, 1d.2l.3e.4i.5d,
1d.2l.3e.4i.5f, 1d.2l.3e.4i.5h, 1d.2l.3e.4i.5i, 1d.2l.3e.4i.5n, 1d.2l.3e.4n.5a,
1d.2l.3e.4n.5b, 1d.2l.3e.4n.5d, 1d.2l.3e.4n.5f, 1d.2l.3e.4n.5h, 1d.2l.3e.4n.5i,
1d.2l.3e.4n.5n, 1d.2l.3e.4p.5a, 1d.2l.3e.4p.5b, 1d.2l.3e.4p.5d, 1d.2l.3e.4p.5f,
1d.2l.3e.4p.5h, 1d.2l.3e.4p.5i, 1d.2l.3e.4p.5n, 1d.2l.3g.4a.5a, 1d.2l.3g.4a.5b,
1d.2l.3g.4a.5d, 1d.2l.3g.4a.5f, 1d.2l.3g.4a.5h, 1d.2l.3g.4a.5i, 1d.2l.3g.4a.5n,
1d.2l.3g.4b.5a, 1d.2l.3g.4b.5b, 1d.2l.3g.4b.5d, 1d.2l.3g.4b.5f, 1d.2l.3g.4b.5h,
1d.2l.3g.4b.5i, 1d.2l.3g.4b.5n, 1d.2l.3g.4d.5a, 1d.2l.3g.4d.5b, 1d.2l.3g.4d.5d,
1d.2l.3g.4d.5f, 1d.2l.3g.4d.5h, 1d.2l.3g.4d.5i, 1d.2l.3g.4d.5n, 1d.2l.3g.4f.5a,
1d.2l.3g.4f.5b, 1d.2l.3g.4f.5d, 1d.2l.3g.4f.5f, 1d.2l.3g.4f.5h, 1d.2l.3g.4f.5i,
1d.2l.3g.4f.5n, 1d.2l.3g.4i.5a, 1d.2l.3g.4i.5b, 1d.2l.3g.4i.5d, 1d.2l.3g.4i.5f,
1d.2l.3g.4i.5h, 1d.2l.3g.4i.5i, 1d.2l.3g.4i.5n, 1d.2l.3g.4n.5a, 1d.2l.3g.4n.5b,
1d.2l.3g.4n.5d, 1d.2l.3g.4n.5f, 1d.2l.3g.4n.5h, 1d.2l.3g.4n.5i, 1d.2l.3g.4n.5n,
1d.2l.3g.4p.5a, 1d.2l.3g.4p.5b, 1d.2l.3g.4p.5d, 1d.2l.3g.4p.5f, 1d.2l.3g.4p.5h,
1d.2l.3g.4p.5i, 1d.2l.3g.4p.5n, 1d.2m.3a.4a.5a, 1d.2m.3a.4a.5b, 1d.2m.3a.4a.5d,
1d.2m.3a.4a.5f, 1d.2m.3a.4a.5h, 1d.2m.3a.4a.5i, 1d.2m.3a.4a.5n, 1d.2m.3a.4b.5a,
1d.2m.3a.4b.5b, 1d.2m.3a.4b.5d, 1d.2m.3a.4b.5f, 1d.2m.3a.4b.5h, 1d.2m.3a.4b.5i,
1d.2m.3a.4b.5n, 1d.2m.3a.4d.5a, 1d.2m.3a.4d.5b, 1d.2m.3a.4d.5d,
1d.2m.3a.4d.5f, 1d.2m.3a.4d.5h, 1d.2m.3a.4d.5i, 1d.2m.3a.4d.5n, 1d.2m.3a.4f.5a,
1d.2m.3a.4f.5b, 1d.2m.3a.4f.5d, 1d.2m.3a.4f.5f, 1d.2m.3a.4f.5h, 1d.2m.3a.4f.5i,
1d.2m.3a.4f.5n, 1d.2m.3a.4i.5a, 1d.2m.3a.4i.5b, 1d.2m.3a.4i.5d, 1d.2m.3a.4i.5f,
1d.2m.3a.4i.5h, 1d.2m.3a.4i.5i, 1d.2m.3a.4i.5n, 1d.2m.3a.4n.5a, 1d.2m.3a.4n.5b,
1d.2m.3a.4n.5d, 1d.2m.3a.4n.5f, 1d.2m.3a.4n.5h, 1d.2m.3a.4n.5i, 1d.2m.3a.4n.5n,
1d.2m.3a.4p.5a, 1d.2m.3a.4p.5b, 1d.2m.3a.4p.5d, 1d.2m.3a.4p.5f,
1d.2m.3a.4p.5h, 1d.2m.3a.4p.5i, 1d.2m.3a.4p.5n, 1d.2m.3c.4a.5a, 1d.2m.3c.4a.5b,
1d.2m.3c.4a.5d, 1d.2m.3c.4a.5f, 1d.2m.3c.4a.5h, 1d.2m.3c.4a.5i, 1d.2m.3c.4a.5n,
1d.2m.3c.4b.5a, 1d.2m.3c.4b.5b, 1d.2m.3c.4b.5d, 1d.2m.3c.4b.5f, 1d.2m.3c.4b.5h,
1d.2m.3c.4b.5i, 1d.2m.3c.4b.5n, 1d.2m.3c.4d.5a, 1d.2m.3c.4d.5b, 1d.2m.3c.4d.5d,
1d.2m.3c.4d.5f, 1d.2m.3c.4d.5h, 1d.2m.3c.4d.5i, 1d.2m.3c.4d.5n, 1d.2m.3c.4f.5a,
1d.2m.3c.4f.5b, 1d.2m.3c.4f.5d, 1d.2m.3c.4f.5f, 1d.2m.3c.4f.5h, 1d.2m.3c.4f.5i,
1d.2m.3c.4f.5n, 1d.2m.3c.4i.5a, 1d.2m.3c.4i.5b, 1d.2m.3c.4i.5d, 1d.2m.3c.4i.5f,
1d.2m.3c.4i.5h, 1d.2m.3c.4i.5i, 1d.2m.3c.4i.5n, 1d.2m.3c.4n.5a, 1d.2m.3c.4n.5b,
1d.2m.3c.4n.5d, 1d.2m.3c.4n.5f, 1d.2m.3c.4n.5h, 1d.2m.3c.4n.5i, 1d.2m.3c.4n.5n,
1d.2m.3c.4p.5a, 1d.2m.3c.4p.5b, 1d.2m.3c.4p.5d, 1d.2m.3c.4p.5f, 1d.2m.3c.4p.5h,
1d.2m.3c.4p.5i, 1d.2m.3c.4p.5n, 1d.2m.3e.4a.5a, 1d.2m.3e.4a.5b, 1d.2m.3e.4a.5d,
1d.2m.3e.4a.5f, 1d.2m.3e.4a.5h, 1d.2m.3e.4a.5i, 1d.2m.3e.4a.5n, 1d.2m.3e.4b.5a,
1d.2m.3e.4b.5b, 1d.2m.3e.4b.5d, 1d.2m.3e.4b.5f, 1d.2m.3e.4b.5h, 1d.2m.3e.4b.5i,
1d.2m.3e.4b.5n, 1d.2m.3e.4d.5a, 1d.2m.3e.4d.5b, 1d.2m.3e.4d.5d, 1d.2m.3e.4d.5f,
1d.2m.3e.4d.5h, 1d.2m.3e.4d.5i, 1d.2m.3e.4d.5n, 1d.2m.3e.4f.5a, 1d.2m.3e.4f.5b,
1d.2m.3e.4f.5d, 1d.2m.3e.4f.5f, 1d.2m.3e.4f.5h, 1d.2m.3e.4f.5i, 1d.2m.3e.4f.5n,
1d.2m.3e.4i.5a, 1d.2m.3e.4i.5b, 1d.2m.3e.4i.5d, 1d.2m.3e.4i.5f, 1d.2m.3e.4i.5h, TABLE 12-continued List of Compound Structures of Formula II 1d.2m.3e.4i.5i, 1d.2m.3e.4i.5n, 1d.2m.3e.4n.5a, 1d.2m.3e.4n.5b, 1d.2m.3e.4n.5d,
1d.2m.3e.4n.5f, 1d.2m.3e.4n.5h, 1d.2m.3e.4n.5i, 1d.2m.3e.4n.5n, 1d.2m.3e.4p.5a,
1d.2m.3e.4p.5b, 1d.2m.3e.4p.5d, 1d.2m.3e.4p.5f, 1d.2m.3e.4p.5h, 1d.2m.3e.4p.5i,
1d.2m.3e.4p.5n, 1d.2m.3g.4a.5a, 1d.2m.3g.4a.5b, 1d.2m.3g.4a.5d, 1d.2m.3g.4a.5f,
1d.2m.3g.4a.5h, 1d.2m.3g.4a.5i, 1d.2m.3g.4a.5n, 1d.2m.3g.4b.5a, 1d.2m.3g.4b.5b,
1d.2m.3g.4b.5d, 1d.2m.3g.4b.5f, 1d.2m.3g.4b.5h, 1d.2m.3g.4b.5i, 1d.2m.3g.4b.5n,
1d.2m.3g.4d.5a, 1d.2m.3g.4d.5b, 1d.2m.3g.4d.5d, 1d.2m.3g.4d.5f,
1d.2m.3g.4d.5h, 1d.2m.3g.4d.5i, 1d.2m.3g.4d.5n, 1d.2m.3g.4f.5a, 1d.2m.3g.4f.5b,
1d.2m.3g.4f.5d, 1d.2m.3g.4f.5f, 1d.2m.3g.4f.5h, 1d.2m.3g.4f.5i, 1d.2m.3g.4f.5n,
1d.2m.3g.4i.5a, 1d.2m.3g.4i.5b, 1d.2m.3g.4i.5d, 1d.2m.3g.4i.5f, 1d.2m.3g.4i.5h,
1d.2m.3g.4i.5i, 1d.2m.3g.4i.5n, 1d.2m.3g.4n.5a, 1d.2m.3g.4n.5b, 1d.2m.3g.4n.5d,
1d.2m.3g.4n.5f, 1d.2m.3g.4n.5h, 1d.2m.3g.4n.5i, 1d.2m.3g.4n.5n, 1d.2m.3g.4p.5a,
1d.2m.3g.4p.5b, 1d.2m.3g.4p.5d, 1d.2m.3g.4p.5f, 1d.2m.3g.4p.5h,
1d.2m.3g.4p.5i, 1d.2m.3g.4p.5n, 1d.2n.3a.4a.5a, 1d.2n.3a.4a.5b, 1d.2n.3a.4a.5d,
1d.2n.3a.4a.5f, 1d.2n.3a.4a.5h, 1d.2n.3a.4a.5i, 1d.2n.3a.4a.5n, 1d.2n.3a.4b.5a,
1d.2n.3a.4b.5b, 1d.2n.3a.4b.5d, 1d.2n.3a.4b.5f, 1d.2n.3a.4b.5h, 1d.2n.3a.4b.5i,
1d.2n.3a.4b.5n, 1d.2n.3a.4d.5a, 1d.2n.3a.4d.5b, 1d.2n.3a.4d.5d, 1d.2n.3a.4d.5f,
1d.2n.3a.4d.5h, 1d.2n.3a.4d.5i, 1d.2n.3a.4d.5n, 1d.2n.3a.4f.5a, 1d.2n.3a.4f.5b,
1d.2n.3a.4f.5d, 1d.2n.3a.4f.5f, 1d.2n.3a.4f.5h, 1d.2n.3a.4f.5i, 1d.2n.3a.4f.5n,
1d.2n.3a.4i.5a, 1d.2n.3a.4i.5b, 1d.2n.3a.4i.5d, 1d.2n.3a.4i.5f, 1d.2n.3a.4i.5h,
1d.2n.3a.4i.5i, 1d.2n.3a.4i.5n, 1d.2n.3a.4n.5a, 1d.2n.3a.4n.5b, 1d.2n.3a.4n.5d,
1d.2n.3a.4n.5f, 1d.2n.3a.4n.5h, 1d.2n.3a.4n.5i, 1d.2n.3a.4n.5n, 1d.2n.3a.4p.5a,
1d.2n.3a.4p.5b, 1d.2n.3a.4p.5d, 1d.2n.3a.4p.5f, 1d.2n.3a.4p.5h, 1d.2n.3a.4p.5i,
1d.2n.3a.4p.5n, 1d.2n.3c.4a.5a, 1d.2n.3c.4a.5b, 1d.2n.3c.4a.5d, 1d.2n.3c.4a.5f,
1d.2n.3c.4a.5h, 1d.2n.3c.4a.5i, 1d.2n.3c.4a.5n, 1d.2n.3c.4b.5a, 1d.2n.3c.4b.5b,
1d.2n.3c.4b.5d, 1d.2n.3c.4b.5f, 1d.2n.3c.4b.5h, 1d.2n.3c.4b.5i, 1d.2n.3c.4b.5n,
1d.2n.3c.4d.5a, 1d.2n.3c.4d.5b, 1d.2n.3c.4d.5d, 1d.2n.3c.4d.5f, 1d.2n.3c.4d.5h,
1d.2n.3c.4d.5i, 1d.2n.3c.4d.5n, 1d.2n.3c.4f.5a, 1d.2n.3c.4f.5b, 1d.2n.3c.4f.5d,
1d.2n.3c.4f.5f, 1d.2n.3c.4f.5h, 1d.2n.3c.4f.5i, 1d.2n.3c.4f.5n, 1d.2n.3c.4i.5a,
1d.2n.3c.4i.5b, 1d.2n.3c.4i.5d, 1d.2n.3c.4i.5f, 1d.2n.3c.4i.5h, 1d.2n.3c.4i.5i,
1d.2n.3c.4i.5n, 1d.2n.3c.4n.5a, 1d.2n.3c.4n.5b, 1d.2n.3c.4n.5d, 1d.2n.3c.4n.5f,
1d.2n.3c.4n.5h, 1d.2n.3c.4n.5i, 1d.2n.3c.4n.5n, 1d.2n.3c.4p.5a, 1d.2n.3c.4p.5b,
1d.2n.3c.4p.5d, 1d.2n.3c.4p.5f, 1d.2n.3c.4p.5h, 1d.2n.3c.4p.5i, 1d.2n.3c.4p.5n,
1d.2n.3e.4a.5a, 1d.2n.3e.4a.5b, 1d.2n.3e.4a.5d, 1d.2n.3e.4a.5f, 1d.2n.3e.4a.5h,
1d.2n.3e.4a.5i, 1d.2n.3e.4a.5n, 1d.2n.3e.4b.5a, 1d.2n.3e.4b.5b, 1d.2n.3e.4b.5d,
1d.2n.3e.4b.5f, 1d.2n.3e.4b.5h, 1d.2n.3e.4b.5i, 1d.2n.3e.4b.5n, 1d.2n.3e.4d.5a,
1d.2n.3e.4d.5b, 1d.2n.3e.4d.5d, 1d.2n.3e.4d.5f, 1d.2n.3e.4d.5h, 1d.2n.3e.4d.5i,
1d.2n.3e.4d.5n, 1d.2n.3e.4f.5a, 1d.2n.3e.4f.5b, 1d.2n.3e.4f.5d, 1d.2n.3e.4f.5f,
1d.2n.3e.4f.5h, 1d.2n.3e.4f.5i, 1d.2n.3e.4f.5n, 1d.2n.3e.4i.5a, 1d.2n.3e.4i.5b,
1d.2n.3e.4i.5d, 1d.2n.3e.4i.5f, 1d.2n.3e.4i.5h, 1d.2n.3e.4i.5i, 1d.2n.3e.4i.5n,
1d.2n.3e.4n.5a, 1d.2n.3e.4n.5b, 1d.2n.3e.4n.5d, 1d.2n.3e.4n.5f, 1d.2n.3e.4n.5h,
1d.2n.3e.4n.5i, 1d.2n.3e.4n.5n, 1d.2n.3e.4p.5a, 1d.2n.3e.4p.5b, 1d.2n.3e.4p.5d,
1d.2n.3e.4p.5f, 1d.2n.3e.4p.5h, 1d.2n.3e.4p.5i, 1d.2n.3e.4p.5n, 1d.2n.3g.4a.5a,
1d.2n.3g.4a.5b, 1d.2n.3g.4a.5d, 1d.2n.3g.4a.5f, 1d.2n.3g.4a.5h, 1d.2n.3g.4a.5i,
1d.2n.3g.4a.5n, 1d.2n.3g.4b.5a, 1d.2n.3g.4b.5b, 1d.2n.3g.4b.5d, 1d.2n.3g.4b.5f,
1d.2n.3g.4b.5h, 1d.2n.3g.4b.5i, 1d.2n.3g.4b.5n, 1d.2n.3g.4d.5a, 1d.2n.3g.4d.5b,
1d.2n.3g.4d.5d, 1d.2n.3g.4d.5f, 1d.2n.3g.4d.5h, 1d.2n.3g.4d.5i, 1d.2n.3g.4d.5n,
1d.2n.3g.4f.5a, 1d.2n.3g.4f.5b, 1d.2n.3g.4f.5d, 1d.2n.3g.4f.5f, 1d.2n.3g.4f.5h,
1d.2n.3g.4f.5i, 1d.2n.3g.4f.5n, 1d.2n.3g.4i.5a, 1d.2n.3g.4i.5b, 1d.2n.3g.4i.5d,
1d.2n.3g.4i.5f, 1d.2n.3g.4i.5h, 1d.2n.3g.4i.5i, 1d.2n.3g.4i.5n, 1d.2n.3g.4n.5a,
1d.2n.3g.4n.5b, 1d.2n.3g.4n.5d, 1d.2n.3g.4n.5f, 1d.2n.3g.4n.5h, 1d.2n.3g.4n.5i,
1d.2n.3g.4n.5n, 1d.2n.3g.4p.5a, 1d.2n.3g.4p.5b, 1d.2n.3g.4p.5d, 1d.2n.3g.4p.5f,
1d.2n.3g.4p.5h, 1d.2n.3g.4p.5i, 1d.2n.3g.4p.5n, 1d.2q.3a.4a.5a, 1d.2q.3a.4a.5b,
1d.2q.3a.4a.5d, 1d.2q.3a.4a.5f, 1d.2q.3a.4a.5h, 1d.2q.3a.4a.5i, 1d.2q.3a.4a.5n,
1d.2q.3a.4b.5a, 1d.2q.3a.4b.5b, 1d.2q.3a.4b.5d, 1d.2q.3a.4b.5f, 1d.2q.3a.4b.5h,
1d.2q.3a.4b.5i, 1d.2q.3a.4b.5n, 1d.2q.3a.4d.5a, 1d.2q.3a.4d.5b, 1d.2q.3a.4d.5d,
1d.2q.3a.4d.5f, 1d.2q.3a.4d.5h, 1d.2q.3a.4d.5i, 1d.2q.3a.4d.5n, 1d.2q.3a.4f.5a,
1d.2q.3a.4f.5b, 1d.2q.3a.4f.5d, 1d.2q.3a.4f.5f, 1d.2q.3a.4f.5h, 1d.2q.3a.4f.5i,
1d.2q.3a.4f.5n, 1d.2q.3a.4i.5a, 1d.2q.3a.4i.5b, 1d.2q.3a.4i.5d, 1d.2q.3a.4i.5f,
1d.2q.3a.4i.5h, 1d.2q.3a.4i.5i, 1d.2q.3a.4i.5n, 1d.2q.3a.4n.5a, 1d.2q.3a.4n.5b,
1d.2q.3a.4n.5d, 1d.2q.3a.4n.5f, 1d.2q.3a.4n.5h, 1d.2q.3a.4n.5i, 1d.2q.3a.4n.5n,
1d.2q.3a.4p.5a, 1d.2q.3a.4p.5b, 1d.2q.3a.4p.5d, 1d.2q.3a.4p.5f, 1d.2q.3a.4p.5h,
1d.2q.3a.4p.5i, 1d.2q.3a.4p.5n, 1d.2q.3c.4a.5a, 1d.2q.3c.4a.5b, 1d.2q.3c.4a.5d,
1d.2q.3c.4a.5f, 1d.2q.3c.4a.5h, 1d.2q.3c.4a.5i, 1d.2q.3c.4a.5n, 1d.2q.3c.4b.5a,
1d.2q.3c.4b.5b, 1d.2q.3c.4b.5d, 1d.2q.3c.4b.5f, 1d.2q.3c.4b.5h, 1d.2q.3c.4b.5i,
1d.2q.3c.4b.5n, 1d.2q.3c.4d.5a, 1d.2q.3c.4d.5b, 1d.2q.3c.4d.5d, 1d.2q.3c.4d.5f,
1d.2q.3c.4d.5h, 1d.2q.3c.4d.5i, 1d.2q.3c.4d.5n, 1d.2q.3c.4f.5a, 1d.2q.3c.4f.5b,
1d.2q.3c.4f.5d, 1d.2q.3c.4f.5f, 1d.2q.3c.4f.5h, 1d.2q.3c.4f.5i, 1d.2q.3c.4f.5n,
1d.2q.3c.4i.5a, 1d.2q.3c.4i.5b, 1d.2q.3c.4i.5d, 1d.2q.3c.4i.5f, 1d.2q.3c.4i.5h,
1d.2q.3c.4i.5i, 1d.2q.3c.4i.5n, 1d.2q.3c.4n.5a, 1d.2q.3c.4n.5b, 1d.2q.3c.4n.5d,
1d.2q.3c.4n.5f, 1d.2q.3c.4n.5h, 1d.2q.3c.4n.5i, 1d.2q.3c.4n.5n, 1d.2q.3c.4p.5a,
1d.2q.3c.4p.5b, 1d.2q.3c.4p.5d, 1d.2q.3c.4p.5f, 1d.2q.3c.4p.5h, 1d.2q.3c.4p.5i,
1d.2q.3c.4p.5n, 1d.2q.3e.4a.5a, 1d.2q.3e.4a.5b, 1d.2q.3e.4a.5d, 1d.2q.3e.4a.5f,
1d.2q.3e.4a.5h, 1d.2q.3e.4a.5i, 1d.2q.3e.4a.5n, 1d.2q.3e.4b.5a, 1d.2q.3e.4b.5b,
1d.2q.3e.4b.5d, 1d.2q.3e.4b.5f, 1d.2q.3e.4b.5h, 1d.2q.3e.4b.5i, 1d.2q.3e.4b.5n,
1d.2q.3e.4d.5a, 1d.2q.3e.4d.5b, 1d.2q.3e.4d.5d, 1d.2q.3e.4d.5f, 1d.2q.3e.4d.5h,
1d.2q.3e.4d.5i, 1d.2q.3e.4d.5n, 1d.2q.3e.4f.5a, 1d.2q.3e.4f.5b, 1d.2q.3e.4f.5d,
1d.2q.3e.4f.5f, 1d.2q.3e.4f.5h, 1d.2q.3e.4f.5i, 1d.2q.3e.4f.5n, 1d.2q.3e.4i.5a, TABLE 12-continued List of Compound Structures of Formula II 1d.2q.3e.4i.5b, 1d.2q.3e.4i.5d, 1d.2q.3e.4i.5f, 1d.2q.3e.4i.5h, 1d.2q.3e.4i.5i,
1d.2q.3e.4i.5n, 1d.2q.3e.4n.5a, 1d.2q.3e.4n.5b, 1d.2q.3e.4n.5d, 1d.2q.3e.4n.5f,
1d.2q.3e.4n.5h, 1d.2q.3e.4n.5i, 1d.2q.3e.4n.5n, 1d.2q.3e.4p.5a, 1d.2q.3e.4p.5b,
1d.2q.3e.4p.5d, 1d.2q.3e.4p.5f, 1d.2q.3e.4p.5h, 1d.2q.3e.4p.5i, 1d.2q.3e.4p.5n,
1d.2q.3g.4a.5a, 1d.2q.3g.4a.5b, 1d.2q.3g.4a.5d, 1d.2q.3g.4a.5f, 1d.2q.3g.4a.5h,
1d.2q.3g.4a.5i, 1d.2q.3g.4a.5n, 1d.2q.3g.4b.5a, 1d.2q.3g.4b.5b, 1d.2q.3g.4b.5d,
1d.2q.3g.4b.5f, 1d.2q.3g.4b.5h, 1d.2q.3g.4b.5i, 1d.2q.3g.4b.5n, 1d.2q.3g.4d.5a,
1d.2q.3g.4d.5b, 1d.2q.3g.4d.5d, 1d.2q.3g.4d.5f, 1d.2q.3g.4d.5h, 1d.2q.3g.4d.5i,
1d.2q.3g.4d.5n, 1d.2q.3g.4f.5a, 1d.2q.3g.4f.5b, 1d.2q.3g.4f.5d, 1d.2q.3g.4f.5f,
1d.2q.3g.4f.5h, 1d.2q.3g.4f.5i, 1d.2q.3g.4f.5n, 1d.2q.3g.4i.5a, 1d.2q.3g.4i.5b,
1d.2q.3g.4i.5d, 1d.2q.3g.4i.5f, 1d.2q.3g.4i.5h, 1d.2q.3g.4i.5i, 1d.2q.3g.4i.5n,
1d.2q.3g.4n.5a, 1d.2q.3g.4n.5b, 1d.2q.3g.4n.5d, 1d.2q.3g.4n.5f, 1d.2q.3g.4n.5h,
1d.2q.3g.4n.5i, 1d.2q.3g.4n.5n, 1d.2q.3g.4p.5a, 1d.2q.3g.4p.5b, 1d.2q.3g.4p.5d,
1d.2q.3g.4p.5f, 1d.2q.3g.4p.5h, 1d.2q.3g.4p.5i, 1d.2q.3g.4p.5n, 1d.2v.3a.4a.5a,
1d.2v.3a.4a.5b, 1d.2v.3a.4a.5d, 1d.2v.3a.4a.5f, 1d.2v.3a.4a.5h, 1d.2v.3a.4a.5i,
1d.2v.3a.4a.5n, 1d.2v.3a.4b.5a, 1d.2v.3a.4b.5b, 1d.2v.3a.4b.5d, 1d.2v.3a.4b.5f,
1d.2v.3a.4b.5h, 1d.2v.3a.4b.5i, 1d.2v.3a.4b.5n, 1d.2v.3a.4d.5a, 1d.2v.3a.4d.5b,
1d.2v.3a.4d.5d, 1d.2v.3a.4d.5f, 1d.2v.3a.4d.5h, 1d.2v.3a.4d.5i, 1d.2v.3a.4d.5n,
1d.2v.3a.4f.5a, 1d.2v.3a.4f.5b, 1d.2v.3a.4f.5d, 1d.2v.3a.4f.5f, 1d.2v.3a.4f.5h,
1d.2v.3a.4f.5i, 1d.2v.3a.4f.5n, 1d.2v.3a.4i.5a, 1d.2v.3a.4i.5b, 1d.2v.3a.4i.5d,
1d.2v.3a.4i.5f, 1d.2v.3a.4i.5h, 1d.2v.3a.4i.5i, 1d.2v.3a.4i.5n, 1d.2v.3a.4n.5a,
1d.2v.3a.4n.5b, 1d.2v.3a.4n.5d, 1d.2v.3a.4n.5f, 1d.2v.3a.4n.5h, 1d.2v.3a.4n.5i,
1d.2v.3a.4n.5n, 1d.2v.3a.4p.5a, 1d.2v.3a.4p.5b, 1d.2v.3a.4p.5d, 1d.2v.3a.4p.5f,
1d.2v.3a.4p.5h, 1d.2v.3a.4p.5i, 1d.2v.3a.4p.5n, 1d.2v.3c.4a.5a, 1d.2v.3c.4a.5b,
1d.2v.3c.4a.5d, 1d.2v.3c.4a.5f, 1d.2v.3c.4a.5h, 1d.2v.3c.4a.5i, 1d.2v.3c.4a.5n,
1d.2v.3c.4b.5a, 1d.2v.3c.4b.5b, 1d.2v.3c.4b.5d, 1d.2v.3c.4b.5f, 1d.2v.3c.4b.5h,
1d.2v.3c.4b.5i, 1d.2v.3c.4b.5n, 1d.2v.3c.4d.5a, 1d.2v.3c.4d.5b, 1d.2v.3c.4d.5d,
1d.2v.3c.4d.5f, 1d.2v.3c.4d.5h, 1d.2v.3c.4d.5i, 1d.2v.3c.4d.5n, 1d.2v.3c.4f.5a,
1d.2v.3c.4f.5b, 1d.2v.3c.4f.5d, 1d.2v.3c.4f.5f, 1d.2v.3c.4f.5h, 1d.2v.3c.4f.5i,
1d.2v.3c.4f.5n, 1d.2v.3c.4i.5a, 1d.2v.3c.4i.5b, 1d.2v.3c.4i.5d, 1d.2v.3c.4i.5f,
1d.2v.3c.4i.5h, 1d.2v.3c.4i.5i, 1d.2v.3c.4i.5n, 1d.2v.3c.4n.5a, 1d.2v.3c.4n.5b,
1d.2v.3c.4n.5d, 1d.2v.3c.4n.5f, 1d.2v.3c.4n.5h, 1d.2v.3c.4n.5i, 1d.2v.3c.4n.5n,
1d.2v.3c.4p.5a, 1d.2v.3c.4p.5b, 1d.2v.3c.4p.5d, 1d.2v.3c.4p.5f, 1d.2v.3c.4p.5h,
1d.2v.3c.4p.5i, 1d.2v.3c.4p.5n, 1d.2v.3e.4a.5a, 1d.2v.3e.4a.5b, 1d.2v.3e.4a.5d,
1d.2v.3e.4a.5f, 1d.2v.3e.4a.5h, 1d.2v.3e.4a.5i, 1d.2v.3e.4a.5n, 1d.2v.3e.4b.5a,
1d.2v.3e.4b.5b, 1d.2v.3e.4b.5d, 1d.2v.3e.4b.5f, 1d.2v.3e.4b.5h, 1d.2v.3e.4b.5i,
1d.2v.3e.4b.5n, 1d.2v.3e.4d.5a, 1d.2v.3e.4d.5b, 1d.2v.3e.4d.5d, 1d.2v.3e.4d.5f,
1d.2v.3e.4d.5h, 1d.2v.3e.4d.5i, 1d.2v.3e.4d.5n, 1d.2v.3e.4f.5a, 1d.2v.3e.4f.5b,
1d.2v.3e.4f.5d, 1d.2v.3e.4f.5f, 1d.2v.3e.4f.5h, 1d.2v.3e.4f.5i, 1d.2v.3e.4f.5n,
1d.2v.3e.4i.5a, 1d.2v.3e.4i.5b, 1d.2v.3e.4i.5d, 1d.2v.3e.4i.5f, 1d.2v.3e.4i.5h,
1d.2v.3e.4i.5i, 1d.2v.3e.4i.5n, 1d.2v.3e.4n.5a, 1d.2v.3e.4n.5b, 1d.2v.3e.4n.5d,
1d.2v.3e.4n.5f, 1d.2v.3e.4n.5h, 1d.2v.3e.4n.5i, 1d.2v.3e.4n.5n, 1d.2v.3e.4p.5a,
1d.2v.3e.4p.5b, 1d.2v.3e.4p.5d, 1d.2v.3e.4p.5f, 1d.2v.3e.4p.5h, 1d.2v.3e.4p.5i,
1d.2v.3e.4p.5n, 1d.2v.3g.4a.5a, 1d.2v.3g.4a.5b, 1d.2v.3g.4a.5d, 1d.2v.3g.4a.5f,
1d.2v.3g.4a.5h, 1d.2v.3g.4a.5i, 1d.2v.3g.4a.5n, 1d.2v.3g.4b.5a, 1d.2v.3g.4b.5b,
1d.2v.3g.4b.5d, 1d.2v.3g.4b.5f, 1d.2v.3g.4b.5h, 1d.2v.3g.4b.5i, 1d.2v.3g.4b.5n,
1d.2v.3g.4d.5a, 1d.2v.3g.4d.5b, 1d.2v.3g.4d.5d, 1d.2v.3g.4d.5f, 1d.2v.3g.4d.5h,
1d.2v.3g.4d.5i, 1d.2v.3g.4d.5n, 1d.2v.3g.4f.5a, 1d.2v.3g.4f.5b, 1d.2v.3g.4f.5d,
1d.2v.3g.4f.5f, 1d.2v.3g.4f.5h, 1d.2v.3g.4f.5i, 1d.2v.3g.4f.5n, 1d.2v.3g.4i.5a,
1d.2v.3g.4i.5b, 1d.2v.3g.4i.5d, 1d.2v.3g.4i.5f, 1d.2v.3g.4i.5h, 1d.2v.3g.4i.5i,
1d.2v.3g.4i.5n, 1d.2v.3g.4n.5a, 1d.2v.3g.4n.5b, 1d.2v.3g.4n.5d, 1d.2v.3g.4n.5f,
1d.2v.3g.4n.5h, 1d.2v.3g.4n.5i, 1d.2v.3g.4n.5n, 1d.2v.3g.4p.5a, 1d.2v.3g.4p.5b,
1d.2v.3g.4p.5d, 1d.2v.3g.4p.5f, 1d.2v.3g.4p.5h, 1d.2v.3g.4p.5i, 1d.2v.3g.4p.5n,
1d.2y.3a.4a.5a, 1d.2y.3a.4a.5b, 1d.2y.3a.4a.5d, 1d.2y.3a.4a.5f, 1d.2y.3a.4a.5h,
1d.2y.3a.4a.5i, 1d.2y.3a.4a.5n, 1d.2y.3a.4b.5a, 1d.2y.3a.4b.5b, 1d.2y.3a.4b.5d,
1d.2y.3a.4b.5f, 1d.2y.3a.4b.5h, 1d.2y.3a.4b.5i, 1d.2y.3a.4b.5n, 1d.2y.3a.4d.5a,
1d.2y.3a.4d.5b, 1d.2y.3a.4d.5d, 1d.2y.3a.4d.5f, 1d.2y.3a.4d.5h, 1d.2y.3a.4d.5i,
1d.2y.3a.4d.5n, 1d.2y.3a.4f.5a, 1d.2y.3a.4f.5b, 1d.2y.3a.4f.5d, 1d.2y.3a.4f.5f,
1d.2y.3a.4f.5h, 1d.2y.3a.4f.5i, 1d.2y.3a.4f.5n, 1d.2y.3a.4i.5a, 1d.2y.3a.4i.5b,
1d.2y.3a.4i.5d, 1d.2y.3a.4i.5f, 1d.2y.3a.4i.5h, 1d.2y.3a.4i.5i, 1d.2y.3a.4i.5n,
1d.2y.3a.4n.5a, 1d.2y.3a.4n.5b, 1d.2y.3a.4n.5d, 1d.2y.3a.4n.5f, 1d.2y.3a.4n.5h,
1d.2y.3a.4n.5i, 1d.2y.3a.4n.5n, 1d.2y.3a.4p.5a, 1d.2y.3a.4p.5b, 1d.2y.3a.4p.5d,
1d.2y.3a.4p.5f, 1d.2y.3a.4p.5h, 1d.2y.3a.4p.5i, 1d.2y.3a.4p.5n, 1d.2y.3c.4a.5a,
1d.2y.3c.4a.5b, 1d.2y.3c.4a.5d, 1d.2y.3c.4a.5f, 1d.2y.3c.4a.5h, 1d.2y.3c.4a.5i,
1d.2y.3c.4a.5n, 1d.2y.3c.4b.5a, 1d.2y.3c.4b.5b, 1d.2y.3c.4b.5d, 1d.2y.3c.4b.5f,
1d.2y.3c.4b.5h, 1d.2y.3c.4b.5i, 1d.2y.3c.4b.5n, 1d.2y.3c.4d.5a, 1d.2y.3c.4d.5b,
1d.2y.3c.4d.5d, 1d.2y.3c.4d.5f, 1d.2y.3c.4d.5h, 1d.2y.3c.4d.5i, 1d.2y.3c.4d.5n,
1d.2y.3c.4f.5a, 1d.2y.3c.4f.5b, 1d.2y.3c.4f.5d, 1d.2y.3c.4f.5f, 1d.2y.3c.4f.5h,
1d.2y.3c.4f.5i, 1d.2y.3c.4f.5n, 1d.2y.3c.4i.5a, 1d.2y.3c.4i.5b, 1d.2y.3c.4i.5d,
1d.2y.3c.4i.5f, 1d.2y.3c.4i.5h, 1d.2y.3c.4i.5i, 1d.2y.3c.4i.5n, 1d.2y.3c.4n.5a,
1d.2y.3c.4n.5b, 1d.2y.3c.4n.5d, 1d.2y.3c.4n.5f, 1d.2y.3c.4n.5h, 1d.2y.3c.4n.5i,
1d.2y.3c.4n.5n, 1d.2y.3c.4p.5a, 1d.2y.3c.4p.5b, 1d.2y.3c.4p.5d, 1d.2y.3c.4p.5f,
1d.2y.3c.4p.5h, 1d.2y.3c.4p.5i, 1d.2y.3c.4p.5n, 1d.2y.3e.4a.5a, 1d.2y.3e.4a.5b,
1d.2y.3e.4a.5d, 1d.2y.3e.4a.5f, 1d.2y.3e.4a.5h, 1d.2y.3e.4a.5i, 1d.2y.3e.4a.5n,
1d.2y.3e.4b.5a, 1d.2y.3e.4b.5b, 1d.2y.3e.4b.5d, 1d.2y.3e.4b.5f, 1d.2y.3e.4b.5h,
1d.2y.3e.4b.5i, 1d.2y.3e.4b.5n, 1d.2y.3e.4d.5a, 1d.2y.3e.4d.5b, 1d.2y.3e.4d.5d,
1d.2y.3e.4d.5f, 1d.2y.3e.4d.5h, 1d.2y.3e.4d.5i, 1d.2y.3e.4d.5n, 1d.2y.3e.4f.5a,
1d.2y.3e.4f.5b, 1d.2y.3e.4f.5d, 1d.2y.3e.4f.5f, 1d.2y.3e.4f.5h, 1d.2y.3e.4f.5i, TABLE 12-continued List of Compound Structures of Formula II 1d.2y.3e.4f.5n, 1d.2y.3e.4i.5a, 1d.2y.3e.4i.5b, 1d.2y.3e.4i.5d, 1d.2y.3e.4i.5f,
1d.2y.3e.4i.5h, 1d.2y.3e.4i.5i, 1d.2y.3e.4i.5n, 1d.2y.3e.4n.5a, 1d.2y.3e.4n.5b,
1d.2y.3e.4n.5d, 1d.2y.3e.4n.5f, 1d.2y.3e.4n.5h, 1d.2y.3e.4n.5i, 1d.2y.3e.4n.5n,
1d.2y.3e.4p.5a, 1d.2y.3e.4p.5b, 1d.2y.3e.4p.5d, 1d.2y.3e.4p.5f, 1d.2y.3e.4p.5h,
1d.2y.3e.4p.5i, 1d.2y.3e.4p.5n, 1d.2y.3g.4a.5a, 1d.2y.3g.4a.5b, 1d.2y.3g.4a.5d,
1d.2y.3g.4a.5f, 1d.2y.3g.4a.5h, 1d.2y.3g.4a.5i, 1d.2y.3g.4a.5n, 1d.2y.3g.4b.5a,
1d.2y.3g.4b.5b, 1d.2y.3g.4b.5d, 1d.2y.3g.4b.5f, 1d.2y.3g.4b.5h, 1d.2y.3g.4b.5i,
1d.2y.3g.4b.5n, 1d.2y.3g.4d.5a, 1d.2y.3g.4d.5b, 1d.2y.3g.4d.5d, 1d.2y.3g.4d.5f,
1d.2y.3g.4d.5h, 1d.2y.3g.4d.5i, 1d.2y.3g.4d.5n, 1d.2y.3g.4f.5a, 1d.2y.3g.4f.5b,
1d.2y.3g.4f.5d, 1d.2y.3g.4f.5f, 1d.2y.3g.4f.5h, 1d.2y.3g.4f.5i, 1d.2y.3g.4f.5n,
1d.2y.3g.4i.5a, 1d.2y.3g.4i.5b, 1d.2y.3g.4i.5d, 1d.2y.3g.4i.5f, 1d.2y.3g.4i.5h,
1d.2y.3g.4i.5i, 1d.2y.3g.4i.5n, 1d.2y.3g.4n.5a, 1d.2y.3g.4n.5b, 1d.2y.3g.4n.5d,
1d.2y.3g.4n.5f, 1d.2y.3g.4n.5h, 1d.2y.3g.4n.5i, 1d.2y.3g.4n.5n, 1d.2y.3g.4p.5a,
1d.2y.3g.4p.5b, 1d.2y.3g.4p.5d, 1d.2y.3g.4p.5f, 1d.2y.3g.4p.5h, 1d.2y.3g.4p.5i,
1d.2y.3g.4p.5n, 1d.2z.3a.4a.5a, 1d.2z.3a.4a.5b, 1d.2z.3a.4a.5d, 1d.2z.3a.4a.5f,
1d.2z.3a.4a.5h, 1d.2z.3a.4a.5i, 1d.2z.3a.4a.5n, 1d.2z.3a.4b.5a, 1d.2z.3a.4b.5b,
1d.2z.3a.4b.5d, 1d.2z.3a.4b.5f, 1d.2z.3a.4b.5h, 1d.2z.3a.4b.5i, 1d.2z.3a.4b.5n,
1d.2z.3a.4d.5a, 1d.2z.3a.4d.5b, 1d.2z.3a.4d.5d, 1d.2z.3a.4d.5f, 1d.2z.3a.4d.5h,
1d.2z.3a.4d.5i, 1d.2z.3a.4d.5n, 1d.2z.3a.4f.5a, 1d.2z.3a.4f.5b, 1d.2z.3a.4f.5d,
1d.2z.3a.4f.5f, 1d.2z.3a.4f.5h, 1d.2z.3a.4f.5i, 1d.2z.3a.4f.5n, 1d.2z.3a.4i.5a,
1d.2z.3a.4i.5b, 1d.2z.3a.4i.5d, 1d.2z.3a.4i.5f, 1d.2z.3a.4i.5h, 1d.2z.3a.4i.5i,
1d.2z.3a.4i.5n, 1d.2z.3a.4n.5a, 1d.2z.3a.4n.5b, 1d.2z.3a.4n.5d, 1d.2z.3a.4n.5f,
1d.2z.3a.4n.5h, 1d.2z.3a.4n.5i, 1d.2z.3a.4n.5n, 1d.2z.3a.4p.5a, 1d.2z.3a.4p.5b,
1d.2z.3a.4p.5d, 1d.2z.3a.4p.5f, 1d.2z.3a.4p.5h, 1d.2z.3a.4p.5i, 1d.2z.3a.4p.5n,
1d.2z.3c.4a.5a, 1d.2z.3c.4a.5b, 1d.2z.3c.4a.5d, 1d.2z.3c.4a.5f, 1d.2z.3c.4a.5h,
1d.2z.3c.4a.5i, 1d.2z.3c.4a.5n, 1d.2z.3c.4b.5a, 1d.2z.3c.4b.5b, 1d.2z.3c.4b.5d,
1d.2z.3c.4b.5f, 1d.2z.3c.4b.5h, 1d.2z.3c.4b.5i, 1d.2z.3c.4b.5n, 1d.2z.3c.4d.5a,
1d.2z.3c.4d.5b, 1d.2z.3c.4d.5d, 1d.2z.3c.4d.5f, 1d.2z.3c.4d.5h, 1d.2z.3c.4d.5i,
1d.2z.3c.4d.5n, 1d.2z.3c.4f.5a, 1d.2z.3c.4f.5b, 1d.2z.3c.4f.5d, 1d.2z.3c.4f.5f,
1d.2z.3c.4f.5h, 1d.2z.3c.4f.5i, 1d.2z.3c.4f.5n, 1d.2z.3c.4i.5a, 1d.2z.3c.4i.5b,
1d.2z.3c.4i.5d, 1d.2z.3c.4i.5f, 1d.2z.3c.4i.5h, 1d.2z.3c.4i.5i, 1d.2z.3c.4i.5n,
1d.2z.3c.4n.5a, 1d.2z.3c.4n.5b, 1d.2z.3c.4n.5d, 1d.2z.3c.4n.5f, 1d.2z.3c.4n.5h,
1d.2z.3c.4n.5i, 1d.2z.3c.4n.5n, 1d.2z.3c.4p.5a, 1d.2z.3c.4p.5b, 1d.2z.3c.4p.5d,
1d.2z.3c.4p.5f, 1d.2z.3c.4p.5h, 1d.2z.3c.4p.5i, 1d.2z.3c.4p.5n, 1d.2z.3e.4a.5a,
1d.2z.3e.4a.5b, 1d.2z.3e.4a.5d, 1d.2z.3e.4a.5f, 1d.2z.3e.4a.5h, 1d.2z.3e.4a.5i,
1d.2z.3e.4a.5n, 1d.2z.3e.4b.5a, 1d.2z.3e.4b.5b, 1d.2z.3e.4b.5d, 1d.2z.3e.4b.5f,
1d.2z.3e.4b.5h, 1d.2z.3e.4b.5i, 1d.2z.3e.4b.5n, 1d.2z.3e.4d.5a, 1d.2z.3e.4d.5b,
1d.2z.3e.4d.5d, 1d.2z.3e.4d.5f, 1d.2z.3e.4d.5h, 1d.2z.3e.4d.5i, 1d.2z.3e.4d.5n,
1d.2z.3e.4f.5a, 1d.2z.3e.4f.5b, 1d.2z.3e.4f.5d, 1d.2z.3e.4f.5f, 1d.2z.3e.4f.5h,
1d.2z.3e.4f.5i, 1d.2z.3e.4f.5n, 1d.2z.3e.4i.5a, 1d.2z.3e.4i.5b, 1d.2z.3e.4i.5d,
1d.2z.3e.4i.5f, 1d.2z.3e.4i.5h, 1d.2z.3e.4i.5i, 1d.2z.3e.4i.5n, 1d.2z.3e.4n.5a,
1d.2z.3e.4n.5b, 1d.2z.3e.4n.5d, 1d.2z.3e.4n.5f, 1d.2z.3e.4n.5h, 1d.2z.3e.4n.5i,
1d.2z.3e.4n.5n, 1d.2z.3e.4p.5a, 1d.2z.3e.4p.5b, 1d.2z.3e.4p.5d, 1d.2z.3e.4p.5f,
1d.2z.3e.4p.5h, 1d.2z.3e.4p.5i, 1d.2z.3e.4p.5n, 1d.2z.3g.4a.5a, 1d.2z.3g.4a.5b,
1d.2z.3g.4a.5d, 1d.2z.3g.4a.5f, 1d.2z.3g.4a.5h, 1d.2z.3g.4a.5i, 1d.2z.3g.4a.5n,
1d.2z.3g.4b.5a, 1d.2z.3g.4b.5b, 1d.2z.3g.4b.5d, 1d.2z.3g.4b.5f, 1d.2z.3g.4b.5h,
1d.2z.3g.4b.5i, 1d.2z.3g.4b.5n, 1d.2z.3g.4d.5a, 1d.2z.3g.4d.5b, 1d.2z.3g.4d.5d,
1d.2z.3g.4d.5f, 1d.2z.3g.4d.5h, 1d.2z.3g.4d.5i, 1d.2z.3g.4d.5n, 1d.2z.3g.4f.5a,
1d.2z.3g.4f.5b, 1d.2z.3g.4f.5d, 1d.2z.3g.4f.5f, 1d.2z.3g.4f.5h, 1d.2z.3g.4f.5i,
1d.2z.3g.4f.5n, 1d.2z.3g.4i.5a, 1d.2z.3g.4i.5b, 1d.2z.3g.4i.5d, 1d.2z.3g.4i.5f,
1d.2z.3g.4i.5h, 1d.2z.3g.4i.5i, 1d.2z.3g.4i.5n, 1d.2z.3g.4n.5a, 1d.2z.3g.4n.5b,
1d.2z.3g.4n.5d, 1d.2z.3g.4n.5f, 1d.2z.3g.4n.5h, 1d.2z.3g.4n.5i, 1d.2z.3g.4n.5n,
1d.2z.3g.4p.5a, 1d.2z.3g.4p.5b, 1d.2z.3g.4p.5d, 1d.2z.3g.4p.5f, 1d.2z.3g.4p.5h,
1d.2z.3g.4p.5i, 1d.2z.3g.4p.5n In still yet another embodiment, the compound of the present invention has an inhibition activity against P450 at a level equal to or better than the inhibition activity of a compound as represented by an $IC_{50}$ of less than about 2000 nM, less than about 1500 nM, less than about 1000 nM, less than about 900 nM, less than about 800 nM, less than about 700 nM, less than about 650 nM, less than about 600 nM, less than about 550 nM, less than about 500 nM, less than about 400 nM, less than about 350 nM, less than about 300 nM, less than about 250 nM, less than about 200 nM, less than about 100 nM, or less than about 50 nM.

In still yet another embodiment, the compound of the present invention has an inhibition activity against an isozyme of P450, e.g., 3A in a range represented by $IC_{50}$ from about 2000 nM to about 100 nM, from about 1000 nM to about 100 nM, from about 900 nM to about 200 nM, from about 800 nM to about 300 nM, from about 700 nM to about 200 nM, from about 600 nM to about 200 nM, from about 500 nM to about 200 nM, from about 700 nM to about 300 nM, from about 600 nM to about 300 nM, from about 700 nM to about 400 nM, from about 600 nM to about 400 nM, from about 400 nM to about 100 nM, from about 300 nM to about 100 nM, or from about 600 nM to about 150 nM.

In still yet another embodiment, the compound of the present invention has an inhibition activity against P450 at a level equal to or better than the inhibition activity of a compound as represented by an $IC_{50}$ of less than about 2000 nM, less than about 1500 nM, less than about 1000 nM, less than about 900 nM, less than about 800 nM, less than about 700 nM, less than about 650 nM, less than about 600 nM, less than about 550 nM, less than about 500 nM, less than about 400 nM, less than about 350 nM, less than about 300 nM, less than about 250 nM, less than about 200 nM, less than about 100 nM, or less than about 50 nM, provided that such compound also does not substantially exhibit biological activities other than its inhibition activity against P450. For example, the compound of the present invention can have a reduced or not significant activity of protease inhibition, including without any limitation a level of protease inhibition as represented by HIV $EC_{50}$ of greater than about 1000 nM, greater than about 900 nM, greater than about 800 nM, greater than about 700 nM, greater than about 600 nM, greater than about 500 nM, greater than about 400 nM, greater than about 300 nM, greater than about 200 nM, greater than about 100 nM, greater than about 50 nM, greater than about 40 nM, greater than about 30 nM, greater than about 20 nM, greater than about 10 nM, greater than about 5 nM, or greater than about 1 nM.

In yet another embodiment, the compound of the present invention has an inhibition activity specifically against one or more isozymes of P450 including without limitation 1A2, 2B6, 2C8, 2C19, 2C9, 2D6, 2E1, and 3A4, 5, 7, etc.

In yet another embodiment, the compound of the present invention has an inhibition activity specifically against an isozyme of P450 that is involved in metabolizing anti-viral drugs, e.g., indinavir, nelfinavir, ritonavir, saquinavir etc.

In still yet another embodiment, the compound of the present invention has an inhibition activity specifically against one or more isozymes of P450, but not the other(s). For example, the compound of the present invention can have an inhibition activity specifically against P450 3A, but a reduced, insubstantial, or minimum inhibition activity against another isozyme of P450, e.g., P450 2C9.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, e.g. a compound of the present invention, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1%, w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil such as arachis oil olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 μm (including particle sizes in a range between 0.1 and 500 μm in increments such as 0.5 μm, 1 μm, 30 μm, 35 μm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients provided by the present invention the formulations of this invention may include other agents conventional in the art having regard to the type of formulation in question, for example those suitable for oral administration may include flavoring agents.

The invention further provides veterinary compositions comprising at least one active ingredient, e.g., a compound of the present invention together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The effective dose of an active ingredient depends at least on the nature of the condition being treated, toxicity, whether the compound is being used prophylactically (lower doses) or against an active disease or condition, the method of delivery, and the pharmaceutical formulation, and will be determined by the clinician using conventional dose escalation studies. The effective dose can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, or between 5 mg and 500 mg, and may take the form of single or multiple doses.

In yet another embodiment, the present application discloses pharmaceutical compositions comprising a compound of the present invention, or a pharmaceutically acceptable salt, solvate, and/or ester thereof, and a pharmaceutically acceptable carrier or exipient.

In yet another embodiment, the present application discloses pharmaceutical compositions comprising a compound of the present invention, or a pharmaceutically acceptable salt, solvate, and/or ester thereof, in combination with at least one additional therapeutic agent, and a pharmaceutically acceptable carrier or exipient.

According to the present invention, the therapeutic agent used in combination with the compound of the present invention can be any agent having a therapeutic effect when used in combination with the compound of the present invention. For example, the therapeutic agent used in combination with the compound of the present invention can be any agent that is accessible to oxidative metabolism by cytochrome P450 enzymes, especially cytochrome P450 monooxygenase, e.g., 1A2, 2B6, 2C8, 2C19, 2C9, 2D6, 2E1, 3A4,5,7, etc.

In another example, the therapeutic agent used in combination with the compound of the present invention can be any anti-viral agent, e.g., anti-HIV, anti-HCV, etc., anti-bacterial agent, anti-fungal agent, immuno-modulator, e.g., immunosuppressant, anti-neoplastic agent, chemotherapeutic agent, agents useful for treating cardiovascular conditions, neurological conditions, etc.

In yet another example, the therapeutic agent used in combination with the compound of the present invention can be any proton pump inhibitor, anti-epileptics, NSAID, oral hypoglycemic agent, angiotensin II, sulfonylureas, beta blocker, antidepressant, antipsychotics, or anesthetics, or a combination thereof.

In yet another example, the therapeutic agent used in combination with the compound of the present invention can be any 1) macrolide antibiotics, e.g., clarithromycin, erythromycin, telithromycin, 2) anti-arrhythmics, e.g., quinidine→3-OH, 3) benzodiazepines, e.g., alprazolam, diazepam→3OH, midazolam, triazolam, 4) immune modulators, e.g., cyclosporine, tacrolimus (FK506), 5) HIV antivirals, e.g., indinavir, nelfinavir, ritonavir, saquinavir, 6) prokinetic, e.g., cisapride, 7) antihistamines, e.g., astemizole, chlorpheniramine, terfenidine, 8) calcium channel blockers, e.g., amlodipine, diltiazem, felodipine lercanidipine, nifedipine, nisoldipine, nitrendipine, verapamil, 9) HMG CoA reductase inhibitors, e.g., atorvastatin, cerivastatin, lovastatin, simvastatin, or 10) steroid 6beta-OH, e.g., estradiol, hydrocortisone, progesterone, testosterone.

In still yet another example, the therapeutic agent used in combination with the compound of the present invention can be any of those selected from alfentanyl, aprepitant, aripiprazole, buspirone, cafergot, caffeine, TMU, cilostazol, cocaine, codeine-N-demethylation, dapsone, dextromethorphan, docetaxel, domperidone, eplerenone, fentanyl, finasteride, gleevec, haloperidol, irinotecan, LAAM, lidocaine, methadone, nateglinide, ondansetron, pimozide, propranolol, quetiapine, quinine, salmeterol, sildenafil, sirolimus, tamoxifen, taxol, terfenadine, trazodone, vincristine, zaleplon, or zolpidem or a combination thereof.

In one embodiment, the present application discloses pharmaceutical compositions comprising a compound of the present invention, or a pharmaceutically acceptable salt, solvate, and/or ester thereof, in combination with at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, non-nucleoside inhibitors of HCV, CCR5 inhibitors, and combinations thereof, and a pharmaceutically acceptable carrier or exipient.

In another embodiment, the present application provides pharmaceutical compositions comprising a compound of the present invention, or a pharmaceutically acceptable salt, solvate, and/or ester thereof, in combination with at least one additional therapeutic agent selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG3S, AG 1859, capravirine, emivirine, delaviridine, efavirenz, nevirapine, (+) calanolide A, etravirine, GW5634, DPC-083, DPC-961, DPC-963, MIV-150, MIV-150, TMC-120, TMC-278 (rilpivirene), BILR 355 BS, VRX 840773, UK-453061, RDEA806, zidovudine, emtricitabine, didanosine, stavudine, zalcitabine, lamivudine, abacavir, amdoxovir, elvucitabine, alovudine, MIV-210, Racivir (±-FTC), D-d4FC, apricitibine (AVX754), phosphazide, fozivudine tidoxil, tenofovir disoproxil fumarate, adefovir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, L-870810, MK-0518 (raltegravir), elvitegravir, BMS-538158, GSK364735C, BMS-707035, MK-2048, BA 011, enfuvirtide, sifuvirtide, FB006M, TRI-1144, AMD-070, SP01A, BMS-488043, BlockAide/CR, immunitin, benzimidazole derivatives, benzo-1,2,4-thiadiazine derivatives, phenylalanine derivatives, A-832, A-689, aplaviroc, vicriviroc, and maraviroc, PRO-140, INCB15050, PF-2332798, CCR5mAB004, BAS-100, SPI-452, REP 9, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDX010 (ipilimumab), PBS 119, ALG 889, PA1050040, pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta, rebetol, copegus, viramidine (taribavirin), NM-283, valopicitabine, R1626, PSI-6130 (R1656), HCV-796, BILB 1941, XTL-2125, MK-0608, NM-107, R7128 (R4048), VCH-759, PF-868554, and GSK625433, SCH-503034 (SCH-7), VX-950 (telaprevir), BILN-2065, BMS-605339, and ITMN-191, MX-3253 (celgosivir), UT-231B, IDN-6556, ME 3738, LB-84451, MitoQ, zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib), cyclosporine, FK-506, rapamycin, taxol, taxotere, clarithromycin, A-77003, A-80987, MK-639, saquinavir; VX-478, AG1343, DMP-323, XM-450, BILA 2011 BS, BILA 1096 BS, BILA 2185 BS, BMS 186,318, LB71262, SC-52151, SC-629 (N,N-dimethylglycyl-N-(2-hydroxy-3-(((4-methoxyphenyl)sulphonyl)(2-methylpropyl)amino)-1-(phenylmethyl)propyl)-3-methyl-L-valinamide), KNI-272, CGP 53437, CGP 57813 and U-103017 and a pharmaceutically acceptable carrier or exipient.

In yet another embodiment, the present application provides a combination pharmaceutical agent comprising:
a) a first pharmaceutical composition comprising a compound of the present invention, or a pharmaceutically acceptable salt, solvate, or ester thereof; and
b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HCV, and other drugs for treating HCV, and combinations thereof.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

In one embodiment, the compounds of the present invention can be used alone, e.g., for inhibiting cytochrome P450 monooxygenase. In another embodiment, the compounds of the present invention are used in combination with other active therapeutic ingredients or agents. Preferably, the other active therapeutic ingredients or agents are metabolized or accessible to the oxidative metabolism by cytochrome P450 enzymes, e.g., monooxygenase enzymes such as 1A2, 2B6, 2C8, 2C19, 2C9, 2D6, 2E1, 3A4,5,7, etc.

Combinations of the compounds of the present invention are typically selected based on the condition to be treated, cross-reactivities of ingredients and pharmaco-properties of the combination. For example, when treating an infection (e.g., HIV or HCV), the compositions of the invention are combined with anti-infective agents (such as those described herein).

In one embodiment, non-limiting examples of suitable combinations include combinations of one or more compounds of the present invention with one or more anti-viral agents, e.g., anti-HIV, anti-HCV, etc., anti-bacterial agents, anti-fungal agents, immuno-modulators, e.g., immunosuppressant, anti-neoplastic agents, chemotherapeutic agents, agents useful for treating cardiovascular conditions, neurological conditions, etc.

In another embodiment, non-limiting examples of suitable combinations include combinations of one or more compounds of the present invention with one or more proton pump inhibitors, anti-epileptics, NSAIDs, oral hypoglycemic agents, angiotensin II, sulfonylureas, beta blockers, antidepressants, antipsychotics, or anesthetics, or a combination thereof.

In yet another embodiment, non-limiting examples of suitable combinations include combinations of one or more compounds of the present invention with one or more 1) macrolide antibiotics, e.g., clarithromycin, erythromycin, telithromycin, 2) anti-arrhythmics, e.g., quinidine→3—OH, 3) benzodiazepines, e.g., alprazolam, diazepam→3OH, midazolam, triazolam, 4) immune modulators, e.g., cyclosporine, tacrolimus (FK506), 5) HIV antivirals, e.g., indinavir, nelfinavir, ritonavir, saquinavir, 6) prokinetic, e.g., cisapride, 7) antihistamines, e.g., astemizole, chlorpheniramine, terfenidine, 8) calcium channel blockers, e.g., amlodipine, diltiazem, felodipine, lercanidipine, nifedipine, nisoldipine, nitrendipine, verapamil, 9) HMG CoA reductase inhibitors, e.g., atorvastatin, cerivastatin, lovastatin, simvastatin, or 10) steroid 6beta-OH, e.g., estradiol, hydrocortisone, progesterone, testosterone.

In still yet another embodiment, non-limiting examples of suitable combinations include combinations of one or more compounds of the present invention with one or more compounds selected from the group consisting of alfentanyl, aprepitant, aripiprazole, buspirone, cafergot, caffeine→TMU, cilostazol, cocaine, codeine-N-demethylation, dapsone, dextromethorphan, docetaxel, domperidone, eplerenone, fentanyl, finasteride, gleevec, haloperidol, irinotecan, LAAM, lidocaine, methadone, nateglinide, odanestron, pimozide, propranolol, quetiapine, quinine, salmeterol, sildenafil, sirolimus, tamoxifen, taxol, terfenadine, trazodone, vincristine, zaleplon, and zolpidem or a combination thereof.

In still yet another embodiment, non-limiting examples of suitable combinations include combinations of one or more compounds of the present invention with one or more HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, and other drugs for treating HIV, interferons, ribavirin analogs, HCV NS3 protease inhibitors, alpha-glucosidase 1 inhibitors, hepatoprotectants, nucleoside or nucleotide inhibitors of HCV, non-nucleoside inhibitors of HCV, and other drugs for treating HCV.

More specifically, one or more compounds of the present invention may be combined with one or more compounds selected from the group consisting of 1) amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, GS-8374, PPL-100, DG35, and AG 1859, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirene), efavirenz, BILR 355 BS, VRX 840773, UK-453061, and RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, apricitibine (AVX754), GS-7340, KP-1461, and fosalvudine tidoxil (formerly HDP 99.0003), 4) a HIV nucleotide inhibitor of reverse transcriptase, e.g., tenofovir and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), elvitegravir, L-870812, and L-870810, MK-0518 (raltegravir), BMS-538158, GSK364735C, BMS-707035, MK-2048, and BA 011, 6) a gp41 inhibitor, e.g., enfuvirtide, sifuvirtide, FB006M, and TRI-1144, 7) a CXCR4 inhibitor, e.g., AMD-070, 8) an entry inhibitor, e.g., SP01A, 9) a gp120 inhibitor, e.g., BMS-488043 or BlockAide/CR, 10) a G6PD and NADH-oxidase inhibitor, e.g., immunitin, 11) a CCR5 inhibitor, e.g., aplaviroc, vicriviroc, maraviroc, PRO-140, INCB15050, PF-232798 (Pfizer), and CCR5mAb004, 12) other drugs for treating HIV, e.g., BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDX10 (ipilimumab), PBS 119, ALG 889, and PA-1050040 (PA-040), 13) an interferon, e.g., pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta, 14) a ribavirin analog, e.g., rebetol, copegus, viramidine (taribavirin), 15) a NS5b polymerase inhibitor, e.g., NM-283, valopicitabine, R1626, PSI-6130 (R1656), HCV-796, BILB 1941, XTL-2125, MK-0608, NM-107, R7128 (R4048), VCH-759, PF-868554, and GSK625433, 16) A NS3 protease inhibitor, e.g., SCH-503034 (SCH-7), VX-950 (telaprevir), BILN-2065, BMS-605339, and ITMN-191, 17) an alpha-glucosidase 1 inhibitor, e.g., MX-3253 (celgosivir), UT-231B, 18) hepatoprotectants, e.g., IDN-6556, ME 3738, LB-84451, and MitoQ, 19) a non-nucleoside inhibitor of HCV, e.g., benzimidazole derivatives, benzo-1,2,4-thiadiazine derivatives, phenylalanine derivatives, A-831, GS-9190, and A-689; and 20) other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

It is also contemplated that the compounds of the present invention can be used with any other active therapeutic agent or ingredient which is appreciably metabolized by cytochrome P450 monooxygenase enzymes, e.g. cytochrome P450 monooxygenase 3A, thereby reducing the amount or rate at which the other active therapeutic agent or ingredient is metabolized, whereby the pharmacokinetics of the other active therapeutic agent or ingredient is improved. The pharmacokinetics of a drug will determine the concentration of the drug at its intended site of therapeutic activity in an organism. Typical, but non-limiting, pharmacokinetic parameters measured are the half-life ($t_{1/2}$), maximum concentration ($C_{max}$), mean residence time (MRT), rate of clearance (CL) and volume of distribution ($V_D$). Non-limiting examples of improved pharmacokinetic parameters would be increased $t_{1/2}$, increased MRT, increased $C_{max}$ and decreased CL. In mammals, these parameters are usually determined by measuring the concentration of the drug in the blood over a period of time using conventional analytical techniques. Pharmacokinetic improvements usually include elevating the blood plasma levels of the other therapeutic agent or ingredient at a given time point or maintaining a therapeutically effective blood plasma level of the other therapeutic active agent or ingredient for a longer time period—compared to blood plasma levels of the other therapeutic agent or ingredient administered without the compound of the present invention. Although the blood may not be the optimal site of therapeutic activity for the drug, the concentration at the site of therapeutic activity is usually proportional to the concentration in the blood at a particular time point for a given dose of drug.

It is also possible to combine any compound of the invention with one or more other active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general during alternation therapy, an effective dosage of each active ingredient is administered sequentially, i.e. serially, whereas in combination therapy, effective dosages of two or more active ingredients are administered together.

In yet another embodiment, the present application provides a method for improving the pharmacokinetics of a drug which is metabolized by cytochrome P450 monooxygenase, comprising administering to a patient treated with said drug, a therapeutically effective amount of a compound of the present invention, or a pharmaceutically acceptable salt, solvate, and/or ester thereof. In another aspect of this embodiment, the $t_{1/2}$ is increased. In another aspect of this embodiment, the $C_{max}$ is increased. In another aspect of this embodiment, the MRT is increased. In another aspect of this embodiment, the CL is decreased. In another aspect of this embodiment, co-administration of a therapeutically effective amount of a compound of Formula I improves at least one of the pharmacokinetic parameters of the drug by at least about 10% to about 500%. In another aspect of this embodiment, co-administration of a therapeutically effective amount of a compound of Formula I improves at least one of the pharmacokinetic parameters of the drug by at least about 10%. In another aspect of this embodiment, co-administration of a therapeutically effective amount of a compound of Formula I improves at least one of the pharmacokinetic parameters of the drug by at least about 25%. In another aspect of this embodiment, co-administration of a therapeutically effective amount of a compound of Formula I improves at least one of the pharmacokinetic parameters of the drug by at least about 50%. In another aspect of this embodiment, co-administration of a therapeutically effective amount of a compound of Formula I improves at least one of the pharmacokinetic parameters of the drug by at least about 100%. In another aspect of this embodiment, co-administration of a therapeutically effective amount of a compound of Formula I improves at least one of the pharmacokinetic parameters of the drug by at least about 200%. In another aspect of this embodiment, co-administration of a therapeutically effective amount of a compound of Formula I improves at least one of the pharmacokinetic parameters of the drug by at least about 500%.

In yet another embodiment, the present application provides a method for improving the pharmacokinetics of a drug which is metabolized by cytochrome P450 monooxygenase, comprising administering to a patient treated with said drug, a therapeutically effective amount of a combination comprising said drug and a compound of the present invention, or a pharmaceutically acceptable salt, solvate, and/or ester thereof. In another aspect of this embodiment, the $t_{1/2}$ is increased. In another aspect of this embodiment, the $C_{max}$ is increased. In another aspect of this embodiment, the MRT is increased. In another aspect of this embodiment, the CL is decreased. In another aspect of this embodiment, the therapeutically effective amount of the combination improves at least one of the pharmacokinetic parameters of the drug by at least about 10% to about 500%. In another aspect of this embodiment, the therapeutically effective amount of the combination improves at least one of the pharmacokinetic parameters of the drug by at least about 10%. In another aspect of this embodiment, the therapeutically effective amount of the combination improves at least one of the pharmacokinetic parameters of the drug by at least about 25%. In another aspect of this embodiment, the therapeutically effective amount of the combination improves at least one of the pharmacokinetic parameters of the drug by at least about 50%. In another aspect of this embodiment, the therapeutically effective amount of the combination improves at least one of the pharmacokinetic parameters of the drug by at least about 100%. In another aspect of this embodiment, the therapeutically effective amount of the combination improves at least one of the pharmacokinetic parameters of the drug by at least about 200%. In another aspect of this embodiment, the therapeutically effective amount of the combination improves at least one of the pharmacokinetic parameters of the drug by at least about 500%.

In yet another embodiment, the present application provides a method for improving the pharmacokinetics of a drug which is metabolized by cytochrome P450 monooxygenase 3A, comprising administering to a patient treated with said drug, a therapeutically effective amount of a compound of the present invention, or a pharmaceutically acceptable salt, solvate, and/or ester thereof. In another aspect of this embodiment, the $t_{1/2}$ is increased. In another aspect of this embodiment, the $C_{max}$ is increased. In another aspect of this embodiment, the MRT is increased. In another aspect of this embodiment, the CL is decreased. In another aspect of this embodiment, co-administration of a therapeutically effective amount of a compound of Formula I improves at least one of the pharmacokinetic parameters of the drug by at least about 10% to about 500%. In another aspect of this embodiment, co-administration of a therapeutically effective amount of a compound of Formula I improves at least one of the pharmacokinetic parameters of the drug by at least about 10%. In another aspect of this embodiment, co-administration of a therapeutically effective amount of a compound of Formula I improves at least one of the pharmacokinetic parameters of the drug by at least about 25%. In another aspect of this embodiment, co-administration of a therapeutically effective amount of a compound of Formula I improves at least one of the pharmacokinetic parameters of the drug by at least about 50%. In another aspect of this embodiment, co-administration of a therapeutically effective amount of a compound of Formula I improves at least one of the pharmacokinetic parameters of the drug by at least about 100%. In another aspect of this embodiment, co-administration of a therapeutically effective amount of a compound of Formula I improves at least one of the pharmacokinetic parameters of the drug by at least about 200%. In another aspect of this embodiment, co-administration of a therapeutically effective amount of a compound of Formula I improves at least one of the pharmacokinetic parameters of the drug by at least about 500%.

In yet another embodiment, the present application provides a method for increasing blood plasma levels of a drug which is metabolized by cytochrome P450 monooxygenase, comprising administering to a patient treated with said drug, a therapeutically effective amount of a compound of the present invention, or a pharmaceutically acceptable salt solvate, and/or ester thereof. In another aspect of this embodiment, co-administration of a therapeutically effective amount of a compound of Formula I increases at least one of the blood plasma levels of the drug by at least about 10% to about 500%. In another aspect of this embodiment, co-administration of a therapeutically effective amount of a compound of Formula I increases at least one of the blood plasma levels of the drug by at least about 10%. In another aspect of this embodiment, co-administration of a therapeutically effective amount of a compound of Formula I increases at least one of the blood plasma levels of the drug by at least about 25%. In another aspect of this embodiment, co-administration of a therapeutically effective amount of a compound of Formula I increases at least one of the blood plasma levels of the drug by at least about 50%. In another aspect of this embodiment, co-administration of a therapeutically effective amount of a compound of Formula I increases at least one of the blood plasma levels of the drug by at least about 100%. In another aspect of this embodiment, co-administration of a therapeutically effective amount of a compound of Formula I increases at least one of the blood plasma levels of the drug by at least about 200%. In another aspect of this embodiment, co-administration of a compound of Formula I increases at least one of the blood plasma levels of the drug by at least about 500%.

In yet another embodiment, the present application provides a method for increasing blood plasma levels of a drug which is metabolized by cytochrome P450 monooxygenase, comprising administering to a patient treated with said drug, a therapeutically effective amount of a combination comprising said drug and a compound of the present invention, or a pharmaceutically acceptable salt, solvate, and/or ester thereof. In another aspect of this embodiment, the therapeutically effective amount of the combination increases at least one of the blood plasma levels of the drug by at least about 10% to about 500%. In another aspect of this embodiment, the therapeutically effective amount of the combination increases at least one of the blood plasma levels of the drug by at least about 10%. In another aspect of this embodiment, the therapeutically effective amount of the combination increases at least one of the blood plasma levels of the drug by at least about 25%. In another aspect of this embodiment, the therapeutically effective amount of the combination increases at least one of the blood plasma levels of the drug by at least about 50%. In another aspect of this embodiment, the therapeutically effective amount of the combination increases at least one of the blood plasma levels of the drug by at least about 100%. In another aspect of this embodiment, the therapeutically effective amount of the combination increases at least one of the blood plasma levels of the drug by at least about 200%. In another aspect of this embodiment, the therapeutically effective amount of the combination increases at least one of the blood plasma levels of the drug by at least about 500%.

In yet another embodiment, the present application provides a method for increasing blood plasma levels of a drug which is metabolized by cytochrome P450 monooxygenase 3A, comprising administering to a patient treated with said drug, a therapeutically effective amount of a compound of the present invention, or a pharmaceutically acceptable salt, solvate, and/or ester thereof. In another aspect of this embodiment, co-administration of a therapeutically effective amount of a compound of Formula I increases at least one of the blood plasma levels of the drug by at least about 10% to about 500%. In another aspect of this embodiment, co-administration of a therapeutically effective amount of a compound of Formula I increases at least one of the blood plasma levels of the drug by at least about 10%. In another aspect of this embodiment, co-administration of a therapeutically effective amount of a compound of Formula I increases at least one of the blood plasma levels of the drug by at least about 25%. In another aspect of this embodiment, co-administration of a therapeutically effective amount of a compound of Formula I increases at least one of the blood plasma levels of the drug by at least about 50%. In another aspect of this embodiment co-administration of a therapeutically effective amount of a compound of Formula I increases at least one of the blood plasma levels of the drug by at least about 100%. In another aspect of this embodiment, co-administration of a therapeutically effective amount of a compound of Formula I increases at least one of the blood plasma levels of the drug by at least about 200%. In another aspect of this embodiment, co-administration of a therapeutically effective amount of a compound of Formula I increases at least one of the blood plasma levels of the drug by at least about 500%.

In yet another embodiment, the present application provides a method for increasing blood plasma levels of a drug which is metabolized by cytochrome P450 monooxygenase, comprising administering to a patient treated with said drug, a therapeutically effective amount of a compound of the present invention, or a pharmaceutically acceptable salt, solvate, and/or ester thereof, and wherein the amount of the compound of the present invention administered is effective to inhibit cytochrome P450 monooxygenase. In another aspect of this embodiment, at least one of the blood plasma levels of the drug is increased by at least about 10% to about 500%. In another aspect of this embodiment, at least one of the blood plasma levels of the drug is increased by at least about 10%. In another aspect of this embodiment, at least one of the blood plasma levels of the drug is increased by at least about 25%. In another aspect of this embodiment, at least one of the blood plasma levels of the drug is increased by at least about 50%. In another aspect of this embodiment, at least one of the blood plasma levels of the drug is increased by at least about 100%. In another aspect of this embodiment, at least one of the blood plasma levels of the drug is increased by at least about 200%. In another aspect of this embodiment, at least one of the blood plasma levels of the drug is increased by at least about 500%.

In yet another embodiment, the present application provides a method for inhibiting cytochrome P450 monooxygenase in a patient comprising administering to a patient in need thereof an amount of a compound of the present invention, or a pharmaceutically acceptable salt, solvate, and/or ester thereof, effective to inhibit cytochrome P450 monooxygenase.

In yet another embodiment, the present application provides a method for inhibiting cytochrome P450 monooxygenase 3A in a patient comprising administering to a patient in need thereof an amount of a compound of the present invention, or a pharmaceutically acceptable salt, solvate, and/or ester thereof, effective to inhibit cytochrome P450 monooxygenase 3A.

In yet another embodiment, the present application provides a method for inhibiting cytochrome P450 monooxygenase comprising contacting cytochrome P450 monooxygenase with an amount of a compound of the present invention, or a pharmaceutically acceptable salt, solvate, and/or ester thereof, effective to inhibit cytochrome P450 monooxygenase.

In yet another embodiment, the present application provides a method for inhibiting cytochrome P450 monooxygenase 3A comprising contacting cytochrome P450 monooxygenase 3A with an amount of a compound of the present invention, or a pharmaceutically acceptable salt, solvate, and/or ester thereof, effective to inhibit cytochrome P450 monooxygenase 3A.

In yet another embodiment, the present application provides a method for treating an HIV infection comprising administering to a patient in need thereof a therapeutically effective amount of a compound of the present invention, or a pharmaceutically acceptable salt solvate, and/or ester thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, and CCR5 inhibitors.

In yet another embodiment, the present application provides a method for treating an HIV infection comprising administering to a patient in need thereof a therapeutically effective amount of a compound of the present invention, or a pharmaceutically acceptable salt, solvate, and/or ester thereof, in combination with a therapeutically effective amount of one or more additional therapeutic agents selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, and GW640385X, DG17, PPL-100, DG35, AG 1859, capravirine, emivirine, delaviridine, efavirenz, nevirapine, (+) calanolide A, etravirine, GW5634, DPC-083, DPC-961, DPC-963, MIV-150, TMC-120, TMC-278 (rilpivirene), efavirenz, BILR 355 BS, VRX 840773, UK-453061, RDEA806, zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, apricitibine (AVX754), amdoxovir, KP-1461, fosalvudine tidoxil (formerly HDP 99.0003), tenofovir, adefovir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, L-870810, elvitegravir, MK-0518 (raltegravir), BMS-538158, GSK364735C, BMS-707035, MK-2048, and BA 011, enfuvirtide, sifuvirtide, FB006M, and TRI-1144, AMD-070, an entry inhibitor, SP01A, BMS-488043, BlockAide/CR, a C6PD and NADH-oxidase inhibitor, immunitin, aplaviroc, vicriviroc, maraviroc, maraviroc, PRO-140, INCB15050, PF-232798 (Pfizer), CCR5mAb004, BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDX010 (ipilimumab), PBS 119, ALG 889, and PA-1050040 (PA-040).

In yet another embodiment, the present application provides a method for treating an HCV infection comprising administering to a patient in need thereof a therapeutically effective amount of a compound of the present invention, or a pharmaceutically acceptable salt, solvate, and/or ester thereof, in combination with a therapeutically effective amount of one or more additional therapeutic agents selected from the group consisting of pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, locteron, albuferon, rebif, Oral interferon alpha, IFNalpha-2b XL, AVI-005, PEG-Infergen, and pegylated IFN-beta, rebetol, copegus, viramidine (taribavirin), NM-283, valopicitabine, R1626, PSI-6130 (R1656), HCV-796, BILB 1941, XTL-2125, MK-0608, NM-107, R7128 (R4048), VCH-759, PF-868554, GSK625433, SCH-503034 (SCH-7), VX-950 (telaprevir), BILN-2065, BMS-605339, ITMN-191, MX-3253 (celgosivir), UT-231B, IDN-6556, ME 3738, LB-84451, MitoQ, benzimidazole derivatives, benzo-1,2,4-thiadiazine derivatives, phenylalanine derivatives, A-831, A-689, zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

In still yet another embodiment, the present application provides for the use of a compound of the present invention, or a pharmaceutically acceptable salt, solvate, and/or ester thereof, for the preparation of a medicament for inhibiting cytochrome P450 monooxygenase in a patient.

In still yet another embodiment, the present application provides for the use of a compound of the present invention, or a pharmaceutically acceptable salt, solvate, and/or ester thereof, for the preparation of a medicament for treating an HIV infection.

In still yet another embodiment, the present application provides for the use of a compound of the present invention, or a pharmaceutically acceptable salt, solvate, and/or ester thereof, for the preparation of a medicament for increasing blood plasma levels of the drug which is metabolized by cytochrome P450 monooxygenase.

In still yet another embodiment, the present application provides for the use of a compound of the present invention, or a pharmaceutically acceptable salt, solvate, and/or ester thereof, for the preparation of a medicament for improving the pharmacokinetics of a drug which is metabolized by cytochrome P450 monooxygenase.

EXAMPLES

Exemplary methods for preparing the compounds of Formula (I) are provided below. These methods are intended to illustrate the nature of such preparations and are not intended to limit the scope of applicable methods. While the examples specify certain reaction conditions, one skilled in the art will understand how to vary the specific reaction conditions to obtain the full scope of the invention.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example; boiling point and molecular weight for distillation and sublimation, presence or absence of polar functional groups for chromatography, stability of materials in acidic and basic media in multiphase extractions; and the like. One skilled in the art will apply techniques most likely to achieve the desired separation.

LIST OF ABBREVIATIONS AND ACRONYMS

| Abbreviation | Meaning |
|---|---|
| AIBN | 2,2'-azobis(2-methylpropionitrile) |
| % AN | % area norm, i.e. % of total area under an integrated curve |
| Bn | benzyl |
| BnBr | benzylbromide |
| BSA | bis(trimethylsilyl)acetamide |
| BzCl | benzoyl chloride |
| CDI | carbonyl diimidazole |
| dba | dibenzylideneacetone |
| DCC | dicyclohexylcarbodiimide |
| DIPEA | di-isopropylethylamine |
| DMAP | 4-dimethylaminopyridine |
| DMA or DMAC | N,N-dimethylacetamide |
| DMTCl | dimethoxytrityl chloride |
| DMSO | dimethylsulfoxide |
| DMF | dimethylformamide |
| EtOAc | ethyl acetate |
| ESI | electrospray ionization |
| HMDS | hexamethyldisilazane |
| HPLC | High pressure liquid chromatography |
| LDA | lithium diisopropylamide |
| LRMS | low resolution mass spectrum |
| mCPBA | meta-chloroperbenzoic acid |
| MeOH | methanol |
| m/z or m/e | mass to charge ratio |
| MH+ | mass plus 1 |
| MH− | mass minus 1 |
| MsOH | methanesulfonic acid |
| MS or ms | mass spectrum |
| NBS | N-bromosuccinimide |
| NMP | N-methylpyrollidinone |
| rt or r.t. | room temperature |
| TMSCl | chlorotrimethylsilane |
| TMSBr | bromotrimethylsilane |
| TMSI | iodotrimethylsilane |
| TEA | triethylamine |
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| δ | parts per million down field from tetramethylsilane |

EXAMPLES

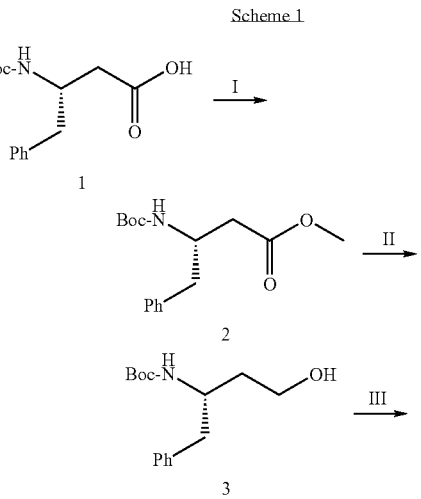

Scheme 1

-continued

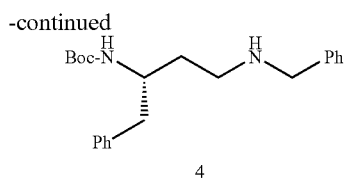

4

I. KHCO₃, MeI, DMF; II. LiAlH₄, THF, 0° C.; III. a. DMSO, TEA, PyrSO₃; b. CH₃CN, BnNH₂, HOAc, NaBH(OAc)₃

Compound 1
Compound 1 is commercially available from Peptech.
Compound 2
Compound 1 (10 mmol) was dissolved in 10 mL of anhydrous DMF. To the resulting solution was added potassium bicarbonate (20 mmol) in one portion. Methyl iodide (12 mmol) was added dropwise after which the reaction mixture was stirred for 12 hours. The reaction mixture was then diluted with ethyl acetate and washed with saturated aqueous sodium chloride solution twice. The resulting organic extract was dried over anhydrous sodium sulfate, concentrated under reduced pressure and dried under high vacuum to give compound 2 (2.9 g).
Compound 3
1M Lithium aluminum hydride in THF (10 mmol) was stirred under nitrogen gas and cooled in an ice bath. Compound 2 (10 mmol) was dissolved in 10 mL of anhydrous THF and added dropwise to the cool LiAlH₄ solution over 60 minutes. The reaction mixture was stirred at the same temperature for an additional 60-90 minutes, upon completion of the addition. Methanol (3 mL) was added slowly to quench the reaction. Then, sodium bicarbonate (3 g) followed by a saturated aqueous solution of potassium sodium tartrate and then ethyl acetate were added. The mixture was stirred for 30 minutes. The organic extract was collected and extracted, and the aqueous phase was again extracted with another portion of ethyl acetate. The combined organic extracts were then washed twice with saturated aqueous sodium bicarbonate solution, followed with a saturated aqueous sodium chloride solution. The organic phase was then dried over anhydrous sodium sulfate and then concentrated under reduced pressure. The resulting oil was dried under high vacuum to give solid Compound 3 (2.6 g).
Compound 4
Compound 3 (3.9 mmol) was dissolved in anhydrous DMSO (13 mL). The solution was stirred under nitrogen gas at 5-10° C. Triethylamine (13.7 mmol) was then added, followed by the addition of sulfur trioxide pyridine complex (14.8 mmol). The reaction mixture was stirred for 60-90 minutes. Ice was added, and the reaction mixture was stirred for 10 minutes. Saturated aqueous sodium bicarbonate solution was added, and the mixture was extracted with ethyl acetate. The organic phase was then washed with saturated aqueous sodium bicarbonate solution followed with water and finally with saturated aqueous sodium chloride solution. The organic phase was dried over anhydrous sodium sulfate and then concentrated under reduced pressure.

The resulting oil was dried under high vacuum to give a solid, which was then dissolved in anhydrous acetonitrile (20 mL). This solution was stirred at room temperature, and then benzylamine (7.8 mmol) and acetic acid (7.8 mmol) were added. The reaction mixture was stirred for 20-30 minutes, and then sodium triacetoxy borohydride (11.7 mmol) was added in one portion. The resulting mixture was stirred for an addition 3 hours. The reaction mixture was concentrated under reduced pressure, then dissolved in ethyl acetate and washed with saturated aqueous sodium bicarbonate solution twice followed with a saturated aqueous sodium chloride solution. The organic phase was dried over anhydrous sodium sulfate and then concentrated under reduced pressure, and purified by flash silica gel column chromatography (0-3% MeOH in dichloromethane) to give Compound 4 (464 mg).

Scheme 2

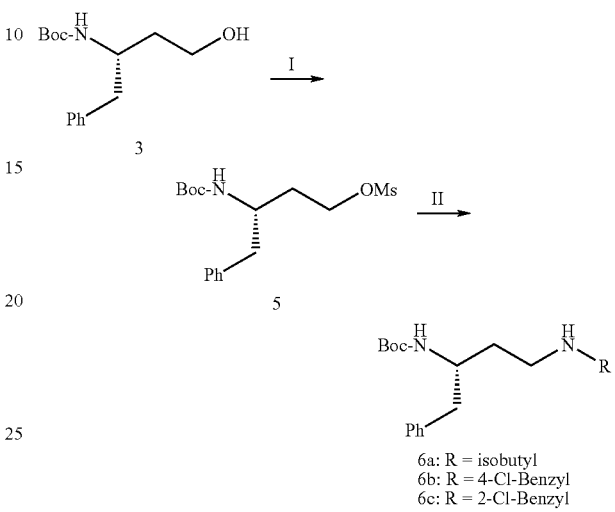

6a: R = isobutyl
6b: R = 4-Cl-Benzyl
6c: R = 2-Cl-Benzyl

I. Ms-Cl, Pyr, DCM; II. DMF, NH₂—R

Compound 5
Compound 3 was dissolved in anhydrous dichloromethane (5 mL) and stirred under nitrogen gas in an ice bath. Pyridine (3 mmol) was then added. Methanesulfonyl chloride (1.2 mmole) in anhydrous dichloromethane (1 mL) was then added dropwise to the reaction mixture. The reaction mixture was stirred for 1 hour and then removed from the ice bath. The reaction mixture was then stirred at room temperature for 2-3 hours, diluted with dichloromethane and washed twice with 5% citric acid aqueous solution followed twice with a water wash. The organic phase was dried over anhydrous sodium sulfate and then concentrated under reduced pressure, and dried under high vacuum to give solid Compound 5 (312 mg).
Compound 6a
Compound 5 (0.91 mmol) was dissolved in anhydrous DMF (5 mL), isobutylamine (45.4 mmol) was added and the mixture was stirred at room temperature for 12 hours. Excess isobutylamine was removed under reduced pressure. The resulting material was diluted with ethyl acetate and washed with saturated aqueous sodium bicarbonate solution twice followed with saturated aqueous sodium chloride solution, the organic phase was dried over anhydrous sodium sulfate, filtered and then concentrated under reduced pressure. The resulting crude material was dried under high vacuum to give solid Compound 6a (293 mg).
Compound 6b
Compound 5 (0.5 mmol) was dissolved in anhydrous DMF (5 mL), 4-chloro benzylamine (2.5 mmol) was added and the reaction mixture was stirred for 16 hours. The mixture was then diluted with ethyl acetate and washed with saturated aqueous sodium chloride solution twice. The organic layer was mixed with water and 5% aqueous citric acid solution was added to give a pH of 7-8. The organic layer was collected and washed with saturated aqueous sodium chloride solution, dried over anhydrous sodium sulfate and then concentrated under reduced pressure. The crude product was purified with flash silica gel column chromatography (0-10% MeOH in DCM) to give Compound 6b (~100 mg).

Compound 6c

Compound 5 (1 mmol) was dissolved in anhydrous DMF (10 mL), then 2-chlorobenzylamine (5 mmol) was added and the mixture was stirred for 20 hours at room temperature. The reaction mixture was stirred at 40° C. for an additional 48 hrs, diluted with ethyl acetate, washed with saturated aqueous sodium chloride solution twice, and then washed with saturated aqueous sodium chloride solution. The organic layer was dried over anhydrous sodium sulfate and then concentrated under reduced pressure. The crude product was purified with flash silica gel column chromatography (0-10% MeOH in DCM) to give Compound 6c (~210 mg).

Scheme 3

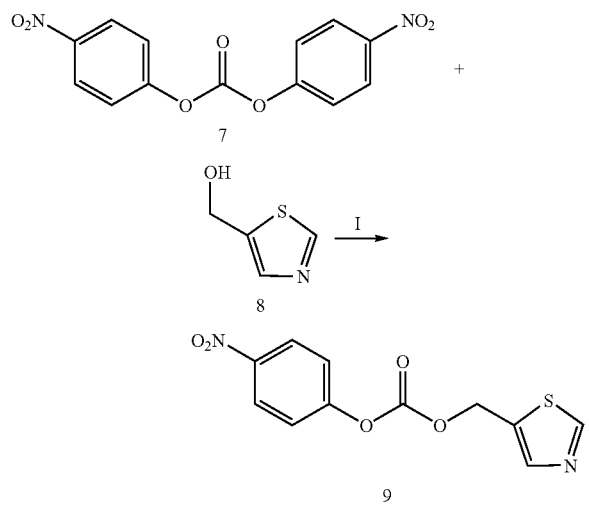

I. Et₃N/DCM

Compound 9

To a solution of Compound 8 (obtained commercially from Molekula) (17 mmol) in DCM (40 mL) was added Compound 7 (19 mmol; purchased from Sigma-Aldrich) followed by triethylamine (26 mmol). The resulting reaction mixture was stirred for 12 hour and concentrated under reduced pressure. The reaction mixture was diluted with EtOAc and washed sequentially with saturated aqueous $Na_2CO_3$, water, and brine. The solvent was removed under reduced pressure. Purification of the residue by flash column chromatography (silica gel, eluent: hexanes/EtOAc=1/1) gave Compound 9 (4.7 g).

Scheme 4

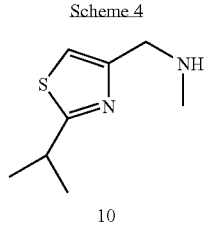

10

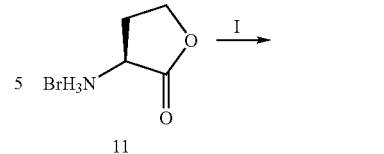

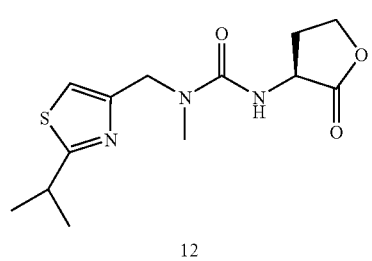

I. a. CDI, DIPEA, MeCN; b. compound 11, MeCN.

Compound 10

Compound 10 was prepared according to the procedures of *J. Med. Chem.* 1998, 41, 602.

Compound 11

Compound 11 is commercially available from Aldrich, and was used as received.

Compound 12

To a suspension of Compound 11 (2.05 g, 11.3 mmol) in $CH_2Cl_2$ (40 mL) was added $iPr_2NEt$ (5.87 mL, 33.9 mmol) followed by CDI (carbonyldiimidazole; 1.86 g, 11.3 mmol). The resulting mixture was stirred at room temperature for 6 h, then Compound 10 (2.33 g, 11.3 mmol) was added. The resulting mixture was stirred for another 10 h before it was evaporated to dryness. The mixture was re-dissolved in $CH_2Cl_2$ and the solid was removed by filtration. The filtrate was evaporated to dryness and purified by CombiFlash (eluted with 20-80% EtOAc/hexanes) to give 3.2 g of Compound 12 as a pale yellow oil, m/z 298.0 $(M+H)^+$.

Scheme 5

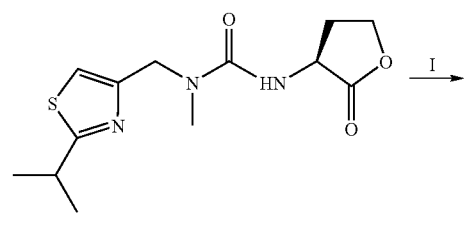

12

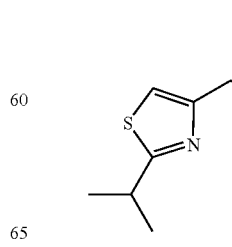

13

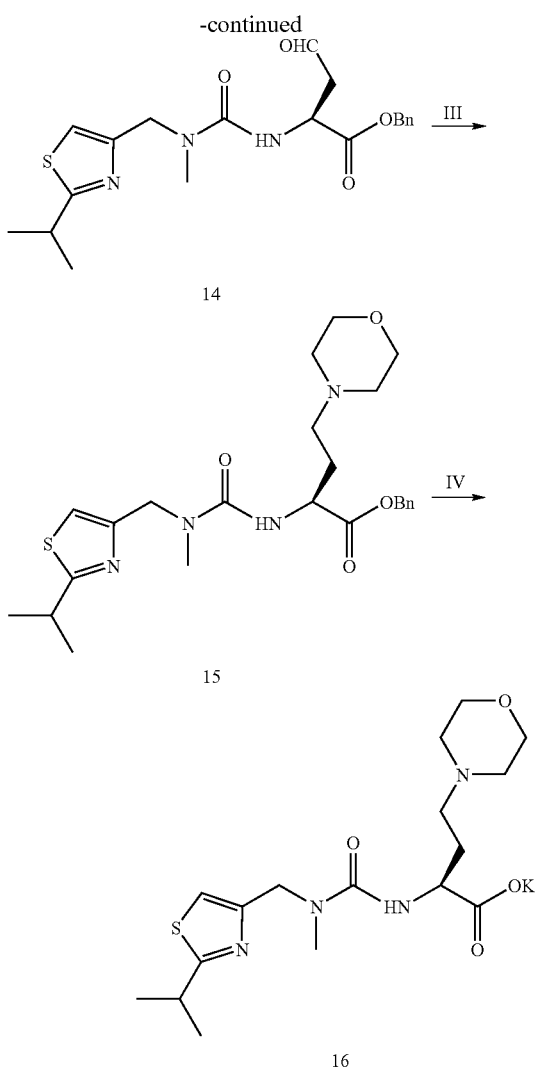

I. a. NaOH/H₂O; b. BnBr; II. SO₃/pyridine; III. morpholine/NaBH(OAc)₃;
IV. a. NaOH; b. HCl c. KOH Compound 13

To a solution of Compound 12 (33 g, 112 mmol) in ethanol (366 mL) at 0° C. was added a solution of sodium hydroxide (4.7 g, 117 mmol) in water (62 mL). The mixture was stirred for one hour at 25° C., and solvents were removed under reduced pressure. The mixture was coevaporated with ethanol (3×400 mL), and dried at 60° C. for two hours under high vacuum to give a white solid. To the solution of above solid in DMF (180 mL) was added benzyl bromide (16.2 mL, 136 mmol). The mixture was stirred for 16 hours under darkness, and was quenched with water (300 mL). The mixture was extracted with EtOAc (4×300 mL). The combined organic phase was washed five times with water and brine, and dried over Na₂SO₄. Concentration gave Compound 13 (48 g), which was used in the next step without further purification.

Compound 14

A mixture of Compound 13 (33 g, 74 mmol) in DMSO (225 mL) and Et₃N (36 mL) was stirred for 30 minutes. The mixture was cooled to 0-10° C. SO₃-pyridine (45 g) was added, and the stirring was continued for 60 minutes. Ice (300 g) was added, and the mixture was stirred for 30 minutes. EtOAc (300 mL) was added and sat. Na₂CO₃ was added until the pH was 9~10. The organic phase was separated from the aqueous phase, and the aqueous phase was extracted with EtOAc (2×300 mL). The combined organic phases were washed twice with sat. Na₂CO₃, three times with water, and then with brine. The mixture was dried over Na₂SO₄ and concentrated to give Compound 14 (32 g), which was used directly in the next step without further purification.

Compound 15

To a solution of Compound 14 (32 g) in CH₃CN (325 mL) was added morpholine (12.9 mL, 148 mmol), with a water bath around the reaction vessel, followed by HOAc (8.9 mL, 148 mmol), and NaBH(OAc)₃ (47 g, 222 mmol). The mixture was stirred for 12 hours. CH₃CN was removed under reduced pressure, and the mixture was diluted with EtOAc (300 mL). Sat. Na₂CO₃ was added until the pH was 9~10. The organic phase was separated from the aqueous phase, and the aqueous phase was extracted with EtOAc (2×300 mL). The combined organic phases were washed twice with sat Na₂CO₃, followed by water, and lastly with brine. The mixture was dried over Na₂SO₄. The resulting residue was concentrated and purified by silica gel column chromatography (EtOAc to DCM/iP-rOH=10/1) to give Compound 15 (30 g).

Compound 16

To a solution of Compound 15 (26.5 g, 56 mmol) in ethanol (160 mL) at 0° C. was added a solution of sodium hydroxide (2.5 g, 62 mmol) in water (30 mL). The mixture was stirred for one hour at 25° C., and solvents were removed under reduced pressure. The mixture was diluted with water (200 mL), and then washed six times with 100 mL of CH₂Cl₂. The water phase was acidified with 12 N HCl (5.2 mL), and was dried under reduced pressure to give a carboxylic acid (22 g).

To the carboxylic acid (384 mg, 1 mmol) in EtOH (5 ml) was added ~17.8M aqueous potassium hydroxide solution (56 ul, 1 mmol). The precipitate was filtered off. The filtrate was concentrated under reduced pressure and was re-dissolved oil in EtOH and concentrated. The resulting oil was dissolved in DCM and concentrated to give foam 16 (224 mg), which was used in the next reaction without purification.

Scheme 6

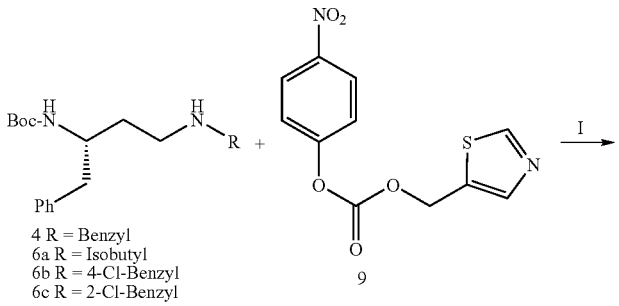

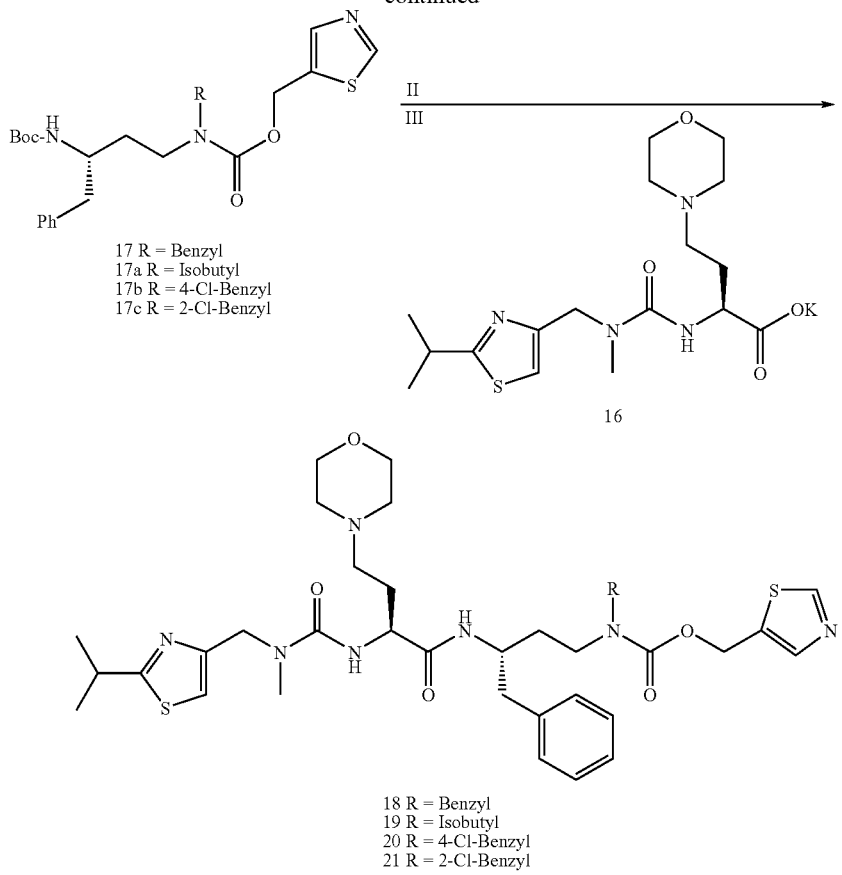

17 R = Benzyl
17a R = Isobutyl
17b R = 4-Cl-Benzyl
17c R = 2-Cl-Benzyl

16

18 R = Benzyl
19 R = Isobutyl
20 R = 4-Cl-Benzyl
21 R = 2-Cl-Benzyl

I. DMF; II. 4N HCl in dioxane; III. EDC, HOBt, TEA, DMF

Compounds 17, 17a, 17b and 17c

Compound 4, 6a, 6b, 6c or 7 was dissolved in anhydrous DMF (5 mL). Compound 9 (1.5-5 mol eq) was added and the mixture was stirred for 3-48 hours. The reaction mixture was then diluted with ethyl acetate and washed twice with saturated aqueous sodium bicarbonate solution followed by saturated an aqueous sodium chloride solution. The organic phase was then dried over anhydrous sodium sulfate and concentrated under reduced pressure. The resulting concentrate was purified by flash silica gel column chromatography (10-30% EtOAc in dichloromethane) to give the desired product (i.e. compound 17, 17a, 17b or 17c, respectively).

Compounds 18, 19, 20 and 21

Compound 17, 17a, 17b or 17c was dissolved in 4N HCl in dioxane (5-10 mL) and stirred for 60-90 minutes. The reaction mixture was concentrated under reduced pressure. THF was added, and the mixture was again concentrated under reduced pressure. Compound 12 (1 mol eq) was dissolved in anhydrous DMF and added to the concentrated material. 1-Hydroxybenzotriazole hydrate (1.5 mol eq), and N-(3-dimethylaminopropyl)-N'-ethylcarbodiimide hydrochloride ("EDC"; 1.5 mol eq) were added and the mixture was stirred for 30-60 minutes. Triethylamine ("TEA"; 1.5 mol eq) was then added, and the mixture was stirred for 2-3 hours. Additional EDC (1.5 mol eq) and TEA (1.5 mol eq) were added and the mixture was stirred for 12-16 hours, then diluted with ethyl acetate and washed twice with saturated aqueous sodium bicarbonate solution followed with saturated aqueous sodium chloride solution. The organic phase was dried over anhydrous sodium sulfate and then concentrated under reduced pressure. The concentrate was then purified by prep $C_{18}$ HPLC to yield the desired compound (i.e., compound 18, 19, 20 or 21, respectively).

Compound 18

$^1$H NMR (CD$_3$OD): δ 8.99 (s, 1H), 7.90 (d, 1H), 7.23 (m, 10H), 5.38 (s, 2H), 4.52 (m, 2H), 4.42 (m, 2H), 4.18 (bs, 1H), 4.05 (bs, 1H), 3.58 (s, 4H), 3.22 (m, 2H), 2.97 (s, 3H), 2.76 (m, 2H), 2.32 (m, 6H), 1.73 (m, 4H), 1.38 (d, J=6.9 Hz, 6H); Mass Spectrum (m/e): (M+H)$^+$ 762.3, (M−H)$^−$ 760.3

Example 19

$^1$H NMR (CD$_3$OD): δ 8.99 (s, 1H), 7.91 (d, 1H), 7.20 (m, 6H), 5.33 (bs, 2H), 4.58 (m, 2H), 4.21 (m, 1H), 4.08 (m, 1H), 4.05 (bs, 1H), 3.61 (s, 4H), 3.31 (m, 4H), 2.99 (s, 3H), 2.80 (m, 2H), 2.40 (m, 6H), 1.80 (m, 5H), 1.38 (d, J=6.9 Hz, 6H), 0.79 (m, 6H); Mass Spectrum (m/e): (M+H)$^+$ 728.3, (M−H)$^−$ 726.3

Example 20

$^1$H NMR (CD$_3$OD): δ 8.99 (s, 1H), 7.89 (d, 1H), 7.19 (m, 10H), 5.37 (s, 2H), 4.51 (m, 4H), 4.18 (bs, 1H), 4.03 (s, 1H), 3.63 (m, 4H), 3.32 (m, 4H), 2.97 (m, 3H), 2.76 (m, 2H), 2.42 (m, 6H), 1.78 (m, 4H), 1.37 (m, 6H); Mass Spectrum (m/e): (M+H)$^+$ 796.2, (M−H)$^−$ 794.2.

Example 21

¹H NMR (CD₃OD): δ 8.96 (s, 1H), 7.89 (d, 1H), 7.19 (m, 9H), 5.37 (s, 2H), 4.52 (m, 4H), 4.17 (m, 2H), 3.57 (m, 4H), 3.31 (m, 4H), 2.96 (s, 3H), 2.77 (m, 2H), 2.31 (m, 6H), 1.82 (m, 4H), 1.36 (m, 6H)

Mass Spectrum (m/e): (M+H)⁺ 796.2, (M−H)⁻ 794.2.

precipitated from ethyl acetate with hexanes to give compound 23 (694 mg, 74%) as a pale solid.

Compound 24

To a solution of compound 23 (350 mg, 0.70 mmol) in methanol (15.0 mL) and ethyl acetate (1.0 mL) was added Pd on carbon (10 wt %, 300 mg). The reaction mixture was stirred at ambient temperature under a hydrogen atmosphere

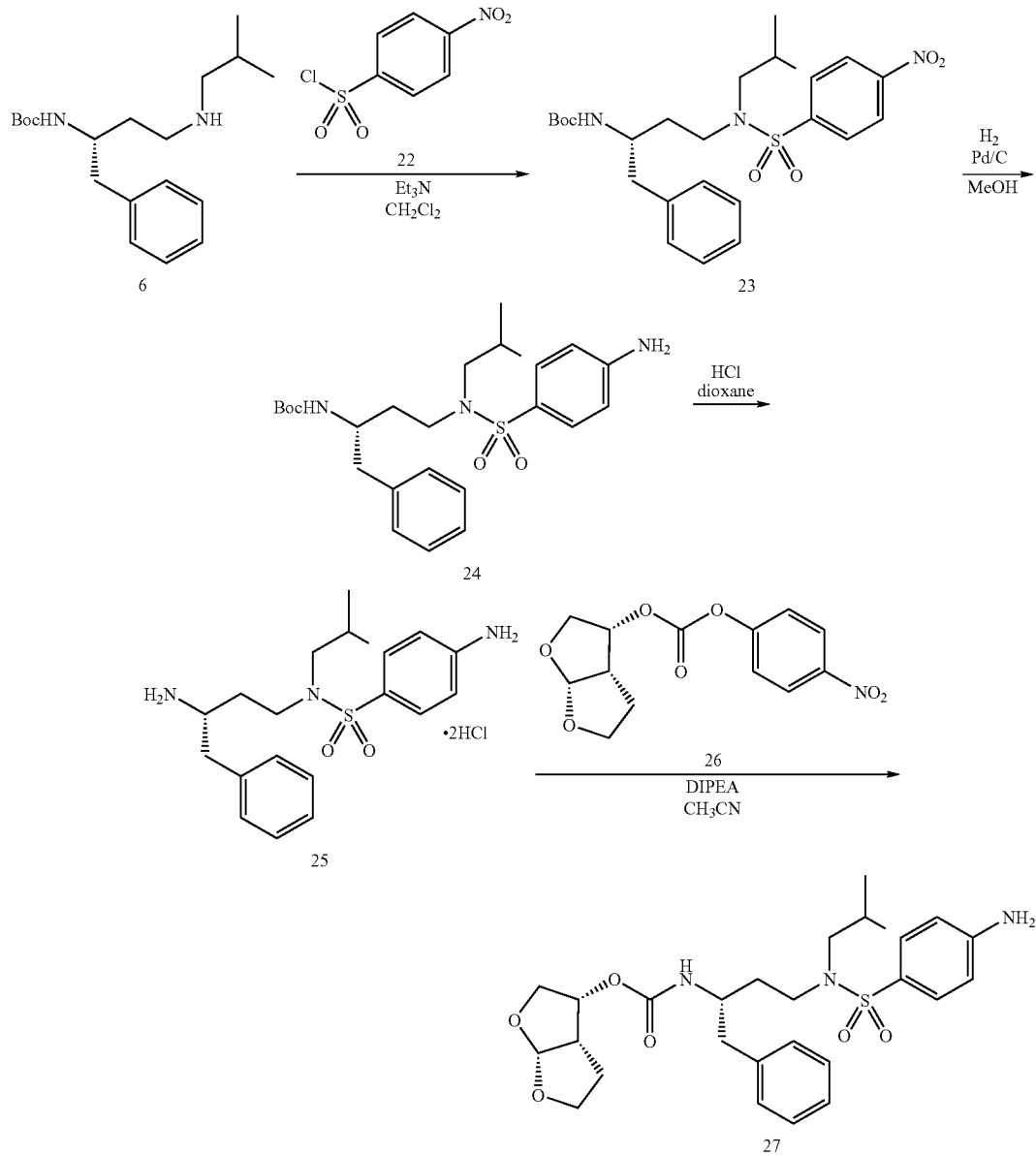

Scheme 7

Compound 23

To a solution of compound 6 (593 mg, 1.85 mmol) in dichloromethane (12.0 mL) at ambient temperature was added triethylamine (280 μL, 2.04 mmol) and 4-nitrobenzenesulfonyl chloride (430 mg, 1.94 mmol, obtained from Aldrich), sequentially. After stirring for 3 h, the reaction mixture was poured into water and extracted with dichloromethane. The organic layer was washed with brine, dried over Na₂SO₄ and concentrated to give a light orange solid. The solid was (via a balloon) for 2 h. The reaction mixture was then filtered through a pad of Celite and concentrated to give an off-white foam (Compound 24) that was used in the next step without further purification.

Compound 25

Solid compound 24 from the previous reaction step was treated at 0° C. with HCl in 1,4-dioxane (12.0 mL of a 4.0 M solution). The reaction was warmed to ambient temperature and stirred for 2 h, after which a precipitate formed. The reaction mixture was concentrated under vacuum to give compound 25 (300 mg, 95% for 2-steps) as an off-white free flowing powder.

Compound 27

To a slurry of compound 25 (80 mg, 0.18 mmol) and 1-(4-nitro-phenyl)-3-hexahydro-furo[2,3-b]furan-3-yl carbonate (Compound 26, 63 mg, 0.21 mmol), prepared according to the procedures described in *Bioorg. Med. Chem. Lett.*, (2005), 3496, in dry acetonitrile (3.0 mL) was added N,N-diisopropylethylamine (95.0 µL, 0.53 mmol) dropwise at ambient temperature. The reaction mixture was stirred overnight poured into brine and extracted with ethyl acetate. The organic layer was washed with brine, dried over $Na_2SO_4$, concentrated and purified by flash column chromatography using 5% methanol in dichloromethane to give a solid. $^1H$ NMR analysis indicated the presence of 4-nitrophenol along with the desired product. The solid that was isolated was dissolved in ethyl acetate and washed three times with 1.0 N aqueous NaOH, water, brine, dried over $Na_2SO_4$ and concentrated to give compound 27 (53 mg, 56%) as an off-white foam.

$^1H$ NMR (300 MHz, $CDCl_3$): δ 0.86 (d, J=6.3 Hz, 3H), 0.87 (d, J=6.3 Hz, 3H), 1.65-1.98 (m, 4H), 2.74-2.90 (m, 4H), 2.94-3.16 (m, 6H), 3.70-4.18 (m, 5E), 4.80 (br d, J=9.0 Hz, 1H), 5.04-5.15 (m, 1H), 5.71 (d, J=5.4 Hz, 1H), 6.67 (d, J=8.4 Hz, 2H), 7.10-7.35 (m, 5H), 7.53 (d, J=8.7 Hz, 2H). LC/MS: 532 (M+1).

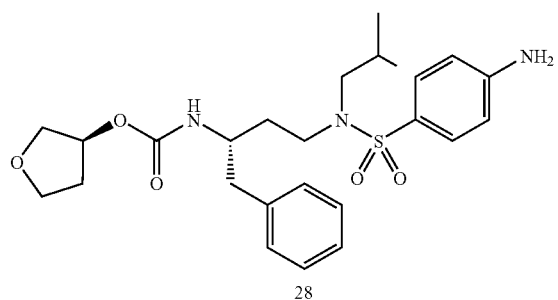

28

Compound 20

To a suspension of compound 25 (90 mg, 0.20 mmol) and carbonic acid 2,5-dioxo-pyrrolidin-1-yl ester tetrahydro-furan-3-yl ester (46 mg, 0.20 mmol), prepared according to the procedures of described in U.S. Pat. No. 5,585,397, WO 94/05639, and WO96/33184, in dry acetonitrile (3.0 mL) was added triethylamine (90.0 µL, 0.64 mmol) dropwise at ambient temperature. The reaction was stirred for 1 h and then diluted with ethyl acetate. The reaction mixture was then washed with water, brine, dried over $Na_2SO_4$ and concentrated to give a solid. Purification by flash column chromatography using 5% methanol in dichloromethane provided compound 28 (41 mg, 42%) as a colorless foam.

$^1H$ NMR (300 MHz, $CDCl_3$): δ 0.85 (d, J=6.3 Hz, 6H), 1.54-2.20 (m, 5H), 2.70-2.86 (m, 4H), 2.96-3.18 (m, 2H), 3.62-3.96 (m, 5H), 4.14 (br s, 2H), 4.72 (br d, J=8.1 Hz, 1H), 5.18 (br s, 1H), 6.64 (d, J=8.4 Hz, 2H), 7.10-7.35 (m, 5H), 7.52 (d, J=8.4 Hz, 2H). LC/MS: 490 (M+1).

Scheme 8

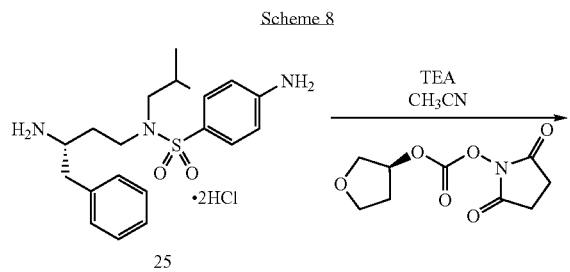

Scheme 9

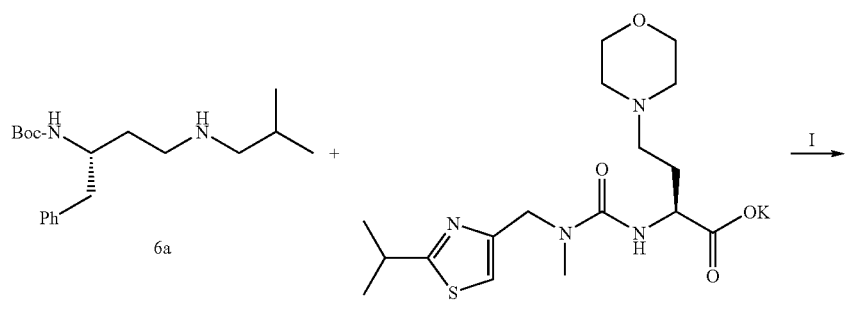

-continued

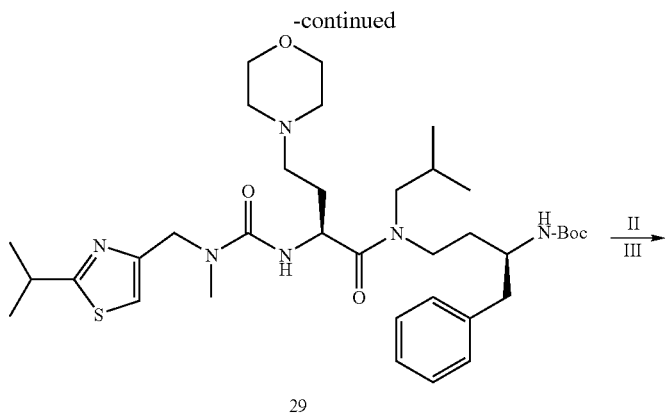

29

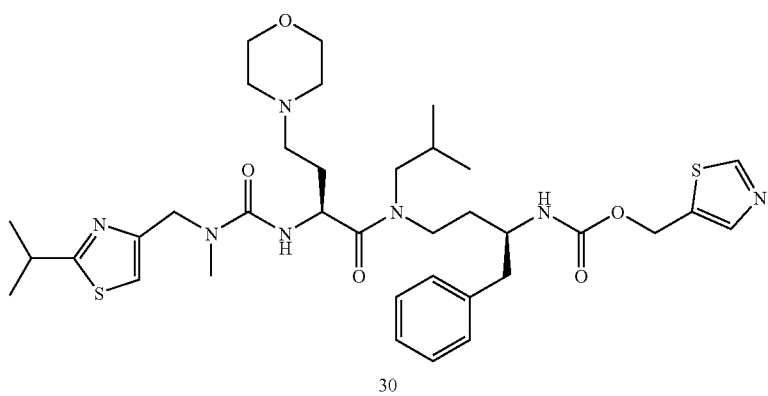

30

I. EDC, HOBt, TEA, DMF; II. 4N HCl in dioxane; III. compound 8, DMF, TEA

Example 29

Amine 6a (1 mmol) was mixed with 1-hydroxybenzotriazole hydrate (1.2 mol eq) and was added Compound 12 (1 mol eq) dissolved anhydrous DMF (5 mL), and N-(3-dimethylaminopropyl)-N'-ethylcarbodiimide (1.2 mol eq). The resulting mixture was stirred for 12-16 hours.

The mixture was diluted with ethyl acetate and washed with saturated aqueous sodium bicarbonate solution twice followed with saturated aqueous sodium chloride solution. It was then dried over anhydrous sodium sulfate, filtered and then concentrated under reduced pressure. The crude material was purified the with flash silica gel column chromatography (0-10% MeOH in DCM) to yield desired compound 29 (470 mg).

Example 30

Compound 29 (0.68 mmol) was dissolved in 4N HCl in dioxane (5-10 mL) and stirred for 45 minutes. The mixture was then concentrated under reduced pressure to give an oil. The resulting oil was re-dissolved in DCM and concentrated under reduced pressure. The resulting material was dissolved in anhydrous DMF (5 mL), compound 8 (1.1 mol eq) and TEA (3 mol. eq) were added, and the mixture was stirred at room temperature for 16 hours.

The mixture was then diluted with ethyl acetate and washed with saturated aqueous sodium bicarbonate solution twice followed with five times with 10% aqueous sodium carbonate solution. The organic was washed with saturated aqueous sodium chloride solution and then dried over anhydrous sodium sulfate, filtered and concentrated under reduced pressure. Purification of the crude material with flash silica gel column chromatography (0-10% MeOH in DCM) and then with prep $C_{18}$ HPLC to yielded compound 30 (110 mg).

$^1$H NMR (CD$_3$OD): δ 8.98 (s, 1H), 7.84 (s, 1H), 7.20 (m, 6H), 5.24 (m, 2H), 4.70 (m, 1H), 4.52 (m, 2H), 3.63 (m, 6H), 3.31 (m, 4H), 2.98 (s, 3H), 2.76 (m, 3H), 2.43 (m, 5H), 1.76 (m, 5H), 1.39 (m, 6H), 0.84 (m, 6H)

Mass Spectrum (m/e): (M+H)$^-$ 728.2, (M–H+HOAc)$^-$ 785.8

Scheme 11

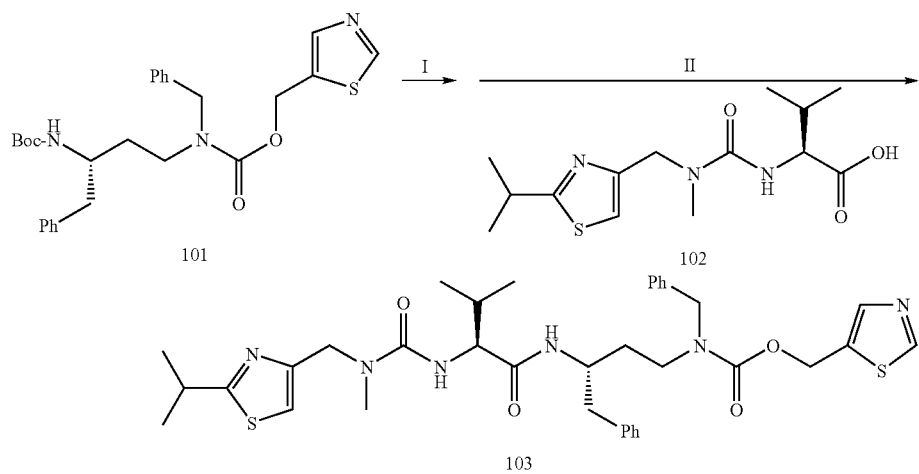

I. 4N HCl in dioxane; II. EDC-HCl, HOBt, DIPEA, DMF

Example 103

Compound (101) was dissolved in 4N HCl in dioxane (10 ml) and stirred for 60 minutes. The reaction solution was concentrated under reduced pressure. The residue was diluted with THF and concentrated under reduced pressure. A solution of compound 102 (1 mol eq) in anhydrous DMF and added to the concentrated reaction mixture. Sequentially, 1-hydroxybenzotriazole hydrate (1.5 mol eq) and N-(3-dimethylaminopropyl)-N'-ethylcarbodiimide hydrochloride (1.2 mol eq) were added to the reaction mixture. After 30 minutes, diisopropylethylamine (2 mol eq) was added and the reaction was stirred for 16 hours. The reaction mixture was diluted with ethyl acetate and washed with saturated aqueous sodium bicarbonate solution twice followed by washing with saturated aqueous sodium chloride solution. The organic phase was dried over anhydrous sodium sulfate and then concentrated under reduced pressure. The residue was purified with prep $C_{18}$ HPLC to yield desired compound 103.

Example 103

$^1$H NMR (CD$_3$OD): δ 9.01 (s, 1H), 7.89 (s, 1H), 7.20 (m, 11H), 6.17 (d, J=8.4 Hz, 1H), 5.38 (s, 2H), 4.47 (m, 4H), 3.98 (m, 2H), 3.26 (m, 4H), 2.96 (s, 3H), 2.74 (m, 2H), 1.90-1.60 (m, 3H), 1.36 (d, J=6.9 Hz, 6H), 0.83 (bs, 6H)

Mass Spectrum (m/e): (M+H)$^+$ 691.2, (M−H)$^−$ 689.2

Scheme 12

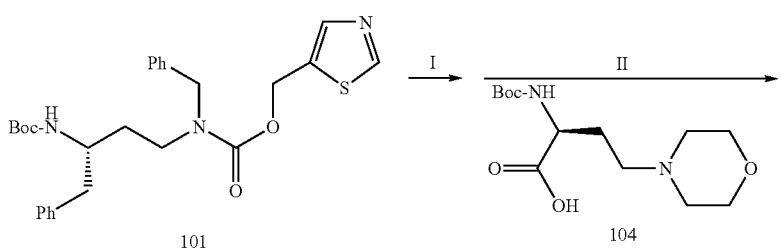

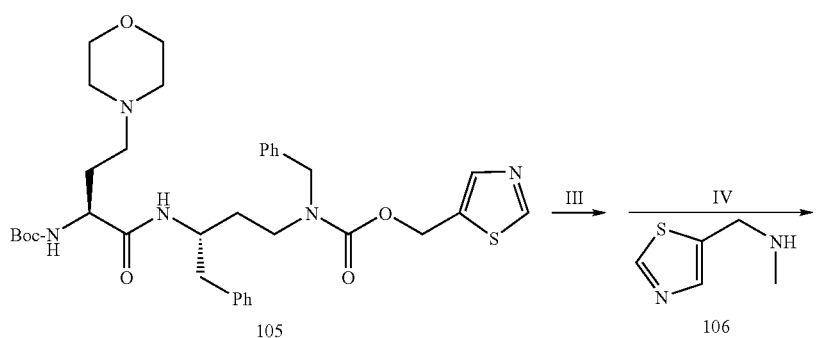

-continued

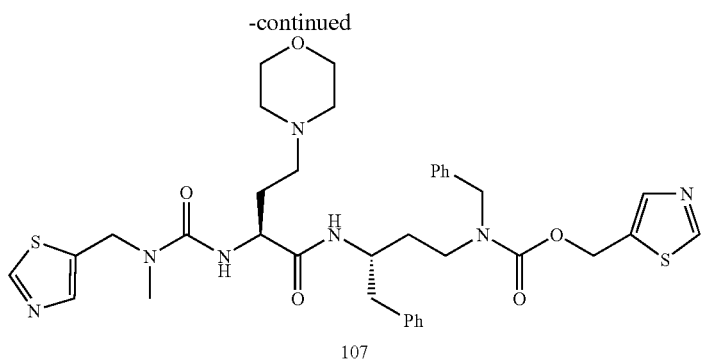

107

I. 4N HCl in dioxane; II. EDC, HOBt, TEA, DMF; III. 4N HCl in dioxane;
IV. CDI, DIPEA, DMF

Example 107

Compound (101) (133 mg, 0.337 mmol) was dissolved in 4N HCl in dioxane (5 mL) and stirred for 60 minutes. The reaction solution was concentrated under reduced pressure. The residue was dissolved in EtOAc and washed with saturated aqueous sodium bicarbonate solution twice followed by washing with saturated aqueous sodium chloride solution. The organic phase was dried over anhydrous sodium sulfate and then concentrated under reduced pressure. The residue was dissolved in anhydrous DMF (5 mL). Sequentially, compound 104 (116 mg, 0.404 mol), 1-hydroxybenzotriazole hydrate (62 mg, 0.404 mol) and N-(3-dimethylaminopropyl)-N'-ethylcarbodiimide (60 uL, 0.404 mol) were added and the mixture stirred for 15 minutes. Triethylamine (94 uL, 0.674 mol) was added and the reaction was stirred for 16 hours.

The reaction mixture was diluted with ethyl acetate and washed with saturated aqueous sodium bicarbonate solution twice followed by washing with saturated aqueous sodium chloride solution. The organic phase was dried over anhydrous sodium sulfate and then concentrated under reduced pressure. The residue was purified with Combiflash column (0-10% MeOH in DCM) and then with prep $C_{18}$ HPLC to yield desired compound (105, 84 mg, 0.126 mmol). Compound 105 was dissolved in 4N HCl in dioxane (5 mL) and stirred for 60 minutes. The reaction solution was concentrated under reduced pressure. The residue was dissolved in EtOAc and washed with saturated aqueous sodium bicarbonate solution twice followed by washing with saturated aqueous sodium chloride solution. The organic phase was dried over anhydrous sodium sulfate and then concentrated under reduced pressure. The residue was dissolved in anhydrous DMF (5 mL) and, sequentially, CDI (19 mg, 0.119 mmol) and DIPEA (34 uL, 0.198 mmol) were added. After 16 hours, additional CDI (19 mg, 0.119 mmol) and DIPEA (34 uL, 0.198 mmol) were added and the reaction stirred for 2 hours. Additional CDI (19 mg, 0.119 mmol) and DIPEA (34 uL, 0.198 mmol) were added and the reaction stirred for 4 hours. A solution of 106 in anhydrous DMF (1 mL) was added to reaction. After 16 hours, the reaction mixture was diluted with ethyl acetate and washed with saturated aqueous sodium bicarbonate solution twice followed by washing with saturated aqueous sodium chloride solution. The organic phase was dried over anhydrous sodium sulfate and then concentrated under reduced pressure. The residue was purified with prep $C_{18}$ HPLC to yield desired compound (107, 36 mg, 0.05 mmol).

Example 107

$^1$H NMR (CD$_3$OD): δ 8.98 (m, 1H), 8.90 (s, 1H), 7.86 (m, 1H), 7.81 (s, 1H), 7.21 (m, 10H), 5.37 (s, 2H), 4.71 (m, 2H), 4.46 (m, 2H), 4.21 (bs, 1H), 4.04 (bs, 1H), 3.62 (m, 4H), 3.22 (m, 2H), 2.93 (s, 3H), 2.76 (m, 2H), 2.32 (m, 6H), 1.78 (m, 4H) Mass Spectrum (m/e): (M+H)$^+$ 720.3, (M−H)$^-$ 718.2

IC$_{50}$ Determinations for Human Liver Cytochrome P450
Materials and General Methods Pooled (n≥15 donors) human hepatic microsomal fraction was obtained from BD-Gentest (Woburn, Mass.) who also supplied hydroxy-terfenadine, 4'-hydroxydiclofenac and NADPH regenerating system. Ritonavir was prepared from commercial Norvir® oral solution (Abbott Laboratories, Abbott Park, Ill.). Other reagents were from Sigma-Aldrich (St. Louis, Mo.) and included terfenadine, fexofenadine, BRL 15572, diclofenac and mefenamic acid.

Incubations were performed in duplicate in 50 mM potassium phosphate buffer, pH 7.4 with NADPH regenerating system used as described by the manufacturer. The final microsomal protein concentrations had previously been determined to be within the linear range for activity and resulted in less than 20% consumption of substrate over the course of the incubation. The final substrate concentrations used were equal to the apparent Km values for the activities determined under the same conditions. Inhibitors were dissolved in DMSO, and the final concentration of DMSO, from both substrate and inhibitor vehicles, was 1% (v/v). Incubations were performed at 37° C. with shaking and were initiated by addition of substrate. Aliquots were then removed at 0, 7 and 15 minutes. Samples were quenched by treatment with an acetonitrile, formic acid, water (94.8%/0.2%/5%, v/v/v) mixture containing internal standard. Precipitated protein was removed by centrifugation at 3000 rpm for 10 min and aliquots of the supernatant were then subjected to LC-MS analysis.

The LC-MS system consisted of a Waters Acquity UPLC, with a binary solvent manager and a refrigerated (8° C.) sample organizer and sample manager, interfaced to a Micromass Quattro Premier tandem mass spectrometer operating in electrospray ionization mode. The column was a Waters Acquity UPLC BEH $C_{18}$ 2.1×50 mm, 1.7 μm pore size. Mobile phases consisted of mixtures of acetonitrile, formic acid and water, the composition for mobile phase A being 1%/0.2%/98.8% (v/v/v) and that for mobile phase B being 94.8%/0.2%/5% (v/v/v). The injection volumes were 5 μL and the flow rate was 0.8 mL/min. Concentrations of metabolites were determined by reference to standard curves generated with authentic analytes under the same conditions as the incubations.

IC$_{50}$ values (the concentration of inhibitor reducing CYP3A activity by 50%) were calculated by non-linear regression using GraphPad Prism 4.0 software and a sigmoidal model.

CYP3A Inhibition Assay

The potencies of the compounds as inhibitors of human hepatic cytochromes P450 of the CYP3A subfamily (particularly CYP3A4) were assessed using terfenadine oxidase, a well-characterized CYP3A-selective activity described in Ling, K.-H. J., et al *Drug Metab. Dispos.* 23, 631-636, (1995) and Jurima-Romet, et al *Drug Metab. Dispos.* 22, 849-857, (1994). The final concentrations of microsomal protein and terfenadine substrate were 0.25 mg/mL and 3 µM, respectively. Metabolic reactions were terminated by treatment with seven volumes of quench solution containing 0.1 µM BRL 15572 as internal standard. A further 8 volumes of water were added before centrifugation and aliquots of the supernatant were removed for analysis.

For LC-MS analysis chromatographic elution was achieved by a series of linear gradients starting at 20% B and holding for 0.1 minutes, then increasing to 80% B over 1.5 minutes, holding for 0.4 minutes and then returning to the starting conditions for 0.05 min. The system was allowed to re-equilibrate for at least 0.25 minutes prior to the next injection. The mass spectrometer was operated in positive ion mode and the following precursor ([M+H]$^+$)/product ion pairs were monitored and quantified using MassLynx 4.0 (SP4, 525) software: hydroxy-terfenadine 488.7/452.4, fexofenadine 502.7/466.4 and BRL 15572 407.5/209.1. Terfenadine oxidase activity was determined from the sum of hydroxy-terfenadine and carboxy-terfenadine (fexofenadine) metabolites.

CYP2C9 Inhibition Assay

The potencies of the compounds as inhibitors of human hepatic CYP2C9 were assessed using diclofenac 4'-hydroxylase, an activity specific for this enzyme, as described in Leeman, T., et al *Life Sci.* 52, 29-34, (1992). The final concentrations of microsomal protein and diclofenac substrate were 0.08 mg/mL and 4 µM, respectively. Metabolic reactions were terminated by treatment with three volumes of quench solution containing 1 µM mefenamic acid as internal standard. After centrifugation a further 4 volumes of water were added. Aliquots of the supernatant were then subjected to LC-MS analysis.

For LC-MS analysis chromatographic elution was achieved by a series of linear gradients starting at 20% B and holding for 0.3 minutes, then increasing to 99% B over 1.2 minutes, holding for 0.5 minutes and then returning to the starting conditions for 0.25 min. The system was allowed to re-equilibrate for at least 0.25 minutes prior to the next injection. The mass spectrometer was operated in negative ion mode and the following precursor ([M−H]$^−$)/product ion pairs were monitored and quantified: 4'-hydroxy-diclofenac 312.4/294.2 and mefenamic acid 242.4/224.2.

Biological Assays Used for the Characterization of HIV Protease Inhibitors

HIV-1 Protease Enzyme Assay (Ki)

The assay is based on the fluorimetric detection of synthetic hexapeptide substrate cleavage by HIV-1 protease in a defined reaction buffer as initially described by M. V. Toth and G. R. Marshall, *Int. J. Peptide Protein Res.* 36, 544 (1990) (herein incorporated by reference in its entirety for all purposes).

The assay employed (2-aminobenzoyl)Thr-Ile-Nle-(p-nitro)Phe-Cln-Arg as the substrate and recombinant HIV-1 protease expressed in *E. Coli* as the enzyme. Both of the reagents were supplied by Bachem California, Inc. (Torrance, Calif.; Cat. no. H-2992). The buffer for this reaction was 100 mM ammonium acetate, pH 5.3, 1 M sodium chloride, 1 mM ethylendiaminetetraacetic acid, 1 mM dithiothreitol, and 10% dimethylsulfoxide.

To determine the inhibition constant Ki, a series of solutions were prepared containing identical amount of the enzyme (1 to 2.5 nM) and the inhibitor to be tested at different concentrations in the reaction buffer. The solutions were subsequently transferred into a white 96-well plate (190 µl each) and pre-incubated for 15 min at 37° C. The substrate was solubilized in 100% dimethylsulfoxide at a concentration of 800 µM and 10 µl of 800 µM substrate was added into each well to reach a final substrate concentration of 40 µM. The real-time reaction kinetics was measured at 37° C. using a Gemini 96-well plate fluorimeter (Molecular Devices, Sunnyvale, Calif.) at λ(Ex)=330 nm and λ(Em)=420 nm. Initial velocities of the reactions with different inhibitor concentrations were determined and the Ki value (in picomolar concentration units) was calculated by using EnzFitter program (Biosoft, Cambridge, U.K.) according to an algorithm for tight-binding competitive inhibition described by Ermolieff J., Lin X., and Tang J., Biochemistry 36, 12364 (1997).

HIV-1 Protease Enzyme Assay (IC50)

As for the $K_i$ assay, above, the $IC_{50}$ assay is based on the fluorimetric detection of synthetic hexapeptide substrate cleavage by HIV-1 protease in a defined reaction buffer as initially described by M. V. Toth and C. R. Marshall, *Int. J. Peptide Protein Res.* 36, 544 (1990).

The assay employed (2-aminobenzoyl)Thr-Ile-Nle-(p-nitro)Phe-Gln-Arg as the substrate and recombinant HIV-1 protease expressed in *E. Coli* as the enzyme. Both of the reagents were supplied by Bachem California, Inc. (Torrance, Calif.; Cat. nos. H-2992 and H-9040, respectively). The buffer for this reaction was 100 mM ammonium acetate, pH 5.5, 1 M sodium chloride, 1 mM ethylendiaminetetraacetic acid, and 1 mM dithiothreitol, and 10% dimethylsulfoxide.

To determine the IC50 value, 170 µL of reaction buffer was transferred into the wells of a white 96-well microtiter plate. A series of 3-fold dilutions in DMSO of the inhibitor to be tested was prepared, and 10 µL of the resulting dilutions was transferred into the wells of the microtiter plate. 10 µL of a 20-50 nM enzyme stock solution in reaction buffer was added to each well of the 96-well plate to provide a final enzyme concentration of 1-2.5 nM. The plates were then preincubated for 10 minutes at 37° C. The substrate was solublized in 100% dimethylsulfoxide at a concentration of 400 µM and 10 µl of the 400 µM substrate was added into each well to reach a final substrate concentration of 20 µM. The real-time reaction kinetics were measured using a Gemini 96-well plate fluorimeter (Molecular Devices, Sunnyvale, Calif.) at λ(Ex)=330 nm and λ(Em)=420 nm. Initial velocities of the reactions with different inhibitor concentrations were determined and the $IC_{50}$ value (in nanomolar concentration units) was calculated by using GraphPad Prism™ software to fit nonlinear regression curves.

Anti-HIV-1 Cell Culture Assay (EC50)

The assay is based on quantification of the HIV-1-associated cytopathic effect by a calorimetric detection of the viability of virus-infected cells in the presence or absence of tested inhibitors. HIV-1-induced cell death was determined using a metabolic substrate 2,3-bis(2-methoxy-4-nitro-5-sulfophenyl)-2H-tetrazolium-5-carboxanilide (XTT) which is converted only by intact cells into a product with specific absorption characteristics as described by Weislow O S, Kiser R, Fine D L, Bader J, Shoemaker R H and Boyd M R, *J. Natl. Cancer Inst.* 81, 577 (1989) (herein incorporated by reference in its entirety for all purposes).

MT2 cells (NIH AIDS reagent program, Cat #237) maintained in RPMI-1640 medium supplemented with 5% fetal bovine serum and antibiotics were infected with the wild-type HIV-1 strain IIIB (Advanced Biotechnologies, Columbia, Md.) for 3 hours at 37° C. using the virus inoculum corresponding to a multiplicity of infection equal to 0.01. The infected cells in culture media were distributed into a 96-well plate (20,000 cells in 100 μl/well), and incubated in the presence of a set of solutions containing 5-fold serial dilutions of the tested inhibitor (100 μl/well) for 5 days at 37° C. Samples with untreated infected and untreated mock-infected control cells were also distributed to the 96-well plate and incubated under the same conditions.

To determine the antiviral activity of the tested inhibitors, a substrate XTT solution (6 mL per assay plate) at a concentration of 2 mg/mL in a phosphate-buffered saline pH 7.4 was heated in water-bath for 5 min at 55° C. before 50 μl of N-methylphenazonium methasulfate (5 μg/mL) was added per 6 mL of XTT solution. After removing 100 μl media from each well on the assay plate, 100 μl of the XTT substrate solution was added to each well. The cells and the XTT solution were incubated at 37° C. for 45 to 60 min in a $CO_2$ incubator. To inactivate the virus, 20 μl of 2% Triton X-100 was added to each well. Viability, as determined by the amount of XTT metabolites produced, was quantified spectrophotometrically by the absorbance at 450 nm (with subtraction of the background absorbance at 650 nm). Data from the assay was expressed as the percentage absorbance relative to untreated control and the fifty percent effective concentration ($EC_{50}$) was calculated as the concentration of compound that effected an increase in the percentage of XTT metabolite production in infected, compound treated cells to 50% of that produced by uninfected, compound-free cells.

Anti-HIV-1 Cell Culture Assay ($EC_{50}$) in Presence of 40% Human Serum or Human Serum Proteins This assay is almost identical to the Anti-HIV-1 Cell Culture Assay described above, except that the infection was made in the presence or absence of 40% human serum (Type AB Male Cambrex 14-498E) or human serum proteins (Human α-acid Glycoprotein, Sigma C-9885; Human Serum Albumin, Sigma A1653, 96-99%) at physiological concentration. The HIV-1-induced cell death was determined as described above, except that the infected cells distributed in the 96-well plate were incubated in 80% Human Serum (2× concentration) or in 2 mg/mL Human α-acid Glycoprotein+ 70 mg/mL HSA (2× concentration) rather than in culture media.

Cytotoxicity Cell Culture Assay ($CC_{30}$)

The assay is based on the evaluation of cytotoxic effect of tested compounds using a metabolic substrate 2,3-bis(2-methoxy-4-nitro-5-sulfophenyl)-2H-tetrazolium-5-carboxanilide (XTT) as described by Weislow O S, Kiser R, Fine D L, Bader J, Shoemaker R H and Boyd M R, *J. Natl. Cancer Inst.* 81, 577 (1989). This assay is almost identical to the previous assay described (Anti-HIV-1 Cell Culture Assay), except that the cells were not infected. The compound induced cell death (or growth reduction) was determined as previously described.

MT-2 cells maintained in RPMI-1640 medium supplemented with 5% fetal bovine serum and antibiotics were distributed into a 96-well plate (20,000 cells in 100 μl/well) and incubated in the presence or absence of 5-fold serial dilutions of the tested inhibitor (100 μl/well) for 5 days at 37° C. Controls included untreated infected cells and infected cells protected by 1 μM of P4405 (Podophyllotoxin, Sigma Cat #P4405).

To determine cytotoxicity, an XTT solution (6 mL per assay plate) at a concentration of 2 mg/mL in phosphate-buffered saline pH 7.4 was heated in the dark in a water-bath for 5 min at 55° C. before 50 μl of N-methylphenazonium methasulfate (5 μg/mL) was added per 6 mL of XTT solution.

After removing 100 μL media from each well on the assay plate, 100 μL of the XTT substrate solution was added to each well. The cells and the XTT solution were incubated at 37° C. for 45 to 60 min in a $CO_2$ incubator. To inactivate the virus, 20 μl of 2% Triton X-100 was added to each well. Viability, as determined by the amount of XTT metabolites produced, is quantified spectrophotometrically by the absorbance at 450 nm (with subtraction of the background absorbance at 650 nm). Data from the assay is expressed as the percentage absorbance relative to untreated control, and the fifty percent cytotoxicity concentration ($EC_{50}$) was calculated as the concentration of compound that affected an increase in the percentage of cell growth in compound treated cells to 50% of the cell growth provided by uninfected, compound-free cells.

Experimental data based on representative Examples demonstrate that the compounds of Formula (I) of the present invention can have a CYP450 3A4 inhibition activity in a range represented by an $IC_{50}$ from about 100 nM to about 4700 nM, and a CYP450 2C9 inhibition activity in a range represented by an $IC_{50}$ from about 100 nM to about 4200 nM. Table 20 shows the activity of representative examples of the compounds of the invention against CYP450 3A4 where category A represents $IC_{50}$'s between 100 and 200 nM, category B represents $IC_{50}$'s between 201 and 500 nM and category C represents $IC_{50}$'s between 501 and 1000 nM.

TABLE 20

| Activity against CYP450 3A4 | |
|---|---|
| Example | CYP450 3A4 $IC_{50}$ |
| 18 | A |
| 19 | A |
| 20 | B |
| 21 | B |
| 30 | A |
| 27 | B |
| 28 | C |
| 103 | A |
| 107 | A |

Experimental data based on representative Examples demonstrate that the compounds of Formula (I) of the present invention can have a protease inhibition activity in a range represented by HIV $EC_{50}$ from about 140 nM to greater than about 1000 nM.

Experimental data based on representative Examples have a CYP450 3A4 inhibition activity in a range represented by an $IC_{50}$ of less than or equal to about 150 nM, a CYP450 2C9 inhibition activity in a range represented by an $IC_{50}$ from about 1000-10,000 nM, and a protease inhibition activity in a range represented by HIV $EC_{50}$ greater than about 20,000 nM.

What is claimed is:

1. A compound of Formula I,

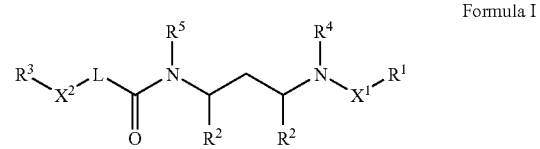

Formula I or a pharmaceutically acceptable salt, wherein,
$X^1$ is selected from the group consisting of —C(O)—O—, —S(O)—, and —S($O_2$)—;

X² is selected from the group consisting of —O—, —NR⁶—C(O)—NR⁶—, —OC(O)NR⁶—, —NR⁶—, and —NR⁶C(O)O—;
L is selected from the group consisting of a covalent bond, alkylene, and —CHR⁷—;
R¹ is selected from the group consisting of aryl, heteroaryl, arylalkyl, and heteroarylalkyl;
each R² is independently selected from the group consisting of H, alkyl, arylalkyl, heterocyclylalkyl, and cycloalkylalkyl wherein at least one R² is arylalkyl;
R³ is selected from the group consisting of heterocyclyl, aryl, heteroaryl, arylalkyl, and heteroarylalkyl;
R⁴ and R⁵ are each independently selected from the group consisting of H, alkyl, cycloalkyl, heterocyclyl, cycloalkylalkyl, arylalkyl, and heterocyclylalkyl;
each R⁶ is independently selected from the group consisting of H, alkyl, and cycloalkyl; and
R⁷ is selected from the group consisting of H, alkyl, substituted alkyl, and heterocyclylalkyl;
wherein each aryl, heteroaryl, cycloalkyl, heterocyclyl, cycloalkylalkyl, heterocyclylalkyl, arylalkyl, and heteroarylalkyl of R¹, R², R³, R⁴, R⁵, R⁶ and R⁷ is unsubstituted or substituted.

2. The compound of claim 1, wherein at least one R² is substituted or unsubstituted phenylmethyl.

3. The compound of claim 1, wherein X¹ is —C(O)—O— or —S(O₂)—.

4. The compound of claim 1, wherein -L-X²- is —CHR⁷—NR⁶—C(O)—NR⁶— or —O—.

5. The compound of claim 1, which is a compound of Formula II or Formula III,

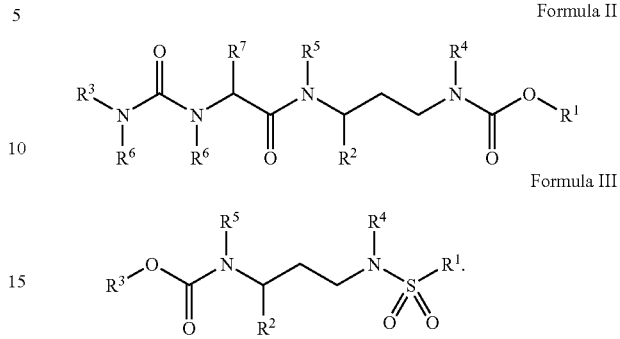

6. The compound of claim 5, wherein R¹ of Formula II is unsubstituted or substituted thiazoylmethyl.

7. The compound of claim 5, wherein R³ is substituted or unsubstituted heterocyclyl or substituted or unsubstituted heteroarylalkyl.

8. The compound of claim 5, wherein R⁷ is unsubstituted or substituted heterocyclylalkyl.

9. The compound of claim 5, wherein R¹ of Formula III is substituted or unsubstituted aryl.

10. A compound according to claim 1 selected from the group consisting of:

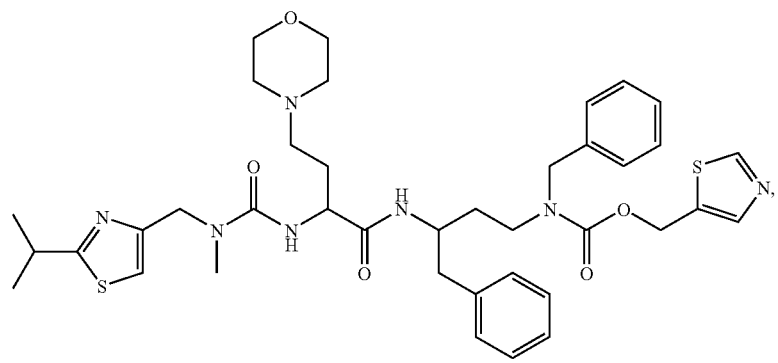

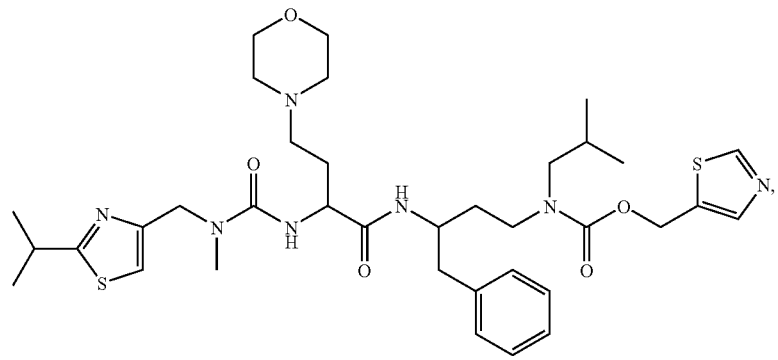

-continued
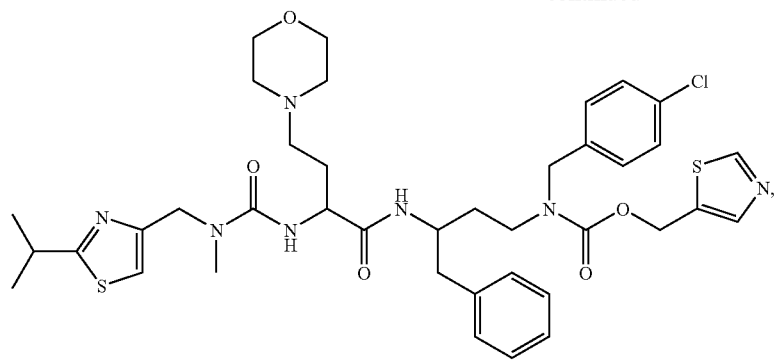
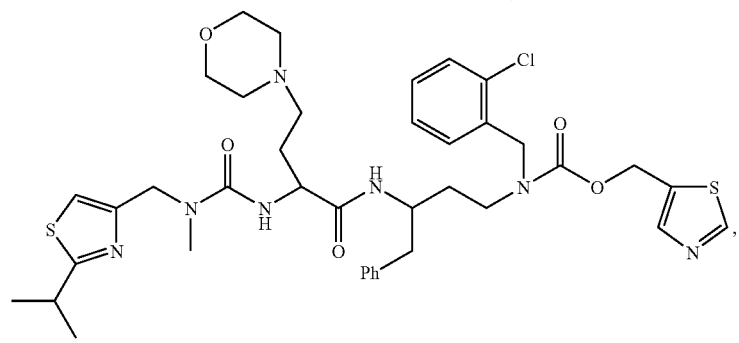
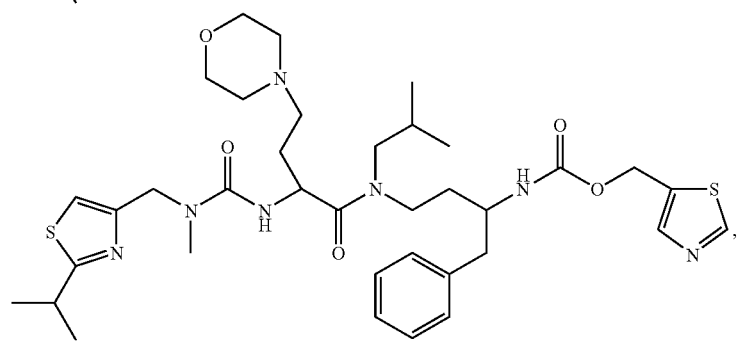
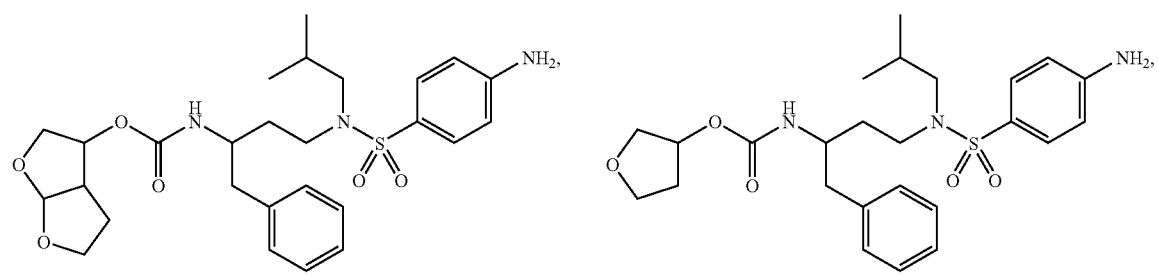
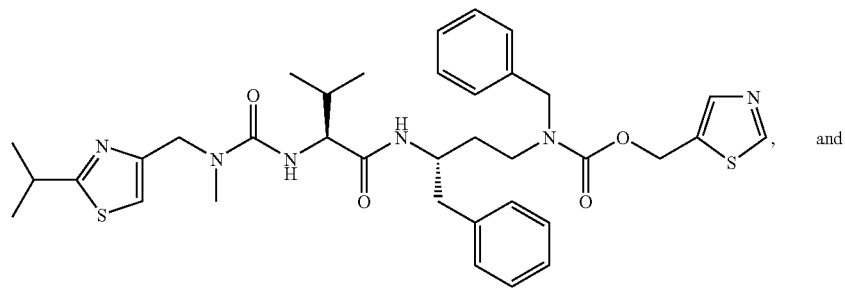
and

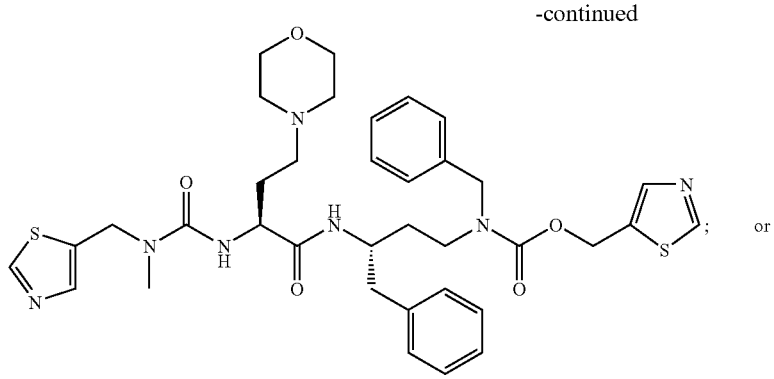

pharmaceutically acceptable salts thereof.

11. A pharmaceutical composition comprising a compound of claim 1, or a pharmaceutically acceptable salt, and a pharmaceutically acceptable carrier or excipient.

12. The pharmaceutical composition of claim 11, further comprising at least one additional therapeutic agent.

13. The pharmaceutical composition of claim 12, wherein the at least one additional therapeutic agent is selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, capsid polymerization inhibitors, interferons, ribavirin, taribavirin, NS3 protease inhibitors, alpha-glucosidase 1 inhibitors, hepatoprotectants, non-nucleoside inhibitors of HCV, other drugs for treating HCV, and combinations thereof.

14. The pharmaceutical composition of claim 13, wherein:
(1) said HIV protease inhibitors are selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859;
(2) said HIV non-nucleoside inhibitors of reverse transcriptase are selected from the group consisting of capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirene), efavirenz, BILR 355 BS, VRX 840773, UK-453061, and RDEA806;
(3) said HIV nucleoside inhibitors of reverse transcriptase are selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), amdoxovir, KP-1461, and fosalvudine tidoxil (formerly HDP 99.0003);
(4) said HIV nucleotide inhibitors of reverse transcriptase are selected from the group consisting of tenofovir and adefovir;
(5) said HIV integrase inhibitors are selected from the group consisting of curcumin, chicoric acid, 3,5-dicaffeoylquinic acid, aurintricarboxylic acid, caffeic acid phenethyl ester, tyrphostin, quercetin, S-1360, AR-177, L-870812, and L-870810, elvitegravir, MK-0518 (raltegravir), BMS-538158, GSK364735C, BMS-707035, MK-2048, and BA 011;
(6) said gp41 inhibitor are selected from the group consisting of enfuvirtide, sifuvirtide, FB006M, and TRI-1144;
(7) said CXCR4 inhibitor is AMD-070;
(8) said entry inhibitor is SP01A;
(9) said gp120 inhibitor is BMS-488043;
(10) said G6PD and NADH-oxidase inhibitor is immunitin;
(11) said CCR5 inhibitors are selected from the group consisting of aplaviroc, vicriviroc, maraviroc, PRO-140, INCB15050, PF-232798 (Pfizer), and CCR5 mAb004;
(12) said other drugs for treating HIV are selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS119, ALG 889, and PA-1050040 (PA-040);
(13) said interferons are selected from the group consisting of pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, and Pegylated IFN-beta; said NS5b polymerase inhibitors are selected from the group consisting of NM-283, valopicitabine, R1626, PSI-6130 (R1656), HCV-796, BILB 1941, XTL-2125, MK-0608, NM-107, R7128 (R4048), VCH-759, PF-868554, and GSK625433;
(15) said NS3 protease inhibitor are selected from the group consisting of SCH-503034 (SCH-7), VX-950 (telaprevir), BILN-2065, BMS-605339, and ITMN-191;
(16) said alpha-glucosidase 1 inhibitors are selected from the group consisting of MX-3253 (celgosivir) and UT-231B;
(17) said hepatoprotectants are selected from the group consisting of IDN-6556, ME 3738, and LB-84451;
(18) said non-nucleoside inhibitors of HCV are selected from the group consisting of A-831, and A-689; and
(19) said other drugs for treating HCV are selected from the group consisting of zadaxin, nitazoxanide, BIVN-401, PYN-17, KPE02003002, CPG-10101, KRN-7000, GI-5005, ANA-975, XTL-6865, ANA 971, NOV-205, EHC-18, NIM811, DEBIO-025, VGX-410C, EMZ-702, AVI 4065, Bavituximab, Oglufanide, and VX-497 (merimepodib).

15. A method for improving the pharmacokinetics or increasing blood plasma levels of a drug which is metabolized by cytochrome P450 monooxygenase, comprising administering to a patient treated with said drug, a pharmacokinetic improving or blood plasma level increasing effective amount of a compound of claim 1, or a pharmaceutically acceptable salt thereof.

16. The method of claim 15 wherein said administering comprises administering a therapeutically effective amount of a combination comprising said drug and the compound of Formula I or a pharmaceutically acceptable salt thereof.

17. The method of claim 16, wherein the drug metabolized by cytochrome P450 is an HIV protease inhibiting compound, an HIV non-nucleoside inhibitor of reverse transcriptase, an HIV nucleoside inhibitor of reverse transcriptase, HIV nucleotide inhibitor of reverse transcriptase, an HIV integrase inhibitor, a gp41 inhibitor, a CXCR4 inhibitor, a gp120 inhibitor, a CCR5 inhibitor, capsid polymerization inhibitors, other drugs for treating HIV, an interferon, ribavirin, taribavirin, NS3 protease inhibitor, alpha-glucosidase 1 inhibitor, hepatoprotectant, non-nucleoside inhibitor of HCV, NS5a inhibitors, NS5b polymerase inhibitors, other drugs for treating HCV, or mixtures thereof.

18. The method of claim 17, wherein the drug is 6-(3-chloro-2-fluorobenzyl)-1-((2S)-1-hydroxy-3-methylbutan-2-yl)-7-methoxy-4-oxo-1,4-dihydroquinoline-3-carboxylic acid or atazanavir.

19. The method of claim 15, wherein the drug and the compound or salt of claim 1 is administered as a single composition to the patient.

20. The method of claim 15, wherein the amount of the compound of Formula I administered is effective to inhibit cytochrome P450 monooxygenase.

21. A method for treating an HIV infection comprising administering to a patient having an HIV infection a therapeutically effective amount of a compound of claim 1, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

22. The method of claim 21, wherein:
(1) said HIV protease inhibitors are selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859;
(2) said HIV non-nucleoside inhibitors of reverse transcriptase are selected from the group consisting of capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirene), efavirenz, BILR 355 BS, VRX 840773, UK-453061, and RDEA806;
(3) said HIV nucleoside inhibitors of reverse transcriptase are selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), amdoxovir, KP-1461, and fosalvudine tidoxil (formerly HDP 99.0003);
(4) said HIV nucleotide inhibitors of reverse transcriptase are selected from the group consisting of tenofovir and adefovir;
(5) said HIV integrase inhibitors are selected from the group consisting of curcumin, chicoric acid, 3,5-dicaffeoylquinic acid, aurintricarboxylic acid, caffeic acid phenethyl ester, tyrphostin, quercetin, S-1360, AR-177, L-870812, and L-870810, elvitegravir, MK-0518 (raltegravir), BMS-538158, GSK364735C, BMS-707035, MK-2048, and BA 011;
(6) said gp41 inhibitor are selected from the group consisting of enfuvirtide, sifuvirtide, FB006M, and TRI-1144;
(7) said CXCR4 inhibitor is AMD-070;
(8) said entry inhibitor is SP01A;
(9) said gp120 inhibitor is BMS-488043;
(10) said G6PD and NADH-oxidase inhibitor is immunitin;
(11) said CCR5 inhibitors are selected from the group consisting of aplaviroc, vicriviroc, maraviroc, PRO-140, INCB15050, PF-232798 (Pfizer), and CCR5 mAb004;
(12) said other drugs for treating HIV are selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS119, ALG 889, and PA-1050040 (PA-040).

23. A method for treating an HCV infection comprising administering to a patient having an HCV infection a therapeutically effective amount of a compound of claim 1, or a pharmaceutically acceptable salt and/or ester thereof, in combination with a therapeutically effective amount of one or more additional therapeutic agents selected from the group consisting of interferons, NS5b polymerase inhibitors, ribavirin, taribavirin, NS3 protease inhibitors, alpha-glucosidase 1 inhibitors, hepatoprotectants, non-nucleoside inhibitors of HCV, and other drugs for treating HCV, or mixtures thereof.

24. The method of claim 23, wherein:
(1) said interferons are selected from the group consisting of pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, and Pegylated IFN-beta;
(2) said NS5b polymerase inhibitors are selected from the group consisting of NM-283, valopicitabine, R1626, PSI-6130 (R1656), HCV-796, BILB 1941, XTL-2125, MK-0608, NM-107, R7128 (R4048), VCH-759, PF-868554, and GSK625433;
(3) said NS3 protease inhibitor are selected from the group consisting of SCH-503034 (SCH-7), VX-950 (telaprevir), BILN-2065, BMS-605339, and ITMN-191;
(4) said alpha-glucosidase 1 inhibitors are selected from the group consisting of MX-3253 (celgosivir) and UT-231B;
(5) said hepatoprotectants are selected from the group consisting of IDN-6556, ME 3738, and LB-84451;
(6) said non-nucleoside inhibitors of HCV are selected from the group consisting of A-831, and A-689; and
(7) said other drugs for treating HCV are selected from the group consisting of zadaxin, nitazoxanide, BIVN-401, PYN-17, KPE02003002, CPG-10101, KRN-7000, GI-5005, ANA-975, XTL-6865, ANA 971, NOV-205, EHC-18, NIM811, DEBIO-025, VGX-410C, EMZ-702, AVI 4065, Bavituximab, Oglufanide, and VX-497 (merimepodib).

* * * * *